United States Patent
Cai et al.

(10) Patent No.: US 10,800,772 B2
(45) Date of Patent: Oct. 13, 2020

(54) THERAPEUTIC COMPOUNDS

(71) Applicant: Gilead Sciences, Inc., Foster City, CA (US)

(72) Inventors: Zhenhong R. Cai, Palo Alto, CA (US); Hongyan Guo, San Mateo, CA (US); Mingzhe Ji, Union City, CA (US); Haolun Jin, Foster City, CA (US); Amy Lee, Palo Alto, CA (US); Ryan McFadden, Foster City, CA (US); Michael L. Mitchell, Castro Valley, CA (US); Manuel Munoz, Vallejo, CA (US); Hyung-Jung Pyun, Fremont, CA (US); Lianhong Xu, Palo Alto, CA (US); Hong Yang, Fremont, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 15/716,431

(22) Filed: Sep. 26, 2017

(65) Prior Publication Data

US 2018/0118734 A1    May 3, 2018

Related U.S. Application Data

(60) Provisional application No. 62/436,256, filed on Dec. 19, 2016, provisional application No. 62/401,015, filed on Sep. 28, 2016.

(51) Int. Cl.

| | |
|---|---|
| *C07D 417/04* | (2006.01) |
| *C07D 471/04* | (2006.01) |
| *C07D 487/04* | (2006.01) |
| *C07D 417/14* | (2006.01) |
| *A61P 31/18* | (2006.01) |
| *A61K 31/428* | (2006.01) |
| *A61K 31/439* | (2006.01) |
| *A61K 31/454* | (2006.01) |
| *A61K 31/4545* | (2006.01) |
| *A61K 31/496* | (2006.01) |
| *A61K 31/4985* | (2006.01) |
| *A61K 31/519* | (2006.01) |
| *A61K 31/5377* | (2006.01) |
| *A61K 31/5383* | (2006.01) |
| *A61K 31/55* | (2006.01) |
| *A61K 31/551* | (2006.01) |
| *A61K 45/06* | (2006.01) |
| *C07D 471/08* | (2006.01) |
| *C07D 487/08* | (2006.01) |
| *C07D 487/10* | (2006.01) |
| *C07D 491/107* | (2006.01) |
| *C07D 498/04* | (2006.01) |

(52) U.S. Cl.
CPC .......... *C07D 417/14* (2013.01); *A61K 31/428* (2013.01); *A61K 31/439* (2013.01); *A61K 31/454* (2013.01); *A61K 31/4545* (2013.01); *A61K 31/496* (2013.01); *A61K 31/4985* (2013.01); *A61K 31/519* (2013.01); *A61K 31/5377* (2013.01); *A61K 31/5383* (2013.01); *A61K 31/55* (2013.01); *A61K 31/551* (2013.01); *A61K 45/06* (2013.01); *A61P 31/18* (2018.01); *C07D 417/04* (2013.01); *C07D 471/04* (2013.01); *C07D 471/08* (2013.01); *C07D 487/04* (2013.01); *C07D 487/08* (2013.01); *C07D 487/10* (2013.01); *C07D 491/107* (2013.01); *C07D 498/04* (2013.01)

(58) Field of Classification Search
CPC ... C07D 417/04; C07D 487/04; C07D 491/04
See application file for complete search history.

(56) References Cited

U.S. PATENT DOCUMENTS

| | | |
|---|---|---|
| 8,987,250 B2 | 3/2015 | Babaoglu et al. |
| 9,006,229 B2 | 4/2015 | Mitchell et al. |
| 9,096,586 B2 | 8/2015 | Babaoglu et al. |

(Continued)

FOREIGN PATENT DOCUMENTS

| | | |
|---|---|---|
| EP | 3604303 A1 | 2/2020 |
| JP | 2018090574 A | 6/2018 |

(Continued)

OTHER PUBLICATIONS

Post-exposure prophylaxis HIV [online], retrieved from the internet on May 13, 2017; URL: http://www.webmd.com/hiv-aids/post-exposure-prophylaxis.*

(Continued)

*Primary Examiner* — Shawquia Jackson

(57) ABSTRACT

Compounds disclosed herein including compounds of Formula I:

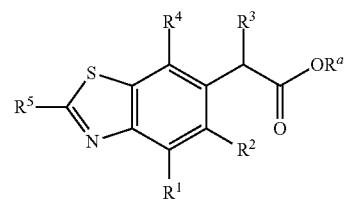

and salts thereof are provided. Pharmaceutical compositions comprising compounds disclosed herein, processes for preparing compounds disclosed herein, intermediates useful for preparing compounds disclosed herein and therapeutic methods for treating an HIV infection using compounds disclosed herein are also provided.

53 Claims, No Drawings

(56) References Cited

U.S. PATENT DOCUMENTS

| | | |
|---|---|---|
| 9,102,614 B2 | 8/2015 | Babaoglu et al. |
| 9,284,323 B2 | 3/2016 | Babaoglu et al. |
| 9,296,758 B2 | 3/2016 | Babaoglu et al. |
| 9,376,392 B2 | 6/2016 | Babaoglu et al. |
| 9,464,096 B2 | 10/2016 | Babaoglu et al. |
| 9,879,023 B2 | 1/2018 | Babaoglu et al. |

FOREIGN PATENT DOCUMENTS

| | | |
|---|---|---|
| WO | WO-2013159064 A1 | 10/2013 |
| WO | WO-2018064080 A1 | 4/2018 |
| WO | WO-2018127800 A1 | 7/2018 |
| WO | WO-2018127801 A1 | 7/2018 |

OTHER PUBLICATIONS

Landovitz, et al. N. Engl. J. Med. 2009, 361:18, 1768-75.*
International Search Report for PCT/US2017/053563, dated Apr. 5, 2018, 3 pgs.
Written Opinion for PCT/US2017/053563, dated Apr. 5, 2018, 5pgs.
AIDS info (2016) "Guidelines for the Use of Antiretroviral Agents in Adults and Adolescents Living with HIV" Downloaded from https://aidsinfo.nih.gov/guidelines on Apr. 9, 2019 pp. A1-A4.
DESCOVY Product Label (Revised Oct. 2017) Gilead Sciences, Inc., 25 Pages.
GENVOYA Product Label (Revised Feb. 2018) Gilead Sciences, Inc., 44 Pages.
Pauwels, R. et al., (1987) "Sensitive and rapid assay on MT-4 cells for detection of antiviral compounds against the AIDS virus" *Journal of Virological Methods*, 16:171-185.
TRUVADA Product Label (Revised May 2018) Gilead Sciences, Inc., 45 Pages.

* cited by examiner

THERAPEUTIC COMPOUNDS

CROSS REFERENCE TO RELATED APPLICATIONS

This application claims priority to and the benefit under 35 U.S.C. 119(e) of U.S. Provisional Patent Application Serial Nos. 62/401,015, filed Sep. 28, 2016 and 62/436,256, filed Dec. 19, 2016, the disclosures of which are hereby incorporated by reference in their entirety.

BACKGROUND

Human immunodeficiency virus (HIV) infection and related diseases are a major public health problem worldwide. Human immunodeficiency virus type 1 (HIV-1) encodes three enzymes which are required for viral replication: reverse transcriptase, protease, and integrase. Although drugs targeting reverse transcriptase and protease are in wide use and have shown effectiveness, particularly when employed in combination, toxicity and development of resistant strains have limited their usefulness (Palella, et al *N. Engl. J. Med.* (1998) 338:853-860; Richman, D. D. *Nature* (2001) 410:995-1001).

Accordingly, there is a need for new agents that inhibit the replication of HIV. There is also a need for agents that are directed against alternate sites in the viral life cycle including agents that target the integrase enzyme. There is also a need for new agents with appropriate levels of metabolic stability.

SUMMARY

The present invention encompasses the recognition that there exists a need for new compounds and methods for treating HIV infection. Accordingly, in some embodiments, the present invention provides a compound of Formula I:

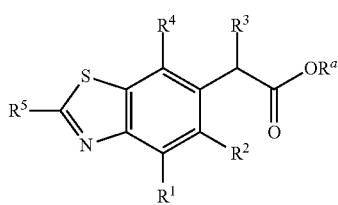

I or a pharmaceutically acceptable salt thereof, wherein:
$R^1$ is H or $(C_1$-$C_6)$alkyl;
$R^2$ is H or $(C_1$-$C_6)$alkyl;
$R^a$ is H or $(C_1$-$C_6)$alkyl;
$R^3$ is $O(C_1$-$C_6)$alkyl or $O(C_1$-$C_6)$cycloalkyl;
$R^4$ is a 3-8 membered saturated, partially unsaturated, or aryl monocyclic ring containing 0-4 heteroatoms independently selected from nitrogen, oxygen, or sulfur, or an 8-13 membered saturated, partially unsaturated, or aryl bicyclic or tricyclic ring containing 0-4 heteroatoms independently selected from nitrogen, oxygen, or sulfur, and wherein $R^4$ is optionally substituted with 1-10 $R^f$;
each $R^f$ is independently halo, $R^X$, $OR^X$, $SR^X$, CN, S(O)$R^X$, SO$_2R^X$, OSO$_2R^X$, N($R^X$)$_2$, NO$_2$, NR$^X$C(O)$R^X$, NR$^X$C(O)(CO)$R^X$, NR$^X$C(O)N($R^X$)$_2$, NR$^X$C(O)OR$^X$, N($R^X$)S(O)$R^X$, N($R^X$)SO$_2R^X$, N($R^X$)SO$_2OR^X$, C(O)$R^X$, C(O)OR$^X$, OC(O)$R^X$, OC(O)OR$^X$, C(O)N($R^X$)$_2$, OC(O)N($R^X$)$_2$, or a 3-8 membered saturated, partially unsaturated, or aryl monocyclic ring containing 0-4 heteroatoms independently selected from nitrogen, oxygen, or sulfur, or two $R^f$ on the same carbon are taken together to form an oxo group;
each $R^X$ is independently H, halo, N($R^Y$)$_2$, C(O)OR$^Y$, $C_{1-8}$ aliphatic, $C_{1-8}$ heteroaliphatic, $(C_3$-$C_6)$cycloalkyl, 3-8 membered heterocycloalkyl containing 1-3 heteroatoms independently selected from nitrogen, oxygen, or sulfur, optionally substituted phenyl, or two $R^X$ on the same nitrogen are taken together to form a 5-6 membered saturated, partially saturated, or heteroaryl ring having 1-3 heteroatoms independently selected from nitrogen, oxygen, and sulfur, or two $R^X$ on the same carbon or on adjacent carbons are optionally taken together to form a $(C_3$-$C_6)$cycloalkyl, or a 3-6 membered saturated fused monocyclic ring containing 0-2 heteroatoms independently selected from nitrogen, oxygen, and sulfur, or two $R^X$ on the same carbon are taken together to form an oxo group;
wherein the $C_{1-8}$ aliphatic, $C_{1-8}$ heteroaliphatic, $(C_3$-$C_6)$cycloalkyl, 3-8 membered heterocycloalkyl, or phenyl is optionally substituted with 1-5 $R^z$;
each $R^z$ is independently halo, $C_{1-8}$ aliphatic, or $C_{1-8}$ heteroaliphatic;
each $R^Y$ is independently H or $(C_1$-$C_6)$alkyl;
$R^5$ is

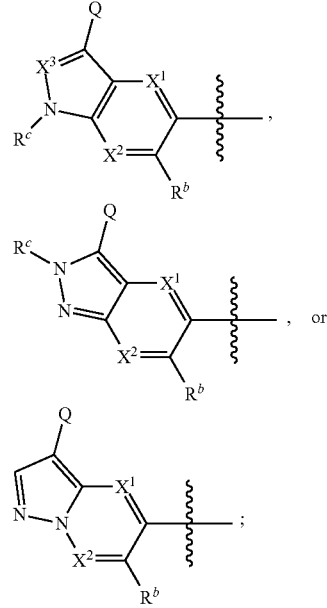

$R^b$ is H or $(C_1$-$C_6)$alkyl;
$R^c$ is H, $(C_1$-$C_6)$alkyl or $(C_3$-$C_6)$cycloalkyl, wherein $R^c$ is optionally substituted with 1-5 groups independently selected from halo, D, OR$^X$, and N($R^X$)$_2$;
Q is a 3-10 membered saturated or partially unsaturated monocyclic or bridged, spirocyclic, or fused bicyclic heterocycloalkyl containing 1-3 heteroatoms independently selected from nitrogen, oxygen, or sulfur, optionally substituted with 1-5 $R^e$;
each $R^e$ is independently H, $(C_1$-$C_6)$alkyl, N($R^X$)$_2$, C(O)$R^X$, C(O)OR$^X$, S(O)$_2R^X$, $(C_3$-$C_6)$cycloalkyl or 3-6 membered heterocycloalkyl containing 1-2 heteroatoms independently selected from nitrogen, oxygen, or sulfur, or two $R^e$ wherein $R^e$ on the same carbon are taken together to form an oxo group, or two $R^e$ wherein $R^e$ on the same carbon are taken together to form ($C_3$-$C_5$)cycloalkyl or 3-4 membered heterocycloalkyl containing 1-2 heteroatoms independently selected from nitrogen, oxygen, or sulfur, wherein $R^e$ is optionally substituted with 1-5 $R^g$;

each $R^g$ is independently halo, $R^X$, $OR^X$, $N(R^X)_2$, $C(O)R^X$, $C(O)OR^X$, $OC(O)R^X$, $OC(O)OR^X$, $S(O)_2R^X$, optionally substituted 3-4 membered heterocycloalkyl containing 1-2 heteroatoms independently selected from nitrogen, oxygen, or sulfur, or two $R^g$ on the same carbon are taken together to form an oxo group, or two $R^g$ on the same sulfur are optionally taken together to form an oxo group;

$X^1$ is N or C(H);

$X^2$ is N or C(H);

$X^3$ is N or C(H); and wherein the compound is not one of the following structures:

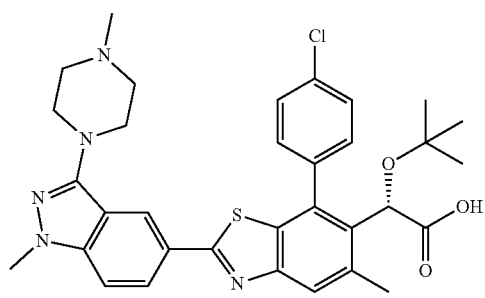

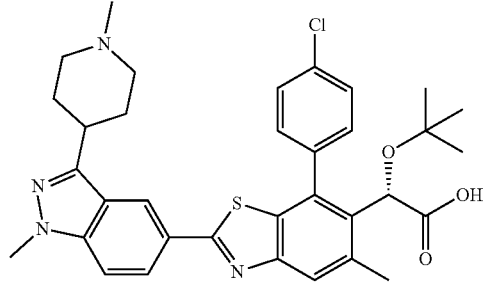

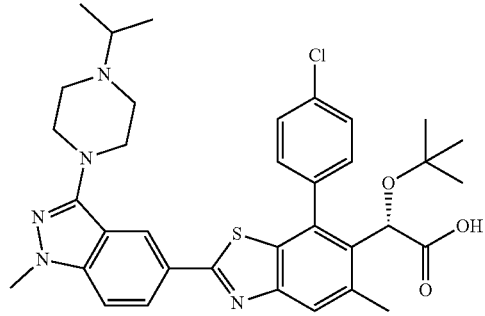

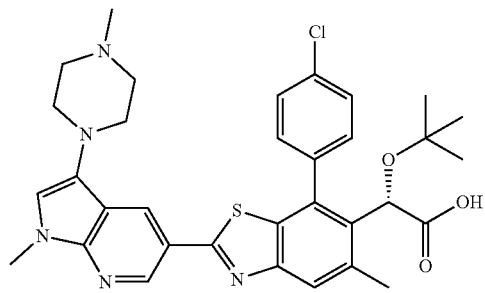

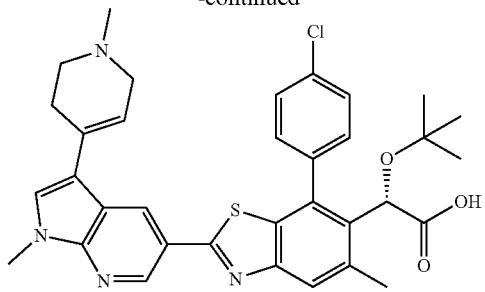

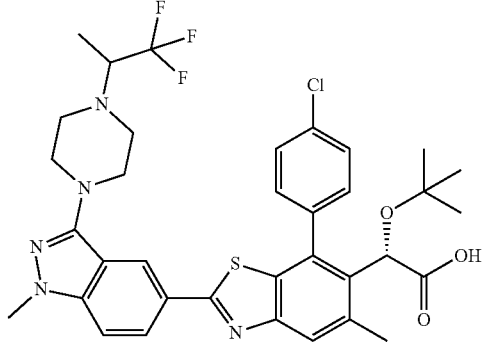

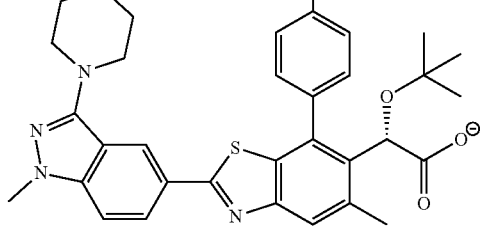

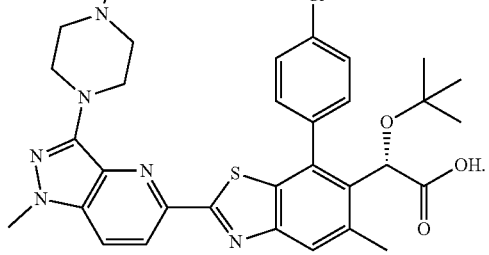

In some embodiments, the present invention provides a pharmaceutical composition comprising a compound disclosed herein (e.g., a compound of Formula I) or a pharmaceutically acceptable salt thereof, and a pharmaceutically acceptable carrier.

In some embodiments, the present invention provides methods for treating the proliferation of the HIV virus, treating AIDS or delaying the onset of AIDS or ARC symptoms in a mammal (e.g., a human), comprising administering a compound disclosed herein (e.g., a compound of Formula I), or a pharmaceutically acceptable salt thereof, to the mammal.

In some embodiments, the present invention provides methods for treating an HIV infection in a mammal (e.g., a human) comprising administering a compound disclosed herein (e.g., a compound of Formula I), or a pharmaceutically acceptable salt thereof, to the mammal.

In some embodiments, the present invention provides methods for treating an HIV infection in a mammal (e.g., a human) comprising administering to the mammal in need thereof a therapeutically effective amount of a compound disclosed herein (e.g., a compound of Formula I), or a pharmaceutically acceptable salt thereof, in combination with a therapeutically effective amount of one or more additional therapeutic agents selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, maturation inhibitors, attachment inhibitors and other drugs for treating HIV, and combinations thereof.

In some embodiments, the present invention provides a compound disclosed herein (e.g., a compound of Formula I), or a pharmaceutically acceptable salt thereof for use in medical therapy (e.g., for use in treating the proliferation of the HIV virus or AIDS or delaying the onset of AIDS or ARC symptoms in a mammal (e.g., a human)).

In some embodiments, the present invention provides a compound disclosed herein (e.g., a compound of Formula I), or a pharmaceutically acceptable salt thereof for use in medical therapy (e.g., for use in treating an HIV infection in a mammal (e.g., a human)).

In some embodiments, the present invention provides a compound disclosed herein (e.g., a compound of Formula I), or a pharmaceutically acceptable salt thereof for use in the manufacture of a medicament for treating the proliferation of the HIV virus or AIDS or delaying the onset of AIDS or ARC symptoms in a mammal (e.g., a human).

In some embodiments, the present invention provides a compound disclosed herein (e.g., a compound of Formula I), or a pharmaceutically acceptable salt thereof, for use in the prophylactic or therapeutic treatment of the proliferation of the HIV virus or AIDS or for use in the therapeutic treatment of delaying the onset of AIDS or ARC symptoms.

In some embodiments, the present invention provides a compound disclosed herein (e.g., a compound of Formula I), or a pharmaceutically acceptable salt thereof, for the manufacture of a medicament for treating an HIV infection in a mammal (e.g., a human).

In some embodiments, the present invention provides a compound disclosed herein (e.g., a compound of Formula I) or a pharmaceutically acceptable salt thereof, for use in the prophylactic or therapeutic treatment of an HIV infection in a mammal (e.g., a human).

In some embodiments, the present invention provides processes and intermediates disclosed herein that are useful for preparing compounds disclosed herein or salts thereof.

DETAILED DESCRIPTION OF CERTAIN EMBODIMENTS

Definitions

Unless stated otherwise, the following terms and phrases as used herein are intended to have the following meanings.

When trade names are used herein, applicants intend to independently include the tradename product and the active pharmaceutical ingredient(s) of the tradename product.

Unless defined otherwise, all technical and scientific terms used herein have the same meaning as commonly understood by one of ordinary skill in the art. A dash at the front or end of a chemical group is a matter of convenience; chemical groups may be depicted with or without one or more dashes without losing their ordinary meaning. A wavy line drawn through a line in a structure indicates a point of attachment of a group. A dashed line indicates an optional bond. A prefix such as "$C_{u\text{-}v}$" or ($C_u$-$C_v$) indicates that the following group has from u to v carbon atoms. For example, "$C_{1\text{-}6}$alkyl" indicates that the alkyl group has from 1 to 6 carbon atoms.

Aliphatic: As used herein, "aliphatic" refers to any group derived from a linear or branched hydrocarbon, including alkyls, alkenyls, and alkynyls. Aliphatic groups include, but are not limited to, methyl, ethyl, propyls such as propan-1-yl, propan-2-yl (iso-propyl), butyls such as butan-1-yl, butan-2-yl (sec-butyl), 2-methyl-propan-1-yl (iso-butyl), 2-methyl-propan-2-yl (t-butyl), pentyls, hexyls, octyls, decyls, ethenyl (vinyl), propenyl (allyl), 1-butenyl, 1,3-butadienyl, ethynyl (—C≡CH), propargyl (—CH$_2$C≡CH), (E)-pent-3-en-1-ynyl, and the like. Unless otherwise specified, an aliphatic group has from 1 to about 10 carbon atoms, for example from 1 to 10 carbon atoms, for example from 1 to 6 carbon atoms, or from about 1 to 4 carbon atoms.

Alkyl: As used herein, the term "alkyl" refers to any group derived from a linear or branched saturated hydrocarbon. Alkyl groups include, but are not limited to, methyl, ethyl, propyls such as propan-1-yl, propan-2-yl (iso-propyl), butyls such as butan-1-yl, butan-2-yl (sec-butyl), 2-methyl-propan-1-yl (iso-butyl), 2-methyl-propan-2-yl (t-butyl), pentyls, hexyls, octyls, decyls, and the like. Unless otherwise specified, an alkyl group has from 1 to about 10 carbon atoms, for example from 1 to 10 carbon atoms, for example from 1 to 6 carbon atoms, for example from 1 to 4 carbon atoms.

Alkenyl: As used herein, "alkenyl" refers to any group derived from a straight or branched hydrocarbon with at least one carbon-carbon double bond. Alkenyl groups include, but are not limited to, ethenyl (vinyl), propenyl (allyl), 1-butenyl, 1,3-butadienyl, and the like. Unless otherwise specified, an alkenyl group has from 2 to about 10 carbon atoms, for example from 2 to 10 carbon atoms, for example from 2 to 6 carbon atoms, for example from 2 to 4 carbon atoms.

Alkynyl: As used herein, "alkynyl" refers to any group derived from a straight or branched hydrocarbon with at least one carbon-carbon triple bond and includes those groups having one triple bond and one double bond. Examples of alkynyl groups include, but are not limited to, ethynyl (—C≡CH), propargyl (—CH$_2$C≡CH), (E)-pent-3-en-1-ynyl, and the like. Unless otherwise specified, an alkynyl group has from 2 to about 10 carbon atoms, for example from 2 to 10 carbon atoms, for example from 2 to 6 carbon atoms, for example from 2 to 4 carbon atoms.

Aryl: As used herein, the term "aryl" used alone or as part of a larger moiety as in "aralkyl", "aralkoxy", or "aryloxyalkyl", refers to monocyclic and bicyclic ring systems having a total of five to fourteen ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl", as it is used herein, is a group in which an aromatic ring is fused to one or more non-aromatic rings, such as indanyl, phthalimidyl, naphthimidyl, phenanthridinyl, or tetrahydronaphthyl, and the like.

Carbocycle: As used herein, the term "carbocycle" or "carbocyclyl" refers to a saturated (i.e., cycloalkyl) or partially unsaturated (e.g., cycloalkenyl, cycloalkadienyl, etc.) ring, having 3 to 7 carbon atoms. In some embodiments the carbocycle is a monocycle comprising 3-6 ring carbons (i.e. ($C_3$-$C_6$)carbocycle). In some embodiments, the term carbocycle includes multicyclic carbocyles having 7 to 12 carbon atoms as a bicycle, and up to about 20 carbon atoms as a polycycle provided that the largest single ring of a multicyclic carbocycle is 7 carbon atoms.

Cycloalkyl: As used herein, the term "cycloalkyl" refers to a cyclic alkyl group. Examples include, but are not limited to, cyclopropyl, cyclobutyl, cyclopentyl, cyclohexyl, adamantyl, and the like.

Halo or halogen: As used herein, the term "halo" or "halogen" refers to fluoro, chloro, bromo and iodo.

Heteroaliphatic: As used herein, the term "heteroaliphatic" refers to an aliphatic group in which one or more of the carbon atoms are each independently replaced with a heteroatom selected from the group consisting of O, N, S, and Si. A heteroatom may optionally be oxidized or alkylated. A heteroatom may be placed at any interior position of the heteroalkyl group or at a position at which the group is attached to the remainder of the molecule. Examples include, but are not limited to, —$CH_2OCH_3$, —$CH_2CH_2NHCH_3$, —$CH_2CH_2N(CH_3)$—$CH_3$, —$CH_2SCH_2CH_3$, —$S(O)CH_3$, —$CH_2CH_2S(O)_2CH_3$, —$CHCHOCH_3$, —$Si(CH_3)_3$, —$CH_2CHNOCH_3$, —$CHCHN(CH_3)CH_3$, —$CH_2NHOCH_3$ and —$CH_2OS(CH_3)_3$.

Heteroalkyl: As used herein, the term "heteroalkyl" refers to an alkyl in which one or more of the carbon atoms are each independently replaced with a heteroatom selected from the group consisting of O, N, S, and Si. A heteroatom may optionally be oxidized or alkylated. A heteroatom may be placed at any interior position of the heteroalkyl group or at a position at which the group is attached to the remainder of the molecule. Examples include, but are not limited to, —$CH_2OCH_3$, —$CH_2CH_2NHCH_3$, —$CH_2CH_2N(CH_3)$—$CH_3$, —$CH_2SCH_2CH_3$, —$S(O)CH_3$, —$CH_2CH_2S(O)_2CH_3$, —$CHCHOCH_3$, —$Si(CH_3)_3$, —$CH_2CHNOCH_3$, —$CHCHN(CH_3)CH_3$, —$CH_2NHOCH_3$ and —$CH_2OS(CH_3)_3$.

Heteroaryl: As used herein, the term "heteroaryl" refers to an aryl group in which one or more of the carbon atoms (and any associated hydrogen atoms) are each independently replaced with the same or different heteroatom, as defined above. Heteroaryl groups include, but are not limited to, groups derived from acridine, benzoimidazole, benzothiophene, benzofuran, benzoxazole, benzothiazole, carbazole, carboline, cinnoline, furan, imidazole, imidazopyridine, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Unless otherwise specified, a heteroaryl group has from 5 to about 20 carbon atoms, for example from 5 to 20 carbon atoms, for example from 5 to 14 carbon atoms, for example from 5 to 10 carbon atoms.

Heteroatom: The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

Heterocycle: As used herein, the terms "heterocycle," "heterocyclic," and "heterocyclyl" refer to a single saturated or partially unsaturated non-aromatic ring with at least one heteroatom, as defined above. Heterocycles include, but are not limited to, groups derived from azetidine, aziridine, imidazolidine, morpholine, oxirane (epoxide), oxetane, piperazine, piperidine, pyrazolidine, piperidine, pyrrolidine, pyrrolidinone, tetrahydrofuran, tetrahydrothiophene, dihydropyridine, tetrahydropyridine, N-bromopyrrolidine, N-chloropiperidine, and the like.

Optionally substituted: Compounds described may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Unless otherwise indicated, suitable monovalent substituents on a substitutable carbon atom of an "optionally substituted" group are independently halogen; —$(CH_2)_{0-4}R^\circ$; —$(CH_2)_{0-4}OR^\circ$; —$O(CH_2)_{0-4}R^\circ$, —$O$—$(CH_2)_{0-4}C(O)OR^\circ$; —$(CH_2)_{0-4}CH(OR^\circ)_2$; —$(CH_2)_{0-4}SR^\circ$; —$(CH_2)_{0-4}Ph$, which may be substituted with $R^\circ$; —$(CH_2)_{0-4}O(CH_2)_{0-1}Ph$ which may be substituted with $R^\circ$; —$CH$=$CHPh$, which may be substituted with $R^\circ$; —$(CH_2)_{0-4}O(CH_2)_{0-1}$— pyridyl which may be substituted with $R^\circ$; —$NO_2$; —$CN$; —$N_3$; —$(CH_2)_{0-4}N(R^\circ)_2$; —$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)SR^\circ$; —$(CH_2)_{0-4}C(O)OSiR^\circ_3$; —$(CH_2)_{0-4}OC(O)R^\circ$; —$OC(O)(CH_2)_{0-4}SR$—, $SC(S)SR^\circ$; —$(CH_2)_{0-4}SC(O)R^\circ$; —$(CH_2)_{0-4}C(O)NR^\circ_2$; —$C(S)NR^\circ_2$; —$C(S)SR^\circ$; —$SC(S)SR^\circ$, —$(CH_2)_{0-4}OC(O)NR^\circ_2$; —$C(O)N(OR^\circ)R^\circ$; —$C(O)C(O)R^\circ$; —$C(O)CH_2C(O)R^\circ$; —$C(NOR^\circ)R^\circ$; —$(CH_2)_{0-4}SSR^\circ$; —$(CH_2)_{0-4}S(O)_2R^\circ$; —$(CH_2)_{0-4}S(O)_2OR^\circ$; —$(CH_2)_{0-4}OS(O)_2R^\circ$; —$S(O)_2NR^\circ_2$; —$(CH_2)_{0-4}S(O)R^\circ$; —$N(R^\circ)S(O)_2NR^\circ_2$; —$N(R^\circ)S(O)_2R^\circ$; —$N(OR^\circ)R^\circ$; —$C(NH)NR^\circ_2$; —$P(O)_2R^\circ$; —$P(O)R^\circ_2$; —$OP(O)R^\circ_2$; —$OP(O)(OR^\circ)_2$; $SiR^\circ_3$; —$(C_{1-4}$ straight or branched alkylene)$O$—$N(R^\circ)_2$; or —$(C_{1-4}$ straight or branched alkylene)$C(O)O$—$N(R^\circ)_2$, wherein each $R^\circ$ may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Unless otherwise indicated, suitable monovalent substituents on $R^\circ$ (or the ring formed by taking two independent occurrences of $R^\circ$ together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include =O and =S.

Unless otherwise indicated, suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Unless otherwise indicated, suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Unless otherwise indicated, suitable substituents on the aliphatic group of R$^\bullet$ include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Unless otherwise indicated, suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Unless otherwise indicated, suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Oxo: As used herein, the term "oxo" refers to a double-bonded oxygen (=O). In compounds where an oxo group is bound to an sp$^2$ nitrogen atom, an N-oxide is indicated.

Provided compound: The term "provided compound," as used herein, refers to a compound of Formula I:

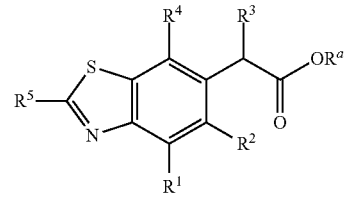

or a pharmaceutically acceptable salt thereof, wherein:
$R^1$ is H or (C$_1$-C$_6$)alkyl;
$R^2$ is H or (C$_1$-C$_6$)alkyl;
$R^a$ is H or (C$_1$-C$_6$)alkyl;
$R^3$ is O(C$_1$-C$_6$)alkyl or O(C$_1$-C$_6$)cycloalkyl;
$R^4$ is a 3-8 membered saturated, partially unsaturated, or aryl monocyclic ring containing 0-4 heteroatoms independently selected from nitrogen, oxygen, or sulfur, or an 8-13 membered saturated, partially unsaturated, or aryl bicyclic or tricyclic ring containing 0-4 heteroatoms independently selected from nitrogen, oxygen, or sulfur, and wherein $R^4$ is optionally substituted with 1-10 $R^f$;
each $R^f$ is independently halo, $R^X$, $OR^X$, $SR^X$, CN, S(O)$R^X$, SO$_2R^X$, OSO$_2R^X$, N(R$^X$)$_2$, NO$_2$, NR$^X$C(O)R$^X$, NR$^X$C(O)(CO)R$^X$, NR$^X$C(O)N(R$^X$)$_2$, NR$^X$C(O)OR$^X$, N(R$^X$)S(O)R$^X$, N(R$^X$)SO$_2$R$^X$, N(R$^X$)SO$_2$OR$^X$, C(O)R$^X$, C(O)OR$^X$, OC(O)R$^X$, OC(O)OR$^X$, C(O)N(R$^X$)$_2$, OC(O)N(R$^X$)$_2$, or a 3-8 membered saturated, partially unsaturated, or aryl monocyclic ring containing 0-4 heteroatoms independently selected from nitrogen, oxygen, or sulfur, or two $R^f$ on the same carbon are taken together to form an oxo group;
each $R^X$ is independently H, halo, N(R$^Y$)$_2$, C(O)OR$^Y$, C$_{1-8}$ aliphatic, C$_{1-8}$ heteroaliphatic, (C$_3$-C$_6$)cycloalkyl, 3-8 membered heterocycloalkyl containing 1-3 heteroatoms independently selected from nitrogen, oxygen, or sulfur, optionally substituted phenyl, or two $R^X$ on the same nitrogen are taken together to form a 5-6 membered saturated, partially saturated, or heteroaryl ring having 1-3 heteroatoms independently selected from nitrogen, oxygen, and sulfur, or two $R^X$ on the same carbon or on adjacent carbons are optionally taken together to form a (C$_3$-C$_6$)cycloalkyl, or a 3-6 membered saturated fused monocyclic ring containing 0-2 heteroatoms independently selected from nitrogen, oxygen, and sulfur, or two $R^X$ on the same carbon are taken together to form an oxo group;
  wherein the C$_{1-8}$ aliphatic, C$_{1-8}$ heteroaliphatic, (C$_3$-C$_6$) cycloalkyl, 3-8 membered heterocycloalkyl, or phenyl is optionally substituted with 1-5 $R^z$;
each $R^z$ is independently halo, C$_{1-8}$ aliphatic, or C$_{1-8}$ heteroaliphatic;

each $R^Y$ is independently H or $(C_1-C_6)$alkyl;

$R^5$ is

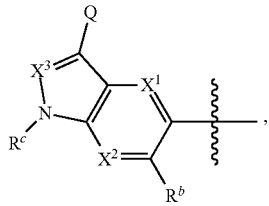

,

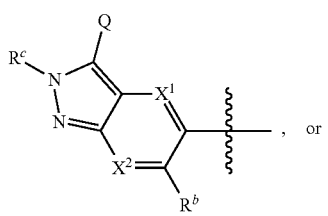

, or

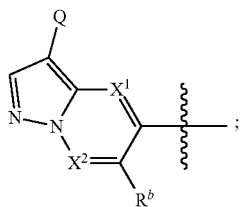

;

$R^b$ is H or $(C_1-C_6)$alkyl;

$R^c$ is H, $(C_1-C_6)$alkyl or $(C_3-C_6)$cycloalkyl, wherein $R^c$ is optionally substituted with 1-5 groups independently selected from halo, D, $OR^X$, and $N(R^X)_2$;

Q is a 3-10 membered saturated or partially unsaturated monocyclic or bicyclic heterocycloalkyl containing 1-3 heteroatoms independently selected from nitrogen, oxygen, or sulfur, optionally substituted with 1-5 $R^e$;

each $R^e$ is independently H, $(C_1-C_6)$alkyl, $N(R^X)_2$, $C(O)R^X$, $C(O)OR^X$, $S(O)_2R^X$, $(C_3-C_6)$cycloalkyl or 3-6 membered heterocycloalkyl containing 1-2 heteroatoms independently selected from nitrogen, oxygen, or sulfur, or two $R^e$ wherein $R^e$ on the same carbon are taken together to form an oxo group, or two $R^e$ wherein $R^e$ on the same carbon are taken together to form $(C_3-C_8)$cycloalkyl or 3-4 membered heterocycloalkyl containing 1-2 heteroatoms independently selected from nitrogen, oxygen, or sulfur, wherein $R^e$ is optionally substituted with 1-5 $R^g$;

each $R^g$ is independently halo, $R^X$, $OR^X$, $N(R^X)_2$, $C(O)R^X$, $C(O)OR^X$, $OC(O)R^X$, $OC(O)OR^X$, $S(O)_2R^X$, optionally substituted 3-4 membered heterocycloalkyl containing 1-2 heteroatoms independently selected from nitrogen, oxygen, or sulfur, or two $R^g$ on the same carbon are taken together to form an oxo group, or two $R^g$ on the same sulfur are optionally taken together to form an oxo group;

$X^1$ is N or C(H);
$X^2$ is N or C(H);
$X^3$ is N or C(H); and wherein the compound is not one of the following structures:

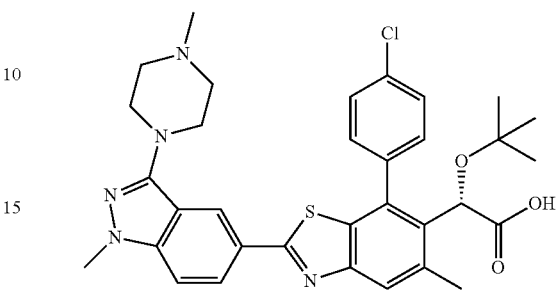

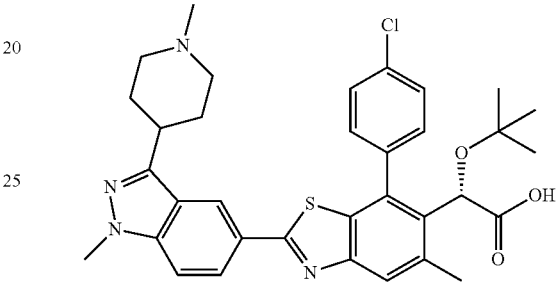

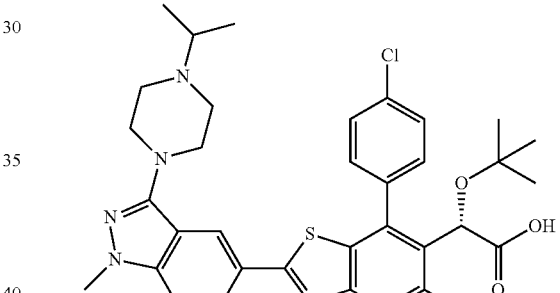

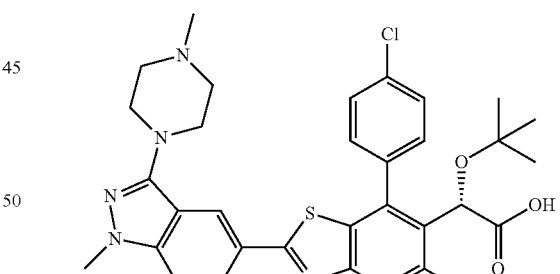

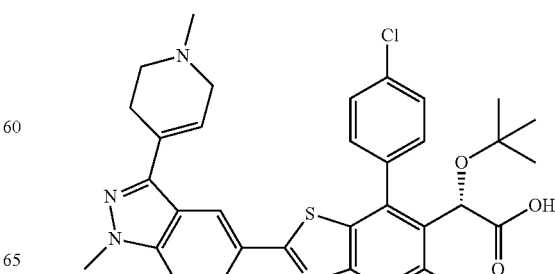

-continued

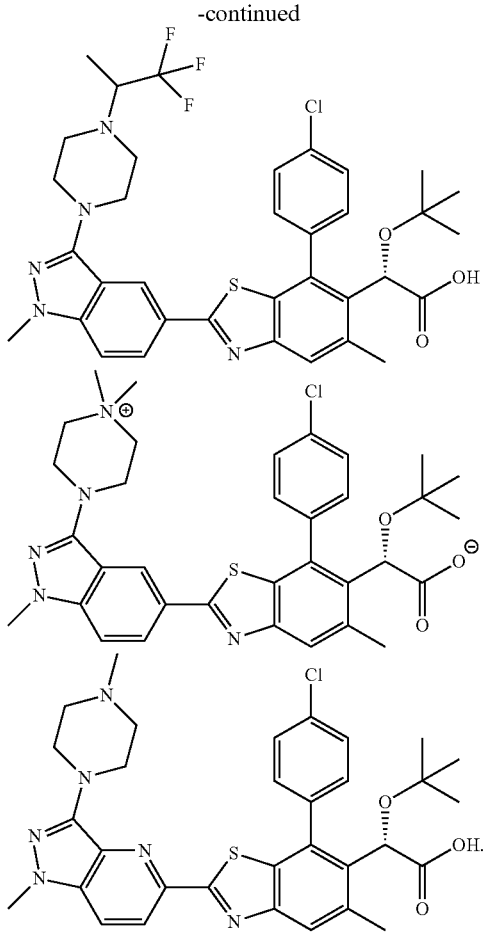

It is to be understood that one or more nitrogen atoms included in either of the five-six fused heteroaryl rings of Formula I can be present in an oxidized form. Accordingly, the invention includes a compound of Formula I (as defined in the summary of the invention) or a salt or N-oxide thereof.

Protecting Groups

In the context of the present disclosure, protecting groups include prodrug moieties and chemical protecting groups.

Protecting Group:

As used herein, the phrase "protecting group" refers to a moiety of a compound that masks or alters the properties of a functional group or the properties of the compound as a whole. Chemical protecting groups and strategies for protection/deprotection are well known in the art. See e.g., *Protective Groups in Organic Chemistry*, Theodora W. Greene, John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g., alcohols, be physiologically acceptable, although in general it is more desirable if the products are pharmacologically innocuous.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis. Protecting groups do not need to be, and generally are not, the same if the compound is substituted with multiple protecting groups. In general, protecting groups will be used to protect functional groups such as carboxyl, hydroxyl, thio, or amino groups and to thus prevent side reactions or to otherwise facilitate the synthetic efficiency. The order of deprotection to yield free deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, phosphonic acid, or other functions) include "ether- or ester-forming groups". Ether- or ester-forming groups are capable of functioning as chemical protecting groups in the synthetic schemes set forth herein. However, some hydroxyl and thio protecting groups are neither ether-nor ester-forming groups, as will be understood by those skilled in the art, and are included with amides, discussed below.

A very large number of hydroxyl protecting groups and amide-forming groups and corresponding chemical cleavage reactions are described in *Protective Groups in Organic Synthesis*, Theodora W. Greene (John Wiley & Sons, Inc., New York, 1991, ISBN 0-471-62301-6) ("Greene"). See also Kocienski, Philip J.; *Protecting Groups* (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene.

Stereoisomers

Compounds of the invention may have chiral centers, e.g., chiral carbon or phosphorus atoms. In some embodiments, compounds of the invention include mixtures of all stereoisomers, including enantiomers, diastereomers, and atropisomers.

Chiral:

As used herein, the term "chiral" refers to molecules which have the property of non-superimposability of the mirror image partner, while the term "achiral" refers to molecules which are superimposable on their mirror image partner.

Diastereoisomer:

As used herein, the term "diastereomer" refers to a stereoisomer with two or more centers or axes of chirality and whose molecules are not mirror images of one another. Diastereomers typically have different physical properties, e.g., melting points, boiling points, spectral properties, and reactivities. Mixtures of diastereomers may separate under high resolution analytical procedures such as electrophoresis and chromatography.

Enantiomer:

As used herein, the term "enantiomer" refers to two stereoisomers of a compound which are non-superimposable mirror images of one another.

Stereoisomers:

As used herein, the term "stereoisomers" refers to compounds which have identical chemical constitution, but differ with regard to the arrangement of the atoms or groups in space.

In some embodiments, compounds of the present invention exist as atropisomers. For example, atropisomers can exist when $R^4$ of Formula I is, e.g., phenyl, and certain substitution patterns are present on the phenyl ring, with such chirality occurring at the site indicated below with an asterisk:

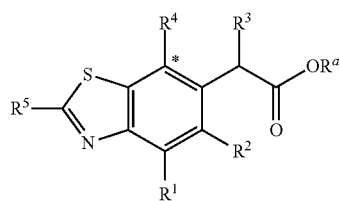

I

In some embodiments, chirality that results from atropisomers (e.g., at the above-depicted asterisk position in Formula I) may be a feature of particular compound(s) of the invention. In some embodiments, the invention may include all atropisomers of a particular compound. In some embodiments, the invention may include mixtures of two or more atropisomers; in some such embodiments, the invention may include mixtures that are enriched in one or more particular atropisomers as compared with one or more other atropisomers. In some embodiments, the present invention provides a single atropisomer of particular compound(s) described herein. In some embodiments, a particular atropisomer, or mixture thereof, may be characterized by one or more characteristics, properties, or activities, as described herein.

In some embodiments, compounds of the invention are greater than 50% a single atropisomer at the asterisk position. In some embodiments, compounds of the invention are at least 60% a single atropisomer at the asterisk position. In some embodiments, compounds of the invention are at least 70% a single atropisomer at the asterisk position. In some embodiments, compounds of the invention are at least 80% a single atropisomer at the asterisk position. In some embodiments, compounds of the invention are at least 90% a single atropisomer at the asterisk position. In some embodiments, compounds of the invention are at least 95% a single atropisomer at the asterisk position. In some embodiments, stereochemistry at the carbon marked with an asterisk as shown above for compounds of the invention (e.g., compounds of Formula I) is in the (R) configuration. In some embodiments, stereochemistry at the carbon marked with an asterisk as shown above for compounds of the invention (e.g., compounds of Formula I) is in the (S) configuration.

In some embodiments, stereochemistry of compounds of the invention occurs at the carbon bearing the $R^3$ substituent, as marked by an asterisk in the formula below.

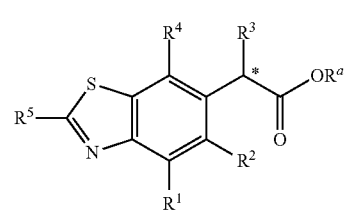

I

In some embodiments, stereochemistry at the carbon marked with an asterisk as shown in the formula above for compounds of the invention is in the (S) configuration. In some embodiments, stereochemistry at the carbon marked with an asterisk as shown in the formula above for compounds of the invention is in the (R) configuration.

In some embodiments, compounds of the invention are greater than 50% a single stereoisomer for the carbon at the asterisk position. In some embodiments, compounds of the invention are at least 60% a single stereoisomer for the carbon at the asterisk position. In some embodiments, compounds of the invention are at least 70% a single stereoisomer for the carbon at the asterisk position. In some embodiments, compounds of the invention are at least 80% a single stereoisomer for the carbon at the asterisk position. In some embodiments, compounds of the invention are at least 90% a single stereoisomer for the carbon at the asterisk position. In some embodiments, compounds of the invention are at least 95% a single stereoisomer for the carbon at the asterisk position.

One skilled in the art will recognize that substituents and other moieties of the compounds disclosed herein should be selected in order to provide a compound which is sufficiently stable to provide a pharmaceutically useful compound which can be formulated into an acceptably stable pharmaceutical composition. Compounds disclosed herein which have such stability are contemplated as falling within the scope of the present invention.

It is to be understood that for compounds disclosed herein when a bond is drawn in a non-stereochemical manner (e.g. flat) the atom to which the bond is attached includes all stereochemical possibilities. It is also to be understood that when a bond is drawn in a stereochemical manner (e.g. bold, bold-wedge, dashed or dashed-wedge) the atom to which the stereochemical bond is attached has the stereochemistry as shown unless otherwise noted.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes (D and L) or (R and S) are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

In some embodiments, compounds of the invention include enriched or resolved optical isomers at any or all asymmetric, chiral atoms. In other words, in some embodiments, one or more chiral centers apparent from the depictions are provided as chiral isomers or racemic mixtures. Both racemic and diastereomeric mixtures, as well as individual optical isomers isolated or synthesized, substantially free of their enantiomeric or diastereomeric partners, are all within the scope of the invention. Racemic mixtures can be separated into individual, substantially optically pure isomers through well-known techniques such as, for example, separation of diastereomeric salts formed with optically active adjuncts, e.g., acids or bases followed by conversion back to the optically active substances. In some embodiments, a desired optical isomer is synthesized by means of stereospecific reactions, beginning with an appropriate stereoisomer of a desired starting material.

In some embodiments, compounds described herein can also exist as tautomeric isomers. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

Salts and Hydrates

Pharmaceutically Acceptable:

As used herein, the phrase "pharmaceutically acceptable" with respect to a substance refers to that substance which is generally regarded as safe and suitable for use without undue toxicity, irritation, allergic response, and the like, commensurate with a reasonable benefit/risk ratio.

Pharmaceutically Acceptable Salt:

In some embodiments, a compound provided herein is used in salt form. As used herein, the phrase "pharmaceutically acceptable salt" refers to a salt of a compound that is pharmaceutically acceptable and that possesses (or can be converted to a form that possesses) the desired pharmacological activity of the parent compound. Such salts include acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic acid, camphorsulfonic acid, citric acid, ethanesulfonic acid, fumaric acid, glucoheptonic acid, gluconic acid, lactic acid, maleic acid, malonic acid, mandelic acid, methanesulfonic acid, 2-naphthalenesulfonic acid, oleic acid, palmitic acid, propionic acid, stearic acid, succinic acid, tartaric acid, p-toluenesulfonic acid, trimethylacetic acid, and the like, and salts formed when an acidic proton present in the parent compound is replaced by either a metal ion, e.g., an alkali metal ion, an alkaline earth ion, or an aluminum ion; or coordinates with an organic base such as diethanolamine, triethanolamine, N-methylglucamine and the like. Also included in this definition are ammonium and substituted or quaternized ammonium salts. Representative non-limiting lists of pharmaceutically acceptable salts can be found in S. M. Berge et al., J. Pharma Sci., 66(1), 1-19 (1977), and Remington: The Science and Practice of Pharmacy, R. Hendrickson, ed., 21st edition, Lippincott, Williams & Wilkins, Philadelphia, Pa., (2005), at p. 732, Table 38-5, both of which are hereby incorporated by reference herein.

Examples of pharmaceutically acceptable salts of compounds described herein include salts derived from an appropriate base, such as an alkali metal (for example, sodium), an alkaline earth metal (for example, magnesium), ammonium and $NX_4^+$ (wherein X is $C_1$-$C_4$ alkyl). Pharmaceutically acceptable salts of a nitrogen atom or an amino group include for example salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, hydrobromic, sulfuric, phosphoric and sulfamic acids. Pharmaceutically acceptable salts of a compound containing a hydroxy group include the anion of said compound in combination with a suitable cation such as $Na^+$ and $NX_4^+$ (wherein X is independently selected from H or a $C_1$-$C_4$ alkyl group).

For therapeutic use, salts of active ingredients of compounds disclosed herein will typically be pharmaceutically acceptable, i.e. they will be salts derived from a physiologically acceptable acid or base. However, in some embodiments, salts of acids or bases which are not pharmaceutically acceptable may also find use, for example, in the preparation or purification of a compound of disclosed herein. All salts, whether or not derived from a physiologically acceptable acid or base, are within the scope of the present invention.

Metal salts can be prepared by reacting a metal hydroxide with a compound disclosed herein. Examples of metal salts which are prepared in this way are salts containing $Li^+$, $Na^+$, and $K^+$. A less soluble metal salt can be precipitated from the solution of a more soluble salt by addition of a suitable metal compound.

In addition, salts may be formed from acid addition of certain organic and inorganic acids, e.g., HCl, HBr, $H_2SO_4$, $H_3PO_4$ or organic sulfonic acids, to basic centers, such as amines. Finally, it is to be understood that compositions herein comprise compounds disclosed herein in their un-ionized, as well as zwitterionic form, and combinations with water as in hydrates. In some embodiments, hydrates include a compound disclosed herein with stoichiometric amounts of water.

Subjects:

As used herein, the terms "subject" and "subjects"" refers to humans, domestic animals (e.g., dogs and cats), farm animals (e.g., cattle, horses, sheep, goats and pigs), laboratory animals (e.g., mice, rats, hamsters, guinea pigs, pigs, rabbits, dogs, and monkeys), and the like.

Therapeutically Effective Amount:

used herein, the term "therapeutically effective amount" means an amount of a substance (e.g., a therapeutic agent, composition, and/or formulation) that elicits a desired biological response when administered as part of a therapeutic regimen. In some embodiments, a therapeutically effective amount of a substance is an amount that is sufficient, when administered to a subject suffering from or susceptible to a disease, disorder, and/or condition, to treat, diagnose, prevent, and/or delay the onset of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. In some embodiments, a therapeutically effective amount is administered in a single dose; in some embodiments, multiple unit doses are required to deliver a therapeutically effective amount.

Treating:

As used herein, the terms "treating" and "treatment" of a disease include the following:

(1) preventing or reducing the risk of developing the disease, i.e., causing the clinical symptoms of the disease not to develop in a subject that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

Isotopes

It is understood by one skilled in the art that, in some embodiments, this invention also includes any compound claimed that may be enriched at any or all atoms above naturally occurring isotopic ratios with one or more isotopes such as, but not limited to, deuterium ($^2$H or D). As a non-limiting example, a —CH$_3$ group may be substituted with —CD$_3$.

Forms

It is contemplated that provided compounds can exist in a variety of physical forms. For example, provided compounds can be in solution, suspension, or in solid form. In certain embodiments, a provided compound is in solid form. In such embodiments, a provided compound may be amorphous, crystalline, or a mixture thereof.

Compounds of Formula I

In some embodiments, the present invention provides a compound of Formula

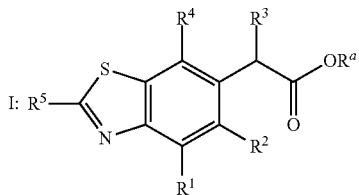

or a pharmaceutically acceptable salt thereof, wherein:
$R^1$ is H or ($C_1$-$C_6$)alkyl;
$R^2$ is H or ($C_1$-$C_6$)alkyl;
$R^a$ is H or ($C_1$-$C_6$)alkyl;
$R^3$ is O($C_1$-$C_6$)alkyl or O($C_1$-$C_6$)cycloalkyl;
$R^4$ is a 3-8 membered saturated, partially unsaturated, or aryl monocyclic ring containing 0-4 heteroatoms independently selected from nitrogen, oxygen, or sulfur, or an 8-13 membered saturated, partially unsaturated, or aryl bicyclic or tricyclic ring containing 0-4 heteroatoms independently selected from nitrogen, oxygen, or sulfur, and wherein $R^4$ is optionally substituted with 1-10 $R^f$;

each $R^f$ is independently halo, $R^X$, $OR^X$, $SR^X$, CN, S(O)$R^X$, SO$_2R^X$, OSO$_2R^X$, N($R^X$)$_2$, NO$_2$, NR$^X$C(O)$R^X$, NR$^X$C(O)(CO)$R^X$, NR$^X$C(O)N($R^X$)$_2$, NR$^X$C(O)O$R^X$, N($R^X$)S(O)$R^X$, N($R^X$)SO$_2R^X$, N($R^X$)SO$_2$O$R^X$, C(O)$R^X$, C(O)O$R^X$, OC(O)$R^X$, OC(O)O$R^X$, C(O)N($R^X$)$_2$, OC(O)N($R^X$)$_2$, or a 3-8 membered saturated, partially unsaturated, or aryl monocyclic ring containing 0-4 heteroatoms independently selected from nitrogen, oxygen, or sulfur, or two $R^f$ on the same carbon are taken together to form an oxo group;

each $R^X$ is independently H, halo, N($R^Y$)$_2$, C(O)O$R^Y$, $C_{1-8}$ aliphatic, $C_{1-8}$ heteroaliphatic, ($C_3$-$C_6$)cycloalkyl, 3-8 membered heterocycloalkyl containing 1-3 heteroatoms independently selected from nitrogen, oxygen, or sulfur, optionally substituted phenyl, or two $R^X$ on the same nitrogen are taken together to form a 5-6 membered saturated, partially saturated, or heteroaryl ring having 1-3 heteroatoms independently selected from nitrogen, oxygen, and sulfur, or two $R^X$ on the same carbon or on adjacent carbons are optionally taken together to form a ($C_3$-$C_6$)cycloalkyl, or a 3-6 membered saturated fused monocyclic ring containing 0-2 heteroatoms independently selected from nitrogen, oxygen, and sulfur, or two $R^X$ on the same carbon are taken together to form an oxo group;

wherein the $C_{1-8}$ aliphatic, $C_{1-8}$ heteroaliphatic, ($C_3$-$C_6$) cycloalkyl, 3-8 membered heterocycloalkyl, or phenyl is optionally substituted with 1-5 $R^z$;

each $R^z$ is independently halo, $C_{1-8}$ aliphatic, or $C_{1-8}$ heteroaliphatic;

each $R^Y$ is independently H or ($C_1$-$C_6$)alkyl;

$R^5$ is

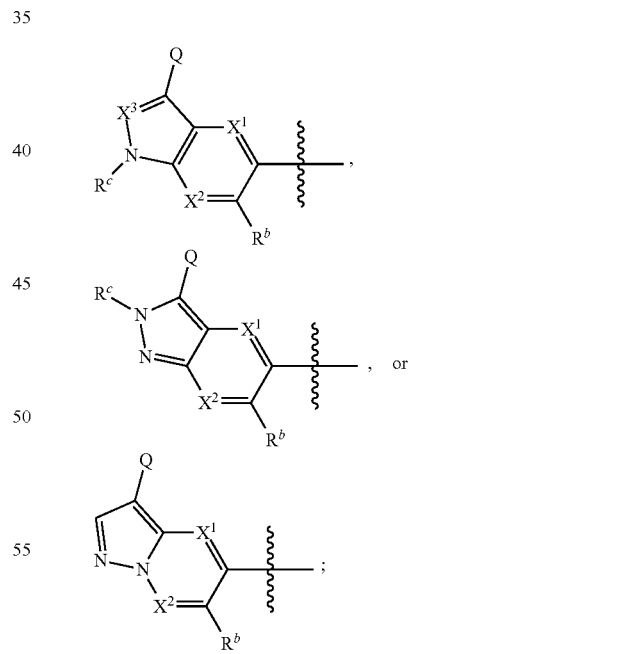

$R^b$ is H or ($C_1$-$C_6$)alkyl;
$R^c$ is H, ($C_1$-$C_6$)alkyl or ($C_3$-$C_6$)cycloalkyl, wherein $R^c$ is optionally substituted with 1-5 groups independently selected from halo, D, O$R^X$, and N($R^X$)$_2$;
Q is a 3-10 membered saturated or partially unsaturated monocyclic or bridged, spirocyclic, or fused bicyclic heterocycloalkyl containing 1-3 heteroatoms independently selected from nitrogen, oxygen, or sulfur, optionally substituted with 1-5 $R^e$;

each $R^e$ is independently H, $(C_1-C_6)$alkyl, $N(R^X)_2$, $C(O)R^X$, $C(O)OR^X$, $S(O)_2R^X$, $(C_3-C_6)$cycloalkyl or 3-6 membered heterocycloalkyl containing 1-2 heteroatoms independently selected from nitrogen, oxygen, or sulfur, or two $R^e$ wherein $R^e$ on the same carbon are taken together to form an oxo group, or two $R^e$ wherein $R^e$ on the same carbon are taken together to form $(C_3-C_8)$cycloalkyl or 3-4 membered heterocycloalkyl containing 1-2 heteroatoms independently selected from nitrogen, oxygen, or sulfur, wherein $R^e$ is optionally substituted with 1-5 $R^g$;

each $R^g$ is independently halo, $R^X$, $OR^X$, $N(R^X)_2$, $C(O)R^X$, $C(O)OR^X$, $OC(O)R^X$, $OC(O)OR^X$, $S(O)_2R^X$, optionally substituted 3-4 membered heterocycloalkyl containing 1-2 heteroatoms independently selected from nitrogen, oxygen, or sulfur, or two $R^g$ on the same carbon are taken together to form an oxo group, or two $R^g$ on the same sulfur are optionally taken together to form an oxo group;

$X^1$ is N or C(H);

$X^2$ is N or C(H);

$X^3$ is N or C(H); and wherein the compound is not one of the following structures:

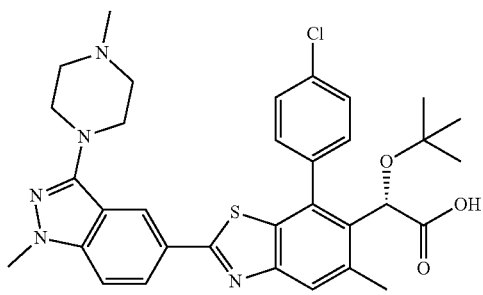

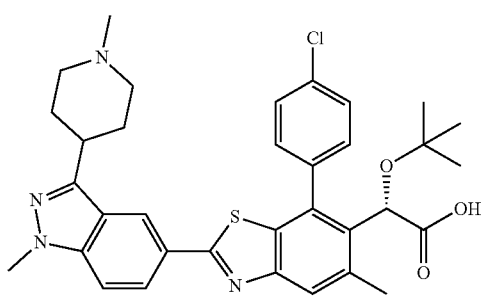

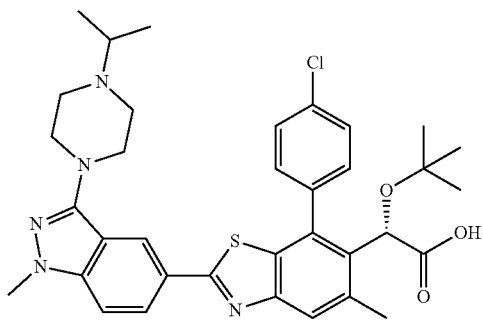

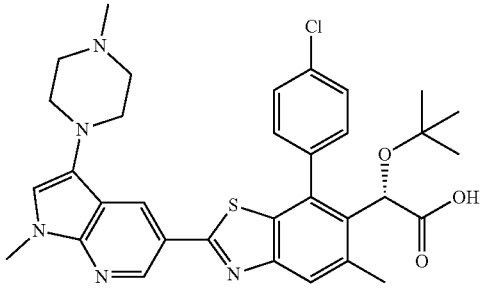

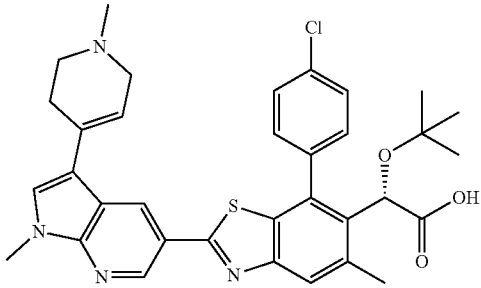

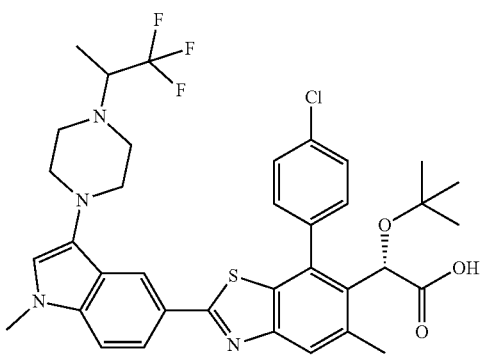

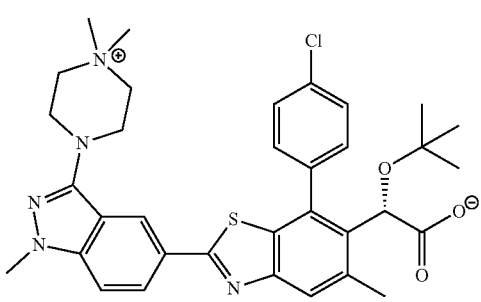

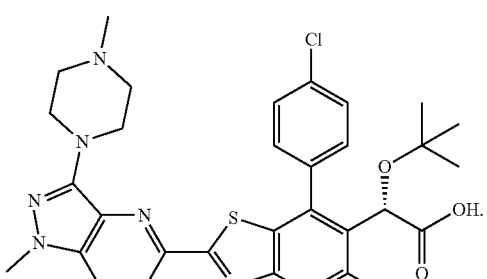

In some embodiments, Q is not one of the following formulae:

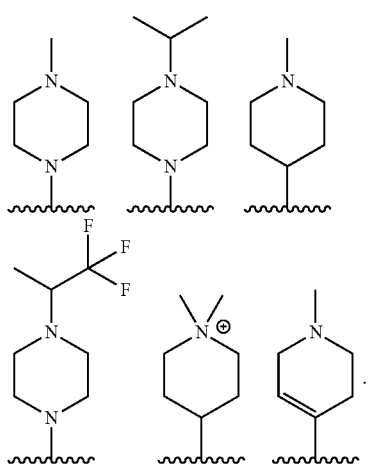

In some embodiments, when Q is piperazine $R^e$ is not an optionally substituted $C_{1-6}$ alkyl group. For instance, in some embodiments, when Q is piperazine $R^e$ is not methyl, isopropyl, or 1,1,1-trifluoroisopropyl.

In some embodiments, when Q is piperidine $R^e$ is not an optionally substituted $C_{1-6}$ alkyl group. For instance, in some embodiments, when Q is piperidine $R^e$ is not methyl.

In some embodiments, when Q is tetrahydropyridine $R^e$ is not an optionally substituted $C_{1-6}$ alkyl group. For instance, in some embodiments, when Q is tetrahydropyridine $R^e$ is not methyl.

In some embodiments, a provided compound is of either of the following formulae:

II

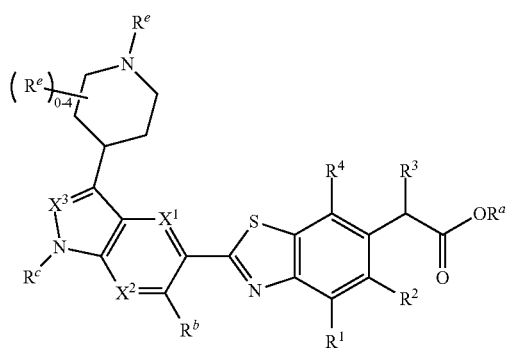

III

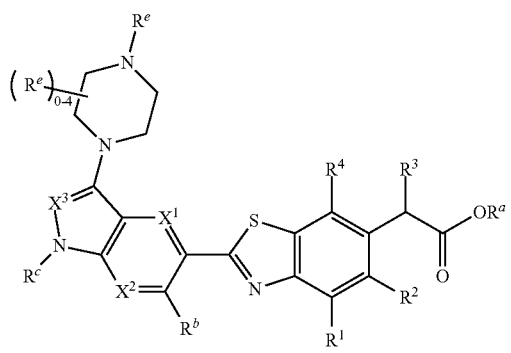

or a pharmaceutically acceptable salt thereof, wherein $R^1$, $R^2$, $R^3$, $R^4$, $R^a$, $R^b$, $R^c$, $R^e$, $X^1$, $X^2$, and $X^3$ are as defined and described above and herein.

In some embodiments, a provided compound is of either of the following formulae:

II-a

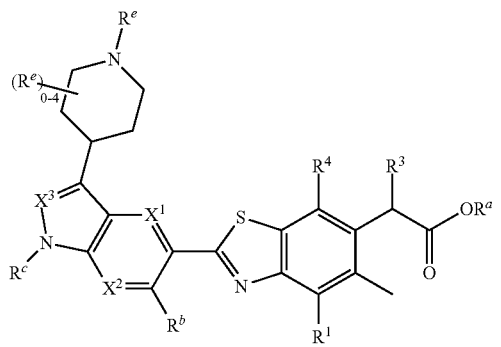

III-a

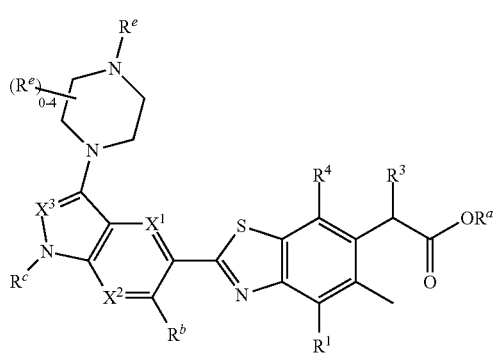

or a pharmaceutically acceptable salt thereof, wherein $R^1$, $R^3$, $R^4$, $R^a$, $R^b$, $R^c$, $R^e$, $X^1$, $X^2$, and $X^3$ are as defined and described above and herein.

In some embodiments, a provided compound is of either of the following formulae:

II-b

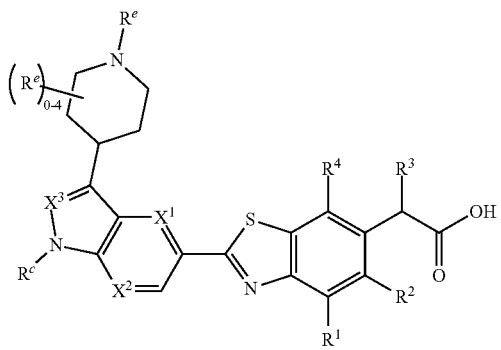

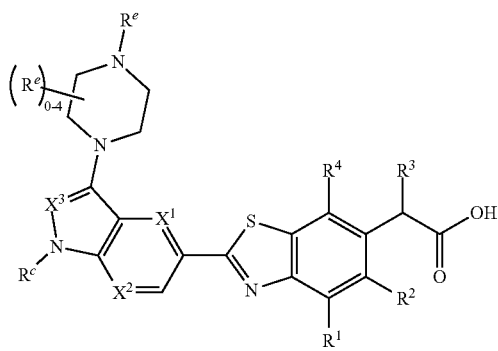

III-b or a pharmaceutically acceptable salt thereof, wherein $R^1$, $R^2$, $R^3$, $R^4$, $R^c$, $R^e$, $X^1$, $X^2$, and $X^3$ are as defined and described above and herein.

In some embodiments, a provided compound is of either of the following formulae:

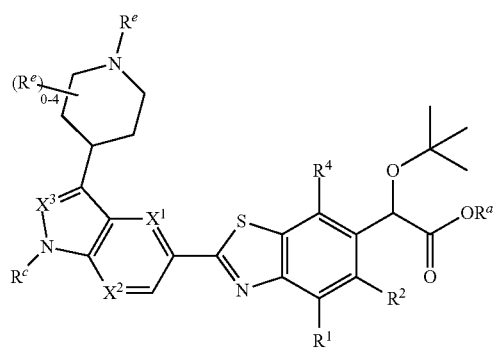

II-c

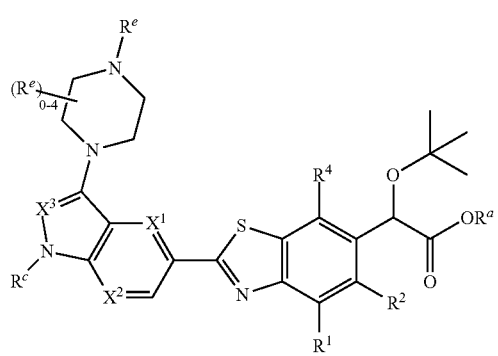

III-c or a pharmaceutically acceptable salt thereof, wherein $R^1$, $R^2$, $R^4$, $R^a$, $R^c$, $R^e$, $X^1$, $X^2$, and $X^3$ are as defined and described above and herein.

In some embodiments, a provided compound is of either of the following formulae:

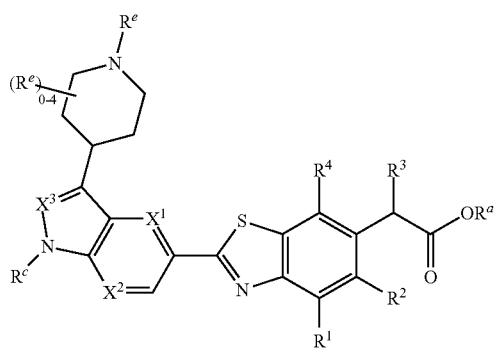

II-d

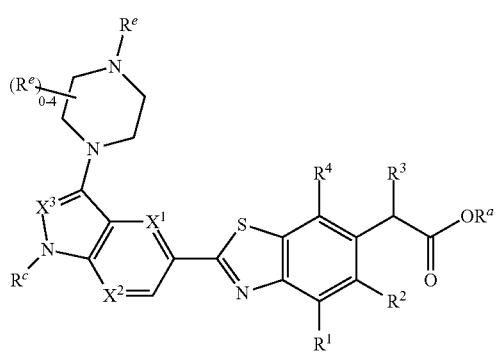

III-d or a pharmaceutically acceptable salt thereof, wherein $R^1$, $R^2$, $R^3$, $R^4$, $R^a$, $R^c$, $R^e$, $X^1$, $X^2$, and $X^3$ are as defined and described above and herein.

In some embodiments, a provided compound is of either of the following formulae:

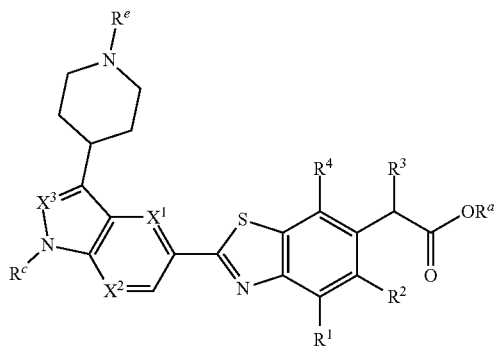

II-e

III-e

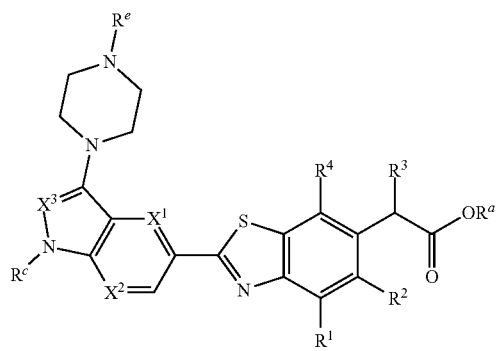

or a pharmaceutically acceptable salt thereof, wherein $R^1$, $R^2$, $R^3$, $R^4$, $R^a$, $R^c$, $R^e$, $X^1$, $X^2$, and $X^3$ are as defined and described above and herein.

In some embodiments, a provided compound is of either of the following formulae:

II-f

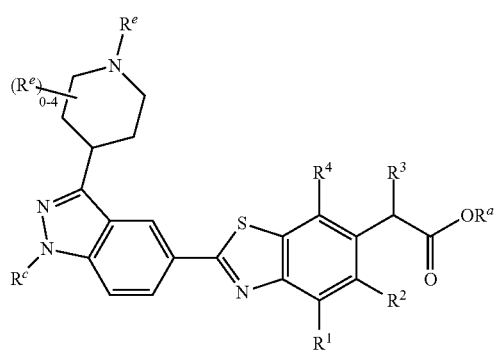

III-f

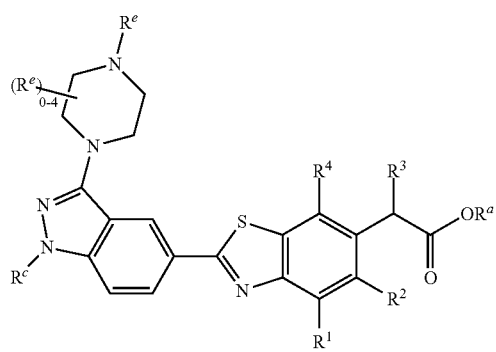

or a pharmaceutically acceptable salt thereof, wherein $R^1$, $R^2$, $R^3$, $R^4$, $R^a$, $R^c$, and $R^e$ are as defined and described above and herein.

In some embodiments, a provided compound is of either of the following formulae:

II-g

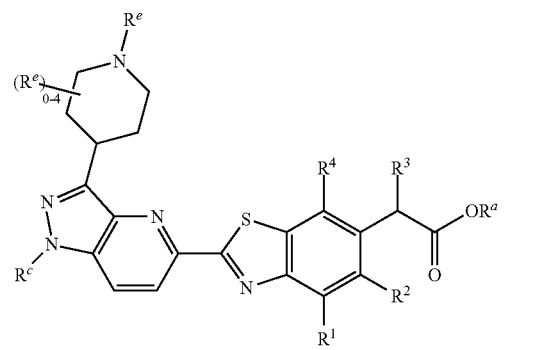

III-g

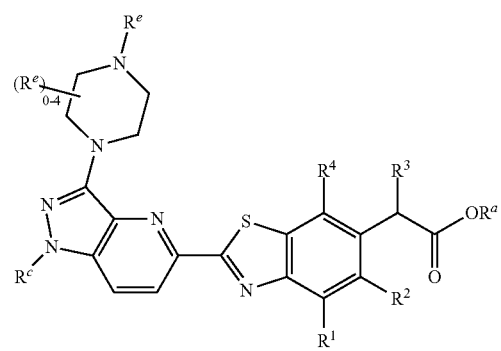

or a pharmaceutically acceptable salt thereof, wherein $R^1$, $R^2$, $R^3$, $R^4$, $R^a$, $R^c$, and $R^e$ are as defined and described above and herein.

In some embodiments, a provided compound is of either of the following formulae:

II-h

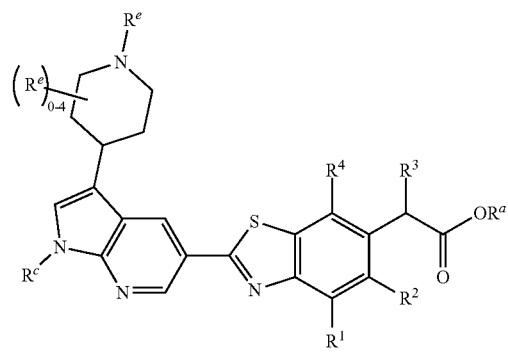

-continued

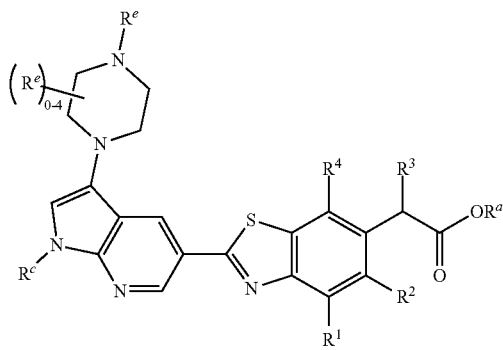

III-h

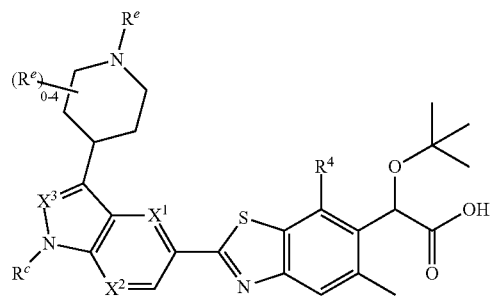

II-j

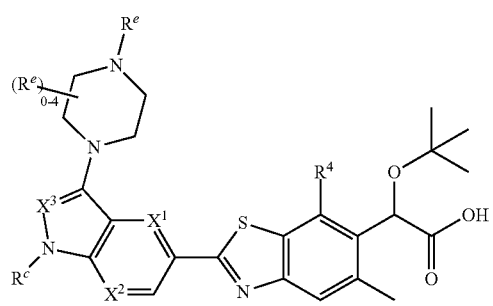

III-j or a pharmaceutically acceptable salt thereof, wherein $R^1$, $R^2$, $R^3$, $R^4$, $R^a$, $R^c$, and $R^e$ are as defined and described above and herein.

In some embodiments, a provided compound is of either of the following formulae:

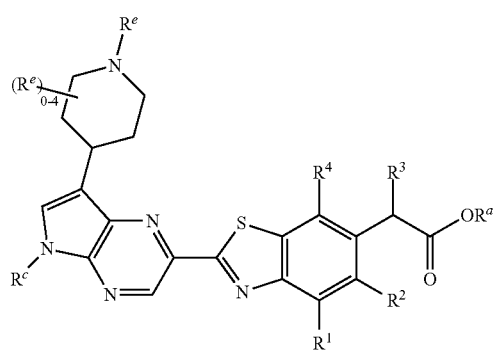

II-i

III-i or a pharmaceutically acceptable salt thereof, wherein $R^4$, $R^c$, $R^e$, $X^1$, $X^2$, and $X^3$ are as defined and described above and herein.

In some embodiments, a provided compound is of either of the following formulae:

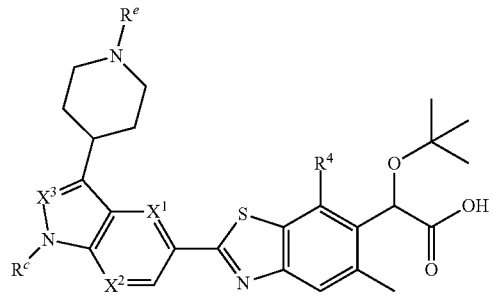

II-k

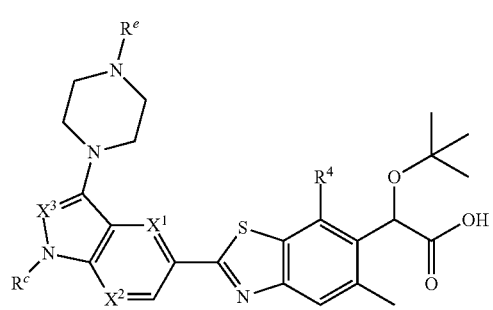

III-k

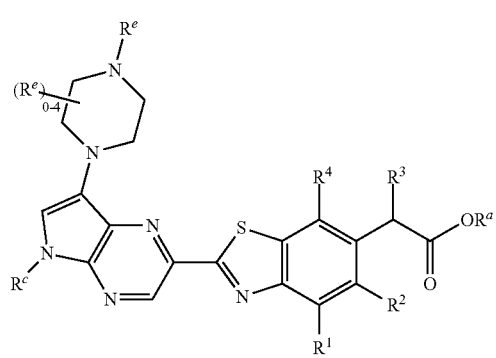

or a pharmaceutically acceptable salt thereof, wherein $R^1$, $R^2$, $R^3$, $R^4$, $R^a$, $R^c$, and $R^e$ are as defined and described above and herein.

In some embodiments, a provided compound is of either of the following formulae:

or a pharmaceutically acceptable salt thereof, wherein $R^4$, $R^c$, $R^e$, $X^1$, $X^2$, and $X^3$ are as defined and described above and herein.

In some embodiments, a provided compound is of either of the following formulae:

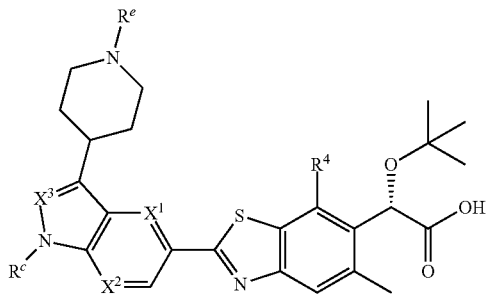

II-l

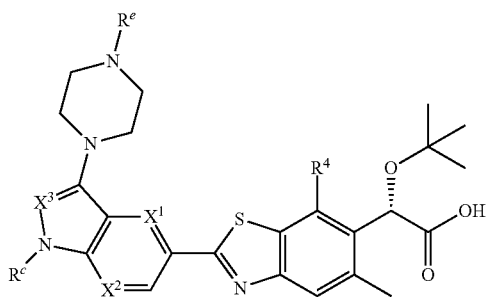

III-l or a pharmaceutically acceptable salt thereof, wherein R⁴, R^c, R^e, X¹, X², and X³ are as defined and described above and herein.

In some embodiments, a provided compound is of either of the following formulae:

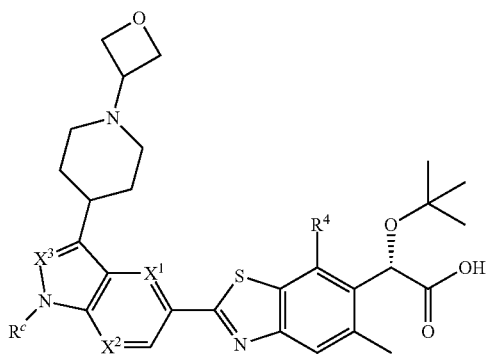

II-m

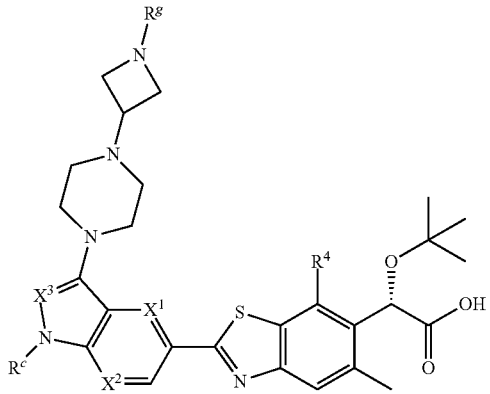

III-m or a pharmaceutically acceptable salt thereof, wherein R⁴, R^c, R^g, X¹, X², and X³ are as defined and described above and herein.

In some embodiments, a provided compound is of either of the following formulae:

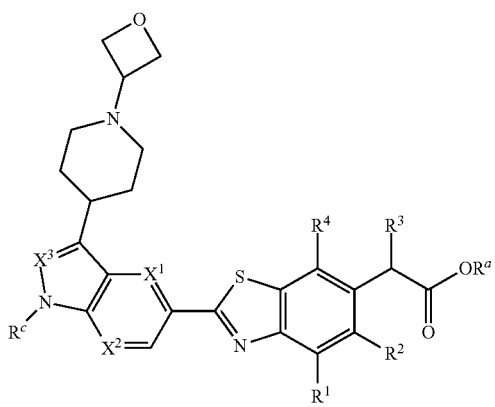

II-n

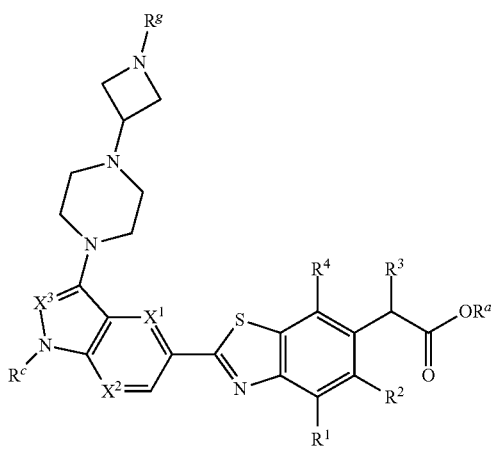

III-n or a pharmaceutically acceptable salt thereof, wherein R¹, R², R³, R⁴, R^a, R^c, R^g, X¹, X², and X³ are as defined and described above and herein.

In some embodiments, a provided compound is of either of the following formulae:

II-o

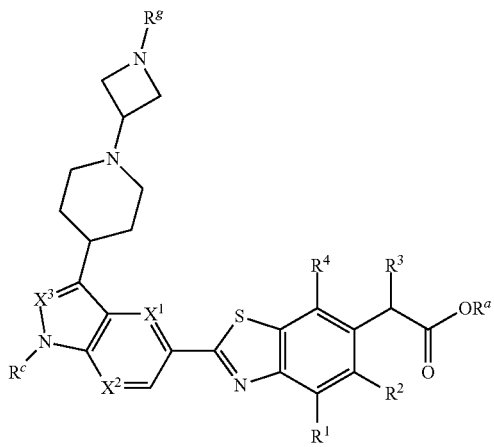

III-p

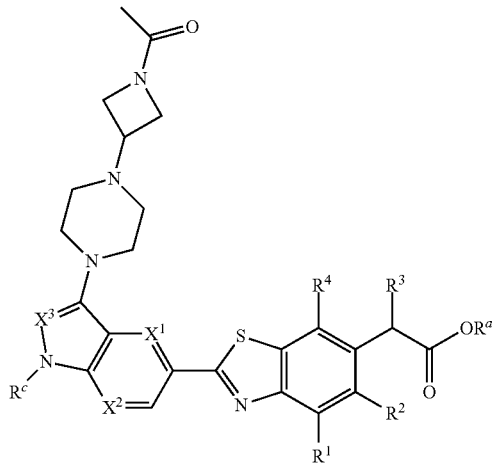

or a pharmaceutically acceptable salt thereof, wherein $R^1$, $R^2$, $R^3$, $R^4$, $R^a$, $R^c$, $X^1$, $X^2$, and $X^3$ are as defined and described above and herein.

In some embodiments, a provided compound is of any of the above depicted formulae and one or more of $R^1$, $R^2$, $R^3$, $R^4$, $R^a$, $R^b$, $R^c$, $R^e$, $X^1$, $X^2$, and $X^3$ are as defined and described above and herein.

In certain embodiments, a provided compound is of formula II-e:

III-o

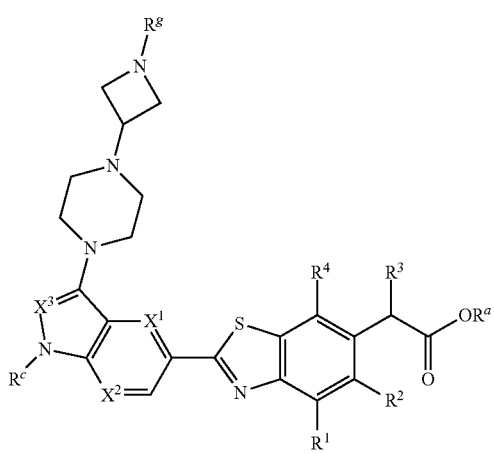

II-e

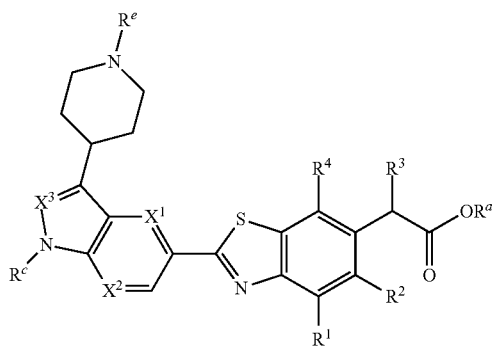

or a pharmaceutically acceptable salt thereof, wherein $R^1$, $R^2$, $R^3$, $R^4$, $R^a$, $R^c$, $X^1$, $X^2$, and $X^3$ are as defined and described above and herein.

In some embodiments, a provided compound is of either of the following formulae:

II-p

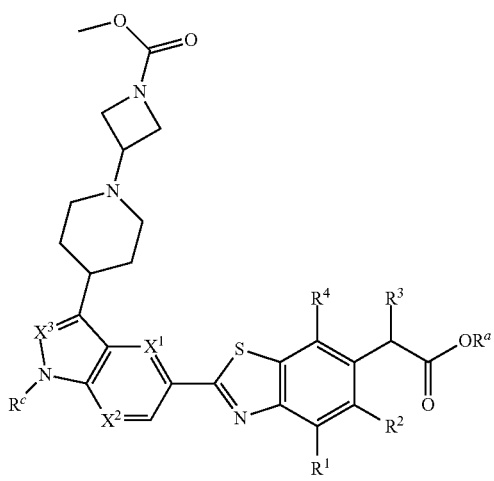

or a pharmaceutically acceptable salt thereof, wherein $X^1$, $X^2$, and $X^3$ are as defined and described above and herein, wherein:
$R^1$ is H;
$R^2$ is $(C_1-C_6)$alkyl;
$R^a$ is H;
$R^3$ is $O(C_1-C_6)$alkyl;
$R^4$ is

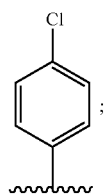 [SMILES: *c1ccc(Cl)cc1]

;

$R^c$ is $(C_1-C_6)$alkyl or $(C_3-C_6)$cycloalkyl, wherein $R^c$ is optionally substituted with 1-5 groups independently selected from halo, D, $OR^X$, and $N(R^X)_2$;

$R^e$ is a 4 membered heterocycloalkyl having one heteroatom selected from N or O, wherein $R^e$ is optionally substituted with 1-2 $R^g$;

each $R^g$ is independently $C(O)R^X$ or $C(O)OR^X$; and each $R^X$ is independently $C_{1-8}$ aliphatic.

In certain embodiments, a provided compound is of formula II-e, wherein $X^1$ is N, $X^2$ is C(H), and $X^3$ is N. In certain embodiments, a provided compound is of formula II-e, wherein $X^1$ is C(H), $X^2$ is C(H), and $X^3$ is N. In certain embodiments, a provided compound is of formula II-e, wherein $X^1$ is C(H), $X^2$ is N, and $X^3$ is C(H). In certain embodiments, a provided compound is of formula II-e, wherein $X^1$ is N, $X^2$ is N, and $X^3$ is C(H).

In certain embodiments, a provided compound is of formula II-e, wherein $R^3$ is

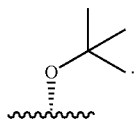

As defined generally above, $R^1$ is H or $(C_1-C_6)$alkyl. In some embodiments, $R^1$ is H. In some embodiments, $R^1$ is $(C_1-C_6)$alkyl. In some such embodiments, $R^1$ is methyl, ethyl, propyl, or butyl.

As defined generally above, $R^2$ is H or $(C_1-C_6)$alkyl. In some embodiments, $R^2$ is H. In some embodiments, $R^2$ is $(C_1-C_6)$alkyl. In some such embodiments, $R^2$ is methyl, ethyl, propyl, or butyl. In some such embodiments, $R^2$ is methyl.

As defined generally above, $R^a$ is H or $(C_1-C_6)$alkyl. In some embodiments, $R^a$ is H. In some embodiments, $R^a$ is $(C_1-C_6)$alkyl. In some such embodiments, $R^a$ is methyl, ethyl, propyl, or butyl.

As defined generally above, $R^3$ is $O(C_1-C_6)$alkyl or $O(C_1-C_6)$cycloalkyl. In some embodiments, $R^3$ is OMe, OEt, O-nPr, O-iPr, O-iBu, O-nBu, O-sBu, O-tBu, or O-cyclopropyl. In some embodiments, $R^3$ is O-nPr, O-iPr, or O-tBu. In certain embodiments, $R^3$ is O-tBu. In certain embodiments, $R^3$ is O-cyclopropyl. In certain embodiments, $R^3$ is

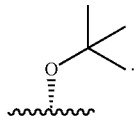

As defined generally above, $R^4$ is a 3-8 membered saturated, partially unsaturated, or aryl monocyclic ring containing 0-4 heteroatoms independently selected from nitrogen, oxygen, or sulfur, or an 8-13 membered saturated, partially unsaturated, or aryl bicyclic or tricyclic ring containing 0-4 heteroatoms independently selected from nitrogen, oxygen, or sulfur, and wherein $R^4$ is optionally substituted with 1-10 $R^f$;

In some embodiments, $R^4$ is an optionally substituted 3-8 membered saturated monocyclic ring having 0-4 heteroatoms independently selected from nitrogen, oxygen, or sulfur. In some embodiments, $R^4$ is an optionally substituted 3-6 membered saturated monocyclic ring having 0-2 heteroatoms independently selected from nitrogen, oxygen, or sulfur. In some embodiments, $R^4$ is an optionally substituted 5-6 membered saturated monocyclic ring having 0-2 heteroatoms independently selected from nitrogen, oxygen, or sulfur. In some embodiments, $R^4$ is an optionally substituted 3-8 membered saturated monocyclic carbocycle.

In some embodiments, $R^4$ is an optionally substituted 3-8 membered partially unsaturated monocyclic ring having 0-4 heteroatoms independently selected from nitrogen, oxygen, or sulfur. In some embodiments, $R^4$ is an optionally substituted 3-6 membered partially unsaturated monocyclic ring having 0-2 heteroatoms independently selected from nitrogen, oxygen, or sulfur. In some embodiments, $R^4$ is an optionally substituted 5-6 membered partially unsaturated monocyclic ring having 0-2 heteroatoms independently selected from nitrogen, oxygen, or sulfur. In some embodiments, $R^4$ is an optionally substituted 3-8 membered partially unsaturated monocyclic carbocycle.

In some embodiments, $R^4$ is an optionally substituted 5-6 membered aryl ring having 0-4 heteroatoms independently selected from nitrogen, oxygen, or sulfur. In some embodiments, $R^4$ is an optionally substituted 5-6 membered aryl ring having 0-2 heteroatoms independently selected from nitrogen, oxygen, or sulfur. In some embodiments, $R^4$ is an optionally substituted 5 membered heteroaryl ring having 1-3 heteroatoms independently selected from nitrogen, oxygen, or sulfur. In some embodiments, $R^4$ is an optionally substituted 6 membered heteroaryl ring having 1-3 nitrogens. In some embodiments, $R^4$ is optionally substituted phenyl. In certain embodiments, $R^4$ is phenyl substituted at the para position relative to the position of connection to the rest of the compound.

In certain embodiments, $R^4$ is phenyl optionally substituted with 1-3 halo. In certain embodiments, $R^4$ is phenyl optionally substituted with 1-3 chloro. In certain embodiments, $R^4$ is phenyl substituted with one chloro. In certain embodiments, $R^4$ is

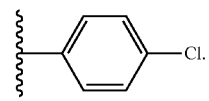

In some embodiments, $R^4$ is an optionally substituted 8-13 membered saturated bicyclic or tricyclic ring having 0-4 heteroatoms independently selected from nitrogen, oxygen, or sulfur. In some embodiments, $R^4$ is an optionally substituted 8-13 membered saturated bicyclic or tricyclic ring having 0-2 heteroatoms independently selected from nitrogen, oxygen, or sulfur. In some embodiments, $R^4$ is an optionally substituted 8-13 membered saturated bicyclic or tricyclic carbocycle.

In some embodiments, $R^4$ is an optionally substituted 8-13 membered partially unsaturated bicyclic or tricyclic ring having 0-4 heteroatoms independently selected from nitrogen, oxygen, or sulfur. In some embodiments, $R^4$ is an optionally substituted 8-13 membered partially unsaturated bicyclic or tricyclic ring having 0-3 heteroatoms independently selected from nitrogen, oxygen, or sulfur. In some embodiments, $R^4$ is an optionally substituted 8-13 membered partially unsaturated bicyclic or tricyclic ring having 1-3 heteroatoms independently selected from nitrogen, oxygen, or sulfur. In some embodiments, $R^4$ is an optionally substituted 8-13 membered partially unsaturated bicyclic or tricyclic carbocycle.

In some embodiments, $R^4$ is an optionally substituted 8-13 membered aryl bicyclic or tricyclic ring having 0-4 heteroatoms independently selected from nitrogen, oxygen, or sulfur. In some embodiments, $R^4$ is an optionally substituted 8-13 membered aryl bicyclic or tricyclic ring having 0-2 heteroatoms independently selected from nitrogen, oxygen, or sulfur. In some embodiments, $R^4$ is an optionally substituted 10 membered aryl bicyclic ring having 0-3 heteroatoms independently selected from nitrogen, oxygen, or sulfur.

As defined generally above, $R^4$ is optionally substituted with 1-10 $R^f$. In some embodiments, $R^4$ is optionally substituted with 1-8 $R^f$. In some embodiments, $R^4$ is optionally substituted with 1-6 $R^f$. In some embodiments, $R^4$ is optionally substituted with 1-4 $R^f$. In some embodiments, $R^4$ is optionally substituted with 1-2 $R^f$. In some embodiments, $R^4$ is optionally substituted with one $R^f$.

As defined generally above, each $R^f$ is independently halo, $R^X$, $OR^X$, $SR^X$, CN, $S(O)R^X$, $SO_2R^X$, $OSO_2R^X$, $N(R^X)_2$, $NO_2$, $NR^XC(O)R^X$, $NR^XC(O)(CO)R^X$, $NR^XC(O)N(R^X)_2$, $NR^XC(O)OR^X$, $N(R^X)S(O)R^X$, $N(R^X)SO_2R^X$, $N(R^X)SO_2R^X$, $C(O)R^X$, $C(O)OR^X$, $OC(O)R^X$, $OC(O)OR^X$, $C(O)N(R^X)_2$, $OC(O)N(R^X)_2$, or a 3-8 membered saturated, partially unsaturated, or aryl monocyclic ring containing 0-4 heteroatoms independently selected from nitrogen, oxygen, or sulfur, or two $R^f$ on the same carbon are taken together to form an oxo group.

In some embodiments, each $R^f$ is independently halo, $R^X$, $OR^X$, $SR^X$, CN, $S(O)R^X$, $SO_2R^X$, $OSO_2R^X$, $N(R^X)_2$, $NO_2$, $NR^XC(O)R^X$, $NR^XC(O)(CO)R^X$, $NR^XC(O)N(R^X)_2$, $NR^XC(O)OR^X$, $N(R^X)S(O)R^X$, $N(R^X)SO_2R^X$, $N(R^X)SO_2OR^X$, $C(O)R^X$, $C(O)OR^X$, $OC(O)R^X$, $OC(O)OR^X$, $C(O)N(R^X)_2$, $OC(O)N(R^X)_2$. In some embodiments, each $R^f$ is independently halo, $R^X$, $OR^X$, $SR^X$, CN, or two $R^f$ on the same carbon are optionally taken together to form an oxo group. In some embodiments, each $R^f$ is independently $R^X$. In some embodiments, each $R^f$ is independently halo. In some embodiments, each $R^f$ is independently chloro.

In some embodiments, each $R^f$ is independently a 3-8 membered saturated, partially unsaturated, or aryl monocyclic ring optionally containing 0-4 heteroatoms independently selected from nitrogen, oxygen, or sulfur.

In some embodiments, $R^4$ is phenyl substituted with 1-5 $R^f$ groups. In certain embodiments, $R^4$ is phenyl substituted with one $R^f$ group. In certain embodiments, $R^4$ is phenyl substituted with two $R^f$ groups. In certain embodiments, $R^4$ is phenyl substituted with three $R^f$ groups. In certain embodiments, $R^4$ is phenyl substituted with four $R^f$ groups. In certain embodiments, $R^4$ is phenyl substituted with five $R^f$ groups.

In some embodiments, $R^4$ is an $R^4$ moiety disclosed in either of US Patent Publication No. 2014/0045818 or US Patent Publication No. 2013/0281433, each of which is incorporated herein by reference in its entirety.

As defined generally above, each $R^X$ is independently H, halo, $N(R^Y)_2$, $C(O)OR^Y$, $C_{1-8}$ aliphatic, $C_{1-8}$ heteroaliphatic, $(C_3-C_6)$cycloalkyl, 3-8 membered heterocycloalkyl containing 1-3 heteroatoms independently selected from nitrogen, oxygen, or sulfur, optionally substituted phenyl, or two $R^X$ on the same nitrogen are taken together to form a 5-6 membered saturated, partially saturated, or heteroaryl ring having 1-3 heteroatoms independently selected from nitrogen, oxygen, and sulfur, or two $R^X$ on the same carbon or on adjacent carbons are optionally taken together to form a $(C_3-C_6)$cycloalkyl, or a 3-6 membered saturated fused monocyclic ring containing 0-2 heteroatoms independently selected from nitrogen, oxygen, and sulfur, or two $R^X$ on the same carbon are taken together to form an oxo group, wherein the $C_{1-8}$ aliphatic, $C_{1-8}$ heteroaliphatic, $(C_3-C_6)$cycloalkyl, 3-8 membered heterocycloalkyl, or phenyl is optionally substituted with 1-5 $R^z$.

In some embodiments, each $R^X$ is independently H, halo, $N(R^Y)_2$, $C(O)OR^Y$, $C_{1-8}$ aliphatic, or $C_{1-8}$ heteroaliphatic. In some embodiments, each $R^X$ is independently H or $C_{1-8}$ aliphatic. In some embodiments, each $R^X$ is H.

As defined generally above, each $R^z$ is independently halo, $C_{1-8}$ aliphatic, or $C_{1-8}$ heteroaliphatic.

As defined generally above, each $R^Y$ is independently H or $(C_1-C_6)$alkyl. In some embodiments, each $R^Y$ is H. In some embodiments, each $R^Y$ is independently $(C_1-C_6)$alkyl.

As defined generally above, $R^5$ is:

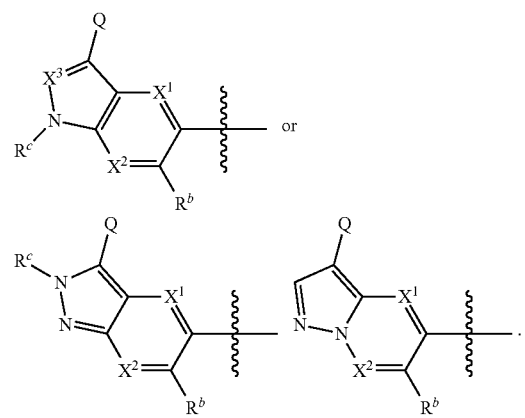

In certain embodiments, $R^5$ is

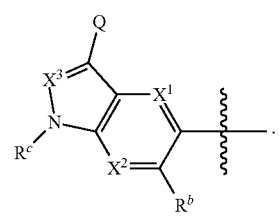

In some such embodiments, $X^1$ is N. In some such embodiments, $X^2$ is not N. In some such embodiments, $X^3$ is N. In some such embodiments, when $X^3$ is N, $X^1$ is also N. In some such embodiments, when $X^3$ is N, $X^2$ is C(H). In certain embodiments, when $R^5$ is

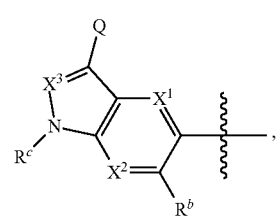

$X^1$ is N, $X^2$ is C(H), and $X^3$ is N.

In some embodiments, $R^5$ is

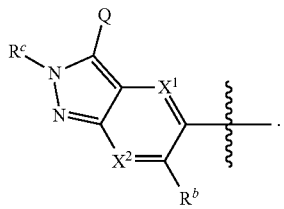

In some embodiments, $R^5$ is

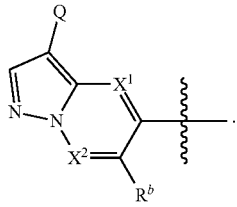

As defined above, Q is a 3-10 membered saturated or partially unsaturated monocyclic or bridged, spirocyclic, or fused bicyclic heterocycloalkyl containing 1-3 heteroatoms independently selected from nitrogen, oxygen, or sulfur, wherein Q is optionally substituted with 1-5 $R^e$.

In some embodiments, Q is a 4-8 membered saturated monocyclic heterocycloalkyl containing 1-2 heteroatoms independently selected from nitrogen, oxygen, or sulfur, wherein Q is optionally substituted with 1-2 $R^e$. In some embodiments, Q is a 5-6 membered saturated monocyclic heterocycloalkyl containing one heteroatom selected from nitrogen, oxygen, or sulfur, wherein Q is optionally substituted with 1-2 $R^e$. In some embodiments, Q is a 5-6 membered saturated monocyclic heterocycloalkyl containing one nitrogen, wherein Q is optionally substituted with 1-2 $R^e$. In some embodiments, Q is a 5 membered saturated monocyclic heterocycloalkyl containing one nitrogen, wherein Q is substituted with one $R^e$. In some such embodiments, Q is N-substituted. In some embodiments, Q is a 6 membered saturated monocyclic heterocycloalkyl containing one nitrogen, wherein Q is substituted with one $R^e$. In some such embodiments, Q is N-substituted.

In some embodiments, Q is of the following formula:

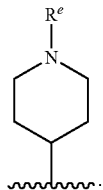

In some embodiments, Q is a 6-10 membered saturated or partially unsaturated bicyclic heterocycloalkyl containing 1-3 heteroatoms independently selected from nitrogen, oxygen, or sulfur, wherein Q is bridged bicyclic. In some embodiments, Q is a 6-10 membered saturated or partially unsaturated bicyclic heterocycloalkyl containing 1-3 heteroatoms independently selected from nitrogen, oxygen, or sulfur, wherein Q is spirocyclic.

As defined generally above, $R^b$ is H or $(C_1-C_6)$alkyl. In some embodiments, $R^b$ is H. In some embodiments, $R^b$ is $(C_1-C_6)$alkyl. In some such embodiments, $R^b$ is methyl, ethyl, propyl, or butyl.

As defined generally above, $R^c$ is H, $(C_1-C_6)$alkyl or $(C_3-C_6)$cycloalkyl, wherein $R^c$ is optionally substituted with 1-5 groups independently selected from halo, D, $OR^X$, and $N(R^X)_2$.

In some embodiments, $R^c$ is $(C_1-C_6)$alkyl optionally substituted with 1-5 groups independently selected from halo, D, $OR^X$, and $N(R^X)_2$. In some embodiments, $R^c$ is $(C_1-C_6)$alkyl optionally substituted with 1-3 groups independently selected from halo, D, $OR^X$, and $N(R^X)_2$. In some embodiments, $R^c$ is methyl optionally substituted with 1-3 groups independently selected from halo, D, $OR^X$, and $N(R^X)_2$. In some embodiments, $R^c$ is methyl. In some embodiments, $R^c$ is methyl optionally substituted with 1-3 fluoro. In some embodiments, R is methyl optionally substituted with three fluoro. In some embodiments, $R^e$ is methyl optionally substituted with two fluoro. In some embodiments, $R^c$ is methyl optionally substituted with one fluoro. In some embodiments, $R^c$ is ethyl optionally substituted with 1-3 groups independently selected from halo, D, $OR^X$, and $N(R^X)_2$. In some embodiments, $R^c$ is ethyl. In some embodiments, $R^c$ is propyl optionally substituted with 1-3 groups independently selected from halo, D, $OR^X$, and $N(R^X)_2$. In some embodiments, R is propyl. In some embodiments, $R^c$ is cyclopropyl optionally substituted with 1-3 groups independently selected from halo, D, $OR^X$, and $N(R^X)_2$. In some embodiments, $R^c$ is cyclopropyl.

As defined generally above, each $R^e$ is independently H, $(C_1-C_6)$alkyl, $N(R^X)_2$, $C(O)R^X$, $C(O)OR^X$, $S(O)_2R^X$, $(C_3-C_6)$cycloalkyl or 3-6 membered heterocycloalkyl containing 1-2 heteroatoms independently selected from nitrogen, oxygen, or sulfur, or two $R^e$ on the same carbon are taken together to form an oxo group, or two $R^e$ on the same carbon are taken together to form a $(C_3-C_8)$cycloalkyl or a 3-4 membered heterocycloalkyl containing 1-2 heteroatoms independently selected from nitrogen, oxygen, or sulfur, wherein $R^e$ is optionally substituted with 1-5 $R^g$.

In some embodiments, one $R^e$ is independently $(C_3-C_6)$cycloalkyl optionally substituted with 1-5 $R^g$. In some embodiments, one $R^e$ is independently $(C_3-C_6)$cycloalkyl optionally substituted with 1-3 $R^9$. In some embodiments, one $R^e$ is independently $(C_3-C_6)$cycloalkyl optionally substituted with 1-2 $R^g$. In some embodiments, one $R^e$ is independently unsubstituted $(C_3-C_6)$cycloalkyl.

In some embodiments, one $R^e$ is independently a 3-6 membered heterocycloalkyl containing 1-2 heteroatoms independently selected from nitrogen, oxygen, or sulfur, wherein $R^e$ is optionally substituted with 1-5 $R^g$. In some embodiments, one $R^e$ is independently a 3-6 membered heterocycloalkyl containing 1-2 heteroatoms independently selected from nitrogen, oxygen, or sulfur, wherein $R^e$ is optionally substituted with 1-3 $R^9$. In some embodiments, one $R^e$ is independently a 3-6 membered heterocycloalkyl containing 1-2 heteroatoms independently selected from nitrogen, oxygen, or sulfur, wherein $R^e$ is optionally substituted with 1-2 $R^g$. In some embodiments, one $R^e$ is independently an unsubstituted 3-6 membered heterocycloalkyl containing 1-2 heteroatoms independently selected from nitrogen, oxygen, or sulfur.

In some embodiments, one $R^e$ is independently a 3-6 membered heterocycloalkyl containing 1-2 heteroatoms independently selected from nitrogen and oxygen, wherein $R^e$ is optionally substituted with 1-5 $R^9$. In some embodiments, one $R^e$ is independently a 3-6 membered heterocycloalkyl containing one heteroatom independently selected from nitrogen and oxygen, wherein $R^e$ is optionally substituted with 1-3 $R^g$. In some embodiments, one $R^e$ is independently a 3-6 membered heterocycloalkyl containing nitrogen. In some such embodiments, one $R^e$ is independently a 3-6 membered heterocycloalkyl containing oxygen.

In some embodiments, one $R^e$ is independently a 4 membered heterocycloalkyl containing one heteroatom independently selected from nitrogen, oxygen or sulfur, wherein $R^e$ is optionally substituted with 1-5 $R^g$. In such some embodiments, $R^e$ is azetidine, wherein $R^e$ is optionally substituted with 1-5 $R^g$. In some such embodiments, $R^e$ is azetidine, wherein $R^e$ is optionally substituted with 1-2 $R^g$. In some such embodiments, $R^e$ is N-substituted azetidine. In certain embodiments, $R^e$ is

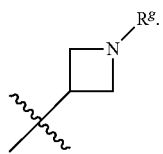

In certain embodiments, $R^e$ is

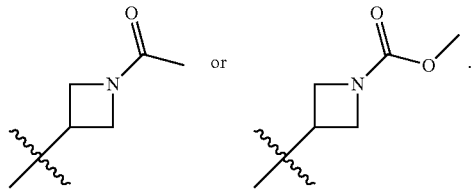

In some embodiments, one $R^e$ is independently oxetane, wherein $R^e$ is optionally substituted with 1-5 $R^g$. In some embodiments, one $R^e$ is independently oxetane, wherein $R^e$ is optionally substituted with 1-2 $R^g$ groups. In some embodiments, one $R^e$ is

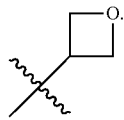

In some embodiments, one $R^e$ is thietane, wherein $R^e$ is optionally substituted with 1-5 $R^g$. In some embodiments, $R^e$ is

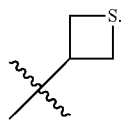

As described above and herein, in some embodiments, each $R^g$ independently halo, $R^X$, $OR^X$, $N(R^X)_2$, $C(O)R^X$, $C(O)OR^X$, $OC(O)R^X$, $OC(O)OR^X$, $S(O)_2R^X$, optionally substituted 3-4 membered heterocycloalkyl containing 1-2 heteroatoms independently selected from nitrogen, oxygen, or sulfur, or two $R^g$ on the same carbon are taken together to form an oxo group, or two $R^g$ on the same sulfur are optionally taken together to form an oxo group;

As described above and herein, in some embodiments, $X^1$ is N or C(H). In certain embodiments, $X^1$ is N. In certain embodiments, $X^1$ is C(H).

As described above and herein, in some embodiments, $X^2$ is N or C(H). In certain embodiments, $X^2$ is N. In certain embodiments, $X^2$ is C(H).

As described above and herein, in some embodiments, $X^3$ is N or C(H). In certain embodiments, $X^3$ is N. In certain embodiments, $X^3$ is C(H).

In some embodiments, a provided compound is as depicted within any of the tables provided at Examples 124 and 125.

In certain embodiments, a provided compound is as depicted below:

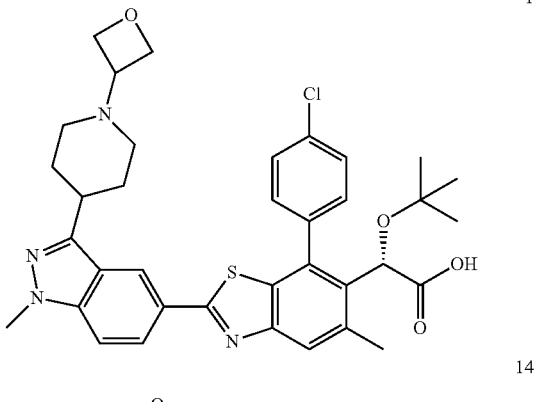

1

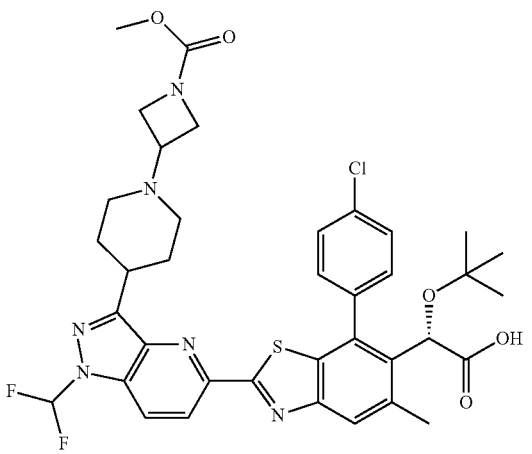

14

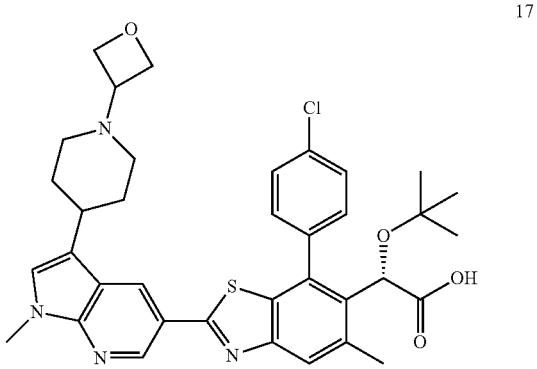

17

35
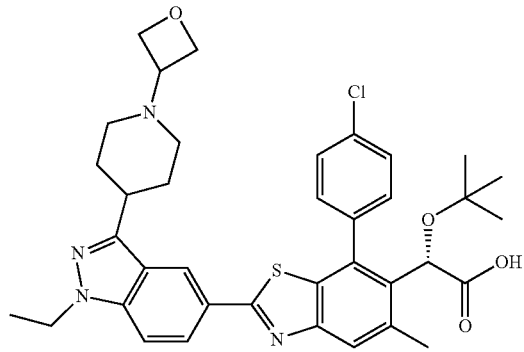
203
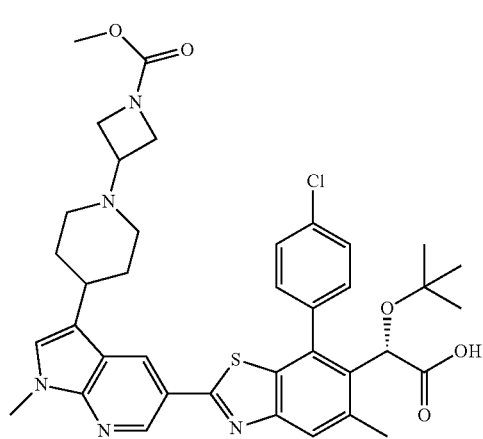
or a pharmaceutically acceptable salt thereof.
In some embodiments, a provided compound is as depicted below:
185
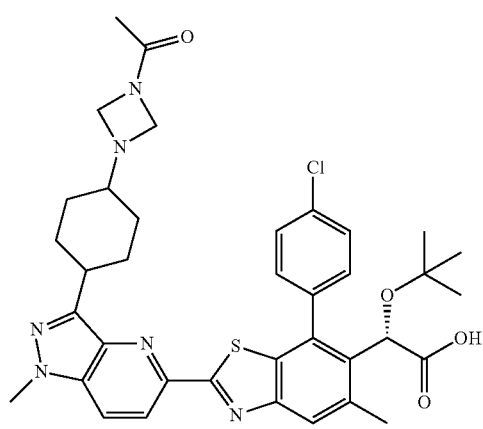
167
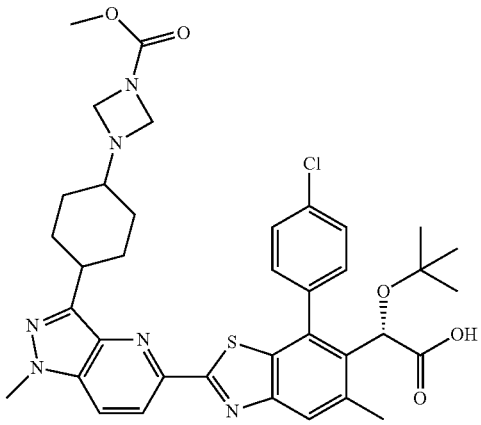
178
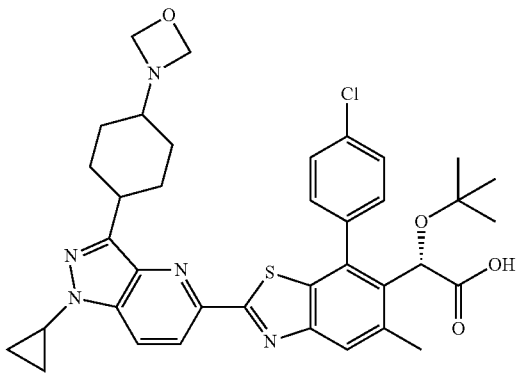
194
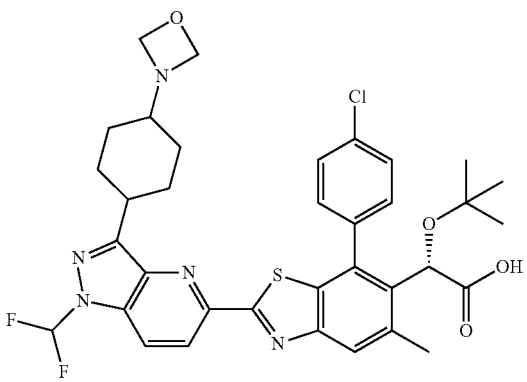
199
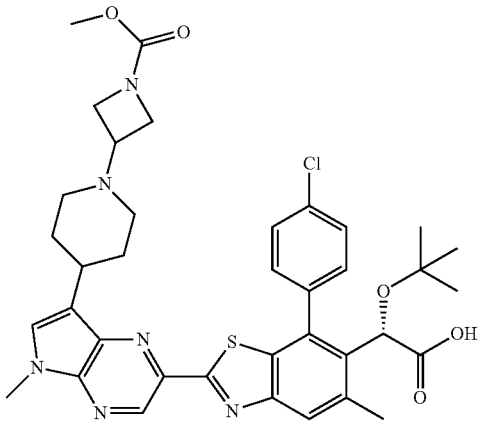

-continued

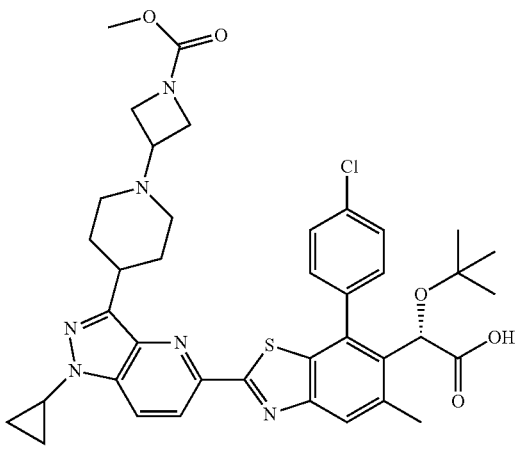

180 or a pharmaceutically acceptable salt thereof.

In certain embodiments, a provided compound is as depicted below:

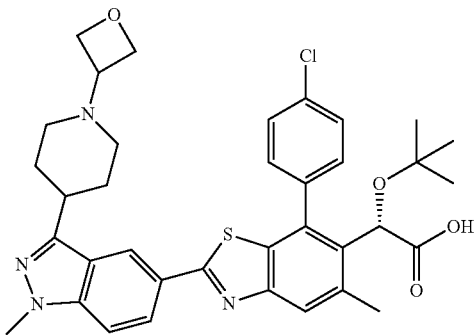

1 or a pharmaceutically acceptable salt thereof.

The compounds disclosed herein are characterized as having antiviral activity against wildtype (WT) HIV-1 (IIIb). In some embodiments, a provided compound is characterized by having an $EC_{50}$ of less than about 20 nM. In some embodiments, a provided compound is characterized by having an $EC_{50}$ of less than about 15 nM. In some embodiments, a provided compound is characterized by having an $EC_{50}$ of less than about 12 nM. In some embodiments, a provided compound is characterized by having an $EC_{50}$ of less than about 11 nM. In some embodiments, a provided compound is characterized by having an $EC_{50}$ of less than about 10 nM. In some embodiments, a provided compound is characterized by having an $EC_{50}$ of less than about 9 nM. In some embodiments, a provided compound is characterized by having an $EC_{50}$ of less than about 8 nM. In some embodiments, a provided compound is characterized by having an $EC_{50}$ of less than about 7 nM. In some embodiments, a provided compound is characterized by having an $EC_{50}$ of less than about 6 nM. In some embodiments, a provided compound is characterized by having an $EC_{50}$ of less than about 5 nM. In some embodiments, a provided compound is characterized by having an $EC_{50}$ of less than about 4 nM. In some embodiments, a provided compound is characterized by having an $EC_{50}$ of less than about 3 nM. In some embodiments, a provided compound is characterized by having an $EC_{50}$ of less than about 2 nM. In some embodiments, a provided compound is characterized by having an $EC_{50}$ of between about 1 nM and about 6 nM. In some embodiments, a provided compound is characterized by having an $EC_{50}$ of between about 2 nM and about 6 nM. In some embodiments, a provided compound is characterized by having an $EC_{50}$ of between about 2 nM and about 5 nM. In some embodiments, a provided compound is characterized by having an $EC_{50}$ 0 of between about 3 nM and about 4 nM.

In certain embodiments, compounds disclosed herein have antiviral activity against mutant HIV-1 viruses. In some cases, these viruses have been identified following development of antiviral resistance in a subject. For example, in certain embodiments, compounds disclosed herein are characterized as having antiviral activity against integrase (IN) T174I HIV-1 virus. In some embodiments, a provided compound is characterized by having an $EC_{50}$ against IN T174I HIV-1 of less than about 1000 nM. In some embodiments, a provided compound is characterized by having an $EC_{50}$ against IN T174I HIV-1 of less than about 750 nM. In some embodiments, a provided compound is characterized by having an $EC_{50}$ against IN T174I HIV-1 of less than about 500 nM. In some embodiments, a provided compound is characterized by having an $EC_{50}$ against IN T174I HIV-1 of less than about 250 nM. In some embodiments, a provided compound is characterized by having an $EC_{50}$ against IN T174I HIV-1 of less than about 100 nM. In some embodiments, a provided compound is characterized by having an $EC_{50}$ against IN T174I HIV-1 of from about 1 nM to about 1000 nM. In some embodiments, a provided compound is characterized by having an $EC_{50}$ against IN T174I HIV-1 of from about 1 nM to about 750 nM. In some embodiments, a provided compound is characterized by having an $EC_{50}$ against IN T174I HIV-1 of from about 1 nM to about 500 nM. In some embodiments, a provided compound is characterized by having an $EC_{50}$ against IN T174I HIV-1 of from about 1 nM to about 250 nM. In some embodiments, a provided compound is characterized by having an $EC_{50}$ against IN T174I HIV-1 of from about 1 nM to about 100 nM.

General Synthetic Procedures

Schemes 1-19 are provided as further embodiments of the invention and illustrate general methods which are used to prepare compounds of the invention and which can be used to prepare additional compounds of the invention.

Scheme 1

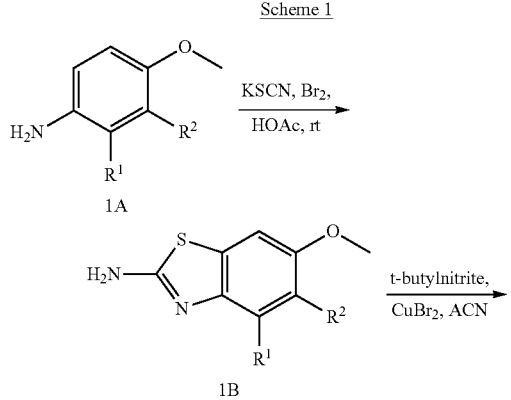

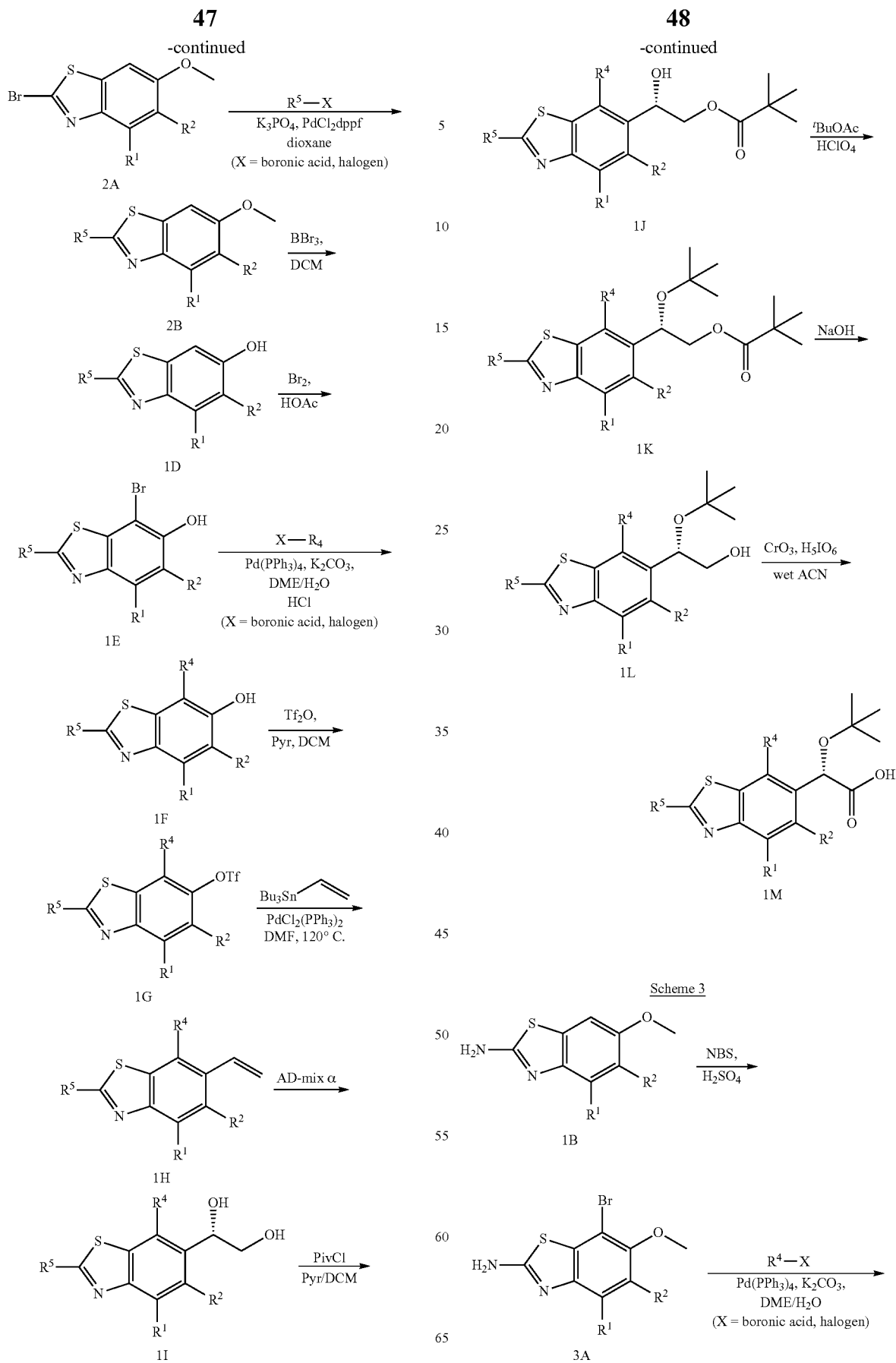

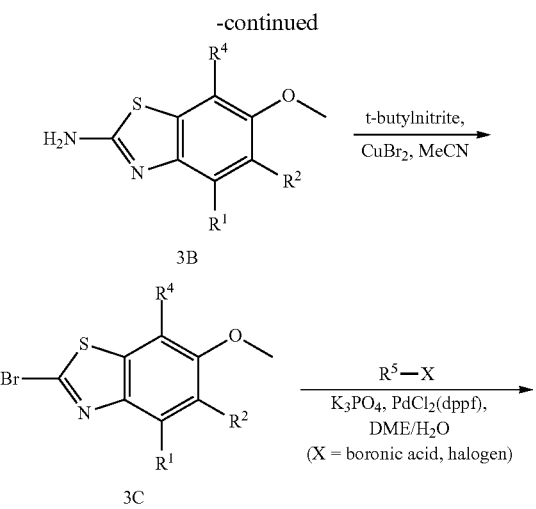

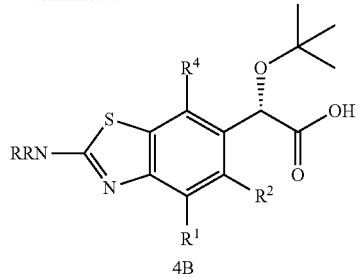

In certain embodiments the benzothiazole intermediate 4A is converted to the final compound 4B by the methods used to convert 2B to 1D and 1F to 1M as outlined in Scheme 1 wherein HNRR a heterocycle (i.e., when R and R taken together with the nitrogen to which they are attached form a ring).

Scheme 5

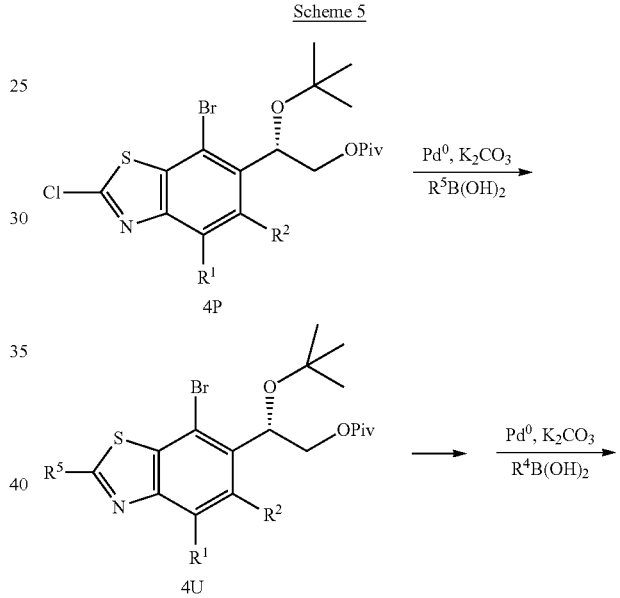

In certain embodiments, the benzothiazole intermediate 3E is converted to the final compound 2C by the methods used to convert 2B to 1D and 1F to 1M as outlined in Scheme 1.

Scheme 4

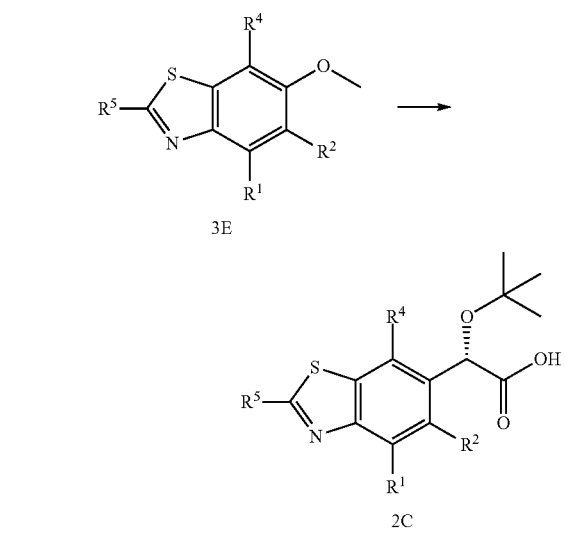

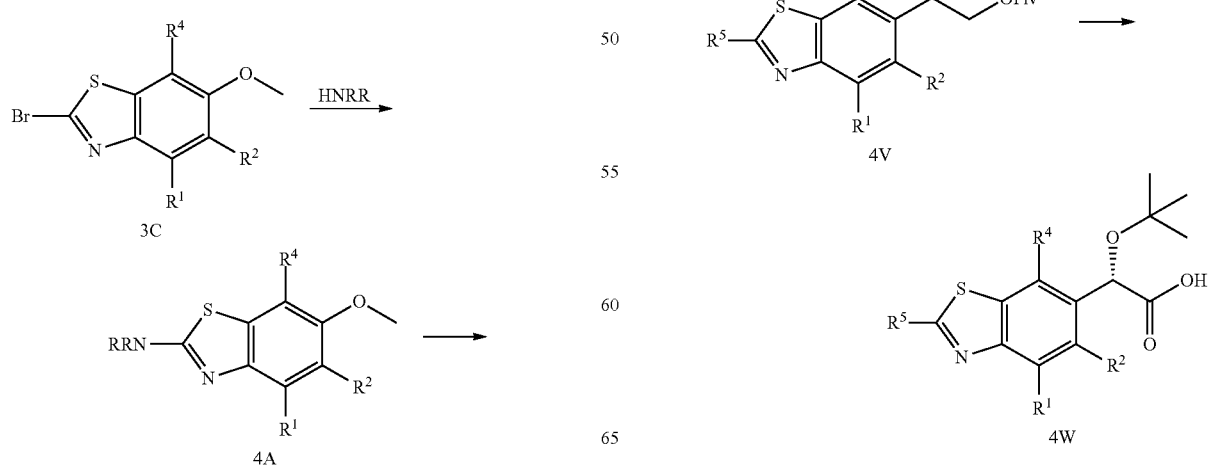

In certain embodiments the benzothiazoline intermediate 4V is converted to the final compound 4W by the methods used to convert 2B to 1M as outlined in Scheme 1.

Scheme 6

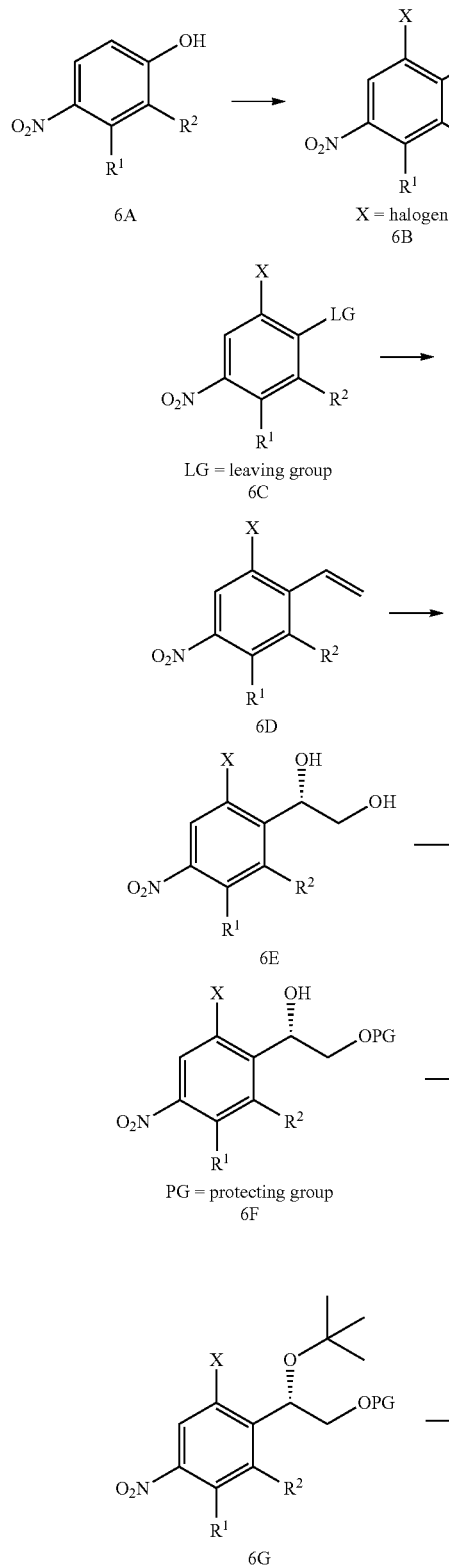

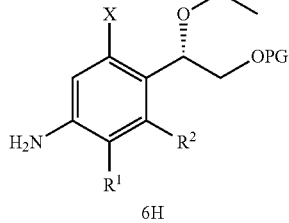

6H

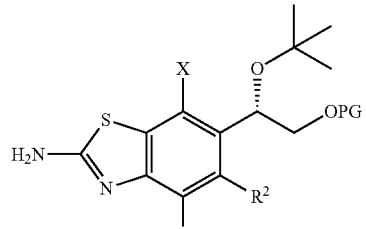

6I

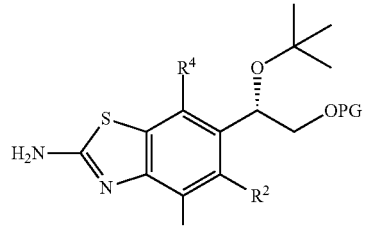

6J

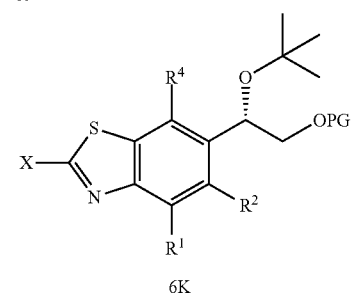

6K

In certain embodiments, an appropriately substituted phenol 6A is halogenated by the treatment of dihalide, for example bromine, in a suitable solvent such as, for example acetic acid. The phenol 6B is converted to a leaving group (e.g., triflate) known to undergo cross-coupling reactions. The corresponding activated phenol 6C undergoes a selective cross-coupling reaction such as, for example Stille cross-coupling using a tin reagent such as tributyl(vinyl)tin and a palladium catalyst such as bis(triphenylphosphine)palladium(II) dichloride to give the corresponding cross-coupled naphthalene such as styrene 6D. The styrene is dihydroxylated to provide 6E by methods known to those skilled in the art such as, Sharpless asymmetric dihydroxylation using, for example, commercially available AD mix-r. The resulting diol 6E is protected at the primary hydroxyl by suitable protecting groups such as pivalate ester using pivaloyl chloride and pyridine to provide 6F. The secondary hydroxyl is converted to the corresponding ether such as tert-butyl ether using methods known to those skilled in the art such as, tert-butyl acetate and perchloric acid to provide 6G.

The nitro group of 6G is reduced to the corresponding aniline 6H by catalytic hydrogenation using platinum on carbon, for example, under a hydrogen atmosphere. Benzothiazole 6I is formed by methods known to those skilled in the art such as potassium thiocyanate and pyridinium perbromide, for example. The resulting benzothiazole undergoes cross-coupling reaction such as Suzuki cross-coupling using a boronic acid or ester and a palladium catalyst such as tetrakis(triphenylphosphine)palladium(0) to give the corresponding cross-coupled benzothiazole 6J. The corresponding halobenzothiazole 6K is formed by methods known to those skilled in the art such as tert-butyl nitrite and a copper(II) halide such as copper(II) bromide, for example.

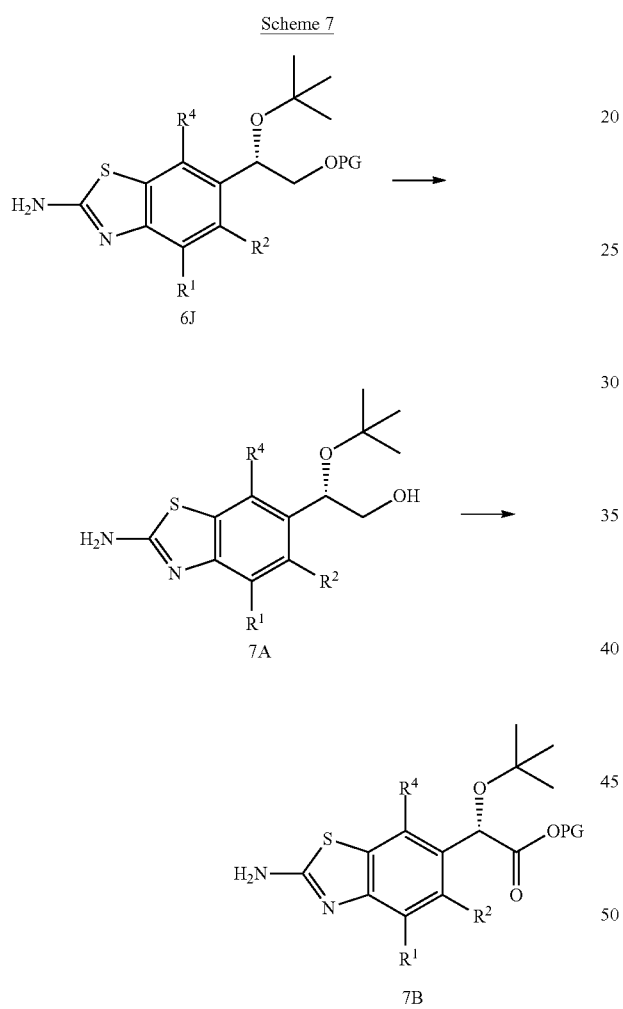

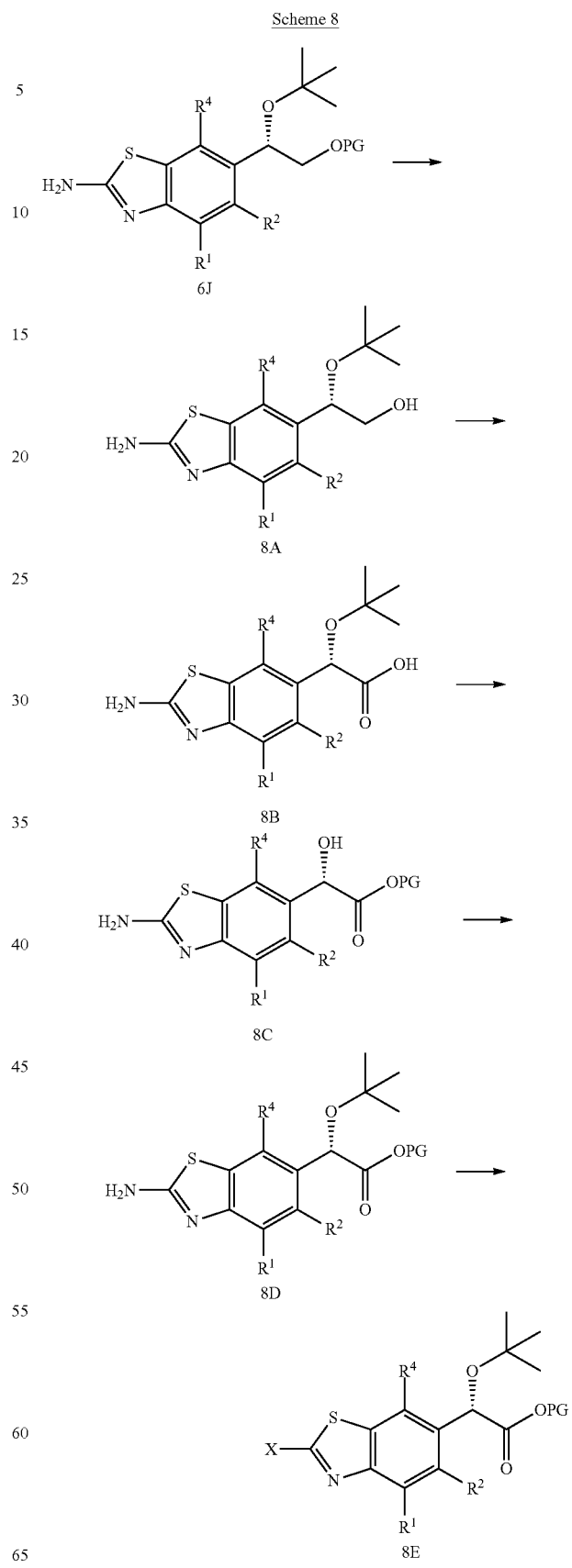

In certain embodiments the protected primary hydroxyl 6J is deprotected by methods known to those skilled in the art such as the deprotection of a pivalate protecting group under basic conditions for example, using sodium hydroxide, to give the corresponding primary hydroxyl compound 7A. The primary hydroxyl is oxidized to the corresponding carboxylic acid 7B by methods known to those skilled in the art such as, for example, periodic acid and chromium trioxide. The resulting carboxylic acid is protected by formation of corresponding carboxylic ester 7B with treatment of, for example, trimethylsilyldiazomethane, to form the corresponding methyl ester.

In certain embodiments the protected primary hydroxyl 6J is deprotected by methods known to those skilled in the art such as the deprotection of a pivalate protecting group under basic conditions for example, using sodium hydroxide, to give the corresponding primary hydroxyl compound 8A. The primary hydroxyl is oxidized to the corresponding carboxylic acid 8B by periodic acid and chromium trioxide, for example. The carboxylic acid is protected as, for example, a methyl ester by treatment with sulfuric acid in methanol. The tert-butyl ether is re-installed by treating 8C with tert-butyl acetate and perchloric acid, for example, to provide 8D. The corresponding halobenzothiazole 8E is formed by methods known to those skilled in the art such as tert-butyl nitrite and a copper(II)halide such as copper(II) bromide, for example.

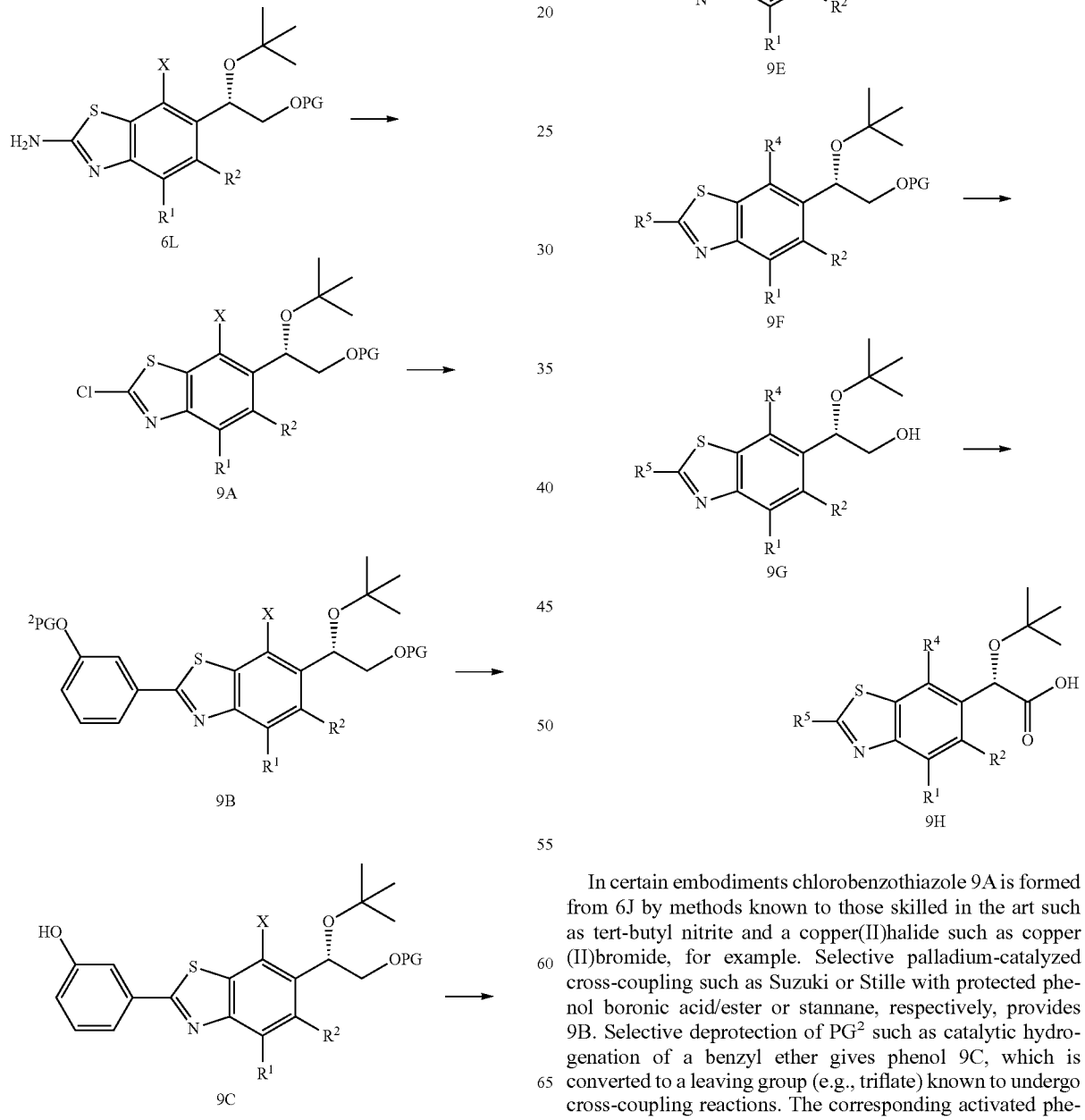

Scheme 9

In certain embodiments chlorobenzothiazole 9A is formed from 6J by methods known to those skilled in the art such as tert-butyl nitrite and a copper(II)halide such as copper (II)bromide, for example. Selective palladium-catalyzed cross-coupling such as Suzuki or Stille with protected phenol boronic acid/ester or stannane, respectively, provides 9B. Selective deprotection of $PG^2$ such as catalytic hydrogenation of a benzyl ether gives phenol 9C, which is converted to a leaving group (e.g., triflate) known to undergo cross-coupling reactions. The corresponding activated phenol 9D undergoes a selective cross-coupling reaction such as, for example Suzuki cross-coupling using a boronic acid or ester and a palladium catalyst such as tetrakis(triphenylphosphine)palladium(0) to give the corresponding cross-coupled benzothiazole 9E.

In certain embodiments the R⁴ moiety is introduced by cross-coupling reaction such as, for example Suzuki cross-coupling using a boronic acid or ester and a palladium catalyst such as tetrakis(triphenylphosphine)palladium(0) to give the corresponding cross-coupled benzothiazole 9F. The protected primary hydroxyl 9F is deprotected by methods known to those skilled in the art such as the deprotection of a pivalate protecting group under basic conditions for example, using sodium hydroxide, to give the corresponding primary hydroxyl compound 9G. The primary hydroxyl is oxidized to the corresponding carboxylic acid 9H by periodic acid and chromium trioxide, for example.

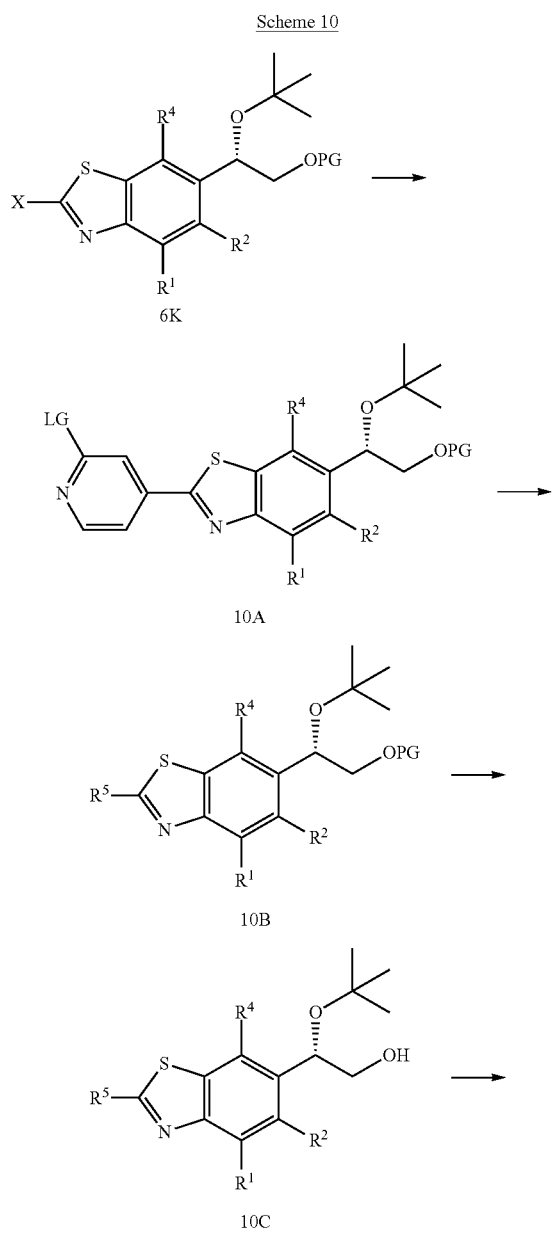

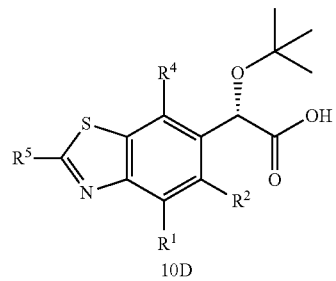

10D

In certain embodiments halobenzothiazole 6K undergoes selective palladium-catalyzed cross-coupling such as Suzuki or Stille with a boronic acid/ester or stannane that also contains a leaving group such as for example, a chloropyridylboronic acid, known to undergo cross-coupling reactions to give 10A. The activated moiety 10A undergoes a cross-coupling reaction such as, for example Suzuki or Stille cross-coupling using a boronic acid/ester or stannane, respectively and a palladium catalyst such as tetrakis(triphenylphosphine)palladium(0) to give the corresponding cross-coupled benzothiazole 10B. The protected primary hydroxyl 10B is deprotected by methods known to those skilled in the art such as the deprotection of a pivalate protecting group under basic conditions for example, using sodium hydroxide, to give the corresponding primary hydroxyl compound 10C. The primary hydroxyl is oxidized to the corresponding carboxylic acid 10D by periodic acid and chromium trioxide, for example.

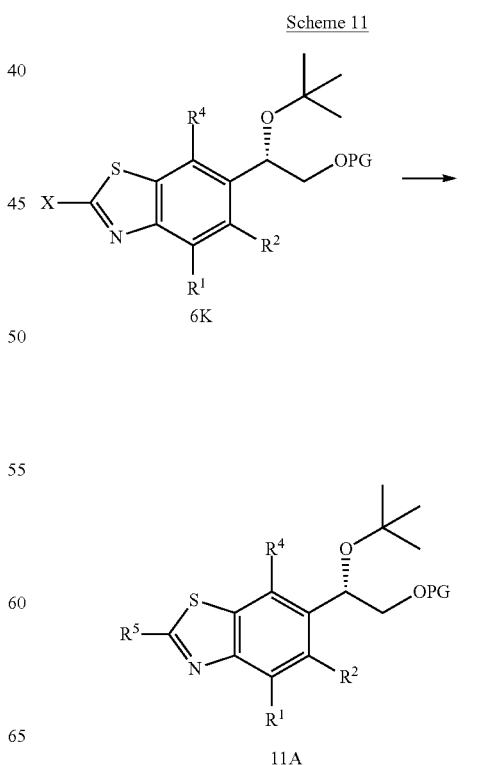

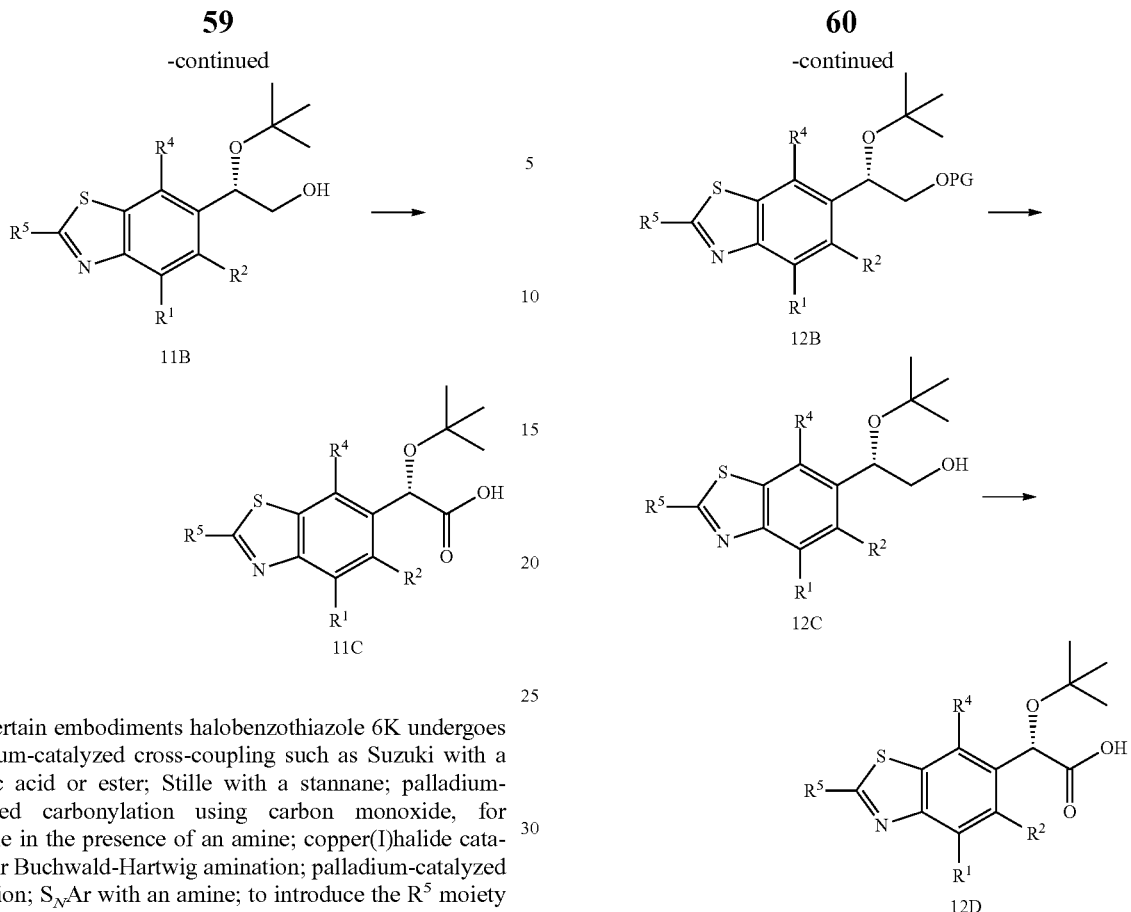

In certain embodiments halobenzothiazole 6K undergoes palladium-catalyzed cross-coupling such as Suzuki with a boronic acid or ester; Stille with a stannane; palladium-catalyzed carbonylation using carbon monoxide, for example in the presence of an amine; copper(I)halide catalyzed or Buchwald-Hartwig amination; palladium-catalyzed amidation; $S_NAr$ with an amine; to introduce the $R^5$ moiety in 11A. The protected primary hydroxyl of 11A is deprotected by methods known to those skilled in the art such as the deprotection of a pivalate protecting group under basic conditions for example, using sodium hydroxide, to give the corresponding primary hydroxyl compound 11B. The primary hydroxyl is oxidized to the corresponding carboxylic acid 11C by periodic acid and chromium trioxide, for example.

In certain embodiments chlorobenzothiazole 9A undergoes selective palladium-catalyzed cross-coupling such as Suzuki or Stille with protected phenol boronic acid/ester or stannane, respectively, to provide 12A. The $R^4$ moiety is introduced by cross-coupling reaction such as, for example Suzuki cross-coupling using a boronic acid or ester and a palladium catalyst such as tetrakis(triphenylphosphine)palladium(0) to give the corresponding cross-coupled benzothiazole 12B. The protected primary hydroxyl in 12B is deprotected by methods known to those skilled in the art such as the deprotection of a pivalate protecting group under basic conditions for example, using sodium hydroxide, to give the corresponding primary hydroxyl compound 12C. The primary hydroxyl is oxidized to the corresponding carboxylic acid 12D by periodic acid and chromium trioxide, for example.

Scheme 12

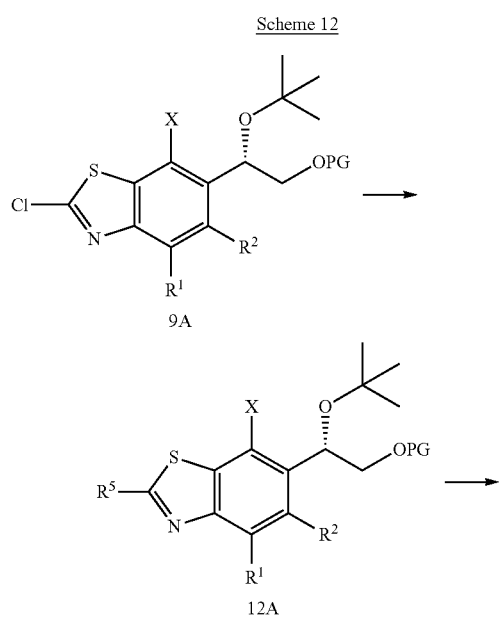

Scheme 13

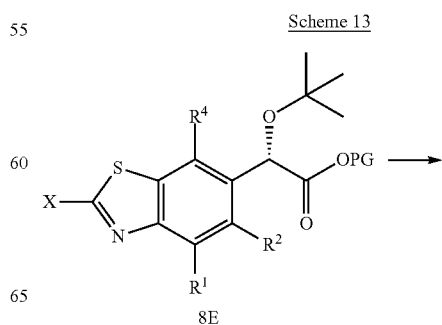

-continued

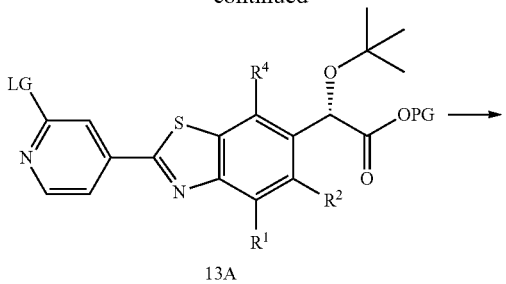

13A

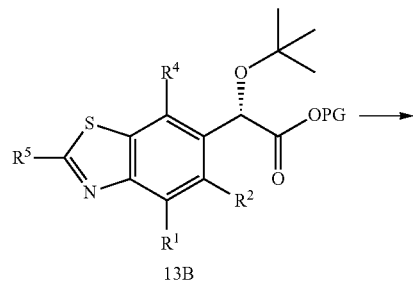

13B

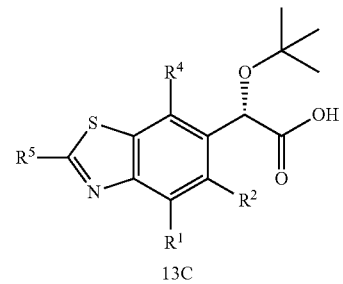

13C

In certain embodiments halobenzothiazole 8E undergoes selective palladium-catalyzed cross-coupling such as Suzuki or Stille with a boronic acid/ester or stannane that also contains a leaving group such as for example, a chloropyridylboronic acid, known to undergo cross-coupling reactions to give 13A. The activated moiety 13A undergoes an $S_NAr$ reaction with for example a secondary amine, or a cross-coupling reaction such as, for example Suzuki or Stille cross-coupling using a boronic acid/ester or stannane, respectively and a palladium catalyst such as tetrakis(triphenylphosphine)palladium(0) to give the corresponding cross-coupled benzothiazole 13B. The protected carboxylic acid 13B is deprotected by methods known to those skilled in the art such as the deprotection of a carboxylic ester under basic conditions for example, using sodium hydroxide, or treatment with lithium iodide in pyridine, to give the corresponding carboxylic acid 13C.

Scheme 14

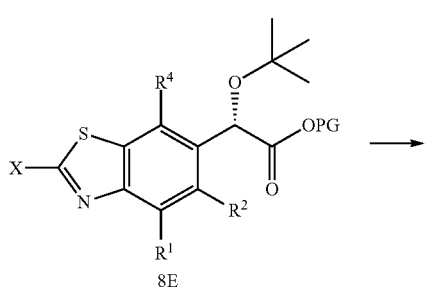

8E

-continued

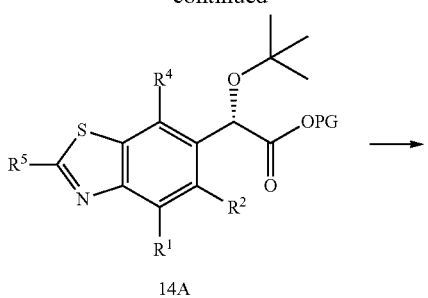

14A

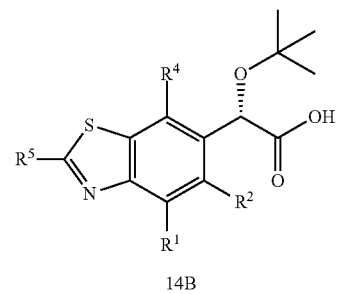

14B

In certain embodiments halobenzothiazole 8E undergoes palladium-catalyzed cross-coupling such as Suzuki with a boronic acid or ester; Stille with a stannane; palladium-catalyzed carbonylation using carbon monoxide, for example in the presence of an amine; copper(I)halide catalyzed or Buchwald-Hartwig amination; palladium-catalyzed amidation; $S_NAr$ with an amine or alcohol; to introduce the $R^5$ moiety in 14A. The protected carboxylic acid 14A is deprotected by methods known to those skilled in the art such as the deprotection of a carboxylic ester under basic conditions for example, using sodium hydroxide, or treatment with lithium iodide in pyridine to give the corresponding carboxylic acid 14B.

Scheme 15

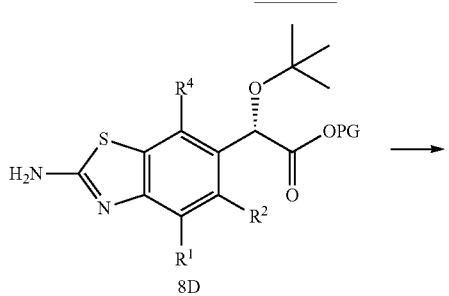

8D

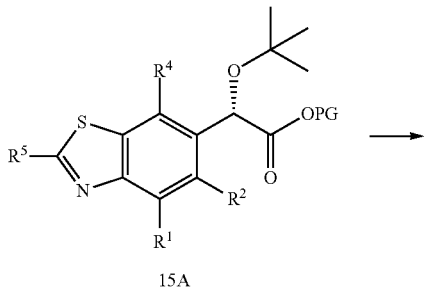

15A

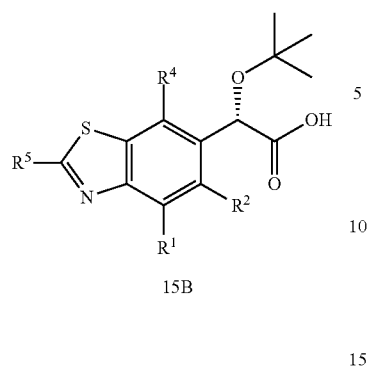

15B

In certain embodiments aminobenzothiazole 8D undergoes reactions known to those skilled in the art such as amide formation using carboxylic acid EDCI, for example; sulfonamide formation using a sulfonyl chloride; urea formation using CDI in the presence of an amine; to introduce the $R^5$ moiety in 15A. The protected carboxylic acid 15A is deprotected by methods known to those skilled in the art such as the deprotection of a carboxylic ester under basic conditions for example, using sodium hydroxide, to give the corresponding carboxylic acid 15B.

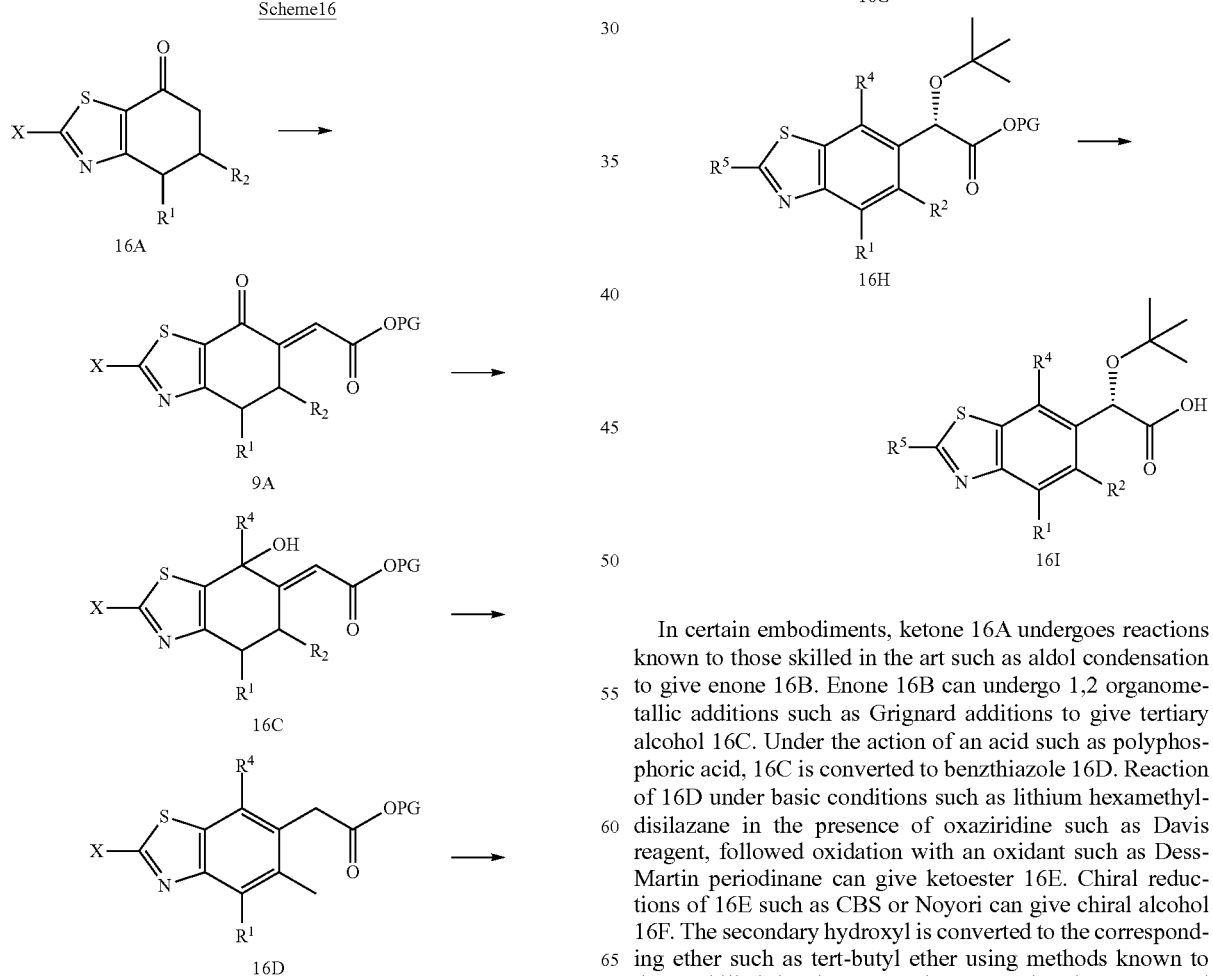

In certain embodiments, ketone 16A undergoes reactions known to those skilled in the art such as aldol condensation to give enone 16B. Enone 16B can undergo 1,2 organometallic additions such as Grignard additions to give tertiary alcohol 16C. Under the action of an acid such as polyphosphoric acid, 16C is converted to benzthiazole 16D. Reaction of 16D under basic conditions such as lithium hexamethyldisilazane in the presence of oxaziridine such as Davis reagent, followed oxidation with an oxidant such as Dess-Martin periodinane can give ketoester 16E. Chiral reductions of 16E such as CBS or Noyori can give chiral alcohol 16F. The secondary hydroxyl is converted to the corresponding ether such as tert-butyl ether using methods known to those skilled in the art such as, tert-butyl acetate and perchloric acid to provide 16G. The activated benzthiazole 16G undergoes a cross-coupling reaction such as, for example Buchwald, Heck, Negishi, Suzuki or Stille cross-coupling using a palladium catalyst such as tetrakis(triphenylphosphine)palladium(0); S$_N$Ar reactions with for example, a secondary amine; to give the corresponding benzothiazole 16H. The protected carboxylic acid 16H is deprotected by methods known to those skilled in the art such as the deprotection of a carboxylic ester under basic conditions for example, using sodium hydroxide, or treatment with lithium iodide in pyridine to give the corresponding carboxylic acid 16I.

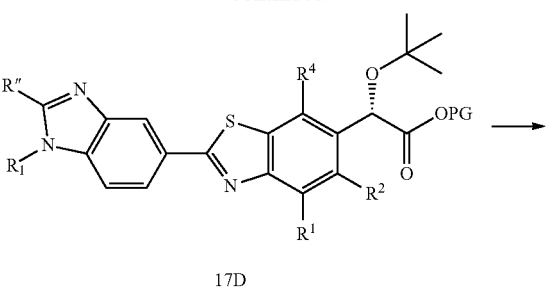

17D

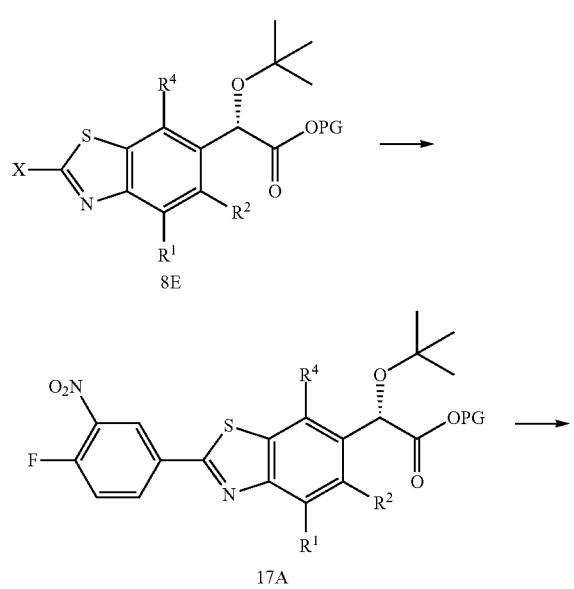

Scheme 17

8E

17A

17B

17C

In certain embodiments, halobenzthiazole 8E undergoes palladium-catalyzed cross-coupling such as Suzuki with a boronic acid or ester, for example 2-(4-fluoro-3-nitrophenyl)-4,4,5,5-tetramethyl-1,3,2-dioxaborolane to give 17A, known to those skilled in the art to undergo SnAr reaction with nucleophiles, such as, for example methylamine, to give 17B. Hydrogenation under platinum on carbon, for example provides the bis-aniline 17C. Cyclization with an orthoformate, such as triethylorthoformate in acetic acid, for example gives benzimidazole 17D. The protected carboxylic acid 17D is deprotected by methods known to those skilled in the art such as the deprotection of a carboxylic ester under basic conditions for example, using sodium hydroxide, or treatment with lithium iodide in pyridine to give the corresponding carboxylic acid 17E.

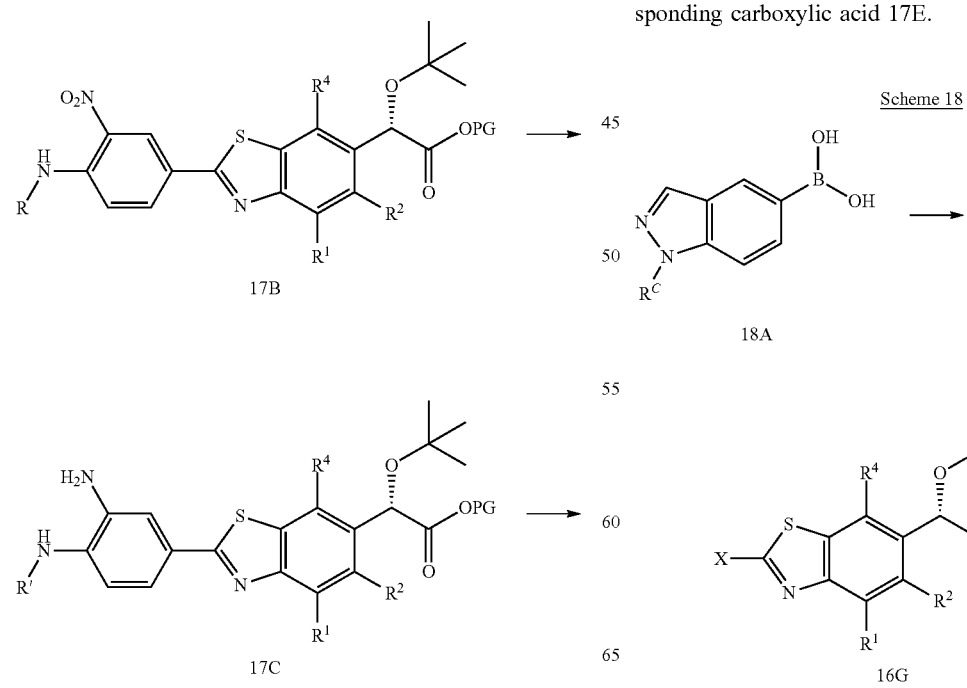

Scheme 18

18A

16G

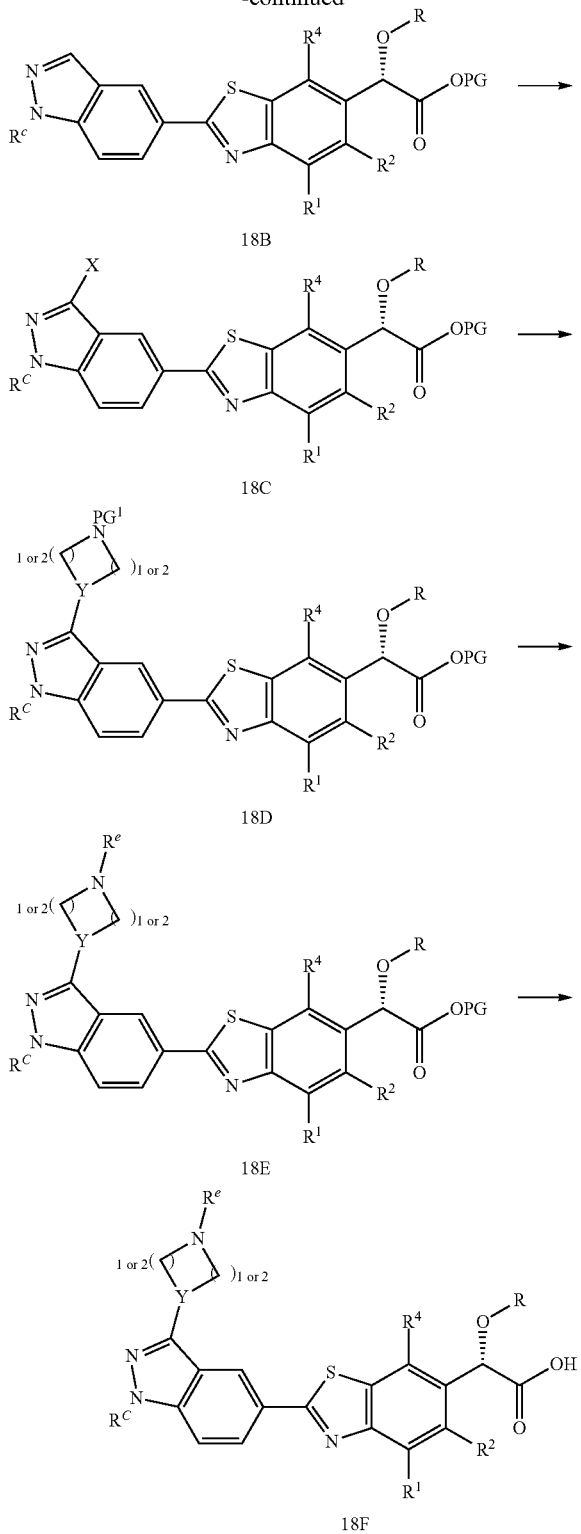

18C. Palladium-catalyzed cross-coupling such as Buchwald coupling with appropriately protected amine or amide or Suzuki reaction with appropriately protected amino vinyl boronic acid or ester followed by hydrogenation with rhodium on alumina, for example, furnishes 18D. Amine deprotection by conditions known to those skilled in the art, such as hydrogen chloride in isopropanol to remove a Boc protecting group, followed by reductive amination with an appropriate aldehyde or acylation with an acid chloride or chloroformate gives 18E. Saponification with an aqueous base such as sodium hydroxide provides 18F.

Scheme 19

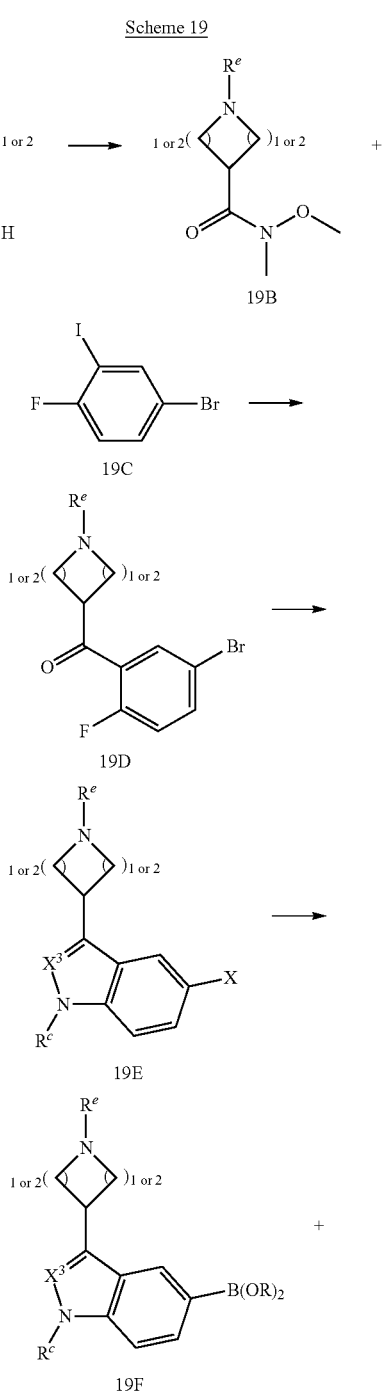

In certain embodiments, halobenzthiazole 16G undergoes palladium-catalyzed cross-coupling such as Suzuki reaction with a boronic acid or ester, for example (1-methyl-1H-indazol-5-yl)boronic acid) or Stille reaction with a stannane; or a Negishi reaction with a heteroaryl halide to give 18B, known to those skilled in the art to undergo halogenation with N-bromosucciimide for example, to give haloindazole

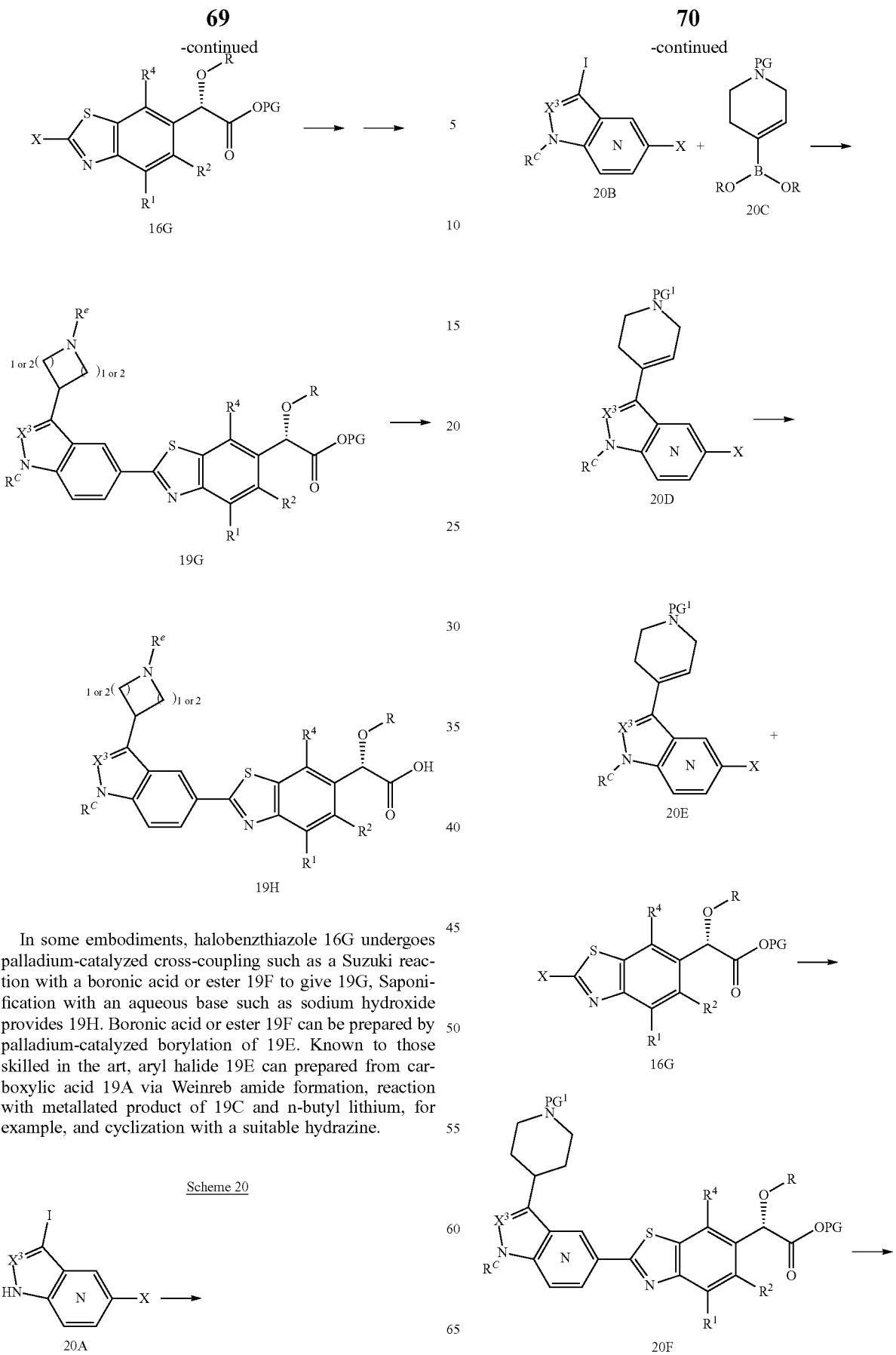

In some embodiments, halobenzthiazole 16G undergoes palladium-catalyzed cross-coupling such as a Suzuki reaction with a boronic acid or ester 19F to give 19G, Saponification with an aqueous base such as sodium hydroxide provides 19H. Boronic acid or ester 19F can be prepared by palladium-catalyzed borylation of 19E. Known to those skilled in the art, aryl halide 19E can prepared from carboxylic acid 19A via Weinreb amide formation, reaction with metallated product of 19C and n-butyl lithium, for example, and cyclization with a suitable hydrazine.

Scheme 20

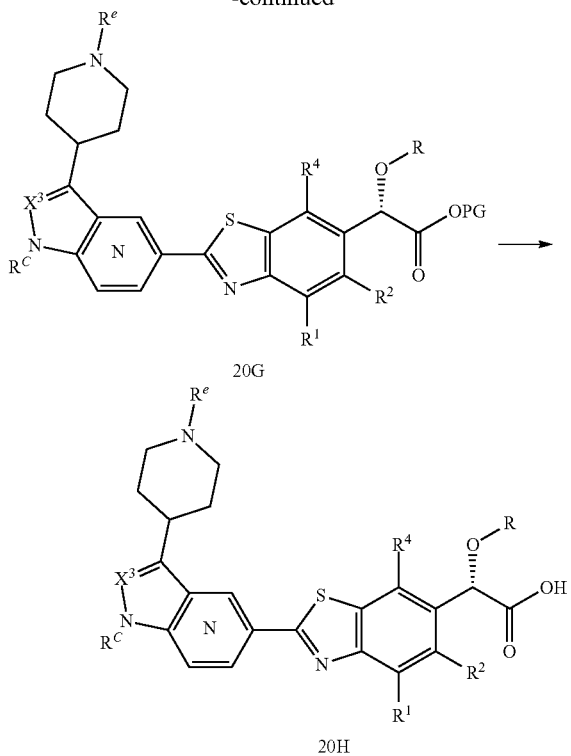

20G

20H

In some embodiments, halobenzthiazole 16G undergoes palladium-catalyzed cross-coupling such as a Negishi reaction with a heteroaryl halide 20E to give 20F, Amine deprotection by conditions known to those skilled in the art, such as hydrogen chloride in isopropanol to remove a Boc protecting group, followed by reductive amination with an appropriate aldehyde or acylation with an acid chloride or chloroformate gives 20G. Saponification with an aqueous base such as sodium hydroxide provides 20H. Known to those skilled in the art, heteroaryl halide 20E can be prepared by alkylation with a base and electrophile such as iodomethane, Suzuki cross-coupling with vinyl boronic acid or ester 20C, catalytic hydrogenation using rhodium on alumina.

Prodrugs

In some embodiments, a prodrug of a compound described herein is provided. A "prodrug" is defined in the pharmaceutical field as a biologically inactive derivative of a drug that upon administration to the human body is converted to the biologically active parent drug according to some chemical or enzymatic pathway. Prodrugs include, for instance, a compound that when administered to a biological system generates a compound of the invention that inhibits the replication of HIV ("the active inhibitory compound"). Such a compound may be formed from the prodrug as a result of, for example: (i) spontaneous chemical reaction(s), (ii) enzyme catalyzed chemical reaction(s), (iii) photolysis, and/or (iv) metabolic chemical reaction(s).

"Prodrug moiety" refers to a labile functional group which separates from an active inhibitory compound during metabolism, systemically, inside a cell, by hydrolysis, enzymatic cleavage, or by some other process (Bundgaard, Hans, "Design and Application of Prodrugs" in *A Textbook of Drug Design and Development* (1991), P. Krogsgaard-Larsen and H. Bundgaard, Eds. Harwood Academic Publishers, pp. 113-191). Enzymes which are capable of an enzymatic activation mechanism with prodrug compounds of the invention include, but are not limited to, amidases, esterases, microbial enzymes, phospholipases, cholinesterases, and phosphases. Prodrug moieties can serve to enhance solubility, absorption and lipophilicity to optimize drug delivery, bioavailability and efficacy. A prodrug moiety may include an active metabolite or drug itself.

Exemplary prodrug moieties include hydrolytically sensitive or labile acyloxymethyl esters —$CH_2OC(=O)R^{99}$ and acyloxymethyl carbonates —$CH_2OC(=O)OR^{99}$ where $R^{99}$ is $C_1$-$C_6$ alkyl, $C_1$-$C_6$ substituted alkyl, $C_6$-$C_{20}$ aryl or $C_6$-$C_{20}$ substituted aryl. Acyloxyalkyl esters were first used as a prodrug strategy for carboxylic acids and then applied to phosphates and phosphonates by Farquhar et al. (1983) *J. Pharm. Sci.* 72: 24; also U.S. Pat. Nos. 4,816,570, 4,968,788, 5,663,159 and 5,792,756. Subsequently, acyloxyalkyl esters were used to deliver phosphonic acids across cell membranes and to enhance oral bioavailability. A close variant of acyloxyalkyl esters, i.e., alkoxycarbonyloxyalkyl esters (carbonates), may also enhance oral bioavailability as prodrug moieties for use in combination with compounds of the invention. An exemplary acyloxymethyl ester is pivaloyloxymethoxy, (POM) —$CH_2OC(=O)C(CH_3)_3$. An exemplary acyloxymethyl carbonate prodrug moiety is pivaloyloxymethylcarbonate (POC) —$CH_2OC(=O)OC(CH_3)_3$.

Combination Therapy

In certain embodiments, a method for treating or preventing an HIV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, or four; or one or two; or one to three; or one to four) additional therapeutic agents. In one embodiment, a method for treating an HIV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, or four; or one or two; or one to three; or one to four) additional therapeutic agents.

In one embodiment, pharmaceutical compositions comprising a compound disclosed herein, or a pharmaceutically acceptable salt thereof, in combination with one or more (e.g., one, two, three, or four; or one or two; or one to three; or one to four) additional therapeutic agents, and a pharmaceutically acceptable excipient are provided.

In certain embodiments, the present disclosure provides a method for treating an HIV infection, comprising administering to a subject in need thereof a therapeutically effective amount of a compound disclosed herein, or a pharmaceutically acceptable salt thereof, in combination with a therapeutically effective amount of one or more additional therapeutic agents which are suitable for treating an HIV infection.

In certain embodiments, a compound disclosed herein, or a pharmaceutically acceptable salt thereof, is combined with one, two, three, four, or more additional therapeutic agents. The one, two, three, four, or more additional therapeutic agents can be different therapeutic agents selected from the same class of therapeutic agents, and/or they can be selected from different classes of therapeutic agents.

Administration of HIV Combination Therapy

In certain embodiments, a compound disclosed herein, or a pharmaceutically acceptable salt thereof, is administered with one or more additional therapeutic agents. Co-administration of a compound disclosed herein, or a pharmaceutically acceptable salt thereof, with one or more additional therapeutic agents generally refers to simultaneous or sequential administration of a compound disclosed herein and one or more additional therapeutic agents, such that therapeutically effective amounts of the compound disclosed herein, or a pharmaceutically acceptable salt thereof, and the one or more additional therapeutic agents are both present in the body of the subject. When administered sequentially, the combination may be administered in two or more administrations.

Co-administration includes administration of unit dosages of the compounds disclosed herein, or pharmaceutically acceptable salts thereof, before or after administration of unit dosages of one or more additional therapeutic agents. For example, the compound disclosed herein, or a pharmaceutically acceptable salt thereof, may be administered within seconds, minutes, or hours of the administration of the one or more additional therapeutic agents. In some embodiments, a unit dose of a compound disclosed herein, or a pharmaceutically acceptable salt thereof, is administered first, followed within seconds or minutes by administration of a unit dose of one or more additional therapeutic agents. Alternatively, a unit dose of one or more additional therapeutic agents is administered first, followed by administration of a unit dose of a compound disclosed herein within seconds or minutes. In other embodiments, a unit dose of a compound disclosed herein is administered first, followed, after a period of hours (e.g., 1-12 hours), by administration of a unit dose of one or more additional therapeutic agents. In yet other embodiments, a unit dose of one or more additional therapeutic agents is administered first, followed, after a period of hours (e.g., 1-12 hours), by administration of a unit dose of a compound disclosed herein.

In certain embodiments, a compound disclosed herein, or a pharmaceutically acceptable salt thereof, is combined with one or more additional therapeutic agents in a unitary dosage form for simultaneous administration to a subject. In certain embodiments, such a unitary dosage form can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intrathecal and epidural), and the like. In certain embodiments, the compounds disclosed can be dosed parenterally. In certain embodiments, the unitary dosage form can be dosed intravenous, subcutaneous, or intramuscular. In certain embodiments, the unitary dosage form is orally bioavailable and can be dosed orally. In certain embodiments, the unitary dosage form can be a solid dosage form for oral administration.

In certain embodiments, a compound disclosed herein, or a pharmaceutically acceptable salt thereof, is formulated as a tablet, which may optionally contain one or more other compounds useful for treating HIV. In certain embodiments, the tablet can one or more other compounds useful for treating HIV, such as HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof.

In certain embodiments, such tablets are suitable for once daily dosing.

HIV Combination Therapy

In the above embodiments, the additional therapeutic agent may be an anti-HIV agent selected from the group consisting of combination drugs for treating HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, HIV vaccines, and combinations thereof.

In some embodiments, the additional therapeutic agent is selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

HIV Combination Drugs

Examples of combination drugs include ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); darunavir, tenofovir alafenamide hemifumarate, emtricitabine, and cobicistat; efavirenz, lamivudine, and tenofovir disoproxil fumarate; lamivudine and tenofovir disoproxil fumarate; tenofovir and lamivudine; tenofovir alafenamide and emtricitabine; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; COMBIVIR® (zidovudine and lamivudine; AZT+3TC); EPZICOM® (LIVEXA®; abacavir sulfate and lamivudine;

ABC+3TC); KALETRA® (ALUVIA®; lopinavir and ritonavir); TRIUMEQ® (dolutegravir, abacavir, and lamivudine); TRIZIVIR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; cabotegravir and rilpivirine; cabotegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dolutegravir+lamivudine; lamivudine+abacavir+zidovudine; lamivudine+abacavir; lamivudine+tenofovir disoproxil fumarate; lamivudine+zidovudine+nevirapine; lopinavir+ritonavir; lopinavir+ritonavir+abacavir+lamivudine; lopinavir+ritonavir+zidovudine+lamivudine; tenofovir+lamivudine; and tenofovir disoproxil fumarate+emtricitabine+rilpivirine hydrochloride; lopinavir, ritonavir, zidovudine and lamivudine; Vacc-4x and romidepsin; and APH-0812.

Other HIV Drugs

Examples of other drugs for treating HIV include acemannan, alisporivir, BanLec, deferiprone, Gamimune, metenkefalin, naltrexone, Prolastin, REP 9, RPI-MN, VSSP, H1viral, SB-728-T, 1,5-dicaffeoylquinic acid, rHIV7-shl-TAR-CCR5RZ, AAV-eCD4-Ig gene therapy, MazF gene therapy, BlockAide, ABX-464, AG-1105, APH-0812, BIT-225, CYT-107, HGTV-43, HPH-116, HS-10234, IMO-3100, IND-02, MK-1376, MK-8507, MK-8591, NOV-205, PA-1050040 (PA-040), PGN-007, SCY-635, SB-9200, SCB-719, TR-452, TEV-90110, TEV-90112, TEV-90111, TEV-90113, RN-18, Immuglo, and VIR-576.

HIV Protease Inhibitors

Examples of HIV protease inhibitors include amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, DG-17, TMB-657 (PPL-100), T-169, BL-008, and TMC-310911.

HIV Reverse Transcriptase Inhibitors

Examples of HIV non-nucleoside or non-nucleotide inhibitors of reverse transcriptase include dapivirine, delavirdine, delavirdine mesylate, doravirine, efavirenz, etravirine, lentinan, nevirapine, rilpivirine, AIC-292, KM-023, and VM-1500.

Examples of HIV nucleoside or nucleotide inhibitors of reverse transcriptase include adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir disoproxil hemifumarate, VIDEX® and VIDEX EC® (didanosine, ddl), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, lamivudine, phosphazid, stavudine, zalcitabine, zidovudine, GS-9131, GS-9148, and KP-1461.

HIV Integrase Inhibitors

Examples of HIV integrase inhibitors include elvitegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, dolutegravir, JTK-351, bictegravir, AVX-15567, diketo quinolin-4-1 derivatives, integrase-LEDGF inhibitor, ledgins, M-522, M-532, NSC-310217, NSC-371056, NSC-48240, NSC-642710, NSC-699171, NSC-699172, NSC-699173, NSC-699174, stilbenedisulfonic acid, T-169 and cabotegravir.

Examples of HIV non-catalytic site, or allosteric, integrase inhibitors (NCINI) include CX-05045, CX-05168, and CX-14442.

HIV Entry Inhibitors

Examples of HIV entry (fusion) inhibitors include cenicriviroc, CCR5 inhibitors, gp41 inhibitors, CD4 attachment inhibitors, gp120 inhibitors, and CXCR4 inhibitors.

Examples of CCR5 inhibitors include aplaviroc, vicriviroc, maraviroc, cenicriviroc, PRO-140, adaptavir (RAP-101), nifeviroc (TD-0232), anti-GP120/CD4 or CCR5 bispecific antibodies, B-07, MB-66, polypeptide C25P, TD-0680, and vMIP (Haimipu).

Examples of gp41 inhibitors include albuvirtide, enfuvirtide, BMS-986197, enfuvirtide biobetter, enfuvirtide biosimilar, HIV-1 fusion inhibitors (P26-Bapc), ITV-1, ITV-2, ITV-3, ITV-4, PIE-12 trimer and sifuvirtide.

Examples of CD4 attachment inhibitors include ibalizumab and CADA analogs

Examples of gp120 inhibitors include Radha-108 (receptol) 3B3-PE38, BanLec, bentonite-based nanomedicine, fostemsavir tromethamine, IQP-0831, and BMS-663068

Examples of CXCR4 inhibitors include plerixafor, ALT-1188, N15 peptide, and vMIP (Haimipu).

HIV Maturation Inhibitors

Examples of HIV maturation inhibitors include BMS-955176 and GSK-2838232.

Latency Reversing Agents

Examples of latency reversing agents include histone deacetylase (HDAC) inhibitors, proteasome inhibitors such as velcade, protein kinase C (PKC) activators, BET-bromodomain 4 (BRD4) inhibitors, ionomycin, PMA, SAHA (suberanilohydroxamic acid, or suberoyl, anilide, and hydroxamic acid), IL-15, JQ1, disulfram, amphotericin B, and ubiquitin inhibitors such as largazole analogs, and GSK-343.

Examples of HDAC inhibitors include romidepsin, vorinostat, and panobinostat.

Examples of PKC activators include indolactam, prostratin, ingenol B, and DAG-lactones.

Capsid Inhibitors

Examples of capsid inhibitors include capsid polymerization inhibitors or capsid disrupting compounds, HIV nucleocapsid p7 (NCp7) inhibitors such as azodicarbonamide, HIV p24 capsid protein inhibitors, AVI-621, AVI-101, AVI-201, AVI-301, and AVI-CAN1-15 series;

Immune-Based Therapies

Examples of immune-based therapies include toll-like receptors modulators such as tlr1, tlr2, tlr3, tlr4, tlr5, tlr6, tlr7, tlr8, tlr9, tlr10, tlr11, tlr12, and tlr13; programmed cell death protein 1 (Pd-1) modulators; programmed death-ligand 1 (Pd-L1) modulators; IL-15 agonists; DermaVir; interleukin-7; plaquenil (hydroxychloroquine); proleukin (aldesleukin, IL-2); interferon alfa; interferon alfa-2b; interferon alfa-n3; pegylated interferon alfa; interferon gamma; hydroxyurea; mycophenolate mofetil (MPA) and its ester derivative mycophenolate mofetil (MMF); ribavirin; rintatolimod, polymer polyethyleneimine (PEI); gepon; rintatolimod; IL-12; WF-10; VGV-1; MOR-22; BMS-936559; CYT-107, interleukin-15/Fc fusion protein, normferon, peginterferon alfa-2a, peginterferon alfa-2b, recombinant interleukin-15, RPI-MN, GS-9620, and IR-103.

Phosphatidylinositol 3-kinase (PI3K) Inhibitors

Examples of PI3K inhibitors include idelalisib, alpelisib, buparlisib, CAI orotate, copanlisib, duvelisib, gedatolisib, neratinib, panulisib, perifosine, pictilisib, pilaralisib, puquitinib mesylate, rigosertib, rigosertib sodium, sonolisib, taselisib, AMG-319, AZD-8186, BAY-1082439, CLR-1401, CLR-457, CUDC-907, DS-7423, EN-3342, GSK-2126458, GSK-2269577, GSK-2636771, INCB-040093, LY-3023414, MLN-1117, PQR-309, RG-7666, RP-6530, RV-1729, SAR-245409, SAR-260301, SF-1126, TGR-1202, UCB-5857, VS-5584, XL-765, and ZSTK-474.

HIV Antibodies, Bispecific Antibodies, and "Antibody-Like" Therapeutic Proteins

Examples of HIV antibodies, bispecific antibodies, and "antibody-like" therapeutic proteins include DARTs®, DUOBODIES®, BITES®, XmAbs®, TandAbs®, Fab derivatives, bnABs (broadly neutralizing HIV-1 antibodies), BMS-936559, TMB-360, and those targeting HIV gp120 or gp41, antibody-Recruiting Molecules targeting HIV, anti-CD63 monoclonal antibodies, anti-GB virus C antibodies, anti-GP120/CD4, CCR5 bispecific antibodies, anti-nef single domain antibodies, anti-Rev antibody, camelid derived anti-CD18 antibodies, camelid-derived anti-ICAM-1 antibodies, DCVax-001, gp140 targeted antibodies, gp41-based HIV therapeutic antibodies, human recombinant mAbs (PGT-121), ibalizumab, Immuglo, MB-66

Examples of those targeting HIV in such a manner include bavituximab, UB-421, C2F5, C2G12, C4E10, C2F5+C2G12+C4E10, 3-BNC-117, PGT145, PGT121, MDX010 (ipilimumab), VRC01, A32, 7B2, 10E8, VRC-07-523, VRC-HIVMAB080-00-AB, MGD-014 and VRC07.

Pharmacokinetic Enhancers

Examples of pharmacokinetic enhancers include cobicistat and ritonavir.

Additional Therapeutic Agents

Examples of additional therapeutic agents include the compounds disclosed in WO 2004/096286 (Gilead Sciences), WO 2006/015261 (Gilead Sciences), WO 2006/110157 (Gilead Sciences), WO 2012/003497 (Gilead Sciences), WO 2012/003498 (Gilead Sciences), WO 2012/145728 (Gilead Sciences), WO 2013/006738 (Gilead Sciences), WO 2013/159064 (Gilead Sciences), WO 2014/100323 (Gilead Sciences), US 2013/0165489 (University of Pennsylvania), US 2014/0221378 (Japan Tobacco), US 2014/0221380 (Japan Tobacco), WO 2009/062285 (Boehringer Ingelheim), WO 2010/130034 (Boehringer Ingelheim), WO 2013/006792 (Pharma Resources), US 20140221356 (Gilead Sciences), US 20100143301 (Gilead Sciences) and WO 2013/091096 (Boehringer Ingelheim).

HIV Vaccines

Examples of HIV vaccines include peptide vaccines, recombinant subunit protein vaccines, live vector vaccines, DNA vaccines, CD4-derived peptide vaccines, vaccine combinations, rgp120 (AIDSVAX), ALVAC HIV (vCP1521)/AIDSVAX B/E (gp120) (RV144), monomeric gp120 HIV-1 subtype C vaccine, Remune, ITV-1, Contre Vir, Ad5-ENVA-48, DCVax-001 (CDX-2401), Vacc-4x, Vacc-C5, VAC-3S, multiclade DNA recombinant adenovirus-5 (rAd5), Pennvax-G, Pennvax-GP, HIV-TriMix-mRNA vaccine, HIV-LAMP-vax, Ad35, Ad35-GRIN, NAcGM3/VSSP ISA-51, poly-ICLC adjuvanted vaccines, TatImmune, GTU-multi-HIV (FIT-06), gp140[delta]V2.TV1+MF-59, rVSVIN HIV-1 gag vaccine, SeV-Gag vaccine, AT-20, DNK-4, ad35-Grin/ENV, TBC-M4, HIVAX, HIVAX-2, NYVAC-HIV-PT1, NYVAC-HIV-PT4, DNA-HIV-PT123, rAAVI-PG9DP, GOVX-B11, GOVX-B21, TVI-HIV-1, Ad-4 (Ad4-env Clade C+Ad4-mGag), EN41-UGR7C, EN41-FPA2, PreVax-Tat, AE-H, MYM-V101, CombiHIVvac, ADVAX, MYM-V201, MVA-CMDR, DNA-Ad5 gag/pol/nef/nev (HVTN505), MVATG-17401, ETV-01, CDX-1401, rcAD26.MOS1.HIV-Env, Ad26.Mod.HIV vaccine, AGS-004, AVX-101, AVX-201, PEP-6409, SAV-001, ThV-01, TL-01, TUTI-16, VGX-3300, IHV-001, and virus-like particle vaccines such as pseudovirion vaccine, CombiVICHvac, LFn-p24 B/C fusion vaccine, GTU-based DNA vaccine, HIV gag/pol/nef/env DNA vaccine, anti-TAT HIV vaccine, conjugate polypeptides vaccine, dendritic-cell vaccines, gag-based DNA vaccine, GI-2010, gp41 HIV-1 vaccine, HIV vaccine (PIKA adjuvant), I i-key/MHC class II epitope hybrid peptide vaccines, ITV-2, ITV-3, ITV-4, LIPO-5, multiclade Env vaccine, MVA vaccine, Pennvax-GP, pp71-deficient HCMV vector HIV gag vaccine, recombinant peptide vaccine (HIV infection), NCI, rgp160 HIV vaccine, RNActive HIV vaccine, SCB-703, Tat Oyi vaccine, TBC-M4, therapeutic HIV vaccine, UBI HIV gp120, Vacc-4x+romidepsin, variant gp120 polypeptide vaccine, rAd5 gag-pol env A/B/C vaccine.

HIV Combination Therapy

In a particular embodiment, a compound disclosed herein, or a pharmaceutically acceptable salt thereof, is combined with one, two, three, four or more additional therapeutic agents selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); adefovir; adefovir dipivoxil; cobicistat; emtricitabine; tenofovir; tenofovir disoproxil; tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir; raltegravir and lamivudine; maraviroc; enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

It will be appreciated by one of skill in the art that the additional therapeutic agents listed above may be included in more than one of the classes listed above. The particular classes are not intended to limit the functionality of those compounds listed in those classes.

In a specific embodiment, a compound disclosed herein, or a pharmaceutically acceptable salt thereof, is combined with one or two HIV nucleoside or nucleotide inhibitors of reverse transcriptase. In a specific embodiment, a compound disclosed herein, or a pharmaceutically acceptable salt thereof, is combined with an HIV nucleoside or nucleotide inhibitor of reverse transcriptase and an HIV non-nucleoside inhibitor of reverse transcriptase. In another specific embodiment, a compound disclosed herein, or a pharmaceutically acceptable salt thereof, is combined with an HIV nucleoside or nucleotide inhibitor of reverse transcriptase, and an HIV protease inhibiting compound. In an additional embodiment, a compound disclosed herein, or a pharmaceutically acceptable salt thereof, is combined with an HIV nucleoside or nucleotide inhibitor of reverse transcriptase, an HIV non-nucleoside inhibitor of reverse transcriptase, and a pharmacokinetic enhancer. In certain embodiments, a compound disclosed herein, or a pharmaceutically acceptable salt thereof, is combined with at least one HIV nucleoside inhibitor of reverse transcriptase, an integrase inhibitor, and a pharmacokinetic enhancer. In another embodiment, a compound disclosed herein, or a pharmaceutically acceptable salt thereof, is combined with two HIV nucleoside or nucleotide inhibitors of reverse transcriptase. In another embodiment, a compound disclosed herein, or a pharmaceutically acceptable salt thereof, is combined with a non-nucleoside inhibitor of reverse transcriptase. In another embodiment, a compound disclosed herein, or a pharmaceutically acceptable salt thereof, is combined with a non-nucleoside inhibitor of reverse transcriptase and an integrase inhibitor.

In a particular embodiment, a compound disclosed herein, or a pharmaceutically acceptable salt thereof, is combined with abacavir sulfate, tenofovir, tenofovir disoproxil, tenofovir disoproxil fumarate, tenofovir disoproxil hemifumarate, tenofovir alafenamide, tenofovir alafenamide fumarate or tenofovir alafenamide hemifumarate.

In a particular embodiment, a compound disclosed herein, or a pharmaceutically acceptable salt thereof, is combined with tenofovir, tenofovir disoproxil, tenofovir disoproxil fumarate, tenofovir alafenamide, tenofovir alafenamide fumarate or tenofovir alafenamide hemifumarate.

In a particular embodiment, a compound disclosed herein, or a pharmaceutically acceptable salt thereof, is combined with a first additional therapeutic agent selected from the group consisting of abacavir sulfate, tenofovir, tenofovir disoproxil, tenofovir disoproxil fumarate, tenofovir alafenamide, tenofovir alafenamide fumarate and tenofovir alafenamide hemifumarate, and a second additional therapeutic agent selected from the group consisting of emtricitabine and lamivudine.

In a particular embodiment, a compound disclosed herein, or a pharmaceutically acceptable salt thereof, is combined with a first additional therapeutic agent selected from the group consisting of tenofovir, tenofovir disoproxil, tenofovir disoproxil fumarate, tenofovir alafenamide, and tenofovir alafenamide hemifumarate, and a second additional therapeutic agent, wherein the second additional therapeutic agent is emtricitabine. In a particular embodiment, a compound disclosed herein, or a pharmaceutically acceptable salt thereof, is combined with a first additional therapeutic agent selected from the group consisting of tenofovir alafenamide fumarate, tenofovir alafenamide, and tenofovir alafenamide hemifumarate, and a second additional therapeutic agent, wherein the second additional therapeutic agent is emtricitabine. In a particular embodiment, a compound disclosed herein, or a pharmaceutically acceptable salt thereof, is combined with a first additional therapeutic agent selected from the group consisting of tenofovir disoproxil fumarate, tenofovir disoproxil, and tenofovir disoproxil hemifumarate, and a second additional therapeutic agent, wherein the second additional therapeutic agent is emtricitabine. In some embodiments, the compound disclosed herein, or a pharmaceutically acceptable salt thereof, and the first and second additional therapeutic agents as disclosed above are administered simultaneously. Optionally, the compound disclosed herein, or a pharmaceutically acceptable salt thereof, and the first and second additional therapeutic agents as disclosed above are combined in a unitary dosage form for simultaneous administration to a subject. In other embodiments, the compound disclosed herein, or a pharmaceutically acceptable salt thereof, and the first and second additional therapeutic agents as disclosed above are administered sequentially.

A compound as disclosed herein may be combined with one or more additional therapeutic agents in any dosage amount of the compound disclosed herein (e.g., from 1 mg to 1000 mg of compound).

In certain embodiments, a compound disclosed herein, or a pharmaceutically acceptable salt thereof, is combined with 5-30 mg tenofovir alafenamide fumarate, tenofovir alafenamide hemifumarate, or tenofovir alafenamide, and 200 mg emtricitabine. In certain embodiments, a compound disclosed, or a pharmaceutically acceptable salt thereof, is combined with 5-10, 5-15, 5-20, 5-25, 25-30, 20-30, 15-30, or 10-30 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 10 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 25 mg tenofovir alafenamide fumarate, tenofovir alafenamide hemifumarate, or tenofovir alafenamide, and 200 mg emtricitabine. A compound as disclosed herein may be combined with the agents provided herein in any dosage amount of the compound (e.g., from 1 mg to 1000 mg of compound) the same as if each combination of dosages were specifically and individually listed.

In certain embodiments, a compound disclosed herein, or a pharmaceutically acceptable salt thereof, is combined with 200-400 mg tenofovir disoproxil fumarate, tenofovir disoproxil hemifumarate, or tenofovir disoproxil, and 200 mg emtricitabine. In certain embodiments, a compound disclosed herein, or a pharmaceutically acceptable salt thereof, is combined with 300 mg tenofovir disoproxil fumarate, tenofovir disoproxil hemifumarate, or tenofovir disoproxil, and 200 mg emtricitabine. A compound as disclosed herein may be combined with the agents provided herein in any dosage amount of the compound (e.g., from 1 mg to 1000 mg of compound) the same as if each combination of dosages were specifically and individually listed.

In one embodiment, kits comprising a compound disclosed herein, or a pharmaceutically acceptable salt thereof, in combination with one or more (e.g., one, two, three, one or two, or one to three) additional therapeutic agents are provided.

Pharmaceutical Formulations

In some embodiments, compounds described herein are formulated with conventional carriers (e.g., inactive ingredient or excipient material) selected in accord with ordinary practice. In some embodiments, tablets contain excipients, including glidants, fillers, binders and the like. In some embodiments, aqueous formulations are prepared in sterile form. In some embodiments, such aqueous formulations are intended for delivery by other than oral administration and are isotonic. In some embodiments, formulations optionally contain excipients such as those set forth in the *Handbook of Pharmaceutical Excipients* (1986). Excipients include, but are not limited to, ascorbic acid and other antioxidants, chelating agents such as EDTA, carbohydrates such as dextrin, hydroxyalkylcellulose, hydroxyalkylmethylcellulose, stearic acid and the like. In some embodiments, the present invention provides formulations in solid dosage form, for example, in solid oral dosage form.

In some embodiments, formulations may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; or parenteral administration, for example, by subcutaneous, intramuscular, intravenous or epidural injection as, for example, a sterile solution or suspension, or sustained-release formulation.

While it is possible for the active ingredients to be administered alone it may be preferable to present them as pharmaceutical formulations (compositions). The formulations, both for veterinary and for human use, of the invention comprise at least one active ingredient, together with one or more acceptable carriers and optionally other therapeutic ingredients. The carrier(s) must be "acceptable" in the sense of being compatible with the other ingredients of the formulation and physiologically innocuous to the recipient thereof.

Formulations include those suitable for the foregoing administration routes. In some embodiments, formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the inactive ingredients (e.g., a carrier, pharmaceutical excipients, etc.) which constitutes one or more accessory ingredients. In some embodiments, formulations are prepared by uniformly and intimately bringing into association the active ingredient with liquid carriers or finely divided solid carriers or both, and then, if necessary, shaping the product.

In some embodiments, formulations described herein that are suitable for oral administration are presented as discrete units including, but not limited to, capsules, cachets or tablets each containing a predetermined amount of the active ingredient.

In some embodiments, pharmaceutical formulations disclosed herein comprise one or more compounds described herein together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

The amount of active ingredient that is combined with one or more inactive ingredients to produce a dosage form will vary depending upon the host treated and the particular mode of administration. For example, in some embodiments, a dosage form for oral administration to humans contains approximately 1 to 1000 mg of active material formulated with an appropriate amount of carrier material (e.g., inactive ingredient or excipient material). In certain embodiments, the carrier material varies from about 5% to about 95% of the total composition (weight:weight).

It should be understood that, in addition to the ingredients particularly mentioned above, formulations of this invention may include other agents conventional in the art having regard to the type of formulation in question, for example those suitable for oral administration may include flavoring agents.

In some embodiments, the present invention provides veterinary compositions comprising at least one active ingredient as above defined together with a veterinary carrier.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Effective dose of active ingredient depends at least on the nature of the condition being treated, toxicity, whether a compound is being used prophylactically (lower doses), the method of delivery, and the pharmaceutical formulation, and will be determined by the clinician using conventional dose escalation studies.

Routes of Administration

One or more compounds described herein (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that a preferred route may vary with, for example, the condition of the recipient. An advantage of the compounds of this invention is that they are orally bioavailable and can be dosed orally.

Identification and/or Characterization of Compounds/Compositions

The antiviral properties of a compound of the invention may be determined using the methods described below.

The specific pharmacological responses observed may vary according to and depending on the particular active compound selected or whether there are present pharmaceutical carriers, as well as the type of formulation and mode of administration employed, and such expected variations or differences in the results are contemplated in accordance with practice of the present invention.

The invention has been described with reference to various specific and preferred embodiments and techniques. However, it should be understood that many variations and modifications may be made while remaining within the spirit and scope of the invention.

The invention will now be illustrated by the following non-limiting examples of compounds (including compounds of the invention) and intermediates useful for preparing compounds of the invention.

EXEMPLIFICATION

Example 1. Preparation of ethyl (S)-2-(2-bromo-7-(4-chlorophenyl)-5-methylbenzo[d]thiazol-6-yl)-2-(tert-butoxy)acetate

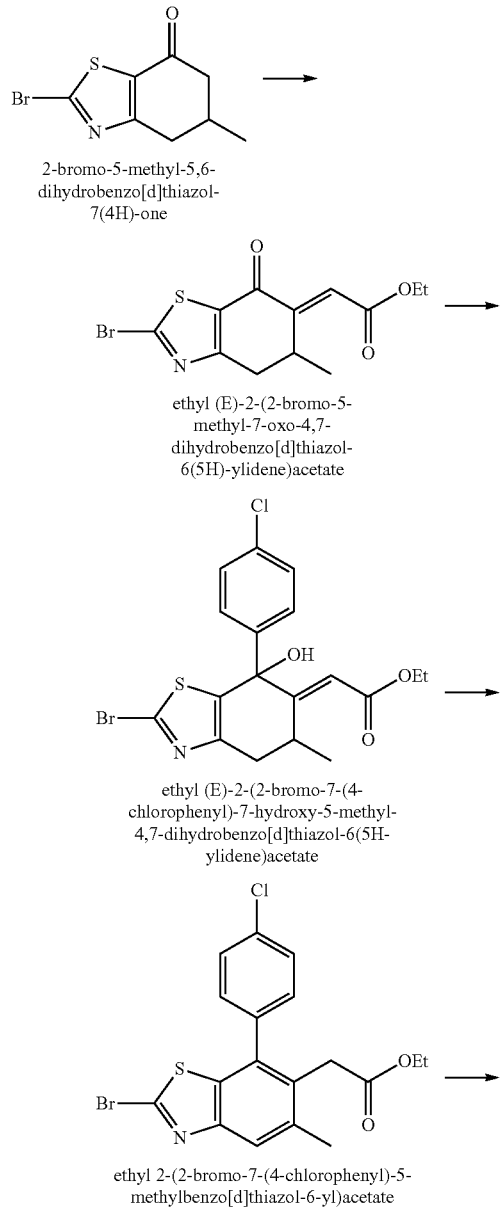

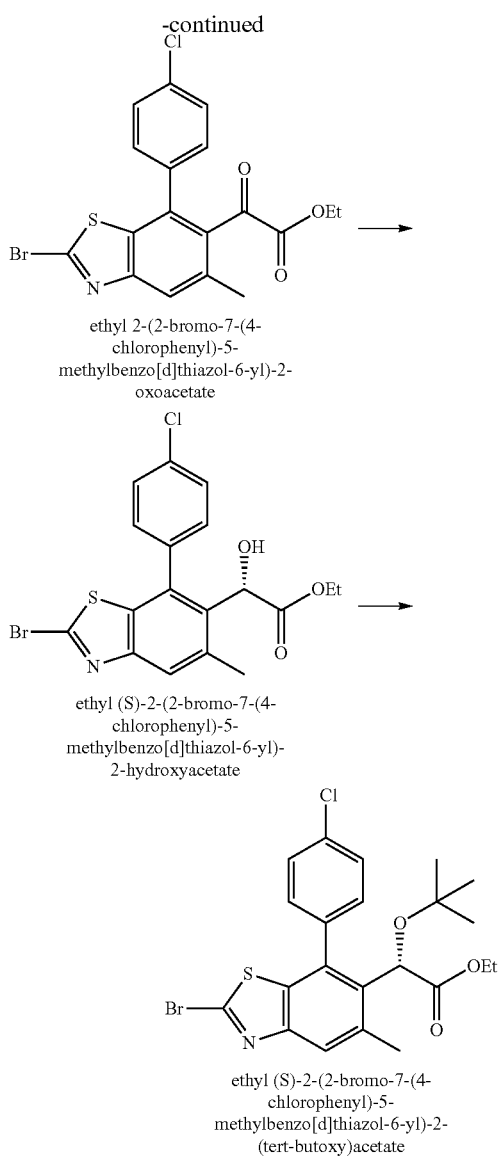

Preparation of ethyl (E)-2-(2-bromo-5-methyl-7-oxo-4,7-dihydrobenzo[d]thiazol-6(5H)-ylidene)acetate: A 3.0 L round-bottom flask was charged with 2-bromo-5-methyl-5,6-dihydrobenzo[d]thiazol-7(4H)-one (75.0 g, 305 mmol, 1.00 equiv), anhydrous THF (750 mL), and a 50% w/v solution of ethylglyoxylate in toluene (211 mL, 1.07 mol, 3.50 equiv). The resulting solution was placed in a water bath. Solid lithium tert-butoxide (48.9 g, 610 mmol, 2.0 equiv) was steadily added over a 1 min period. The reaction was capped and stirred for 4.5 h. TLC (20% EtOAc/80% hexane indicated full consumption of 2-bromo-5-methyl-5,6-dihydrobenzo[d]thiazol-7(4H)-one). Saturated aqueous NH₄Cl (750 mL) was added quickly. The reaction was stirred for 15 min. H₂O (250 mL) was added. Most of the solids dissolved. 1.0 M aqueous HCl (180 mL) was added over a 5 min period. After a short time the pH of the aqueous layer was ~3.5. The organic phase was collected, and the aqueous layer was extracted with EtOAc (2×375 mL). Combined organic layers were washed with brine (500 mL), dried (MgSO₄), filtered, and concentrated to a minimum volume with a bath temperature of 50-60° C. and 10 mmHg vacuum. DCM (40 mL) was added. The resulting solution was transferred to a Combiflash XL solid loading cartridge by gravity loading. The solid cartridge was assembled in line with a 1.5 kg Combiflash XL silica gel column equilibrated with hexane. The following gradient elution sequence was used: [100% Hexane (5 column volumes, isocratic)→10% EtOAc/90% Hexane (10 column volumes, linear gradient) →10% EtOAc/90% Hexane (7 column volumes, isocratic)) →100% EtOAc (8 column volumes, isocratic)]. Fractions containing product were combined, concentrated, and dried under high vacuum to give desired product. LCMS-ESI+ calc'd for $C_{12}H_{12}BrNO_3S$: 330.0 and 332.0 (M+H+); found: 330.0 and 332.0 (M+H+). $^1$H NMR (400 MHz, CDCl$_3$): δ 6.77 (s, 1H), 4.60-4.53 (m, 1H), 4.30-4.21 (m, 2H), 3.23 (dd, J=17.6, 5.8 Hz, 1H), 3.07 (d, J=5.8 Hz, 1H), 1.33 (t, J=7.2 Hz, 3H), 1.23 (d, J=7.0 Hz, 3H).

Preparation of ethyl (E)-2-(2-bromo-7-(4-chlorophenyl)-7-hydroxy-5-methyl-4,7-dihydrobenzo[d]thiazol-6(5H)-ylidene)acetate: A 3-liter flask equipped with a mechanical stirrer, addition funnel, and nitrogen inlet was charged with ethyl (E)-2-(2-bromo-5-methyl-7-oxo-4,7-dihydrobenzo[d]thiazol-6(5H)-ylidene)acetate (24.1 g, 73 mmol, 1.0 equiv) and then diluted with THF (800 mL). To the resulting solution was added 0.6M LaCl$_3$.2LiCl (243 mL, 146 mmol, 2.0 equiv) and then the reaction mixture was cooled to −65° C. by the aid of a dry-ice acetone bath. The addition funnel was then charged with 1.0M 4-chlorophenylmagnesium bromide (146 mL, 146 mmol, 2.0 equiv) and then slowly added to the reaction mixture over a 25 minute period. Upon completion of the addition, TLC analysis showed full consumption of the starting material (TLC of the starting material in 20% EtOAc/Hex has Rf=0.50; TLC of the product in 20% EtOAc/Hex has Rf=0.38), and the reaction was quenched with saturated NH$_4$Cl (100 mL) and then diluted with EtOAc (1 L) and H$_2$O (1.5 L). The cooling bath was removed and the mixture was allowed to warm to room temperature with stirring. The layers were separated and the aqueous extract was washed with EtOAc (1 L). The combined organics were dried over Na$_2$SO$_4$, filtered through a small plug of silica gel eluting with EtOAc, and then concentrated in vacuo. The resulting crude residue was chromatographed using a 330 g RediSep normal phase silica gel cartridge (EtOAc/Hex, 5%→15%) on a CombiFlash system to afford desired product. TLC (20% EtOAc/Hex) Rf=0.38; $^1$H NMR (400 MHz, CDCl3) δ 7.31 (d, J=8.6 Hz, 2H), 7.26 (d, J=8.6 Hz, 2H), 5.62 (s, 1H), 4.57-4.40 (m, 1H) 4.22-4.04 (m, 2H), 3.03 (qd, J=16.6, 3.8 Hz, 2H), 2.61 (br s, 1H), 1.38 (d, J=7.2 Hz, 3H), 1.25 (t, J=7.1 Hz, 3H).

Preparation of ethyl 2-(2-bromo-7-(4-chlorophenyl)-5-methylbenzo[d]thiazol-6-yl)acetate: Polyphosphoric acid (PPA) (140 g) and THF (210 mL) were heated to 75° C. in a 1 L recovery flask. Ethyl (E)-2-(2-bromo-7-(4-chlorophenyl)-7-hydroxy-5-methyl-4,7-dihydrobenzo[d]thiazol-6 (5H)-ylidene)acetate (31.0 g, 70.0 mmol) was added via addition funnel in THF (70 mL) over 2 min. The funnel was rinsed with THF (20 mL). The reaction mixture was heated at 80° C. for 2.5 h. After cooling to rt, the mixture was poured onto a 1 M K$_2$HPO$_4$ (1.5 L) solution followed by EtOAc (700 mL). The layers were separated, and the organic layer was washed with brine (500 mL). The organic layer was dried, filtered, and concentrated in vacuo to give desired product that was used without further purification. $^1$H NMR (400 MHz, CDCl$_3$): δ 7.81 (s, 1H), 7.45 (d, 2H, J=8 Hz), 7.29 (d, 2H, J=8 Hz), 4.13 (q, 2H, J=7 Hz), 3.57 (s, 2H), 2.45 (s, 3H), 1.23 (t, 3H, J=7 Hz).

Preparation of ethyl 2-(2-bromo-7-(4-chlorophenyl)-5-methylbenzo[d]thiazol-6-yl)-2-oxoacetate: To a solution of the ethyl 2-(2-bromo-7-(4-chlorophenyl)-5-methylbenzo[d] thiazol-6-yl)acetate (15.4 g, 36.4 mmol) in THF (146 mL) at −78° C. was added a solution of KHMDS (1 M in THF, 43.6 mmol, 43.6 mL) over 5 min. After 30 min, a solution of 3-phenyl-2-(phenylsulfonyl)-1,2-oxaziridine (11.4 g, 43.6 mmol) in THF (29 mL) was added. After 1 h, a saturated solution of NH$_4$Cl was added (200 mL). The reaction mixture was warmed to rt. The layers were separated, and the aqueous layer was extracted with EtOAc. The combined organic layers were dried, filtered, and concentrated in vacuo and were used without further purification.

To the above residue was added CH$_2$Cl$_2$ (240 mL) followed by Dess-Martin periodinane (16.9 g, 40.0 mmol). After 2 h, a saturated solution of Na$_2$S$_2$O$_3$ (150 mL) and a saturated solution of NaHCO$_3$ (150 mL) and water (100 mL) were added. The mixture was stirred at room temperature for 2 h. The layers were separated, and the aqueous layer was extracted with CH$_2$Cl$_2$. The combined organic layers were dried, filtered, and concentrated in vacuo. A mixture of hexanes/EtOAc (9:1) was added. The mixture was filtered, the solids were washed with additional hex/EtOAc (9:1), and the filtrate was concentrated. The crude oil was purified by column chromatography (5%-10% EtOAc/hex) to give desired product. $^1$H NMR (400 MHz, CDCl$_3$): δ 7.88 (s, 1H), 7.45 (d, 2H, J=8 Hz), 7.28 (d, 2H, J=8 Hz), 3.91 (q, 2H, J=7 Hz), 2.52 (s, 3H), 1.08 (t, 3H, J=7 Hz).

Preparation of ethyl (S)-2-(2-bromo-7-(4-chlorophenyl)-5-methylbenzo[d]thiazol-6-yl)-2-hydroxyacetate: Catalyst Preparation: A 25 mL flask was charged with dichloro (pentamethylcyclopentadienyl)rhodium(III) dimer (94 mg, 0.15 mmol, 1.0 equiv) and the ligand N-((1S,2S)-2-amino-1,2-diphenylethyl)-4-nitrobenzenesulfonamide (153 mg, 0.39 mmol, 2.6 equiv) and sealed with a rubber septum. The flask was purged with argon and then ACN (1.5 mL) and NEt$_3$ (0.15 mL) were added to the flask and an additional septum was fitted. The resulting red solution was stirred at room temperature under argon for a minimum of 45 minutes, but not more than 6 hours, which resulted in a heterogeneous orange suspension.

A 100 mL flask was charged with ethyl 2-(2-bromo-7-(4-chlorophenyl)-5-methylbenzo[d]thiazol-6-yl)-2-oxoacetate (2.4 g, 5.5 mmol, 1.0 equiv) and sealed with a rubber septum. The flask was purged with argon and to this was charged ACN (11 mL) and NEt$_3$ (1.9 mL, 13.6 mmol, 2.5 equiv) and stirring was initiated. The solution was cooled to 0° C. and then HCO$_2$H (0.63 mL, 16.7 mmol, 3.0 equiv) was added to the solution at a rate to maintain an internal temperature not more than 20° C. Upon completion of the addition, the solution was allowed to cool back to 0° C. Argon was then bubbled through the solution using a porous gas dispersion unit. To the stirring solution at 0° C. was charged the prepared catalyst solution (0.5 mL, 0.05 equiv) from the catalyst preparation above. The solution was stirred at 0° C. with the bubbling of argon through the solution until TLC indicated complete consumption of starting material (10-18 h). The reaction was quenched with H$_2$O then diluted with EtOAc and allowed to warm to room temperature. The layers were separated and the organic extract was washed once more with H$_2$O. The organic extract was then dried over Na$_2$SO$_4$, filtered through a small pad of silica gel eluting with EtOAc, and concentrated in vacuo. The resulting crude residue was chromatographed using a 80 g RediSep normal phase silica gel cartridge (EtOAc/Hex, 5%→20%) on a CombiFlash system to give the desired product. TLC (20% EtOAc/Hex) Rf=0.27; $^1$H NMR (400 MHz, CDCl$_3$) δ 7.79 (s, 1H), 7.53-7.43 (m, 2H), 7.37 (m, 2H), 5.23 (d, J=2.2 Hz, 1H), 4.19 (m, 2H), 3.29 (d, J=2.2 Hz, 1H), 2.48 (d, J=0.5 Hz, 3H), 1.21 (t, J=7.1 Hz, 3H).

Alternative preparation of ethyl (S)-2-(2-bromo-7-(4-chlorophenyl)-5-methylbenzo[d]thiazol-6-yl)-2-hydroxyacetate: A solution of ethyl 2-(2-bromo-7-(4-chlorophenyl)-5-methylbenzo[d]thiazol-6-yl)-2-oxoacetate (10.60 g, 25.0 mmol) in PhMe (100 mL) was cooled to −30° C. (R)-Me-CBS catalyst (1.39 g, 5.00 mmol) was added, followed immediately by distilled catecholborane (4.00 mL, 37.5 mmol). At 1.2 h, additional (R)-Me-CBS catalyst (1.39 g, 5.00 mmol) was added. After another 1 h had passed, additional (R)-Me-CBS catalyst (700 mg, 2.50 mmol) was added. After 30 min, the reaction was quenched with EtOAc (30 mL). Saturated aqueous NaHCO$_3$ (50 mL) was added, and the reaction was warmed to 23° C. and stirred for an additional 30 min. The organic phase was collected, washed with saturated aqueous NaHCO$_3$ (1×), dried (MgSO$_4$), filtered, and concentrated. Benzene was added and the resulting solution was purified by silica gel column, eluting by 0-100% EtOAc in hexanes to give the product. LCMS-ESI$^+$: calc'd for C$_{18}$H$_{15}$BrClNO$_3$S: 440.0, 442.0, 440.0 (M+H$^+$); Found: 440.2, 442.1, 444.1 (M+H$^+$). $^1$H NMR (400 MHz, CDCl$_3$) δ: 7.80 (s, 1H), 7.54-7.43 (m, 2H), 7.42-7.32 (m, 2H), 5.23 (s, 1H), 4.31-4.12 (m, 2H), 2.47 (s, 3H), 1.23 (t, J=7.1 Hz, 3H).

Preparation of ethyl (S)-2-(2-bromo-7-(4-chlorophenyl)-5-methylbenzo[d]thiazol-6-yl)-2-(tert-butoxy)acetate: A suspension of ethyl (S)-2-(2-bromo-7-(4-chlorophenyl)-5-methylbenzo[d]thiazol-6-yl)-2-hydroxyacetate (7.20 g, 16.9 mmol) in tert-butyl acetate (100 mL) was cooled to 0° C. in an ice bath. 70% w/v aqueous HClO$_4$ (293 μL, 3.4 mmol) was added dropwise over 5 min. The reaction was warmed to 23° C., then stirred for 2.3 h. At this point the reaction was transferred to an addition funnel. The reaction was added to a 23° C. solution of sat aqueous NaHCO$_3$ (400 mL) over 30 min. Once addition was complete, the reaction was stirred for another 15 min. The resulting system was extracted with EtOAc (2×150 mL). Combined organic layers were dried (Na$_2$SO$_4$), filtered, and concentrated in vacuo. Some residual tert-butyl acetate remained. Hexane (200 mL) was added and the slurry was concentrated once more. The resulting residue (reasonably free of tert-butyl acetate) was treated with benzene and loaded onto a 330 g "gold" ISCO silica gel column. The following gradient elution sequence was used: [100% Hexane (5 column volumes, isocratic) →10% EtOAc/90% Hexane (5 column volumes, linear gradient→10% EtOAc/90% Hexane (5 column volumes) →100% EtOAc (10 column volumes)]. Product-containing fractions were pooled, concentrated, co-evarported with Et$_2$O (100 mL) to give desired product. LCMS-ESI+ calc'd for C$_{22}$H$_{23}$BrClNO$_3$S: 496.0, 498.0 and 500.0 (M+H+); found: 496.2, 498.2, and 500.1 (M+H+). $^1$H NMR (400 MHz, CDCl$_3$): δ 7.77 (s, 1H), 7.48 (m, 3H), 7.37 (m, 1H), 5.12 (s, 1H), 4.20 (m, 2H), 2.57 (s, 3H), 1.24 (t, 3H, J=7 Hz), 0.96 (s, 9H).

Example 2. Preparation of ethyl (S)-2-(2-bromo-7-(4-chlorophenyl)-5-methylbenzo[d]thiazol-6-yl)-2-cyclopropoxyacetate

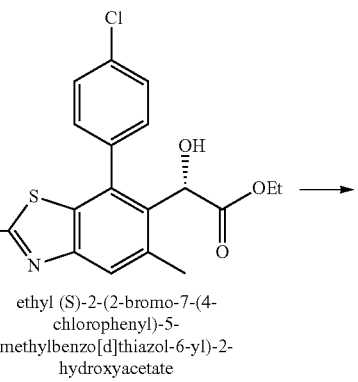

ethyl (S)-2-(2-bromo-7-(4-chlorophenyl)-5-methylbenzo[d]thiazol-6-yl)-2-hydroxyacetate

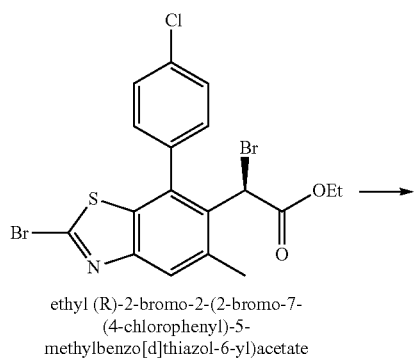

ethyl (R)-2-bromo-2-(2-bromo-7-(4-chlorophenyl)-5-methylbenzo[d]thiazol-6-yl)acetate

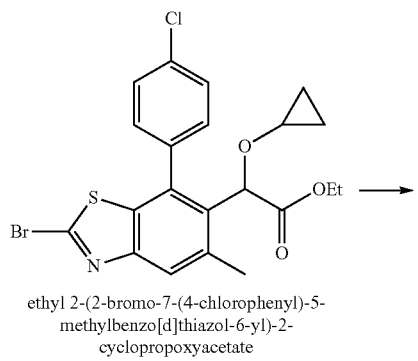

ethyl 2-(2-bromo-7-(4-chlorophenyl)-5-methylbenzo[d]thiazol-6-yl)-2-cyclopropoxyacetate

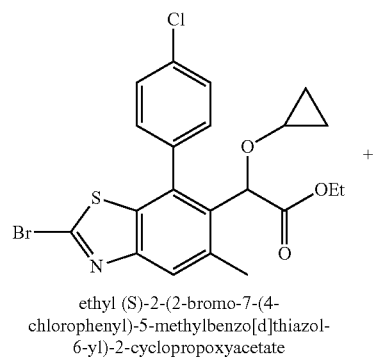

ethyl (S)-2-(2-bromo-7-(4-chlorophenyl)-5-methylbenzo[d]thiazol-6-yl)-2-cyclopropoxyacetate -continued

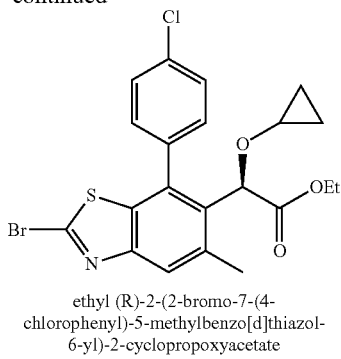

ethyl (R)-2-(2-bromo-7-(4-chlorophenyl)-5-methylbenzo[d]thiazol-6-yl)-2-cyclopropoxyacetate Preparation of ethyl (R)-2-bromo-2-(2-bromo-7-(4-chlorophenyl)-5-methylbenzo[d]thiazol-6-yl)acetate: Two reactions were run in parallel: To a solution of ethyl (S)-2-(2-bromo-7-(4-chlorophenyl)-5-methylbenzo[d]thiazol-6-yl)-2-hydroxyacetate (23 g, 52.2 mmol, 1.0 eq) in DCM (350 mL) was added a mixture solution of 1H-benzotriazole (6.84 g, 57.4 mmol, 1.1 eq) and SOBr$_2$ (11.9 g, 57.4 mmol, 1.1 eq) in DCM (50 mL) at 15° C. The reaction was stirred for 2 hrs at 15° C. TLC (Petroleum ether/Ethyl acetate=5/1, Rf=0.5) showed ethyl (S)-2-(2-bromo-7-(4-chlorophenyl)-5-methylbenzo[d]thiazol-6-yl)-2-hydroxyacetate was consumed completely, four new spots. Two reactions were combined for workup. The reaction mixture was filtered, concentrated in vacuo to remove DCM. The crude product was purified by silica gel chromatography eluted with Petroleum ether: Ethyl acetate (20:1) to give ethyl (R)-2-bromo-2-(2-bromo-7-(4-chlorophenyl)-5-methylbenzo[d]thiazol-6-yl)acetate. LCMS-ESI$^+$: calc'd for $C_{18}H_{15}Br_2ClNO_2S$: 501.9 (M+H)$^+$; found: 502.0 (M+H)$^+$.

Preparation of ethyl 2-(2-bromo-7-(4-chlorophenyl)-5-methylbenzo[d]thiazol-6-yl)-2-cyclopropoxyacetate: Two reactions were carried out in parallel. A mixture of ethyl (R)-2-bromo-2-(2-bromo-7-(4-chlorophenyl)-5-methylbenzo[d]thiazol-6-yl)acetate (20 g, 39.7 mmol, 1 eq) and cyclopropanol (6.9 g, 119 mmol, 3 eq) in DCE (300 ml, freshly distilled from P$_2$O$_5$) was stirred with 4 Å molecular sieves (15 g) for 0.5 hr at 15° C. To a suspension of AgOTf (30.6 g, 119 mmol, 3 eq) in DCE (300 ml, freshly distilled from P$_2$O$_5$) was added 4 Å molecular sieves (15 g). The mixture was stirred at 15° C. for 0.5 hr in dark. The two mixtures were mixed together and stirred at 80° C. in dark for 1.5 hrs. LC-MS showed the reaction was complete. Two reactions were combined for workup. The reaction mixture was filtered, concentrated in vacuo. The residue was purified by silica gel chromatography eluted with Petroleum ether: Ethyl acetate (20:1) to give pure product. To the solid was added Petroleum ether (70 mL). The mixture was stirred at 15° C. for 0.5 hr. The mixture was filtered. The solid was dried in vacuo to afford ethyl 2-(2-bromo-7-(4-chlorophenyl)-5-methylbenzo[d]thiazol-6-yl)-2-cyclopropoxyacetate. LCMS-ESI: calc'd for $C_{21}H_{20}BrClNO_3S$: 480.0 (M+H)$^+$; found: 480.0 (M+H)$^+$.

Individual enantiomers were separated using chiral SFC (OJ (250 mm*30 mm, 5 um); Neu-MeOH) to give ethyl (S)-2-(2-bromo-7-(4-chlorophenyl)-5-methylbenzo[d]thiazol-6-yl)-2-cyclopropoxyacetate (peak 1, $[\alpha]_D^{20}$ -103.59° (c 1.0, CHCl$_3$)) and ethyl (R)-2-(2-bromo-7-(4-chlorophenyl)-5-methylbenzo[d]thiazol-6-yl)-2-cyclopropoxyacetate (peak 2, $[\alpha]_D^{20}$ +98.220 (c 1.0, CHCl$_3$)).

Example 3. Preparation of ethyl (S)-2-(2-(3-bromo-1-methyl-1H-indazol-5-yl)-7-(4-chlorophenyl)-5-methylbenzo[d]thiazol-6-yl)-2-(tert-butoxy)acetate

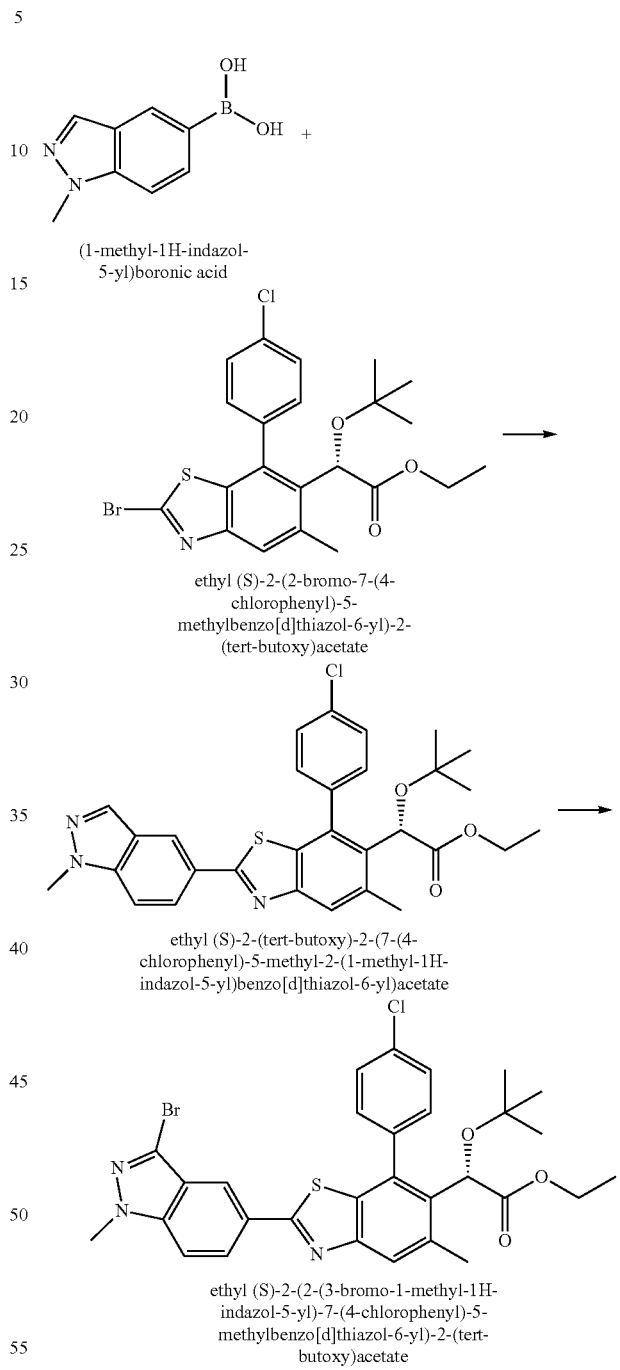

Preparation of ethyl (S)-2-(tert-butoxy)-2-(7-(4-chlorophenyl)-5-methyl-2-(1-methyl-1H-indazol-5-yl)benzo[d]thiazol-6-yl)acetate: A flask containing ethyl (S)-2-(2-bromo-7-(4-chlorophenyl)-5-methylbenzo[d]thiazol-6-yl)-2-(tert-butoxy)acetate (2503 mg, 5.038 mmol), (1-methyl-1H-indazol-5-yl)boronic acid (1773 mg, 10.09 mmol), potassium carbonate (2087 mg, 15.1 mmol), and tetrakis(triphenylphosphine)palladium(0) (585 mg, 0.506 mmol) was purged with Argon gas for 5 min and then added water (6 mL) and dioxane (24 mL). After additional ~1 min purging with Argon gas, the flask was kept tightly with septum and heated at 95° C. bath for 1.25 h. After the mixture was filtered through celite and washed with dioxane, the filtrate and washing were concentrated to dryness. After the residue was stirred with dichloromethane (~200 mL), the solution was dried (MgSO$_4$) and concentrated. The residue was purified by CombiFlash (120 g, Gold, 0-40% EtOAc/Hex) to obtain the title product. LCMS-ESI$^+$: calc'd for $C_{30}H_{31}ClN_3O_3S$: 548.18 (M+H)$^+$; found: 548.29 (M+H)$^+$.

Preparation of ethyl (S)-2-(2-(3-bromo-1-methyl-1H-indazol-5-yl)-7-(4-chlorophenyl)-5-methylbenzo[d]thiazol-6-yl)-2-(tert-butoxy)acetate: A solution of ethyl (S)-2-(tert-butoxy)-2-(7-(4-chlorophenyl)-5-methyl-2-(1-methyl-1H-indazol-5-yl)benzo[d]thiazol-6-yl)acetate (2357 mg, 4.3 mmol) in acetonitrile (22 mL) was stirred at 0° C. as N-bromosucciimide (843 mg, 4.73 mmol) was added. After 5 min, the mixture was stirred at rt. After 17 h, the reaction mixture was diluted with dichloromethane (150 mL) and washed with saturated aqueous NaHCO$_3$ (200 mL×1) and water (200 mL×1). After the aqueous layers were extracted with dichloromethane (100 mL×1), the two organic layers were combined, dried (MgSO$_4$), and concentrated to dryness. The residue was purified by Combiflash (120 g, Gold, 0-35% EtOAc/Hex) to obtain the title product. LCMS-ESI: calc'd for $C_{30}H_{30}BrCl\ N_3O_3S$: 626.09 (M+H)$^+$; found: 626.25 (M+H)$^+$.

Method A

Example 4. Preparation of (S)-2-(tert-butoxy)-2-(7-(4-chlorophenyl)-5-methyl-2-(1-methyl-3-(1-(oxetan-3-yl)piperidin-4-yl)-1H-indazol-5-yl)benzo[d]thiazol-6-yl)acetic Acid (1)

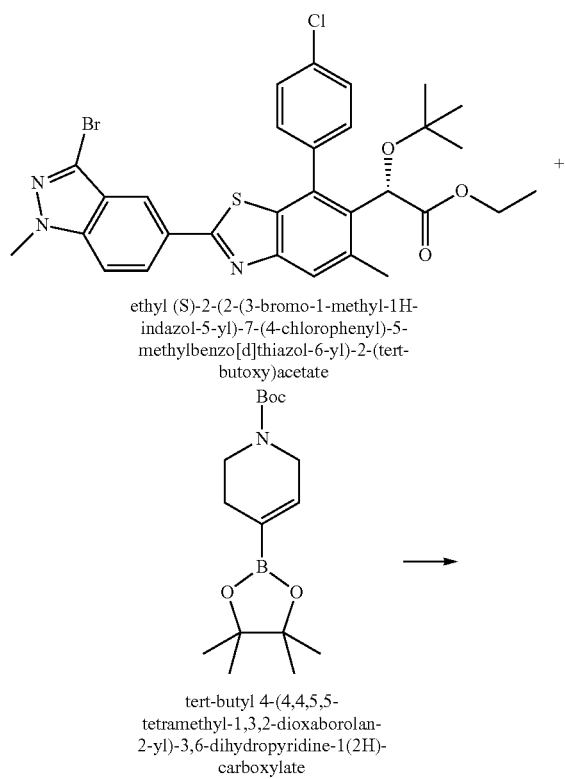

ethyl (S)-2-(2-(3-bromo-1-methyl-1H-indazol-5-yl)-7-(4-chlorophenyl)-5-methylbenzo[d]thiazol-6-yl)-2-(tert-butoxy)acetate tert-butyl 4-(4,4,5,5-tetramethyl-1,3,2-dioxaborolan-2-yl)-3,6-dihydropyridine-1(2H)-carboxylate

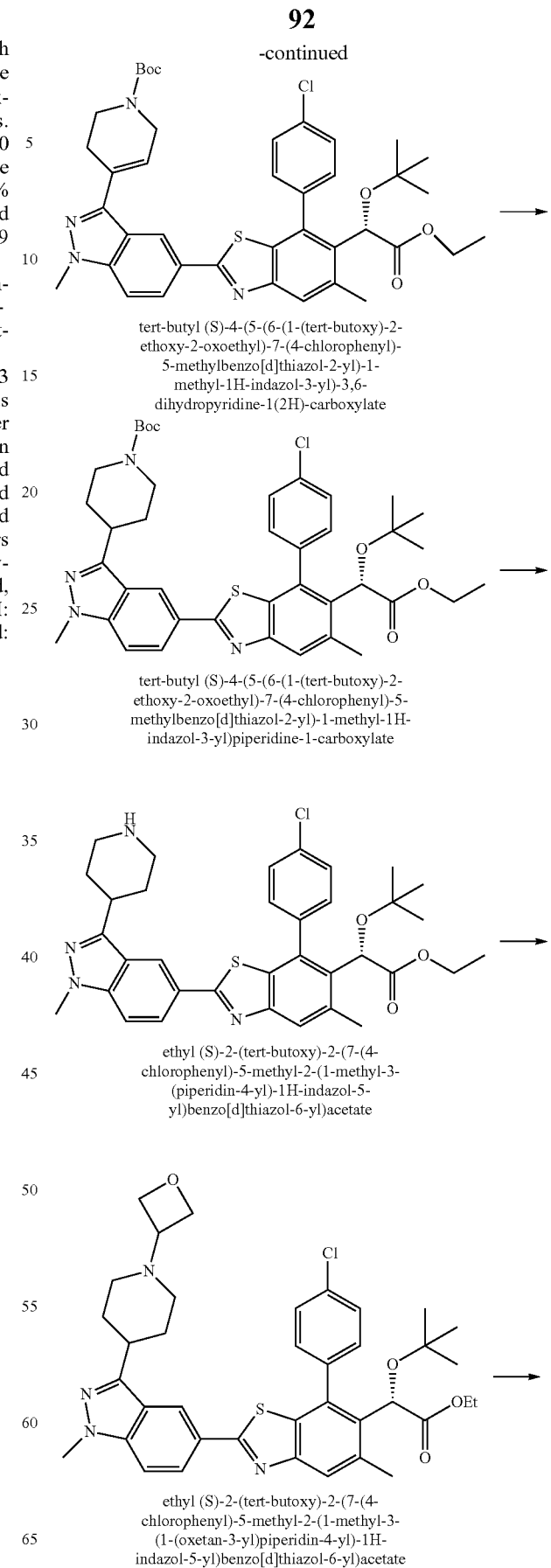

tert-butyl (S)-4-(5-(6-(1-(tert-butoxy)-2-ethoxy-2-oxoethyl)-7-(4-chlorophenyl)-5-methylbenzo[d]thiazol-2-yl)-1-methyl-1H-indazol-3-yl)-3,6-dihydropyridine-1(2H)-carboxylate tert-butyl (S)-4-(5-(6-(1-(tert-butoxy)-2-ethoxy-2-oxoethyl)-7-(4-chlorophenyl)-5-methylbenzo[d]thiazol-2-yl)-1-methyl-1H-indazol-3-yl)piperidine-1-carboxylate ethyl (S)-2-(tert-butoxy)-2-(7-(4-chlorophenyl)-5-methyl-2-(1-methyl-3-(piperidin-4-yl)-1H-indazol-5-yl)benzo[d]thiazol-6-yl)acetate ethyl (S)-2-(tert-butoxy)-2-(7-(4-chlorophenyl)-5-methyl-2-(1-methyl-3-(1-(oxetan-3-yl)piperidin-4-yl)-1H-indazol-5-yl)benzo[d]thiazol-6-yl)acetate

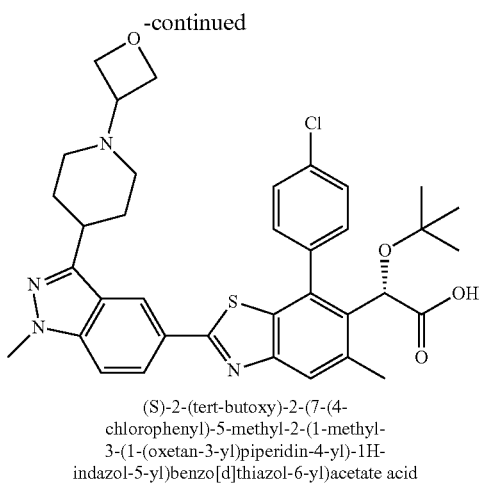

(S)-2-(tert-butoxy)-2-(7-(4-chlorophenyl)-5-methyl-2-(1-methyl-3-(1-(oxetan-3-yl)piperidin-4-yl)-1H-indazol-5-yl)benzo[d]thiazol-6-yl)acetate acid Preparation of tert-butyl (S)-4-(5-(6-(1-(tert-butoxy)-2-ethoxy-2-oxoethyl)-7-(4-chlorophenyl)-5-methylbenzo[d]thiazol-2-yl)-1-methyl-1H-indazol-3-yl)-3,6-dihydropyridine-1(2H)-carboxylate: To a microwave vial containing ethyl (S)-2-(2-(3-bromo-1-methyl-1H-indazol-5-yl)-7-(4-chlorophenyl)-5-methylbenzo[d]thiazol-6-yl)-2-(tert-butoxy)acetate (250 mg, 0.40 mmol), tert-butyl 4-(4,4,5,5-tetramethyl-1,3,2-dioxaborolan-2-yl)-3,6-dihydropyridine-1(2H)-carboxylate (185 mg, 0.60 mmol), potassium carbonate (165.3 mg, 1.2 mmol), and tetrakis(triphenylphosphine)palladium(0) (46 mg, 0.04 mmol) was added water (1 mL) and dioxane (4 mL). It was purged with Argon gas for 10 min. The mixture was capped and microwaved at 110° C. bath for 2 h. After the reaction was completed and cooled to room temperature, the mixture was filtered through celite and washed with ethyl acetate. The filtrate was washed with brine. The organic phase was dried (MgSO$_4$) and concentrated. The residue was purified by CombiFlash (40 g, Gold, 0-50% EtOAc/Hex) to give the desired product. LCMS-ESI+: calc'd for: $C_{40}H_{46}ClN_4O_5S$; 729.3 (M+H)$^+$; found: 729.1 (M+H)$^+$.

Preparation of tert-butyl (S)-4-(5-(6-(1-(tert-butoxy)-2-ethoxy-2-oxoethyl)-7-(4-chlorophenyl)-5-methylbenzo[d]thiazol-2-yl)-1-methyl-1H-indazol-3-yl)piperidine-1-carboxylate: A mixture of tert-butyl (S)-4-(5-(6-(1-(tert-butoxy)-2-ethoxy-2-oxoethyl)-7-(4-chlorophenyl)-5-methylbenzo[d]thiazol-2-yl)-1-methyl-1H-indazol-3-yl)-3,6-dihydropyridine-1(2H)-carboxylate (263 mg, 0.361 mmol), rhodium on alumina, 5 wt % (111 mg, 0.054 mmol) in ethanol (40 mL) was evacuated and back-filled with hydrogen (3×). Reaction mixture was stirred overnight, filtered through a pad of Celite and concentrated to give desired product as colorless oil. LCMS-ESI+: calc'd for $C_{40}H_{48}ClN_4O_5S$; 731.3 (M+H)$^+$; found: 731.1 (M+H)$^+$.

Preparation of ethyl (S)-2-(tert-butoxy)-2-(7-(4-chlorophenyl)-5-methyl-2-(1-methyl-3-(piperidin-4-yl)-1H-indazol-5-yl)benzo[d]thiazol-6-yl)acetate: A solution of tert-butyl (S)-4-(5-(6-(1-(tert-butoxy)-2-ethoxy-2-oxoethyl)-7-(4-chlorophenyl)-5-methylbenzo[d]thiazol-2-yl)-1-methyl-1H-indazol-3-yl)piperidine-1-carboxylate (214 mg, 0.293 mmol) in 1.25 HCl in isopropanol (5.0 mL) was stirred overnight at room temperature. Reaction mixture was quenched with saturated sodium bicarbonate solution carefully and extracted with ethyl acetate (2×). Combined organic layer was dried (MgSO$_4$), filtered and concentrated to give crude desired product that was used in the next step without further purification. LCMS-ESI+: calc'd for $C_{35}H_{40}ClN_4O_3S$; 631.2 (M+H)$^+$; found: 631.3 (M+H)$^+$.

Preparation of ethyl (S)-2-(tert-butoxy)-2-(7-(4-chlorophenyl)-5-methyl-2-(1-methyl-3-(1-(oxetan-3-yl)piperidin-4-yl)-1H-indazol-5-yl)benzo[d]thiazol-6-yl)acetate: A solution of (S)-2-(tert-butoxy)-2-(7-(4-chlorophenyl)-5-methyl-2-(1-methyl-3-(piperidin-4-yl)-1H-indazol-5-yl)benzo[d]thiazol-6-yl)acetate (36 mg, 0.057 mmol), 3-oxetanone (41 mg, 0.57 mmol), acetic acid (2 drops) and sodium cyanoborohydride (35.8 mg, 0.57 mmol) in methanol (1 mL) was stirred for 18 hours at room temperature. LCMS showed complete conversion. Reaction mixture was carried to the next step directly. LCMS-ESI+: calc'd for $C_{38}H_{44}ClN_4O_4S$: 687.3 (M+H)$^+$; found: 687.4 (M+H)$^+$.

Preparation of (S)-2-(tert-butoxy)-2-(7-(4-chlorophenyl)-5-methyl-2-(1-methyl-3-(1-(oxetan-3-yl)piperidin-4-yl)-1H-indazol-5-yl)benzo[d]thiazol-6-yl)acetic acid: To above reaction mixture of ethyl (S)-2-(tert-butoxy)-2-(7-(4-chlorophenyl)-5-methyl-2-(1-methyl-3-(1-(oxetan-3-yl)piperidin-4-yl)-1H-indazol-5-yl)benzo[d]thiazol-6-yl)acetate (0.057 mmol) was added THF (1 mL), MeOH (1 mL) and 50% Sodium hydroxide (1 mL) at rt. The mixture was stirred at 60° C. for 1.5 h. The reaction mixture was cooled by ice and acidified with 3 N HCl. The resulting mixture was extracted with ethyl acetate (2×). Combined organic layer was dried (MgSO$_4$), filtered and concentrated to give crude mixture which was purified by Gilson HPLC (Phenomenex Gemini 250×21.2 10μ C18 column, 40-100% ACN/H$_2$O+0.1% TFA) to give a yellow powder after lyophilization. $^1$H NMR (400 MHz, Chloroform-d) δ 8.30 (s, 1H), 7.96 (d, J=8.5 Hz, 1H), 7.81 (s, 1H), 7.69 (d, J=8.0 Hz, 1H), 7.54-7.40 (m, 3H), 7.35 (d, J=8.9 Hz, 1H), 5.21 (s, 1H), 4.91-4.77 (m, 2H), 4.74 (t, J=7.1 Hz, 2H), 3.96 (s, 3H), 3.17 (d, J=11.2 Hz, 2H), 2.55 (s, 3H), 2.17 (s, 4H), 0.94 (s, 9H). LCMS-ESI+: calc'd for $C_{36}H_{40}ClN_4O_4S$; 659.2 (M+H)$^+$; found: 659.4 (M+H)$^+$.

Method B

Example 5. (S)-2-(tert-butoxy)-2-(7-(4-chlorophenyl)-2-(3-(3-methoxyazetidin-1-yl)-1-methyl-1H-indazol-5-yl)-5-methylbenzo[d]thiazol-6-yl)acetic Acid (2)

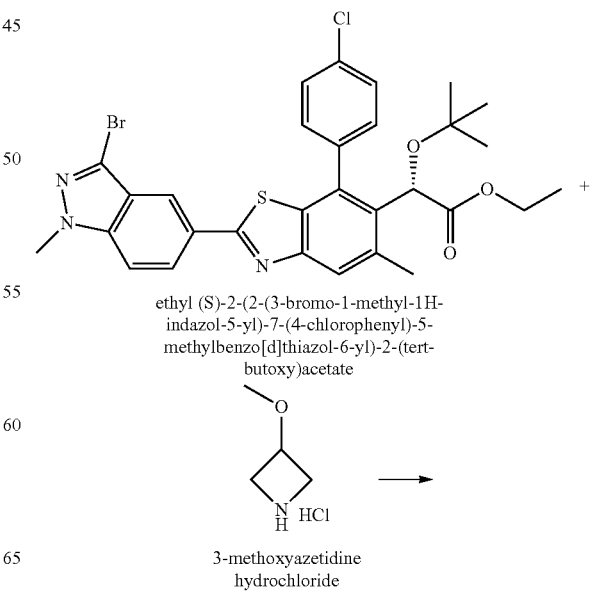

ethyl (S)-2-(2-(3-bromo-1-methyl-1H-indazol-5-yl)-7-(4-chlorophenyl)-5-methylbenzo[d]thiazol-6-yl)-2-(tert-butoxy)acetate 3-methoxyazetidine hydrochloride -continued

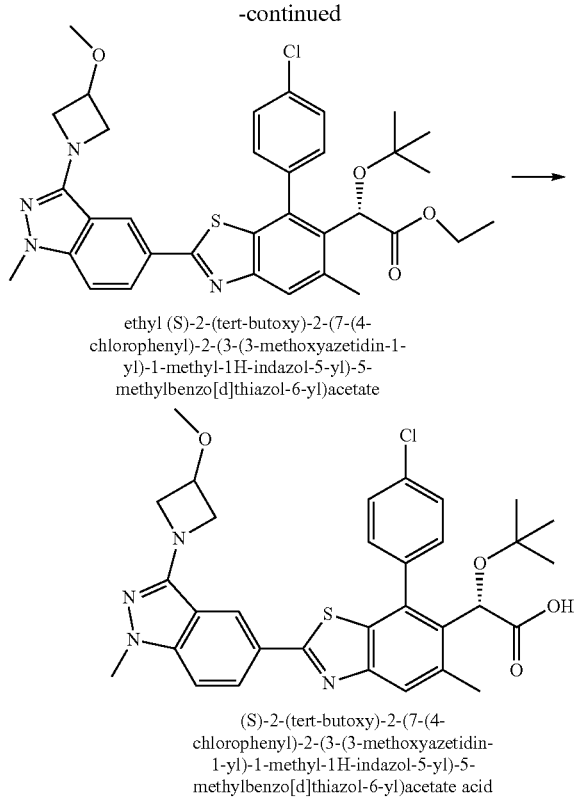

ethyl (S)-2-(tert-butoxy)-2-(7-(4-chlorophenyl)-2-(3-(3-methoxyazetidin-1-yl)-1-methyl-1H-indazol-5-yl)-5-methylbenzo[d]thiazol-6-yl)acetate (S)-2-(tert-butoxy)-2-(7-(4-chlorophenyl)-2-(3-(3-methoxyazetidin-1-yl)-1-methyl-1H-indazol-5-yl)-5-methylbenzo[d]thiazol-6-yl)acetate acid Preparation of ethyl (S)-2-(tert-butoxy)-2-(7-(4-chlorophenyl)-2-(3-(3-methoxyazetidin-1-yl)-1-methyl-1H-indazol-5-yl)-5-methylbenzo[d]thiazol-6-yl)acetate: A microwave vial containing Tris(dibenzylideneacetone) dipalladium (0) (6.57 mg, 7.18 µmol), 2-(Dicyclohexylphosphino)-2',4',6'-triisopropylbiphenyl (3.42 mg, 7.18 µmol) and cesium carbonate (78.0 mg, 239 µmol) in 1,4-dioxane (1 mL) was purged with Argon for 5 min. Ethyl (S)-2-(2-(3-bromo-1-methyl-1H-indazol-5-yl)-7-(4-chlorophenyl)-5-methylbenzo[d]thiazol-6-yl)-2-(tert-butoxy)acetate (30 mg, 0.05 mmol) and 3-methoxyazetidine hydrochloride (17.74 mg, 0.14 mmol) were added and reaction mixture was sealed and heated in a microwave reactor at 100° C. for 1 h. After cooling to room temperature, the resulting mixture was diluted ethyl acetate. The mixture was washed with brine, organic phase was dried ($Na_2SO_4$) and concentrated. The residue was purified by CombiFlash (40 g, Gold, 0-50% EtOAc/Hex plus 0.1% TEA) to give desired product. LCMS-ESI+: calc'd for: $C_{34}H_{37}ClN_4O_4S$; 633.2 $(M+H)^+$; found: 633.3 $(M+H)^+$.

Preparation of (S)-2-(tert-butoxy)-2-(7-(4-chlorophenyl)-2-(3-(3-methoxyazetidin-1-yl)-1-methyl-1H-indazol-5-yl)-5-methylbenzo[d]thiazol-6-yl)acetic acid: To ethyl (S)-2-(tert-butoxy)-2-(7-(4-chlorophenyl)-2-(3-(3-methoxyazetidin-1-yl)-1-methyl-1H-indazol-5-yl)-5-methylbenzo[d]thiazol-6-yl)acetate (20 mg, 0.03 mmol) was added THF (1.5 mL), MeOH (0.2 mL) and 50% aqueous sodium hydroxide (0.4 mL) at room temperature. The mixture was stirred at 60° C. for 2 h. The reaction mixture was cooled by ice and acidified with 3 N HCl. The resulting mixture was extracted with ethyl acetate (2×). Combined organic layer was dried ($MgSO_4$), filtered and concentrated to give crude mixture which was purified by Gilson HPLC (Phenomenex Gemini 250×21.2 10µ C18 column, 40-100% ACN/$H_2O$+0.1% TFA) to give a yellow powder after lyophilization. $^1H$ NMR (400 MHz, Chloroform-d) δ 8.16 (s, 1H), 7.95 (d, J=8.9 Hz, 1H), 7.81 (s, 1H), 7.69-7.62 (m, 1H), 7.46 (d, J=6.9 Hz, 3H), 7.16 (d, J=9.0 Hz, 1H), 5.24 (d, J=5.7 Hz, 1H), 4.49-3.96 (m, 5H), 3.83 (s, 3H), 3.29 (s, 3H), 2.50 (s, 3H), 0.94 (s, 9H). LCMS-ESI+: calc'd for $C_{32}H_{33}ClN_4O_4S$; 605.2 $(M+H)^+$; found: 605.3 $(M+H)^+$.

Method C

Example 6. Preparation of (S)-2-(tert-butoxy)-2-(7-(4-chlorophenyl)-5-methyl-2-(1-methyl-3-(2-oxoazetidin-1-yl)-1H-indazol-5-yl)benzo[d]thiazol-6-yl) acetic Acid (3)

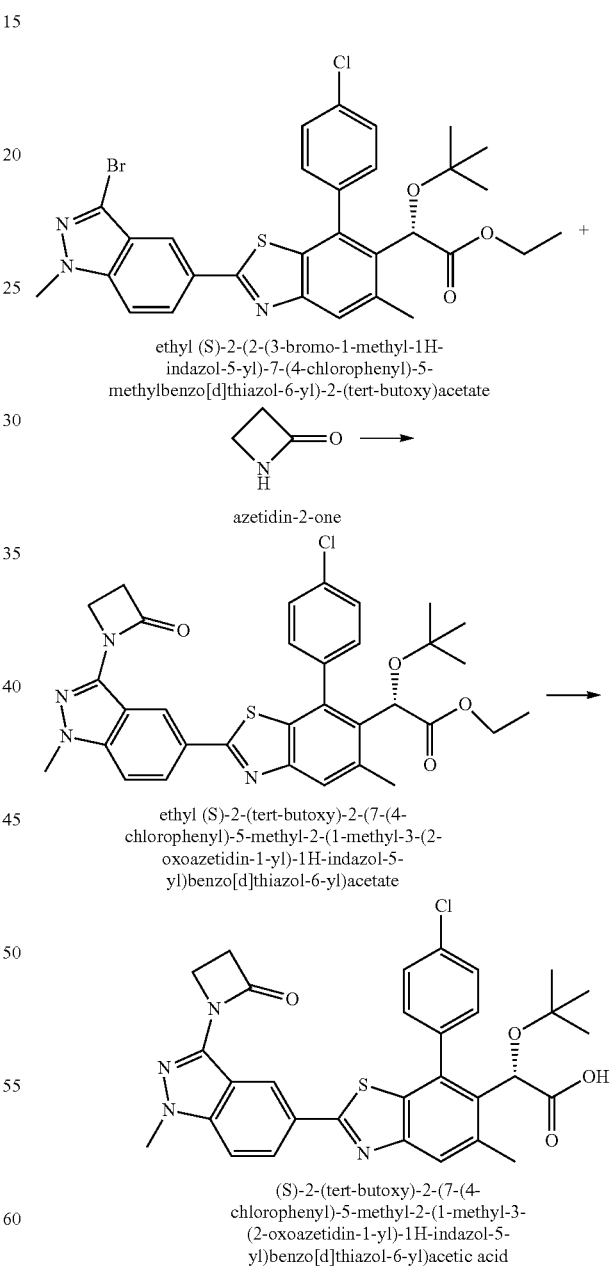

ethyl (S)-2-(2-(3-bromo-1-methyl-1H-indazol-5-yl)-7-(4-chlorophenyl)-5-methylbenzo[d]thiazol-6-yl)-2-(tert-butoxy)acetate azetidin-2-one ethyl (S)-2-(tert-butoxy)-2-(7-(4-chlorophenyl)-5-methyl-2-(1-methyl-3-(2-oxoazetidin-1-yl)-1H-indazol-5-yl)benzo[d]thiazol-6-yl)acetate (S)-2-(tert-butoxy)-2-(7-(4-chlorophenyl)-5-methyl-2-(1-methyl-3-(2-oxoazetidin-1-yl)-1H-indazol-5-yl)benzo[d]thiazol-6-yl)acetic acid Preparation of ethyl (S)-2-(tert-butoxy)-2-(7-(4-chlorophenyl)-5-methyl-2-(1-methyl-3-(2-oxoazetidin-1-yl)-1H-indazol-5-yl)benzo[d]thiazol-6-yl)acetate: A microwave vial containing Tris(dibenzylideneacetone) dipalladium (0) (4.4 mg, 5 µmol), 2-(Dicyclohexylphosphino)-2',4',6'-triisopropylbiphenyl (2.3 mg, 5.0 µmol) and cesium carbonate (52 mg, 160 µmol) in 1,4-dioxane (1 mL) was purged with Argon for 5 min. Ethyl (S)-2-(2-(3-bromo-1-methyl-1H-indazol-5-yl)-7-(4-chlorophenyl)-5-methylbenzo[d]thiazol-6-yl)-2-(tert-butoxy)acetate (20 mg, 0.032 mmol) and azetidin-2-one (6.8 mg, 0.096 mmol) were added and mixture was sealed and heated in a microwave reactor at 100° C. for 1 h. To test the solvent effect, two additional reactions were set up with exact same reagents and amounts in Toluene and t-BuOH separately which gave same results. After cooling to room temperature, the resulting three reaction mixtures were combined, diluted ethyl acetate. The mixture was washed with brine. The organic phase was dried (Na$_2$SO$_4$) and concentrated. The residue was purified by CombiFlash (40 g, Gold, 0-10% MeOH/CH$_2$Cl$_2$) to give desired product (containing impurity from catalyst). LCMS-ESI+: calc'd for: C$_{33}$H$_{33}$ClN$_4$O$_4$S; 617.2 (M+H)$^+$; found: 617.3 (M+H)$^+$.

Preparation of (S)-2-(tert-butoxy)-2-(7-(4-chlorophenyl)-2-(3-(3-methoxyazetidin-1-yl)-1-methyl-1H-indazol-5-yl)-5-methylbenzo[d]thiazol-6-yl)acetic acid: To ethyl (S)-2-(tert-butoxy)-2-(7-(4-chlorophenyl)-5-methyl-2-(1-methyl-3-(2-oxoazetidin-1-yl)-1H-indazol-5-yl)benzo[d]thiazol-6-yl)acetate in pyridine (1.5 ml) was added lithium iodide hydrate (240 mg, 1.58 mmol) at room temperature. The mixture was microwaved at 170° C. for 3 h. The reaction mixture was cooled by ice and acidified with 3 N HCl. The resulting mixture was extracted with ethyl acetate. The organic layer was washed by sat'd NH$_4$Cl, dried (MgSO$_4$), filtered and concentrated to give crude mixture which was purified by Gilson HPLC (Phenomenex Gemini 250×21.2 10µ C18 column, 40-100% ACN/H$_2$O+0.1% TFA) to give a yellow powder after lyophilization. $^1$H NMR (400 MHz, Chloroform-d) δ 9.14 (s, 1H), 8.88 (s, 1H), 8.14-8.00 (m, 1H), 7.83 (s, 1H), 7.73-7.63 (m, 1H), 7.59-7.42 (m, 3H), 7.35 (d, J=9.0 Hz, 1H), 6.51 (t, J=22.6 Hz, 6H), 5.88 (dd, J=10.4, 1.4 Hz, 1H), 5.31 (s, 1H), 3.97 (s, 3H), 2.55 (s, 3H), 1.26 (d, J=2.4 Hz, 1H), 0.99 (s, 9H). LCMS-ESI+: calc'd for C$_{31}$H$_{29}$ClN$_4$O$_4$S; 589.2 (M+H)$^+$; found: 589.3 (M+H)$^+$.

Method D

Example 7. Preparation of (S)-2-(tert-butoxy)-2-(7-(4-chlorophenyl)-2-(3-((S)-hexahydropyrazino[2,1-c][1,4]oxazin-8(1H)-yl)-1-methyl-1H-indazol-5-yl)-5-methylbenzo[d]thiazol-6-yl)acetic Acid (4)

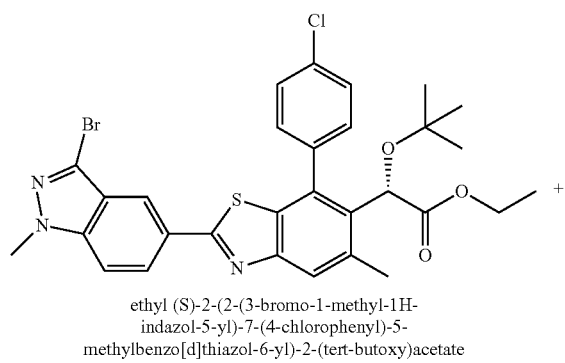

ethyl (S)-2-(2-(3-bromo-1-methyl-1H-indazol-5-yl)-7-(4-chlorophenyl)-5-methylbenzo[d]thiazol-6-yl)-2-(tert-butoxy)acetate

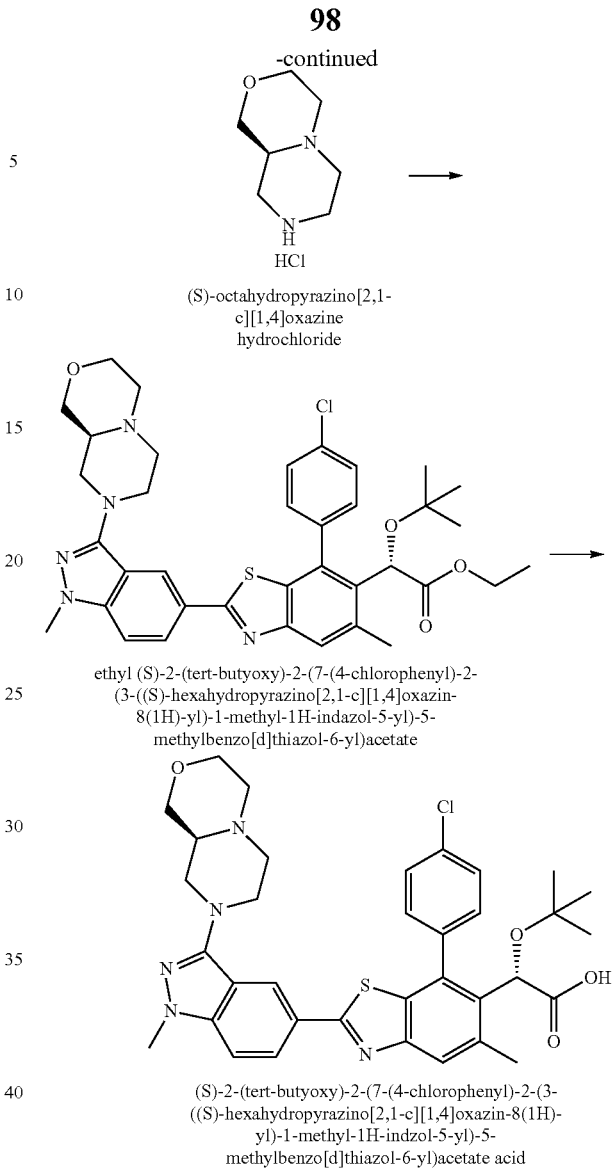

(S)-octahydropyrazino[2,1-c][1,4]oxazine hydrochloride ethyl (S)-2-(tert-butyoxy)-2-(7-(4-chlorophenyl)-2-(3-((S)-hexahydropyrazino[2,1-c][1,4]oxazin-8(1H)-yl)-1-methyl-1H-indazol-5-yl)-5-methylbenzo[d]thiazol-6-yl)acetate (S)-2-(tert-butyoxy)-2-(7-(4-chlorophenyl)-2-(3-((S)-hexahydropyrazino[2,1-c][1,4]oxazin-8(1H)-yl)-1-methyl-1H-indzol-5-yl)-5-methylbenzo[d]thiazol-6-yl)acetate acid Preparation of (S)-2-(tert-butoxy)-2-(7-(4-chlorophenyl)-2-(3-((S)-hexahydropyrazino[2,1-c][1,4]oxazin-8(1H)-yl)-1-methyl-1H-indazol-5-yl)-5-methylbenzo[d]thiazol-6-yl) acetic acid: A mixture of ethyl (S)-2-(2-(3-bromo-1-methyl-1H-indazol-5-yl)-7-(4-chlorophenyl)-5-methylbenzo[d]thiazol-6-yl)-2-(tert-butoxy)acetate (110 mg, 0.175 mmol), (S)-Octahydropyrazino[2,1-c][1,4]oxazine hydrochloride (87 µl, 0.53 mmol), SPhos Pd G2 (24 mg, 0.035 mmol), and potassium t-butoxide (104 mg, 1.2 mmol) in 1,2-dimethoxyethane (2 mL) was placed in a microwave vial and reacted under microwave at 100° C. for 1 h. The resulting mixture was cooled to room temperature, diluted in methanol, filtered through a pad of Celite, washed with EtOAc, and concentrated. To this crude mixture was added THF (1.5 mL), MeOH (0.2 mL) and 50% aqueous sodium hydroxide (0.4 mL). The mixture was stirred at 60° C. for 2 h. The reaction mixture was cooled by ice and acidified with 3 N HCl. The resulting mixture was extracted with ethyl acetate (2×). Combined organic layer was dried (MgSO$_4$), filtered and concentrated to give crude mixture which was purified by Gilson HPLC (Phenomenex Gemini 250×21.2 10µ C18 column, 40-100% ACN/H$_2$O+0.1% TFA) to give a yellow powder after lyophilization. ¹H NMR (400 MHz, Chloroform-d) δ 8.57 (s, 1H), 7.91 (s, 1H), 7.84 (d, J=8.9 Hz, 1H), 7.71 (d, J=8.1 Hz, 1H), 7.60-7.51 (m, 2H), 7.47 (d, J=7.9 Hz, 1H), 7.33 (d, J=8.9 Hz, 1H), 5.31 (s, 1H), 4.09 (q, J=12.2, 10.1 Hz, 3H), 3.93 (s, 4H), 3.66 (dt, J=28.8, 12.7 Hz, 3H), 3.45 (t, J=12.3 Hz, 1H), 3.28 (s, 1H), 3.04 (s, 1H), 2.58 (s, 3H), 1.25 (m, 2H), 1.01 (s, 9H), 0.93-0.77 (m, 3H). LCMS-ESI+: calc'd for $C_{35}H_{38}ClN_5O_4S$; 660.2 (M+H)⁺; found: 660.4 (M+H)⁺.

Method E

Example 8. Preparation of (S)-2-(tert-butoxy)-2-(7-(4-chlorophenyl)-2-(3-(1-(((R)-1-(methoxycarbonyl)azetidin-2-yl)methyl)piperidin-4-yl)-1-methyl-1H-indazol-5-yl)-5-methylbenzo[d]thiazol-6-yl)acetic Acid (5)

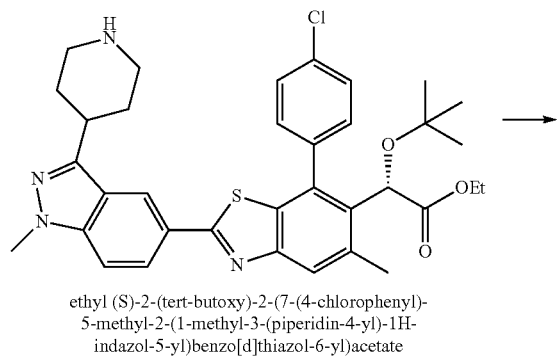

ethyl (S)-2-(tert-butoxy)-2-(7-(4-chlorophenyl)-5-methyl-2-(1-methyl-3-(piperidin-4-yl)-1H-indazol-5-yl)benzo[d]thiazol-6-yl)acetate

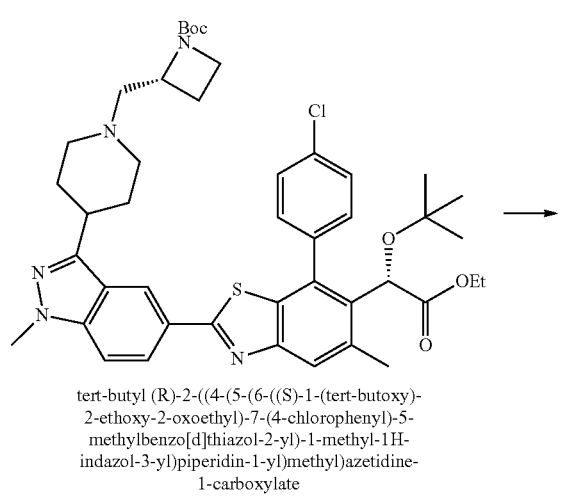

tert-butyl (R)-2-((4-(5-(6-((S)-1-(tert-butoxy)-2-ethoxy-2-oxoethyl)-7-(4-chlorophenyl)-5-methylbenzo[d]thiazol-2-yl)-1-methyl-1H-indazol-3-yl)piperidin-1-yl)methyl)azetidine-1-carboxylate

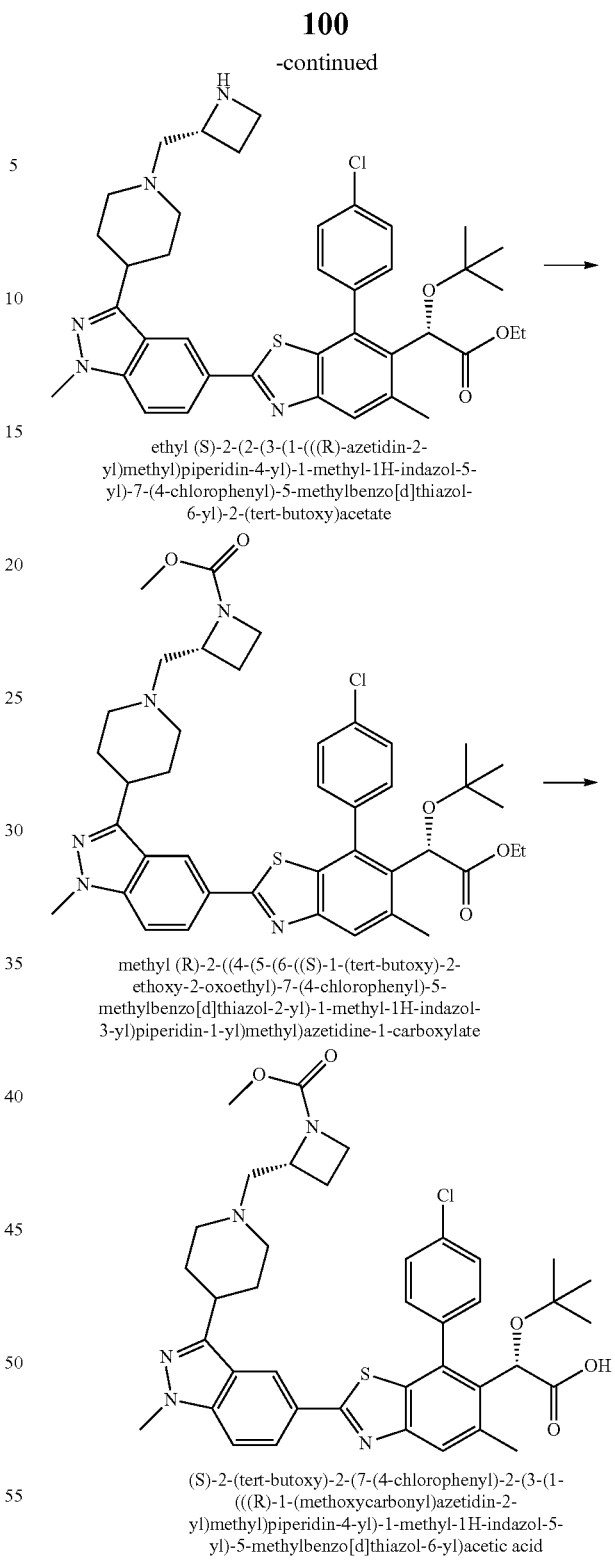

ethyl (S)-2-(2-(3-(1-(((R)-azetidin-2-yl)methyl)piperidin-4-yl)-1-methyl-1H-indazol-5-yl)-7-(4-chlorophenyl)-5-methylbenzo[d]thiazol-6-yl)-2-(tert-butoxy)acetate methyl (R)-2-((4-(5-(6-((S)-1-(tert-butoxy)-2-ethoxy-2-oxoethyl)-7-(4-chlorophenyl)-5-methylbenzo[d]thiazol-2-yl)-1-methyl-1H-indazol-3-yl)piperidin-1-yl)methyl)azetidine-1-carboxylate (S)-2-(tert-butoxy)-2-(7-(4-chlorophenyl)-2-(3-(1-(((R)-1-(methoxycarbonyl)azetidin-2-yl)methyl)piperidin-4-yl)-1-methyl-1H-indazol-5-yl)-5-methylbenzo[d]thiazol-6-yl)acetic acid Preparation of tert-butyl (R)-2-((4-(5-(6-((S)-1-(tert-butoxy)-2-ethoxy-2-oxoethyl)-7-(4-chlorophenyl)-5-methylbenzo[d]thiazol-2-yl)-1-methyl-1H-indazol-3-yl)piperidin-1-yl)methyl)azetidine-1-carboxylate: To a solution of ethyl (S)-2-(tert-butoxy)-2-(7-(4-chlorophenyl)-5-methyl-2-(1-methyl-3-(piperidin-4-yl)-1H-indazol-5-yl)benzo[d]thiazol-6-yl)acetate (100 mg, 0.160 mmol) in acetonitrile (4.0 mL) at room temperature was added cesium carbonate (284 mg, 0.870 mmol) and tert-butyl (R)-2-(bromomethyl)azetidine-1-carboxylate (198 mg, 0.790 mmol) and reaction mixture was stirred at 95° C. for 3 hours. Once complete, reaction mixture was allowed to cool to room temperature and quenched with saturated sodium bicarbonate and extracted with ethyl acetate (3×). Combined organic layer was washed with saturated sodium chloride, dried ($Na_2SO_4$) and concentrated. The residue was purified by CombiFlash (0-15% $MeOH/CH_2Cl_2$) and concentrated to give desired product. LCMS-ESI+: calc'd for $C_{44}H_{55}ClN_5O_5S$: 800.36 $(M+H)^+$; found: 800.39 $(M+H)^+$.

Preparation of ethyl (S)-2-(2-(3-(1-(((R)-azetidin-2-yl)methyl)piperidin-4-yl)-1-methyl-1H-indazol-5-yl)-7-(4-chlorophenyl)-5-methylbenzo[d]thiazol-6-yl)-2-(tert-butoxy)acetate: A solution of tert-butyl (R)-2-((4-(5-(6-((S)-1-(tert-butoxy)-2-ethoxy-2-oxoethyl)-7-(4-chlorophenyl)-5-methylbenzo[d]thiazol-2-yl)-1-methyl-1H-indazol-3-yl)piperidin-1-yl)methyl)azetidine-1-carboxylate (88 mg, 0.011 mmol) in 1.25 M HCl in isopropanol (5.0 mL) was stirred for 36 hours at room temperature. Reaction mixture was quenched with saturated sodium bicarbonate and concentrated. Residue was diluted with water and extracted with dichloromethane (3×). Combined organic layer was washed with saturated sodium chloride, dried ($Na_2SO_4$), and concentrated to give (S)-2-(2-(3-(1-(((R)-azetidin-2-yl)methyl)piperidin-4-yl)-1-methyl-1H-indazol-5-yl)-7-(4-chlorophenyl)-5-methylbenzo[d]thiazol-6-yl)-2-(tert-butoxy)acetate that was used in the next step without purification. LCMS-ESI+: calc'd for $C_{39}H_{47}ClN_5O_3S$: 700.31 $(M+H)^+$; found: 700.68 $(M+H)^+$.

Preparation of methyl (R)-2-((4-(5-(6-((S)-1-(tert-butoxy)-2-ethoxy-2-oxoethyl)-7-(4-chlorophenyl)-5-methylbenzo[d]thiazol-2-yl)-1-methyl-1H-indazol-3-yl)piperidin-1-yl)methyl)azetidine-1-carboxylate: To a solution of ethyl (S)-2-(2-(3-(1-(((R)-azetidin-2-yl)methyl)piperidin-4-yl)-1-methyl-1H-indazol-5-yl)-7-(4-chlorophenyl)-5-methylbenzo[d]thiazol-6-yl)-2-(tert-butoxy)acetate (15 mg, 0.021 mmol) in dichloromethane (0.5 mL) was added N,N-diisopropylethylamine (0.037 mL, 0.21 mmol) at 0° C. followed by the addition of methyl chloroformate (0.008 mL, 0.1 mmol) and stirred for 1 hour. The reaction mixture was quenched with saturated sodium bicarbonate at 0° C. and extracted with dichloromethane (3×). Combined organic layer was washed with saturated sodium chloride, dried ($Na_2SO_4$), and concentrated. Residue was purified by CombiFlash (0-15% $MeOH/CH_2Cl_2$) and concentrated to give desired product. LCMS-ESI+: calc'd for $C_{41}H_{49}ClN_5O_5S$: 758.31 $(M+H)^+$; found: 758.66 $(M+H)^+$.

Preparation of (S)-2-(tert-butoxy)-2-(7-(4-chlorophenyl)-2-(3-(1-(((R)-1-(methoxycarbonyl)azetidin-2-yl)methyl)piperidin-4-yl)-1-methyl-1H-indazol-5-yl)-5-methylbenzo[d]thiazol-6-yl)acetic acid: A solution of (R)-2-((4-(5-(6-((S)-1-(tert-butoxy)-2-ethoxy-2-oxoethyl)-7-(4-chlorophenyl)-5-methylbenzo[d]thiazol-2-yl)-1-methyl-1H-indazol-3-yl)piperidin-1-yl)methyl)azetidine-1-carboxylate (10 mg, 0.013 mmol) and 2.5 M sodium hydroxide (0.040 mL, 0.11 mmol) in methanol (0.5 mL) was stirred at 50° C. for one hour. Reaction mixture was concentrated, dissolved in DMF/methanol, filtered through syringe filter and purified by Gilson HPLC (Gemini, 5-100% $ACN/H_2O+0.1\%$ TFA) to give a yellow powder after lyophilization. $^1H$ NMR (400 MHz, Methanol-$d_4$) δ 8.46 (s, 1H), 8.12 (d, J=9.0, 1.5 Hz, 1H), 7.82 (s, 1H), 7.72-7.66 (m, 1H), 7.66-7.57 (m, 4H), 5.26 (s, 1H), 4.14-4.02 (m, 4H), 4.02-3.91 (m, 1H), 3.78-3.34 (m, 8H), 3.24-3.10 (m, 1H), 2.62 (s, 3H), 2.58-2.06 (m, 7H), 1.35-1.17 (m, 1H), 0.98 (s, 9H). LCMS-ESI+: calc'd for $C_{39}H_{45}ClN_5S$: 730.28 $(M+H)^+$; found: 730.71 $(M+H)^+$.

Example 9. Preparation of (2S)-2-(tert-butoxy)-2-(7-(4-chlorophenyl)-5-methyl-2-(1-methyl-3-(1-(oxetan-2-ylmethyl)piperidin-4-yl)-1H-indazol-5-yl)benzo[d]thiazol-6-yl)acetic Acid (6)

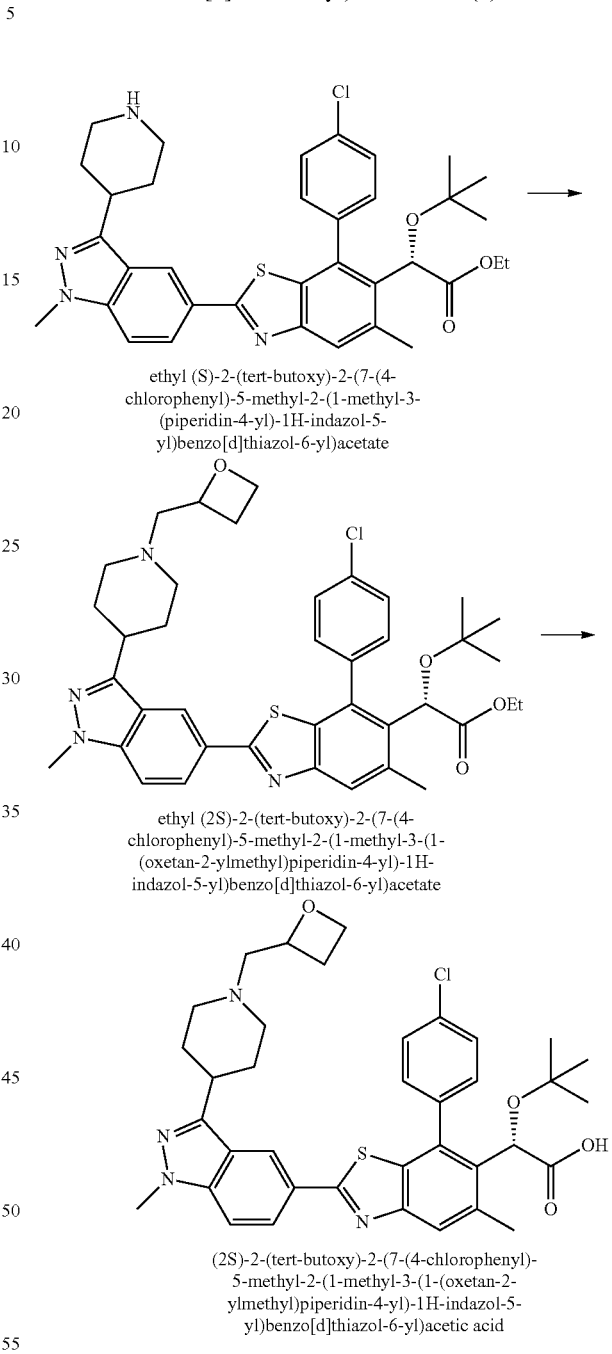

ethyl (S)-2-(tert-butoxy)-2-(7-(4-chlorophenyl)-5-methyl-2-(1-methyl-3-(piperidin-4-yl)-1H-indazol-5-yl)benzo[d]thiazol-6-yl)acetate ethyl (2S)-2-(tert-butoxy)-2-(7-(4-chlorophenyl)-5-methyl-2-(1-methyl-3-(1-(oxetan-2-ylmethyl)piperidin-4-yl)-1H-indazol-5-yl)benzo[d]thiazol-6-yl)acetate (2S)-2-(tert-butoxy)-2-(7-(4-chlorophenyl)-5-methyl-2-(1-methyl-3-(1-(oxetan-2-ylmethyl)piperidin-4-yl)-1H-indazol-5-yl)benzo[d]thiazol-6-yl)acetic acid Preparation of ethyl (2S)-2-(tert-butoxy)-2-(7-(4-chlorophenyl)-5-methyl-2-(1-methyl-3-(1-(oxetan-2-ylmethyl)piperidin-4-yl)-1H-indazol-5-yl)benzo[d]thiazol-6-yl)acetate: To a solution of ethyl (S)-2-(tert-butoxy)-2-(7-(4-chlorophenyl)-5-methyl-2-(1-methyl-3-(piperidin-4-yl)-1H-indazol-5-yl)benzo[d]thiazol-6-yl)acetate (10 mg, 0.016 mmol) and 2-(bromomethyl)oxetane (4.8 mg, 0.032 mmol) in DMF (0.5 mL) at room temperature was added cesium carbonate (11 mg, 0.035 mmol) and reaction mixture was stirred at 90° C. for 3 hours. Once complete, reaction mixture was allowed to cool to room temperature and quenched with saturated sodium bicarbonate and concentrated. Diluted with water and extracted with ethyl acetate (3×). Combined organic layer was washed with saturated sodium chloride, dried (Na$_2$SO$_4$) and concentrated. Crude reaction mixture was dissolved in DMF/methanol, filtered through syringe filter and purified by Gilson HPLC (Gemini, 5-100% ACN/H$_2$O+ 0.1% TFA) to give a yellow powder after lyophilization. LCMS-ESI$^+$: calc'd for C$_{39}$H$_{46}$ClN$_4$O$_4$S: 701.29 (M+H)$^+$; found: 701.63 (M+H)$^+$.

Preparation of (2S)-2-(tert-butoxy)-2-(7-(4-chlorophenyl)-5-methyl-2-(1-methyl-3-(1-(oxetan-2-ylmethyl)piperidin-4-yl)-1H-indazol-5-yl)benzo[d]thiazol-6-yl)acetic acid: A solution of ethyl (2S)-2-(tert-butoxy)-2-(7-(4-chlorophenyl)-5-methyl-2-(1-methyl-3-(1-(oxetan-2-ylmethyl)piperidin-4-yl)-1H-indazol-5-yl)benzo[d]thiazol-6-yl)acetate (5.9 mg, 0.0084 mmol) and 2.0 M sodium hydroxide (0.04 mL, 0.08 mmol) in methanol (0.5 mL) was stirred at 50° C. for three hours. Reaction mixture was concentrated, dissolved in DMF/methanol, filtered through syringe filter and purified by Gilson HPLC (Gemini, 5-100% ACN/H$_2$O+0.1% TFA) to give a yellow powder after lyophilization. $^1$H NMR (400 MHz, Methanol-d$_4$) δ 8.46 (s, 1H), 8.12 (d, 1H), 7.82 (s, 1H), 7.72-7.66 (m, 1H), 7.66-7.55 (m, 4H), 5.33-5.22 (m, 2H), 4.79-4.72 (m, 1H), 4.71-4.59 (m, 1H), 4.05 (d, 3H), 3.82-3.63 (m, 3H), 3.61-3.35 (m, 3H), 3.29-3.20 (m, 1H), 2.96-2.84 (m, 1H), 2.62 (s, 3H), 2.60-2.47 (m, 1H), 2.44-2.12 (m, 4H), 0.99 (s, 9H). LCMS-ESI$^+$: calc'd for C$_{37}$H$_{42}$ClN$_4$O$_4$S: 673.26 (M+H)$^+$; found: 673.62 (M+H)$^+$.

Method F

Example 10. Preparation of (S)-2-(tert-butoxy)-2-(7-(4-chlorophenyl)-5-methyl-2-(1-methyl-3-(1-(1-propionylazetidin-3-yl)piperidin-4-yl)-1H-indazol-5-yl)benzo[d]thiazol-6-yl)acetic Acid (7)

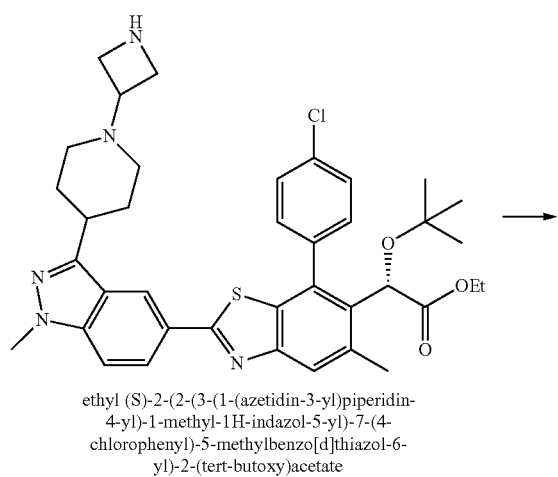

ethyl (S)-2-(2-(3-(1-(azetidin-3-yl)piperidin-4-yl)-1-methyl-1H-indazol-5-yl)-7-(4-chlorophenyl)-5-methylbenzo[d]thiazol-6-yl)-2-(tert-butoxy)acetate

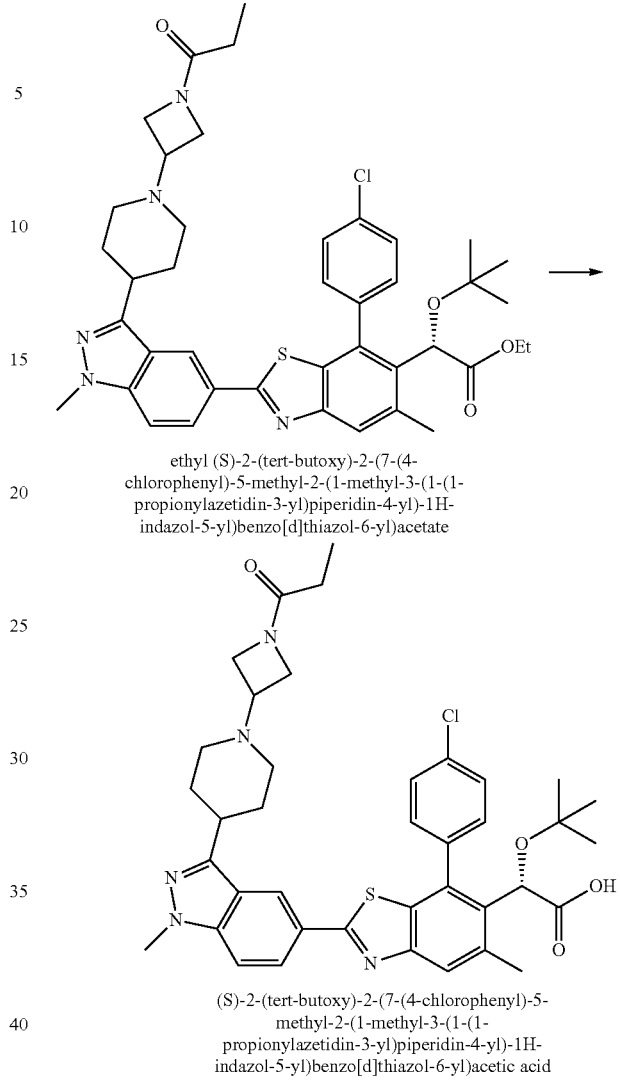

ethyl (S)-2-(tert-butoxy)-2-(7-(4-chlorophenyl)-5-methyl-2-(1-methyl-3-(1-(1-propionylazetidin-3-yl)piperidin-4-yl)-1H-indazol-5-yl)benzo[d]thiazol-6-yl)acetate (S)-2-(tert-butoxy)-2-(7-(4-chlorophenyl)-5-methyl-2-(1-methyl-3-(1-(1-propionylazetidin-3-yl)piperidin-4-yl)-1H-indazol-5-yl)benzo[d]thiazol-6-yl)acetic acid Preparation of ethyl (S)-2-(tert-butoxy)-2-(7-(4-chlorophenyl)-5-methyl-2-(1-methyl-3-(1-(1-propionylazetidin-3-yl)piperidin-4-yl)-1H-indazol-5-yl)benzo[d]thiazol-6-yl)acetate: To a solution of ethyl (S)-2-(2-(3-(1-(azetidin-3-yl)piperidin-4-yl)-1-methyl-1H-indazol-5-yl)-7-(4-chlorophenyl)-5-methylbenzo[d]thiazol-6-yl)-2-(tert-butoxy)acetate (10 mg, 0.015 mmol) and N,N-Diisopropylethylamine (0.051 mL, 0.29 mmol) in methanol (0.5 mL) was added propionyl chloride (0.013 mL, 0.15 mmol) and reaction mixture was allowed to stir for one hour. Reaction mixture was quenched with saturated sodium bicarbonate and concentrated. Diluted with water and extracted with ethyl acetate (3×). Combined organic layer was washed with saturated sodium chloride, dried (Na$_2$SO$_4$) and concentrated to give ethyl (S)-2-(tert-butoxy)-2-(7-(4-chlorophenyl)-5-methyl-2-(1-methyl-3-(1-(1-propionylazetidin-3-yl)piperidin-4-yl)-1H-indazol-5-yl)benzo[d]thiazol-6-yl)acetate that was used in the next step without further purification. LCMS-ESI$^+$: calc'd for C$_{41}$H$_{49}$ClN$_5$O$_4$S: 742.32 (M+H)$^+$; found: 742.68 (M+H)$^+$.

Preparation of (S)-2-(tert-butoxy)-2-(7-(4-chlorophenyl)-5-methyl-2-(1-methyl-3-(1-(1-propionylazetidin-3-yl)piperidin-4-yl)-1H-indazol-5-yl)benzo[d]thiazol-6-yl)acetic acid: A solution of (S)-2-(tert-butoxy)-2-(7-(4-chlorophenyl)-5-methyl-2-(1-methyl-3-(1-(1-propionylazetidin-3-yl)piperidin-4-yl)-1H-indazol-5-yl)benzo[d]thiazol-6-yl)acetate (11 mg, 0.15 mmol) and 2.0 M sodium hydroxide (0.11 mL, 0.22 mmol) in methanol (0.5 mL) was stirred at 50° C. for three hours. Reaction mixture was concentrated, dissolved in DMF/methanol, filtered through syringe filter and purified by Gilson HPLC (Gemini, 5-100% ACN/H$_2$O+ 0.1% TFA) to give a yellow powder after lyophilization. $^1$H NMR (400 MHz, Methanol-d$_4$) δ 8.47 (s, 1H), 8.13 (d, J=8.9 Hz, 1H), 7.82 (s, 1H), 7.73-7.56 (m, 5H), 5.26 (s, 1H), 4.63-4.53 (m, 1H), 4.49-4.40 (m, 1H), 4.37-4.30 (m, 1H), 4.25-4.15 (m, 2H), 4.06 (s, 3H), 3.77-3.47 (m, 2H), 3.27-3.08 (m, 2H), 2.62 (s, 3H), 2.46-2.17 (m, 5H), 1.36 (d, J=6.8 Hz, 1H), 1.22 (d, J=6.6 Hz, 1H), 1.13 (t, J=7.5 Hz, 3H), 0.98 (s, 9H). LCMS-ESI$^+$: calc'd for C$_{39}$H$_{45}$ClN$_5$O$_4$S: 714.29 (M+H)$^+$; found: 714.66 (M+H)$^+$.

Method G

Example 11. Preparation of (2S)-2-(tert-butoxy)-2-(7-(4-chlorophenyl)-5-methyl-2-(1-methyl-3-(1-(1-(1,1,1-trifluoropropan-2-yl)azetidin-3-yl)piperidin-4-yl)-1H-indazol-5-yl)benzo[d]thiazol-6-yl)acetic Acid (8)

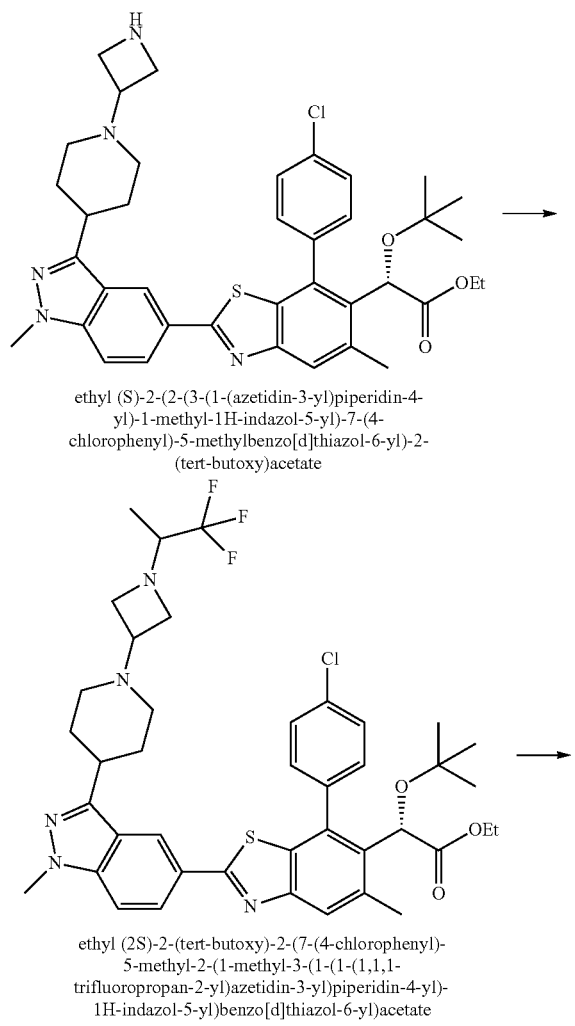

ethyl (S)-2-(2-(3-(1-(azetidin-3-yl)piperidin-4-yl)-1-methyl-1H-indazol-5-yl)-7-(4-chlorophenyl)-5-methylbenzo[d]thiazol-6-yl)-2-(tert-butoxy)acetate ethyl (2S)-2-(tert-butoxy)-2-(7-(4-chlorophenyl)-5-methyl-2-(1-methyl-3-(1-(1-(1,1,1-trifluoropropan-2-yl)azetidin-3-yl)piperidin-4-yl)-1H-indazol-5-yl)benzo[d]thiazol-6-yl)acetate

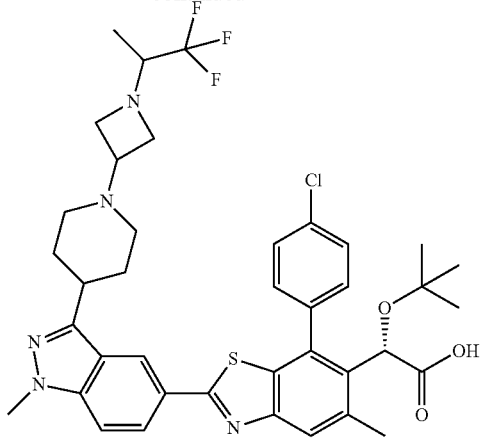

(2S)-2-(tert-butoxy)-2-(7-(4-chlorophenyl)-5-methyl-2-(1-methyl-3-(1-(1-(1,1,1-trifluoropropan-2-yl)azetidin-3-yl)piperidin-4-yl)-1H-indazol-5-yl)benzo[d]thiazol-6-yl)acetic acid Preparation of ethyl (2S)-2-(tert-butoxy)-2-(7-(4-chlorophenyl)-5-methyl-2-(1-methyl-3-(1-(1-(1,1,1-trifluoropropan-2-yl)azetidin-3-yl)piperidin-4-yl)-1H-indazol-5-yl)benzo[d]thiazol-6-yl)acetate: To a solution of ethyl (S)-2-(2-(3-(1-(azetidin-3-yl)piperidin-4-yl)-1-methyl-1H-indazol-5-yl)-7-(4-chlorophenyl)-5-methylbenzo[d]thiazol-6-yl)-2-(tert-butoxy)acetate (10 mg, 0.015 mmol) and 1,1,1-trifluoropropan-2-one (0.013 mL, 0.15 mmol) in methanol (0.5 mL) at 0° C. was added sodium cyanoborohydride (9.2 mg, 0.15 mmol) and acetic acid (0.004 mL, 0.07 mmol). Reaction mixture was allowed to stir for 5 minutes, then removed from ice bath and stirred for one additional hour. Reaction mixture was quenched with saturated sodium bicarbonate and concentrated. Residue was diluted with water and extracted with ethyl acetate (3×). Combined organic layer was washed with saturated sodium chloride, dried (Na$_2$SO$_4$), and concentrated to give ethyl (2S)-2-(tert-butoxy)-2-(7-(4-chlorophenyl)-5-methyl-2-(1-methyl-3-(1-(1-(1,1,1-trifluoropropan-2-yl)azetidin-3-yl)piperidin-4-yl)-1H-indazol-5-yl)benzo[d]thiazol-6-yl)acetate that was used in the next step without further purification. LCMS-ESI$^+$: calc'd for C$_{41}$H$_{48}$ClF$_3$N$_5$O$_3$S: 782.31 (M+H)$^+$; found: 782.58 (M+H)$^+$.

Preparation of (2S)-2-(tert-butoxy)-2-(7-(4-chlorophenyl)-5-methyl-2-(1-methyl-3-(1-(1-(1,1,1-trifluoropropan-2-yl)azetidin-3-yl)piperidin-4-yl)-1H-indazol-5-yl)benzo[d]thiazol-6-yl)acetic acid: To a solution of ethyl (2S)-2-(tert-butoxy)-2-(7-(4-chlorophenyl)-5-methyl-2-(1-methyl-3-(1-(1-(1,1,1-trifluoropropan-2-yl)azetidin-3-yl)piperidin-4-yl)-1H-indazol-5-yl)benzo[d]thiazol-6-yl)acetate (10 mg, 0.013 mmol) in methanol (0.5 mL) was added 2.0 M sodium hydroxide (0.096 mL, 0.19 mmol) and heated to 50° C. for one hour. Reaction mixture was concentrated, dissolved in DMF/methanol, filtered through syringe filter and purified by Gilson HPLC (Gemini, 5-100% ACN/H$_2$O+0.1% TFA) to give a yellow powder after lyophilization. $^1$H NMR (400 MHz, Methanol-d$_4$) δ 8.46 (s, 1H), 8.12 (d, J=8.7 Hz, 1H), 7.82 (s, 1H), 7.72-7.52 (m, 5H), 5.26 (s, 1H), 4.05 (s, 3H), 4.02-3.39 (m, 8H), 3.23-3.02 (m, 3H), 2.62 (s, 3H), 2.43-2.13 (m, 4H), 1.19 (d, J=6.3 Hz, 3H), 0.98 (s, 9H). LCMS-ESI$^+$: calc'd for C$_{39}$H$_{44}$ClF$_3$N$_5$O$_3$S: 754.28 (M+H)$^+$; found: 754.57 (M+H)$^+$.

Method H

Example 12. Preparation of (S)-2-(tert-butoxy)-2-(7-(4-chlorophenyl)-5-methyl-2-(1-methyl-3-(1-((R)-tetrahydrofuran-2-carbonyl)piperidin-4-yl)-1H-indazol-5-yl)benzo[d]thiazol-6-yl)acetic Acid (9)

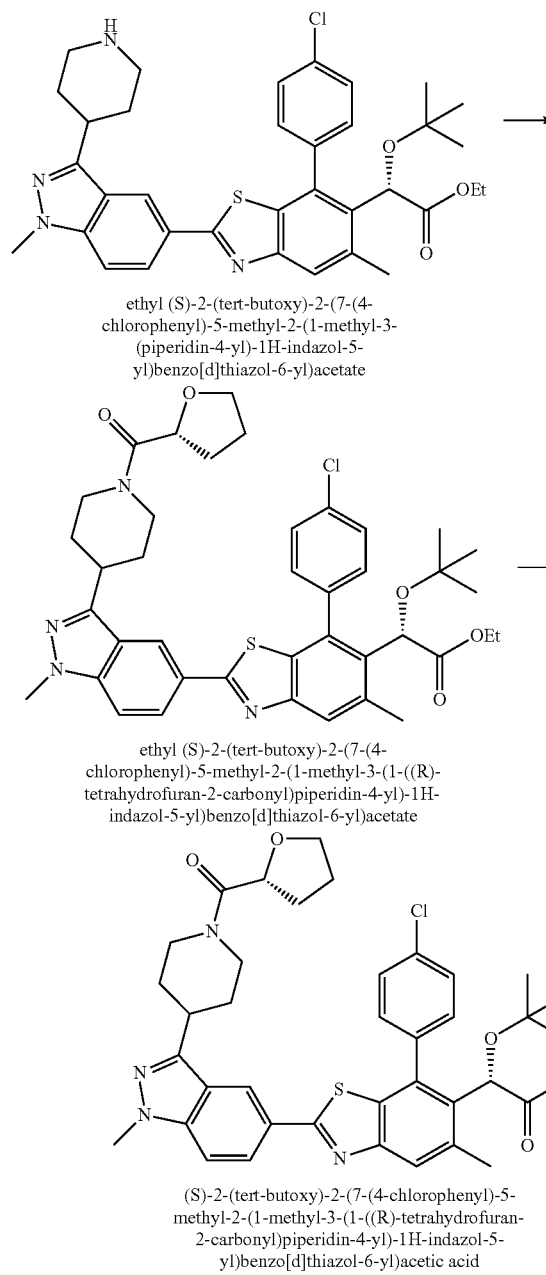

ethyl (S)-2-(tert-butoxy)-2-(7-(4-chlorophenyl)-5-methyl-2-(1-methyl-3-(piperidin-4-yl)-1H-indazol-5-yl)benzo[d]thiazol-6-yl)acetate ethyl (S)-2-(tert-butoxy)-2-(7-(4-chlorophenyl)-5-methyl-2-(1-methyl-3-(1-((R)-tetrahydrofuran-2-carbonyl)piperidin-4-yl)-1H-indazol-5-yl)benzo[d]thiazol-6-yl)acetate (S)-2-(tert-butoxy)-2-(7-(4-chlorophenyl)-5-methyl-2-(1-methyl-3-(1-((R)-tetrahydrofuran-2-carbonyl)piperidin-4-yl)-1H-indazol-5-yl)benzo[d]thiazol-6-yl)acetic acid Preparation of ethyl (S)-2-(tert-butoxy)-2-(7-(4-chlorophenyl)-5-methyl-2-(1-methyl-3-(1-((R)-tetrahydrofuran-2-carbonyl)piperidin-4-yl)-1H-indazol-5-yl)benzo[d]thiazol-6-yl)acetate: To a solution of (R)-tetrahydrofuran-2-carboxylic acid (18 mg, 0.16 mmol) in DMF (1.5 mL) was added HATU (21 mg, 0.16 mmol) and reaction mixture was stirred for 30 minutes followed by the addition of ethyl (S)-2-(tert-butoxy)-2-(7-(4-chlorophenyl)-5-methyl-2-(1-methyl-3-(piperidin-4-yl)-1H-indazol-5-yl)benzo[d]thiazol-6-yl)acetate (20 mg, 0.032 mmol) and N,N-Diisopropylethylamine (0.028 mL, 0.16 mmol) and stirred for an additional 1 hour. Reaction mixture was quenched with saturated sodium bicarbonate and extracted with ethyl acetate (3×). Combined organic layer was washed with saturated sodium chloride, dried ($Na_2SO_4$), and concentrated. Residue was purified by CombiFlash (0-100% EtOAc/Hex) and concentrated to give desired product. LCMS-ESI$^+$: calc'd for $C_{40}H_{46}ClN_4O_5S$: 729.29 (M+H)$^+$; found: 729.49 (M+H)$^+$.

Preparation of (S)-2-(tert-butoxy)-2-(7-(4-chlorophenyl)-5-methyl-2-(1-methyl-3-(1-((R)-tetrahydrofuran-2-carbonyl)piperidin-4-yl)-1H-indazol-5-yl)benzo[d]thiazol-6-yl)acetic acid: A solution of ethyl (S)-2-(tert-butoxy)-2-(7-(4-chlorophenyl)-5-methyl-2-(1-methyl-3-(1-((R)-tetrahydrofuran-2-carbonyl)piperidin-4-yl)-1H-indazol-5-yl)benzo[d]thiazol-6-yl)acetate (19 mg, 0.026 mmol) and 2.0 M sodium hydroxide (0.19 mL) in methanol (1.0 mL) was stirred at 60° C. for 3 hours. Reaction mixture was concentrated, dissolved in DMF/methanol, filtered through syringe filter and purified by Gilson HPLC (Gemini, 5-100% ACN/$H_2O$+0.1% TFA) to give desired product. $^1$H NMR (400 MHz, Methanol-$d_4$) δ 8.38 (s, 1H), 8.09-8.00 (m, 1H), 7.79 (s, 1H), 7.72-7.67 (m, 1H), 7.61-7.51 (m, 4H), 5.25 (s, 1H), 4.82-4.74 (m, 1H), 4.65-4.54 (m, 1H), 4.25-4.09 (m, 1H), 4.01-3.80 (m, 5H), 3.51-3.32 (m, 1H), 3.26 (d, J=11.5 Hz, 0H), 2.99-2.85 (m, 1H), 2.61 (s, 3H), 2.31-1.75 (m, 9H), 0.98 (s, 9H). LCMS-ESI$^+$: calc'd for $C_{38}H_{42}ClN_4O_5S$: 701.26 (M+H)$^+$; found: 701.33 (M+H)$^+$.

Example 13. Preparation of (S)-2-(tert-butoxy)-2-(7-(4-chlorophenyl)-2-(3-(1-(1,1-dioxidothietan-3-yl)piperidin-4-yl)-1-methyl-1H-indazol-5-yl)-5-methylbenzo[d]thiazol-6-yl)acetic Acid (10)

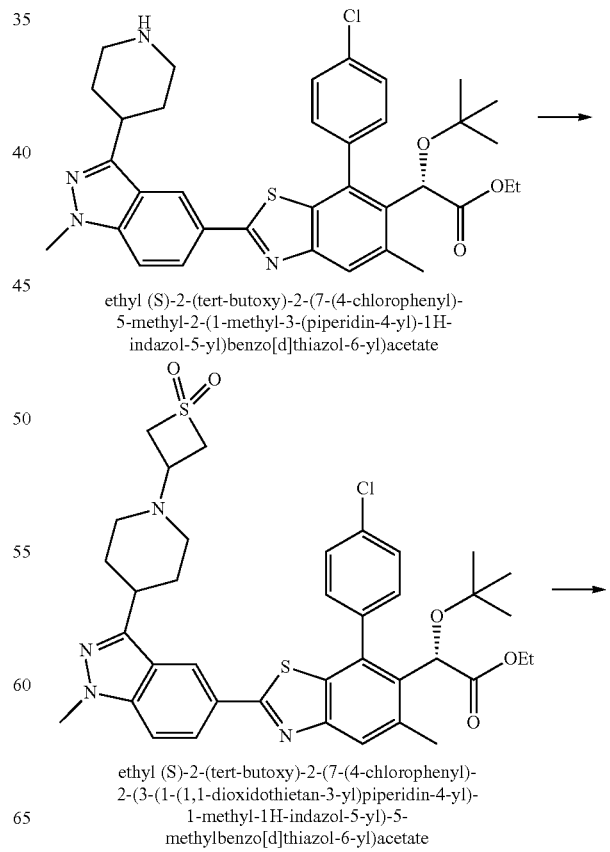

ethyl (S)-2-(tert-butoxy)-2-(7-(4-chlorophenyl)-5-methyl-2-(1-methyl-3-(piperidin-4-yl)-1H-indazol-5-yl)benzo[d]thiazol-6-yl)acetate ethyl (S)-2-(tert-butoxy)-2-(7-(4-chlorophenyl)-2-(3-(1-(1,1-dioxidothietan-3-yl)piperidin-4-yl)-1-methyl-1H-indazol-5-yl)-5-methylbenzo[d]thiazol-6-yl)acetate

109

-continued

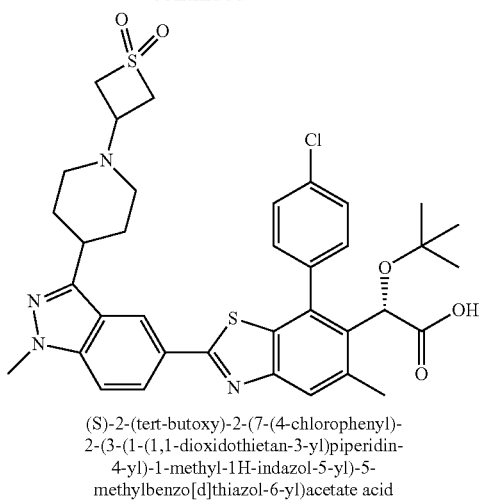

(S)-2-(tert-butoxy)-2-(7-(4-chlorophenyl)-
2-(3-(1-(1,1-dioxidothietan-3-yl)piperidin-
4-yl)-1-methyl-1H-indazol-5-yl)-5-
methylbenzo[d]thiazol-6-yl)acetate acid Preparation of ethyl (S)-2-(tert-butoxy)-2-(7-(4-chlorophenyl)-2-(3-(1-(1,1-dioxidothietan-3-yl)piperidin-4-yl)-1-methyl-1H-indazol-5-yl)-5-methylbenzo[d]thiazol-6-yl)acetate: To a solution of ethyl (S)-2-(tert-butoxy)-2-(7-(4-chlorophenyl)-5-methyl-2-(1-methyl-3-(piperidin-4-yl)-1H-indazol-5-yl)benzo[d]thiazol-6-yl)acetate (10 mg, 0.016 mmol) and thietan-3-one 1,1-dioxide (1.9 mg, 0.016 mmol) in tetrahydrofuran (0.2 mL) was added titanium(IV) isopropixide (0.006 mL, 0.02 mmol) at room temperature and reaction mixture was stirred for 1.5 hours, followed by the addition of sodium cyanoborohydride (2.0 mg, 0.032 mmol). After one hour, reaction mixture was quenched with saturated sodium bicarbonate and extracted with ethyl acetate (3×). Combined organic layer was washed with saturated sodium chloride, dried (Na$_2$SO$_4$), and concentrated. Residue was purified by CombiFlash (0-100% EtOAc/Hex) and concentrated to give desired product. LCMS-ESI$^+$: calc'd for C$_{38}$H$_{44}$ClN$_4$O$_5$S$_2$: 735.24 (M+H)$^+$; found: 736.97 (M+H)$^+$.

Preparation of (S)-2-(tert-butoxy)-2-(7-(4-chlorophenyl)-2-(3-(1-(1,1-dioxidothietan-3-yl)piperidin-4-yl)-1-methyl-1H-indazol-5-yl)-5-methylbenzo[d]thiazol-6-yl)acetic acid: A solution of ethyl (S)-2-(tert-butoxy)-2-(7-(4-chlorophenyl)-2-(3-(1-(1,1-dioxidothietan-3-yl)piperidin-4-yl)-1-methyl-1H-indazol-5-yl)-5-methylbenzo[d]thiazol-6-yl)acetate (2.7 mg, 0.0037 mmol) and 2.0 M sodium hydroxide (0.018 mL) in methanol (0.5 mL) was stirred at 50° C. for 3 hours. Reaction mixture was diluted with DMF/methanol, filtered through syringe filter and purified by Gilson HPLC (Gemini, 5-100% ACN/H$_2$O+0.1% TFA) to give desired product. $^1$H NMR (400 MHz, Methanol-d$_4$) δ 8.47 (s, 1H), 8.12 (dd, J=8.9, 1.6 Hz, 1H), 7.82 (s, 1H), 7.72-7.58 (m, 5H), 5.26 (s, 1H), 4.54-4.39 (m, 3H), 4.05 (s, 3H), 3.57-3.36 (m, 4H), 2.91 (s, 2H), 2.62 (s, 3H), 2.34-2.12 (m, 5H), 0.98 (s, 9H). LCMS-ESI$^+$: calc'd for C$_{36}$H$_{40}$ClN$_4$O$_5$S$_2$ 707.21 (M+H)$^+$; found: 707.36 (M+H)$^+$.

110

Method I

Example 14. Preparation of (S)-2-(2-(3-(1-((S)-1-acetylpyrrolidin-3-yl)piperidin-4-yl)-1-methyl-1H-indazol-5-yl)-7-(4-chlorophenyl)-5-methylbenzo[d]thiazol-6-yl)-2-(tert-butoxy)acetic Acid (11)

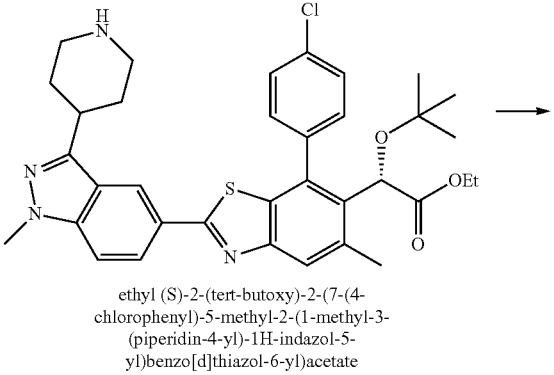

ethyl (S)-2-(tert-butoxy)-2-(7-(4-chlorophenyl)-5-methyl-2-(1-methyl-3-(piperidin-4-yl)-1H-indazol-5-yl)benzo[d]thiazol-6-yl)acetate

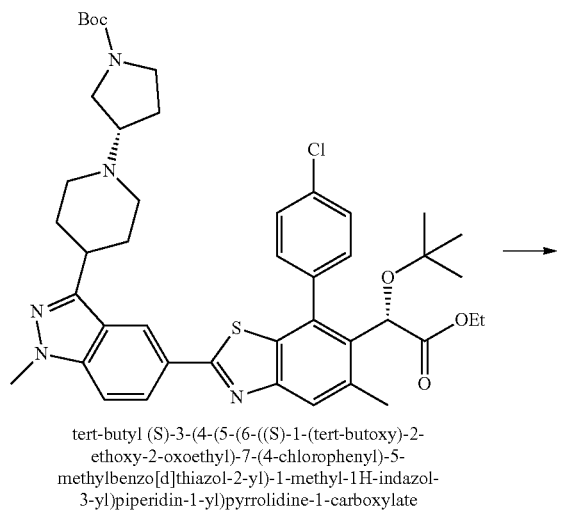

tert-butyl (S)-3-(4-(5-(6-((S)-1-(tert-butoxy)-2-ethoxy-2-oxoethyl)-7-(4-chlorophenyl)-5-methylbenzo[d]thiazol-2-yl)-1-methyl-1H-indazol-3-yl)piperidin-1-yl)pyrrolidine-1-carboxylate

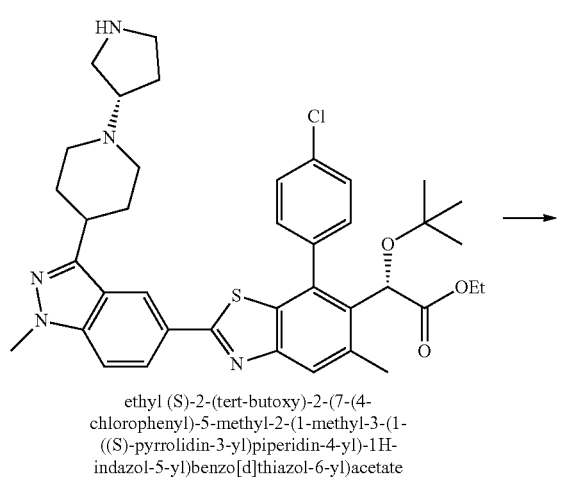

ethyl (S)-2-(tert-butoxy)-2-(7-(4-chlorophenyl)-5-methyl-2-(1-methyl-3-(1-((S)-pyrrolidin-3-yl)piperidin-4-yl)-1H-indazol-5-yl)benzo[d]thiazol-6-yl)acetate

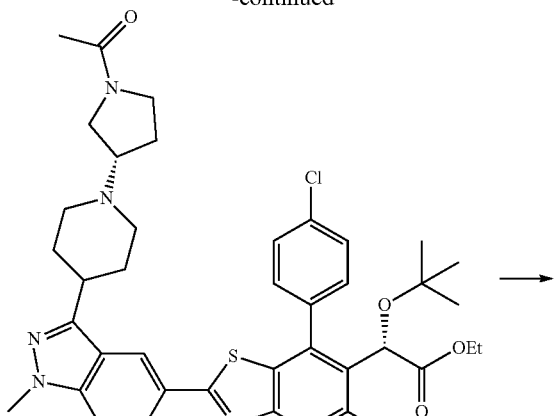

ethyl (S)-2-(2-(3-(1-((S)-1-acetylpyrrolidin-3-yl)piperidin-4-yl)-1-methyl-1H-indazol-5-yl)-7-(4-chlorophenyl)-5-methylbenzo[d]thiazol-6-yl)-2-(tert-butoxy)acetate

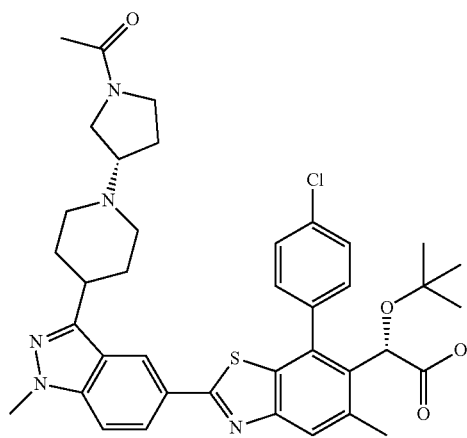

(S)-2-(2-(3-(1-((S)-1-acetylpyrrolidin-3-yl)piperidin-4-yl)-1-methyl-1H-indazol-5-yl)-7-(4-chlorophenyl)-5-methylbenzo[d]thiazol-6-yl)-2-(tert-butoxy)acetate acid Preparation of tert-butyl (S)-3-(4-(5-(6-((S)-1-(tert-butoxy)-2-ethoxy-2-oxoethyl)-7-(4-chlorophenyl)-5-methylbenzo[d]thiazol-2-yl)-1-methyl-1H-indazol-3-yl)piperidin-1-yl)pyrrolidine-1-carboxylate: To a solution of ethyl (S)-2-(tert-butoxy)-2-(7-(4-chlorophenyl)-5-methyl-2-(1-methyl-3-(piperidin-4-yl)-1H-indazol-5-yl)benzo[d]thiazol-6-yl)acetate (1.0 g, 1.6 mmol), tert-butyl 3-oxopyrrolidine-1-carboxylate (2.9 g, 16 mmol), and acetic acid (0.45 mL, 7.9 mmol) in 1,2-dichloroethane (12.0 mL) was added sodium triacetoxyborohydride (1.7 g, 7.9 mmol) and reaction mixture was stirred for 90 minutes. Reaction mixture was quenched with saturated sodium bicarbonate and extracted with dichloromethane (3×). Combined organic layer was washed with saturated sodium chloride, dried (Na$_2$SO$_4$) and concentrated. The residue was purified by CombiFlash (0-20% MeOH/DCM) to give desired product. Diastereomers were separated by Chiralpak IC. LCMS-ESI$^+$: calc'd for C$_{44}$H$_{55}$ClN$_5$O$_5$S: 800.36 (M+H)$^+$; found: 800.41 (M+H)$^+$.

Preparation of ethyl (S)-2-(tert-butoxy)-2-(7-(4-chlorophenyl)-5-methyl-2-(1-methyl-3-(1-((S)-pyrrolidin-3-yl)piperidin-4-yl)-1H-indazol-5-yl)benzo[d]thiazol-6-yl)acetate: tert-Butyl (S)-3-(4-(5-(6-((S)-1-(tert-butoxy)-2-ethoxy-2-oxoethyl)-7-(4-chlorophenyl)-5-methylbenzo[d]thiazol-2-yl)-1-methyl-1H-indazol-3-yl)piperidin-1-yl)pyrrolidine-1-carboxylate (430 mg, 0.537 mmol) was dissolved in 1.25 M HCl in isopropanol (50.0 mL) and stirred for 48 hours. Reaction mixture was quenched with saturated sodium bicarbonate and concentrated. Residue was diluted with water and extracted with ethyl acetate (3×). Combined organic layer was washed with saturated sodium chloride, dried (Na$_2$SO$_4$) and concentrated to give ethyl (S)-2-(tert-butoxy)-2-(7-(4-chlorophenyl)-5-methyl-2-(1-methyl-3-(1-((S)-pyrrolidin-3-yl)piperidin-4-yl)-1H-indazol-5-yl)benzo[d]thiazol-6-yl)acetate that was used in the next step without further purification.

Preparation of ethyl (S)-2-(2-(3-(1-((S)-1-acetylpyrrolidin-3-yl)piperidin-4-yl)-1-methyl-1H-indazol-5-yl)-7-(4-chlorophenyl)-5-methylbenzo[d]thiazol-6-yl)-2-(tert-butoxy)acetate: To a solution of ethyl (S)-2-(tert-butoxy)-2-(7-(4-chlorophenyl)-5-methyl-2-(1-methyl-3-(1-((S)-pyrrolidin-3-yl)piperidin-4-yl)-1H-indazol-5-yl)benzo[d]thiazol-6-yl)acetate (51 mg, 0.073 mmol) and N,N-Diisopropylethylamine (0.13 mL, 0.73 mmol) in dichloromethane (2.5 mL) was added acetyl chloride (0.03 mL, 0.4 mmol) and reaction mixture was stirred for 30 minutes. Reaction mixture was quenched with saturated sodium bicarbonate and extracted with dichloromethane (3×). Combined organic layer was washed with saturated sodium chloride, dried (Na$_2$SO$_4$) and concentrated to give ethyl (S)-2-(2-(3-(1-((S)-1-acetylpyrrolidin-3-yl)piperidin-4-yl)-1-methyl-1H-indazol-5-yl)-7-(4-chlorophenyl)-5-methylbenzo[d]thiazol-6-yl)-2-(tert-butoxy)acetate that was used in the next step without further purification.

Preparation of (S)-2-(2-(3-(1-((S)-1-acetylpyrrolidin-3-yl)piperidin-4-yl)-1-methyl-1H-indazol-5-yl)-7-(4-chlorophenyl)-5-methylbenzo[d]thiazol-6-yl)-2-(tert-butoxy)acetic acid: A solution of ethyl (S)-2-(2-(3-(1-((S)-1-acetylpyrrolidin-3-yl)piperidin-4-yl)-1-methyl-1H-indazol-5-yl)-7-(4-chlorophenyl)-5-methylbenzo[d]thiazol-6-yl)-2-(tert-butoxy)acetate (54 mg, 0.073 mmol) and 2.5 M sodium hydroxide (0.15 mL) in methanol (2.0 mL) was stirred at 55° C. for two hours. Reaction mixture was diluted with DMF/methanol, filtered through syringe filter and purified by Gilson HPLC (Gemini, 5-100% ACN/H$_2$O+0.1% TFA) to give desired product. $^1$H NMR (400 MHz, Methanol-d$_4$) δ 8.46 (s, 1H), 8.12 (d, J=8.9 Hz, 1H), 7.82 (s, 1H), 7.71-7.57 (m, 5H), 5.26 (s, 1H), 4.20-3.91 (m, 6H), 3.92-3.30 (m, 7H), 2.62 (s, 3H), 2.59-2.15 (m, 6H), 2.12 (d, J=11.3 Hz, 3H), 0.98 (s, 9H). LCMS-ESI$^+$: calc'd for C$_{39}$H$_{45}$ClN$_5$O$_4$S: 714.29 (M+H)$^+$; found: 714.33 (M+H)$^+$.

Method J

Example 15. Preparation of (S)-2-(2-(3-(1-((R)-1-acetylpyrrolidin-3-yl)piperidin-4-yl)-1-methyl-1H-indazol-5-yl)-7-(4-chlorophenyl)-5-methylbenzo[d]thiazol-6-yl)-2-(tert-butoxy)acetic Acid (12)

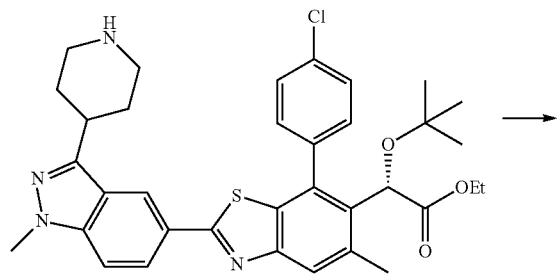

ethyl (S)-2-(tert-butoxy)-2-(7-(4-chlorophenyl)-5-methyl-2-(1-methyl-3-(piperidin-4-yl)-1H-indazol-5-yl)benzo[d]thiazol-6-yl)acetate

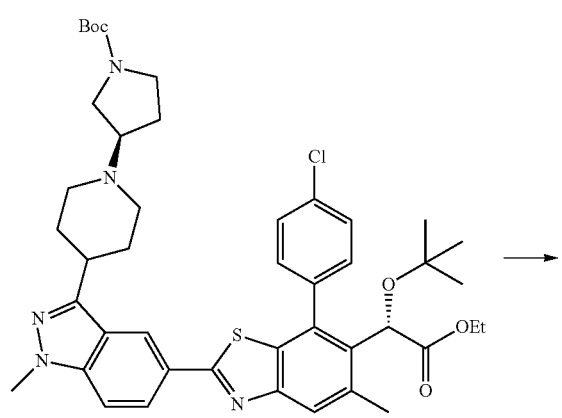

tert-butyl (R)-3-(4-(5-(6-((S)-1-(tert-butoxy)-2-ethoxy-2-oxoethyl)-7-(4-chlorophenyl)-5-methylbenzo[d]thiazol-2-yl)-1-methyl-1H-indzol-3-yl)piperidin-1-yl)pyrrolidine-1-carboxylate

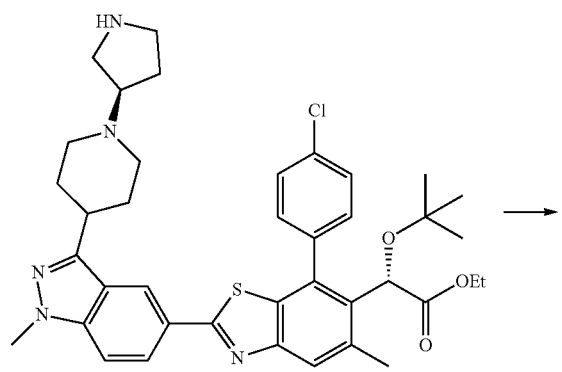

ethyl (S)-2-(tert-butoxy)-2-(7-(4-chlorophenyl)-5-methyl-2-(1-methyl-3-(1-((R)-pyrrolidin-3-yl)piperidin-4-yl)-1H-indazol-5-yl)benzo[d]thiazol-6-yl)acetate

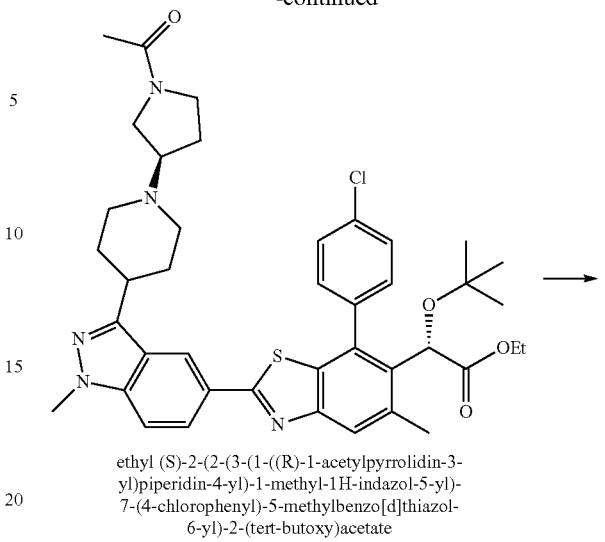

ethyl (S)-2-(2-(3-(1-((R)-1-acetylpyrrolidin-3-yl)piperidin-4-yl)-1-methyl-1H-indazol-5-yl)-7-(4-chlorophenyl)-5-methylbenzo[d]thiazol-6-yl)-2-(tert-butoxy)acetate

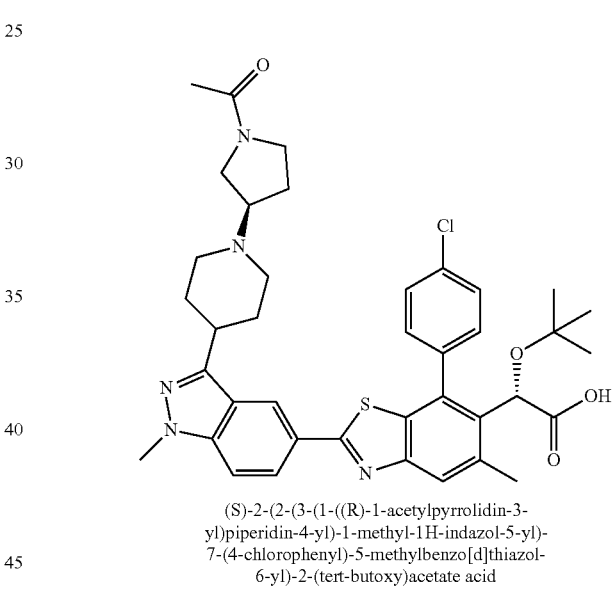

(S)-2-(2-(3-(1-((R)-1-acetylpyrrolidin-3-yl)piperidin-4-yl)-1-methyl-1H-indazol-5-yl)-7-(4-chlorophenyl)-5-methylbenzo[d]thiazol-6-yl)-2-(tert-butoxy)acetate acid Preparation of tert-butyl (R)-3-(4-(5-(6-((S)-1-(tert-butoxy)-2-ethoxy-2-oxoethyl)-7-(4-chlorophenyl)-5-methylbenzo[d]thiazol-2-yl)-1-methyl-1H-indazol-3-yl)piperidin-1-yl)pyrrolidine-1-carboxylate: To a solution of ethyl (S)-2-(tert-butoxy)-2-(7-(4-chlorophenyl)-5-methyl-2-(1-methyl-3-(piperidin-4-yl)-1H-indazol-5-yl)benzo[d]thiazol-6-yl) acetate (1.0 g, 1.6 mmol), tert-butyl 3-oxopyrrolidine-1-carboxylate (2.9 g, 16 mmol), and acetic acid (0.45 mL, 7.9 mmol) in 1,2-dichloroethane (12.0 mL) was added sodium triacetoxyhorohydride (1.7 g, 7.9 mmol) and reaction mixture was stirred for 90 minutes. Reaction mixture was quenched with saturated sodium bicarbonate and extracted with dichloromethane (3×). Combined organic layer was washed with saturated sodium chloride, dried ($Na_2SO_4$) and concentrated. The residue was purified by CombiFlash (0-20% MeOH/DCM) to give desired product. Diastereomers were separated by Chiralpak IC. LCMS-ESI+: calc'd for $C_{44}H_{55}ClN_5O_5S$: 800.36 (M+H)+; found: 800.41 (M+H)+.

Preparation of ethyl (S)-2-(tert-butoxy)-2-(7-(4-chlorophenyl)-5-methyl-2-(1-methyl-3-(1-((R)-pyrrolidin-3-yl)piperidin-4-yl)-1H-indazol-5-yl)benzo[d]thiazol-6-yl)acetate: tert-Butyl (R)-3-(4-(5-(6-((S)-1-(tert-butoxy)-2-ethoxy-2-oxoethyl)-7-(4-chlorophenyl)-5-methylbenzo[d]thiazol-2-yl)-1-methyl-1H-indazol-3-yl)piperidin-1-yl)pyrrolidine-1-carboxylate (430 mg, 0.537 mmol) was dissolved in 1.25 M HCl in isopropanol (50.0 mL) and stirred for 48 hours. Reaction mixture was quenched with saturated sodium bicarbonate and concentrated. Residue was diluted with water and extracted with ethyl acetate (3×). Combined organic layer was washed with saturated sodium chloride, dried ($Na_2SO_4$) and concentrated to give ethyl (S)-2-(tert-butoxy)-2-(7-(4-chlorophenyl)-5-methyl-2-(1-methyl-3-(1-((R)-pyrrolidin-3-yl)piperidin-4-yl)-1H-indazol-5-yl)benzo[d]thiazol-6-yl)acetate that was used in the next step without further purification.

Preparation of ethyl (S)-2-(2-(3-(1-((R)-1-acetylpyrrolidin-3-yl)piperidin-4-yl)-1-methyl-1H-indazol-5-yl)-7-(4-chlorophenyl)-5-methylbenzo[d]thiazol-6-yl)-2-(tert butoxy)acetate: To a solution of ethyl (S)-2-(tert-butoxy)-2-(7-(4-chlorophenyl)-5-methyl-2-(1-methyl-3-(1-((R)-pyrrolidin-3-yl)piperidin-4-yl)-1H-indazol-5-yl)benzo[d]thiazol-6-yl)acetate (51 mg, 0.073 mmol) and N,N-Diisopropylethylamine (0.13 mL, 0.73 mmol) in dichloromethane (2.50 mL) was added acetyl chloride (0.03 mL, 0.4 mmol) and reaction mixture was stirred for 30 minutes. Reaction mixture was quenched with saturated sodium bicarbonate and extracted with dichloromethane (3×). Combined organic layer was washed with saturated sodium chloride, dried ($Na_2SO_4$) and concentrated to give ethyl (S)-2-(2-(3-(1-((R)-1-acetylpyrrolidin-3-yl)piperidin-4-yl)-1-methyl-1H-indazol-5-yl)-7-(4-chlorophenyl)-5-methylbenzo[d]thiazol-6-yl)-2-(tert-butoxy)acetate that was used in the next step without further purification.

Preparation of (S)-2-(2-(3-(1-((R)-1-acetylpyrrolidin-3-yl)piperidin-4-yl)-1-methyl-1H-indazol-5-yl)-7-(4-chlorophenyl)-5-methylbenzo[d]thiazol-6-yl)-2-(tert-butoxy)acetic acid: A solution of ethyl (S)-2-(2-(3-(1-((R)-1-acetylpyrrolidin-3-yl)piperidin-4-yl)-1-methyl-1H-indazol-5-yl)-7-(4-chlorophenyl)-5-methylbenzo[d]thiazol-6-yl)-2-(tert-butoxy)acetate (54 mg, 0.073 mmol) and 2.5 M sodium hydroxide (0.15 mL) in methanol (2.0 mL) was stirred at 55° C. for two hours. Reaction mixture was diluted with DMF/methanol, filtered through syringe filter and purified by Gilson HPLC (Gemini, 5-100% ACN/$H_2O$+0.1% TFA) to give desired product. $^1$H NMR (400 MHz, Methanol-$d_4$) δ 8.46 (s, 1H), 8.13 (d, J=8.9 Hz, 1H), 7.82 (d, J=0.8 Hz, 1H), 7.72-7.56 (m, 5H), 5.26 (s, 1H), 4.23-3.93 (m, 5H), 3.92-3.30 (m, 8H), 2.62 (s, 3H), 2.61-2.16 (m, 6H), 2.12 (d, J=11.3 Hz, 3H), 0.99 (s, 9H). LCMS-ESI+: calc'd for $C_{39}H_{45}ClN_5O_4S$: 714.29 (M+H)+; found: 714.33 (M+H)+.

Method K

Example 16. Preparation of (2S)-2-(tert-butoxy)-2-(7-(4-chlorophenyl)-5-methyl-2-(1-methyl-3-(3-(oxetan-3-yl)-3,8-diazabicyclo[3.2.1]octan-8-yl)-1H-indazol-5-yl)benzo[d]thiazol-6-yl)acetic Acid (13)

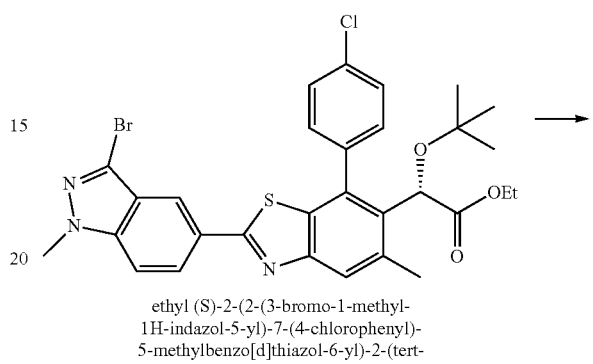

ethyl (S)-2-(2-(3-bromo-1-methyl-1H-indazol-5-yl)-7-(4-chlorophenyl)-5-methylbenzo[d]thiazol-6-yl)-2-(tert-butoxy)acetate

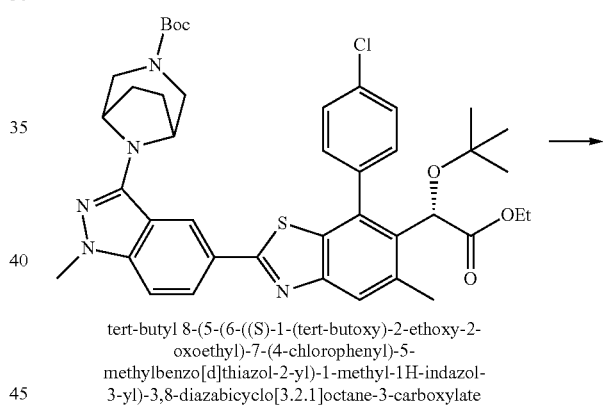

tert-butyl 8-(5-(6-((S)-1-(tert-butoxy)-2-ethoxy-2-oxoethyl)-7-(4-chlorophenyl)-5-methylbenzo[d]thiazol-2-yl)-1-methyl-1H-indazol-3-yl)-3,8-diazabicyclo[3.2.1]octane-3-carboxylate

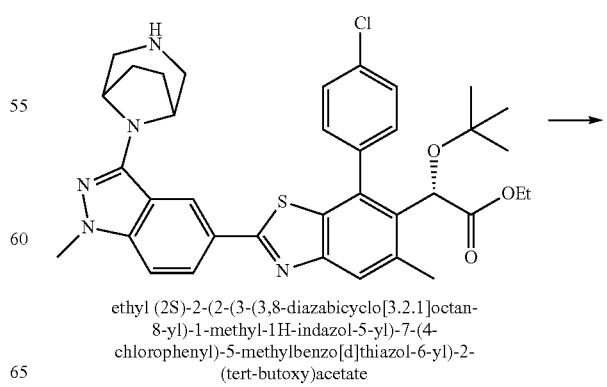

ethyl (2S)-2-(2-(3-(3,8-diazabicyclo[3.2.1]octan-8-yl)-1-methyl-1H-indazol-5-yl)-7-(4-chlorophenyl)-5-methylbenzo[d]thiazol-6-yl)-2-(tert-butoxy)acetate

117

-continued

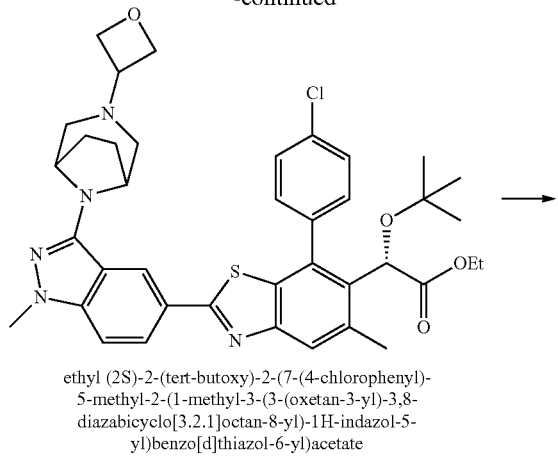

ethyl (2S)-2-(tert-butoxy)-2-(7-(4-chlorophenyl)-
5-methyl-2-(1-methyl-3-(3-(oxetan-3-yl)-3,8-
diazabicyclo[3.2.1]octan-8-yl)-1H-indazol-5-
yl)benzo[d]thiazol-6-yl)acetate

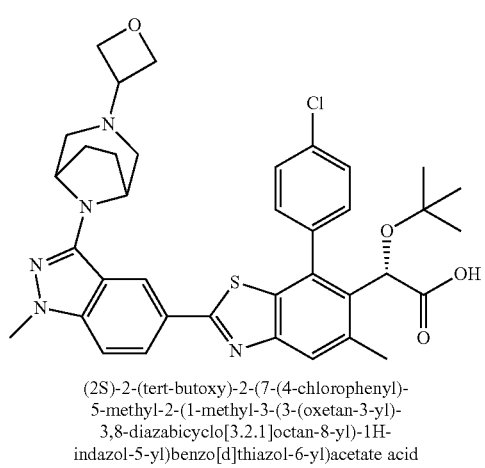 [SMILES: Cc1cc2nc(-c3ccc4c(c3)c(N3C5CCC3CN(C3COC3)C5)nn4C)sc2c(-c2ccc(Cl)cc2)c1[C@H](OC(C)(C)C)C(=O)O]

(2S)-2-(tert-butoxy)-2-(7-(4-chlorophenyl)-
5-methyl-2-(1-methyl-3-(3-(oxetan-3-yl)-
3,8-diazabicyclo[3.2.1]octan-8-yl)-1H-
indazol-5-yl)benzo[d]thiazol-6-yl)acetate acid Preparation of tert-butyl 8-(5-(6-((S)-1-(tert-butoxy)-2-ethoxy-2-oxoethyl)-7-(4-chlorophenyl)-5-methylbenzo[d]thiazol-2-yl)-1-methyl-1H-indazol-3-yl)-3,8-diazabicyclo[3.2.1]octane-3-carboxylate: A suspension of $Pd_2(dba)_3$ (7 mg, 0.008 mmol), XPhos (4 mg, 0.008 mmol), and cesium carbonate (130 mg, 0.400 mmol) in dioxane (2.0 mL) was stirred for 30 minutes, followed by the addition of ethyl (S)-2-(2-(3-bromo-1-methyl-1H-indazol-5-yl)-7-(4-chlorophenyl)-5-methylbenzo[d]thiazol-6-yl)-2-(tert-butoxy)acetate (50 mg, 0.080 mmol) and tert-butyl 3,8-diazabicyclo[3.2.1]octane-3-carboxylate (51 mg, 0.24 mmol). Reaction mixture was sparged with argon and heated to 100° C. for one hour. Reaction mixture was quenched with saturated sodium bicarbonate and extracted with ethyl acetate (3×). Combined organic layer was washed with saturated sodium chloride, dried ($Na_2SO_4$) and concentrated. The residue was purified by CombiFlash (0-100% EtOAc/Hex) and concentrated to give desired product. LCMS-ESI⁺: calc'd for $C_{41}H_{49}ClN_5O_5S$: 738.31 (M+H)⁺; found: 757.41 (M+H)⁺.

118

Preparation of ethyl (2S)-2-(2-(3-(3,8-diazabicyclo[3.2.1]octan-8-yl)-1-methyl-1H-indazol-5-yl)-7-(4-chlorophenyl)-5-methylbenzo[d]thiazol-6-yl)-2-(tert-butoxy)acetate: A solution of tert-butyl 8-(5-(6-((S)-1-(tert-butoxy)-2-ethoxy-2-oxoethyl)-7-(4-chlorophenyl)-5-methylbenzo[d]thiazol-2-yl)-1-methyl-1H-indazol-3-yl)-3,8-diazabicyclo[3.2.1]octane-3-carboxylate (32 mg, 0.042 mmol) in 1.25 M HCl in isopropanol (5.0 mL) was stirred for 36 hours. Reaction mixture was quenched with saturated sedum bicarbonate and concentrated. Residue was diluted with water and extracted with ethyl acetate (3×). Combined organic layer was washed with saturated sodium chloride, dried ($Na_2SO_4$) and concentrated. Reaction mixture was dissolved in DMF/methanol, filtered through syringe filter and purified by Gilson HPLC (Gemini, 5-100% ACN/$H_2O$+0.1% TFA). LCMS-ESI⁺: calc'd for $C_{36}H_{41}ClN_5O_3S$: 658.26 (M+H)⁺; found: 658.54 (M+H)⁺.

Preparation of ethyl (2S)-2-(tert-butoxy)-2-(7-(4-chlorophenyl)-5-methyl-2-(1-methyl-3-(3-(oxetan-3-yl)-3,8-diazabicyclo[3.2.1]octan-8-yl)-1H-indazol-5-yl)benzo[d]thiazol-6-yl)acetate: To a solution of ethyl (2S)-2-(2-(3-(3,8-diazabicyclo[3.2.1]octan-8-yl)-1-methyl-1H-indazol-5-yl)-7-(4-chlorophenyl)-5-methylbenzo[d]thiazol-6-yl)-2-(tert-butoxy)acetate (25 mg, 0.040 mmol) and oxetan-3-one (41 mg, 0.57 mmol) in methanol (1.0 mL) at 0° C. was added acetic acid (0.012 mL, 0.21 mmol) and sodium cyanoborohydride (24 mg, 0.38 mmol). Reaction mixture was stirred and allowed to warm to room temperature over 16 hours. Reaction mixture was quenched with saturated sodium bicarbonate and extracted with ethyl acetate (3×). Combined organic layer was washed with saturated sodium chloride, dried ($Na_2SO_4$) and concentrated. Residue was purified by CombiFlash (0-100% EtOAc/Hex) to give desired product. LCMS-ESI⁺: calc'd for $C_{39}H_{45}ClN_5O_4S$: 714.29 (M+H)⁺; found: 714.04 (M+H)⁺.

Preparation of (2S)-2-(tert-butoxy)-2-(7-(4-chlorophenyl)-5-methyl-2-(1-methyl-3-(3-(oxetan-3-yl)-3,8-diazabicyclo[3.2.1]octan-8-yl)-1H-indazol-5-yl)benzo[d]thiazol-6-yl)acetic acid: A solution of ethyl (2S)-2-(tert-butoxy)-2-(7-(4-chlorophenyl)-5-methyl-2-(1-methyl-3-(3-(oxetan-3-yl)-3,8-diazabicyclo[3.2.1]octan-8-yl)-1H-indazol-5-yl)benzo[d]thiazol-6-yl)acetate (15 mg, 0.022 mmol), 2.0 M sodium hydroxide (0.54 mL), and ethylene glycol (0.2 mL) in methanol (1.0 mL) was stirred at 60° C. for three hours. Reaction mixture was diluted with DMF/methanol, filtered through syringe filter and purified by Gilson HPLC (Gemini, 5-100% ACN/$H_2O$+0.1% TFA) without workup to give desired product. ¹H NMR (400 MHz, Methanol-d₄) δ 8.38 (s, 1H), 8.01 (dd, J=8.9, 1.6 Hz, 1H), 7.78 (s, 1H), 7.71-7.66 (m, 1H), 7.61-7.54 (m, 3H), 7.50 (d, J=8.9 Hz, 1H), 5.25 (s, 1H), 4.89-4.76 (m, 4H), 4.66 (s, 2H), 4.43 (p, J=6.5 Hz, 1H), 3.91 (s, 3H), 3.52 (d, J=12.8 Hz, 2H), 3.44-3.36 (m, 2H), 2.61 (s, 3H), 2.41-2.31 (m, 2H), 2.17-2.10 (m, 2H), 0.98 (s, 9H). LCMS-ESI⁺: calc'd for $C_{37}H_{41}ClN_5O_4S$: 686.26 (M+H)⁺; found: 686.22 (M+H)⁺.

Method L
Example 17. Preparation of (S)-2-(tert-butoxy)-2-(7-(4-chlorophenyl)-2-(1-(difluoromethyl)-3-(1-(1-(methoxycarbonyl)azetidin-3-yl)piperidin-4-yl)-1H-pyrazolo[4,3-b]pyridin-5-yl)-5-methylbenzo[d]thiazol-6-yl)acetic Acid (14)
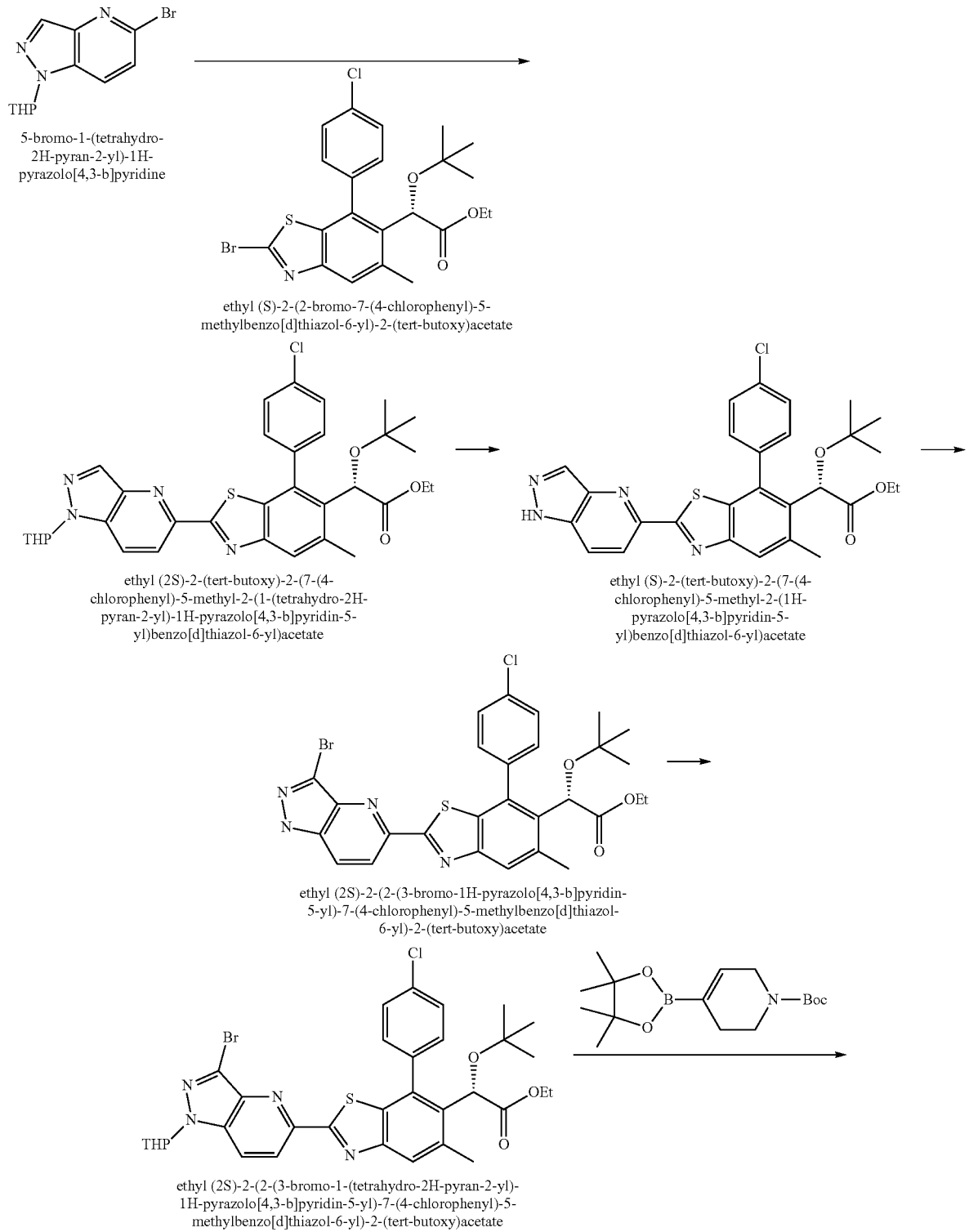

-continued

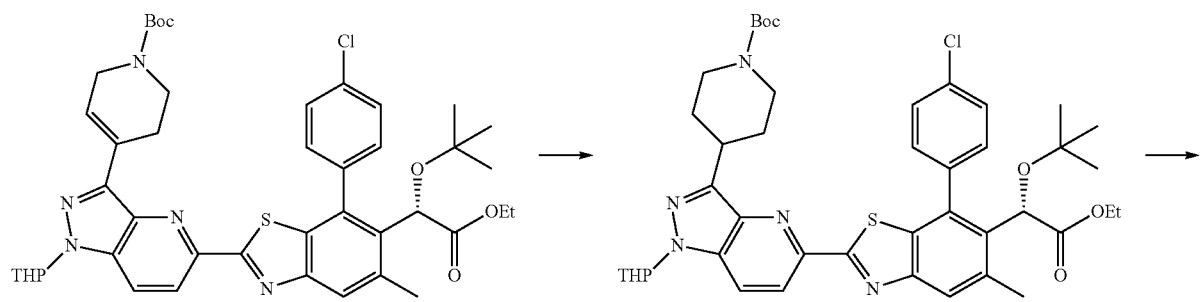

121 tert-butyl 4-(5-(6-((S)-1-(tert-butoxy)-2-ethoxy-2-
oxoethyl)-7-(4-chlorophenyl)-5-methylbenzo[d]thiazol-
2-yl)-1-(tetrahydro-2H-pyran-2-yl)-1H-pyrazolo[4,3-
b]pyridin-3-yl)-3,6-dihydropyridine-1(2H)-carboxylate

122 tert-butyl 4-(5-(6-((S)-1-(tert-butoxy)-2-ethoxy-2-
oxoethyl)-7-(4-chlorophenyl)-5-methylbenzo[d]thiazol-
2-yl)-1-(tetrahydro-2H-pyran-2-yl)-1H-pyrazolo[4,3-
b]pyridin-3-yl)piperidine-1-carboxylate

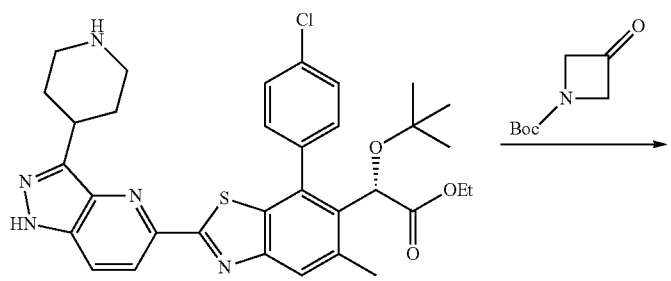

ethyl (S)-2-(tert-butoxy)-2-(7-(4-
chlorophenyl)-5-methyl-2-(3-(piperidin-
4-yl)-1H-pyrazolo[4,3-b]pyridin-5-
yl)benzo[d]thiazol-6-yl)acetate

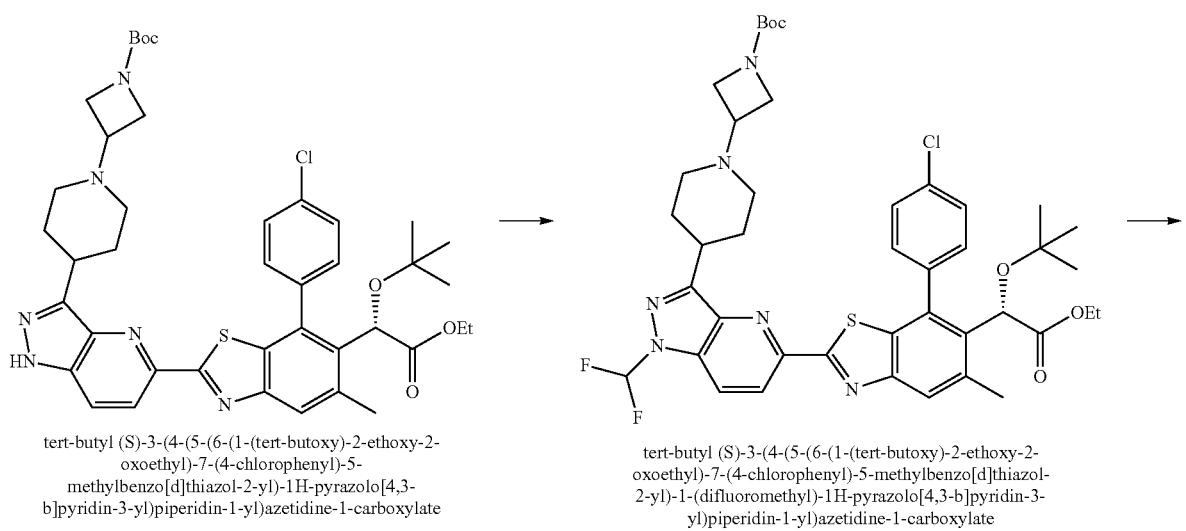

tert-butyl (S)-3-(4-(5-(6-(1-(tert-butoxy)-2-ethoxy-2-
oxoethyl)-7-(4-chlorophenyl)-5-
methylbenzo[d]thiazol-2-yl)-1H-pyrazolo[4,3-
b]pyridin-3-yl)piperidin-1-yl)azetidine-1-carboxylate tert-butyl (S)-3-(4-(5-(6-(1-(tert-butoxy)-2-ethoxy-2-
oxoethyl)-7-(4-chlorophenyl)-5-methylbenzo[d]thiazol-
2-yl)-1-(difluoromethyl)-1H-pyrazolo[4,3-b]pyridin-3-
yl)piperidin-1-yl)azetidine-1-carboxylate

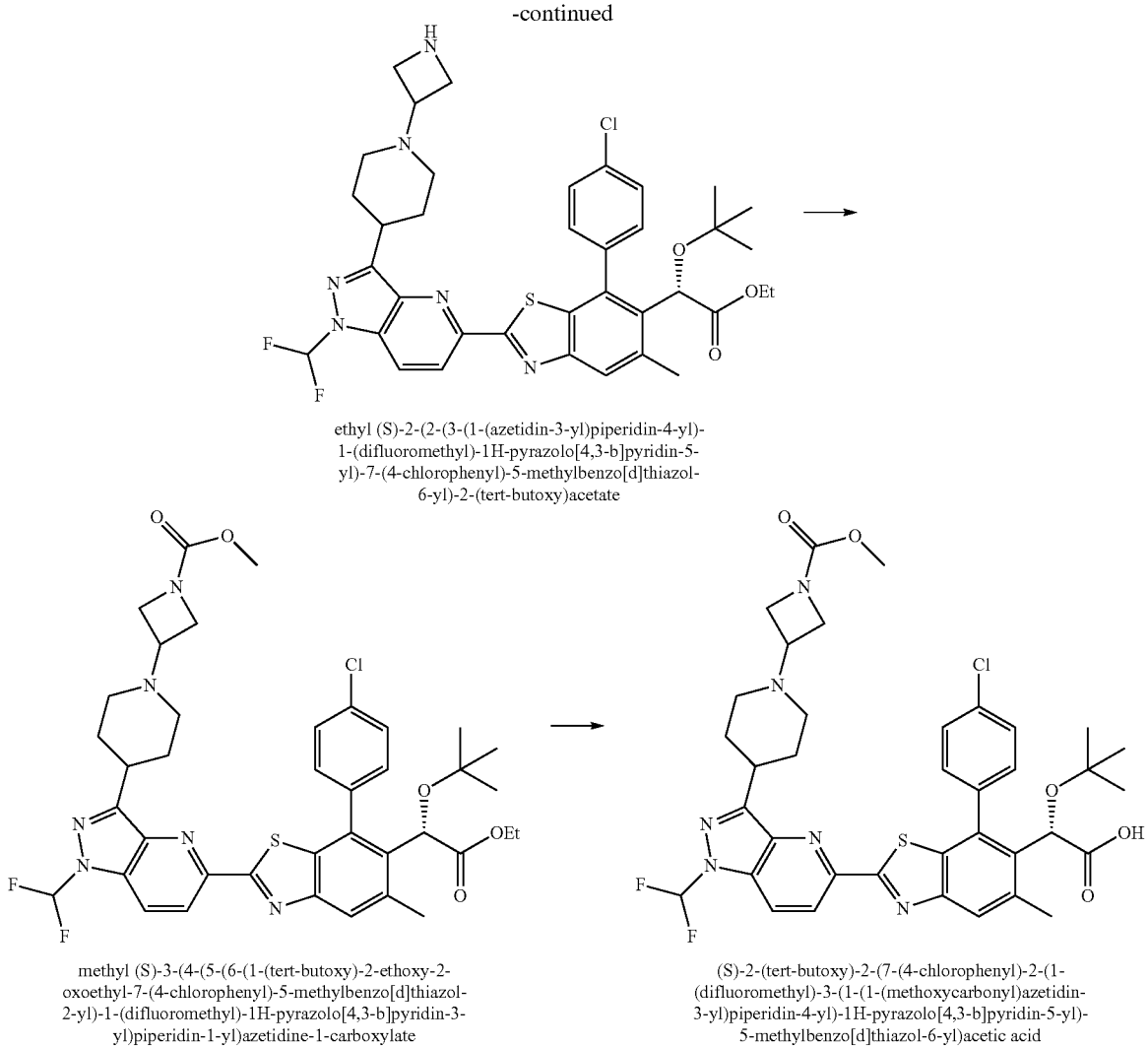

ethyl (S)-2-(2-(3-(1-(azetidin-3-yl)piperidin-4-yl)-1-(difluoromethyl)-1H-pyrazolo[4,3-b]pyridin-5-yl)-7-(4-chlorophenyl)-5-methylbenzo[d]thiazol-6-yl)-2-(tert-butoxy)acetate methyl (S)-3-(4-(5-(6-(1-(tert-butoxy)-2-ethoxy-2-oxoethyl)-7-(4-chlorophenyl)-5-methylbenzo[d]thiazol-2-yl)-1-(difluoromethyl)-1H-pyrazolo[4,3-b]pyridin-3-yl)piperidin-1-yl)azetidine-1-carboxylate (S)-2-(tert-butoxy)-2-(7-(4-chlorophenyl)-2-(1-(difluoromethyl)-3-(1-(1-(methoxycarbonyl)azetidin-3-yl)piperidin-4-yl)-1H-pyrazolo[4,3-b]pyridin-5-yl)-5-methylbenzo[d]thiazol-6-yl)acetic acid Preparation of ethyl (2S)-2-(tert-butoxy)-2-(7-(4-chlorophenyl)-5-methyl-2-(1-(tetrahydro-2H-pyran-2-yl)-1H-pyrazolo[4,3-b]pyridin-5-yl)benzo[d]thiazol-6-yl)acetate:
To an oven-dried round bottom flask was charged 5-bromo-1-(tetrahydro-2H-pyran-2-yl)-1H-pyrazolo[4,3-b]pyridine (4.09 g, 14.5 mmol, 1.80 equiv), which was then dissolved in 5:1 toluene:hexanes (48 mL). The reaction solution was then cooled to −40° C. and a solution of n-butyllithium in hexanes (2.50 M, 6.12 mL, 15.3 mmol, 1.90 equiv) was added dropwise. Upon completion of addition, the reaction mixture was immediately cooled to −78° C. and stirred for 4.5 h. A solution of zinc chloride in 2-methyltetrahydrofuran (1.90 M, 8.90 mL, 16.9 mmol, 2.10 equiv) was then added, followed by 22 mL of tetrahydrofuran. After stirring at −78° C. for 25 min, the reaction mixture was warmed to 0° C. and stirred for an additional 1.5 h. The reaction was then allowed to warm to room temperature and was stirred for an additional 1 h. Ethyl (S)-2-(2-bromo-7-(4-chlorophenyl)-5-methylbenzo[d]thiazol-6-yl)-2-(tert-butoxy)acetate (4.00 g, 8.05 mmol, 1.00 equiv) and Pd(PPh$_3$)$_4$ (930 mg, 0.810 mmol, 0.10 equiv) were then added. The reaction mixture was sparged with argon for 10 min and subsequently heated to 60° C. After stirring for 1 h, the reaction was cooled to room temperature. 1 M hydrochloric acid was added until all solids dissolved. Saturated aqueous NaHCO$_3$ was added until pH-7 was reached. The reaction was then diluted with EtOAc (60 mL) and the organic and aqueous layers were separated. The aqueous layer was extracted with additional EtOAc (3×30 mL) and the organic layers were all combined, washed with brine (50 mL), dried over anhydrous MgSO$_4$, filtered, and concentrated. The crude product was purified via CombiFlash (Peeke Scientific, silica gel, gradient: 0-100% EtOAc/hex) to afford the desired product as a pale yellow flocculent solid as a 1:1 mixture of diastereomers. 1H NMR (400 MHz, CDCl$_3$) δ 8.61-8.38 (m, 2H), 8.28 (s, 2H), 8.09 (d, J=8.9 Hz, 2H), 7.93 (s, 2H), 7.51 (d, J=14.8 Hz, 8H), 5.77 (dt, J=8.3, 2.3 Hz, 2H), 5.19 (s, 2H), 4.21 (qd, J=7.1, 3.5 Hz, 4H), 4.07-3.96 (m, 2H), 3.86-3.71 (m, 2H), 2.61 (s, 6H), 2.56-2.39 (m, 2H), 2.23-2.07 (m, 4H), 1.89-1.62 (m, 6H), 1.25 (t, J=7.1 Hz, 6H), 0.99 (s, 18H). LCMS-ESI+: calc'd for C$_{33}$H$_{36}$ClN$_4$O$_4$S: 619.21 [M+H]$^+$; found: 619.11.

Preparation of ethyl (S)-2-(tert-butoxy)-2-(7-(4-chlorophenyl)-5-methyl-2-(1H-pyrazolo[4,3-b]pyridin-5-yl)benzo[d]thiazol-6-yl)acetate: To a round bottom flask was charged ethyl (2S)-2-(tert-butoxy)-2-(7-(4-chlorophenyl)-5-methyl-2-(1-(tetrahydro-2H-pyran-2-yl)-1H-pyrazolo[4,3-b]pyridin-5-yl)benzo[d]thiazol-6-yl)acetate (2.00 g, 3.23 mmol, 1.00 equiv), followed by a solution of hydrochloric acid in isopropanol (1.25 M, 129 mL). The reaction was allowed to stir at room temperature for 2 days and was subsequently quenched with saturated aqueous NaHCO$_3$ until pH-7. The reaction was concentrated in vacuo to remove all volatiles, then diluted with EtOAc (100 mL) and water (100 mL). The organic and aqueous layers were separated. The aqueous layer was extracted with additional EtOAc (3×80 mL) and the organic layers were all combined, washed with brine (150 mL), dried over anhydrous MgSO$_4$, filtered, and concentrated. The crude product was purified via CombiFlash (Peeke Scientific, silica gel, gradient: 0-100% EtOAc/hex) to afford the desired product. $^1$H NMR (400 MHz, CDCl$_3$) δ 8.62-8.41 (m, 1H), 8.35 (s, 1H), 7.98-7.85 (m, 2H), 7.59-7.43 (m, 4H), 5.20 (s, 1H), 4.23 (qt, J=7.0, 3.5 Hz, 2H), 2.61 (s, 3H), 1.26 (t, J=7.1 Hz, 3H), 0.99 (d, J=0.9 Hz, 9H). LCMS-ESI+: calc'd for C$_{28}$H$_{28}$ClN$_4$O$_3$S: 535.16 [M+H]$^+$; found: 535.19.

Preparation of ethyl (S)-2-(2-(3-bromo-1H-pyrazolo[4,3-b]pyridin-5-yl)-7-(4-chlorophenyl)-5-methylbenzo[d]thiazol-6-yl)-2-(tert-butoxy)acetate: To a round-bottom flask was charged ethyl (S)-2-(tert-butoxy)-2-(7-(4-chlorophenyl)-5-methyl-2-(1H-pyrazolo[4,3-b]pyridin-5-yl)benzo[d]thiazol-6-yl)acetate (1.73 g, 3.23 mmol, 1.00 equiv), which was then dissolved in dichloromethane (35 mL). The solution was cooled to 0° C., then NaHCO$_3$ (326 mg, 3.90 mmol, 1.20 equiv) was added. A 1 M stock solution of bromine in dichloromethane was then added dropwise (3.88 mL, 3.90 mmol, 1.20 equiv). The reaction was warmed to room temperature and stirred for 1 day. The reaction was quenched with saturated aqueous Na$_2$S$_2$O$_3$ (15 mL) and the organic and aqueous layers were separated. The aqueous layer was extracted with additional dichloromethane (3×40 mL) and the organic layers were combined, dried over anhydrous MgSO$_4$, filtered, and concentrated. The crude product was purified via CombiFlash (Peeke Scientific, silica gel, gradient: 0-100% EtOAc/hex) to afford the desired product as a pale flocculent yellow solid. $^1$H NMR (400 MHz, CDCl$_3$) δ 11.15 (br s, 1H), 8.35 (d, J=8.9 Hz, 1H), 7.80-7.65 (m, 2H), 7.59-7.41 (m, 4H), 5.23 (s, 1H), 4.26 (qd, J=7.1, 2.0 Hz, 2H), 2.57 (s, 3H), 1.29 (t, J=7.0 Hz, 3H), 0.99 (s, 9H). LCMS-ESI+: calc'd for C$_{28}$H$_{27}$BrClN$_4$O$_3$S: 613.07 [M+H]$^+$; found: 613.03.

Preparation of ethyl (2S)-2-(2-(3-bromo-1-(tetrahydro-2H-pyran-2-yl)-1H-pyrazolo[4,3-b]pyridin-5-yl)-7-(4-chlorophenyl)-5-methylbenzo[d]thiazol-6-yl)-2-(tert-butoxy)acetate: To a round bottom flask with stir bar was added ethyl (S)-2-(2-(3-bromo-1H-pyrazolo[4,3-b]pyridin-5-yl)-7-(4-chlorophenyl)-5-methylbenzo[d]thiazol-6-yl)-2-(tert-butoxy)acetate (807 mg, 1.31 mmol, 1.00 equiv), followed by dichloromethane (12 mL). 3,4-Dihydro-2H-pyran (144 μL, 1.58 mmol, 1.20 equiv), and p-TsOH (23 mg, 0.13 mmol, 0.10 equiv) were then added. The reaction mixture was heated to 45° C. and stirred for 4 h. After cooling to room temperature, the reaction was quenched with saturated aqueous NaHCO$_3$. The organic and aqueous layers were separated and the aqueous layer was extracted with additional dichloromethane (3×10 mL). The organic layers were combined, dried over anhydrous MgSO$_4$, filtered, and concentrated. The crude product was purified via CombiFlash (Peeke Scientific, silica gel, gradient: 0-100% EtOAc/hex) to yield the product as a 1:1 mixture of diastereomers as a flocculent solid. $^1$H NMR (400 MHz, CDCl$_3$) δ 8.49 (d, J=8.9 Hz, 2H), 8.06 (dd, J=9.0, 2.1 Hz, 2H), 7.90 (s, 2H), 7.62-7.42 (m, 8H), 5.72 (dt, J=8.7, 2.8 Hz, 2H), 5.18 (s, 2H), 4.22 (qt, J=7.1, 3.9 Hz, 4H), 4.05-3.95 (m, 2H), 3.75 (t, J=9.4 Hz, 2H), 2.61 (s, 6H), 2.54-2.38 (m, 2H), 2.19-2.06 (m, 4H), 1.71 (td, J=16.5, 16.1, 10.3 Hz, 6H), 1.26 (t, J=6.9 Hz, 3H), 1.25 (t, J=7.1 Hz, 3H), 0.98 (s, 18H). LCMS-ESI+: calc'd for C$_{33}$H$_{35}$BrClN$_4$O$_4$S: 697.13 [M+H]$^+$; found: 696.98.

Preparation of tert-butyl 4-(5-(6-((S)-1-(tert-butoxy)-2-ethoxy-2-oxoethyl)-7-(4-chlorophenyl)-5-methylbenzo[d]thiazol-2-yl)-1-(tetrahydro-2H-pyran-2-yl)-1H-pyrazolo[4,3-b]pyridin-3-yl)-3,6-dihydropyridine-1(2H)-carboxylate: To a microwave tube was charged ethyl (2S)-2-(2-(3-bromo-1-(tetrahydro-2H-pyran-2-yl)-1H-pyrazolo[4,3-b]pyridin-5-yl)-7-(4-chlorophenyl)-5-methylbenzo[d]thiazol-6-yl)-2-(tert-butoxy)acetate (900 mg, 1.29 mmol, 1.00 equiv), tert-butyl 4-(4,4,5,5-tetramethyl-1,3,2-dioxaborolan-2-yl)-3,6-dihydropyridine-1(2H)-carboxylate (598 mg, 1.93 mmol, 1.50 equiv), Pd(PPh$_3$)$_4$ (220 mg, 0.19 mmol, 0.15 equiv), and 2 M K$_2$CO$_3$ (1.93 mL, 3.87 mmol, 3.00 equiv). Dioxane (13 mL) was added and the reaction mixture was sparged with argon for 10 min before sealing and heating to 110° C., followed by stirring for 4 h. After cooling to room temperature, water (15 mL) and EtOAc (30 mL) were added to the reaction. The organic and aqueous layers were separated and the aqueous layer was extracted with additional EtOAc (3×20 mL). The organic layers were combined, washed with brine (50 mL), dried over anhydrous MgSO$_4$, filtered, and concentrated. The crude product was purified via CombiFlash (Peeke Scientific, silica gel, gradient: 0-100% EtOAc/hex) to yield the product as a pale yellow flocculent solid. $^1$H NMR (400 MHz, CDCl$_3$) δ 8.41 (d, J=8.8 Hz, 2H), 8.01 (dd, J=8.9, 2.7 Hz, 2H), 7.88 (s, 2H), 7.64-7.46 (m, 8H), 7.48-7.32 (m, 2H), 5.71 (dt, J=9.2, 3.0 Hz, 2H), 5.17 (s, 2H), 4.28-4.13 (m, 8H), 4.06-3.94 (m, 2H), 3.81-3.58 (m, 8H), 2.92-2.69 (m, 4H), 2.61 (s, 6H), 2.57-2.38 (m, 2H), 2.21-2.04 (m, 4H), 1.84-1.60 (m, 4H), 1.51 (s, 18H), 1.26 (t, J=7.1 Hz, 6H), 0.98 (s, 18H). LCMS-ESI+: calc'd for C$_{43}$H$_{51}$ClN$_5$O$_6$S: 800.32 [M+H]$^+$; found: 799.87.

Preparation of tert-butyl 4-(5-(6-((S)-1-(tert-butoxy)-2-ethoxy-2-oxoethyl)-7-(4-chlorophenyl)-5-methylbenzo[d]thiazol-2-yl)-1-(tetrahydro-2H-pyran-2-yl)-1H-pyrazolo[4,3-b]pyridin-3-yl)piperidine-1-carboxylate: To a round-bottom flask was added tert-butyl 4-(5-(6-((S)-1-(tert-butoxy)-2-ethoxy-2-oxoethyl)-7-(4-chlorophenyl)-5-methylbenzo[d]thiazol-2-yl)-1-(tetrahydro-2H-pyran-2-yl)-1H-pyrazolo[4,3-b]pyridin-3-yl)-3,6-dihydropyridine-1(2H)-carboxylate (2.17 g, 2.71 mmol, 1.00 equiv), followed by EtOH (100 mL). Rhodium on alumina (5 wt. % loading, 1.67 g, 0.813 mmol, 0.30 equiv) was then added and the reaction vessel was equipped with a hydrogen balloon. Evacuation of the flask followed by backfilling with hydrogen gas was conducted three times. The reaction mixture was allowed to stir for 12 h, then an additional portion of rhodium on alumina (1.9 g) was added. Every 3 h, the reaction vessel was charged with 2 g of rhodium on alumina for a total of three additional portions. After stirring for an additional 12 h, the reaction was filtered through a pad of Celite and concentrated. The crude product was purified via CombiFlash (Peeke Scientific, silica gel, gradient: 0-100% EtOAc/hex) to yield the product as a flocculent solid. $^1$H NMR (400 MHz, CDCl$_3$) δ 8.62-8.48 (m, 2H), 8.09-7.90 (m, 4H), 7.65-7.44 (m, 8H), 5.77-5.60 (m, 2H), 5.16 (s, 2H), 4.32-4.15 (m, 4H), 4.04 (d, J=11.5 Hz, 2H), 3.76 (t, J=10.5 Hz, 2H), 3.48-3.33 (m, 4H), 3.01 (t, J=12.4 Hz, 4H), 2.61 (s, 6H), 2.56-2.39 (m, 2H), 2.21-1.88 (m, 10H), 1.86-1.53 (m, 10H), 1.48 (s, 18H), 1.34-1.17 (m, 6H), 1.01-0.89 (m, 18H). LCMS-ESI+: calc'd for C$_{43}$H$_{53}$ClN$_5$O$_6$S: 802.34 [M+H]$^+$; found: 802.03.

Preparation of ethyl (S)-2-(tert-butoxy)-2-(7-(4-chlorophenyl)-5-methyl-2-(3-(piperidin-4-yl)-1H-pyrazolo[4,3-b]pyridin-5-yl)benzo[d]thiazol-6-yl)acetate: To a round bottom flask was added tert-butyl 4-(5-(6-((S)-1-(tert-butoxy)-2-ethoxy-2-oxoethyl)-7-(4-chlorophenyl)-5-methylbenzo[d]thiazol-2-yl)-1-(tetrahydro-2H-pyran-2-yl)-1H-pyrazolo[4,3-b]pyridin-3-yl)piperidine-1-carboxylate (1.58 g, 1.97 mmol, 1.00 equiv), followed by a solution of hydrochloric acid in isopropanol (1.25 M, 79 mL). The reaction was allowed to stir at room temperature for 3 days and was subsequently quenched with saturated aqueous NaHCO$_3$ until pH-7. The reaction was concentrated in vacuo to remove all volatiles, then diluted with EtOAc (100 mL) and water (100 mL). The organic and aqueous layers were separated. The aqueous layer was extracted with additional EtOAc (3×80 mL) and the organic layers were all combined, washed with brine (150 mL), dried over anhydrous MgSO$_4$, filtered, and concentrated. The crude product was carried on to the next step without further purification. $^1$H NMR (400 MHz, CDCl$_3$) δ 8.39 (d, J=8.9 Hz, 1H), 7.91-7.77 (m, 2H), 7.62-7.44 (m, 4H), 5.17 (s, 1H), 4.23 (ddp, J=10.8, 7.1, 3.6 Hz, 2H), 3.54-3.42 (m, 1H), 3.34-3.19 (m, 2H), 2.99-2.88 (m, 2H), 2.60 (s, 3H), 2.19 (d, J=13.2 Hz, 2H), 2.04-1.87 (m, 2H), 1.26 (t, J=7.1 Hz, 3H), 0.98 (s, 9H). LCMS-ESI+: calc'd for C$_{33}$H$_{37}$ClN$_5$O$_3$S: 618.23 [M+H]$^+$; found: 618.58.

Preparation of tert-butyl (S)-3-(4-(5-(6-(1-(tert-butoxy)-2-ethoxy-2-oxoethyl)-7-(4-chlorophenyl)-5-methylbenzo[d]thiazol-2-yl)-1H-pyrazolo[4,3-b]pyridin-3-yl)piperidin-1-yl)azetidine-1-carboxylate: To a round bottom flask was added ethyl (S)-2-(tert-butoxy)-2-(7-(4-chlorophenyl)-5-methyl-2-(3-(piperidin-4-yl)-1H-pyrazolo[4,3-b]pyridin-5-yl)benzo[d]thiazol-6-yl)acetate (800 mg, 1.29 mmol, 1.00 equiv) and tert-butyl 3-oxoazetidine-1-carboxylate (2.22 g, 12.9 mmol, 10.0 equiv), which were then dissolved in dichloroethane (13 mL). Acetic acid (593 μL, 10.4 mmol, 8.00 equiv), then sodium triacetoxyborohydride (1.37 g, 6.47 mmol, 5.00 equiv), were added. The reaction was stirred at room temperature for 6 h and was subsequently quenched with saturated aqueous NaHCO$_3$ (10 mL) and diluted with dichloromethane (10 mL). The organic and aqueous layers were separated. The aqueous layer was extracted with additional dichloromethane (3×10 mL) and the organic layers were all combined, dried over anhydrous MgSO$_4$, filtered, and concentrated. The crude product was purified via CombiFlash (Peeke Scientific, silica gel, gradient: 0-100% EtOAc/hex, then 0-20% MeOH/CH$_2$Cl$_2$) to yield the desired product as a flocculent solid. $^1$H NMR (400 MHz, CDCl$_3$) δ 8.38 (d, J=8.8 Hz, 1H), 7.85 (d, J=9.7 Hz, 2H), 7.62-7.43 (m, 4H), 5.17 (s, 1H), 4.59 (d, J=8.3 Hz, 1H), 4.22 (dhept, J=10.9, 3.8 Hz, 2H), 4.04-3.93 (m, 4H), 3.38 (t, J=12.6 Hz, 1H), 3.29 (dt, J=13.5, 7.2 Hz, 1H), 3.12-2.95 (m, 2H), 2.59 (s, 3H), 2.29 (d, J=11.5 Hz, 2H), 2.22-2.06 (m, 1H), 1.44 (s, 9H), 1.25 (t, J=7.1 Hz, 3H), 0.98 (s, 9H). LCMS-ESI+: calc'd for C$_{41}$H$_{50}$ClN$_6$O$_5$S: 773.33 [M+H]$^+$; found: 773.46.

Preparation of tert-butyl (S)-3-(4-(5-(6-(1-(tert-butoxy)-2-ethoxy-2-oxoethyl)-7-(4-chlorophenyl)-5-methylbenzo[d]thiazol-2-yl)-1-(difluoromethyl)-1H-pyrazolo[4,3-b]pyridin-3-yl)piperidin-1-yl)azetidine-1-carboxylate: To a round-bottom flask was added tert-butyl (S)-3-(4-(5-(6-(1-(tert-butoxy)-2-ethoxy-2-oxoethyl)-7-(4-chlorophenyl)-5-methylbenzo[d]thiazol-2-yl)-1H-pyrazolo[4,3-b]pyridin-3-yl)piperidin-1-yl)azetidine-1-carboxylate (128 mg, 0.166 mmol, 1.00 equiv) and DMF (2 mL). The solution was cooled to 0° C. and sodium hydride (60% dispersion in mineral oil, 33.0 mg, 0.828 mmol, 5.00 equiv) was added. After stirring at 0° C. for 30 min, a solution of difluoroiodomethane in THF (10 wt. %, 982 μL, 1.33 mmol, 8.00 equiv) was added. The reaction was stirred for an additional 20 min before adding saturated aqueous NH$_4$Cl and diluting with EtOAc (5 mL). The organic and aqueous layers were separated. The aqueous layer was extracted with additional EtOAc (3×5 mL) and the organic layers were all combined, washed with brine (20 mL), dried over anhydrous MgSO$_4$, filtered, and concentrated. The crude product was purified via Gilson HPLC (Gemini, 5-100% MeCN/H$_2$O+0.1% TFA) to afford a pale yellow solid after concentration. $^1$H NMR (400 MHz, CD$_3$OD) δ 8.58 (d, J=8.9 Hz, 1H), 8.38 (d, J=8.8 Hz, 1H), 8.01-7.66 (m, 2H), 7.66-7.47 (m, 4H), 5.24 (s, 1H), 4.38-4.01 (m, 7H), 3.80-3.58 (m, 3H), 3.27-3.07 (m, 2H), 2.60 (s, 3H), 2.56 (d, J=9.8 Hz, 2H), 2.36-2.12 (m, 2H), 1.47 (s, 9H), 1.25 (t, J=7.1 Hz, 3H), 0.99 (s, 9H). LCMS-ESI+: calc'd for C$_{42}$H$_{50}$ClF$_2$N$_6$O$_5$S: 823.32 [M+H]$^+$; found: 823.19.

Preparation of ethyl (S)-2-(2-(3-(1-(azetidin-3-yl)piperidin-4-yl)-1-(difluoromethyl)-1H-pyrazolo[4,3-b]pyridin-5-yl)-7-(4-chlorophenyl)-5-methylbenzo[d]thiazol-6-yl)-2-(tert-butoxy)acetate: To a round-bottom flask with stir bar was added tert-butyl (S)-3-(4-(5-(6-(1-(tert-butoxy)-2-ethoxy-2-oxoethyl)-7-(4-chlorophenyl)-5-methylbenzo[d]thiazol-2-yl)-1-(difluoromethyl)-1H-pyrazolo[4,3-b]pyridin-3-yl)piperidin-1-yl)azetidine-1-carboxylate (52.0 mg, 0.0630 mmol, 1.00 equiv), followed by a solution of hydrochloric acid in isopropanol (1.25 M, 2.5 mL). The reaction was allowed to stir at room temperature for 2 days and was subsequently quenched with saturated aqueous NaHCO$_3$ until pH>10. The reaction was concentrated in vacuo to remove all volatiles, then diluted with EtOAc (5 mL) and water (5 mL). The organic and aqueous layers were separated. The aqueous layer was extracted with additional EtOAc (3×5 mL) and dichloromethane (3×5 mL), and the organic layers were all combined, washed with brine (10 mL), dried over anhydrous MgSO$_4$, filtered, and rotavapped. The crude product was carried on to the next step without further purification. LCMS-ESI+: calc'd for C$_{37}$H$_{42}$ClF$_2$N$_6$O$_3$S: 723.27 [M+H]$^+$; found: 723.58.

Preparation of methyl (S)-3-(4-(5-(6-(1-(tert-butoxy)-2-ethoxy-2-oxoethyl)-7-(4-chlorophenyl)-5-methylbenzo[d]thiazol-2-yl)-1-(difluoromethyl)-1H-pyrazolo[4,3-b]pyridin-3-yl)piperidin-1-yl)azetidine-1-carboxylate: To a vial with stir bar was added ethyl (S)-2-(2-(3-(1-(azetidin-3-yl)piperidin-4-yl)-1-(difluoromethyl)-1H-pyrazolo[4,3-b]pyridin-5-yl)-7-(4-chlorophenyl)-5-methylbenzo[d]thiazol-6-yl)-2-(tert-butoxy)acetate (13.5 mg, 0.0187 mmol, 1.00 equiv) and dichloromethane (500 μL). N,N-Diisopropylethylamine (32.5 μL, 0.187 mmol, 10.0 equiv), followed by methyl chloroformate (7.2 μL, 0.093 mmol, 5.0 equiv), were then added. After stirring for 40 min, water (1 mL) and EtOAc (1 mL) were added to the reaction mixture. The organic and aqueous layers were separated. The aqueous layer was extracted with additional EtOAc (3×1 mL) and the organic layers were all combined, washed with brine (2 mL), dried over anhydrous MgSO$_4$, filtered, and concentrated. The crude product was carried on to the next step without further purification. LCMS-ESI+: calc'd for C$_{39}$H$_{44}$ClF$_2$N$_6$O$_5$S: 781.28 [M+H]$^+$; found: 781.59.

Preparation of (S)-2-(tert-butoxy)-2-(7-(4-chlorophenyl)-2-(1-(difluoromethyl)-3-(1-(1-(methoxycarbonyl)azetidin-3-yl)piperidin-4-yl)-1H-pyrazolo[4,3-b]pyridin-5-yl)-5-methylbenzo[d]thiazol-6-yl)acetic acid: To a vial with stir bar was added crude methyl (S)-3-(4-(5-(6-(1-(tert-butoxy)-2-ethoxy-2-oxoethyl)-7-(4-chlorophenyl)-5-methylbenzo[d]thiazol-2-yl)-1-(difluoromethyl)-1H-pyrazolo[4,3-b]pyridin-3-yl)piperidin-1-yl)azetidine-1-carboxylate (14.6 mg, 0.0187 mmol, 1.00 equiv), THF (1 mL), and three drops of methanol. An aqueous 2.5 M NaOH solution (23 μL, 0.056 mmol, 3.0 equiv) was then added and the reaction was heated to 60° C. for 20 min. After cooling to room temperature, the reaction mixture was filtered and purified directly by Gilson HPLC (Gemini, 5-100% MeCN/H₂O+0.1% TFA) to afford a pale yellow solid after lyophilization. $^1$H NMR (400 MHz, CD$_3$OD) δ 8.58 (d, J=8.9 Hz, 1H), 8.38 (d, J=8.9 Hz, 1H), 8.03-7.65 (m, 3H), 7.65-7.52 (m, 3H), 5.25 (s, 1H), 4.42-4.27 (m, 2H), 4.27-4.17 (m, 2H), 4.17-4.07 (m, 1H), 3.72 (s, 3H), 3.70-3.59 (m, 3H), 3.25-3.08 (m, 2H), 2.61 (s, 3H), 2.60-2.50 (m, 2H), 2.34-2.13 (m, 2H), 0.98 (s, 9H). LCMS-ESI+: calc'd for C$_{37}$H$_{40}$ClF$_2$N$_6$O$_5$S: 753.24 [M+H]⁺; found: 753.91.

Method M

Example 18. Preparation of (S)-2-(tert-butoxy)-2-(7-(4-chlorophenyl)-5-methyl-2-(1-methyl-3-(4-(oxetan-3-yl)piperazin-1-yl)-1H-pyrazolo[4,3-b]pyridin-5-yl)benzo[d]thiazol-6-yl)acetic Acid (15)

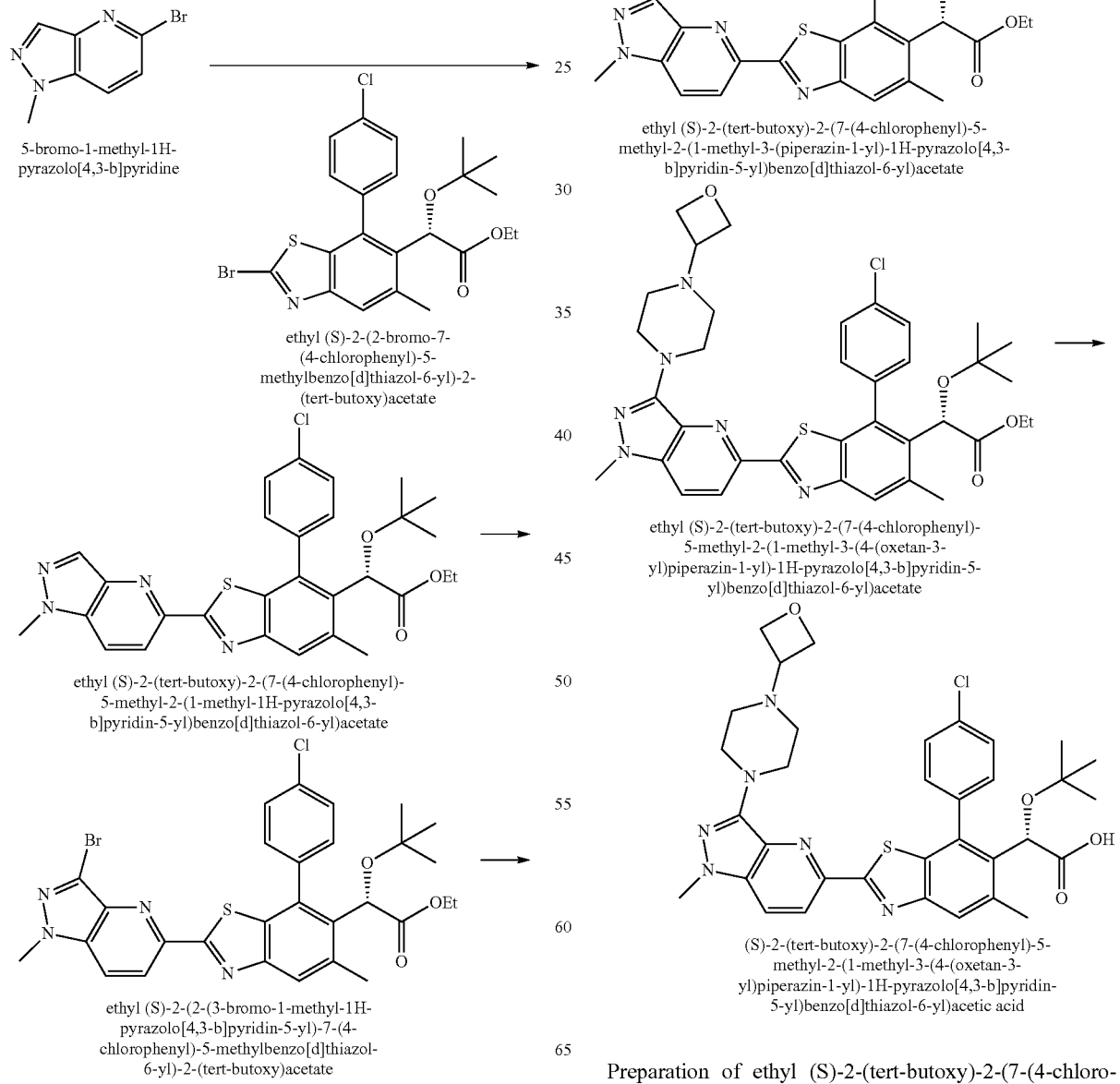

Preparation of ethyl (S)-2-(tert-butoxy)-2-(7-(4-chlorophenyl)-5-methyl-2-(1-methyl-1H-pyrazolo[4,3-b]pyridin- 5-yl)benzo[d]thiazol-6-yl)acetate: To an oven-dried round bottom flask was charged 5-bromo-1-methyl-1H-pyrazolo [4,3-b]pyridine (1.71 g, 8.06 mmol, 2.00 equiv), which was then dissolved in 5:1 toluene:hexanes (32 mL). The reaction solution was then cooled to −40° C. and a solution of n-butyllithium in hexanes (2.50 M, 3.54 mL, 8.86 mmol, 2.20 equiv) was added dropwise. Upon completion of addition, the reaction mixture was immediately cooled to −78° C. and stirred for 3 h. A solution of zinc chloride in 2-methyltetrahydrofuran (1.90 M, 4.87 mL, 9.23 mmol, 2.30 equiv) was then added, followed by 14 mL of tetrahydrofuran. After stirring at −78° C. for 10 min, the reaction mixture was warmed to 0° C. and stirred for an additional 30 min. The reaction was then allowed to warm to room temperature and was stirred for an additional 35 min. Ethyl (S)-2-(2-bromo-7-(4-chlorophenyl)-5-methylbenzo[d]thiazol-6-yl)-2-(tert-butoxy)acetate (2.00 g, 4.03 mmol, 1.00 equiv) and Pd(PPh$_3$)$_4$ (465 mg, 0.403 mmol, 0.10 equiv) were then added. The reaction mixture was sparged with argon for 10 min and subsequently heated to 60° C. After stirring for 1 h, the reaction was cooled to room temperature. 1 M hydrochloric acid was added until all solids dissolved. Saturated aqueous NaHCO$_3$ was added until pH-7 was reached. The reaction was then diluted with EtOAc (60 mL) and the organic and aqueous layers were separated. The aqueous layer was extracted with additional EtOAc (3×30 mL) and the organic layers were all combined, washed with brine (50 mL), dried over anhydrous MgSO$_4$, filtered, and concentrated. The crude product was purified via Combi-Flash (Peeke Scientific, silica gel, gradient: 0-100% EtOAc/ hex) to afford the desired product as a pale yellow flocculent solid. LCMS-ESI+: calc'd for C$_{29}$H$_{30}$ClN$_4$O$_3$S: 549.17 [M+H]$^+$; found: 549.30.

Preparation of ethyl (S)-2-(2-(3-bromo-1-methyl-1H-pyrazolo[4,3-b]pyridin-5-yl)-7-(4-chlorophenyl)-5-methylbenzo[d]thiazol-6-yl)-2-(tert-butoxy)acetate: To a round bottom flask with stir bar was added ethyl (S)-2-(tert-butoxy)-2-(7-(4-chlorophenyl)-5-methyl-2-(1-methyl-1H-pyrazolo[4,3-b]pyridin-5-yl)benzo[d]thiazol-6-yl)acetate (931 mg, 1.70 mmol, 1.00 equiv) and acetonitrile (18 mL). The solution was cooled to 0° C. and 2,6-lutidine (711 μL, 6.10 mmol, 3.60 equiv), followed by a 1 M stock solution of bromine in acetonitrile (6.10 mL, 6.10 mmol, 3.60 equiv), were added. The reaction was allowed to warm to room temperature and was stirred for 7 h before additional 2,6-lutidine (180 μL) and 1 M bromine in acetonitrile (1.5 mL) were added. After stirring for 12 h, the reaction was quenched with saturated aqueous NaHCO$_3$ and saturated aqueous Na$_2$S$_2$O$_3$, followed by dilution with EtOAc (30 mL). The organic and aqueous layers were separated. The aqueous layer was extracted with additional EtOAc (3×25 mL) and the organic layers were combined, washed with brine (50 mL), dried over anhydrous MgSO$_4$, filtered, and concentrated. The crude product was purified via Combi-Flash (Peeke Scientific, silica gel, gradient: 0-100% EtOAc/ hex) to afford the desired product as a pale yellow flocculent solid. LCMS-ESI+: calc'd for C$_{29}$H$_{29}$BrClN$_4$O$_3$S: 627.08 [M+H]$^+$; found: 627.14.

Preparation of tert-butyl (S)-4-(5-(6-(1-(tert-butoxy)-2-ethoxy-2-oxoethyl)-7-(4-chlorophenyl)-5-methylbenzo[d] thiazol-2-yl)-1-methyl-1H-pyrazolo[4,3-b]pyridin-3-yl)piperazine-1-carboxylate: To a microwave tube was charged ethyl (S)-2-(2-(3-bromo-1-methyl-1H-pyrazolo[4,3-b]pyridin-5-yl)-7-(4-chlorophenyl)-5-methylbenzo[d]thiazol-6-yl)-2-(tert-butoxy)acetate (99.0 mg, 0.158 mmol, 1.00 equiv), tert-butyl piperazine-1-carboxylate (88.1 mg, 0.473 mmol, 3.00 equiv), tris(dibenzylideneacetone)dipalladium (0) (28.9 mg, 0.0315 mmol, 0.20 equiv), 2-dicyclohexylphosphino-2',4',6'-triisopropylbiphenyl (15.0 mg, 0.0315 mmol, 0.20 equiv), cesium carbonate (257 mg, 0.788 mmol, 5.00 equiv), and dioxane (4 mL). The reaction mixture was sparged with argon for 10 min and then heated to 100° C. for 3 h. After cooling to room temperature, saturated aqueous NaHCO$_3$ (2 mL) and EtOAc (8 mL) were added to the reaction mixture. The organic and aqueous layers were separated. The aqueous layer was extracted with additional EtOAc (3×5 mL) and the organic layers were combined, washed with brine (10 mL), dried over anhydrous MgSO$_4$, filtered, and concentrated. The crude product was purified via CombiFlash (Peeke Scientific, silica gel, gradient: 0-100% EtOAc/hex) to afford the desired product. LCMS-ESI+: calc'd for C$_{38}$H$_{46}$ClN$_6$O$_5$S: 733.29 [M+H]$^+$; found: 732.65.

Preparation of ethyl (S)-2-(tert-butoxy)-2-(7-(4-chlorophenyl)-5-methyl-2-(1-methyl-3-(piperazin-1-yl)-1H-pyrazolo[4,3-b]pyridin-5-yl)benzo[d]thiazol-6-yl)acetate: To a round-bottom flask with stir bar was added tert-butyl (S)-4-(5-(6-(1-(tert-butoxy)-2-ethoxy-2-oxoethyl)-7-(4-chlorophenyl)-5-methylbenzo[d]thiazol-2-yl)-1-methyl-1H-pyrazolo[4,3-b]pyridin-3-yl)piperazine-1-carboxylate and a solution of hydrochloric acid in isopropanol (1.25 M, 4.1 mL). The reaction was allowed to stir at room temperature for 2 days and was subsequently quenched with saturated aqueous NaHCO$_3$ until pH>10. The reaction was concentrated in vacuo to remove all volatiles, then diluted with EtOAc (5 mL) and water (5 mL). The organic and aqueous layers were separated. The aqueous layer was extracted with additional EtOAc (3×5 mL) and the organic layers were all combined, washed with brine (10 mL), dried over anhydrous MgSO$_4$, filtered, and concentrated. The crude product was carried on to the next step without further purification. LCMS-ESI+: calc'd for C$_{33}$H$_{38}$ClN$_6$O$_3$S: 633.24 [M+H]$^+$; found: 633.50.

Preparation of ethyl (S)-2-(tert-butoxy)-2-(7-(4-chlorophenyl)-5-methyl-2-(1-methyl-3-(4-(oxetan-3-yl)piperazin-1-yl)-1H-pyrazolo[4,3-b]pyridin-5-yl)benzo[d]thiazol-6-yl) acetate: To a vial with stir bar was added ethyl (S)-2-(tert-butoxy)-2-(7-(4-chlorophenyl)-5-methyl-2-(1-methyl-3-(piperazin-1-yl)-1H-pyrazolo[4,3-b]pyridin-5-yl)benzo[d] thiazol-6-yl)acetate (9.0 mg, 0.014 mmol, 1.0 equiv), 3-oxetanone (9.0 μL, 0.14 mmol, 10 equiv), and methanol (500 μL). The reaction was cooled to 0° C., then acetic acid (4.5 μL, 0.078 mmol, 5.5 equiv) and sodium cyanoborohydride (8.9 mg, 0.14 mmol, 10 equiv) were added. The reaction was warmed to room temperature and stirred for 8 h before quenching with saturated aqueous NaHCO$_3$ until pH>10. The reaction was concentrated in vacuo to remove all volatiles, then diluted with EtOAc (2 mL) and water (2 mL). The organic and aqueous layers were separated. The aqueous layer was extracted with additional EtOAc (3×2 mL) and the organic layers were all combined, washed with brine (5 mL), dried over anhydrous MgSO$_4$, filtered, and rotavapped. The crude product was purified via CombiFlash (Peeke Scientific, silica gel, gradient: 0-100% EtOAc/hex, then 0-20% MeOH/CH$_2$Cl$_2$) to afford the desired product as a pale yellow solid. LCMS-ESI+: calc'd for C$_{36}$H$_{42}$ClN$_6$O$_4$S: 689.27 [M+H]$^+$; found: 689.41.

Preparation of (S)-2-(tert-butoxy)-2-(7-(4-chlorophenyl)-5-methyl-2-(1-methyl-3-(4-(oxetan-3-yl)piperazin-1-yl)-1H-pyrazolo[4,3-b]pyridin-5-yl)benzo[d]thiazol-6-yl)acetic acid: To a vial with stir bar was added ethyl (S)-2-(tert-butoxy)-2-(7-(4-chlorophenyl)-5-methyl-2-(1-methyl-3-(4-(oxetan-3-yl)piperazin-1-yl)-1H-pyrazolo[4,3-b]pyridin-5-yl)benzo[d]thiazol-6-yl)acetate (7.3 mg, 0.011 mmol, 1.0 equiv), THF (500 µL), and three drops of methanol. An aqueous 25% NaOH solution (53 µL, 0.11 mmol, 10 equiv) was then added and the reaction was heated to 60° C. for 3 h. Additional 50% NaOH solution (100 µL) was added before heating for 3 h. After cooling to room temperature, the reaction mixture was filtered and purified directly by Gilson HPLC (Gemini, 5-100% MeCN/H$_2$O+0.1% TFA) to afford a pale yellow solid after lyophilization. $^1$H NMR (400 MHz, CD$_3$OD) δ 8.36 (d, J=9.0 Hz, 1H), 8.00 (d, J=9.0 Hz, 1H), 7.86 (s, 1H), 7.73-7.63 (m, 1H), 7.63-7.50 (m, 3H), 5.22 (s, 1H), 4.96-4.86 (m, 2H), 4.84-4.76 (m, 2H), 4.44 (p, J=6.3 Hz, 1H), 3.94 (s, 3H), 3.55-3.31 (m, 8H), 2.61 (s, 3H), 0.97 (s, 9H). LCMS-ESI+: calc'd for C$_{34}$H$_{38}$ClN$_6$O$_5$S$_2$: 661.24 [M+H]$^+$; found: 662.11.

Method N

Example 19. Preparation of (S)-2-(tert-butoxy)-2-(7-(4-chlorophenyl)-5-methyl-2-(5-methyl-7-(1-(oxetan-3-yl)piperidin-4-yl)-5H-pyrrolo[2,3-b]pyrazin-2-yl)benzo[d]thiazol-6-yl)acetic Acid (16)

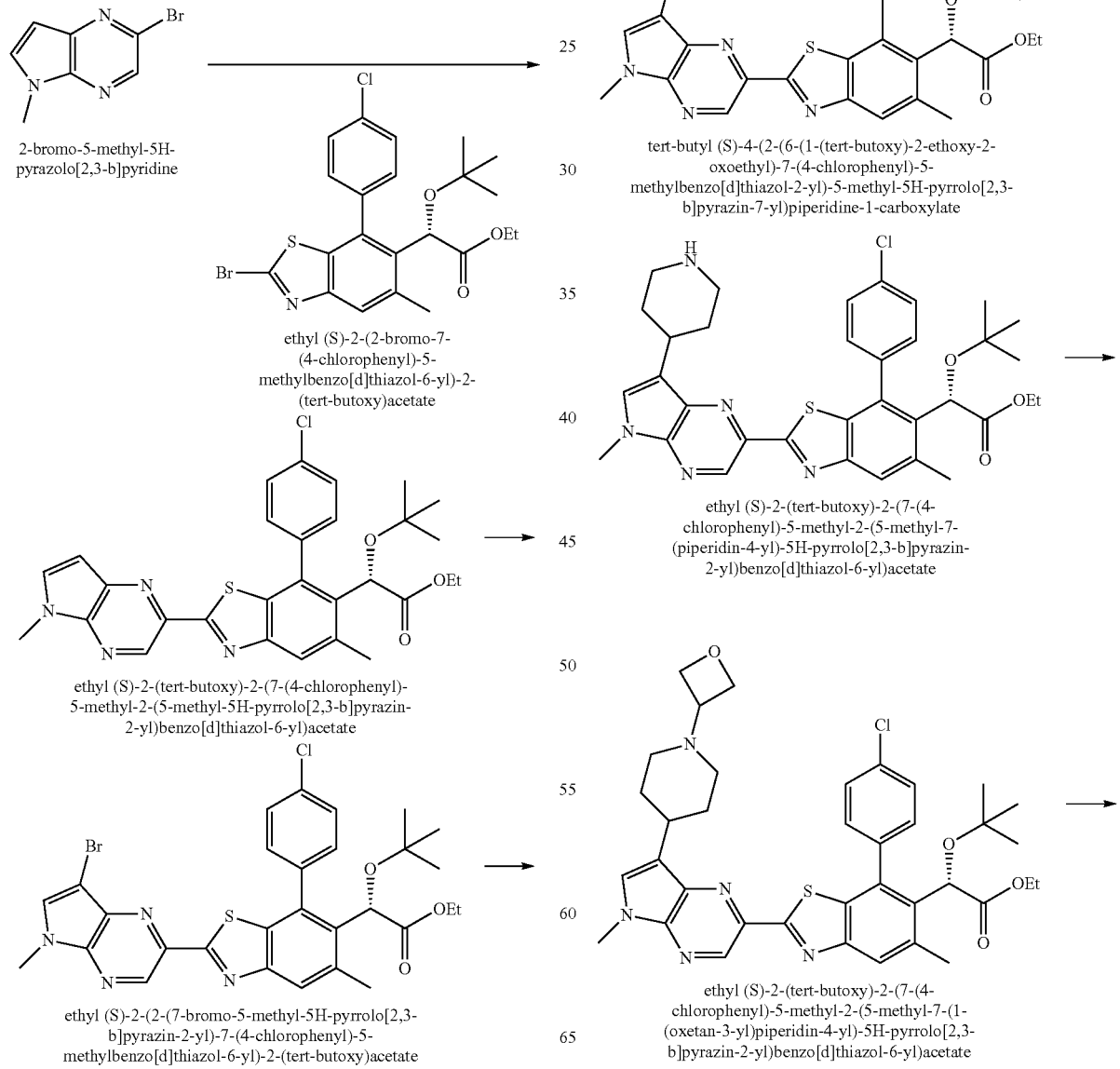

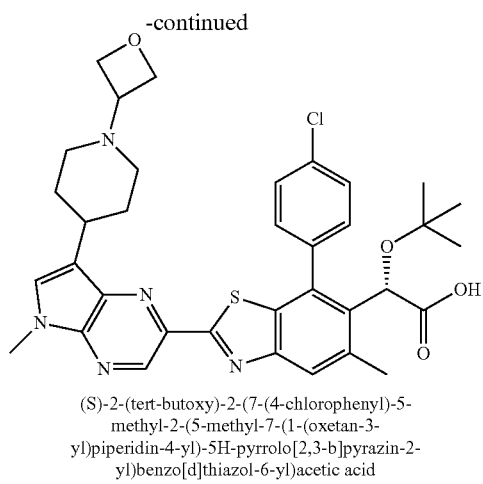

(S)-2-(tert-butoxy)-2-(7-(4-chlorophenyl)-5-methyl-2-(5-methyl-7-(1-(oxetan-3-yl)piperidin-4-yl)-5H-pyrrolo[2,3-b]pyrazin-2-yl)benzo[d]thiazol-6-yl)acetic acid Preparation of ethyl (S)-2-(tert-butoxy)-2-(7-(4-chlorophenyl)-5-methyl-2-(5-methyl-5H-pyrrolo[2,3-b]pyrazin-2-yl)benzo[d]thiazol-6-yl)acetate: To an oven-dried round bottom flask was charged 2-bromo-5-methyl-5H-pyrrolo[2,3-b]pyrazine (896 mg, 4.23 mmol, 2.00 equiv), which was then dissolved in 3:1 toluene:hexanes (12 mL). The reaction solution was then cooled to −78° C. and a solution of n-butyllithium in hexanes (2.50 M, 1.86 mL, 4.65 mmol, 2.20 equiv) was added dropwise. After stirring for 1.5 h, a solution of zinc chloride in 2-methyltetrahydrofuran (1.90 M, 2.56 mL, 4.86 mmol, 2.30 equiv) was then added, followed by 10 mL of tetrahydrofuran. After stirring at −78° C. for 25 min, the reaction mixture was warmed to 0° C. and stirred for an additional 35 min. The reaction was then allowed to warm to room temperature and was stirred for an additional 2 h. Ethyl (S)-2-(2-bromo-7-(4-chlorophenyl)-5-methylbenzo[d]thiazol-6-yl)-2-(tert-butoxy)acetate (1.05 g, 2.11 mmol, 1.00 equiv) and Pd(PPh$_3$)$_4$ (244 mg, 0.211 mmol, 0.10 equiv) were then added. The reaction mixture was sparged with argon for 10 min and subsequently heated to 60° C. After stirring for 3 h, the reaction was cooled to room temperature. 1 M hydrochloric acid was added until all solids dissolved. Saturated aqueous NaHCO$_3$ was added until pH-7 was reached. The reaction was then diluted with EtOAc (30 mL) and the organic and aqueous layers were separated. The aqueous layer was extracted with additional EtOAc (3×15 mL) and the organic layers were all combined, washed with brine (30 mL), dried over anhydrous MgSO$_4$, filtered, and concentrated. The crude product was purified via CombiFlash (Peeke Scientific, silica gel, gradient: 0-100% EtOAc/hex) to afford the desired product as a pale yellow flocculent solid. LCMS-ESI+: calc'd for C$_{29}$H$_{30}$ClN$_4$O$_3$S: 549.17 [M+H]$^+$; found: 549.19.

Preparation of ethyl (S)-2-(2-(7-bromo-5-methyl-5H-pyrrolo[2,3-b]pyrazin-2-yl)-7-(4-chlorophenyl)-5-methylbenzo[d]thiazol-6-yl)-2-(tert-butoxy)acetate: To a round bottom flask with stir bar was added ethyl (S)-2-(tert-butoxy)-2-(7-(4-chlorophenyl)-5-methyl-2-(5-methyl-5H-pyrrolo[2,3-b]pyrazin-2-yl)benzo[d]thiazol-6-yl)acetate (1.18 g, 2.15 mmol, 1.00 equiv) and acetonitrile (25 mL). The solution was cooled to 0° C. and N-bromosuccinimide (421 mg, 2.36 mmol, 1.10 equiv) was added. The reaction was allowed to warm to room temperature and was stirred for 25 min before quenching with saturated aqueous NaHCO$_3$ (10 mL) and diluting with EtOAc (50 mL). The aqueous layer was extracted with additional EtOAc (3×25 mL) and the organic layers were combined, washed with brine (70 mL), dried over anhydrous MgSO$_4$, filtered, and concentrated. The crude product was purified via CombiFlash (Peeke Scientific, silica gel, gradient: 0-100% EtOAc/hex) to afford the desired product as a pale yellow flocculent solid. LCMS-ESI+: calc'd for C$_{29}$H$_{29}$BrClN$_4$O$_3$S: 627.08 [M+H]$^+$; found: 627.06.

Preparation of tert-butyl (S)-4-(2-(6-(1-(tert-butoxy)-2-ethoxy-2-oxoethyl)-7-(4-chlorophenyl)-5-methylbenzo[d]thiazol-2-yl)-5-methyl-5H-pyrrolo[2,3-b]pyrazin-7-yl)-3,6-dihydropyridine-1(2H)-carboxylate: To a microwave tube was charged ethyl (S)-2-(2-(7-bromo-5-methyl-5H-pyrrolo[2,3-b]pyrazin-2-yl)-7-(4-chlorophenyl)-5-methylbenzo[d]thiazol-6-yl)-2-(tert-butoxy)acetate (820 mg, 1.31 mmol, 1.00 equiv), tert-butyl 4-(4,4,5,5-tetramethyl-1,3,2-dioxaborolan-2-yl)-3,6-dihydropyridine-1(2H)-carboxylate (606 mg, 1.96 mmol, 1.50 equiv), Pd(PPh$_3$)$_4$ (226 mg, 0.196 mmol, 0.15 equiv), and 2 M K$_2$CO$_3$ (1.95 mL, 3.92 mmol, 3.00 equiv). Dioxane (18 mL) was added and the reaction mixture was sparged with argon for 10 min before sealing and heating to 110° C. and stirring for 2.5 h. After cooling to room temperature, water (15 mL) and EtOAc (40 mL) were added to the reaction. The organic and aqueous layers were separated and the aqueous layer was extracted with additional EtOAc (3×20 mL). The organic layers were combined, washed with brine (50 mL), dried over anhydrous MgSO$_4$, filtered, and concentrated. The crude product was purified via CombiFlash (Peeke Scientific, silica gel, gradient: 0-100% EtOAc/hex) to yield the product as a pale yellow flocculent solid. LCMS-ESI+: calc'd for C$_{39}$H$_{45}$ClN$_5$O$_5$S: 730.28 [M+H]$^+$; found: 729.77.

Preparation of tert-butyl (S)-4-(2-(6-(1-(tert-butoxy)-2-ethoxy-2-oxoethyl)-7-(4-chlorophenyl)-5-methylbenzo[d]thiazol-2-yl)-5-methyl-5H-pyrrolo[2,3-b]pyrazin-7-yl)piperidine-1-carboxylate: To a round bottom flask was added tert-butyl (S)-4-(2-(6-(1-(tert-butoxy)-2-ethoxy-2-oxoethyl)-7-(4-chlorophenyl)-5-methylbenzo[d]thiazol-2-yl)-5-methyl-5H-pyrrolo[2,3-b]pyrazin-7-yl)-3,6-dihydropyridine-(2H)-carboxylate (933 mg, 1.28 mmol, 1.00 equiv), followed by EtOH (50 mL). Rhodium on alumina (5 wt. % loading, 394 mg, 0.192 mmol, 0.15 equiv) was then added and the reaction vessel was equipped with a hydrogen balloon. Evacuation of the flask followed by backfilling with hydrogen gas was conducted three times. The reaction mixture was allowed to stir for 12 h, then an additional portion of rhodium on alumina (200 mg) was added. After stirring for an additional 24 h, the reaction was filtered through a pad of Celite and concentrated. The crude product was purified via CombiFlash (Peeke Scientific, silica gel, gradient: 0-100% EtOAc/hex) to yield the product as a flocculent solid. LCMS-ESI+: calc'd for C$_{39}$H$_{47}$ClN$_5$O$_5$S: 732.30 [M+H]$^+$; found: 731.87.

Preparation of ethyl (S)-2-(tert-butoxy)-2-(7-(4-chlorophenyl)-5-methyl-2-(5-methyl-7-(piperidin-4-yl)-5H-pyrrolo[2,3-b]pyrazin-2-yl)benzo[d]thiazol-6-yl)acetate: To a round bottom flask was added tert-butyl (S)-4-(2-(6-(1-(tert-butoxy)-2-ethoxy-2-oxoethyl)-7-(4-chlorophenyl)-5-methylbenzo[d]thiazol-2-yl)-5-methyl-5H-pyrrolo[2,3-b]pyrazin-7-yl)piperidine-1-carboxylate (819 mg, 1.12 mmol, 1.00 equiv), followed by a solution of hydrochloric acid in isopropanol (1.25 M, 27 mL). The reaction was allowed to stir at room temperature for 2 days and was subsequently quenched with saturated aqueous NaHCO$_3$ until pH>10. The reaction was concentrated in vacuo to remove all volatiles, then diluted with EtOAc (50 mL) and water (50 mL). The organic and aqueous layers were separated. The aqueous layer was extracted with additional EtOAc (3×20 mL) and the organic layers were all combined, washed with brine (50 mL), dried over anhydrous MgSO$_4$, filtered, and concentrated. The crude product was carried on to the next step without further purification. LCMS-ESI+: calc'd for C$_{34}$H$_{39}$ClN$_5$O$_3$S: 632.25 [M+H]$^+$; found: 632.47.

Preparation of ethyl (S)-2-(tert-butoxy)-2-(7-(4-chlorophenyl)-5-methyl-2-(5-methyl-7-(1-(oxetan-3-yl)piperidin-4-yl)-5H-pyrrolo[2,3-b]pyrazin-2-yl)benzo[d]thiazol-6-yl)acetate: To a vial with stir bar was added ethyl (S)-2-(tert-butoxy)-2-(7-(4-chlorophenyl)-5-methyl-2-(5-methyl-7-(piperidin-4-yl)-5H-pyrrolo[2,3-b]pyrazin-2-yl)benzo[d]thiazol-6-yl)acetate (70.0 mg, 0.111 mmol, 1.00 equiv), 3-oxetanone (71 µL, 1.1 mmol, 10 equiv), and methanol (1 mL). The reaction was cooled to 0° C., then acetic acid (35 µL, 0.61 mmol, 5.5 equiv) and sodium cyanoborohydride (70.0 mg, 1.11 mmol, 10.0 equiv) were added. The reaction was warmed to room temperature and stirred for 12 h before additional 3-oxetanone (70 µL), acetic acid (30 µL), and sodium cyanoborohydride (55 mg) were added. After stirring for an additional 12 h, saturated aqueous NaHCO$_3$ was added until pH>10. The reaction was concentrated in vacuo to remove all volatiles, then diluted with EtOAc (2 mL) and water (2 mL). The organic and aqueous layers were separated. The aqueous layer was extracted with additional EtOAc (3×2 mL) and the organic layers were all combined, washed with brine (5 mL), dried over anhydrous MgSO$_4$, filtered, and concentrated. The crude product was purified via CombiFlash (Peeke Scientific, silica gel, gradient: 0-100% EtOAc/hex, then 0-20% MeOH/CH$_2$Cl$_2$) to afford the desired product as a pale yellow solid. LCMS-ESI+: calc'd for C$_{37}$H$_{43}$ClN$_5$O$_4$S: 688.27 [M+H]$^+$; found: 688.60.

Preparation of (S)-2-(tert-butoxy)-2-(7-(4-chlorophenyl)-5-methyl-2-(5-methyl-7-(1-(oxetan-3-yl)piperidin-4-yl)-5H-pyrrolo[2,3-b]pyrazin-2-yl)benzo[d]thiazol-6-yl)acetic acid: To a vial with stir bar was added ethyl (S)-2-(tert-butoxy)-2-(7-(4-chlorophenyl)-5-methyl-2-(5-methyl-7-(1-(oxetan-3-yl)piperidin-4-yl)-5H-pyrrolo[2,3-b]pyrazin-2-yl)benzo[d]thiazol-6-yl)acetate (52.3 mg, 0.0760 mmol, 1.00 equiv), THF (600 µL), and three drops of methanol. An aqueous 2.5 M NaOH solution (152 µL, 0.380 mmol, 5.00 equiv) was then added and the reaction was heated to 60° C. for 2 h. After cooling to room temperature, the reaction mixture was filtered and purified directly by Gilson HPLC (Gemini, 5-100% MeCN/H$_2$O+0.1% TFA) to afford a pale yellow solid after lyophilization. $^1$H NMR (400 MHz, CD$_3$OD) δ 9.07 (s, 1H), 7.78 (s, 1H), 7.73-7.64 (m, 1H), 7.61 (d, J=8.2 Hz, 4H), 5.25 (s, 1H), 4.89-4.64 (m, 4H), 4.55-4.32 (m, 1H), 3.76 (s, 3H), 3.69-3.43 (m, 2H), 3.30-3.16 (m, 1H), 3.16-2.91 (m, 2H), 2.62 (s, 3H), 2.53-2.23 (m, 2H), 2.21-1.90 (m, 2H), 0.98 (s, 9H). LCMS-ESI+: calc'd for C$_{35}$H$_{39}$ClN$_5$O$_4$S: 660.24 [M+H]$^+$; found: 660.59.

Method O

Example 20. Preparation of (S)-2-(tert-butoxy)-2-(7-(4-chlorophenyl)-5-methyl-2-(1-methyl-3-(1-(oxetan-3-yl)piperidin-4-yl)-1H-pyrrolo[2,3-b]pyridin-5-yl)benzo[d]thiazol-6-yl)acetic Acid (17)

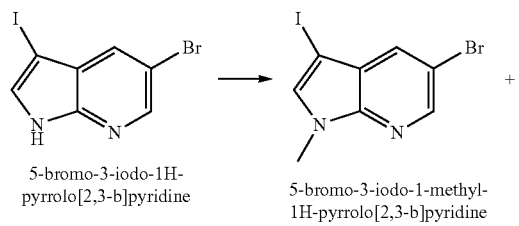

5-bromo-3-iodo-1H-pyrrolo[2,3-b]pyridine 5-bromo-3-iodo-1-methyl-1H-pyrrolo[2,3-b]pyridine

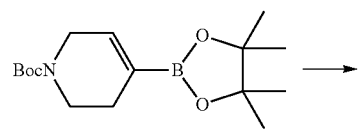

tert-butyl 4-(4,4,5,5-tetramethyl-1,3,2-dioxaborolan-2-yl)-3,6-dihydropyridine-1(2H)-carboxylate

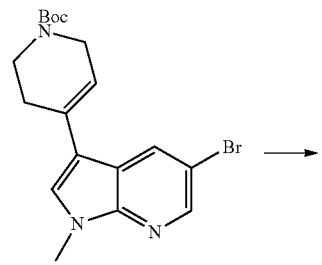

tert-butyl 4-(5-bromo-1-methyl-1H-pyrrolo[2,3-b]pyridin-3-yl)-3,6-dihydropyridine-1(2H)-carboxylate

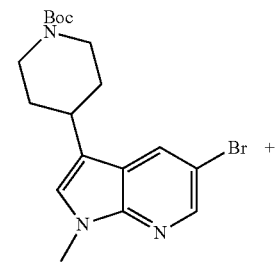

tert-butyl 4-(5-bromo-1-methyl-1H-pyrrolo[2,3-b]pyridin-3-yl)piperidine-1-carboxylate

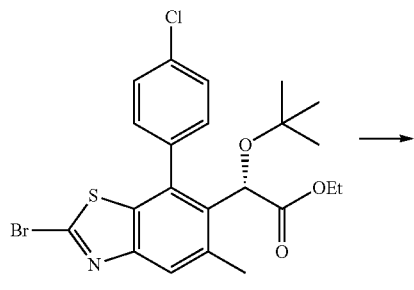

ethyl (S)-2-(2-bromo-7-(4-chlorophenyl)-5-methylbenzo[d]thiazol-6-yl)-2-(tert-butoxy)acelate

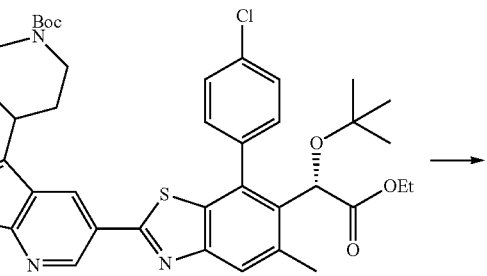

tert-butyl (S)-4-(5-(6-(1-(tert-butoxy)-2-ethoxy-2-oxoethyl)-7-(4-chlorophenyl)-5-methylbenzo[d]thiazol-2-yl)-1-methyl-1H-pyrrolo[2,3-b]pyridin-3-yl)piperidine-1-carboxylate

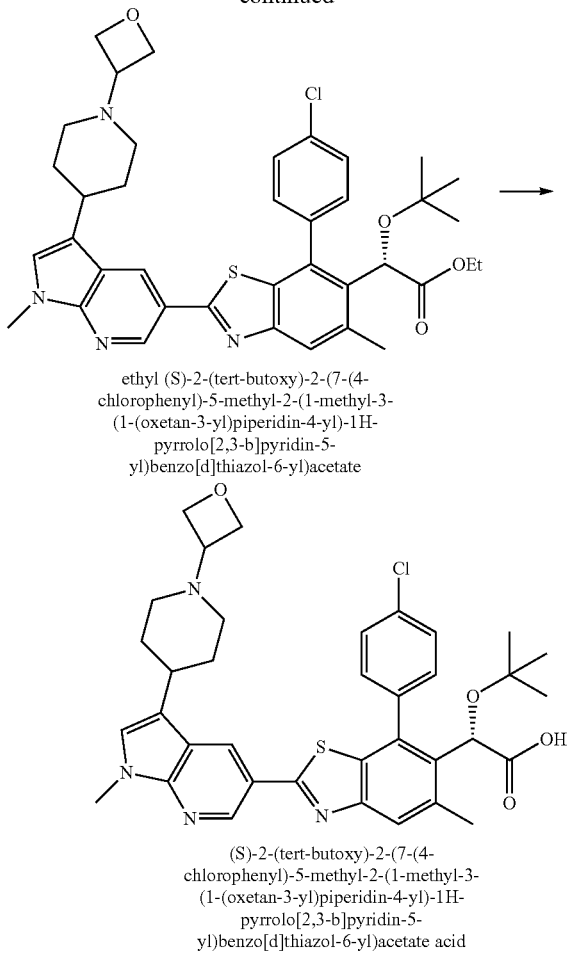

ethyl (S)-2-(tert-butoxy)-2-(7-(4-chlorophenyl)-5-methyl-2-(1-methyl-3-(1-(oxetan-3-yl)piperidin-4-yl)-1H-pyrrolo[2,3-b]pyridin-5-yl)benzo[d]thiazol-6-yl)acetate (S)-2-(tert-butoxy)-2-(7-(4-chlorophenyl)-5-methyl-2-(1-methyl-3-(1-(oxetan-3-yl)piperidin-4-yl)-1H-pyrrolo[2,3-b]pyridin-5-yl)benzo[d]thiazol-6-yl)acetate acid Preparation of 5-bromo-3-iodo-1-methyl-1H-pyrrolo[2,3-b]pyridine: To a solution of 5-bromo-3-iodo-1H-pyrrolo[2,3-b]pyridine (4.23 g, 13.1 mmol) in anhydrous DMF (100 mL) at 0° C. was added 60% sodium hydride (0.629 g, 15.7 mmol) and reaction mixture was stirred for 15 minutes. Iodomethane (0.98 mL, 15.7 mmol) was added and reaction mixture was stirred at 0° C. for 1.5 hours. Reaction was complete by LCMS analysis. Reaction mixture was concentrated, suspended in EtOAc/CH$_2$Cl$_2$) and washed with saturated ammonium chloride (2×). Organic layer was dried (MgSO$_4$), filtered, concentrated and purified by CombiFlash (120 g, Gold, 0-20% EtOAc/Hex) to give a yellow solid. LCMS-ESI$^+$: calc'd for $C_8H_7BrIN_2$: 338.9 (M+H)+; found: 339.1 (M+H)$^+$.

Preparation of tert-butyl 4-(5-bromo-1-methyl-1H-pyrrolo[2,3-b]pyridin-3-yl)-5,6-dihydropyridine-1(2H)-carboxylate: A 100 mL round bottom flask was charged with 5-bromo-3-iodo-1-methyl-1H-pyrrolo[2,3-b]pyridine (2.44 g, 7.24 mmol), tert-butyl 4-(4,4,5,5-tetramethyl-1,3,2-dioxaborolan-2-yl)-5,6-dihydropyridine-1(2H)-carboxylate (2.46 g, 7.97 mmol), dichloro 1,1-bis(diphenylphosphino)ferrocene palladium(II) dichloromethane (591 mg, 0.724 mmol) and potassium phosphate (7.7 g, 36 mmol). The flask was flushed with nitrogen for 5 minutes, then anhydrous dioxane (50 mL) was added and flask was placed into an oil bath pre-heated to 70° C. Reaction mixture was stirred for 5 hours. LCMS shows multiple reaction products in addition to desired product. Reaction mixture was filtered through a pad of Celite, concentrated and purified by CombiFlash (120 g, 0-30% EtOAc/Hex) to give impure product. Repurification by CombiFlash (120 g Gold, 5-20% EtOAc/Hex) gave desire product. LCMS-ESI$^+$: calc'd for $C_{18}H_{23}BrN_3O_2$: 392.1 (M+H)$^+$; found: 392.1 (M+H)$^+$.

Preparation of tert-butyl 4-(5-bromo-1-methyl-1H-pyrrolo[2,3-b]pyridin-3-yl)piperidine-1-carboxylate: A flask containing a mixture of tert-butyl 4-(5-bromo-1-methyl-1H-pyrrolo[2,3-b]pyridin-3-yl)-5,6-dihydropyridine-1(2H)-carboxylate (135 mg, 0.344 mmol), rhodium on alumina, 5 wt % (130 mg, 0.063 mmol) in ethanol (5 mL) was evacuated and back-filled with hydrogen (3×). Reaction mixture was stirred overnight, filtered through a pad of Celite and concentrated. The colorless residue was purified by CombiFlash (12 g, Gold, 2-25% EtOAc/Hex) to give a colorless oil. LCMS-ESI+: calc'd for $C_{18}H_{25}BrN_3O_2$: 394.1 (M+H)$^+$; found: 394.1 (M+H)$^+$.

Preparation of tert-butyl (S)-4-(5-(6-(1-(tert-butoxy)-2-ethoxy-2-oxoethyl)-7-(4-chlorophenyl)-5-methylbenzo[d]thiazol-2-yl)-1-methyl-1H-pyrrolo[2,3-b]pyridin-3-yl)piperidine-1-carboxylate: A 25 mL round bottom flask was charged with the tert-butyl 4-(5-bromo-1-methyl-1H-pyrrolo[2,3-b]pyridin-3-yl)piperidine-1-carboxylate (71 mg, 0.18 mmol), bis(neopentyl glycolato)diboron (53 mg, 0.234 mmol), PdCl$_2$(Amphos)$_2$ (13 mg, 0.018 mmol) and potassium propionate (91 mg, 0.81 mmol) and flushed with nitrogen. De-gassed dioxane (2.0 mL) was added under a nitrogen atmosphere and reaction mixture was heated to 80° C. for 2 h. The reaction turned to a heterogeneous yellow color. LCMS showed mass corresponding to (3-(1-(tert-butoxycarbonyl)piperidin-4-yl)-1-methyl-1H-pyrrolo[2,3-b]pyridin-5-yl)boronic acid (~33%) and dimer mass (~66%). Reaction mixture was cooled to ~50° C. Potassium carbonate (2M, 0.223 mL, 0.446 mmol) and ethyl (S)-2-(2-bromo-7-(4-chlorophenyl)-5-methylbenzo[d]thiazol-6-yl)-2-(tert-butoxy)acetate (59 mg, 0.119 mmol) were added and the reaction heated to 80° C. After 2 h, LCMS showed desired product mass. Reaction was cooled to room temperature, filtered through a pad of Celite and concentrated. The residue was purified by CombiFlash (12 g Gold, 0-100% EtOAc/Hex) and concentrated to give impure product. Repurified by CombiFlash (12 g Gold, 10-40% EtOAc/Hex) and concentrated to desired product with some impurity. LCMS-ESI+: calc'd for $C_{40}H_{48}ClN_4O_5S$: 731.3 (M+H)$^+$; found: 731.1 (M+H)$^+$.

Preparation of ethyl (S)-2-(tert-butoxy)-2-(7-(4-chlorophenyl)-5-methyl-2-(1-methyl-3-(1-(oxetan-3-yl)piperidin-4-yl)-1H-pyrrolo[2,3-b]pyridin-5-yl)benzo[d]thiazol-6-yl)acetate: A solution of tert-butyl (S)-4-(5-(6-(1-(tert-butoxy)-2-ethoxy-2-oxoethyl)-7-(4-chlorophenyl)-5-methylbenzo[d]thiazol-2-yl)-1-methyl-1H-pyrrolo[2,3-b]pyridin-3-yl)piperidine-1-carboxylate (7.5 mg, 0.010 mmol) in 1.25 HCl in isopropanol (1.0 mL) was stirred overnight at room temperature. Reaction mixture was quenched with saturated sodium bicarbonate solution and extracted with ethyl acetate (2×). Combined organic layer was dried (MgSO$_4$), filtered and concentrated to give ethyl (S)-2-(tert-butoxy)-2-(7-(4-chlorophenyl)-5-methyl-2-(1-methyl-3-(piperidin-4-yl)-1H-pyrrolo[2,3-b]pyridin-5-yl)benzo[d]thiazol-6-yl)acetate that was used in the next step without further purification.

A solution of ethyl (S)-2-(tert-butoxy)-2-(7-(4-chlorophenyl)-5-methyl-2-(1-methyl-3-(piperidin-4-yl)-1H-pyrrolo[2,3-b]pyridin-5-yl)benzo[d]thiazol-6-yl)acetate (6.6 mg, 0.01 mmol), 3-oxetanone (6.7 µL, 0.105 mmol), acetic acid (3.0 µL, 0.052 mmol) and sodium cyanoborohydride (6.6 mg, 0.105 mmol) in ethanol was stirred for 8 hours at room temperature. LCMS showed about 50% conversion. Added 3-oxetanone (6.7 μL, 0.105 mmol), acetic acid (3.0 μL, 0.052 mmol) and sodium cyanoborohydride (6.6 mg, 0.105 mmol) and stirred overnight. LCMS showed complete conversion. Reaction was quenched with saturated sodium bicarbonate solution and brine and stirred for 1.5 hours. The mixture was extracted with ethyl acetate (2×) and combined organic layer was dried (MgSO$_4$), filtered and concentrated. The residue was purified by CombiFlash (4 g, Gold, 0-10% MeOH/CH$_2$Cl$_2$) to give a colorless film. LCMS-ESI+: calc'd for C$_{38}$H$_{44}$ClN$_4$O$_4$S: 687.3 (M+H)$^+$; found: 687.3 (M+H)$^+$.

Preparation of (S)-2-(tert-butoxy)-2-(7-(4-chlorophenyl)-5-methyl-2-(1-methyl-3-(1-(oxetan-3-yl)piperidin-4-yl)-1H-pyrrolo[2,3-b]pyridin-5-yl)benzo[d]thiazol-6-yl)acetic acid: A solution of ethyl (S)-2-(tert-butoxy)-2-(7-(4-chlorophenyl)-5-methyl-2-(1-methyl-3-(1-(oxetan-3-yl)piperidin-4-yl)-1H-pyrrolo[2,3-b]pyridin-5-yl)benzo[d]thiazol-6-yl)acetate (3.4 mg, 0.005 mmol) and 5M sodium hydroxide (10 μL, 0.050 mmol) in THF (0.5 mL) and methanol (0.1 mL) was stirred at 45° C. for 4 hours. Additional 5M sodium hydroxide (5 ILL, 0.025 mmol) was added and reaction mixture was stirred for 2 hours. Reaction mixture was concentrated, dissolved in DMF/methanol, filtered through syringe filter and purified by Gilson HPLC (Gemini, 5-100% ACN/H$_2$O+0.1% TFA) to give a yellow powder after lyophilization.

$^1$H NMR (400 MHz, Methanol-d$_4$) δ 8.95 (d, J=2.0 Hz, 1H), 8.64 (d, J=2.0 Hz, 1H), 7.83 (s, 1H), 7.72-7.65 (m, 1H), 7.60 (dd, J=7.0, 1.5 Hz, 3H), 7.37 (s, 1H), 5.26 (s, 1H), 4.94 (t, J=7.7 Hz, 2H), 4.45 (s, 1H), 3.87 (s, 3H), 3.62 (d, J=13.5 Hz, 2H), 3.25 (d, J=11.0 Hz, 1H), 3.16-3.01 (m, 2H), 2.62 (s, 3H), 2.36 (d, J=14.1 Hz, 2H), 2.17-1.99 (m, 2H), 0.98 (s, 9H). LCMS-ESI$^+$: calc'd for C$_{36}$H$_{40}$ClN$_4$O$_4$S: 659.2 (M+H)$^+$; found: 659.2 (M+H)$^+$.

Example 21. Preparation of (S)-2-(tert-butoxy)-2-(7-(4-chlorophenyl)-2-(3-(3,6-dihydro-2H-pyran-4-yl)-1-methyl-1H-indazol-5-yl)-5-methylbenzo[d]thiazol-6-yl)acetic Acid (18)

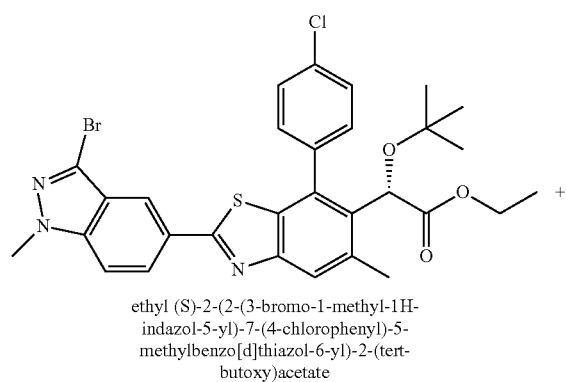

ethyl (S)-2-(2-(3-bromo-1-methyl-1H-indazol-5-yl)-7-(4-chlorophenyl)-5-methylbenzo[d]thiazol-6-yl)-2-(tert-butoxy)acetate

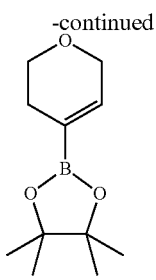

2-(3,6-dihydro-2H-pyran-4-yl)-4,4,5,5-tetramethyl-1,3,2-dioxaborolane

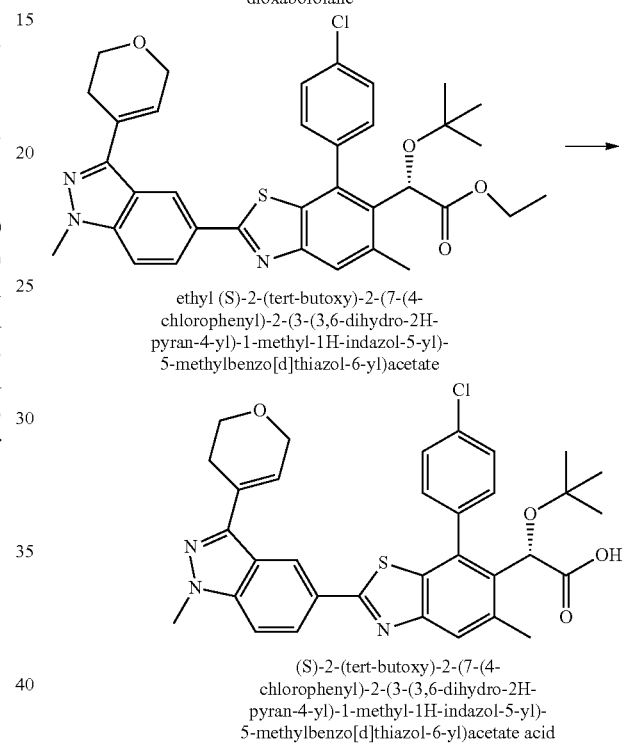

ethyl (S)-2-(tert-butoxy)-2-(7-(4-chlorophenyl)-2-(3-(3,6-dihydro-2H-pyran-4-yl)-1-methyl-1H-indazol-5-yl)-5-methylbenzo[d]thiazol-6-yl)acetate (S)-2-(tert-butoxy)-2-(7-(4-chlorophenyl)-2-(3-(3,6-dihydro-2H-pyran-4-yl)-1-methyl-1H-indazol-5-yl)-5-methylbenzo[d]thiazol-6-yl)acetate acid Preparation of ethyl (S)-2-(tert-butoxy)-2-(7-(4-chlorophenyl)-2-(3-(3,6-dihydro-2H-pyran-4-yl)-1-methyl-1H-indazol-5-yl)-5-methylbenzo[d]thiazol-6-yl)acetate: A mixture of ethyl (S)-2-(2-(3-bromo-1-methyl-1H-indazol-5-yl)-7-(4-chlorophenyl)-5-methylbenzo[d]thiazol-6-yl)-2-(tert-butoxy)acetate (70.3 mg, 0.112 mmol), 2-(3,6-dihydro-2H-pyran-4-yl)-4,4,5,5-tetramethyl-1,3,2-dioxaborolane (42.1 mg, 0.200 mmol), tetrakis(triphenylphosphine)palladium(0) (13.43 mg, 0.012 mmol), and potassium carbonate (46.94 mg, 0.340 mmol) in a microwave vial was purged with argon gas for ~3 min and water (0.3 mL) and dioxane (1.2 mL) were added. The resulting mixture was reacted in a microwave reactor for 20 min at 110° C. To the reaction mixture was added water (0.5 mL) and the resulting mixture was again reacted in a microwave reactor for 20 min at 110° C. After the reaction mixture was diluted with ethyl acetate and washed with water (×2), and the aqueous layer was extracted with ethyl acetate (×1), the organic layers were combined and concentrated. The residue was purified by Combiflash (12 g, Gold, 0-60% EtOAc/Hex) to obtain the title product. LCMS-ESI: calc'd for C$_{35}$H$_{37}$ClN$_3$O$_4$S: 630.22 (M+H)$^+$; found: 630.36 (M+H)$^+$.

Preparation of (S)-2-(tert-butoxy)-2-(7-(4-chlorophenyl)-2-(3-(3,6-dihydro-2H-pyran-4-yl)-1-methyl-1H-indazol-5- yl)-5-methylbenzo[d]thiazol-6-yl)acetic acid: To a solution of ethyl (S)-2-(tert-butoxy)-2-(7-(4-chlorophenyl)-2-(3-(3,6-dihydro-2H-pyran-4-yl)-1-methyl-1H-indazol-5-yl)-5-methylbenzo[d]thiazol-6-yl)acetate (28.5 mg, 0.045 mmol) in THF (1 mL) and MeOH (1 mL) was added 2 N NaOH (1 mL) at room temperature and kept tightly before the mixture was stirred at 70° C. for 1.5 h. The reaction mixture was concentrated to remove organic solvent and acidified with 2 N HCl. The resulting mixture was dissolved with DMF and MeCN (total ~5 mL), filtered through syringe filter, and purified by Gilson HPLC (Phenomenex Gemini, 60-100% ACN/H$_2$O+0.1% TFA) to obtain the title product after lyophilization. $^1$H NMR (400 MHz, Acetonitrile-d$_3$) δ 8.48 (dd, J=1.6, 0.8 Hz, 1H), 8.08 (dd, J=8.9, 1.6 Hz, 1H), 7.83 (d, J=1.0 Hz, 1H), 7.70-7.63 (m, 1H), 7.63-7.57 (m, 3H), 7.54 (dd, J=8.8, 0.8 Hz, 1H), 6.59 (dt, J=3.0, 1.5 Hz, 1H), 5.28 (s, 1H), 4.35 (q, J=2.8 Hz, 2H), 4.00 (s, 3H), 3.91 (t, J=5.5 Hz, 2H), 2.69 (dq, J=5.4, 2.9 Hz, 2H), 2.58 (d, J=0.9 Hz, 3H), 0.99 (s, 9H). LCMS-ESI$^+$: calc'd for C$_{33}$H$_{33}$ClN$_3$O$_4$S: 602.19 (M+H)$^+$; found: 602.28 (M+H)$^+$.

Example 22. Preparation of (S)-2-(tert-butoxy)-2-(7-(4-chlorophenyl)-5-methyl-2-(1-methyl-3-(tetrahydro-2H-pyran-4-yl)-1H-indazol-5-yl)benzo[d]thiazol-6-yl)acetic Acid (19)

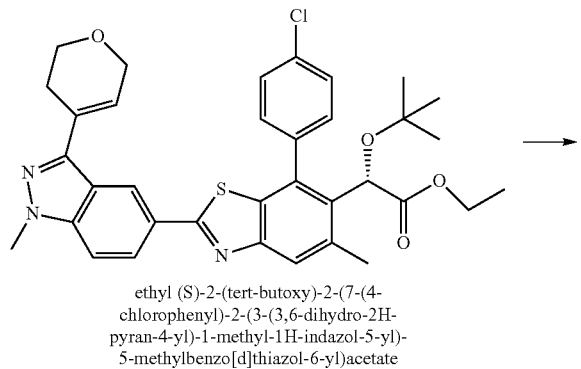

ethyl (S)-2-(tert-butoxy)-2-(7-(4-chlorophenyl)-2-(3-(3,6-dihydro-2H-pyran-4-yl)-1-methyl-1H-indazol-5-yl)-5-methylbenzo[d]thiazol-6-yl)acetate

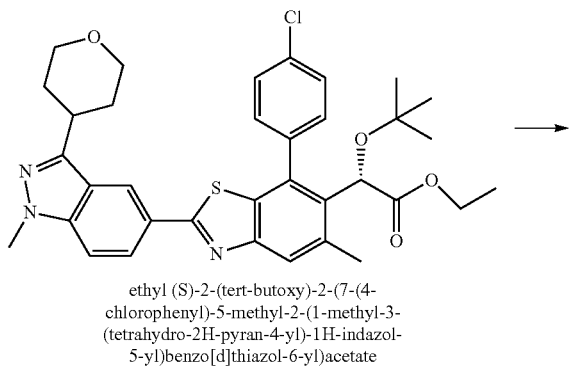

ethyl (S)-2-(tert-butoxy)-2-(7-(4-chlorophenyl)-5-methyl-2-(1-methyl-3-(tetrahydro-2H-pyran-4-yl)-1H-indazol-5-yl)benzo[d]thiazol-6-yl)acetate

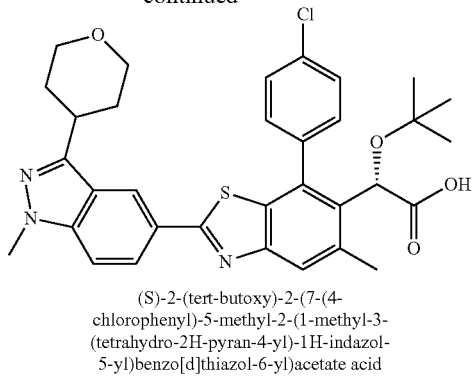

(S)-2-(tert-butoxy)-2-(7-(4-chlorophenyl)-5-methyl-2-(1-methyl-3-(tetrahydro-2H-pyran-4-yl)-1H-indazol-5-yl)benzo[d]thiazol-6-yl)acetate acid Preparation of ethyl (S)-2-(tert-butoxy)-2-(7-(4-chlorophenyl)-5-methyl-2-(1-methyl-3-(tetrahydro-2H-pyran-4-yl)-1H-indazol-5-yl)benzo[d]thiazol-6-yl)acetate: A mixture of ethyl (S)-2-(tert-butoxy)-2-(7-(4-chlorophenyl)-2-(3-(3,6-dihydro-2H-pyran-4-yl)-1-methyl-1H-indazol-5-yl)-5-methylbenzo[d]thiazol-6-yl)acetate (29.3 mg, 0.046 mmol) and 5% Rhodium on alumina (22 mg) in ethanol (3 mL) was stirred under H$_2$ atmosphere for 5 h. The reaction mixture was filtered through celite pad and the filtrate was concentrated to dryness to get the crude title product. LCMS-ESI$^+$: calc'd for C$_{35}$H$_{39}$ClN$_3$O$_4$S: 632.23 (M+H)$^+$; found: 632.38 (M+H)$^+$.

Preparation of (S)-2-(tert-butoxy)-2-(7-(4-chlorophenyl)-5-methyl-2-(1-methyl-3-(tetrahydro-2H-pyran-4-yl)-1H-indazol-5-yl)benzo[d]thiazol-6-yl)acetic acid: To a solution of the above crude ethyl (S)-2-(tert-butoxy)-2-(7-(4-chlorophenyl)-5-methyl-2-(1-methyl-3-(tetrahydro-2H-pyran-4-yl)-1H-indazol-5-yl)benzo[d]thiazol-6-yl)acetate in THF (1 mL) and MeOH (1 mL) was added 2 N NaOH (1 mL) at room temperature and kept tightly before the mixture was stirred at 70° C. for 1.5 h. The reaction mixture was concentrated to remove organic solvent and acidified with 2 N HCl. The resulting mixture was dissolved with DMF and MeCN (total 6 mL), filtered through syringe filter, and purified by Gilson HPLC (Phenomenex Gemini, 60-100% ACN/H$_2$O+0.1% TFA) to obtain the title product after lyophilization. $^1$H NMR (400 MHz, Acetonitrile-d$_3$) δ 8.40 (dd, J=1.6, 0.9 Hz, 1H), 8.07 (dt, J=8.9, 1.4 Hz, 1H), 7.85 (d, J=1.2 Hz, 1H), 7.69-7.64 (m, 1H), 7.63-7.56 (m, 3H), 7.53 (dt, J=8.9, 0.9 Hz, 1H), 5.29 (s, 1H), 4.02 (dp, J=8.9, 2.6 Hz, 2H), 3.98 (d, J=0.9 Hz, 3H), 3.65-3.52 (m, 2H), 3.39 (ddd, J=15.6, 10.2, 6.3 Hz, 1H), 2.58 (d, J=0.8 Hz, 3H), 2.06-1.87 (m, 4H), 0.99 (s, 9H). LCMS-ESI$^+$: calc'd for C$_{33}$H$_{35}$ClN$_3$O$_4$S: 604.20 (M+H)$^+$; found: 604.31 (M+H)$^+$.

Example 23. Preparation of (S)-2-(tert-butoxy)-2-(7-(4-chlorophenyl)-5-methyl-2-(1-methyl-3-(1-(3-methyloxetan-3-yl)piperidin-4-yl)-1H-indazol-5-yl)benzo[d]thiazol-6-yl)acetic Acid (20)

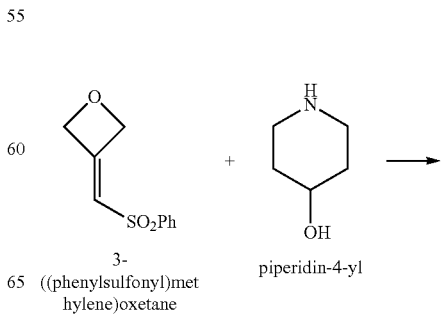

3-((phenylsulfonyl)methylene)oxetane piperidin-4-yl

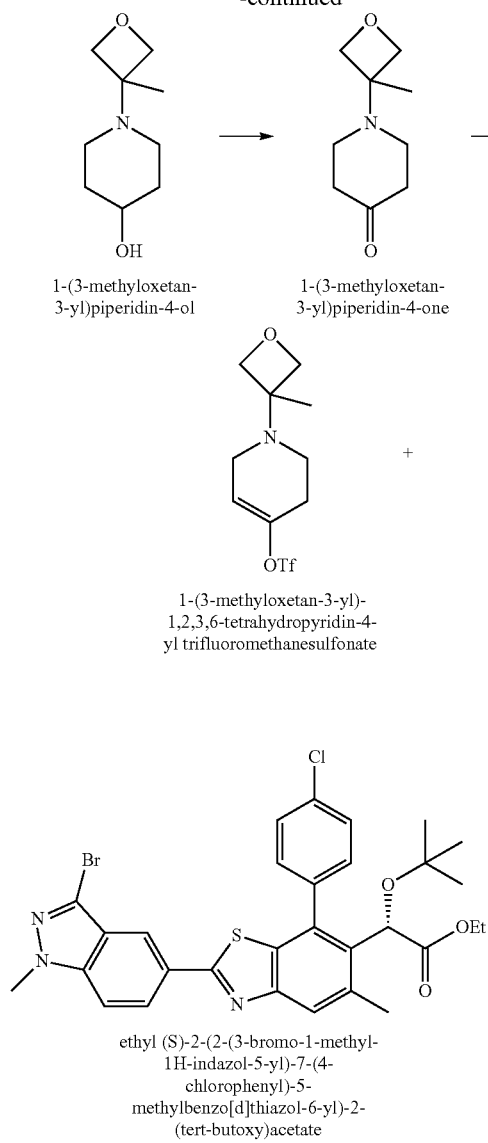

1-(3-methyloxetan-3-yl)piperidin-4-ol 1-(3-methyloxetan-3-yl)piperidin-4-one 1-(3-methyloxetan-3-yl)-1,2,3,6-tetrahydropyridin-4-yl trifluoromethanesulfonate ethyl (S)-2-(2-(3-bromo-1-methyl-1H-indazol-5-yl)-7-(4-chlorophenyl)-5-methylbenzo[d]thiazol-6-yl)-2-(tert-butoxy)acetate ethyl (S)-2-(tert-butoxy)-2-(7-(4-chlorophenyl)-5-methyl-2-(1-methyl-3-(1-(3-methyloxetan-3-yl)-1,2,3,6-tetrahydropyridin-4-yl)-1H-indazol-5-yl)benzo[d]thiazol-6-yl)acetate

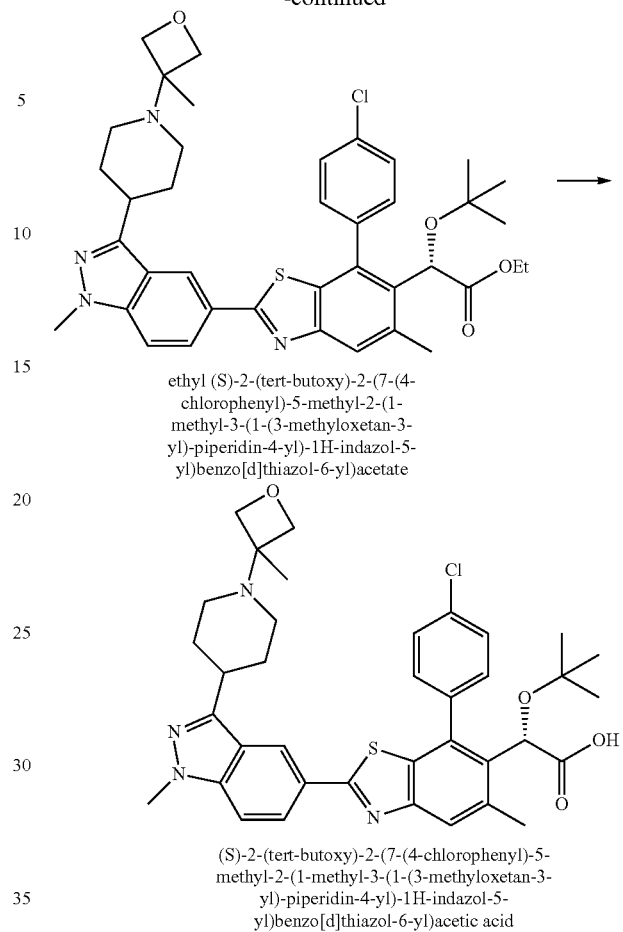

ethyl (S)-2-(tert-butoxy)-2-(7-(4-chlorophenyl)-5-methyl-2-(1-methyl-3-(1-(3-methyloxetan-3-yl)-piperidin-4-yl)-1H-indazol-5-yl)benzo[d]thiazol-6-yl)acetate (S)-2-(tert-butoxy)-2-(7-(4-chlorophenyl)-5-methyl-2-(1-methyl-3-(1-(3-methyloxetan-3-yl)-piperidin-4-yl)-1H-indazol-5-yl)benzo[d]thiazol-6-yl)acetic acid Preparation of 1-(3-methyloxetan-3-yl)piperidin-4-ol: A solution of 3-(phenylsulfonylmethylene)oxetane (2.1 g, 10 mmol) and piperidin-4-ol (1.11 g, 11 mmol) in methanol (100 mL) was stirred at 50° C. for 5 hours. LCMS shows desired product, trace starting material. Reaction mixture was telescoped into next reaction. Magnesium turnings (1.2 g, 50 mmol) were treated with chloro trimethylsilane (0.5 mL), followed by anhydrous methanol (5 mL). The mixture was gently swirled resulting in vigorous bubbling. After 30 seconds, mixture was decanted, anhydrous methanol (5 mL) was added, swirled for 30 seconds and decanted. The activated magnesium was added to above reaction mixture and stirred at 50° C. for 12 h. LCMS shows desired product mass. Reaction mixture was diluted with methanol, filtered through a pad of Celite and the filtrate concentrated. Crude 1-(3-methyloxetan-3-yl)piperidin-4-ol was dissolved in methanol and was applied to a Amberlite column. The column was washed with methanol and product was eluted off using 2M ammonia in methanol. Product containing fractions were concentrated and dried under house vacuum to give a yellow residue. LCMS-ESI+: calc'd for $C_9H_{18}NO_2$: 172.1 (M+H)+; found: 172.2 (M+H)+.

Preparation of 1-(3-methyloxetan-3-yl)piperidin-4-one: To a solution of oxalyl chloride (0.24 mL, 2.84 mmol) in dichloromethane (10 mL) at −78° C. was added dropwise DMSO (0.37 mL, 5.20 mmol). Reaction mixture was stirred for 15 minutes, and then a solution of 1-(3-methyloxetan-3-yl)piperidin-4-ol (0.41 g, 2.37 mmol) in dichloromethane (1.5 mL) was added dropwise. Reaction mixture was stirred

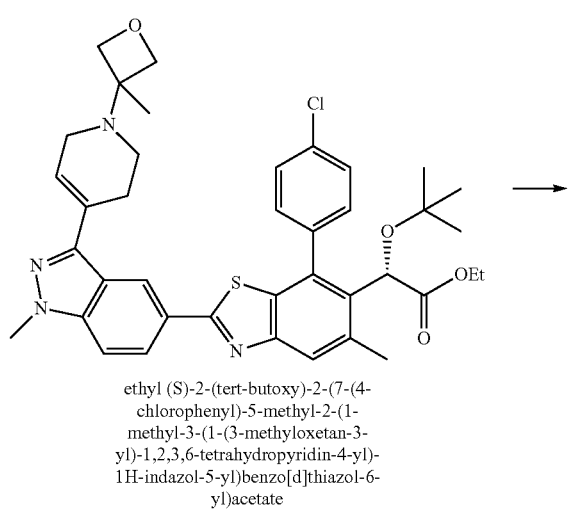

for 5 minutes, and then triethylamine (1.65 mL, 11.8 mmol) was added. Reaction mixture was stirred at −78° for 30 minutes, then warmed to room temperature over 1 hour. Reaction mixture was filtered and filtrate was concentrated and stored in the freezer over the weekend. Purified by CombiFlash (24 g Gold, 0-20% MeOH/EtOAc, staining with DNP) to give a yellow residue. LCMS-ESI+: calc'd for $C_9H_{16}NO_2$: 170.1 (M+H)+; found: 170.1 (M+H)+.

Preparation of 1-(3-methyloxetan-3-yl)-1,2,3,6-tetrahydropyridin-4-yl trifluoromethanesulfonate: To a solution of 1.0M lithium hexamethyldisilazide in THF (2.0 mL) in THF (2 mL) at −78° C. was added a solution of 1-(3-methyloxetan-3-yl)piperidin-4-one (0.221 g, 1.30 mmol) in THF (2 mL) over 5 minutes. Reaction mixture was warmed to room temperature over 2 hours, then cooled to −78° C. n-Phenyltrifluoromethanesulfonimide (0.56 g, 1.56 mmol) was added and reaction mixture was warmed to room temperature over 2 hours. The reaction mixture was quenched with ammonium chloride and stirred for 20 minutes. The organic component was removed by rotovap and the white mixture was extracted with ethyl acetate (2×). Combined organic layer was dried ($MgSO_4$), filtered and concentrated. The yellow residue was purified by CombiFlash (12 g Gold, 10-60-100% EtOAc/Hex) to give desired product plus 1-(3-methyloxetan-3-yl)piperidin-4-one. LCMS-ESI+: calc'd for $C_{10}H_{15}F_3NO_4S$: 302.1 (M+H)+; found: 302.0 (M+H)+.

Preparation of ethyl (S)-2-(tert-butoxy)-2-(7-(4-chlorophenyl)-5-methyl-2-(1-methyl-3-(1-(3-methyloxetan-3-yl)-1,2,3,6-tetrahydropyridin-4-yl)-1H-indazol-5-yl)benzo[d]thiazol-6-yl)acetate: A mixture of 1-(3-methyloxetan-3-yl)-1,2,3,6-tetrahydropyridin-4-yl trifluoromethanesulfonate (250 mg, 0.830 mmol), bis(pinacolato)diboron (309 mg, 3.15 mmol), [1,1'-bis(diphenylphosphino)ferrocene]dichloropalladium(II), complex with dichloromethane (19 mg, 0.027 mmol), and 1,1'-bis(diphenylphosphino)ferrocene (15 mg, 0.027 mmol) in dioxane (8.0 mL) was sparged with nitrogen for 20 minutes. Reaction mixture was heated at 80° C. for 3 hours. LCMS shows some desired product mass, majority is dimer. Cooled to room temperature and stored in freezer over the weekend.

The mixture was allowed to thaw for 1 hour. 2M Potassium carbonate (0.48 mL, 0.96 mmol) was added and reaction mixture was sparged with nitrogen for 5 minutes. $PdCl_2(Amphos)_2$ (11 mg, 0.016 mmol) and ethyl (S)-2-(2-(3-bromo-1-methyl-1H-indazol-5-yl)-7-(4-chlorophenyl)-5-methylbenzo[d]thiazol-6-yl)-2-(tert-butoxy)acetate (59 mg, 0.119 mmol) (100 mg, 0.129 mmol) were added and reaction mixture was heated at 80° C. for 4 hours. LCMS showed desired product mass. Reaction mixture was cooled to room temperature, diluted with ethyl acetate and washed with brine. The aqueous layer was back-extracted and combined organic layer was dried ($MgSO_4$), filtered and concentrated to give a dark brown residue. Purification by CombiFlash (12 g, Gold, 0-100% EtOAc/hex) gave a yellow film. LCMS-ESI+: calc'd for $C_{39}H_{44}ClN_4O_4S$: 699.3 (M+H)+; found: 699.2 (M+H)+.

Preparation of ethyl (S)-2-(tert-butoxy)-2-(7-(4-chlorophenyl)-5-methyl-2-(1-methyl-3-(1-(3-methyloxetan-3-yl)piperidin-4-yl)-1H-indazol-5-yl)benzo[d]thiazol-6-yl)acetate: A mixture of ethyl (S)-2-(tert-butoxy)-2-(7-(4-chlorophenyl)-5-methyl-2-(1-methyl-3-(1-(3-methyloxetan-3-yl)-1,2,3,6-tetrahydropyridin-4-yl)-1H-indazol-5-yl)benzo[d]thiazol-6-yl)acetate (46 mg, 0.066 mmol) and 5% rhodium on alumina (40 mg, 0.019 mmol) in ethanol (4.0 mL) was stirred under hydrogen atmosphere for 36 hours. LCMS showed reaction was complete. Reaction mixture was filtered through a pad of Celite, concentrated and purified by CombiFlash (4 g, Gold, 0-70% Hex/(20% MeOH in EtOAc)) to give a colorless film. LCMS-ESI+: calc'd for $C_{39}H_{46}ClN_4O_4S$: 701.3 (M+H)+; found: 701.3 (M+H)+.

Preparation of (S)-2-(tert-butoxy)-2-(7-(4-chlorophenyl)-5-methyl-2-(1-methyl-3-(1-(3-methyloxetan-3-yl)piperidin-4-yl)-1H-indazol-5-yl)benzo[d]thiazol-6-yl)acetic acid: A solution of ethyl (S)-2-(tert-butoxy)-2-(7-(4-chlorophenyl)-5-methyl-2-(1-methyl-3-(1-(3-methyloxetan-3-yl)piperidin-4-yl)-1H-indazol-5-yl)benzo[d]thiazol-6-yl)acetate (25 mg, 0.036 mmol) and 5M sodium hydroxide (36 µL, 0.18 mmol) in THF (1.0 mL) and MeOH (0.1 mL) was stirred at 60° C. for 3 hours. Reaction mixture was cooled to room temperature, diluted with DMF (0.5 mL), concentrated to ~0.5 mL, diluted with methanol, filtered through a syringe filter and purified by Gilson HPLC (Gemini, 5-100% ACN/$H_2O$+ 0.1% TFA). Product was lyophilized to give a yellow powder. $^1$H NMR (400 MHz, Methanol-$d_4$) δ 8.46 (s, 1H), 8.13 (d, J=8.9 Hz, 1H), 7.82 (s, 1H), 7.75-7.48 (m, 5H), 5.25 (s, 1H), 4.89 (d, J=7.9 Hz, 2H), 4.54 (d, J=7.8 Hz, 2H), 4.05 (s, 3H), 3.64-3.32 (m, 4H), 2.61 (s, 3H), 2.48-2.14 (m, 4H), 1.81 (s, 3H), 0.98 (s, 9H). LCMS-ESI+: calc'd for $C_{37}H_{42}ClN_4O_4S$: 673.3 (M+H)+; found: 673.2 (M+H)+.

Example 24. Preparation of (S)-2-(7-(4-chlorophenyl)-5-methyl-2-(1-methyl-3-(1-(oxetan-3-yl)piperidin-4-yl)-1H-indazol-5-yl)benzo[d]thiazol-6-yl)-2-((2-(methyl-$d_3$)propan-2-yl-1,1,1,3,3,3-$d_6$)oxy)acetic Acid (21)

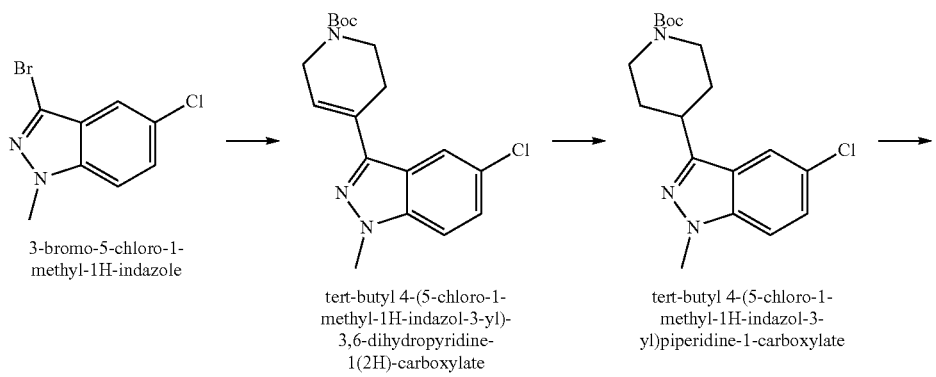

3-bromo-5-chloro-1-methyl-1H-indazole tert-butyl 4-(5-chloro-1-methyl-1H-indazol-3-yl)-3,6-dihydropyridine-1(2H)-carboxylate tert-butyl 4-(5-chloro-1-methyl-1H-indazol-3-yl)piperidine-1-carboxylate

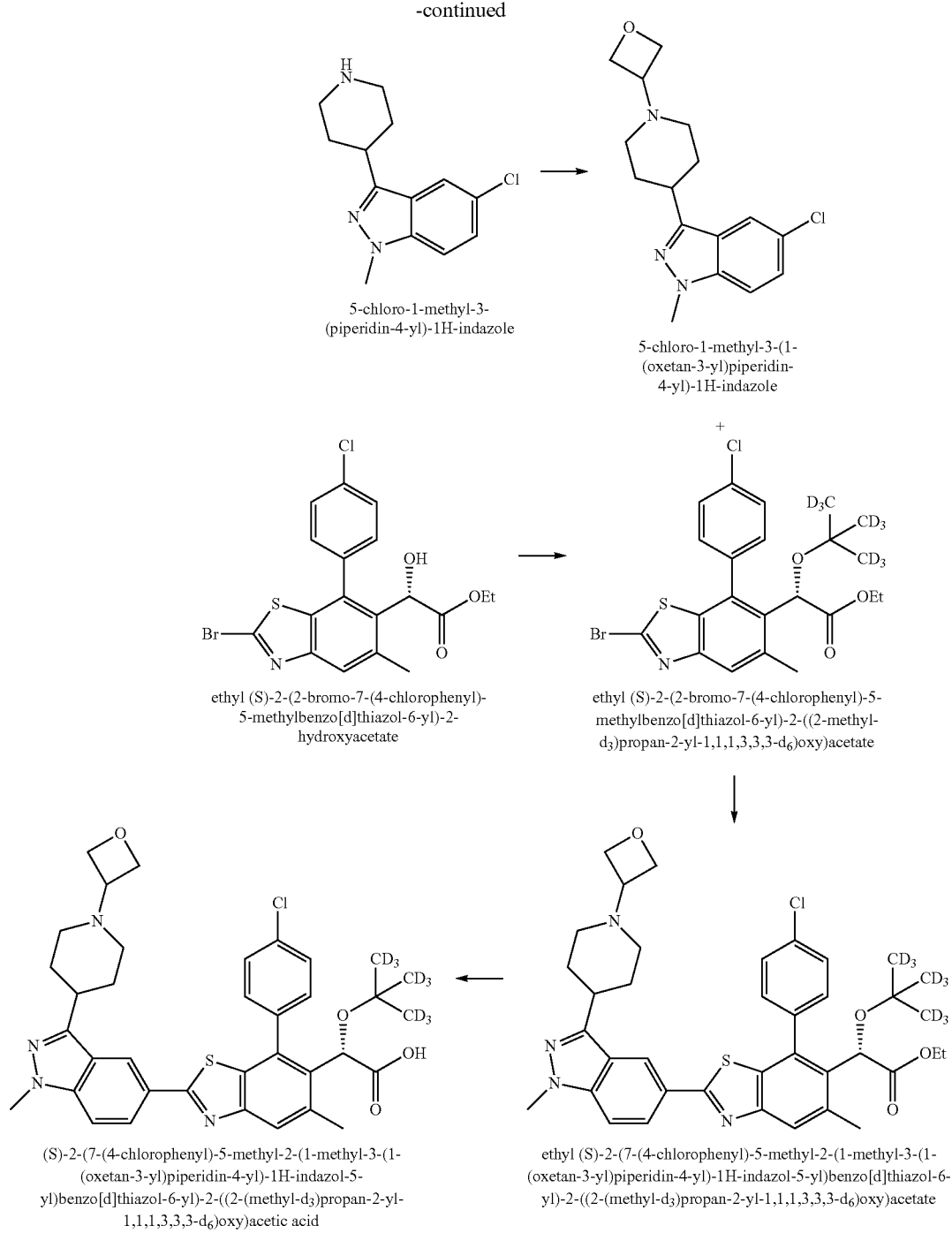

Preparation of tert-butyl 4-(5-chloro-1-methyl-1H-indazol-3-yl)-5,6-dihydropyridine-1(2H)-carboxylate: A 100 mL round bottom flask was charged with 3-bromo-5-chloro-1-methyl-1H-indazole (2.00 g, 8.15 mmol), tert-butyl 4-(4,4,5,5-tetramethyl-1,3,2-dioxaborolan-2-yl)-5,6-dihydropyridine-1(2H)-carboxylate (3.02 mg, 9.78 mmol), dichloro 1,1-bis(diphenylphosphino)ferrocene palladium(II) dichloromethane (665 mg, 0.815 mmol) and potassium phosphate 8.65 g, 40.7 mmol). The flask was flushed with nitrogen for 5 minutes, then anhydrous dioxane (40 mL) was added and flask was placed into an oil bath pre-heated to 90° C. Reaction mixture was stirred for 5 hours. LCMS shows nearly complete conversion. Reaction mixture was filtered through a pad of Celite, concentrated and purified by CombiFlash (120 g, 10-25% EtOAc/Hex) to give a yellow residue. LCMS-ESI+: calc'd for $C_{14}H_{15}ClN_3O_2$: 292.1 (M-tBu+H)$^+$; found: 292.2 (M-tBu+H)$^+$.

Preparation of tert-butyl 4-(5-chloro-1-methyl-1H-indazol-3-yl)piperidine-1-carboxylate: A mixture of tert-butyl 4-(5-chloro-1-methyl-1H-indazol-3-yl)-5,6-dihydropyridine-1(2H)-carboxylate (2.61 g, 7.50 mmol), rhodium on alumina (5%, 2.01 g, 0.977 mmol) in ethanol (40 mL) was stirred under a hydrogen atmosphere for 8 hours. Reaction mixture was filtered through Celite and the filtrate was concentrated. The residue was purified by CombiFlash (120 g, Gold, 0-25% EtOAc/Hex) to give a colorless oil. LCMS-ESI+: calc'd for $C_{14}H_{17}ClN_3O_2$: 294.1 (M-tBu+H)+; found: 294.1 (M+H)+.

Preparation of 5-chloro-1-methyl-3-(piperidin-4-yl)-1H-indazole: To a solution of tert-butyl 4-(5-chloro-1-methyl-1H-indazol-3-yl)piperidine-1-carboxylate (0.495 g, 1.42 mmol) in dichloromethane (4.0 mL) was added trifluoroacetic acid (1.0 mL). The reaction mixture turned orange immediately. Reaction mixture was stirred for 1 hour, then concentrated. The residue was suspended in 10% dichloromethane in hexane, resulting solid collected by filtration and dried on house vacuum to give desired product as a TFA salt. LCMS-ESI+: calc'd for $C_{13}H_{18}ClN_3$: 250.1 (M+H)+; found: 250.2 (M+H)+.

Preparation of 5-chloro-1-methyl-3-(1-(oxetan-3-yl)piperidin-4-yl)-1H-indazole: A solution of 5-chloro-1-methyl-3-(piperidin-4-yl)-1H-indazole TFA salt (291 mg, 0.80 mmol), oxetan-3-one (0.37 mL, 5.834 mmol), acetic acid (0.334 mL, 5.83 mmol), and sodium triacetoxyborohydride (1.24 g, 5.83 mmol) in DMF (3.0 mL) was stirred at 60° C. for 1 hour. LCMS show no starting material. Reaction mixture was quenched with saturated sodium bicarbonate, and extracted with EtOAc. Organic layer was washed with 5% lithium chloride solution (3×), brine and dried (MgSO$_4$). Concentration and purification by CombiFlash (12 g, Gold, 0-5% MeOH/EtOAc) gave desired product. The aqueous layer was back-extracted with ethyl acetate (3×), dried (MgSO$_4$), filtered and concentrated. The residue was dried over the weekend under house vacuum and purified by CombiFlash (12 g, Gold, 0-5% MeOH/EtOAc) to give additional product. LCMS-ESI+: calc'd for $C_{16}H_{21}ClN_3O$: 306.1 (M+H)+; found: 306.2 (M+H)+.

Preparation of ethyl (S)-2-(2-bromo-7-(4-chlorophenyl)-5-methylbenzo[d]thiazol-6-yl)-2-((2-(methyl-d$_3$)propan-2-yl-1,1,1,3,3,3-d$_6$)oxy)acetate: Two parallel reactions: to a solution of ethyl (S)-2-(2-bromo-7-(4-chlorophenyl)-5-methylbenzo[d]thiazol-6-yl)-2-hydroxyacetate (1.10 g, 2.50 mmol) in tert-butanol, d$_{10}$ (11 mL) and dichloromethane (2.2 mL) at −10° C. was added trifluoromethanesulfonic anhydride (5 g, 17.7 mmol) over 5 minutes. The internal temperature rose to 37° C. but cooled back down to below 0° C. Reaction mixture was stirred at this temperature for 1 hour, then quenched with triethylamine (4.5 mL) and stirred for 10 minutes. Reaction mixture was diluted with ethyl acetate, poured into 5M NaOH and washed with brine (2×). The organic layers from both reactions were combined, dried (MgSO$_4$) and concentrated to give a white paste that was adsorbed onto silica gel using dichloromethane and methanol. Purification by CombiFlash (40 g, Gold, 0-25% EtOAc/Hex) gave the desired product. LCMS-ESI+: calc'd for $C_{22}H_{15}D_9BrClNO_3S$: 505.1 (M+H)+; found: 505.1 (M+H)+.

Preparation of ethyl (S)-2-(7-(4-chlorophenyl)-5-methyl-2-(1-methyl-3-(1-(oxetan-3-yl)piperidin-4-yl)-1H-indazol-5-yl)benzo[d]thiazol-6-yl)-2-((2-(methyl-d$_3$)propan-2-yl-1,1,1,3,3,3-d$_6$)oxy)acetate: A 10 mL round bottom flash was charged with the 5-chloro-1-methyl-3-(1-(oxetan-3-yl)piperidin-4-yl)-1H-indazole (105 mg, 0.343 mmol), bis(neopentyl glycolato)diboron (101 mg, 0.446 mmol), PdCl$_2$(Amphos)$_2$ (24 mg, 0.034 mmol) and potassium propionate (173 mg, 1.55 mmol) and flushed with nitrogen. De-gassed dioxane (3.0 mL) was added under a nitrogen atmosphere and reaction mixture was heated to 80° C. for 2 h. The reaction turned from a heterogeneous yellow color to a dark brown color. To the above reaction mixture, 2M potassium carbonate (1.28 mL, 2.56 mmol) and ethyl (S)-2-(2-bromo-7-(4-chlorophenyl)-5-methylbenzo[d]thiazol-6-yl)-2-((2-(methyl-d$_3$)propan-2-yl-1,1,1,3,3,3-d$_6$)oxy)acetate (262 mg, 0.342 mmol) were added and the reaction heated to 80° C. After 2 h, LCMS showed desired product mass. Reaction was cooled to room temperature, filtered through a pad of Celite, concentrated. The residue was purified by CombiFlash (4 g Gold, 5-40% EtOAc/Hex) and concentrated to give a white film. LCMS-ESI+: calc'd for $C_{38}H_{35}D_9ClN_4O_4S$: 696.3 (M+H)+; found: 696.5 (M+H)+.

Preparation of (S)-2-(7-(4-chlorophenyl)-5-methyl-2-(1-methyl-3-(1-(oxetan-3-yl)piperidin-4-yl)-1H-indazol-5-yl)benzo[d]thiazol-6-yl)-2-((2-(methyl-d$_3$)propan-2-yl-1,1,1,3,3,3-d$_6$)oxy)acetic acid: A solution of ethyl (S)-2-(7-(4-chlorophenyl)-5-methyl-2-(1-methyl-3-(1-(oxetan-3-yl)piperidin-4-yl)-1H-indazol-5-yl)benzo[d]thiazol-6-yl)-2-((2-(methyl-d$_3$)propan-2-yl-1,1,1,3,3,3-d$_6$)oxy)acetate (131 mg, 0.139 mmol) and 5M sodium hydroxide (0.278 mL, 1.39 mmol) in THF (3.0 mL) and MeOH (0.5 mL) was heated at 50° C. for 3 hours. Reaction mixture was diluted with ethyl acetate, washed with brine, dried (MgSO$_4$), filtered and concentrated. Residue was dissolved in methanol and purified by Gilson HPLC (5-100% ACN/H$_2$O) and product-containing fractions were lyophilized to give a yellow powder. $^1$H NMR (400 MHz, Methanol-d$_4$) δ 8.46 (s, 1H), 8.12 (d, J=8.7 Hz, 1H), 7.81 (s, 1H), 7.73-7.56 (m, 5H), 5.24 (s, 1H), 4.98-4.89 (m, 3H), 4.86-4.79 (m, 3H), 4.47 (s, 1H), 4.05 (s, 3H), 3.65 (d, J=9.8 Hz, 2H), 3.50 (d, J=19.5 Hz, 1H), 3.21-3.03 (m, 2H), 2.61 (s, 3H), 2.39 (d, J=12.9 Hz, 2H), 2.33-2.14 (m, 2H). LCMS-ESI+: calc'd for $C_{36}H_{31}D_9ClN_4O_4S$: 668.3 (M+H)+; found: 668.3 (M+H)+.

Example 25. Preparation of (S)-2-(7-(4-chlorophenyl)-5-methyl-2-(1-methyl-3-(1-(oxetan-3-yl)piperidin-4-yl)-1H-indazol-5-yl)benzo[d]thiazol-6-yl)-2-cyclopropoxyacetic Acid (22)

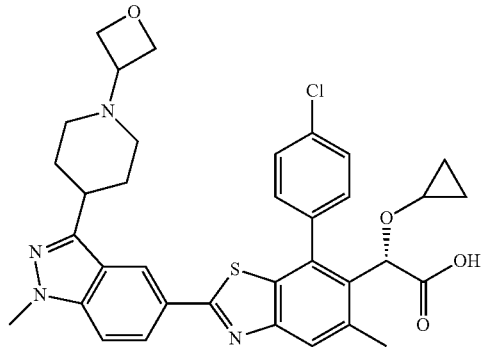

(S)-2-(7-(4-chlorophenyl)-5-methyl-2-(1-methyl-3-(1-(oxetan-3-yl)piperidin-4-yl)-1H-indazol-5-yl)benzo[d]thiazol-6-yl)-2-cyclopropoxyacetic acid Preparation of (S)-2-(7-(4-chlorophenyl)-5-methyl-2-(1-methyl-3-(1-(oxetan-3-yl)piperidin-4-yl)-1H-indazol-5-yl)benzo[d]thiazol-6-yl)-2-cyclopropoxyacetic acid: Prepared in a similar manner as (S)-2-(7-(4-chlorophenyl)-5-methyl-2-(1-methyl-3-(1-(oxetan-3-yl)piperidin-4-yl)-1H-indazol-5-yl)benzo[d]thiazol-6-yl)-2-((2-(methyl-d$_3$)propan-2-yl-1,1,1,3,3,3-d$_6$)oxy)acetic acid, except using bis(pinacolato)diboron instead of bis(neopentyl glycolato)diboron. $^1$H NMR (400 MHz, Methanol-d4) δ 8.39 (s, 1H), 8.04 (dd, J=8.9, 1.6 Hz, 1H), 7.79 (s, 1H), 7.60-7.44 (m, 5H), 5.15 (s, 1H), 4.96-4.81 (m, 4H), 4.48 (p, J=6.6 Hz, 1H), 4.00 (s, 3H), 3.60 (s, 1H), 3.50 (s, 1H), 3.26 (m, 1H), 3.12 (m, 2H), 2.65 (m, 1H), 2.54 (s, 3H), 2.40-2.20 (m, 4H), 0.46-0.21 (m, 4H).

Example 26. Preparation of (S)-2-(tert-butoxy)-2-(2-(3-(1-(tert-butoxycarbonyl)piperidin-4-yl)-1-methyl-1H-indazol-5-yl)-7-(4-chlorophenyl)-5-methylbenzo[d]thiazol-6-yl)acetic Acid (23)

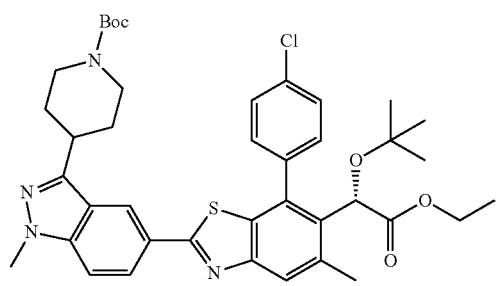

tert-butyl (S)-4-(5-(6-(1-(tert-butoxy)-2-ethoxy-2-oxoethyl)-7-(4-chlorophenyl)-5-methylbenzo[d]thiazol-2-yl)-1-methyl-1H-indazol-3-yl)piperidine-1-carboxylate

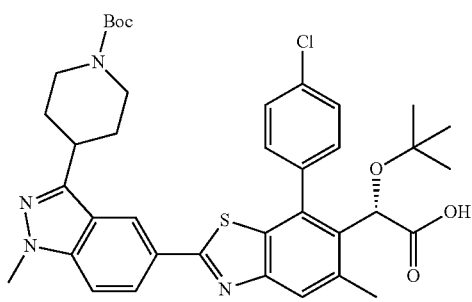

(S)-2-(tert-butoxy)-2-(2-(3-(1-(tert-butoxycarbonyl)piperidin-4-yl)-1-methyl-1H-indazol-5-yl)-7-(4-chlorophenyl)-5-methylbenzo[d]thiazol-6-yl)acetic acid Preparation of (S)-2-(tert-butoxy)-2-(2-(3-(1-(tert-butoxycarbonyl)piperidin-4-yl)-1-methyl-1H-indazol-5-yl)-7-(4-chlorophenyl)-5-methylbenzo[d]thiazol-6-yl)acetic acid: To tert-butyl (S)-4-(5-(6-(1-(tert-butoxy)-2-ethoxy-2-oxoethyl)-7-(4-chlorophenyl)-5-methylbenzo[d]thiazol-2-yl)-1-methyl-1H-indazol-3-yl)piperidine-1-carboxylate (20 mg, 0.027 mmol) was added THF (1 mL), MeOH (0.2 mL) and 50% Sodium hydroxide (0.2 mL) at rt. The mixture was stirred at 60° C. for 1 h. The reaction mixture was cooled by ice and acidified with 2 N HCl. The resulting mixture was extracted with ethyl acetate (2×). Combined organic layer was dried (MgSO$_4$), filtered and concentrated to give crude mixture which was purified by Gilson HPLC (Phenomenex Gemini 250×21.2 10µ C18 column, 40-100% ACN/H$_2$O+ 0.1% TFA) to give a yellow powder after lyophilization. $^1$H NMR (400 MHz, Chloroform-d) δ 8.32 (s, 1H), 8.04 (d, J=8.0 Hz, 1H), 7.84 (s, 1H), 7.63-7.31 (m, 3H), 5.27 (s, 1H), 4.25 (s, 2H), 4.02 (s, 3H), 3.24 (t, J=11.2 Hz, 1H), 2.93 (s, 2H), 2.54 (s, 3H), 2.02-1.82 (m, 4H), 1.48 (s, 9H), 0.96 (s, 9H). LCMS-ESI+: calc'd for C$_{38}$H$_{44}$ClN$_4$O$_5$S; 703.2 (M+H)$^+$; found: 703.0 (M+H)$^+$.

Example 27. Preparation of (S)-2-(tert-butoxy)-2-(2-(3-(1-(tert-butoxycarbonyl)piperidin-4-yl)-1-methyl-1H-indazol-5-yl)-7-(4-chlorophenyl)-5-methylbenzo[d]thiazol-6-yl)acetic Acid (24)

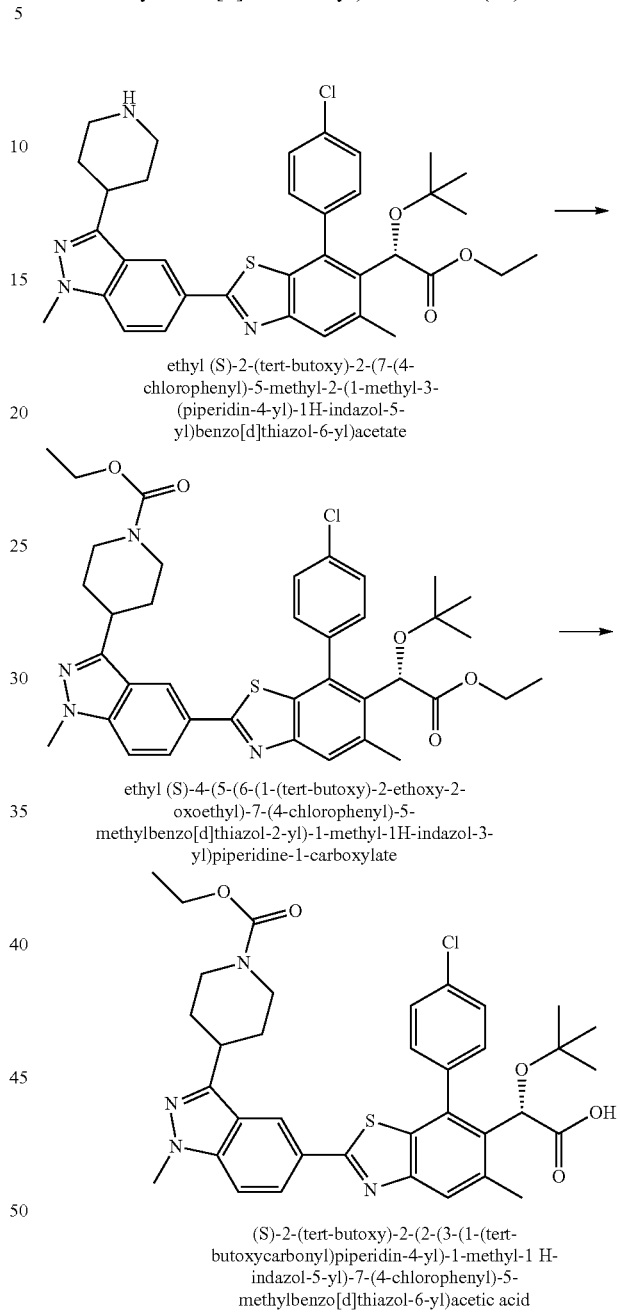

ethyl (S)-2-(tert-butoxy)-2-(7-(4-chlorophenyl)-5-methyl-2-(1-methyl-3-(piperidin-4-yl)-1H-indazol-5-yl)benzo[d]thiazol-6-yl)acetate ethyl (S)-4-(5-(6-(1-(tert-butoxy)-2-ethoxy-2-oxoethyl)-7-(4-chlorophenyl)-5-methylbenzo[d]thiazol-2-yl)-1-methyl-1H-indazol-3-yl)piperidine-1-carboxylate (S)-2-(tert-butoxy)-2-(2-(3-(1-(tert-butoxycarbonyl)piperidin-4-yl)-1-methyl-1H-indazol-5-yl)-7-(4-chlorophenyl)-5-methylbenzo[d]thiazol-6-yl)acetic acid Preparation of ethyl (S)-4-(5-(6-(1-(tert-butoxy)-2-ethoxy-2-oxoethyl)-7-(4-chlorophenyl)-5-methylbenzo[d]thiazol-2-yl)-1-methyl-1H-indazol-3-yl)piperidine-1-carboxylate: To a flask containing ethyl (S)-2-(tert-butoxy)-2-(7-(4-chlorophenyl)-5-methyl-2-(1-methyl-3-(piperidin-4-yl)-1H-indazol-5-yl)benzo[d]thiazol-6-yl)acetate (36 mg, 0.057 mmol) in THF (1 mL) and 1N sodium hydroxide (0.5 mL) was added Ethyl chloroformate (20 µl, 0.21 mmol). The mixture was stirred at room temperature for 18 h. The reaction was completed and carried to the next step directly. LCMS-ESI+: calc'd for: C$_{38}$H$_{44}$ClN$_4$O$_5$S; 703.3 (M+H)$^+$; found: 703.5 (M+H)$^+$.

Preparation of (S)-2-(tert-butoxy)-2-(2-(3-(1-(tert-butoxycarbonyl)piperidin-4-yl)-1-methyl-1H-indazol-5-yl)-7-(4-chlorophenyl)-5-methylbenzo[d]thiazol-6-yl)acetic acid: To above reaction mixture containing crude ethyl (S)-4-(5-(6-(1-(tert-butoxy)-2-ethoxy-2-oxoethyl)-7-(4-chlorophenyl)-5-methylbenzo[d]thiazol-2-yl)-1-methyl-1H-indazol-3-yl)piperidine-1-carboxylate (0.057 mmol) was added MeOH (0.5 mL) and 50% Sodium hydroxide (0.2 mL) at rt. The mixture was stirred at 60° C. for 1 h. The reaction mixture was cooled by ice bath and acidified with 3N HCl. The resulting mixture was extracted with ethyl acetate (2×). Combined organic layer was dried (MgSO$_4$), filtered and concentrated to give crude mixture which was purified by Gilson HPLC (Phenomenex Gemini 250×21.2 10μ C18 column, 40-100% ACN/H$_2$O+0.1% TFA) to give a yellow powder after lyophilization. $^1$H NMR (400 MHz, Chloroform-d) δ 8.36 (d, J=1.6 Hz, 1H), 8.03 (dd, J=8.8, 1.5 Hz, 1H), 7.89 (s, 1H), 7.72 (d, J=8.1 Hz, 1H), 7.59-7.47 (m, 3H), 7.39 (d, J=8.8 Hz, 1H), 5.32 (s, 1H), 4.30 (s, 2H), 4.17 (q, J=7.1 Hz, 2H), 4.03 (s, 3H), 3.36-3.16 (m, 1H), 3.00 (t, J=12.4 Hz, 2H), 2.59 (s, 3H), 2.14-1.82 (m, 4H), 1.29 (t, J=7.1 Hz, H), 1.01 (s, 9H). LCMS-ESI+: calc'd for C$_{36}$H$_{40}$ClN$_4$O$_5$S; 675.4 (M+H)$^+$; found: 675.3 (M+H)$^+$.

Example 28. Preparation of (S)-2-(tert-butoxy)-2-(2-(3-(1-(tert-butoxycarbonyl)piperidin-4-yl)-1-methyl-1H-indazol-5-yl)-7-(4-chlorophenyl)-5-methylbenzo[d]thiazol-6-yl)acetic Acid (25)

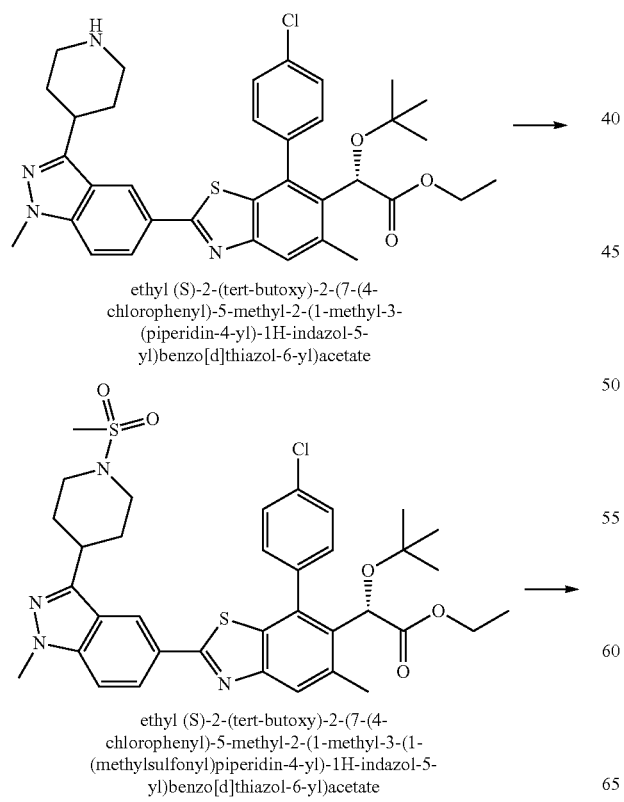

ethyl (S)-2-(tert-butoxy)-2-(7-(4-chlorophenyl)-5-methyl-2-(1-methyl-3-(piperidin-4-yl)-1H-indazol-5-yl)benzo[d]thiazol-6-yl)acetate ethyl (S)-2-(tert-butoxy)-2-(7-(4-chlorophenyl)-5-methyl-2-(1-methyl-3-(1-(methylsulfonyl)piperidin-4-yl)-1H-indazol-5-yl)benzo[d]thiazol-6-yl)acetate

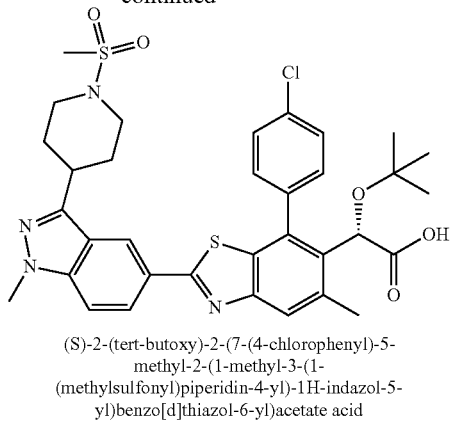

(S)-2-(tert-butoxy)-2-(7-(4-chlorophenyl)-5-methyl-2-(1-methyl-3-(1-(methylsulfonyl)piperidin-4-yl)-1H-indazol-5-yl)benzo[d]thiazol-6-yl)acetate acid Preparation of ethyl (S)-2-(tert-butoxy)-2-(7-(4-chlorophenyl)-5-methyl-2-(1-methyl-3-(1-(methylsulfonyl)piperidin-4-yl)-1H-indazol-5-yl)benzo[d]thiazol-6-yl)acetate: To a flask containing ethyl (S)-2-(tert-butoxy)-2-(7-(4-chlorophenyl)-5-methyl-2-(1-methyl-3-(piperidin-4-yl)-1H-indazol-5-yl)benzo[d]thiazol-6-yl)acetate (40 mg, 0.063 mmol) in dichloromethane (2 mL) and Triethylamine (70.66 μl, 506.95 μmol) was added Methanesulfonyl chloride (7.36 μl, 95.05 μmol) at 0° C. It was stirred and warmed to room temperature overnight (18 h). The reaction was complete and carried to the next step directly. LCMS-ESI+: calc'd for: C$_{36}$H$_{42}$ClN$_4$O$_5$S$_2$; 709.2 (M+H)$^+$; found: 709.4 (M+H)$^+$.

Preparation of (S)-2-(tert-butoxy)-2-(7-(4-chlorophenyl)-5-methyl-2-(1-methyl-3-(1-(methylsulfonyl)piperidin-4-yl)-1H-indazol-5-yl)benzo[d]thiazol-6-yl)acetic acid: To above reaction mixture containing crude ethyl (S)-2-(tert-butoxy)-2-(7-(4-chlorophenyl)-5-methyl-2-(1-methyl-3-(1-(methylsulfonyl)piperidin-4-yl)-1H-indazol-5-yl)benzo[d]thiazol-6-yl)acetate (0.063 mmol) was added THF (2 mL), MeOH (0.5 mL) and 50% Sodium hydroxide (0.5 mL) at rt. The mixture was stirred at 60° C. for 2 h. The reaction mixture was cooled by ice and acidified with 3 N HCl. The resulting mixture was extracted with ethyl acetate (2×). Combined organic layer was dried (MgSO$_4$), filtered and concentrated to give crude mixture which was purified by Gilson HPLC (Phenomenex Gemini 250×21.2 10μ C18 column, 40-100% ACN/H$_2$O+0.1% TFA) to give a yellow powder after lyophilization. $^1$H NMR (400 MHz, Chloroform-d) δ 8.42 (s, 1H), 8.06-7.88 (m, 2H), 7.73 (d, J=8.2 Hz, 1H), 7.62-7.47 (m, 3H), 7.41 (d, J=8.8 Hz, 1H), 5.33 (s, 1H), 4.04 (s, 3H), 3.95 (d, J=11.9 Hz, 2H), 3.23 (dd, J=10.2, 4.8 Hz, 1H), 3.01-2.87 (m, 2H), 2.86 (s, 3H), 2.59 (s, 3H), 2.16 (p, J=3.9 Hz, 4H), 1.02 (s, 9H). LCMS-ESI+: calc'd for $C_{34}H_{38}ClN_4O_5S_2$; 681.2 (M+H)+; found: 681.4 (M+H)+.

Example 29. Preparation of (S)-2-(tert-butoxy)-2-(7-(4-chlorophenyl)-5-methyl-2-(1-methyl-3-(1-((S)-tetrahydrofuran-3-yl)piperidin-4-yl)-1H-indazol-5-yl)benzo[d]thiazol-6-yl)acetic Acid (26)

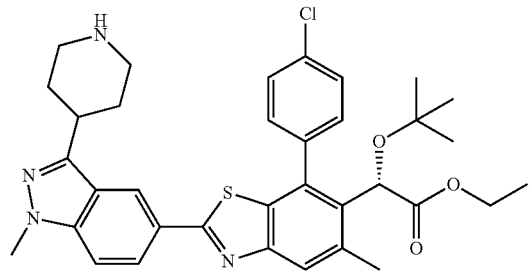

ethyl (S)-2-(tert-butoxy)-2-(7-(4-chlorophenyl)-5-methyl-2-(1-methyl-3-(piperidin-4-yl)-1H-indazol-5-yl)benzo[d]thiazol-6-yl)acetate ture was microwaved at 100° C. for another 2 h. The reaction was complete and carried to the next step directly after cooled to room temperature. LCMS-ESI+: calc'd for: $C_{39}H_{46}ClN_4O_4S$; 701.3 (M+H)+; found: 701.4 (M+H)+.

Preparation of (S)-2-(tert-butoxy)-2-(7-(4-chlorophenyl)-5-methyl-2-(1-methyl-3-(1-((S)-tetrahydrofuran-3-yl)piperidin-4-yl)-1H-indazol-5-yl)benzo[d]thiazol-6-yl)acetic acid: To above reaction mixture containing crude ethyl (S)-2-(tert-butoxy)-2-(7-(4-chlorophenyl)-5-methyl-2-(1-methyl-3-(1-(methylsulfonyl)piperidin-4-yl)-1H-indazol-5-

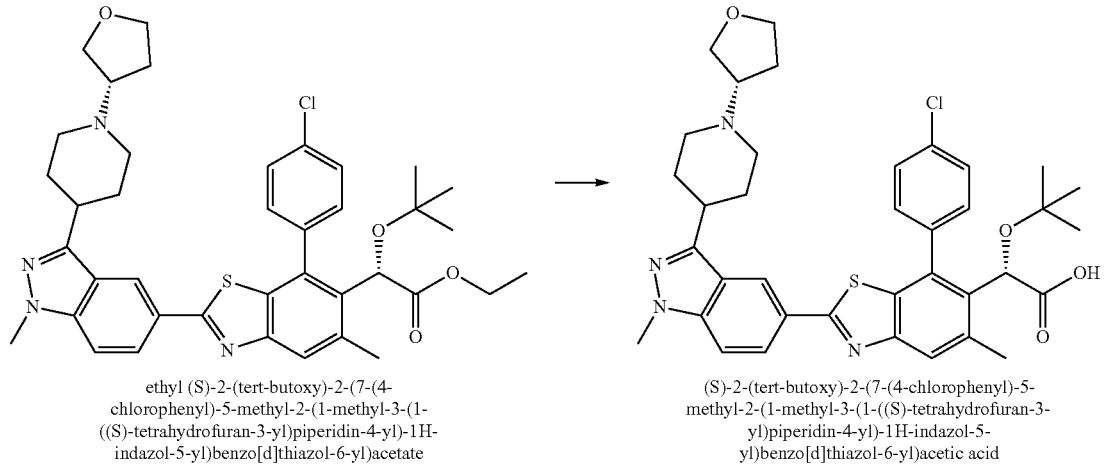

ethyl (S)-2-(tert-butoxy)-2-(7-(4-chlorophenyl)-5-methyl-2-(1-methyl-3-(1-((S)-tetrahydrofuran-3-yl)piperidin-4-yl)-1H-indazol-5-yl)benzo[d]thiazol-6-yl)acetate (S)-2-(tert-butoxy)-2-(7-(4-chlorophenyl)-5-methyl-2-(1-methyl-3-(1-((S)-tetrahydrofuran-3-yl)piperidin-4-yl)-1H-indazol-5-yl)benzo[d]thiazol-6-yl)acetic acid Preparation of ethyl (S)-2-(tert-butoxy)-2-(7-(4-chlorophenyl)-5-methyl-2-(1-methyl-3-(1-((S)-tetrahydrofuran-3-yl)piperidin-4-yl)-1H-indazol-5-yl)benzo[d]thiazol-6-yl)acetate: To a microwave vial containing ethyl (S)-2-(tert-butoxy)-2-(7-(4-chlorophenyl)-5-methyl-2-(1-methyl-3-(piperidin-4-yl)-1H-indazol-5-yl)benzo[d]thiazol-6-yl) acetate (50 mg, 0.079 mmol) in acetonitrile (2 mL) was added (S)-tetrahydrofuran-3-yl methanesulfonate (40 mg, 0.241 mmol) and Potassium carbonate (30 mg, 475 μmol). The mixture was microwaved at 100° C. for 1 h. Additional cesium carbonate (63.17 mg, 475 mmol), 40 mg of (S)-tetrahydrofuran-3-yl methanesulfonate were added and mixyl)benzo[d]thiazol-6-yl)acetate (0.079 mmol) was added THF (2 mL), MeOH (0.5 mL) and 50% Sodium hydroxide (0.5 mL) at rt. The mixture was stirred at 60° C. for 2 h. The reaction mixture was cooled by ice and acidified with 3 N HCl. The resulting mixture was extracted with ethyl acetate (2×). Combined organic layer was dried (MgSO4), filtered and concentrated to give crude mixture which was purified by Gilson HPLC (Phenomenex Gemini 250×21.2 10 g C18 column, 40-100% ACN/H2O+0.1% TFA) to give a yellow powder after lyophilization. $^1$H NMR (400 MHz, Chloroform-d) δ 8.24 (d, J=35.9 Hz, 1H), 7.96 (dd, J=36.3, 8.8 Hz, 1H), 7.78 (s, 1H), 7.70-7.57 (m, 1H), 7.52-7.37 (m, 3H), 7.33 (t, J=10.1 Hz, 1H), 5.33-5.10 (m, 1H), 4.18 (t, J=8.9 Hz, 1H), 4.06-3.80 (m, 3H), 3.80-2.72 (m, 8H), 2.49 (s, 3H), 2.35-2.03 (m, 6H), 1.28-1.05 (m, 1H), 0.93 (s, 9H). LCMS-ESI+: calc'd for $C_{37}H_{42}ClN_4O_4S$; 673.3 (M+H)+; found: 673.3 (M+H)+.

Example 30. Preparation of (S)-2-(tert-butoxy)-2-(7-(4-chlorophenyl)-5-methyl-2-(1-methyl-3-(1-((R)-tetrahydrofuran-3-yl)piperidin-4-yl)-1H-indazol-5-yl)benzo[d]thiazol-6-yl)acetic Acid (27)

Preparation of (S)-2-(tert-butoxy)-2-(7-(4-chlorophenyl)-5-methyl-2-(1-methyl-3-(1-((R)-tetrahydrofuran-3-yl)piperidin-4-yl)-1H-indazol-5-yl)benzo[d]thiazol-6-yl)acetic acid: To above reaction mixture containing crude ethyl (S)-2-(tert-butoxy)-2-(7-(4-chlorophenyl)-5-methyl-2-(1-methyl-3-(1-((R)-tetrahydrofuran-3-yl)piperidin-4-yl)-1H-indazol-5-yl)benzo[d]thiazol-6-yl)acetate (0.079 mmol) was added THF (2 mL), MeOH (0.5 mL) and 50% Sodium hydroxide (0.5 mL) at rt. The mixture was stirred at 60° C. for 2 h. The reaction mixture was cooled by ice and acidified with 3 N HCl. The resulting mixture was extracted with ethyl acetate (2×). Combined organic layer was dried

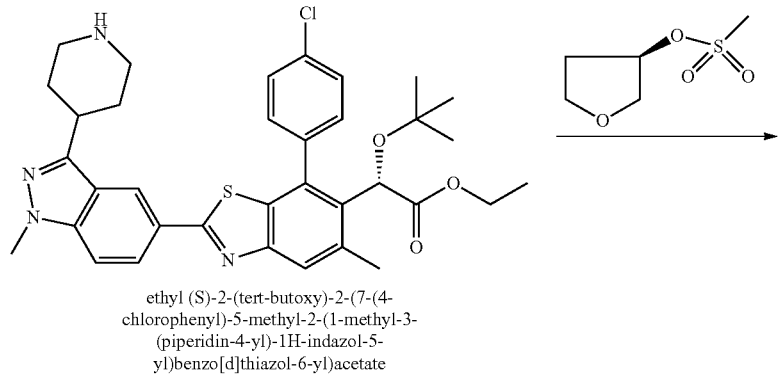

ethyl (S)-2-(tert-butoxy)-2-(7-(4-chlorophenyl)-5-methyl-2-(1-methyl-3-(piperidin-4-yl)-1H-indazol-5-yl)benzo[d]thiazol-6-yl)acetate

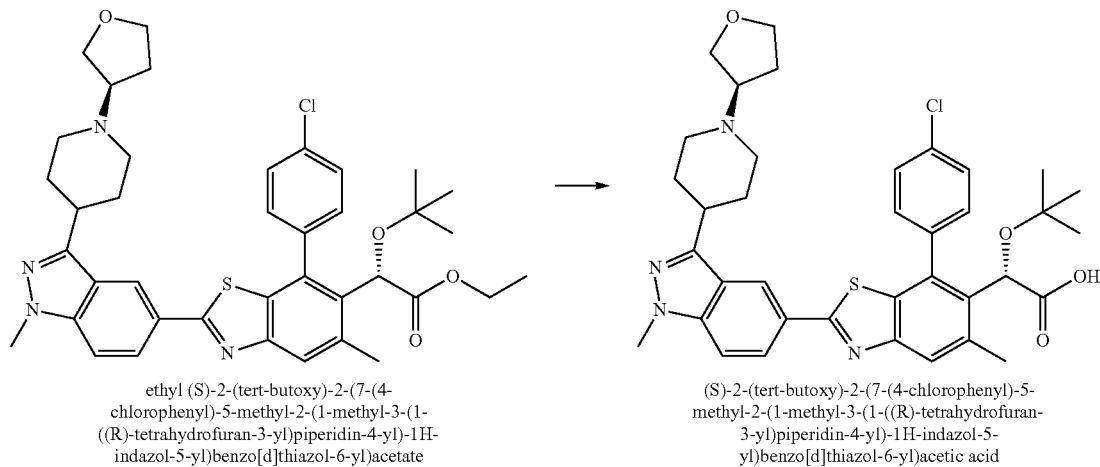

ethyl (S)-2-(tert-butoxy)-2-(7-(4-chlorophenyl)-5-methyl-2-(1-methyl-3-(1-((R)-tetrahydrofuran-3-yl)piperidin-4-yl)-1H-indazol-5-yl)benzo[d]thiazol-6-yl)acetate (S)-2-(tert-butoxy)-2-(7-(4-chlorophenyl)-5-methyl-2-(1-methyl-3-(1-((R)-tetrahydrofuran-3-yl)piperidin-4-yl)-1H-indazol-5-yl)benzo[d]thiazol-6-yl)acetic acid Preparation of ethyl (S)-2-(tert-butoxy)-2-(7-(4-chlorophenyl)-5-methyl-2-(1-methyl-3-(1-((R)-tetrahydrofuran-3-yl)piperidin-4-yl)-1H-indazol-5-yl)benzo[d]thiazol-6-yl)acetate: To a microwave vial containing ethyl (S)-2-(tert-butoxy)-2-(7-(4-chlorophenyl)-5-methyl-2-(1-methyl-3-(piperidin-4-yl)-1H-indazol-5-yl)benzo[d]thiazol-6-yl) acetate (50 mg, 0.079 mmol) in acetonitrile (2 mL) was added (R)-tetrahydrofuran-3-yl methanesulfonate (40 mg, 0.241 mmol) and Cesium carbonate (63.17 mg, 475 mmol). The mixture was microwaved at 100° C. for 4 h. The reaction was completed and carried to the next step directly after cooled to room temperature. LCMS-ESI+: calc'd for: $C_{39}H_{46}ClN_4O_4S$; 701.3 (M+H)+; found: 701.4 (M+H)+.

(MgSO4), filtered and concentrated to give crude mixture which was purified by Gilson HPLC (Phenomenex Gemini 250×21.2 10µ C18 column, 40-100% ACN/H2O+0.1% TFA) to give a yellow powder after lyophilization. 1H NMR (400 MHz, Chloroform-d) δ 8.23 (d, J=24.7 Hz, 1H), 7.97 (dd, J=30.7, 8.8 Hz, 1H), 7.79 (s, 1H), 7.64 (d, J=8.1 Hz, 1H), 7.51-7.39 (m, 3H), 7.33 (t, J=9.5 Hz, 1H), 5.24 (s, 1H), 4.20 (d, J=10.0 Hz, 1H), 3.96 (d, J=15.5 Hz, 3H), 3.81-3.48 (m, 6H), 3.40 (m, 2H), 3.23 (d, J=33.5 Hz, 2H), 2.84 (d, J=11.8 Hz, 1H), 2.50 (s, 3H), 2.36-2.02 (m, 4H), 0.93 (s, 9H). LCMS-ESI+: calc'd for $C_{37}H_{42}ClN_4O_4S$; 673.3 (M+H)+; found: 673.4 (M+H)+.

Example 31. Preparation of (S)-2-(tert-butoxy)-2-(2-(3-(1-(1-(tert-butoxycarbonyl)azetidin-3-yl)piperidin-4-yl)-1-methyl-1H-indazol-5-yl)-7-(4-chlorophenyl)-5-methylbenzo[d]thiazol-6-yl)acetic Acid (28)

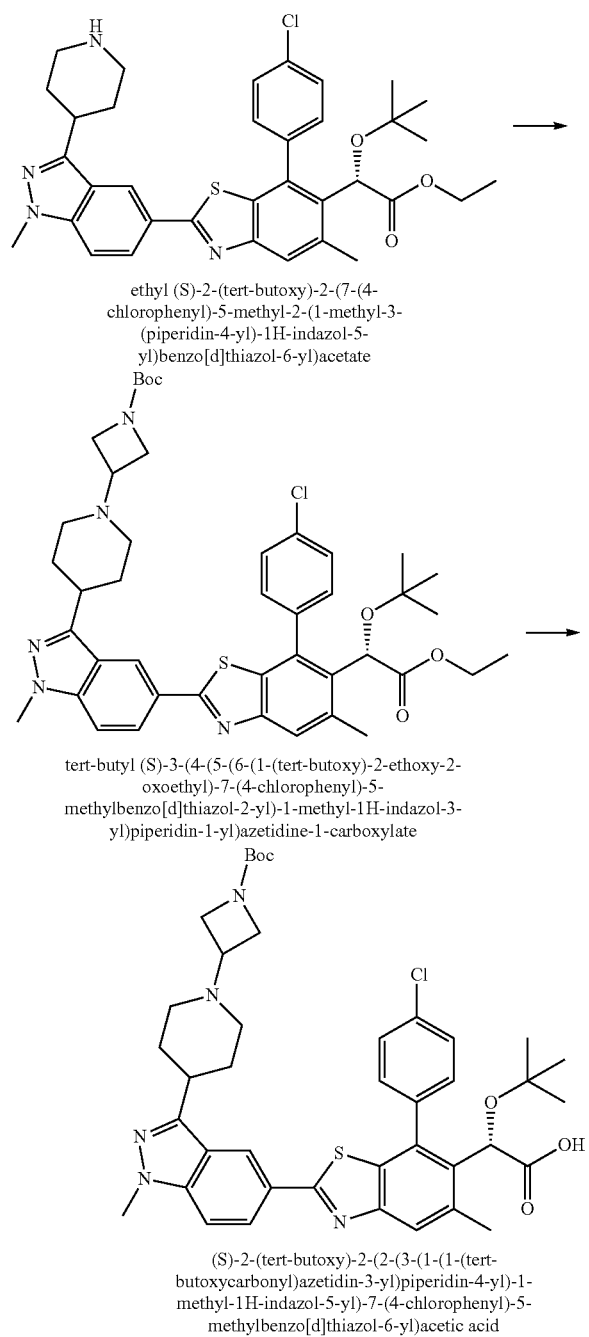

ethyl (S)-2-(tert-butoxy)-2-(7-(4-chlorophenyl)-5-methyl-2-(1-methyl-3-(piperidin-4-yl)-1H-indazol-5-yl)benzo[d]thiazol-6-yl)acetate tert-butyl (S)-3-(4-(5-(6-(1-(tert-butoxy)-2-ethoxy-2-oxoethyl)-7-(4-chlorophenyl)-5-methylbenzo[d]thiazol-2-yl)-1-methyl-1H-indazol-3-yl)piperidin-1-yl)azetidine-1-carboxylate (S)-2-(tert-butoxy)-2-(2-(3-(1-(1-(tert-butoxycarbonyl)azetidin-3-yl)piperidin-4-yl)-1-methyl-1H-indazol-5-yl)-7-(4-chlorophenyl)-5-methylbenzo[d]thiazol-6-yl)acetic acid Preparation of tert-butyl (S)-3-(4-(5-(6-(1-(tert-butoxy)-2-ethoxy-2-oxoethyl)-7-(4-chlorophenyl)-5-methylbenzo[d]thiazol-2-yl)-1-methyl-1H-indazol-3-yl)piperidin-1-yl)azetidine-1-carboxylate: A solution of (S)-2-(tert-butoxy)-2-(7-(4-chlorophenyl)-5-methyl-2-(1-methyl-3-(piperidin-4-yl)-1H-indazol-5-yl)benzo[d]thiazol-6-yl)acetate (260 mg, 0.412 mmol), N-Boc-3-oxoazetidine (380 mg, 2.22 mmol), acetic acid (0.2 mL, 3.5 mmol)) and sodium cyanoborohydride (300 mg, 4.77 mmol) in methanol (10 mL) was stirred for 24 hours at room temperature. Reaction was quenched with saturated sodium bicarbonate solution and brine. The mixture was extracted with ethyl acetate (2×) and combined organic layer was dried (MgSO$_4$), filtered and concentrated. The residue was purified by CombiFlash (40 g, Gold, 0-10% MeOH/CH$_2$Cl$_2$) to give the desired product. $^1$H NMR (400 MHz, Chloroform-d) δ 8.35-8.27 (m, 1H), 8.06 (dd, J=8.9, 1.6 Hz, 1H), 7.85 (d, J=1.0 Hz, 1H), 7.59-7.44 (m, 4H), 7.44-7.34 (m, 1H), 5.16 (s, 1H), 4.21 (tq, J=7.1, 3.5 Hz, 2H), 4.02 (s, 3H), 3.96-3.57 (m, 7H), 3.51-3.28 (m, 3H), 3.08 (q, J=7.3 Hz, 1H), 3.00-2.67 (m, 4H), 2.60 (s, 3H), 2.42-2.18 (m, 4H), 1.43 (s, 1H), 1.35 (td, J=7.3, 2.9 Hz, 5H), 1.25 (t, J=7.1 Hz, 5H), 0.98 (s, 9H). LCMS-ESI+: calc'd for C$_{43}$H$_{53}$ClN$_5$O$_5$S: 786.3 (M+H)$^+$; found: 786.2 (M+H)$^+$.

Preparation of (S)-2-(tert-butoxy)-2-(2-(3-(1-(1-(tert-butoxycarbonyl)azetidin-3-yl)piperidin-4-yl)-1-methyl-1H-indazol-5-yl)-7-(4-chlorophenyl)-5-methylbenzo[d]thiazol-6-yl)acetic acid: To a flask containing tert-butyl (S)-3-(4-(5-(6-(1-(tert-butoxy)-2-ethoxy-2-oxoethyl)-7-(4-chlorophenyl)-5-methylbenzo[d]thiazol-2-yl)-1-methyl-1H-indazol-3-yl)piperidin-1-yl)azetidine-1-carboxylate (10 mg, 0.013 mmol) was added THF (1 mL), MeOH (0.2 mL) and 50% Sodium hydroxide (0.2 mL) at rt. The mixture was stirred at 60° C. for 2 h. The reaction mixture was cooled by ice bath and acidified with 2 N HCl. The resulting mixture was extracted with ethyl acetate (2×). Combined organic layer was dried (MgSO$_4$), filtered and concentrated to give crude mixture which was purified by Gilson HPLC (Phenomenex Gemini 250×21.2 10μ C18 column, 40-100% ACN/H$_2$O+0.1% TFA) to a yellow powder after lyophilization. $^1$H NMR (400 MHz, Chloroform-d) δ 8.38 (s, 1H), 8.05 (d, J=9.0 Hz, 1H), 7.87 (s, 1H), 7.72 (d, J=8.1 Hz, 1H), 7.53 (dd, J=10.9, 3.3 Hz, 3H), 7.39 (d, J=8.5 Hz, 1H), 5.32 (s, 1H), 4.30-4.08 (m, 1H), 4.03 (s, 3H), 3.99-3.77 (m, 2H), 3.76-3.53 (m, 2H), 3.09 (d, J=81.1 Hz, 1H), 2.58 (s, 3H), 2.28-1.92 (m, 6H), 1.72-1.53 (m, 2H), 1.45 (s, 9H), 1.01 (s, 9H). LCMS-ESI+: calc'd for C$_{41}$H$_{49}$ClN$_5$O$_5$S; 758.3 (M+H)$^+$; found: 758.1 (M+H)$^+$.

Example 32. Preparation of (S)-2-(2-(3-(1-(azetidin-3-yl)piperidin-4-yl)-1-methyl-1H-indazol-5-yl)-7-(4-chlorophenyl)-5-methylbenzo[d]thiazol-6-yl)-2-(tert-butoxy)acetic Acid (29)

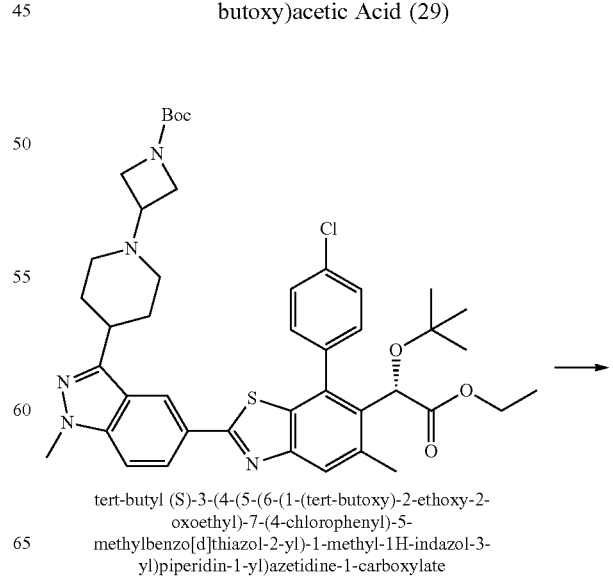

tert-butyl (S)-3-(4-(5-(6-(1-(tert-butoxy)-2-ethoxy-2-oxoethyl)-7-(4-chlorophenyl)-5-methylbenzo[d]thiazol-2-yl)-1-methyl-1H-indazol-3-yl)piperidin-1-yl)azetidine-1-carboxylate

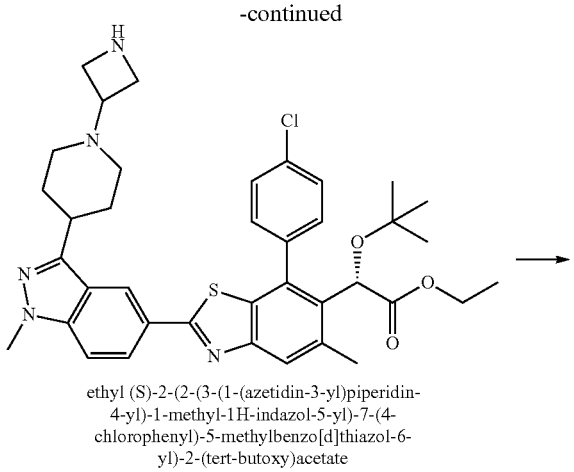

ethyl (S)-2-(2-(3-(1-(azetidin-3-yl)piperidin-4-yl)-1-methyl-1H-indazol-5-yl)-7-(4-chlorophenyl)-5-methylbenzo[d]thiazol-6-yl)-2-(tert-butoxy)acetate

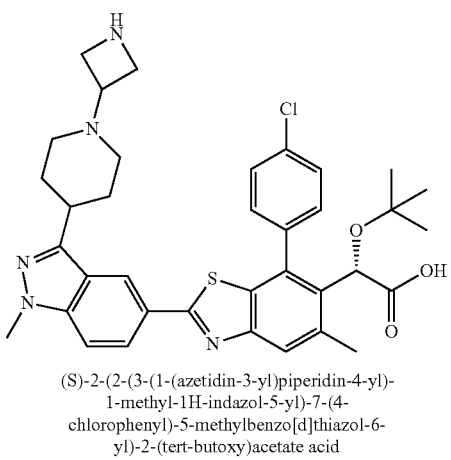

(S)-2-(2-(3-(1-(azetidin-3-yl)piperidin-4-yl)-1-methyl-1H-indazol-5-yl)-7-(4-chlorophenyl)-5-methylbenzo[d]thiazol-6-yl)-2-(tert-butoxy)acetate acid Preparation of ethyl (S)-2-(2-(3-(1-(azetidin-3-yl)piperidin-4-yl)-1-methyl-1H-indazol-5-yl)-7-(4-chlorophenyl)-5-methylbenzo[d]thiazol-6-yl)-2-(tert-butoxy)acetate: A solution tert-butyl (S)-3-(4-(5-(6-(1-(tert-butoxy)-2-ethoxy-2-oxoethyl)-7-(4-chlorophenyl)-5-methylbenzo[d]thiazol-2-yl)-1-methyl-1H-indazol-3-yl)piperidin-1-yl)azetidine-1-carboxylate (95 mg, 0.121 mmol) in 1.25 HCl in isopropanol (5.0 mL) (not well soluble) was stirred overnight at room temperature. The reaction had only 33% conversion. Additional MeOH (2 mL), 1.25M HCl/iPrOH (5 mL) and CH$_2$Cl$_2$ (5 mL) were added so the reaction solution became clear. The reaction was stirred for another 18 h. Reaction mixture was quenched with saturated sodium bicarbonate solution carefully and extracted with ethyl acetate (2×). Combined organic layer was dried (MgSO$_4$), filtered and concentrated to give crude desired product that was used in the next step without further purification. LCMS-ESI+: calc'd for C$_{38}$H$_{45}$ClN$_5$O$_3$S; 686.3 (M+H)$^+$; found: 686.2 (M+H)$^+$.

Preparation of (S)-2-(2-(3-(1-(azetidin-3-yl)piperidin-4-yl)-1-methyl-1H-indazol-5-yl)-7-(4-chlorophenyl)-5-methylbenzo[d]thiazol-6-yl)-2-(tert-butoxy)acetic acid: To a flask containing of ethyl (S)-2-(2-(3-(1-(azetidin-3-yl)piperidin-4-yl)-1-methyl-1H-indazol-5-yl)-7-(4-chlorophenyl)-5-methylbenzo[d]thiazol-6-yl)-2-(tert-butoxy)acetate (15 mg, 0.022 mmol) was added THF (1 mL), MeOH (0.2 mL) and 50% Sodium hydroxide (0.2 mL) at rt. The mixture was stirred at 60° C. for 2 h. The reaction mixture was cooled by ice and acidified with 2 N HCl. The resulting mixture was extracted with ethyl acetate (2×). Combined organic layer was dried (MgSO$_4$), filtered and concentrated to give crude mixture which was purified by Gilson HPLC (Phenomenex Gemini 250×21.2 10μ C18 column, 40-100% ACN/H$_2$O+ 0.1% TFA) to give a yellow powder after lyophilization. $^1$H NMR (400 MHz, Chloroform-d) δ 8.27 (s, 1H), 7.92 (dd, J=9.0, 1.5 Hz, 1H), 7.75 (s, 1H), 7.59 (dd, J=8.5, 2.0 Hz, 1H), 7.44 (td, J=6.0, 2.9 Hz, 3H), 7.36 (d, J=8.9 Hz, 1H), 5.16 (s, 1H), 4.43 (d, J=65.3 Hz, 4H), 3.95 (s, 3H), 3.48-2.89 (m, 7H), 2.54 (d, J=13.0 Hz, 6H), 2.39-2.16 (m, 3H), 0.90 (s, 9H). LCMS-ESI+: calc'd for C$_{36}$H$_{41}$ClN$_5$O$_3$S; 658.3 (M+H)$^+$; found: 658.3 (M+H)$^+$.

Example 33. Preparation of (S)-2-(2-(3-(1-(1-acetylazetidin-3-yl)piperidin-4-yl)-1-methyl-1H-indazol-5-yl)-7-(4-chlorophenyl)-5-methylbenzo[d]thiazol-6-yl)-2-(tert-butoxy)acetic Acid (30)

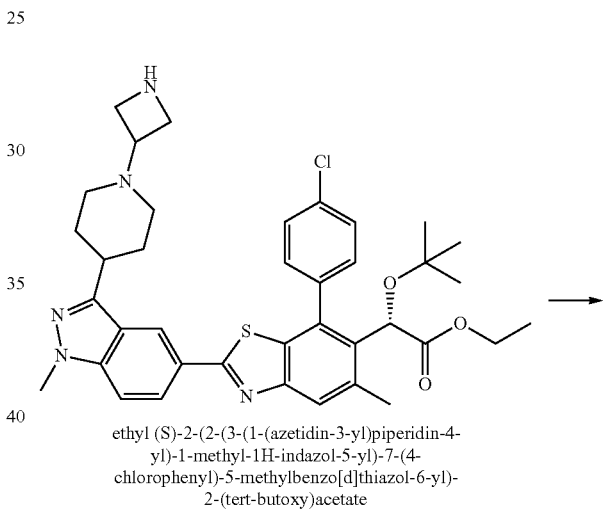

ethyl (S)-2-(2-(3-(1-(azetidin-3-yl)piperidin-4-yl)-1-methyl-1H-indazol-5-yl)-7-(4-chlorophenyl)-5-methylbenzo[d]thiazol-6-yl)-2-(tert-butoxy)acetate

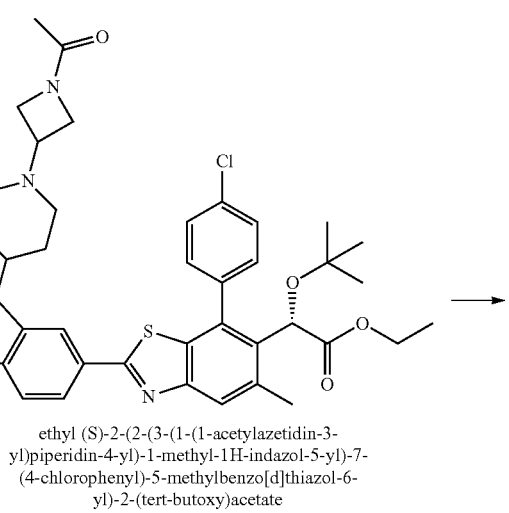

ethyl (S)-2-(2-(3-(1-(1-acetylazetidin-3-yl)piperidin-4-yl)-1-methyl-1H-indazol-5-yl)-7-(4-chlorophenyl)-5-methylbenzo[d]thiazol-6-yl)-2-(tert-butoxy)acetate

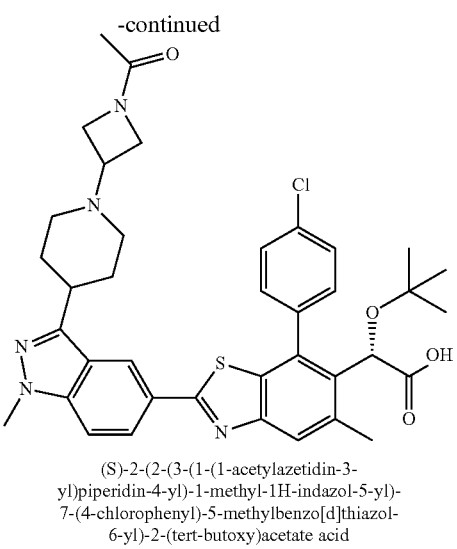

(S)-2-(2-(3-(1-(1-acetylazetidin-3-yl)piperidin-4-yl)-1-methyl-1H-indazol-5-yl)-7-(4-chlorophenyl)-5-methylbenzo[d]thiazol-6-yl)-2-(tert-butoxy)acetate acid Preparation of ethyl (S)-2-(2-(3-(1-(1-acetylazetidin-3-yl)piperidin-4-yl-1-methyl-1H-indazol-5-yl)-7-(4-chlorophenyl)-5-methylbenzo[d]thiazol-6-yl)-2-(tert-butoxy)acetate: To a flask containing ethyl (S)-2-(2-(3-(1-(azetidin-3-yl)piperidin-4-yl)-1-methyl-1H-indazol-5-yl)-7-(4-chlorophenyl)-5-methylbenzo[d]thiazol-6-yl)-2-(tert-butoxy)acetate (20 mg, 0.029 mmol) in THF (2 mL) were added N-Ethyldiisopropylamine (101.52 µl, 582.83 µmol) and Acetyl chloride (20.72 µl, 291.42 µmol). The mixture was stirred at room temperature overnight. The reaction was complete and carried to the next step directly. LCMS-ESI+: calc'd for: $C_{40}H_{47}ClN_5O_4S$; 728.3 $(M+H)^+$; found: 728.3 $(M+H)^+$.

Preparation of (S)-2-(2-(3-(1-(1-acetylazetidin-3-yl)piperidin-4-yl)-1-methyl-1H-indazol-5-yl)-7-(4-chlorophenyl)-5-methylbenzo[d]thiazol-6-yl)-2-(tert-butoxy)acetic acid: To above reaction mixture containing crude ethyl (S)-2-(2-(3-(1-(1-acetylazetidin-3-yl)piperidin-4-yl)-1-methyl-1H-indazol-5-yl)-7-(4-chlorophenyl)-5-methylbenzo[d]thiazol-6-yl)-2-(tert-butoxy)acetate (0.029 mmol) was added MeOH (0.5 mL) and 50% Sodium hydroxide (0.5 mL) at rt. The mixture was stirred at 60° C. for 2 h. The reaction mixture was cooled by ice and acidified with 3 N HCl. The resulting mixture was extracted with ethyl acetate (2×). Combined organic layer was dried (MgSO₄), filtered and concentrated to give crude mixture which was purified by Gilson HPLC (Phenomenex Gemini 250×21.2 10µ C18 column, 40-100% ACN/H₂O+0.1% TFA) to give a yellow powder after lyophilization. ¹H NMR (400 MHz, Chloroform-d) δ 8.24 (s, 1H), 7.95 (d, J=8.8 Hz, 1H), 7.76 (s, 1H), 7.63-7.55 (m, 1H), 7.50-7.39 (m, 3H), 7.35 (d, J=8.8 Hz, 1H), 5.18 (s, 1H), 4.75-4.06 (m, 4H), 3.96 (s, 3H), 3.86 (d, J=8.1 Hz, 1H), 3.45 (s, 4H), 3.13-2.94 (m, 2H), 2.53 (s, 3H), 2.29 (d, J=23.0 Hz, 4H), 1.82 (s, 3H), 1.19 (d, J=11.8 Hz, 1H), 0.91 (s, 9H). LCMS-ESI+: calc'd for $C_{38}H_{43}ClN_5O_4S$; 700.3 $(M+H)^+$; found: 700.3 $(M+H)^+$.

Example 34. Preparation of (S)-2-(tert-butoxy)-2-(7-(4-chlorophenyl)-5-methyl-2-(1-methyl-3-(1-(1-methylazetidin-3-yl)piperidin-4-yl)-1H-indazol-5-yl)benzo[d]thiazol-6-yl)acetic Acid (31)

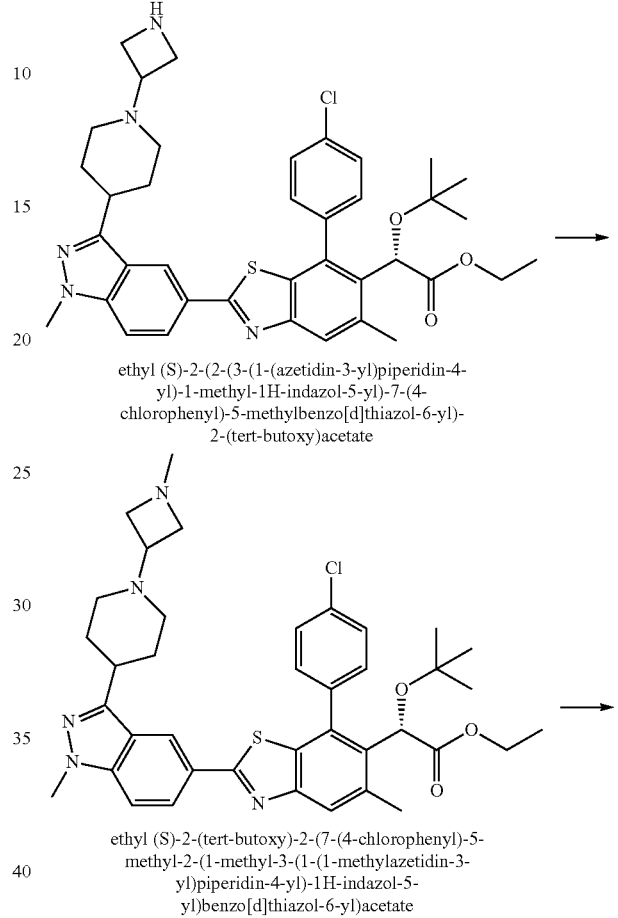

ethyl (S)-2-(2-(3-(1-(azetidin-3-yl)piperidin-4-yl)-1-methyl-1H-indazol-5-yl)-7-(4-chlorophenyl)-5-methylbenzo[d]thiazol-6-yl)-2-(tert-butoxy)acetate ethyl (S)-2-(tert-butoxy)-2-(7-(4-chlorophenyl)-5-methyl-2-(1-methyl-3-(1-(1-methylazetidin-3-yl)piperidin-4-yl)-1H-indazol-5-yl)benzo[d]thiazol-6-yl)acetate

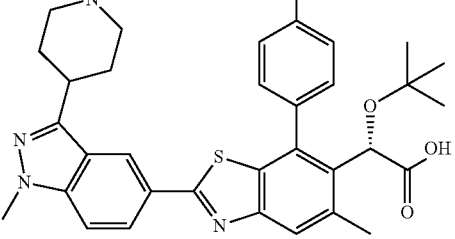

(S)-2-(tert-butoxy)-2-(7-(4-chlorophenyl)-5-methyl-2-(1-methyl-3-(1-(1-methylazetidin-3-yl)piperidin-4-yl)-1H-indazol-5-yl)benzo[d]thiazol-6-yl)acetic acid Preparation of ethyl (S)-2-(tert-butoxy)-2-(7-(4-chlorophenyl)-5-methyl-2-(1-methyl-3-(1-(1-methylazetidin-3-yl)piperidin-4-yl)-1H-indazol-5-yl)benzo[d]thiazol-6-yl)acetate: A solution of ethyl (S)-2-(2-(3-(1-(azetidin-3-yl)piperidin-4-yl)-1-methyl-1H-indazol-5-yl)-7-(4-chlorophenyl)-5-methylbenzo[d]thiazol-6-yl)-2-(tert-butoxy)acetate (44 mg, 0.064 mmol) in acetonitrile (2 mL) was stirred at 0° C. bath as 37% formaldehyde (0.175 mL, 2.36 mmol), and sodium cyanoborohydride (88 mg, 1.4 mmol) were added. To the reaction mixture was added ~2 drops of acetic acid. After 1 h, the reaction was completed and carried to the next step directly. LCMS-ESI+: calc'd for: $C_{39}H_{47}ClN_5O_3S$; 700.3 (M+H)+; found: 700.2 (M+H)+.

Preparation of (S)-2-(tert-butoxy)-2-(7-(4-chlorophenyl)-5-methyl-2-(1-methyl-3-(1-(1-methylazetidin-3-yl)piperidin-4-yl)-1H-indazol-5-yl)benzo[d]thiazol-6-yl)acetic acid: To above reaction mixture containing ethyl (S)-2-(tert-butoxy)-2-(7-(4-chlorophenyl)-5-methyl-2-(1-methyl-3-(1-(1-methylazetidin-3-yl)piperidin-4-yl)-1H-indazol-5-yl)benzo[d]thiazol-6-yl)acetate (0.064 mmol) were added THF (2 mL), MeOH (0.5 mL) and 50% Sodium hydroxide (0.5 mL) at rt. The mixture was stirred at 60° C. for 2 h. The reaction mixture was cooled by ice bath and acidified with 3 N HCl. The resulting mixture was extracted with ethyl acetate (2×). Combined organic layer was dried (MgSO₄), filtered and concentrated to give crude mixture which was purified by Gilson HPLC (Phenomenex Gemini 250×21.2 10μ C18 column, 40-100% ACN/H₂O+0.1% TFA) to give a yellow powder after lyophilization. ¹H NMR (400 MHz, Chloroform-d) δ 8.33-8.19 (m, 1H), 7.95 (dd, J=8.8, 1.6 Hz, 1H), 7.78 (s, 1H), 7.61 (dd, J=8.6, 2.1 Hz, 1H), 7.46 (td, J=5.9, 2.9 Hz, 3H), 7.37 (d, J=8.9 Hz, 1H), 5.19 (s, 1H), 4.48 (dt, J=18.0, 9.1 Hz, 4H), 4.28-4.10 (m, 1H), 3.97 (s, 3H), 3.36-3.07 (m, 4H), 2.92 (s+m, 4H), 2.54 (s, 3H), 2.26 (ddd, J=19.8, 9.9, 4.8 Hz, 4H), 0.92 (s, 9H). LCMS-ESI+: calc'd for $C_{37}H_{43}ClN_5O_3S$; 672.3 (M+H)+; found: 772.3 (M+H)+.

Example 35. (S)-2-(tert-butoxy)-2-(7-(4-chlorophenyl)-2-(1-(2-(dimethylamino)ethyl)-3-(1-(oxetan-3-yl)piperidin-4-yl)-1H-pyrrolo[2,3-b]pyridin-5-yl)-5-methylbenzo[d]thiazol-6-yl)acetic Acid (32)

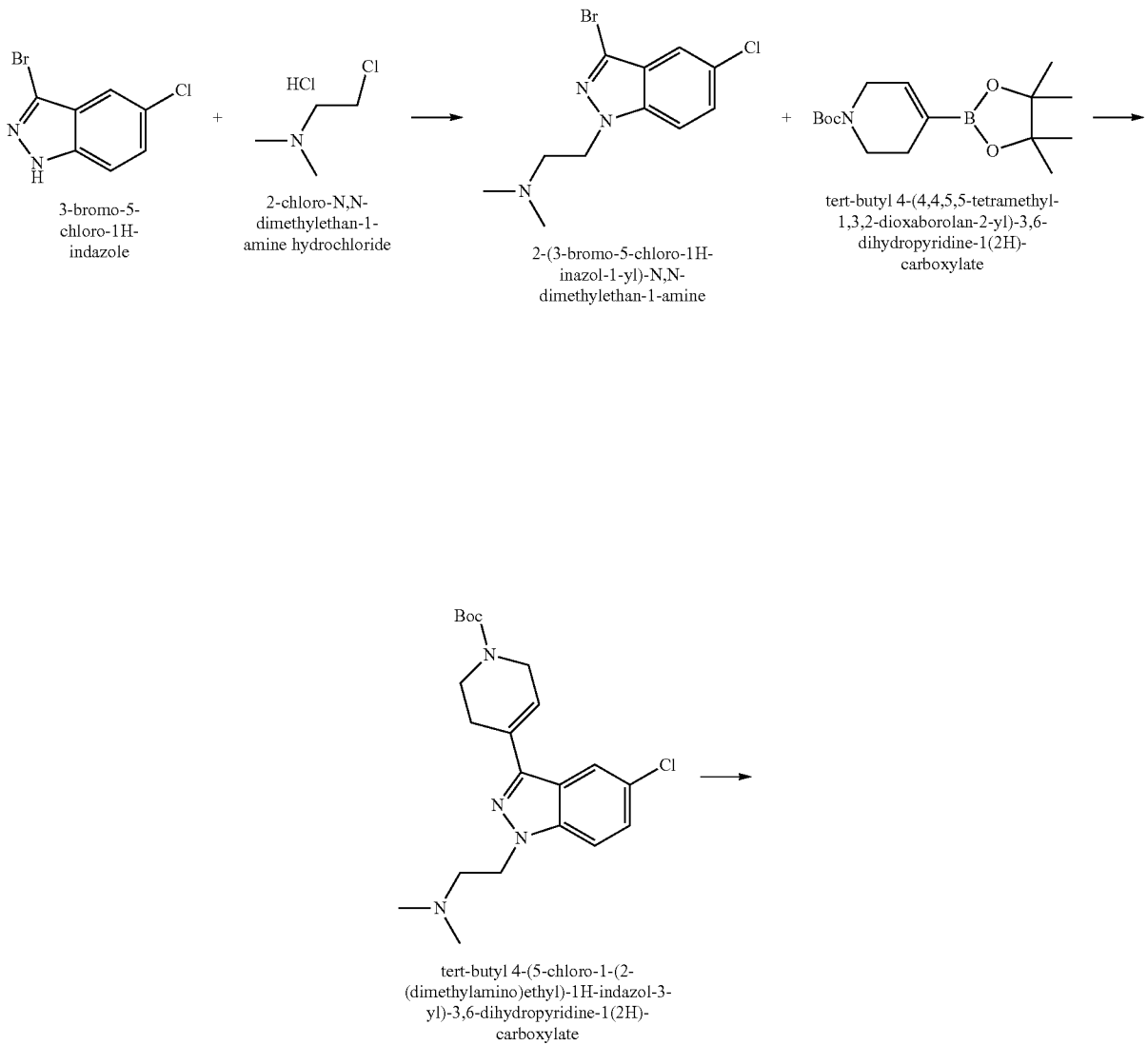

-continued

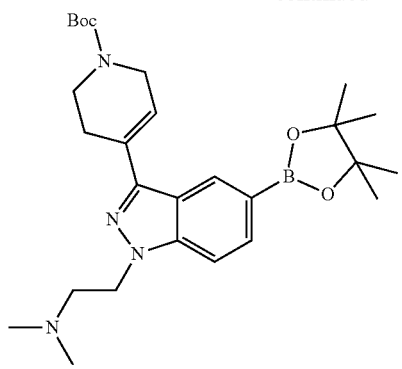

tert-butyl 4-(1-(2-(dimethylamino)ethyl)-5-(4,4,5,5-tetramethyl-1,3,2-dioxaborolan-2-yl)-1H-indazol-3-yl)-3,6-dihydropyridine-1(2H)-carboxylate and

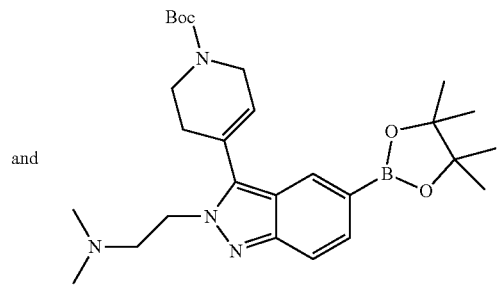

tert-butyl 4-(2-(2-(dimethylamino)ethyl)-5-(4,4,5,5-tetramethyl-1,3,2-dioxaborolan-2-yl)-2H-indazol-3-yl)-3,6-dihydropyridine-1(2H)-carboxylate

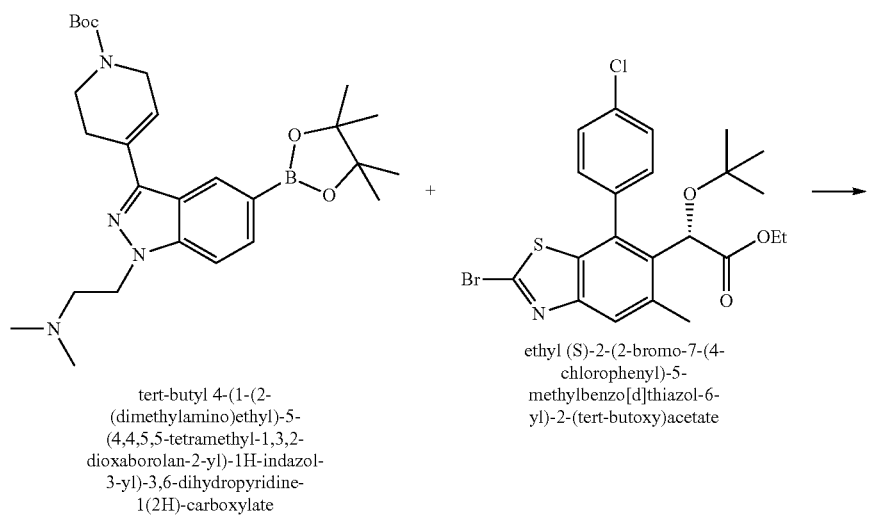

tert-butyl 4-(1-(2-(dimethylamino)ethyl)-5-(4,4,5,5-tetramethyl-1,3,2-dioxaborolan-2-yl)-1H-indazol-3-yl)-3,6-dihydropyridine-1(2H)-carboxylate ethyl (S)-2-(2-bromo-7-(4-chlorophenyl)-5-methylbenzo[d]thiazol-6-yl)-2-(tert-butoxy)acetate

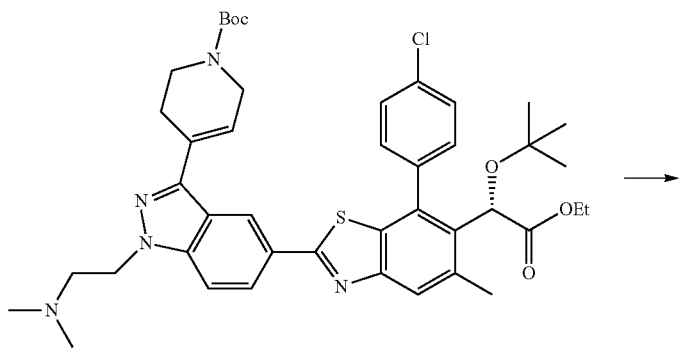

tert-butyl (S)-4-(5-(6-(1-(tert-butoxy)-2-ethoxy-2-oxoethyl)-7-(4-chlorophenyl)-5-methylbenzo[d]thiazol-2-yl)-1-(2-(dimethylamino)ethyl)-1H-indazol-3-yl)-3,6-dihydropyridine-1(2H)-carboxylate -continued

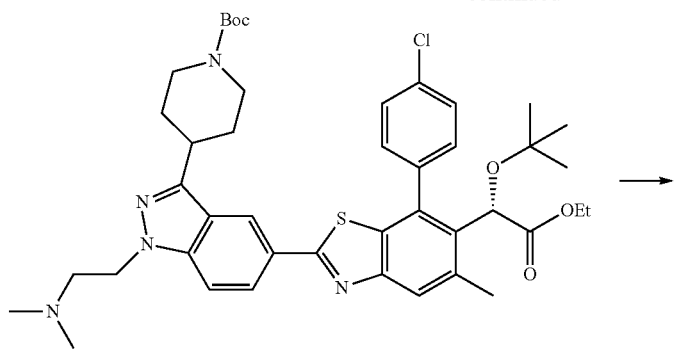

tert-butyl (S)-4-(5-(6-(1-(tert-butoxy)-2-ethoxy-2-
oxoethyl)-7-(4-chlorophenyl)-5-methylbenzo[d]thiazol-
2-yl)-1-(2-(dimethylamino)ethyl)-1H-indazol-3-
yl)piperidine-1-carboxylate

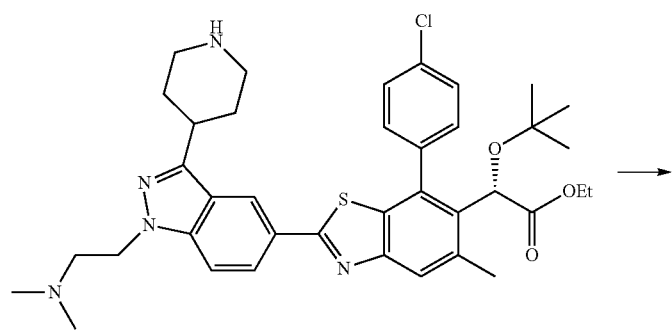

ethyl (S)-2-(tert-butoxy)-2-(7-(4-
chlorophenyl)-2-(1-(2-(dimethylamino)ethyl)-
3-(piperidin-4-yl)-1H-indazol-5-yl)-5-
methylbenzo[d]thiazol-6-yl)acetate

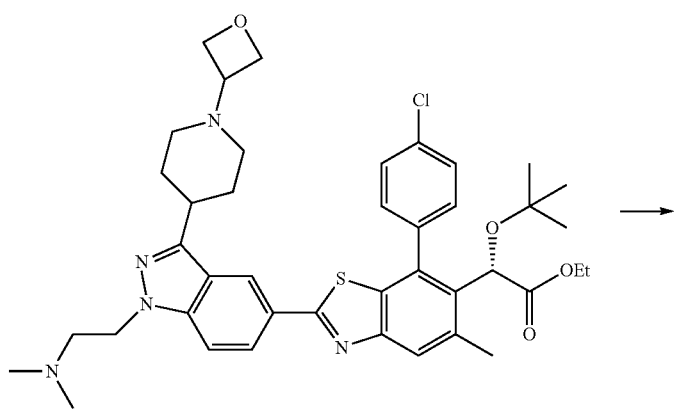

ethyl (S)-2-(tert-butoxy)-2-(7-(4-chlorophenyl)-2-(1-
(2-(dimethylamino)ethyl)-3-(1-(oxetan-3-
yl)piperidin-4-yl)-1H-indazol-5-yl)-5-
methylbenzo[d]thiazol-6-yl)acetate

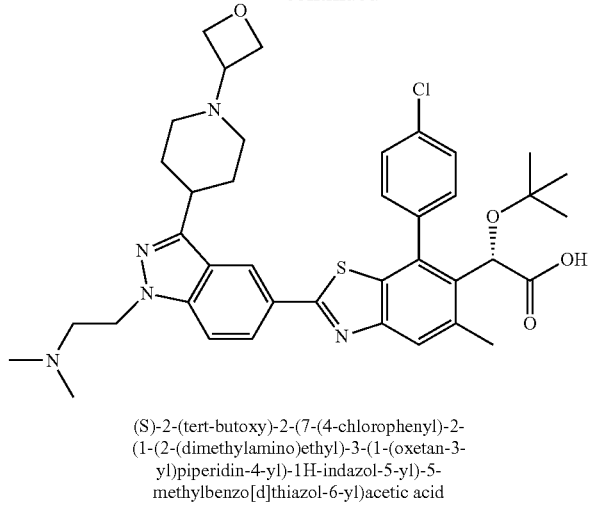

(S)-2-(tert-butoxy)-2-(7-(4-chlorophenyl)-2-
(1-(2-(dimethylamino)ethyl)-3-(1-(oxetan-3-
yl)piperidin-4-yl)-1H-indazol-5-yl)-5-
methylbenzo[d]thiazol-6-yl)acetic acid Preparation of 2-(3-bromo-5-chloro-1H-indazol-1-yl)-N,N-dimethylethane-1-amine (isomer a): To a solution of 3-bromo-5-chloro-1H-indazole (1 g, 4.32 mmol) in anhydrous DMF (10 mL) at room temperature was added cesium carbonate (3.66 g, 11.23 mmol), followed by 2-dimethylamino-ethyl chloride hydrochloride (0.81 g, 5.62 mmol). The reaction was heated to 100° C. for 18 h. It was diluted with water (10 mL) and 3% LiCl (50 mL), then extracted with EtOAc. The organic layer was washed with brine, dried over sodium sulfate, and concentrated. The crude mixture was purified by CombiFlash (40 g, Gold, 0-20% MeOH/$CH_2Cl_2$) to give an oily material (isomer ratio=6:1 by NMR). 1H NMR (400 MHz, Chloroform-d) δ 7.58 (dd, J=1.6, 0.9 Hz, 1H), 7.36 (dd, J=2.1, 1.3 Hz, 2H), 4.42 (t, J=6.9 Hz, 2H), 2.81 (t, J=6.9 Hz, 2H), 2.29 (s, 6H). LCMS-ESI+: calc'd for $C_{11}H_{14}BrClN_3$: 302.0 (M+H)+; found: 303.9 (M+H)+.

Preparation of tert-butyl 4-(5-chloro-1-(2-(dimethylamino)ethyl)-1H-indazol-3-yl)-3,6-dihydropyridine-1(2H)-carboxylate: A 20 mL microwave vial was charged with 2-(3-bromo-5-chloro-1H-indazol-1-yl)-N,N-dimethylethane-1-amine (0.5 g, 1.65 mmol), tert-butyl 4-(4,4,5,5-tetramethyl-1,3,2-dioxaborolan-2-yl)-5,6-dihydropyridine-1(2H)-carboxylate (766.4 mg, 2.45 mmol), Palladium (0) tetrakis(triphenylphosphine) (190.94 mg, 0.17 mmol), and Potassium carbonate (685.09 mg, 4.96 mmol) in water (2 mL) and dioxane (8 mL). It was flushed with nitrogen for 5 minutes, then microwaved at 100° C. for 60 min. Reaction mixture was filtered through a pad of Celite, concentrated and purified by CombiFlash (40 g, 0-20% MeOH/$CH_2Cl_2$) to give desire product. The above reaction was repeated 3 times to generate enough material for the next step. LCMS-ESI: calc'd for $C_{21}H_{30}ClN_4O_2$: 405.2 (M+H)+; found: 405.2 (M+H)+.

Preparation of tert-butyl 4-(1-(2-(dimethylamino)ethyl)-5-(4,4,5,5-tetramethyl-1,3,2-dioxaborolan-2-yl)-1H-indazol-3-yl)-3,6-dihydropyridine-1(2H)-carboxylate and tert-butyl 4-(2-(2-(dimethylamino)ethyl)-5-(4,4,5,5-tetramethyl-1,3,2-dioxaborolan-2-yl)-2H-indazol-3-yl)-3,6-dihydropyridine-1(2H)-carboxylate: To a flask charged with tert-butyl 4-(5-chloro-1-(2-(dimethylamino)ethyl)-1H-indazol-3-yl)-3,6-dihydropyridine-1(2H)-carboxylate (1.76 g, 4.35 mmol) were added [Bis (Pinacolato) Diboron (3.22 g, 13.4 mmol), potassium acetate (1.28 g, 13.04 mmol), Palladium acetate trimer (48.79 mg, 0.22 mmol) and 2-(Dicyclohexylphosphino)-2',4',6'-triisopropylbiphenyl (207.2 mg, 0.43 mmol). 1,4-Dioxane (20 mL) was added and the mixture was flushed with nitrogen for 10 min. The reaction mixture was heated to 100° C. for 4 h under a nitrogen atmosphere. It was cooled to room temperature, filtered through a pad of Celite and concentrated. The residue was purified by CombiFlash (80 g Gold, 0-20% MeOH/$CH_2Cl_2$ (twice). It was still black colored and treated with Activated Carbon to remove the black palladium residues.

tert-Butyl 4-(1-(2-(dimethylamino)ethyl)-5-(4,4,5,5-tetramethyl-1,3,2-dioxaborolan-2-yl)-1H-indazol-3-yl)-3,6-dihydropyridine-1(2H)-carboxylate: $^1$H NMR (400 MHz, Chloroform-d) δ 8.44-8.27 (m, 1H), 7.80 (dd, J=8.5, 0.9 Hz, 1H), 7.40 (d, J=8.4 Hz, 1H), 6.50 (s, 1H), 4.59-4.37 (m, 2H), 4.20 (d, J=4.0 Hz, 2H), 3.68 (t, J=5.7 Hz, 2H), 2.94 (t, J=7.3 Hz, 2H), 2.77 (d, J=6.2 Hz, 2H), 2.35 (s, 6H), 1.52 (d, J=8.6 Hz, 9H), 1.36 (d, J=3.9 Hz, 12H). LCMS-ESI+: calc'd for $C_{27}H_{42}BN_4O_4$: 497.3 (M+H)+; found: 497.3 (M+H)+.

tert-Butyl 4-(2-(2-(dimethylamino)ethyl)-5-(4,4,5,5-tetramethyl-1,3,2-dioxaborolan-2-yl)-2H-indazol-3-yl)-3,6-dihydropyridine-1(2H)-carboxylate: $^1$H NMR (400 MHz, Chloroform-d) δ 8.36 (d, J=0.9 Hz, 1H), 7.78 (dd, J=8.5, 0.9 Hz, 1H), 7.37 (dd, J=8.4, 0.9 Hz, 1H), 6.50 (s, 1H), 4.44 (dd, J=8.4, 6.0 Hz, 2H), 4.33-4.07 (m, 2H), 3.68 (t, J=5.7 Hz, 2H), 2.89-2.63 (m, 4H), 2.30 (s, 6H), 1.50 (s, 9H), 1.37 (s, 12H). LCMS-ESI+: calc'd for $C_{27}H_{42}BN_4O_4$: 497.3 (M+H)+; found: 497.3 (M+H)+.

Preparation of tert-butyl (S)-4-(5-(6-(1-(tert-butoxy)-2-ethoxy-2-oxoethyl)-7-(4-chlorophenyl)-5-methylbenzo[d]thiazol-2-yl)-1-(2-(dimethylamino)ethyl)-1H-indazol-3-yl)-3,6-dihydropyridine-1(2H)-carboxylate: A 100 mL round bottom flask was charged with ethyl (S)-2-(2-bromo-7-(4-chlorophenyl)-5-methylbenzo[d]thiazol-6-yl)-2-(tert-butoxy)acetate (0.65 g, 1.31 mmol), tert-butyl 4-(1-(2-(dimethylamino)ethyl)-5-(4,4,5,5-tetramethyl-1,3,2-dioxaborolan-2-yl)-1H-indazol-3-yl)-3,6-dihydropyridine-1(2H)-carboxylate (0.8 g, 1.61 mmol), Pd(PPh$_3$)$_4$ (200 mg, 0.17 mmol) and potassium phosphate (0.545 g, 2 mmol). Then 1,4-dioxane (15 mL) and water (3ML) were added and the flask was flushed with nitrogen for 10 minutes. The flask was placed into a pre-heated heating block to 100° C. and stirred for 3 hours. Cooled to rt, it was diluted with EtOAc, washed with brine. The organic phase was dried over Na₂SO₄ and concentrated. The crude residue was purification by CombiFlash (80 g Gold, 0-10% MeOH/CH₂Cl₂) gave the desire product. ¹H NMR (400 MHz, Chloroform-d) δ 8.48 (s, 1H), 8.08 (d, J=8.8 Hz, 1H), 7.86 (s, 1H), 7.61-7.45 (m, 4H), 6.49 (s, 1H), 5.16 (d, J=2.4 Hz, 1H), 4.53 (s, 2H), 4.21 (dq, J=7.2, 3.6 Hz, 4H), 3.70 (d, J=7.7 Hz, 2H), 2.78 (s, 1H), 2.65-2.52 (m, 2H), 2.37 (s, 6H), 1.91 (s, 1H), 1.53 (d, J=7.2 Hz, 3H), 1.24 (s, 9H), 0.98 (d, J=1.4 Hz, 9H). LCMS-ESI⁺: calc'd for C₄₃H₅₃ClN₅O₅S: 786.3 (M+H)⁺; found: 786.3 (M+H)⁺.

Preparation of tert-butyl (S)-4-(5-(6-(1-(tert-butoxy)-2-ethoxy-2-oxoethyl)-7-(4-chlorophenyl)-5-methylbenzo[d]thiazol-2-yl)-1-(2-(dimethylamino)ethyl)-1H-indazol-3-yl)piperidine-1-carboxylate: A flask containing a mixture of tert-butyl (S)-4-(5-(6-(1-(tert-butoxy)-2-ethoxy-2-oxoethyl)-7-(4-chlorophenyl)-5-methylbenzo[d]thiazol-2-yl)-1-(2-(dimethylamino)ethyl)-1H-indazol-3-yl)-3,6-dihydropyridine-1(2H)-carboxylate (1000 mg, 1.272 mmol), rhodium on alumina, 5 wt % (400 mg, 0.194 mmol) in ethanol (200 mL) was evacuated and back-filled with hydrogen (3×). Reaction mixture was stirred overnight under hydrogen atmosphere vigorously; ¹H NMR showed that the product was about 50% formed. It was filtered through a pad of Celite and added 500 mg of fresh catalyst. The resulting mixture was stirred under hydrogen atmosphere vigorously over the weekend. LCMS showed mostly the desired product with a very small amount of de-chlorinated product peak. The mixture was filtered through a pad of Celite and concentrated. The residue was purified by CombiFlash (120 g, Gold, 0-22% MeOH/CH₂Cl₂) gave the desire product. LCMS-ESI+: calc'd for C₄₃H₅₅ClN₅O₅S: 788.3 (M+H)⁺; found: 788.1 (M+H)⁺.

Preparation of ethyl (S)-2-(tert-butoxy)-2-(7-(4-chlorophenyl)-2-(1-(2-(dimethylamino)ethyl)-3-(piperidin-4-yl)-1H-indazol-5-yl)-5-methylbenzo[d]thiazol-6-yl)acetate: A solution of tert-butyl (S)-4-(5-(6-(1-(tert-butoxy)-2-ethoxy-2-oxoethyl)-7-(4-chlorophenyl)-5-methylbenzo[d]thiazol-2-yl)-1-(2-(dimethylamino)ethyl)-1H-indazol-3-yl)piperidine-1-carboxylate (800 mg, 1.015 mmol) in 1.25 HCl in isopropanol (20 mL) was stirred overnight at room temperature. Reaction mixture was quenched with saturated sodium bicarbonate solution and extracted with ethyl acetate (2×). Combined organic layer was dried over sodium sulfate, filtered and concentrated to give the desire product that was used in the next step without further purification. LCMS-ESI+: calc'd for C₃₈H₄₇ClN₅O₃S: 688.3 (M+H)⁺; found: 688.1 (M+H)⁺.

Preparation of ethyl (S)-2-(tert-butoxy)-2-(7-(4-chlorophenyl)-2-(1-(2-(dimethylamino)ethyl)-3-(1-(oxetan-3-yl)piperidin-4-yl)-1H-indazol-5-yl)-5-methylbenzo[d]thiazol-6-yl)acetate: A solution of ethyl (S)-2-(tert-butoxy)-2-(7-(4-chlorophenyl)-2-(1-(2-(dimethylamino)ethyl)-3-(piperidin-4-yl)-1H-indazol-5-yl)-5-methylbenzo[d]thiazol-6-yl)acetate (250 mg, 0.363 mmol), 3-Oxetanone (350 μl, 5.46 mmol), acetic acid (100 μL, 1.75 mmol) and sodium cyanoborohydride (456.5 mg, 7.26 mmol) in methanol (5 mL) was stirred for 5 hours at room temperature. LCMS showed complete conversion. Reaction was quenched with saturated sodium bicarbonate solution and brine and stirred for 1.5 hours. The mixture was extracted with ethyl acetate (2×) and combined organic layer was dried (MgSO₄), filtered and concentrated. The residue was purified by CombiFlash (40 g, Gold, 0-10% MeOH/CH₂Cl₂) to give the desire product. LCMS-ESI+: calc'd for C₄₁H₅₅ClN₅O₄S: 744.3 (M+H)⁺; found: 744.4 (M+H)⁺.

Preparation of (S)-2-(tert-butoxy)-2-(7-(4-chlorophenyl)-2-(1-(2-(dimethylamino)ethyl)-3-(1-(oxetan-3-yl)piperidin-4-yl)-1H-indazol-5-yl)-5-methylbenzo[d]thiazol-6-yl)acetic acid: To ethyl (S)-2-(tert-butoxy)-2-(7-(4-chlorophenyl)-2-(1-(2-(dimethylamino)ethyl)-3-(1-(oxetan-3-yl)piperidin-4-yl)-1H-indazol-5-yl)-5-methylbenzo[d]thiazol-6-yl)acetate (200 mg, 0.269 mmol) was added THF (2 mL), MeOH (0.5 mL) and 50% Sodium hydroxide (0.5 mL) at room temperature. The mixture was stirred at 60° C. for 2 h. The reaction mixture was cooled by ice and acidified with 3 N HCl. The resulting mixture was extracted with ethyl acetate (2×). Combined organic layer was dried (MgSO₄), filtered and concentrated to give crude mixture which was purified by Gilson HPLC (Phenomenex Gemini 250×21.2 10μ C18 column, 40-100% ACN/H₂O+0.1% TFA) to give a yellow powder after lyophilization. ¹H NMR (400 MHz, Chloroform-d) δ 8.30 (s, 1H), 8.01 (d, J=8.8 Hz, 1H), 7.81 (s, 1H), 7.68 (d, J=8.2 Hz, 1H), 7.53 (q, J=9.0 Hz, 4H), 5.28 (s, 1H), 5.10 (t, J=7.0 Hz, 2H), 4.78 (dt, J=13.1, 6.9 Hz, 4H), 4.28 (s, 1H), 3.80-3.18 (m, 5H), 2.83 (s, 6H), 2.57 (s, 3H), 2.34 (m, 4H), 0.98 (s, 9H). LCMS-ESI+: calc'd for C₃₉H₄₇ClN₅O₄S; 716.3 (M+H)⁺; found: 716.2 (M+H)⁺.

Example 36. Preparation of (S)-2-(2-(3-(1-(1-acetylazetidin-3-yl)piperidin-4-yl)-1-(2-(dimethylamino)ethyl)-1H-pyrrolo[2,3-b]pyridin-5-yl)-7-(4-chlorophenyl)-5-methylbenzo[d]thiazol-6-yl)-2-(tert-butoxy)acetic Acid (33)

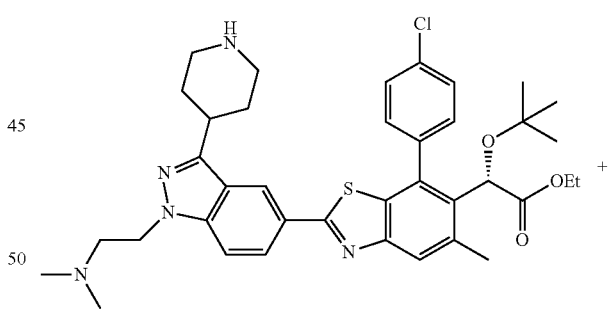

ethyl (S)-2-(tert-butoxy)-2-(7-(4-chlorophenyl)-2-(1-(2-(dimethylamino)ethyl)-3-(piperidin-4-yl)-1H-indazol-5-yl)-5-methylbenzo[d]thiazol-6-yl)acetate

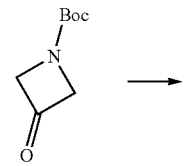

tert-butyl 3-oxoazetidine-1-carboxylate

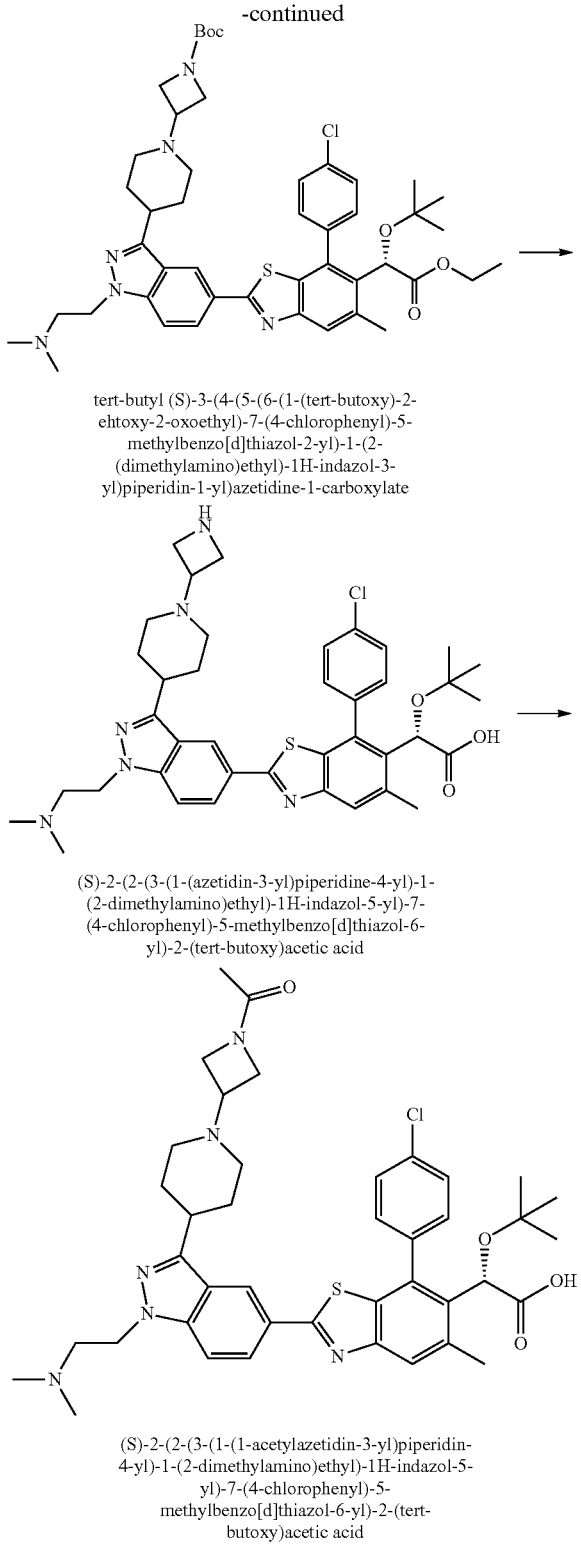

tert-butyl (S)-3-(4-(5-(6-(1-(tert-butoxy)-2-ethoxy-2-oxoethyl)-7-(4-chlorophenyl)-5-methylbenzo[d]thiazol-2-yl)-1-(2-(dimethylamino)ethyl)-1H-indazol-3-yl)piperidin-1-yl)azetidine-1-carboxylate (S)-2-(2-(3-(1-(azetidin-3-yl)piperidine-4-yl)-1-(2-dimethylamino)ethyl)-1H-indazol-5-yl)-7-(4-chlorophenyl)-5-methylbenzo[d]thiazol-6-yl)-2-(tert-butoxy)acetic acid (S)-2-(2-(3-(1-(1-acetylazetidin-3-yl)piperidin-4-yl)-1-(2-dimethylamino)ethyl)-1H-indazol-5-yl)-7-(4-chlorophenyl)-5-methylbenzo[d]thiazol-6-yl)-2-(tert-butoxy)acetic acid Preparation of tert-butyl (S)-3-(4-(5-(6-(1-(tert-butoxy)-2-ethoxy-2-oxoethyl)-7-(4-chlorophenyl)-5-methylbenzo[d]thiazol-2-yl)-1-(2-(dimethylamino)ethyl)-1H-indazol-3-yl)piperidin-1-yl)azetidine-1-carboxylate: A solution of ethyl (S)-2-(tert-butoxy)-2-(7-(4-chlorophenyl)-2-(1-(2-(dimethylamino)ethyl)-3-(piperidin-4-yl)-1H-indazol-5-yl)-5-methylbenzo[d]thiazol-6-yl)acetate (250 mg, 363.2 μmol), 1-Boc-3-azetidinone (186.53 mg, 1.01 mmol), acetic acid (0.1 mL, 1.75 mmol)) and sodium cyanoborohydride (228 mg, 3.63 mmol) in methanol (5 mL) was stirred for 24 hours at room temperature. Reaction was quenched with saturated sodium bicarbonate solution and brine. The mixture was extracted with ethyl acetate (2×) and combined organic layer was dried (MgSO$_4$), filtered and concentrated. The residue was purified by CombiFlash (40 g, Gold, 0-10% MeOH/CH$_2$Cl$_2$) to give impure product. LCMS-ESI+: calc'd for C$_{46}$H$_{60}$ClN$_6$O$_5$S: 843.4 (M+H)$^+$; found: 843.1 (M+H)$^+$.

Preparation of (S)-2-(2-(3-(1-(azetidin-3-yl)piperidin-4-yl)-1-(2-(dimethylamino)ethyl)-1H-indazol-5-yl)-7-(4-chlorophenyl)-5-methylbenzo[d]thiazol-6-yl)-2-(tert-butoxy) acetic acid: A solution of tert-butyl (S)-3-(4-(5-(6-(1-(tert-butoxy)-2-ethoxy-2-oxoethyl)-7-(4-chlorophenyl)-5-methylbenzo[d]thiazol-2-yl)-1-(2-(dimethylamino)ethyl)-1H-indazol-3-yl)piperidin-1-yl)azetidine-1-carboxylate (600 mg, from previous step) in 1.25 HCl in isopropanol (10 mL) (not well soluble) was stirred overnight at room temperature. Reaction mixture was quenched with saturated sodium bicarbonate solution carefully and extracted with ethyl acetate (2×). Combined organic layer was dried (MgSO$_4$), filtered and concentrated to give 264 mg of crude product as borate-chelate as shown by LCMS. This material was added THF (5 mL), MeOH (10 mL), ethylene glycol (5 ml) and 50% Sodium hydroxide (4 mL). The mixture was stirred at 60° C. for 3 h, then room temperature overnight to break the borate complex. Reaction mixture was concentrated down, and then DMF/MeOH/CH$_3$CN were added, producing a gel-like solid. After filtration and concentration, the residue was purified by Gilson HPLC (Phenomenex Gemini 250×21.2 10μ C18 column, 40-100% ACN/H$_2$O+ 0.1% TFA) to give a yellow powder after lyophilization. LCMS-ESI+: calc'd for C$_{39}$H$_{48}$ClN$_6$O$_3$S; 715.3 (M+H)$^+$; found: 715.2 (M+H)$^+$.

Preparation of (S)-2-(2-(3-(1-(1-acetylazetidin-3-yl)piperidin-4-yl)-1-(2-(dimethylamino)ethyl)-1H-indazol-5-yl)-7-(4-chlorophenyl)-5-methylbenzo[d]thiazol-6-yl)-2-(tert-butoxy)acetic acid: To a flask containing (S)-2-(2-(3-(1-(azetidin-3-yl)piperidin-4-yl)-1-(2-(dimethylamino)ethyl)-1H-indazol-5-yl)-7-(4-chlorophenyl)-5-methylbenzo[d] thiazol-6-yl)-2-(tert-butoxy)acetic acid (22 mg, 0.024 mmol) in THF (2 mL) were added N-Ethyldiisopropylamine (200 μl, 1.15 mmol) and Acetyl chloride (35 μl, 0.49 mmol). The mixture was stirred at room temperature for 1 h. The reaction mixture was cooled to 0° C., acidified with 3N HCl, and concentrated to remove the organic solvent. The residue was purified by Gilson HPLC (Phenomenex Gemini 250× 21.2 10μ C18 column, 40-100% ACN/H$_2$O+0.1% TFA) to give a yellow powder after lyophilization. LCMS-ESI+: calc'd for C$_{41}$H$_{50}$ClN$_6$O$_4$S; 757.3 (M+H)$^+$; found: 757.3 (M+H)$^+$.

Example 37. (S)-2-(tert-butoxy)-2-(7-(4-chlorophenyl)-5-methyl-2-(3-(1-(oxetan-3-yl)piperidin-4-yl)-1H-indazol-5-yl)benzo[d]thiazol-6-yl)acetic Acid (34)

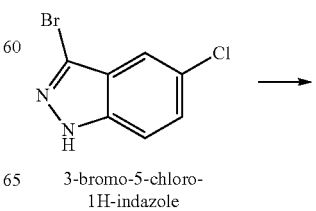

3-bromo-5-chloro-1H-indazole

179
-continued

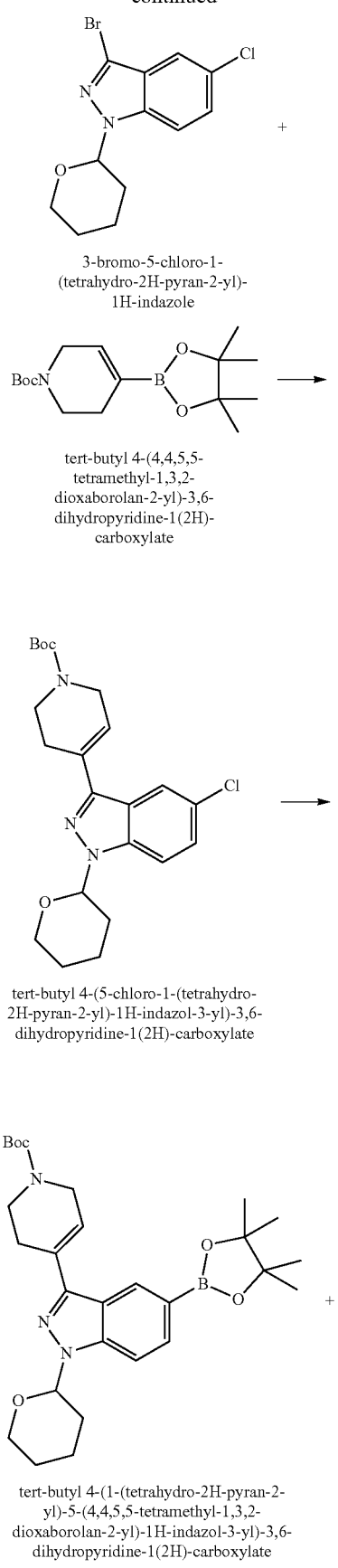

3-bromo-5-chloro-1-(tetrahydro-2H-pyran-2-yl)-1H-indazole tert-butyl 4-(4,4,5,5-tetramethyl-1,3,2-dioxaborolan-2-yl)-3,6-dihydropyridine-1(2H)-carboxylate tert-butyl 4-(5-chloro-1-(tetrahydro-2H-pyran-2-yl)-1H-indazol-3-yl)-3,6-dihydropyridine-1(2H)-carboxylate tert-butyl 4-(1-(tetrahydro-2H-pyran-2-yl)-5-(4,4,5,5-tetramethyl-1,3,2-dioxaborolan-2-yl)-1H-indazol-3-yl)-3,6-dihydropyridine-1(2H)-carboxylate 180
-continued

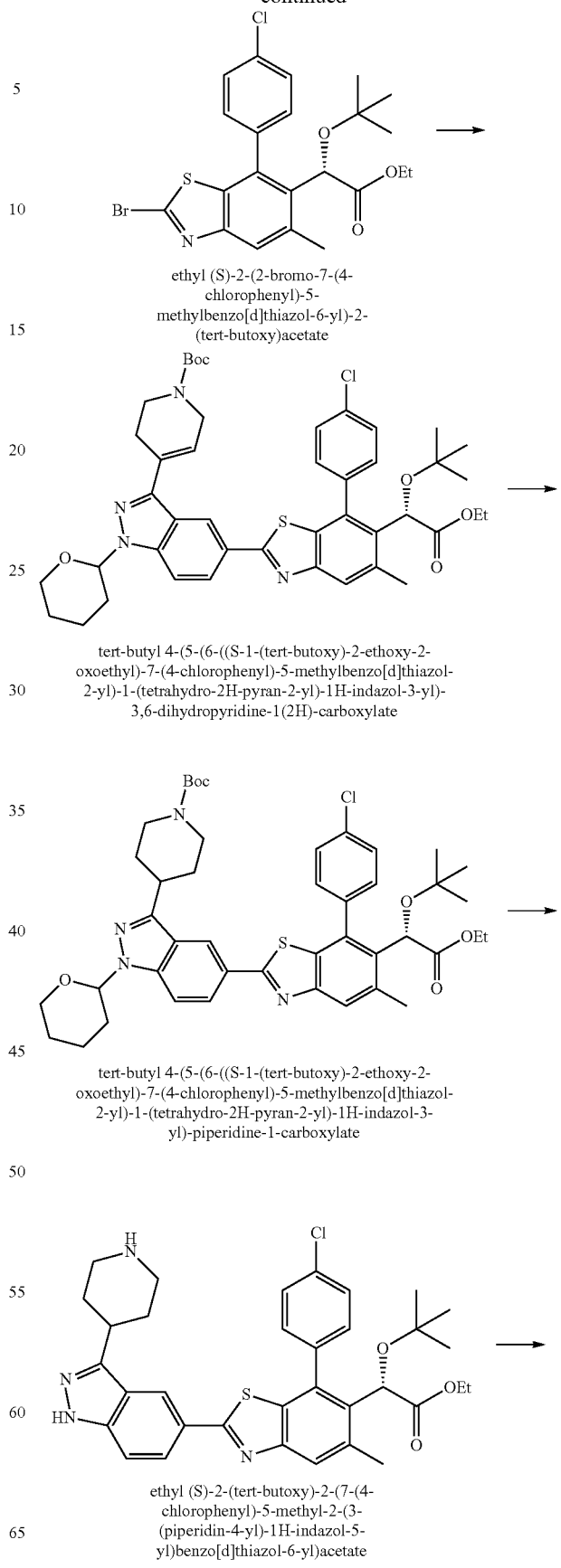

ethyl (S)-2-(2-bromo-7-(4-chlorophenyl)-5-methylbenzo[d]thiazol-6-yl)-2-(tert-butoxy)acetate tert-butyl 4-(5-(6-((S-1-(tert-butoxy)-2-ethoxy-2-oxoethyl)-7-(4-chlorophenyl)-5-methylbenzo[d]thiazol-2-yl)-1-(tetrahydro-2H-pyran-2-yl)-1H-indazol-3-yl)-3,6-dihydropyridine-1(2H)-carboxylate tert-butyl 4-(5-(6-((S-1-(tert-butoxy)-2-ethoxy-2-oxoethyl)-7-(4-chlorophenyl)-5-methylbenzo[d]thiazol-2-yl)-1-(tetrahydro-2H-pyran-2-yl)-1H-indazol-3-yl)-piperidine-1-carboxylate ethyl (S)-2-(tert-butoxy)-2-(7-(4-chlorophenyl)-5-methyl-2-(3-(piperidin-4-yl)-1H-indazol-5-yl)benzo[d]thiazol-6-yl)acetate

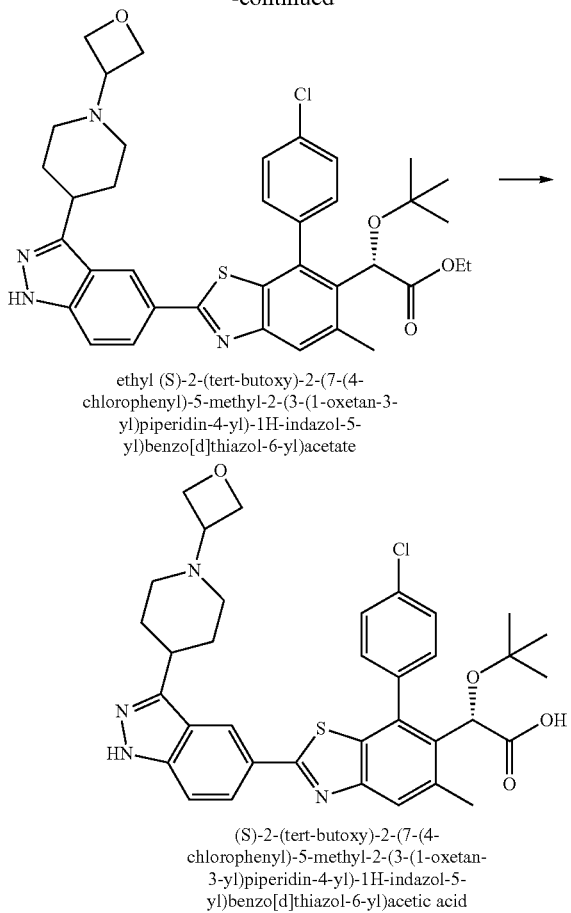

ethyl (S)-2-(tert-butoxy)-2-(7-(4-chlorophenyl)-5-methyl-2-(3-(1-oxetan-3-yl)piperidin-4-yl)-1H-indazol-5-yl)benzo[d]thiazol-6-yl)acetate (S)-2-(tert-butoxy)-2-(7-(4-chlorophenyl)-5-methyl-2-(3-(1-oxetan-3-yl)piperidin-4-yl)-1H-indazol-5-yl)benzo[d]thiazol-6-yl)acetic acid Preparation of 3-bromo-5-chloro-1-(tetrahydro-2H-pyran-2-yl)-1H-indazole: To a solution of 3-bromo-5-chloro-1H-indazole (3 g, 12.96 mmol) dissolved in EtOAc (25 mL) were added a catalytic amount of p-Toluenesulfonic acid (0.22 g, 1.3 mmol) and 3,4-Dihydro-2H-pyran (2.36 ml, 25.92 mmol). The reaction mixture was heated to reflux (100° C.) for 2 h. LC-MS indicates the reaction was done. It was cooled to RT, quenched with sat'd NaHCO$_3$ (50 mL), then extracted with EtOAc. The organic extracts were washed with brine, dried over sodium sulfate, concentrated. The crude mixture was purified by CombiFlash (120 g, Gold, 0-5% MeOH/CH$_2$Cl$_2$) to give a white solid (isomer ratio=1:1 by NMR). $^1$H NMR (400 MHz, Chloroform-d) δ 7.59 (dd, J=2.0, 0.7 Hz, 1H), 7.52 (dd, J=8.9, 0.7 Hz, 1H), 7.38 (dd, J=8.9, 1.9 Hz, 1H), 5.65 (dd, J=9.0, 2.8 Hz, 1H), 3.99 (dtd, J=11.5, 3.7, 1.5 Hz, 1H), 3.80-3.61 (m, 1H), 2.50 (dddd, J=13.4, 11.0, 8.9, 4.1 Hz, 1H), 2.26-1.95 (m, 2H), 1.87-1.59 (m, 3H). LCMS-ESI$^+$: calc'd for C$_{12}$H$_{13}$BrClN$_2$O: 316.6 (M+H)+; found: 316.7 (M+H)$^+$.

Preparation of tert-butyl 4-(5-chloro-1-(tetrahydro-2H-pyran-2-yl)-1H-indazol-3-yl)-3,6-dihydropyridine-1 (2H)-carboxylate: A solution of 3-bromo-5-chloro-1-(tetrahydro-2H-pyran-2-yl)-1H-indazole (4 g, 12.67 mmol), tert-butyl 4-(4,4,5,5-tetramethyl-1,3,2-dioxaborolan-2-yl)-3,6-dihydropyridine-1(2H)-carboxylate (6 g, 19.4 mmol), Palladium (0) tetrakis(triphenylphosphine) (2 g, 1.73 mmol), Potassium carbonate (6 g, 43.4 mmol) in water (10 mL) and 1,4-dioxane (40 mL) in a 500 mL RBF was flushed with argon for 10 minutes, then sealed, and heated to 100° C. for 3 h. Reaction mixture was cooled to room temperature, filtered through a pad of Celite, concentrated and purified by CombiFlash (220 g, using 0-30% EtOAc/Hexane) to give desired product as isomer mixture. LCMS-ESI$^+$: calc'd for C$_{22}$H$_{29}$ClN$_3$O$_3$: 417.2 (M+H)$^+$; found: 417.9 (M+H)$^+$.

Preparation of tert-butyl 4-(1-(tetrahydro-2H-pyran-2-yl)-5-(4,4,5,5-tetramethyl-1,3,2-dioxaborolan-2-yl)-1H-indazol-3-yl)-3,6-dihydropyridine-1(2H)-carboxylate: To a flask with tert-butyl 4-(5-chloro-1-(tetrahydro-2H-pyran-2-yl)-1H-indazol-3-yl)-3,6-dihydropyridine-1(2H)-carboxylate (4.0 g, 9.57 mmol) in 1,4-Dioxane (60 ml) were added Bis (Pinacolato) Diboron (5.4 g, 21.26 mmol), potassium acetate (2.8 g, 28.7 mmol), Palladium acetate trimer (215 mg, 0.96 mmol) and 2-(Dicyclohexylphosphino)-2',4',6'-triisopropylbiphenyl (913 mg, 1.91 mmol). The mixture was flushed with nitrogen for 10 min, and heated to 100° C. for 3 h under a nitrogen atmosphere. It was cooled to room temperature, filtered through a pad of Celite and concentrated. The residue was purified by CombiFlash (80 g Gold, 0 to 50% EtOAc/Hex) to give desired product as isomer mixture. LCMS-ESI$^+$: calc'd for C$_{28}$H$_{41}$BN$_3$O$_5$: 510.5 (M+H)$^+$; found: 510.1 (M+H)$^+$.

Preparation of tert-butyl 4-(5-(6-((S)-1-(tert-butoxy)-2-ethoxy-2-oxoethyl)-7-(4-chlorophenyl)-5-methylbenzo[d]thiazol-2-yl)-1-(tetrahydro-2H-pyran-2-yl)-1H-indazol-3-yl)-3,6-dihydropyridine-(2H)-carboxylate: A flask was charged with ethyl (S)-2-(2-bromo-7-(4-chlorophenyl)-5-methylbenzo[d]thiazol-6-yl)-2-(tert-butoxy)acetate (2.6 g, 5.23 mmol), tert-butyl 4-(1-(tetrahydro-2H-pyran-2-yl)-5-(4,4,5,5-tetramethyl-1,3,2-dioxaborolan-2-yl)-1H-indazol-3-yl)-3,6-dihydropyridine-1(2H)-carboxylate (3.2 g, 6.28 mmol), Pd(PPh$_3$)$_4$ (605 mg, 0.523 mmol) and potassium phosphate (2.17 g, 15.7 mmol). Then 1,4-dioxane (50 mL) and water (10 mL) were added. The mixture was flushed with nitrogen for 10 minutes. It was heated to 100° C. for 4 hours. Cooled to rt, it was diluted with EtOAc, washed with brine. The organic phase was dried over Na$_2$SO$_4$ and concentrated. The crude residue was purification by CombiFlash (80 g Gold, 0-10% MeOH/CH$_2$Cl$_2$) gave the desire product as regioisomeric mixture. $^1$H NMR (400 MHz, Chloroform-d) δ 8.52 (s, 1H), 8.07 (d, J=8.8 Hz, 1H), 7.88 (s, 1H), 7.61 (d, J=8.8 Hz, 1H), 7.59-7.46 (m, 4H), 6.52 (s, 1H), 5.71 (dd, J=9.2, 2.8 Hz, 1H), 5.16 (s, 1H), 4.21 (dd, J=7.1, 2.9 Hz, 3H), 4.03 (d, J=11.3 Hz, 1H), 3.81-3.58 (m, 3H), 2.81 (d, J=17.3 Hz, 2H), 2.60 (d, J=0.8 Hz, 3H), 2.57-2.41 (m, 1H), 2.24-2.05 (m, 1H), 1.85-1.60 (m, 3H), 1.52 (s, 9H), 1.26 (td, J=7.1, 2.0 Hz, 4H), 0.98 (s, 9H). LCMS-ESI$^+$: calc'd for C$_{44}$H$_{52}$ClN$_4$O$_6$S: 799.4 (M+H)$^+$; found: 799.1 (M+H)$^+$.

Preparation of tert-butyl 4-(5-(6-((S)-1-(tert-butoxy)-2-ethoxy-2-oxoethyl)-7-(4-chlorophenyl)-5-methylbenzo[d] thiazol-2-yl)-1-(tetrahydro-2H-pyran-2-yl)-1H-indazol-3-yl)piperidine-1-carboxylate: A flask containing a mixture of tert-butyl 4-(5-(6-((S)-1-(tert-butoxy)-2-ethoxy-2-oxoethyl)-7-(4-chlorophenyl)-5-methylbenzo[d]thiazol-2-yl)-1-(tetrahydro-2H-pyran-2-yl)-1H-indazol-3-yl)-3,6-dihydropyridine-1(2H)-carboxylate (2.27 g, 2.84 mmol), rhodium on alumina (5 wt %, 2 g, 0.972 mmol) in ethanol (200 mL) was evacuated and back-filled with hydrogen (3×). Reaction mixture was stirred under hydrogen atmosphere vigorously for 3 days. LCMS showed mostly the desired product with a very small amount of de-chlorinated by-product peak. The mixture was filtered through a pad of Celite and concentrated. The residue was purified by CombiFlash (120 g, Gold, 0-22% MeOH/CH$_2$Cl$_2$) to give the desire product. 1H NMR (400 MHz, Chloroform-d) δ 8.42 (s, 1H), 8.07 (d, J=8.6 Hz, 1H), 7.92 (s, 1H), 7.62-7.42 (m, 5H), 5.66 (dd, J=9.5, 2.7 Hz, 1H), 5.16 (s, 1H), 4.21 (dd, J=7.1, 2.5 Hz, 2H), 4.05 (d, J=11.6 Hz, 1H), 3.76 (d, J=9.9 Hz, 1H), 3.26 (d, J=11.0 Hz, 1H), 2.96 (s, 2H), 2.60 (s, 3H), 2.51 (m, 1H), 2.15 (s, 1H), 2.08-1.86 (m, 4H), 1.70 (d, J=43.6 Hz, 2H), 1.49 (s, 9H), 1.25 (td, J=7.1, 2.5 Hz, 4H), 0.98 (s, 9H). LCMS-ESI+: calc'd for $C_{44}H_{54}ClN_4O_6S$: 801.4 (M+H)$^+$; found: 801.2 (M+H)$^+$.

Preparation of ethyl (S)-2-(tert-butoxy)-2-(7-(4-chlorophenyl)-5-methyl-2-(3-(piperidin-4-yl)-1H-indazol-5-yl)benzo[d]thiazol-6-yl)acetate: A solution of tert-butyl 4-(5-(6-((S)-1-(tert-butoxy)-2-ethoxy-2-oxoethyl)-7-(4-chlorophenyl)-5-methylbenzo[d]thiazol-2-yl)-1-(tetrahydro-2H-pyran-2-yl)-1H-indazol-3-yl)piperidine-1-carboxylate (2.15 g, 2.68 mmol) in 1.25 HCl in isopropanol (150 mL) was stirred at room temperature for 48 h. Reaction was quenched carefully with 1N Sodium hydroxide at 0° C. to pH>8. It was extracted with ethyl acetate (2×). Combined organic layer was dried over sodium sulfate, filtered and concentrated to give the desired product as a solid. It was used in the next step without further purification. An analytical sample was prepared by HPLC purification to give the bis-TFA salt. $^1$H NMR (400 MHz, Chloroform-d) δ 10.28 (s, 1H), 9.02 (s, 1H), 8.34 (s, 1H), 7.91 (d, J=8.7 Hz, 1H), 7.76 (s, 1H), 7.53-7.32 (m, 5H), 5.09 (s, 1H), 4.14 (qt, J=6.9, 3.6 Hz, 2H), 3.57 (m, 2H), 3.48 (m, 1H), 3.20 (m, 2H), 2.52 (s, 3H), 2.27 (m, 4H), 1.18 (t, J=7.1 Hz, 3H), 0.90 (s, 9H). LCMS-ESI+: calc'd for $C_{34}H_{38}ClN_4O_3S$: 617.2 (M+H)$^+$; found: 617.4 (M+H)$^+$.

Preparation of ethyl (S)-2-(tert-butoxy)-2-(7-(4-chlorophenyl)-5-methyl-2-(3-(1-(oxetan-3-yl)piperidin-4-yl)-1H-indazol-5-yl)benzo[d]thiazol-6-yl)acetate: A solution of ethyl (S)-2-(tert-butoxy)-2-(7-(4-chlorophenyl)-5-methyl-2-(3-(piperidin-4-yl)-1H-indazol-5-yl)benzo[d]thiazol-6-yl)acetate (1 g, 1.62 mmol), 3-Oxetanone (1.04 ml, 16.2 mmol), acetic acid (600 µL) and sodium cyanoborohydride (2.04 g, 32.4 mmol) in methanol (14 mL) was stirred for 24 hours at room temperature. LCMS showed complete conversion. Reaction was quenched with saturated sodium bicarbonate solution and brine and stirred for 1.5 hours. The mixture was extracted with ethyl acetate (2×) and combined organic layer was dried (MgSO$_4$), filtered and concentrated. The residue was purified by crude mixture which was purified by Gilson HPLC (Phenomenex Gemini 250×21.2 10µ C18 column, 40-100% ACN/H$_2$O+0.1% TFA) to give the desired product. $^1$H NMR (400 MHz, Chloroform-d) δ 8.38 (s, 1H), 8.04 (d, J=11.0 Hz, 1H), 7.84 (d, J=8.0 Hz, 1H), 7.60-7.37 (m, 5H), 5.15 (d, J=3.7 Hz, 1H), 4.69 (d, J=4.7 Hz, 3H), 4.20 (d, J=6.6 Hz, 2H), 3.70-2.70 (d, J=86.9 Hz, 3H), 2.59 (d, J=4.6 Hz, 3H), 2.09 (s, 6H), 1.24 (q, J=6.8 Hz, 3H), 0.97 (d, J=4.1 Hz, 9H). LCMS-ESI+: calc'd for $C_{37}H_{42}ClN_4O_4S$: 673.3 (M+H)$^+$; found: 673.3 (M+H)$^+$.

Preparation of (S)-2-(tert-butoxy)-2-(7-(4-chlorophenyl)-5-methyl-2-(3-(1-(oxetan-3-yl)piperidin-4-yl)-1H-indazol-5-yl)benzo[d]thiazol-6-yl)acetic acid: To ethyl (S)-2-(tert-butoxy)-2-(7-(4-chlorophenyl)-5-methyl-2-(3-(1-(oxetan-3-yl)piperidin-4-yl)-1H-indazol-5-yl)benzo[d]thiazol-6-yl)acetate (50 mg, 0.074 mmol) was added DMF (2 mL), MeOH (0.5 mL) and 50% Sodium hydroxide (0.5 mL) at room temperature. The mixture was stirred at 60° C. for 2 h. The reaction mixture was cooled by ice and acidified with 3 N HCl. The resulting mixture was extracted with ethyl acetate (2×). Combined organic layer was dried (MgSO$_4$), filtered and concentrated to give crude mixture which was purified by Gilson HPLC (Phenomenex Gemini 250×21.2 10µ C18 column, 40-100% ACN/H$_2$O+0.1% TFA) to give a yellow powder after lyophilization. $^1$H NMR (400 MHz, Chloroform-d) δ 8.37 (d, J=1.5 Hz, 1H), 8.19 (s, 2H), 8.01 (dd, J=8.8, 1.6 Hz, 1H), 7.89-7.79 (m, 1H), 7.72 (d, J=8.2 Hz, 1H), 7.60-7.45 (m, 4H), 5.32 (s, 1H), 5.05 (t, J=6.8 Hz, 2H), 4.79 (t, J=7.2 Hz, 2H), 4.03 (t, J=6.7 Hz, 1H), 3.36 (m, 3H), 2.96-2.85 (m, 1H), 2.58 (s, 3H), 2.50 (d, J=29.6 Hz, 2H), 2.33 (s, 1H), 1.25 (d, J=3.5 Hz, 1H), 1.01 (s, 9H), 0.87 (d, J=11.2 Hz, 1H). LCMS-ESI+: calc'd for $C_{35}H_{38}ClN_4O_4S$; 645.2 (M+H)$^+$; found: 645.3 (M+H)$^+$.

Example 38A and 38B. Preparation of (S)-2-(tert-butoxy)-2-(7-(4-chlorophenyl)-2-(1-ethyl-3-(1-(oxetan-3-yl)piperidin-4-yl)-1H-indazol-5-yl)-5-methylbenzo[d]thiazol-6-yl)acetic Acid (35) and ethyl (S)-2-(tert-butoxy)-2-(7-(4-chlorophenyl)-2-(2-ethyl-3-(1-(oxetan-3-yl)piperidin-4-yl)-2H-indazol-5-yl)-5-methylbenzo[d]thiazol-6-yl)acetate (36)

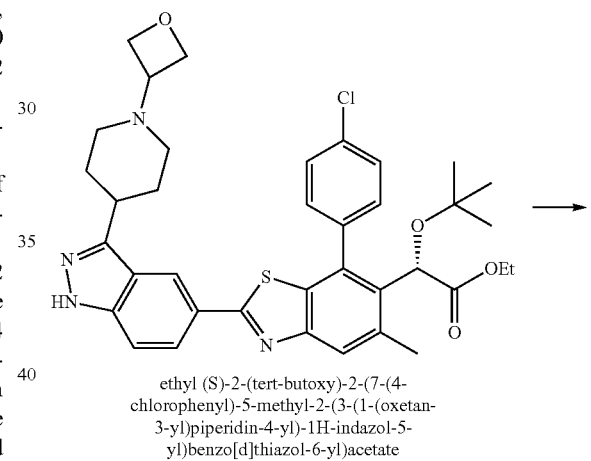

ethyl (S)-2-(tert-butoxy)-2-(7-(4-chlorophenyl)-5-methyl-2-(3-(1-(oxetan-3-yl)piperidin-4-yl)-1H-indazol-5-yl)benzo[d]thiazol-6-yl)acetate and

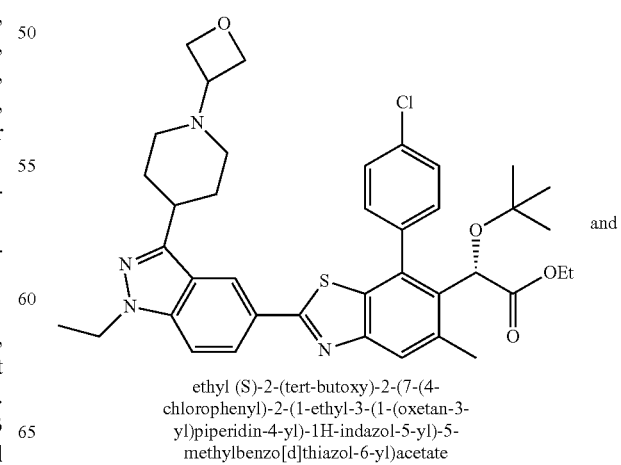

ethyl (S)-2-(tert-butoxy)-2-(7-(4-chlorophenyl)-2-(1-ethyl-3-(1-(oxetan-3-yl)piperidin-4-yl)-1H-indazol-5-yl)-5-methylbenzo[d]thiazol-6-yl)acetate -continued

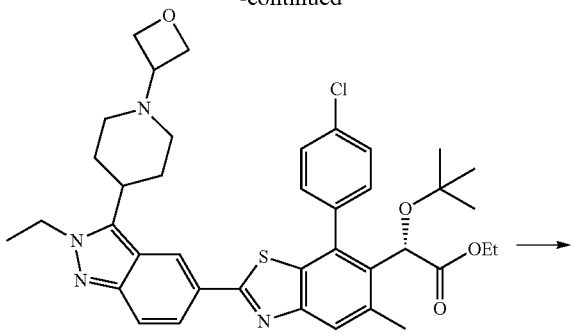

ethyl (S)-2-(tert-butoxy)-2-(7-(4-chlorophenyl)-2-(2-ethyl-3-(1-(oxetan-3-yl)piperidin-4-yl)-2H-indazol-5-yl)-5-methylbenzo[d]thiazol-6-yl)acetate

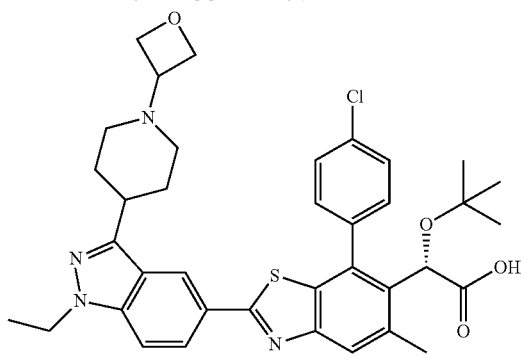

(S)-2-(tert-butoxy)-2-(7-(4-chlorophenyl)-2-(1-ethyl-3-(1-(oxetan-3-yl)piperidin-4-yl)-1H-indazol-5-yl)-5-methylbenzo[d]thiazol-6-yl)acetate acid

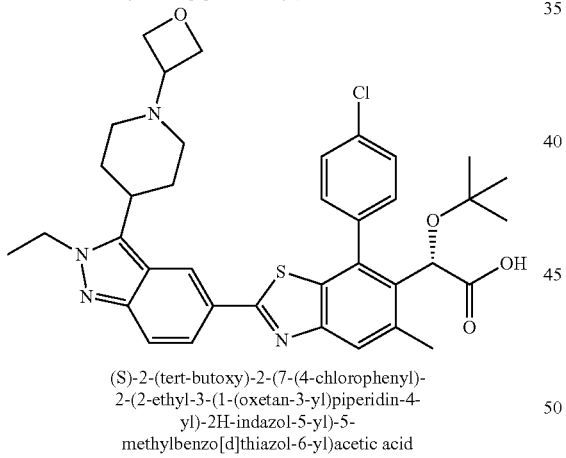

(S)-2-(tert-butoxy)-2-(7-(4-chlorophenyl)-2-(2-ethyl-3-(1-(oxetan-3-yl)piperidin-4-yl)-2H-indazol-5-yl)-5-methylbenzo[d]thiazol-6-yl)acetic acid Preparation of (S)-2-(tert-butoxy)-2-(7-(4-chlorophenyl)-2-(1-ethyl-3-(1-(oxetan-3-yl)piperidin-4-yl)-1H-indazol-5-yl)-5-methylbenzo[d]thiazol-6-yl)acetic acid and (S)-2-(tert-butoxy)-2-(7-(4-chlorophenyl)-2-(2-ethyl-3-(1-(oxetan-3-yl)piperidin-4-yl)-2H-indazol-5-yl)-5-methylbenzo[d]thiazol-6-yl)acetic acid: To a solution of ethyl (S)-2-(tert-butoxy)-2-(7-(4-chlorophenyl)-5-methyl-2-(3-(1-(oxetan-3-yl)piperidin-4-yl)-1H-indazol-5-yl)benzo[d]thiazol-6-yl)acetate (600 mg, 0.891 mmol) in anhydrous DMF (10 mL) was added sodium hydride (60% disp. in oil. 106.93 mg, 2.67 mmol) and stirred for 20 min at to 0° C. under argon. Iodoethane (500 µl, 6.2 mmol) was added. The reaction mixture was kept at 0° C. for 20 min, then at room temperature for 1 h. Reaction was complete by LCMS analysis and used in next step directly. LCMS-ESI+: calc'd for $C_{39}H_{46}ClN_4O_4S$: 701.3 (M+H)+; found: 701.4 (M+H)+.

To above reaction mixture was added MeOH (10 mL) and 50% Sodium hydroxide (5 mL) at room temperature. The mixture was stirred at 60° C. for 1 h. The reaction mixture was cooled by ice and acidified with 3 N HCl. The resulting mixture was extracted with ethyl acetate (2×). Combined organic layer was dried (MgSO$_4$), filtered and concentrated to give crude mixture which was purified by Gilson HPLC (Phenomenex Gemini 250×21.2 10µ C18 column, 40-100% ACN/H$_2$O+0.1% TFA)

(S)-2-(tert-butoxy)-2-(7-(4-chlorophenyl)-2-(1-ethyl-3-(1-(oxetan-3-yl)piperidin-4-yl)-1H-indazol-5-yl)-5-methyl-benzo[d]thiazol-6-yl)acetic acid: $^1$H NMR (400 MHz, Chloroform-d) δ 8.27 (s, 1H), 8.00 (d, J=9.0 Hz, 1H), 7.82 (s, 1H), 7.65 (d, J=8.6 Hz, 1H), 7.53-7.44 (m, 3H), 7.41 (d, J=8.9 Hz, 1H), 5.24 (s, 1H), 5.08 (d, J=6.7 Hz, 2H), 4.78 (t, J=7.2 Hz, 2H), 4.34 (t, J=7.2 Hz, 2H), 4.27 (s, 1H), 3.61-2.83 (m, 5H), 2.58 (s, Hz, 3H), 2.41 (d, J=38.9 Hz, 4H), 1.47 (t, J=7.2 Hz, 3H), 0.96 (s, 9H). LCMS-ESI+: calc'd for $C_{37}H_{42}BN_4O_4S$: 673.3 (M+H)+; found: 673.4 (M+H)+.

(S)-2-(tert-butoxy)-2-(7-(4-chlorophenyl)-2-(2-ethyl-3-(1-(oxetan-3-yl)piperidin-4-yl)-2H-indazol-5-yl)-5-methyl-benzo[d]thiazol-6-yl)acetic acid: $^1$H NMR (400 MHz, Chloroform-d) δ 8.60 (s, 1H), 7.91 (s, 1H), 7.82 (d, J=9.1 Hz, 1H), 7.71 (d, J=9.1 Hz, 1H), 7.53 (dd, J=10.6, 2.9 Hz, 4H), 5.33 (s, 1H), 5.13 (m, 2H), 4.85 (t, J=7.2 Hz, 2H), 4.53 (d, J=7.3 Hz, 2H), 4.29 (m, 1H), 3.62 (d, J=9.5 Hz, 3H), 3.01-2.77 (m, 1H), 2.59 (s, 3H), 3.00-2.15 (br, 2H), 2.14 (d, J=13.2 Hz, 2H), 1.60 (t, J=6.9 Hz, 3H), 1.23 (d, J=17.9 Hz, 1H), 1.01 (s, 9H). LCMS-ESI+: calc'd for $C_{37}H_{42}BN_4O_4S$: 673.3 (M+H)+; found: 673.4 (M+H)+.

Example 39. Preparation of (S)-2-(tert-butoxy)-2-(7-(4-chlorophenyl)-2-(1-(2 hydroxyethyl)-3-(1-(oxetan-3-yl)piperidin-4-yl)-1H-indazol-5-yl)-5-methylbenzo[d]thiazol-6-yl)acetic Acid (37)

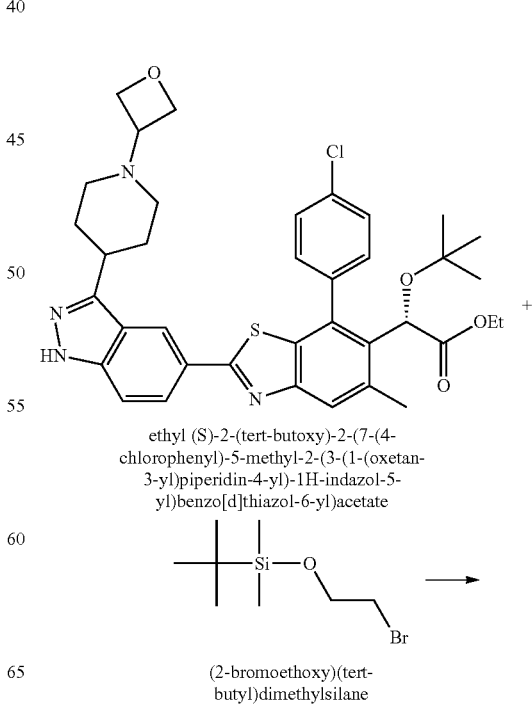

ethyl (S)-2-(tert-butoxy)-2-(7-(4-chlorophenyl)-5-methyl-2-(3-(1-(oxetan-3-yl)piperidin-4-yl)-1H-indazol-5-yl)benzo[d]thiazol-6-yl)acetate (2-bromoethoxy)(tert-butyl)dimethylsilane

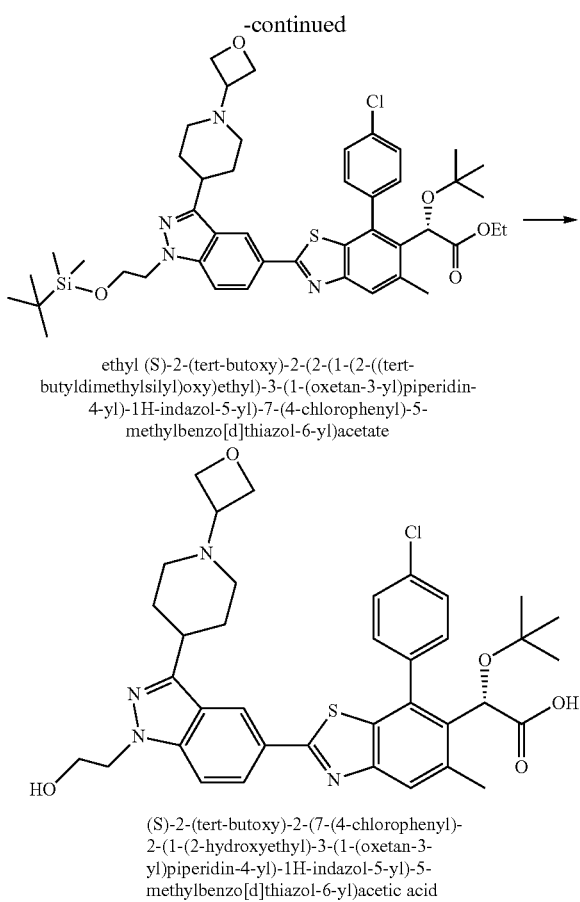

ethyl (S)-2-(tert-butoxy)-2-(2-(1-(2-((tert-butyldimethylsilyl)oxy)ethyl)-3-(1-(oxetan-3-yl)piperidin-4-yl)-1H-indazol-5-yl)-7-(4-chlorophenyl)-5-methylbenzo[d]thiazol-6-yl)acetate (S)-2-(tert-butoxy)-2-(7-(4-chlorophenyl)-2-(1-(2-hydroxyethyl)-3-(1-(oxetan-3-yl)piperidin-4-yl)-1H-indazol-5-yl)-5-methylbenzo[d]thiazol-6-yl)acetic acid Preparation of ethyl (S)-2-(tert-butoxy)-2-(2-(1-(2-((tert-butyldimethylsilyl)oxy)ethyl)-3-(1-(oxetan-3-yl)piperidin-4-yl)-1H-indazol-5-yl)-7-(4-chlorophenyl)-5-methylbenzo[d]thiazol-6-yl)acetate: To a solution of ethyl (S)-2-(tert-butoxy)-2-(7-(4-chlorophenyl)-5-methyl-2-(3-(1-(oxetan-3-yl)piperidin-4-yl)-1H-indazol-5-yl)benzo[d]thiazol-6-yl) acetate (50 mg, 0.074 mmol) in anhydrous DMF (10 mL) was added sodium hydride (60% disp. in oil, 10 mg, 0.417 mmol) and stirred for 20 min at to 0° C. under argon. (2-Bromoethoxy)-tert-butyldimethylsilane (50 μl, 233.04 μmol) was added. The reaction mixture was kept at 0° C. for 20 min, then at room temperature for 16 h. Reaction was complete by LCMS analysis and used in the next step directly. LCMS-ESI$^+$: calc'd for $C_{45}H_{60}ClN_4O_5SSi$: 831.6 (M+H)+; found: 831.4 (M+H)$^+$.

Preparation of (S)-2-(tert-butoxy)-2-(7-(4-chlorophenyl)-2-(1-(2-hydroxyethyl)-3-(1-(oxetan-3-yl)piperidin-4-yl)-1H-indazol-5-yl)-5-methylbenzo[d]thiazol-6-yl)acetic acid: To above reaction mixture was added MeOH (1 mL) and 50% Sodium hydroxide (0.5 mL) at room temperature. The mixture was stirred at 60° C. for 1 h. The reaction mixture was cooled by ice and acidified with 3 N HCl. The resulting mixture was extracted with ethyl acetate (2×). Combined organic layer was dried (MgSO$_4$), filtered and concentrated to give crude mixture which was purified by Gilson HPLC (Phenomenex Gemini 250×21.2 10μ C18 column, 40-100% ACN/H$_2$O+0.1% TFA) to give a yellow powder after lyophilization. $^1$H NMR (400 MHz, Chloroform-d) δ 8.03 (s, 1H), 7.87 (s, 1H), 7.71 (s, 1H), 7.51 (dd, J=16.9, 8.7 Hz, 3H), 5.33 (s, 1H), 5.13 (d, J=7.1 Hz, 2H), 4.81 (d, J=7.7 Hz, 2H), 4.46 (s, 2H), 4.25 (d, J=6.6 Hz, 1H), 4.13 (t, J=4.9 Hz, 2H), 2.59 (s, 3H), 2.6-1.9 (br, 8H) 1.01 (s, 9H). LCMS-ESI+: calc'd for $C_{37}H_{42}ClN_4O_5S$; 689.3 (M+H)$^+$; found: 689.3 (M+H)$^+$.

Example 40. Preparation of (S)-2-(tert-butoxy)-2-(7-(4-chlorophenyl)-2-(1-cyclopropyl-3-(1-(oxetan-3-yl)piperidin-4-yl)-1H-indazol-5-yl)-5-methylbenzo[d]thiazol-6-yl)acetic Acid (38)

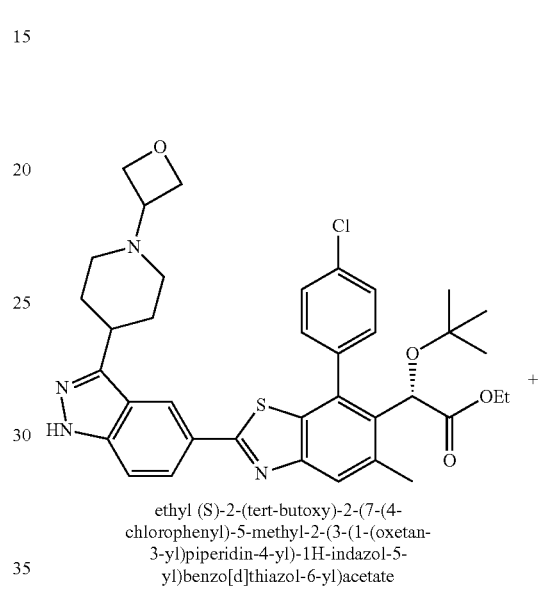

ethyl (S)-2-(tert-butoxy)-2-(7-(4-chlorophenyl)-5-methyl-2-(3-(1-(oxetan-3-yl)piperidin-4-yl)-1H-indazol-5-yl)benzo[d]thiazol-6-yl)acetate

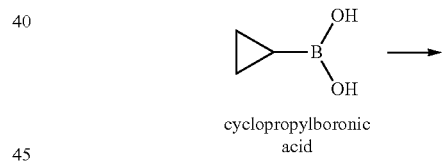

cyclopropylboronic acid

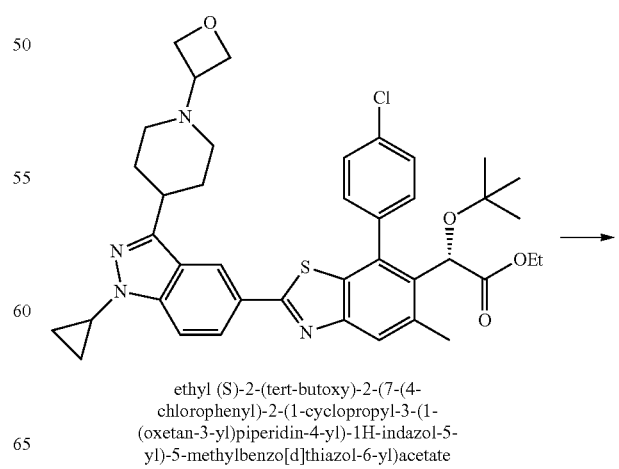

ethyl (S)-2-(tert-butoxy)-2-(7-(4-chlorophenyl)-2-(1-cyclopropyl-3-(1-(oxetan-3-yl)piperidin-4-yl)-1H-indazol-5-yl)-5-methylbenzo[d]thiazol-6-yl)acetate

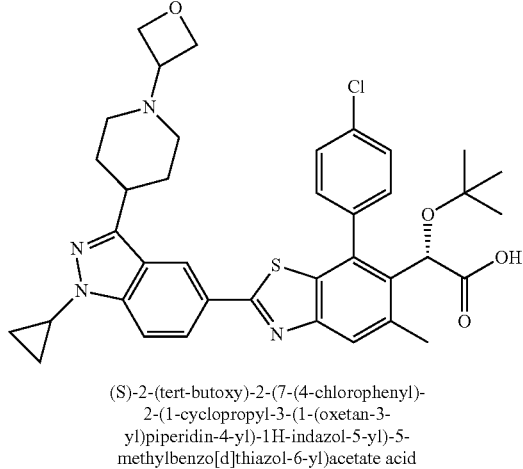

(S)-2-(tert-butoxy)-2-(7-(4-chlorophenyl)-
2-(1-cyclopropyl-3-(1-(oxetan-3-
yl)piperidin-4-yl)-1H-indazol-5-yl)-5-
methylbenzo[d]thiazol-6-yl)acetate acid Preparation of ethyl (S)-2-(tert-butoxy)-2-(7-(4-chlorophenyl)-2-(1-cyclopropyl-3-(1-(oxetan-3-yl)piperidin-4-yl)-1H-indazol-5-yl)-5-methylbenzo[d]thiazol-6-yl)acetate: To a microwave vial with ethyl (S)-2-(tert-butoxy)-2-(7-(4-chlorophenyl)-5-methyl-2-(3-(1-(oxetan-3-yl)piperidin-4-yl)-1H-indazol-5-yl)benzo[d]thiazol-6-yl)acetate (95 mg, 141.1 μmol) in THF (3 mL) was added Cyclopropylboronic acid (60.6 mg, 705.5 μmol), anhydrous cupric acetate, (76.9 mg, 423.35 μmol), triethylamine (0.12 ml, 847 μmol) and pyridine (0.09 ml, 1129 μmol). The mixture was heated in microwave at 140° C. for 30 min. The reaction mixture was cooled to room temperature and used as is for the next step. LCMS-ESI+: calc'd for $C_{40}H_{46}ClN_4O_4S$: 713.3 (M+H)+; found: 713.4 (M+H)+.

Preparation of (S)-2-(tert-butoxy)-2-(7-(4-chlorophenyl)-2-(1-cyclopropyl-3-(1-(oxetan-3-yl)piperidin-4-yl)-1H-indazol-5-yl)-5-methylbenzo[d]thiazol-6-yl)acetic acid: To above reaction mixture was added MeOH (1 mL) and 50% Sodium hydroxide (0.5 mL) at room temperature. The mixture was stirred at 60° C. for 1 h. The reaction mixture was cooled by ice and acidified with 3 N HCl. The resulting mixture was extracted with ethyl acetate (2×). Combined organic layer was dried ($MgSO_4$), filtered and concentrated to give crude mixture which was purified by Gilson HPLC (Phenomenex Gemini 250×21.2 10μ C18 column, 40-100% ACN/$H_2O$+0.1% TFA) to give a yellow powder after lyophilization. $^1$H NMR (400 MHz, Chloroform-d) δ 8.40 (dd, J=72.4, 34.3 Hz, 1H), 8.12-7.90 (m, 1H), 7.89 (s, 1H), 7.72 (d, J=8.1 Hz, 1H), 7.62 (d, J=8.8 Hz, 1H), 7.58-7.43 (m, 2H), 5.32 (s, 1H), 5.11 (t, J=7.1 Hz, 2H), 4.81 (t, J=7.6 Hz, 2H), 4.28 (t, J=6.8 Hz, 1H), 3.85-2.66 (m, 5H), 2.58 (s, 3H), 2.53-2.13 (m, 5H), 1.20 (s, 4H), 1.01 (s, 9H). LCMS-ESI+: calc'd for $C_{38}H_{42}ClN_4O_4S$; 685.3 (M+H)+; found: 685.3 (M+H)+.

Example 41. Preparation of (S)-2-(tert-butoxy)-2-(7-(4-chlorophenyl)-2-(1-(difluoromethyl)-3-(1-(oxetan-3-yl)piperidin-4-yl)-1H-indazol-5-yl)-5-methyl-benzo[d]thiazol-6-yl)acetic Acid (39)

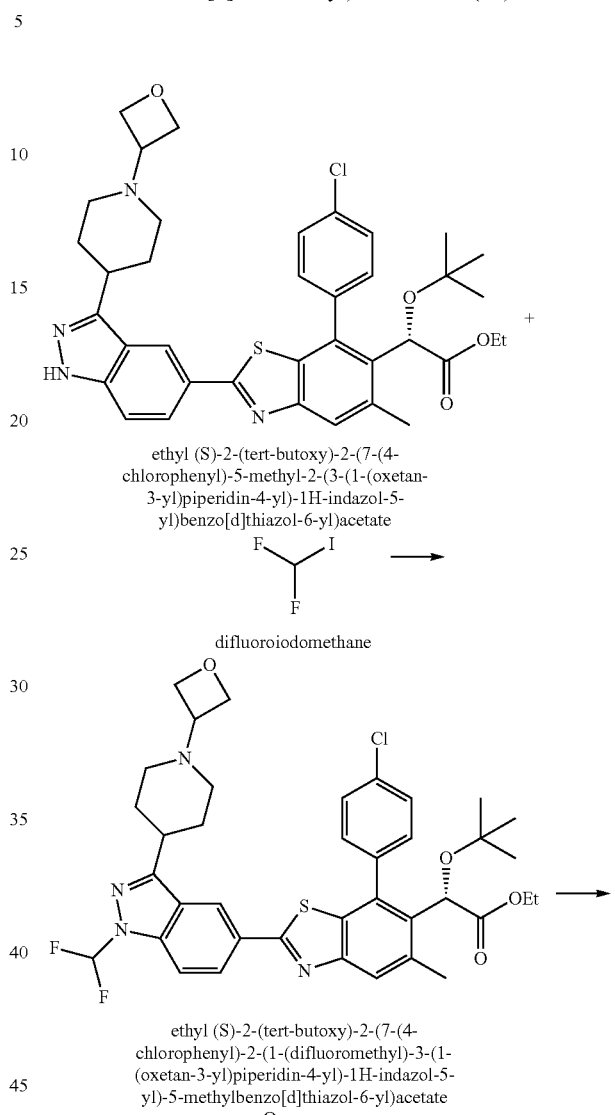

ethyl (S)-2-(tert-butoxy)-2-(7-(4-chlorophenyl)-5-methyl-2-(3-(1-(oxetan-3-yl)piperidin-4-yl)-1H-indazol-5-yl)benzo[d]thiazol-6-yl)acetate difluoroiodomethane ethyl (S)-2-(tert-butoxy)-2-(7-(4-chlorophenyl)-2-(1-(difluoromethyl)-3-(1-(oxetan-3-yl)piperidin-4-yl)-1H-indazol-5-yl)-5-methylbenzo[d]thiazol-6-yl)acetate

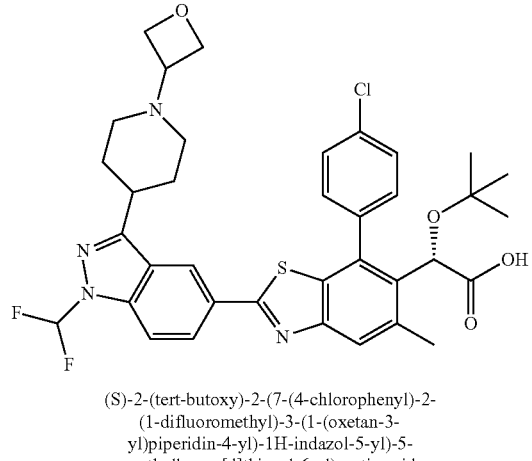

(S)-2-(tert-butoxy)-2-(7-(4-chlorophenyl)-2-(1-difluoromethyl)-3-(1-(oxetan-3-yl)piperidin-4-yl)-1H-indazol-5-yl)-5-methylbenzo[d]thiazol-6-yl)acetic acid Preparation of ethyl (S)-2-(tert-butoxy)-2-(7-(4-chlorophenyl)-2-(1-(difluoromethyl)-3-(1-(oxetan-3-yl)piperidin- 4-yl)-1H-indazol-5-yl)-5-methylbenzo[d]thiazol-6-yl)acetate: To a 50 mL pressure vessel with a stir bar was added ethyl (S)-2-(tert-butoxy)-2-(7-(4-chlorophenyl)-5-methyl-2-(3-(1-(oxetan-3-yl)piperidin-4-yl)-1H-indazol-5-yl)benzo[d]thiazol-6-yl)acetate (77 mg, 0.114 mmol), difluoroiodomethane (430.65 µl, 0.23 mmol) in THF (2 ml) and cesium carbonate (111.79 mg, 0.34 mmol). The vessel was sealed and heated to 40° C. for 24 h. LCMS showed little desired product was formed. Additional difluoroiodomethane (430.65 µl, 0.23 mmol) and cesium carbonate (111.79 mg, 0.34 mmol) were added and mixture heated at 40° C. for another 24 h. Additional product formed, but still greater than half of SM remained by LCMS analysis. The reaction mixture was cooled room temperature. It was taken to the next step directly. LCMS-ESI⁺: calc'd for $C_{38}H_{42}ClF_2N_4O_4S$: 723.3 (M+H)+; found: 723.4 (M+H)⁺.

Preparation of (S)-2-(tert-butoxy)-2-(7-(4-chlorophenyl)-2-(1-(difluoromethyl)-3-(1-(oxetan-3-yl)piperidin-4-yl)-1H-indazol-5-yl)-5-methylbenzo[d]thiazol-6-yl)acetic acid: To above reaction mixture was added MeOH (1 mL) and 50% Sodium hydroxide (0.5 mL) at room temperature. The mixture was stirred at 60° C. for 1 h. The reaction mixture was cooled by ice and acidified with 3 N HCl. The resulting mixture was extracted with ethyl acetate (2×). Combined organic layer was dried (MgSO₄), filtered and concentrated to give crude mixture which was purified by Gilson HPLC (Phenomenex Gemini 250×21.2 10µ C18 column, 40-100% ACN/H₂O+0.1% TFA) to give a yellow powder after lyophilization. ¹H NMR (400 MHz, Chloroform-d) δ 8.39 (d, J=7.0 Hz, 1H), 8.10 (dd, J=28.7, 8.8 Hz, 1H), 7.88 (s, 1H), 7.80 (dd, J=8.8, 5.7 Hz, 1H), 7.72 (d, J=8.2 Hz, 1H), 7.60-7.35 (m, 4H), 5.33 (s, 1H), 5.11 (t, J=7.0 Hz, 2H), 4.80 (t, J=7.6 Hz, 2H), 4.33-4.16 (m, 1H), 3.80-3.04 (m, 4H), 2.58 (s, 3H), 2.38 (d, J=36.9 Hz, 4H), 1.01 (d, J=1.8 Hz, 9H). 19F NMR (376 MHz, Chloroform-d) δ −76.25, −95.25 (d, J=58.9 Hz). LCMS-ESI+: calc'd for $C_{36}H_{38}ClF_2N_4O_4S$; 695.2 (M+H)⁺; found: 695.3 (M+H)⁺.

Example 42. Preparation of (S)-2-(tert-butoxy)-2-(7-(4-chlorophenyl)-2-(1-(2-hydroxyethyl)-3-(1-(oxetan-3-yl)piperidin-4-yl)-1H-indazol-5-yl)-5-methylbenzo[d]thiazol-6-yl)acetic Acid (40)

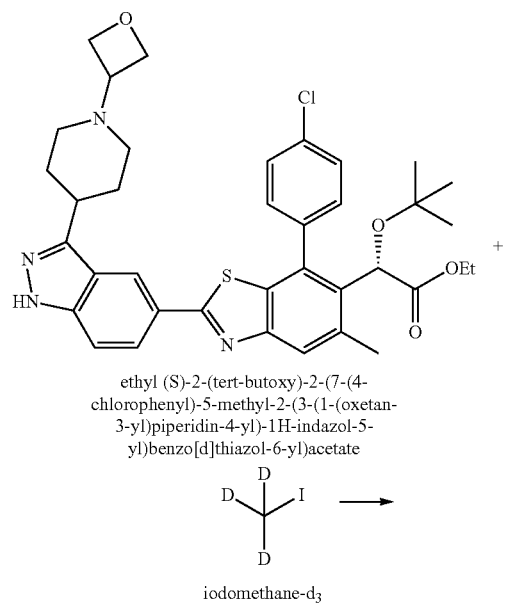

ethyl (S)-2-(tert-butoxy)-2-(7-(4-chlorophenyl)-5-methyl-2-(3-(1-(oxetan-3-yl)piperidin-4-yl)-1H-indazol-5-yl)benzo[d]thiazol-6-yl)acetate iodomethane-d₃

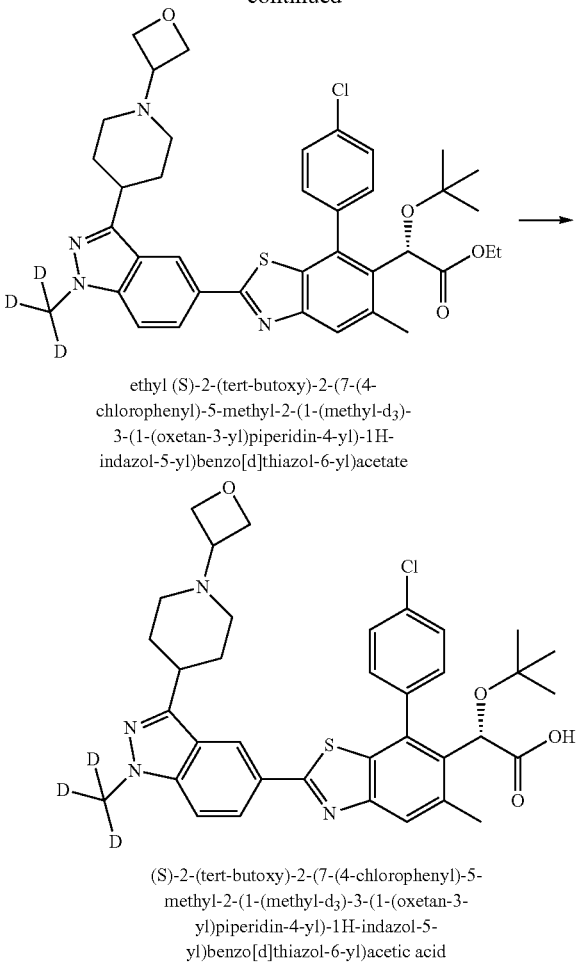

ethyl (S)-2-(tert-butoxy)-2-(7-(4-chlorophenyl)-5-methyl-2-(1-(methyl-d₃)-3-(1-(oxetan-3-yl)piperidin-4-yl)-1H-indazol-5-yl)benzo[d]thiazol-6-yl)acetate (S)-2-(tert-butoxy)-2-(7-(4-chlorophenyl)-5-methyl-2-(1-(methyl-d₃)-3-(1-(oxetan-3-yl)piperidin-4-yl)-1H-indazol-5-yl)benzo[d]thiazol-6-yl)acetic acid Preparation of ethyl (S)-2-(tert-butoxy)-2-(7-(4-chlorophenyl)-5-methyl-2-(1-(methyl-d3)-3-(1-(oxetan-3-yl)piperidin-4-yl)-1H-indazol-5-yl)benzo[d]thiazol-6-yl)acetate: To a solution of ethyl (S)-2-(tert-butoxy)-2-(7-(4-chlorophenyl)-5-methyl-2-(3-(1-(oxetan-3-yl)piperidin-4-yl)-1H-indazol-5-yl)benzo[d]thiazol-6-yl)acetate (33 mg, 0.049 mmol) in anhydrous THF (1 mL) was added sodium hydride (60% disp. in oil, 10 mg, 0.417 mmol) and stirred for 20 min at to 0° C. under argon. Iodomethane-d3 (21.3 mg, 0.147 mmol) was added. The reaction mixture was kept at 0° C. for 20 min, then at room temperature for 1 h. Reaction was complete by LCMS analysis and used in the next step directly. LCMS-ESI⁺: calc'd for $C_{45}H_{60}ClN_4O_5SSi$: 831.6 (M+H)+; found: 690.4 (M+H)⁺.

Preparation of (S)-2-(tert-butoxy)-2-(7-(4-chlorophenyl)-5-methyl-2-(1-(methyl-d3)-3-(1-(oxetan-3-yl)piperidin-4-yl)-1H-indazol-5-yl)benzo[d]thiazol-6-yl)acetic acid: To above reaction mixture was added MeOH (1 mL) and 50% Sodium hydroxide (0.5 mL) at room temperature. The mixture was stirred at 60° C. for 1 h. The reaction mixture was cooled by ice and acidified with 3 N HCl. The resulting mixture was extracted with ethyl acetate (2×). Combined organic layer was dried (MgSO₄), filtered and concentrated to give crude mixture which was purified by Gilson HPLC (Phenomenex Gemini 250×21.2 10µ C18 column, 40-100% ACN/H₂O+0.1% TFA) to give a yellow powder after lyophilization. ¹H NMR (400 MHz, Chloroform-d) δ 8.24 (s, 1H), 7.98 (s, 1H), 7.79 (s, 1H), 7.63 (s, 1H), 7.45 (d, J=8.6

Hz, 3H), 7.33 (d, J=8.6 Hz, 1H), 5.24 (s, 1H), 5.06 (t, J=7.1 Hz, 2H), 4.71 (t, J=7.6 Hz, 2H), 4.18 (s, 1H), 2.50 (s, 3H), 2.45 (d, J=14.7 Hz, 2H), 2.30 (s, 6H), 0.93 (s, 9H). LCMS-ESI+: calc'd for $C_{36}H_{37}D_3ClN_4O_4S$; 662.3 (M+H)$^+$; found: 662.3 (M+H)$^+$.

Example 43. Preparation of (S)-2-(tert-butoxy)-2-(7-(4-chlorophenyl)-5-methyl-2-(3-(1-(oxetan-3-yl)piperidin-4-yl)-1-(2,2,2-trifluoroethyl)-1H-indazol-5-yl)benzo[d]thiazol-6-yl)acetic Acid (41)

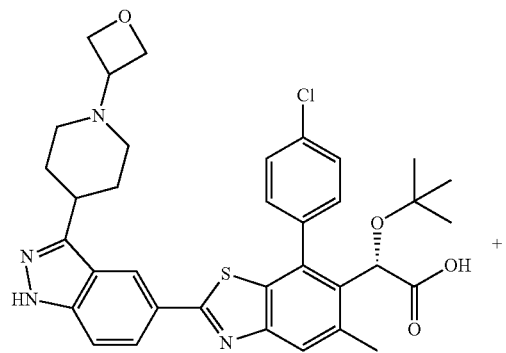

(S)-2-(tert-butoxy)-2-(7-(4-chlorophenyl)-5-methyl-2-(3-(1-(oxetan-3-yl)piperidin-4-yl)-1H-indazol-5-yl)benzo[d]thiazol-6-yl)acetate acid

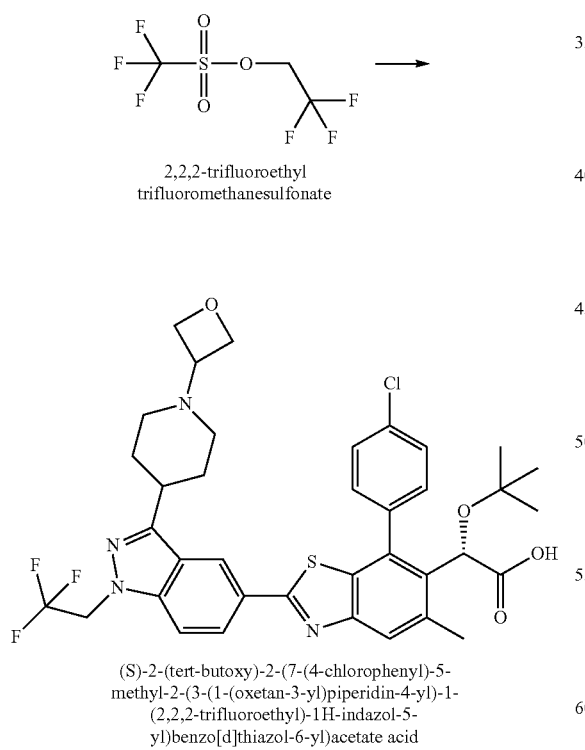

2,2,2-trifluoroethyl trifluoromethanesulfonate (S)-2-(tert-butoxy)-2-(7-(4-chlorophenyl)-5-methyl-2-(3-(1-(oxetan-3-yl)piperidin-4-yl)-1-(2,2,2-trifluoroethyl)-1H-indazol-5-yl)benzo[d]thiazol-6-yl)acetate acid Preparation of (S)-2-(tert-butoxy)-2-(7-(4-chlorophenyl)-5-methyl-2-(3-(1-(oxetan-3-yl)piperidin-4-yl)-1-(2,2,2-trifluoroethyl)-1H-indazol-5-yl)benzo[d]thiazol-6-yl)acetic acid: To a solution of (S)-2-(tert-butoxy)-2-(7-(4-chlorophe- nyl)-5-methyl-2-(3-(1-(oxetan-3-yl)piperidin-4-yl)-1H-indazol-5-yl)benzo[d]thiazol-6-yl)acetic acid (26 mg, 0.040 mmol) in anhydrous DMF (1 mL) was added sodium hydride (60% disp. in oil, 3.2 mg, 0.08 mmol) and stirred for 20 min at to 0° C. under argon. 2,2,2-Trifluoroethyl trifluoromethanesulfonate (11.61 µl, 0.080 mmol) was added. The reaction mixture was kept at 0° C. for 20 min, then at room temperature for 1 h. Reaction was complete by LCMS analysis. The reaction mixture was cooled to 0° C., acidified with 3N HCl, extracted with EtOAc, washed with 3% LiCl and brine. After drying over MgSO$_4$, organic layer was concentrated to remove the organic solvent. The residue was purified by HPLC purified by Gilson HPLC (Phenomenex Gemini 250×21.2 10µ C18 column, 40-100% ACN/H$_2$O+ 0.1% TFA) to give a yellow powder after lyophilization. $^1$H NMR (400 MHz, Chloroform-d) δ 7.88 (s, 1H), 7.45 (d, J=14.2 Hz, 7H), 5.23 (s, 1H), 4.82 (m, 2H), 4.59 (dd, J=12.9, 7.8 Hz, 3H), 4.46-4.24 (m, 1H), 4.04 (t, J=7.0 Hz, 1H), 3.68 (m, 1H), 2.77 (m, 1H), 2.46 (s, 3H), 2.12 (d, J=17.3 Hz, 5H), 1.30-1.09 (m, 1H), 0.97 (s, 9H). 19F NMR (377 MHz, Chloroform-d) δ -74.15 (t, J=8.5 Hz), -75.73. LCMS-ESI+: calc'd for $C_{37}H_{39}ClF_3N_4O_4S$; 727.2 (M+H)$^+$; found: 727.4 (M+H)$^+$.

Example 44. Preparation of (S)-2-(tert-butoxy)-2-(7-(4-chlorophenyl)-2-(1-(2,2-difluoroethyl)-3-(1-(oxetan-3-yl)piperidin-4-yl)-1H-indazol-5-yl)-5-methylbenzo[d]thiazol-6-yl)acetic Acid (42)

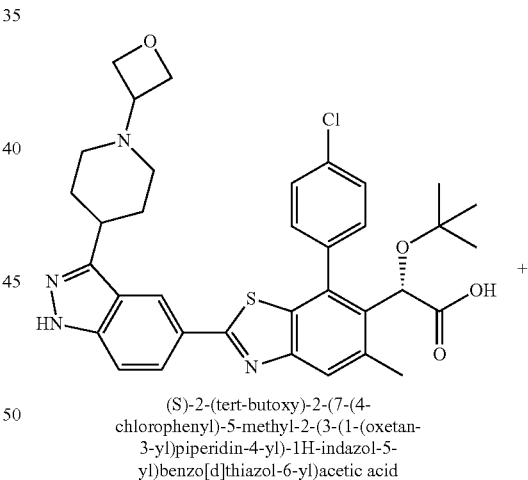

(S)-2-(tert-butoxy)-2-(7-(4-chlorophenyl)-5-methyl-2-(3-(1-(oxetan-3-yl)piperidin-4-yl)-1H-indazol-5-yl)benzo[d]thiazol-6-yl)acetic acid

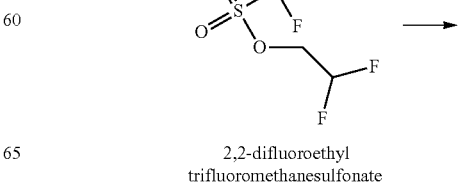

2,2-difluoroethyl trifluoromethanesulfonate

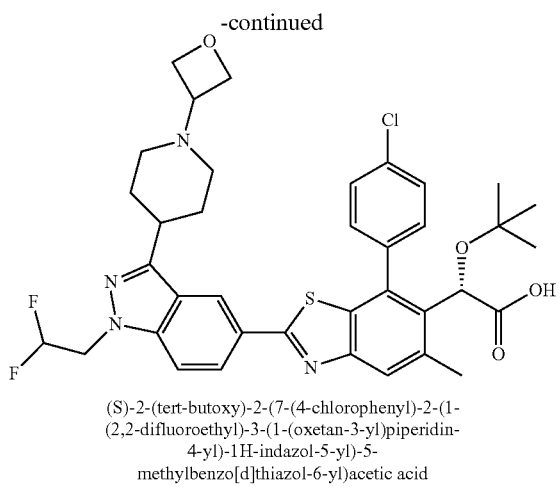

(S)-2-(tert-butoxy)-2-(7-(4-chlorophenyl)-2-(1-(2,2-difluoroethyl)-3-(1-(oxetan-3-yl)piperidin-4-yl)-1H-indazol-5-yl)-5-methylbenzo[d]thiazol-6-yl)acetic acid Preparation of (S)-2-(tert-butoxy)-2-(7-(4-chlorophenyl)-2-(1-(2,2-difluoroethyl)-3-(1-(oxetan-3-yl)piperidin-4-yl)-1H-indazol-5-yl)-5-methylbenzo[d]thiazol-6-yl)acetic acid: To a flask with a stir bar was added (S)-2-(tert-butoxy)-2-(7-(4-chlorophenyl)-5-methyl-2-(3-(1-(oxetan-3-yl)piperidin-4-yl)-1H-indazol-5-yl)benzo[d]thiazol-6-yl)acetic acid (25 mg, 0.03 mmol) in DMF (1 mL), 2,2-Difluoroethyl trifluoromethanesulfonate (31.89 mg, 0.15 mmol) and cesium carbonate (97.06 mg, 0.3 mmol). The mixture was stirred at 80° C. for 5 h. The reaction mixture was cooled to 0° C., acidified with 3N HCl. It was extracted with EtOAc, washed with 3% LiCl and brine. After dried over MgSO$_4$, it was concentrated to remove the organic solvent. The residue was purified by HPLC purified by Gilson HPLC (Phenomenex Gemini 250×21.2 10μ C18 column, 40-100% ACN/H$_2$O+0.1% TFA) to give a yellow powder after lyophilization. $^1$H NMR (400 MHz, Chloroform-d) δ 7.82 (m, 2H), 7.43 (d, J=17.9 Hz, 6H), 6.10-5.60 (m, 1H), 5.19 (s, 1H), 4.87 (m, 2H), 4.63 (m, 2H), 4.44-3.92 (m, 3H), 3.62-2.61 (m, 5H), 2.48 (s, 3H), 2.18 (s, 4H), 0.94 (s, 9H). 19F NMR (377 MHz, Chloroform-d) δ −76.02, −126.24 (ddt, J=56.5, 28.6, 13.8 Hz). LCMS-ESI+: calc'd for C$_{37}$H$_{40}$ClF$_2$N$_4$O$_4$S; 709.3 (M+H)$^+$; found: 709.4 (M+H)$^+$.

Example 45. (S)-2-(2-(3-(1-(1-acetylazetidin-3-yl)piperidin-4-yl)-1-(difluoromethyl)-1H-indazol-5-yl)-7-(4-chlorophenyl)-5-methylbenzo[d]thiazol-6-yl)-2-(tert-butoxy)acetic Acid (43)

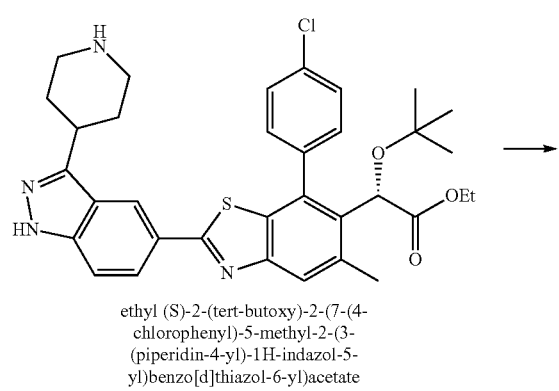

ethyl (S)-2-(tert-butoxy)-2-(7-(4-chlorophenyl)-5-methyl-2-(3-(piperidin-4-yl)-1H-indazol-5-yl)benzo[d]thiazol-6-yl)acetate

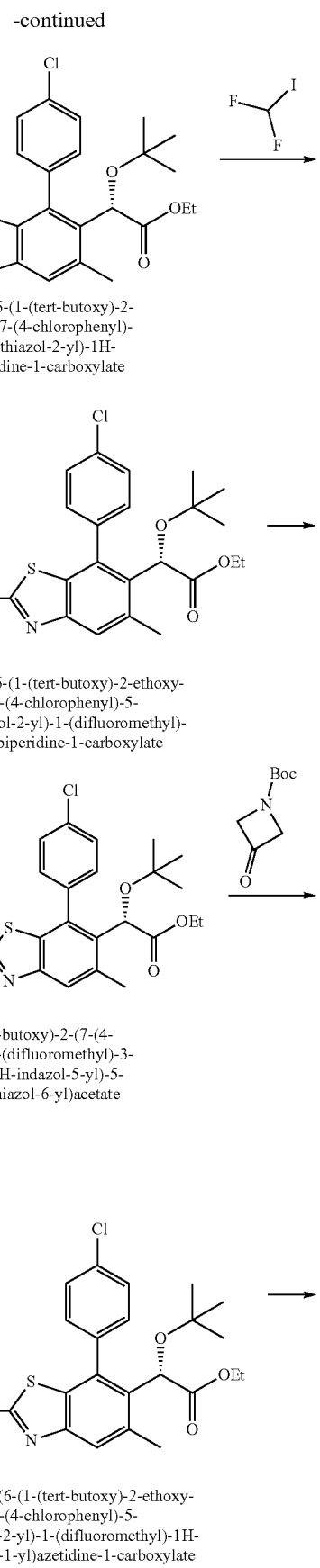

tert-butyl (S)-4-(5-(6-(1-(tert-butoxy)-2-ethoxy-2-oxoethyl)-7-(4-chlorophenyl)-5-methylbenzo[d]thiazol-2-yl)-1H-indazol-3-yl)piperidine-1-carboxylate tert-butyl (S)-4-(5-(6-(1-(tert-butoxy)-2-ethoxy-2-oxoethyl)-7-(4-chlorophenyl)-5-methylbenzo[d]thiazol-2-yl)-1-(difluoromethyl)-1H-indazol-3-yl)piperidine-1-carboxylate ethyl (S)-2-(tert-butoxy)-2-(7-(4-chlorophenyl)-2-(1-(difluoromethyl)-3-(piperidin-4-yl)-1H-indazol-5-yl)-5-methylbenzo[d]thiazol-6-yl)acetate tert-butyl (S)-3-(4-(5-(6-(1-(tert-butoxy)-2-ethoxy-2-oxoethyl)-7-(4-chlorophenyl)-5-methylbenzo[d]thiazol-2-yl)-1-(difluoromethyl)-1H-indazol-3-yl)piperidin-1-yl)azetidine-1-carboxylate

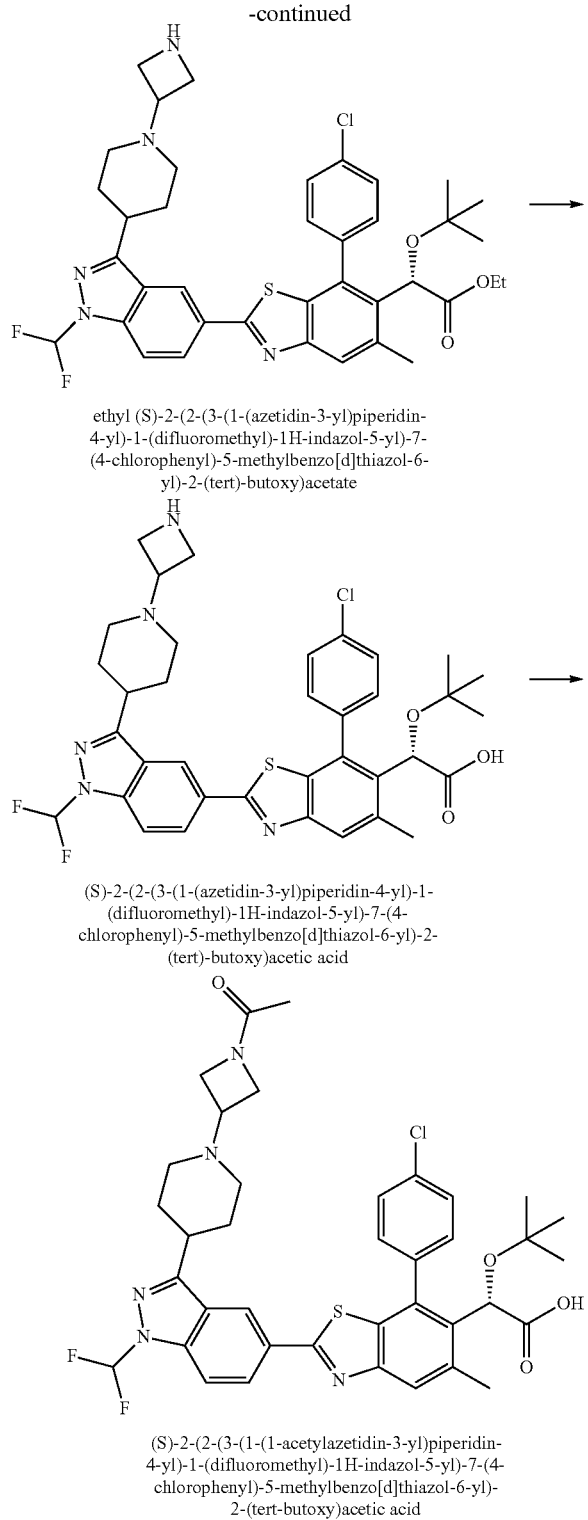

ethyl (S)-2-(2-(3-(1-(azetidin-3-yl)piperidin-4-yl)-1-(difluoromethyl)-1H-indazol-5-yl)-7-(4-chlorophenyl)-5-methylbenzo[d]thiazol-6-yl)-2-(tert)-butoxy)acetate (S)-2-(2-(3-(1-(azetidin-3-yl)piperidin-4-yl)-1-(difluoromethyl)-1H-indazol-5-yl)-7-(4-chlorophenyl)-5-methylbenzo[d]thiazol-6-yl)-2-(tert)-butoxy)acetic acid (S)-2-(2-(3-(1-(1-acetylazetidin-3-yl)piperidin-4-yl)-1-(difluoromethyl)-1H-indazol-5-yl)-7-(4-chlorophenyl)-5-methylbenzo[d]thiazol-6-yl)-2-(tert-butoxy)acetic acid Preparation of tert-butyl (S)-4-(5-(6-(1-(tert-butoxy)-2-ethoxy-2-oxoethyl)-7-(4-chlorophenyl)-5-methylbenzo[d]thiazol-2-yl)-1H-indazol-3-yl)piperidine-1-carboxylate: To a solution of ethyl (S)-2-(tert-butoxy)-2-(7-(4-chlorophenyl)-5-methyl-2-(3-(piperidin-4-yl)-1H-indazol-5-yl)benzo[d]thiazol-6-yl)acetate (0.7 g, 1.13 mmol) in dichloromethane (14 mL) was added Di-tert-butyl dicarbonate (0.37 g, 1.7 mmol) and N,N-Diisopropylethylamine (0.6 ml). The reaction mixture was kept at room temperature for 18 h. Reaction was complete by LCMS analysis. The reaction mixture was quenched with sat'd NaHCO$_3$, extracted with EtOAc, dried (MgSO$_4$) and concentrated to give desired product. LCMS-ESI+: calc'd for C$_{39}$H$_{46}$ClN$_4$O$_5$S; 717.32 (M+H)$^+$; found: 717.1 (M+H)$^+$.

Preparation of tert-butyl (S)-4-(5-(6-(1-(tert-butoxy)-2-ethoxy-2-oxoethyl)-7-(4-chlorophenyl)-5-methylbenzo[d]thiazol-2-yl)-1-(difluoromethyl)-1H-indazol-3-yl)piperidine-1-carboxylate: To a solution of tert-butyl (S)-4-(5-(6-(1-(tert-butoxy)-2-ethoxy-2-oxoethyl)-7-(4-chlorophenyl)-5-methylbenzo[d]thiazol-2-yl)-1H-indazol-3-yl)piperidine-1-carboxylate (325 mg, 0.453 mmol) in anhydrous DMF (5 mL) was added sodium hydride (60% disp. in oil, 21.75 mg, 0.91 mmol) and stirred for 20 min at to 0° C. under argon. Difluoroiodomethane (1279.55 µl, 0.68 mmol) in THF was added. The reaction mixture was kept at 0° C. for 20 min, then at room temperature for 2 h. LCMS showed about ⅓ of starting material remained. The reaction mixture was cooled to 0° C. under argon again, and additional NaH (60% disp. in oil, 21.75 mg, 0.91 mmol) was added, followed by difluoroiodomethane (1279.55 µl, 0.68 mmol) as before. After another 2 h at RT, the reaction was completed. The reaction mixture was cooled to 0° C., then added 1N HCl until pH about 7. It was extracted with EtOAc, washed with 3% LiCl and brine. The organic layer was dried over Na$_2$SO$_4$ and concentrated. The residue was purified by CombiFlash (40 g, Gold, 0-100% EtOAc/Hexane) gave the desired regioisomer product (faster runner on TLC). $^1$H NMR (400 MHz, Chloroform-d) δ 8.39 (dd, J=1.6, 0.8 Hz, 1H), 8.14 (dd, J=8.8, 1.6 Hz, 1H), 7.89 (d, J=0.9 Hz, 1H), 7.77 (d, J=8.7 Hz, 1H), 7.60-7.35 (m, 5H), 5.16 (s, 1H), 4.22 (tt, J=7.1, 3.6 Hz, 4H), 4.12 (q, J=7.1 Hz, 2H), 3.25 (tt, J=11.6, 3.9 Hz, 1H), 2.97 (t, J=12.7 Hz, 2H), 2.61 (d, J=0.7 Hz, 3H), 1.92 (qd, J=12.1, 4.4 Hz, 2H), 1.49 (s, 9H), 1.26 (t, J=7.1 Hz, 3H), 0.99 (s, 9H). LCMS-ESI+: calc'd for C$_{40}$H$_{46}$ClF$_2$N$_4$O$_5$S: 767.3 (M+H)$^+$; found: 767.1 (M+H)$^+$.

Preparation of ethyl (S)-2-(tert-butoxy)-2-(7-(4-chlorophenyl)-2-(1-(difluoromethyl)-3-(piperidin-4-yl)-1H-indazol-5-yl)-5-methylbenzo[d]thiazol-6-yl)acetate: A solution of tert-butyl (S)-4-(5-(6-(1-(tert-butoxy)-2-ethoxy-2-oxoethyl)-7-(4-chlorophenyl)-5-methylbenzo[d]thiazol-2-yl)-1-(difluoromethyl)-1H-indazol-3-yl)piperidine-1-carboxylate (100 mg, 0.13 mmol) in 1.25 HCl in isopropanol (3 mL) was stirred at room temperature for 16 h. Reaction was quenched carefully with 1N sodium hydroxide at 0° C. to pH>8. It was extracted with ethyl acetate (2x). Combined organic layer was dried over sodium sulfate, filtered and concentrated to give desire product. It was used in the next step without further purification. LCMS-ESI+: calc'd for C$_{35}$H$_{38}$ClF$_2$N$_4$O$_3$S: 667.2 (M+H)$^+$; found: 667.4 (M+H)$^+$.

Preparation of tert-butyl (S)-3-(4-(5-(6-(1-(tert-butoxy)-2-ethoxy-2-oxoethyl)-7-(4-chlorophenyl)-5-methylbenzo[d]thiazol-2-yl)-1-(difluoromethyl)-1H-indazol-3-yl)piperidin-1-yl)azetidine-1-carboxylate: A solution of ethyl (S)-2-(tert-butoxy)-2-(7-(4-chlorophenyl)-2-(1-(difluoromethyl)-3-(piperidin-4-yl)-1H-indazol-5-yl)-5-methylbenzo[d]thiazol-6-yl)acetate (40 mg, 60 µmol), 1-Boc-3-azetidinone (102 mg, 0.6 mmol), acetic acid (2 drops) and sodium cyanoborohydride (64 mg, 0.3 mmol) in methanol (5 mL) was stirred for 5 hours at room temperature. Reaction was quenched with saturated sodium bicarbonate solution and brine. The mixture was extracted with ethyl acetate (2x) and combined organic layer was dried (MgSO$_4$), filtered and concentrated. The residue was purified by CombiFlash (40 g, Gold, 0-10% MeOH/CH$_2$Cl$_2$) to give desired product. LCMS-ESI+: calc'd for C$_{43}$H$_{51}$ClF$_2$N$_5$O$_5$S: 822.4 (M+H)$^+$; found: 822.1 (M+H)$^+$.

Preparation of ethyl (S)-2-(2-(3-(1-(azetidin-3-yl)piperidin-4-yl)-1-(difluoromethyl)-1H-indazol-5-yl)-7-(4-chlorophenyl)-5-methylbenzo[d]thiazol-6-yl)-2-(tert-butoxy)acetate: A solution of tert-butyl (S)-3-(4-(5-(6-(1-(tert-butoxy)-2-ethoxy-2-oxoethyl)-7-(4-chlorophenyl)-5-methylbenzo[d]thiazol-2-yl)-1-(difluoromethyl)-1H-indazol-3-yl)piperidin-1-yl)azetidine-1-carboxylate (49 mg, 0.06 mmol) in 1.25 HCl in isopropanol (3 mL) was stirred at room temperature for 16 h. Reaction was quenched carefully with 1N sodium hydroxide at 0° C. to pH>8. It was extracted with ethyl acetate (2×). Combined organic layer was dried over sodium sulfate, filtered and concentrated to give desire product. It was used in the next step without further purification. LCMS-ESI+: calc'd for C$_{38}$H$_{43}$ClF$_2$N$_5$O$_3$S: 722.3 (M+H)$^+$; found: 722.2 (M+H)$^+$.

Preparation of (S)-2-(2-(3-(1-(azetidin-3-yl)piperidin-4-yl)-1-(difluoromethyl)-1H-indazol-5-yl)-7-(4-chlorophenyl)-5-methylbenzo[d]thiazol-6-yl)-2-(tert-butoxy)acetic acid: To the ethyl (S)-2-(2-(3-(1-(azetidin-3-yl)piperidin-4-yl)-1-(difluoromethyl)-1H-indazol-5-yl)-7-(4-chlorophenyl)-5-methylbenzo[d]thiazol-6-yl)-2-(tert-butoxy)acetate (15 mg, 0.020 mmol) was added THF (2 mL), MeOH (1 mL) and 50% sodium hydroxide (0.5 mL) at room temperature. The mixture was stirred at 60° C. for 1 h. The reaction mixture was cooled by ice and acidified with 3N HCl to pH=6. It was concentrated to remove the organic solvent. Used as is in next step. LCMS-ESI+: calc'd for C$_{36}$H$_{38}$ClF$_2$N$_5$O$_3$S; 694.2 (M+H)$^+$; found: 694.2 (M+H)$^+$.

Preparation of (S)-2-(2-(3-(1-(1-acetylazetidin-3-yl)piperidin-4-yl)-1-(difluoromethyl)-1H-indazol-5-yl)-7-(4-chlorophenyl)-5-methylbenzo[d]thiazol-6-yl)-2-(tert-butoxy) acetic acid: To a flask containing (S)-2-(2-(3-(1-(azetidin-3-yl)piperidin-4-yl)-1-(difluoromethyl)-1H-indazol-5-yl)-7-(4-chlorophenyl)-5-methylbenzo[d]thiazol-6-yl)-2-(tert-butoxy)acetic acid (14 mg, 0.020 mmol) in dichloromethane (10 mL) and water (5 mL) were added, followed by Sodium carbonate (62.02 mg, 2 mol) and Acetyl chloride (14.22 μl, 200 μmol). The mixture was stirred at room temperature for 20 h. The desired acid product LCMS [m+1]=736.27 was formed as major, along with the corresponding mixed anhydride side-product (LCMS[m+1]=778.02). The layers were separated and the organic layer was dried (MgSO$_4$), and concentrated. To the residue was added MeOH (1 mL), THF (2 mL) and 1N Sodium hydroxide (0.1 mL), stirred at RT for 1 h to hydrolyze corresponding mixed anhydride side-product. After the completion, the reaction mixture was cooled to 0° C., acidified with 3N HCl to pH=4. The mixture was then concentrated to give crude mixture which was purified by Gilson HPLC (Phenomenex Gemini 250×21.2 10μ C18 column, 40-100% ACN/H$_2$O+0.1% TFA) to give a yellow powder after lyophilization. $^1$H NMR (400 MHz, Chloroform-d) δ 8.39 (d, J=7.0 Hz, 1H), 8.10 (dd, J=28.7, 8.8 Hz, 1H), 7.88 (s, 1H), 7.80 (dd, J=8.8, 5.7 Hz, 1H), 7.72 (d, J=8.2 Hz, 1H), 7.60-7.35 (m, 4H), 5.33 (s, 1H), 5.11 (t, J=7.0 Hz, 2H), 4.80 (t, J=7.6 Hz, 2H), 4.33-4.16 (m, 1H), 3.80-3.04 (m, 4H), 2.58 (s, 3H), 2.38 (d, J=36.9 Hz, 4H), 1.01 (d, J=1.8 Hz, 9H). 19F NMR (376 MHz, Chloroform-d) δ −76.25, −95.25 (d, J=58.9 Hz). 19F NMR (376 MHz, Chloroform-d) δ −76.48, −95.40 (d, J=58.0 Hz). LCMS-ESI+: calc'd for C$_{38}$H$_{41}$ClF$_2$N$_5$O$_4$S; 736.3 (M+H)$^+$; found: 736.2 (M+H)$^+$.

Example 46. (S)-2-(tert-butoxy)-2-(7-(4-chlorophenyl)-2-(1-(difluoromethyl)-3-(1-(1-(methoxycarbonyl)azetidin-3-yl)piperidin-4-yl)-1H-indazol-5-yl)-5-methylbenzo[d]thiazol-6-yl)acetic Acid (44)

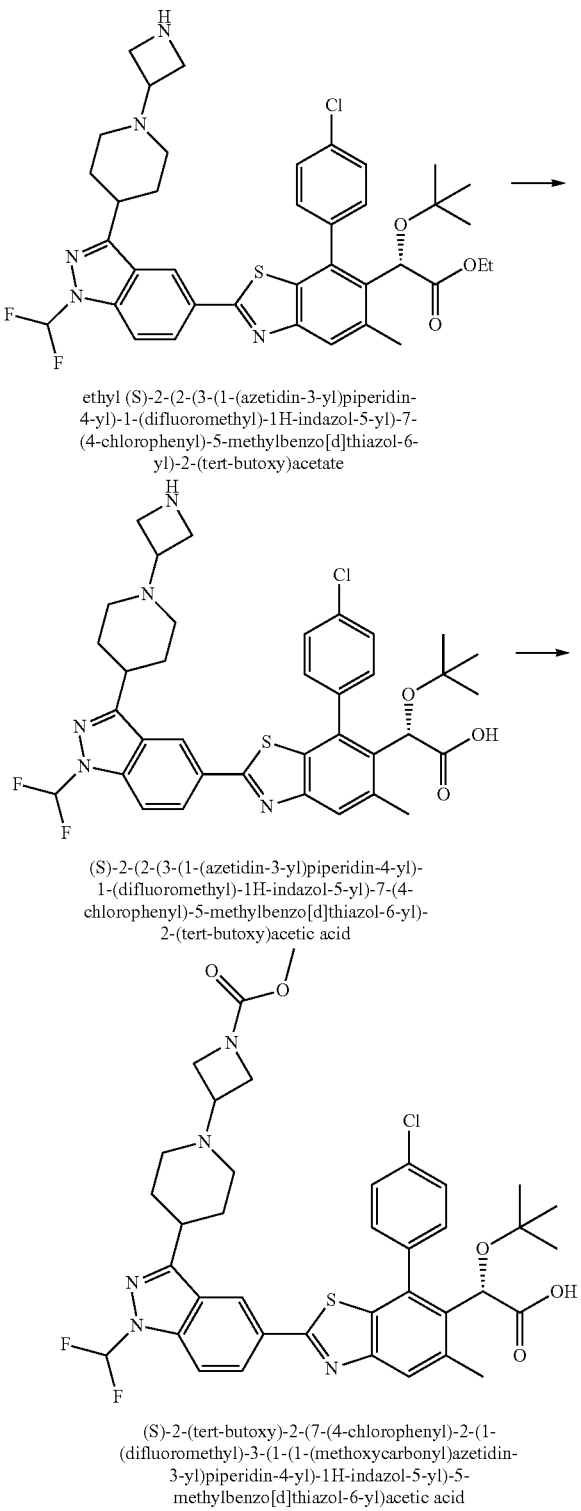

ethyl (S)-2-(2-(3-(1-(azetidin-3-yl)piperidin-4-yl)-1-(difluoromethyl)-1H-indazol-5-yl)-7-(4-chlorophenyl)-5-methylbenzo[d]thiazol-6-yl)-2-(tert-butoxy)acetate (S)-2-(2-(3-(1-(azetidin-3-yl)piperidin-4-yl)-1-(difluoromethyl)-1H-indazol-5-yl)-7-(4-chlorophenyl)-5-methylbenzo[d]thiazol-6-yl)-2-(tert-butoxy)acetic acid (S)-2-(tert-butoxy)-2-(7-(4-chlorophenyl)-2-(1-(difluoromethyl)-3-(1-(1-(methoxycarbonyl)azetidin-3-yl)piperidin-4-yl)-1H-indazol-5-yl)-5-methylbenzo[d]thiazol-6-yl)acetic acid Preparation of (S)-2-(2-(3-(1-(azetidin-3-yl)piperidin-4-yl)-1-(difluoromethyl)-1H-indazol-5-yl)-7-(4-chlorophenyl)-5-methylbenzo[d]thiazol-6-yl)-2-(tert-butoxy)acetic acid: To the ethyl (S)-2-(2-(3-(1-(azetidin-3-yl)piperidin-4-yl)-1-(difluoromethyl)-1H-indazol-5-yl)-7-(4-chlorophenyl)-5-methylbenzo[d]thiazol-6-yl)-2-(tert-butoxy)acetate (15 mg, 0.020 mmol) was added THF (2 mL), MeOH (1 mL) and 50% Sodium hydroxide (0.5 mL) at room temperature. The mixture was stirred at 60° C. for 1 h. The reaction mixture was cooled by ice and acidified with 3N HCl to pH=6. It was concentrated to remove the organic solvent and used as is in next step. LCMS-ESI+: calc'd for $C_{36}H_{38}ClF_2NO_{53}S$; 694.2 (M+H)$^+$; found: 694.2 (M+H)$^+$.

Preparation of (S)-2-(tert-butoxy)-2-(7-(4-chlorophenyl)-2-(1-(difluoromethyl)-3-(1-(1-(methoxycarbonyl)azetidin-3-yl)piperidin-4-yl)-1H-indazol-5-yl)-5-methylbenzo[d]thiazol-6-yl)acetic acid: To a flask containing crude (S)-2-(2-(3-(1-(azetidin-3-yl)piperidin-4-yl)-1-(difluoromethyl)-1H-indazol-5-yl)-7-(4-chlorophenyl)-5-methylbenzo[d]thiazol-6-yl)-2-(tert-butoxy)acetic acid (14 mg, 0.020 mmol) in dichloromethane (10 mL) and water (5 mL) were added Sodium carbonate (100 mg, 3 mmol) and Methyl chloroformate (50 µl, 647.11 µmol). The mixture was stirred at room temperature for 20 h. The corresponding mixed anhydride by-product (LCMS[m+1]=810.15) was major. The biphasic layers were separated, the organic layer was dried over MgSO$_4$, and concentrated. To the residue was added MeOH (1 mL) and THF (2 mL) and 1N Sodium hydroxide (0.1 mL), stirred at RT for 1 h to hydrolyze the mixed anhydride by-product. After the completion, the reaction mixture was cooled to 0° C., acidified with 3N HCl to pH=4. The mixture was then concentrated to give crude mixture which was purified by Gilson HPLC (Phenomenex Gemini 250×21.2 10µ C18 column, 40-100% ACN/H$_2$O+0.1% TFA) to give a yellow powder after lyophilization. $^1$H NMR (400 MHz, Chloroform-d) δ 8.89 (s, 1H), 8.03-7.79 (m, 3H), 7.71 (s, 1H), 7.65-7.39 (m, 4H), 5.34 (s, 1H), 4.50 (s, 2H), 4.30 (s, 2H), 3.95 (m, 1H), 3.81 (m, 2H), 3.73 (s, 3H), 3.68-3.20 (m, 2H), 2.99 (s, 1H), 2.63 (s, 3H), 2.40 (d, J=7.1 Hz, 4H), 1.02 (s, 9H), 1.00-0.83 (m, 3H). 19F NMR (376 MHz, Chloroform-d) δ −76.39, −95.49 (d, J=58.9 Hz). LCMS-ESI+: calc'd for $C_{38}H_{41}ClF_2N_5O_5S$; 752.3 (M+H)$^+$; found: 752.2 (M+H)$^+$.

Example 47. Preparation of (S)-2-(2-(3-(1-(1-acetylazetidin-3-yl)piperidin-4-yl)-1-cyclopropyl-1H-indazol-5-yl)-7-(4-chlorophenyl)-5-methylbenzo[d]thiazol-6-yl)-2-(tert-butoxy)acetic Acid (45)

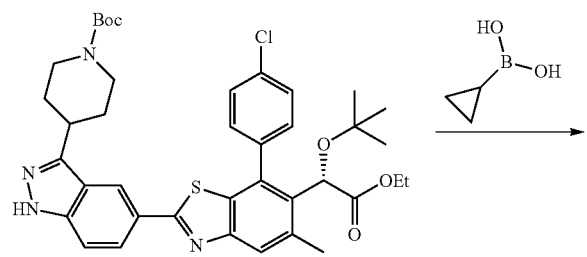

tert-butyl (S)-4-(5-(6-(1-(tert-butoxy)-2-ethoxy-2-oxoethyl)-7-(4-chlorophenyl)-5-methylbenzo[d]thiazol-2-yl)-1H-indazol-3-yl)piperidine-1-carboxylate

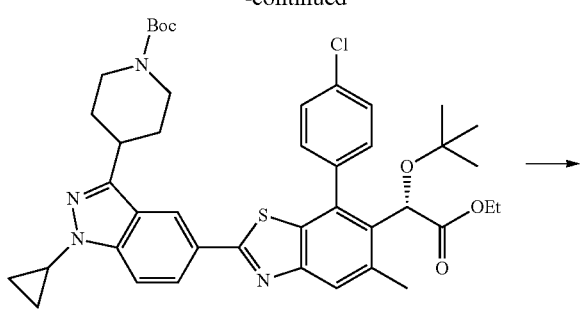

tert-butyl (S)-4-(5-(6-(1-tert-butoxy)-2-ethoxy-2-oxoethyl)-7-(4-chlorophenyl)-5-methylbenzo[d]thiazol-2-yl)-1-cyclopropyl-1H-indazol-3-yl)piperidine-1-carboxylate

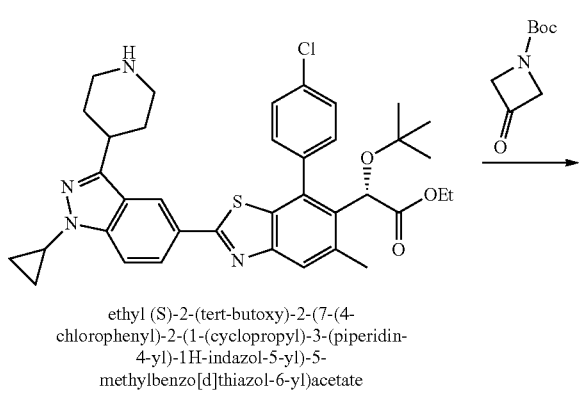

ethyl (S)-2-(tert-butoxy)-2-(7-(4-chlorophenyl)-2-(1-(cyclopropyl)-3-(piperidin-4-yl)-1H-indazol-5-yl)-5-methylbenzo[d]thiazol-6-yl)acetate

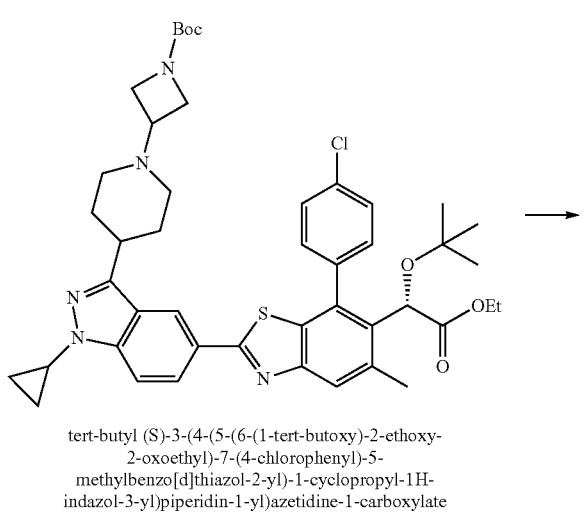

tert-butyl (S)-3-(4-(5-(6-(1-tert-butoxy)-2-ethoxy-2-oxoethyl)-7-(4-chlorophenyl)-5-methylbenzo[d]thiazol-2-yl)-1-cyclopropyl-1H-indazol-3-yl)piperidin-1-yl)azetidine-1-carboxylate

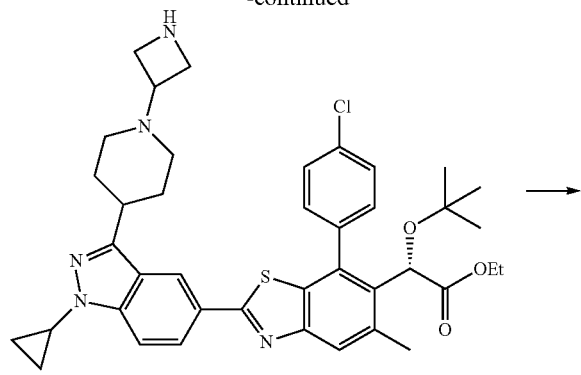

ethyl (S)-2-(2-(3-(1-(azetidin-3-yl)piperidin-
4-yl)-1-cyclopropyl-1H-indazol-5-yl)-7-(4-
chlorophenyl)-5-methylbenzo[d]thiazol-6-
yl)-2-(tert-butoxy)acetate

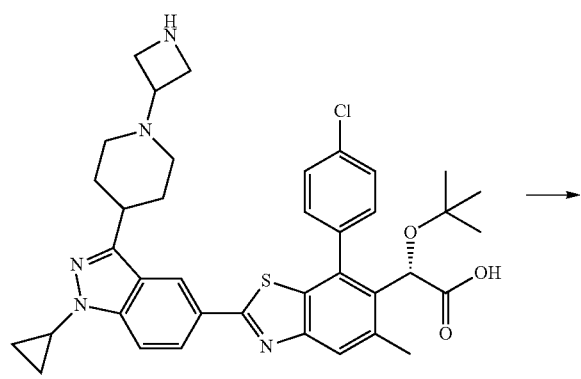

(S)-2-(2-(3-(1-(azetidin-3-yl)piperidin-4-yl)-1-
cyclopropyl-1H-indazol-5-yl)-7-(4-chlorophenyl)-
5-methylbenzo[d]thiazol-6-yl)-2-(tert-
butoxy)acetic acid

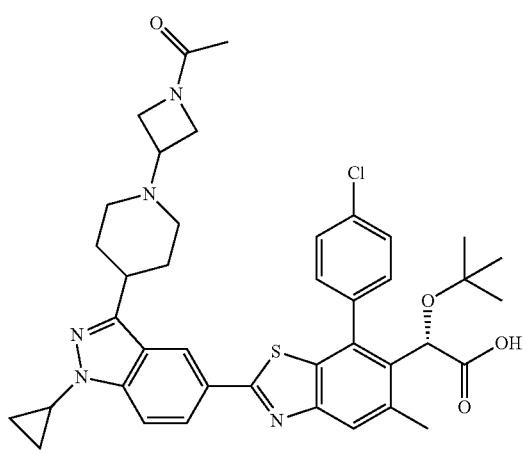

(S)-2-(2-(3-(1-(1-acetylazetidin-3-yl)piperidin-
4-yl)-1-cyclopropyl-1H-indazol-5-yl)-7-(4-
chlorophenyl)-5-methylbenzo[d]thiazol-6-yl)-
2-(tert-butoxy)acetic acid Preparation of tert-butyl (S)-4-(5-(6-(1-(tert-butoxy)-2-ethoxy-2-oxoethyl)-7-(4-chlorophenyl)-5-methylbenzo[d]thiazol-2-yl)-1-cyclopropyl-1H-indazol-3-yl)piperidine-1-carboxylate: To a microwave vial with tert-butyl (S)-4-(5-(6-(1-(tert-butoxy)-2-ethoxy-2-oxoethyl)-7-(4-chlorophenyl)-5-methylbenzo[d]thiazol-2-yl)-1H-indazol-3-yl)piperidine-1-carboxylate (170 mg, 237 µmol) in THF (3 mL) was added Cyclopropylboronic acid (101.79 mg, 1185 µmol), anhydrous Cupric acetate, (129 mg, 711 µmol), Triethylamine (198 µl, 1422 µmol) and pyridine (153 µl, 1896 µmol). The mixture was heated in microwave at 140° C. for 30 min. The reaction mixture was cooled to room temperature, filtered through a pad of Celite and concentrated. The residue was purified by CombiFlash (40 g, Gold, 0-100% EtOAc/Hexane) to give desired product. LCMS-ESI+: calc'd for $C_{42}H_{49}ClN_4O_5S$: 757.4 (M+H)+; found: 757.2 (M+H)+.

Preparation of ethyl (S)-2-(tert-butoxy)-2-(7-(4-chlorophenyl)-2-(1-cyclopropyl-3-(piperidin-4-yl)-1H-indazol-5-yl)-5-methylbenzo[d]thiazol-6-yl)acetate: A solution of tert-butyl (S)-4-(5-(6-(1-(tert-butoxy)-2-ethoxy-2-oxoethyl)-7-(4-chlorophenyl)-5-methylbenzo[d]thiazol-2-yl)-1-cyclopropyl-1H-indazol-3-yl)piperidine-1-carboxylate (132 mg, 0.174 mmol) in 1.25 HCl in isopropanol (4 mL) was stirred at room temperature for 16 h. Reaction was quenched carefully with sat'd $NaHCO_3$. It was extracted with ethyl acetate (2×). Combined organic layer was dried over sodium sulfate, filtered and concentrated to give desired product. It was used in the next step without further purification. LCMS-ESI+: calc'd for $C_{37}H_{41}ClN_4O_3S$: 657.3 (M+H)+; found: 657.4 (M+H)+.

Preparation of ethyl (S)-2-(2-(3-(1-(azetidin-3-yl)piperidin-4-yl)-1-cyclopropyl-1H-indazol-5-yl)-7-(4-chlorophenyl)-5-methylbenzo[d]thiazol-6-yl)-2-(tert-butoxy)acetate: It was made by the same conditions and procedures as for (S)-2-(2-(3-(1-(1-acetylazetidin-3-yl)piperidin-4-yl)-1-(difluoromethyl)-1H-indazol-5-yl)-7-(4-chlorophenyl)-5-methylbenzo[d]thiazol-6-yl)-2-(tert-butoxy)acetic acid. Reductive amination of ethyl (S)-2-(tert-butoxy)-2-(7-(4-chlorophenyl)-2-(1-cyclopropyl-3-(piperidin-4-yl)-1H-indazol-5-yl)-5-methylbenzo[d]thiazol-6-yl)acetate with 1-Boc-3-azetidinone followed by de-Boc in 1.25 HCl in isopropanol to give desired product. LCMS-ESI+: calc'd for $C_{40}H_{46}ClN_5O_3S$: 712.4 (M+H)+; found: 712.3 (M+H)+.

Preparation of ethyl (S)-2-(2-(3-(1-(1-acetylazetidin-3-yl)piperidin-4-yl)-1-cyclopropyl-1H-indazol-5-yl)-7-(4-chlorophenyl)-5-methylbenzo[d]thiazol-6-yl)-2-(tert-butoxy)acetic acid: It was prepared using similar procedure as for (S)-2-(2-(3-(1-(1-acetylazetidin-3-yl)piperidin-4-yl)-1-(difluoromethyl)-1H-indazol-5-yl)-7-(4-chlorophenyl)-5-methylbenzo[d]thiazol-6-yl)-2-(tert-butoxy)acetic acid. $^1$H NMR (400 MHz, DMSO-d6) δ 8.44 (s, 1H), 8.15 (d, J=8.9 Hz, 1H), 7.85 (s, 1H), 7.77 (d, J=8.8 Hz, 1H), 7.73-7.52 (m, 4H), 5.05 (s, 1H), 4.51-3.68 (m, 5H), 3.55 (s, 3H), 3.03 (s, 1H), 2.53 (s, 3H), 2.16 (t, J=7.4 Hz, 4H), 1.80 (s, 3H), 1.45 (d, J=7.4 Hz, 4H), 1.16-1.01 (m, 4H), 0.89 (s, 9H), 0.87-0.78 (m, 6H). LCMS-ESI+: calc'd for $C_{40}H_{44}ClN_5O_4S$; 726.3 (M+H)+; found: 726.3 (M+H)+.

Example 48. (S)-2-(tert-butoxy)-2-(7-(4-chlorophenyl)-2-(1-cyclopropyl-3-(1-(1-(methoxycarbonyl)azetidin-3-yl)piperidin-4-yl)-1H-indazol-5-yl)-5-methylbenzo[d]thiazol-6-yl)acetic Acid (46)

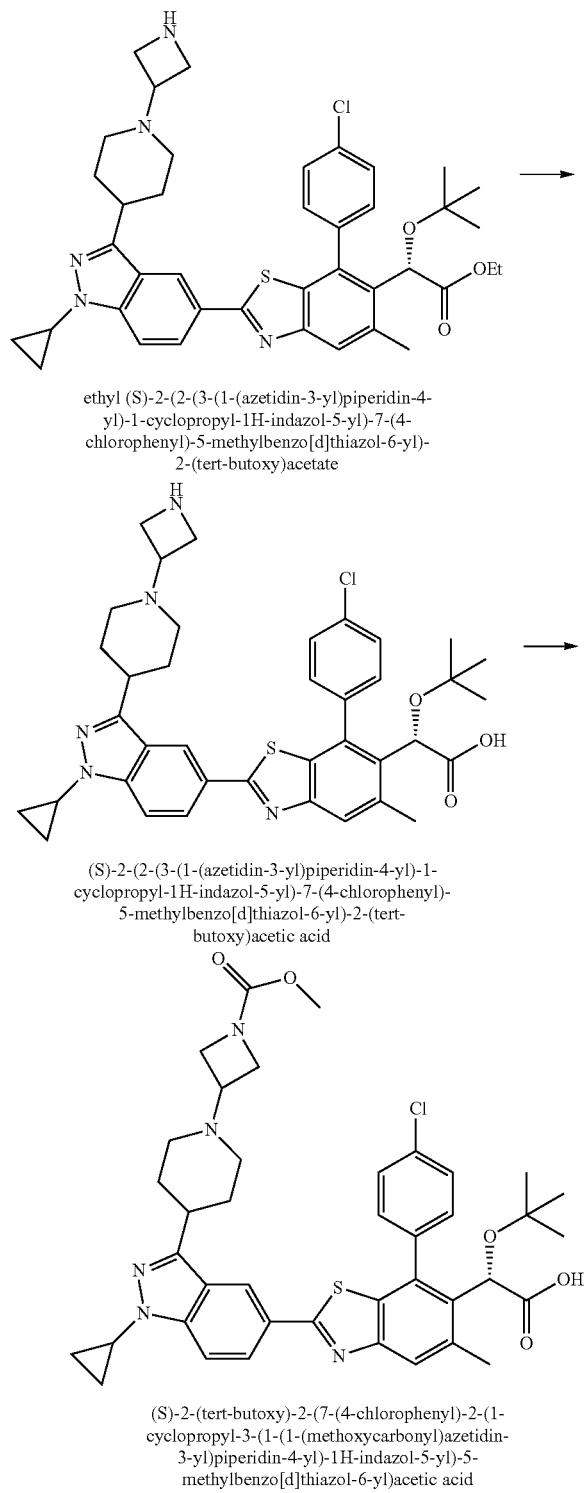

ethyl (S)-2-(2-(3-(1-(azetidin-3-yl)piperidin-4-yl)-1-cyclopropyl-1H-indazol-5-yl)-7-(4-chlorophenyl)-5-methylbenzo[d]thiazol-6-yl)-2-(tert-butoxy)acetate (S)-2-(2-(3-(1-(azetidin-3-yl)piperidin-4-yl)-1-cyclopropyl-1H-indazol-5-yl)-7-(4-chlorophenyl)-5-methylbenzo[d]thiazol-6-yl)-2-(tert-butoxy)acetic acid (S)-2-(tert-butoxy)-2-(7-(4-chlorophenyl)-2-(1-cyclopropyl-3-(1-(1-(methoxycarbonyl)azetidin-3-yl)piperidin-4-yl)-1H-indazol-5-yl)-5-methylbenzo[d]thiazol-6-yl)acetic acid Preparation of (S)-2-(tert-butoxy)-2-(7-(4-chlorophenyl)-2-(1-cyclopropyl-3-(1-(1-(methoxycarbonyl)azetidin-3-yl)piperidin-4-yl)-1H-indazol-5-yl)-5-methylbenzo[d]thiazol- 6-yl)acetic acid: It was prepared using similar procedure as for (S)-2-(2-(3-(1-(1-acetylazetidin-3-yl)piperidin-4-yl)-1-(difluoromethyl)-1H-indazol-5-yl)-7-(4-chlorophenyl)-5-methylbenzo[d]thiazol-6-yl)-2-(tert-butoxy)acetic acid. $^1$H NMR (400 MHz, DMSO-d6) δ 8.44 (d, J=1.5 Hz, 1H), 8.20-8.06 (m, 1H), 7.85 (s, 1H), 7.76 (d, J=8.9 Hz, 1H), 7.73-7.51 (m, 4H), 5.05 (s, 1H), 4.18 (s, 4H), 3.74 (d, J=4.1 Hz, 1H), 3.60 (s, 3H), 3.55 (s, 3H), 3.00 (m, 1H), 2.53 (s, 3H), 2.16 (t, J=7.4 Hz, 4H), 2.04 (m, 1H), 1.46 (t, J=7.2 Hz, 4H), 1.16-0.99 (m, 4H), 0.89 (s, 9H), 0.86-0.80 (m, 6H). LCMS-ESI+: calc'd for $C_{40}H_{44}ClN_5S$; 742.3 $(M+H)^+$; found: 742.24 $(M+H)^+$.

Example 49. Preparation of (S)-2-(2-(3-(1-(1-acetylazetidin-3-yl)piperidin-4-yl)-1-ethyl-1H-indazol-5-yl)-7-(4-chlorophenyl)-5-methylbenzo[d]thiazol-6-yl)-2-(tert-butoxy)acetic Acid (47)

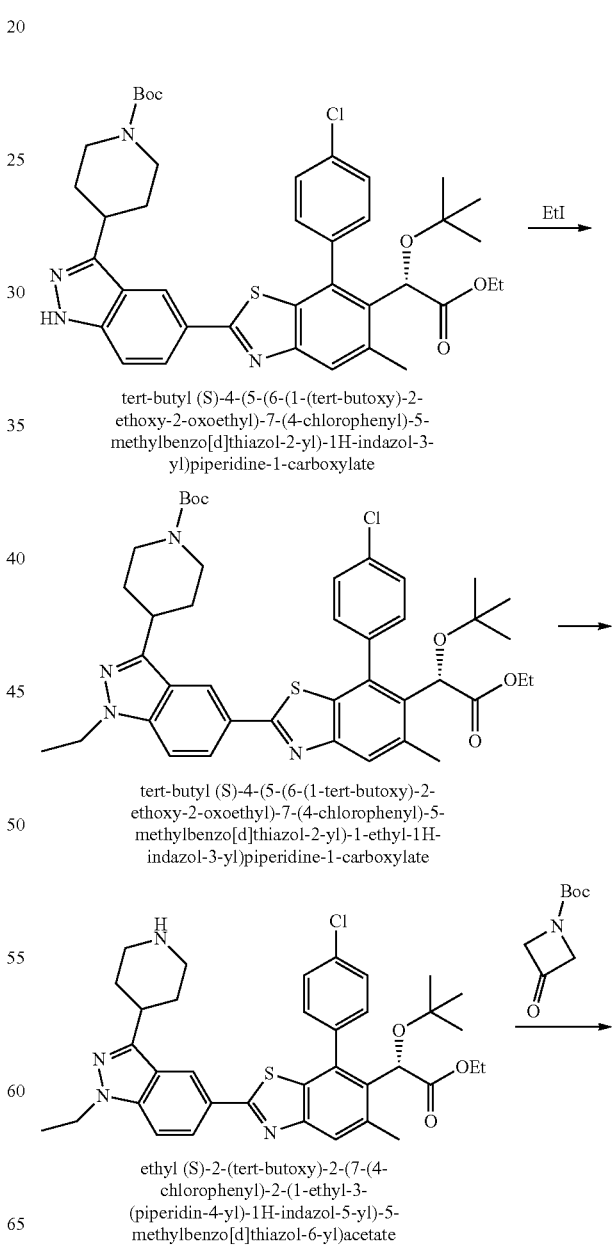

tert-butyl (S)-4-(5-(6-(1-(tert-butoxy)-2-ethoxy-2-oxoethyl)-7-(4-chlorophenyl)-5-methylbenzo[d]thiazol-2-yl)-1H-indazol-3-yl)piperidine-1-carboxylate tert-butyl (S)-4-(5-(6-(1-tert-butoxy)-2-ethoxy-2-oxoethyl)-7-(4-chlorophenyl)-5-methylbenzo[d]thiazol-2-yl)-1-ethyl-1H-indazol-3-yl)piperidine-1-carboxylate ethyl (S)-2-(tert-butoxy)-2-(7-(4-chlorophenyl)-2-(1-ethyl-3-(piperidin-4-yl)-1H-indazol-5-yl)-5-methylbenzo[d]thiazol-6-yl)acetate 207
-continued

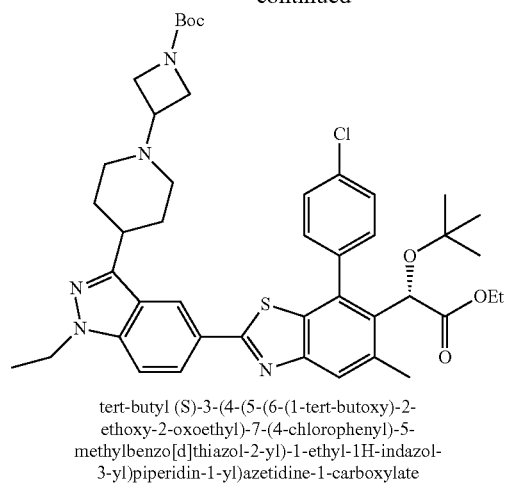

tert-butyl (S)-3-(4-(5-(6-(1-tert-butoxy)-2-
ethoxy-2-oxoethyl)-7-(4-chlorophenyl)-5-
methylbenzo[d]thiazol-2-yl)-1-ethyl-1H-indazol-
3-yl)piperidin-1-yl)azetidine-1-carboxylate

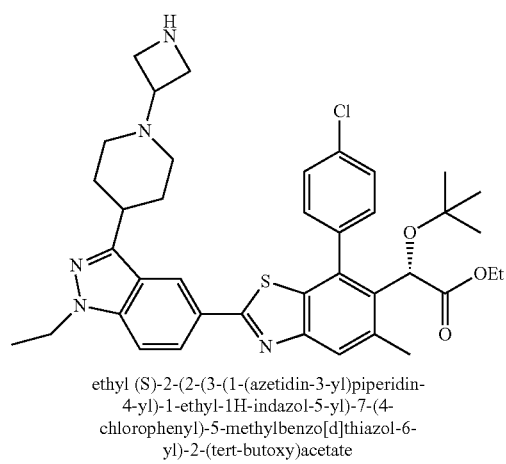

ethyl (S)-2-(2-(3-(1-(azetidin-3-yl)piperidin-
4-yl)-1-ethyl-1H-indazol-5-yl)-7-(4-
chlorophenyl)-5-methylbenzo[d]thiazol-6-
yl)-2-(tert-butoxy)acetate

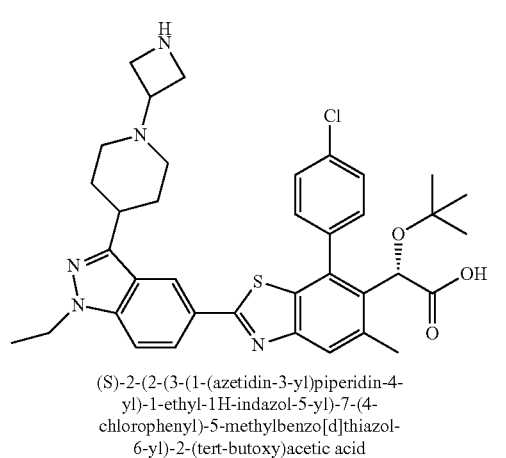

(S)-2-(2-(3-(1-(azetidin-3-yl)piperidin-4-
yl)-1-ethyl-1H-indazol-5-yl)-7-(4-
chlorophenyl)-5-methylbenzo[d]thiazol-
6-yl)-2-(tert-butoxy)acetic acid 208
-continued

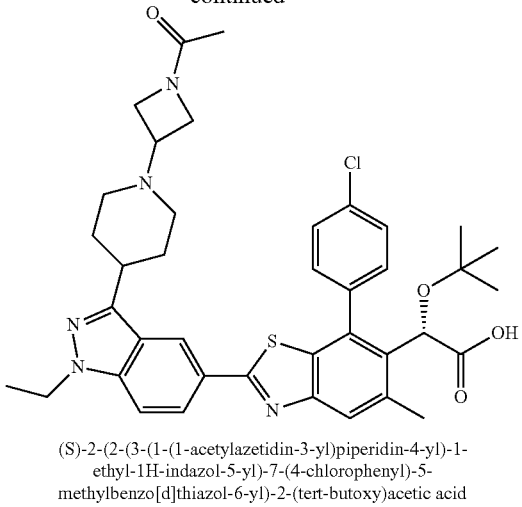

(S)-2-(2-(3-(1-(1-acetylazetidin-3-yl)piperidin-4-yl)-1-
ethyl-1H-indazol-5-yl)-7-(4-chlorophenyl)-5-
methylbenzo[d]thiazol-6-yl)-2-(tert-butoxy)acetic acid Preparation of tert-butyl (S)-4-(5-(6-(1-(tert-butoxy)-2-ethoxy-2-oxoethyl)-7-(4-chlorophenyl)-5-methylbenzo[d]thiazol-2-yl)-1-ethyl-1H-indazol-3-yl)piperidine-1-carboxylate: To a solution of tert-butyl (S)-4-(5-(6-(1-(tert-butoxy)-2-ethoxy-2-oxoethyl)-7-(4-chlorophenyl)-5-methylbenzo[d]thiazol-2-yl)-1H-indazol-3-yl)piperidine-1-carboxylate (180 mg, 0.25 mmol) in anhydrous DMF (3 mL) was added sodium hydride (60% disp. in oil, 30 mg, 0.75 mmol) and stirred for 20 min at to 0° C. under argon. Iodoethane (121 μl, 1.5 mmol) was added. The reaction mixture was kept at 0° C. for 20 min, then at room temperature for 1 h. Reaction was complete by LCMS analysis. 1N HCl was added to adjust pH to 7-8, then it was extracted with EtOAc. The organic layer was washed with 3% LiCl and dried over $MgSO_4$ and concentrated. The residue was purified by CombiFlash (40 g, Gold, 0-100% EtOAc/Hexane) to give desired major isomer product. $^1$H NMR (400 MHz, Chloroform-d) δ 8.31 (dd, J=1.6, 0.7 Hz, 1H), 8.03 (dd, J=8.8, 1.6 Hz, 1H), 7.84 (d, J=0.9 Hz, 1H), 7.59-7.41 (m, 4H), 7.37 (dd, J=8.8, 0.7 Hz, 1H), 5.14 (s, 1H), 4.35 (q, J=7.3 Hz, 2H), 4.19 (dq, J=7.2, 3.6 Hz, 2H), 3.32-3.12 (m, 1H), 2.92 (s, 2H), 2.58 (d, J=0.8 Hz, 3H), 1.99-1.83 (m, 3H), 1.47 (s+m, 12H), 1.23 (td, J=7.1, 0.7 Hz, 4H), 0.96 (s, 9H). LCMS-ESI$^+$: calc'd for $C_{41}H_{49}ClN_4O_5S$: 745.4 (M+H)+; found: 745.2 (M+H)$^+$.

Minor regioisomer. $^1$H NMR (400 MHz, Chloroform-d) δ 8.30 (d, J=1.3 Hz, 1H), 7.93 (dd, J=9.0, 1.6 Hz, 1H), 7.84 (d, J=0.9 Hz, 1H), 7.67 (dd, J=9.1, 0.8 Hz, 1H), 7.58-7.40 (m, 4H), 5.14 (s, 1H), 4.52-4.04 (m, 6H), 3.30-3.01 (m, 1H), 2.86 (t, J=13.0 Hz, 2H), 2.58 (d, J=0.8 Hz, 3H), 2.16 (dt, J=13.1, 5.3 Hz, 2H), 1.88 (d, J=13.2 Hz, 2H), 1.66 (s, 2H), 1.56 (t, J=7.3 Hz, 3H), 1.51 (s, 9H), 1.23 (t, J=7.1 Hz, 3H), 0.97 (s, 9H).

Preparation of ethyl (S)-2-(tert-butoxy)-2-(7-(4-chlorophenyl)-2-(1-ethyl-3-(piperidin-4-yl)-1H-indazol-5-yl)-5-methylbenzo[d]thiazol-6-yl)acetate: A solution of tert-butyl (S)-4-(5-(6-(1-(tert-butoxy)-2-ethoxy-2-oxoethyl)-7-(4-chlorophenyl)-5-methylbenzo[d]thiazol-2-yl)-1-ethyl-1H-indazol-3-yl)piperidine-1-carboxylate (126 mg, 0.169 mmol) in 1.25 HCl in isopropanol (4 mL) was stirred at room temperature for 16 h. Reaction was quenched carefully with sat'd NaHCO₃ and extracted with ethyl acetate (2×). Combined organic layer was dried over sodium sulfate, filtered and concentrated to give desired product. It was used in the next step without further purification. LCMS-ESI+: calc'd for C₃₆H₄₁ClN₄O₃S: 645.3 (M+H)⁺; found: 645.4 (M+H)⁺.

Preparation of (S)-2-(2-(3-(1-(azetidin-3-yl)piperidin-4-yl)-1-ethyl-1H-indazol-5-yl)-7-(4-chlorophenyl)-5-methylbenzo[d]thiazol-6-yl)-2-(tert-butoxy)acetic acid: Prepared using similar procedure as for (S)-2-(2-(3-(1-(1-acetylazetidin-3-yl)piperidin-4-yl)-1-(difluoromethyl)-1H-indazol-5-yl)-7-(4-chlorophenyl)-5-methylbenzo[d]thiazol-6-yl)-2-(tert-butoxy)acetic acid. Reductive amination of ethyl (S)-2-(tert-butoxy)-2-(7-(4-chlorophenyl)-2-(1-ethyl-3-(piperidin-4-yl)-1H-indazol-5-yl)-5-methylbenzo[d]thiazol-6-yl)acetate with 1-Boc-3-azetidinone followed by de-Boc in 1.25 HCl in isopropanol and hydrolysis with 50% Sodium hydroxide to give desired product. LCMS-ESI+: calc'd for C₃₇H₄₂ClN₅O₃S: 672.3 (M+H)⁺; found: 672.3 (M+H)⁺.

Preparation of (S)-2-(2-(3-(1-(1-acetylazetidin-3-yl)piperidin-4-yl)-1-ethyl-1H-indazol-5-yl)-7-(4-chlorophenyl)-5-methylbenzo[d]thiazol-6-yl)-2-(tert-butoxy)acetic acid: To a flask containing (S)-2-(2-(3-(1-(azetidin-3-yl)piperidin-4-yl)-1-ethyl-1H-indazol-5-yl)-7-(4-chlorophenyl)-5-methylbenzo[d]thiazol-6-yl)-2-(tert-butoxy)acetic acid (67 mg, 0.1 mmol) in DMF (2 mL) and EtOAc (10 mL) were added sat'd aq. sodium bicarbonate (10 mL) and Acetyl chloride (200 μl, 2.8 mmol). The mixture was stirred at room temperature for 20 h. LCMS analysis indicated that only the desired acid product was formed. The reaction mixture was cooled to 0° C., acidified with 3N HCl to pH=4 and extracted with EtOAc. The organic layer was concentrated to give crude mixture which was purified by Gilson HPLC (Phenomenex Gemini 250×21.2 10μ C18 column, 40-100% ACN/H₂O+ 0.1% TFA) to give a yellow powder after lyophilization. 1H NMR (400 MHz, Chloroform-d) δ 8.24 (s, 1H), 7.95 (d, J=9.3 Hz, 1H), 7.78 (s, 1H), 7.63 (d, J=8.2 Hz, 1H), 7.44 (d, J=8.4 Hz, 3H), 7.35 (d, J=8.9 Hz, 1H), 5.24 (s, 1H), 4.72 (dd, J=9.9, 5.2 Hz, 1H), 4.42-4.06 (m, 5H), 3.59 (d, J=135.5 Hz, 6H), 2.50 (s, 3H), 2.28 (d, J=22.2 Hz, 3H), 1.81 (s, 3H), 1.43 (t, J=7.2 Hz, 3H), 1.15 (d, J=17.4 Hz, 1H), 0.93 (s, 9H). LCMS-ESI+: calc'd for C₃₉H₄₄ClN₅O₄S; 714.3 (M+H)⁺; found: 714.3 (M+H)⁺.

Example 50. Preparation of (S)-2-(tert-butoxy)-2-(7-(4-chlorophenyl)-2-(1-ethyl-3-(1-(1-(methoxycarbonyl)azetidin-3-yl)piperidin-4-yl)-1H-indazol-5-yl)-5-methylbenzo[d]thiazol-6-yl)acetic Acid (48)

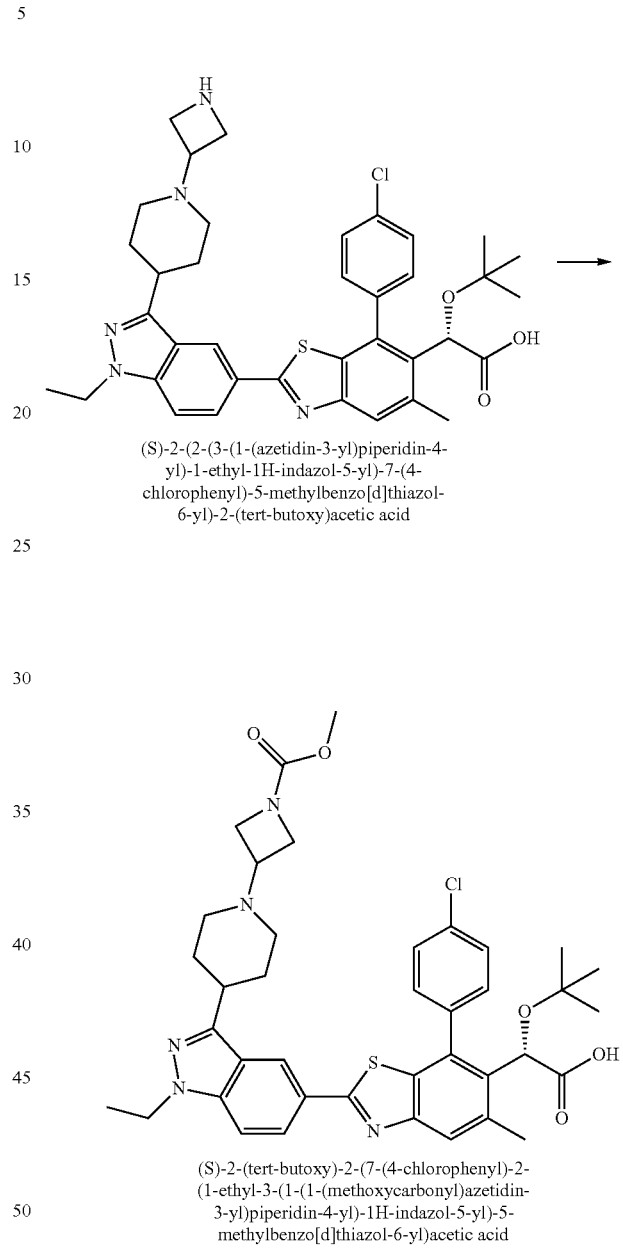

(S)-2-(2-(3-(1-(azetidin-3-yl)piperidin-4-yl)-1-ethyl-1H-indazol-5-yl)-7-(4-chlorophenyl)-5-methylbenzo[d]thiazol-6-yl)-2-(tert-butoxy)acetic acid (S)-2-(tert-butoxy)-2-(7-(4-chlorophenyl)-2-(1-ethyl-3-(1-(1-(methoxycarbonyl)azetidin-3-yl)piperidin-4-yl)-1H-indazol-5-yl)-5-methylbenzo[d]thiazol-6-yl)acetic acid Preparation of (S)-2-(tert-butoxy)-2-(7-(4-chlorophenyl)-2-(1-ethyl-3-(1-(1-(methoxycarbonyl)azetidin-3-yl)piperidin-4-yl)-1H-indazol-5-yl)-5-methylbenzo[d]thiazol-6-yl) acetic acid: To a flask containing (S)-2-(2-(3-(1-(azetidin-3-yl)piperidin-4-yl)-1-ethyl-1H-indazol-5-yl)-7-(4-chlorophenyl)-5-methylbenzo[d]thiazol-6-yl)-2-(tert-butoxy)acetic acid (67 mg, 0.1 mmol) in DMF (2 mL) and EtOAc (10 mL) were added sat'd aq. sodium bicarbonate (10 mL) and Methyl chloroformate (100 μl, 1.29 mmol). The mixture was stirred at room temperature for 20 h. LCMS analysis indicated that only the desired acid product was formed. The reaction mixture was cooled to 0° C., acidified with 3N HCl to pH=4 and extracted with EtOAc. The organic layer was concentrated to give crude mixture which was purified by Gilson HPLC (Phenomenex Gemini 250× 21.2 10μ C18 column, 40-100% ACN/H$_2$O+0.1% TFA) to give a yellow powder after lyophilization. $^1$H NMR (400 MHz, Chloroform-d) δ 8.32 (s, 1H), 8.03 (s, 1H), 7.86 (s, 1H), 7.71 (d, J=8.1 Hz, 1H), 7.58-7.47 (m, 3H), 7.43 (d, J=8.9 Hz, 1H), 5.31 (s, 1H), 4.48 (s, 2H), 4.38 (q, J=7.2 Hz, 2H), 4.19 (t, J=8.9 Hz, 2H), 4.04-3.92 (m, 3H), 3.85 (s, 1H), 3.68 (d, J=1.8 Hz, 3H), 3.43 (d, J=50.1 Hz, 3H), 2.76 (s, 1H), 2.57 (s, 3H), 2.34 (m, 3H), 1.50 (t, J=7.2 Hz, 3H), 1.20 (d, J=6.2 Hz, 5H), 1.00 (s, 9H). LCMS-ESI+: calc'd for C$_{39}$H$_{44}$ClN$_5$O$_5$S; 730.3 (M+H)$^+$; found: 730.4 (M+H)$^+$.

Example 51. (S)-2-(tert-butoxy)-2-(7-(4-chlorophenyl)-2-(1-ethyl-3-(1-((S)-1-(methoxycarbonyl)pyrrolidin-3-yl)piperidin-4-yl)-1H-indazol-5-yl)-5-methylbenzo[d]thiazol-6-yl)acetic Acid (49)

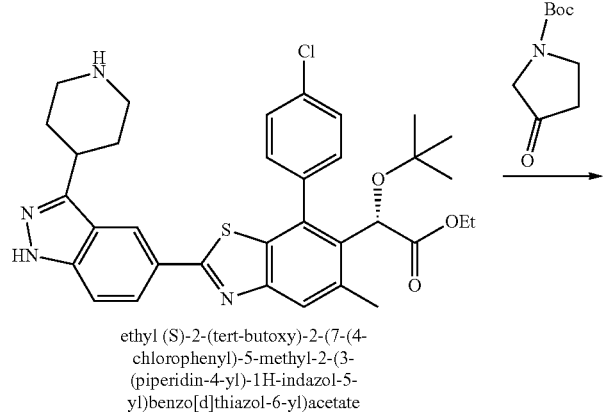

ethyl (S)-2-(tert-butoxy)-2-(7-(4-chlorophenyl)-5-methyl-2-(3-(piperidin-4-yl)-1H-indazol-5-yl)benzo[d]thiazol-6-yl)acetate

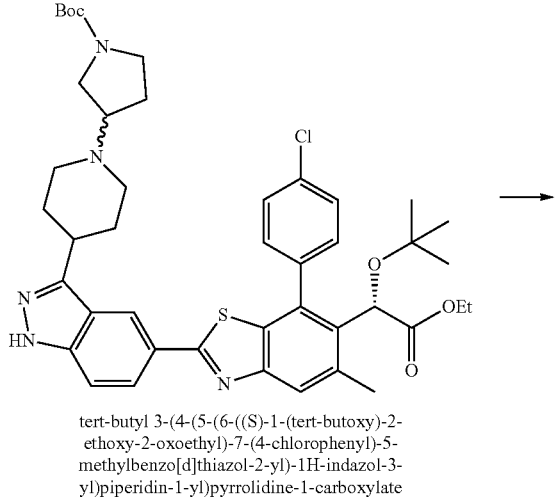

tert-butyl 3-(4-(5-(6-((S)-1-(tert-butoxy)-2-ethoxy-2-oxoethyl)-7-(4-chlorophenyl)-5-methylbenzo[d]thiazol-2-yl)-1H-indazol-3-yl)piperidin-1-yl)pyrrolidine-1-carboxylate

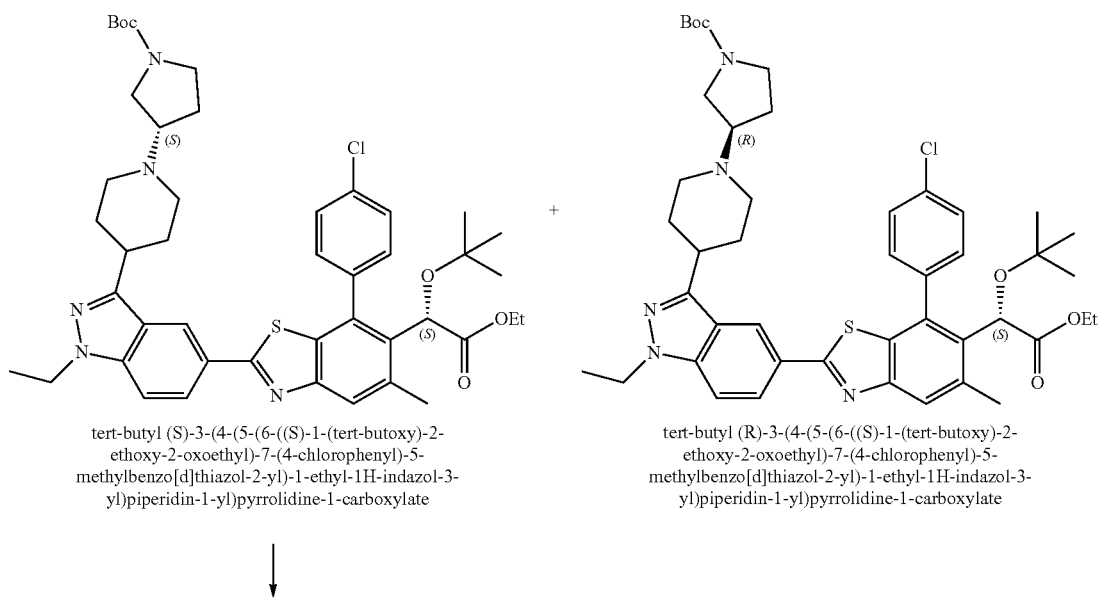

tert-butyl (S)-3-(4-(5-(6-((S)-1-(tert-butoxy)-2-ethoxy-2-oxoethyl)-7-(4-chlorophenyl)-5-methylbenzo[d]thiazol-2-yl)-1-ethyl-1H-indazol-3-yl)piperidin-1-yl)pyrrolidine-1-carboxylate tert-butyl (R)-3-(4-(5-(6-((S)-1-(tert-butoxy)-2-ethoxy-2-oxoethyl)-7-(4-chlorophenyl)-5-methylbenzo[d]thiazol-2-yl)-1-ethyl-1H-indazol-3-yl)piperidin-1-yl)pyrrolidine-1-carboxylate

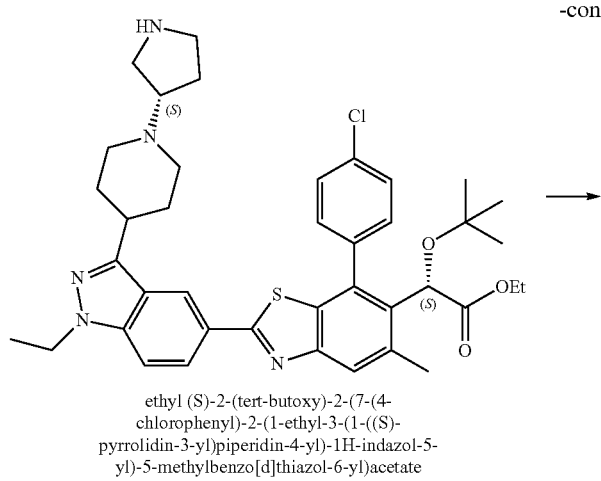

ethyl (S)-2-(tert-butoxy)-2-(7-(4-chlorophenyl)-2-(1-ethyl-3-(1-((S)-pyrrolidin-3-yl)piperidin-4-yl)-1H-indazol-5-yl)-5-methylbenzo[d]thiazol-6-yl)acetate (S)-2-(tert-butoxy)-2-(7-(4-chlorophenyl)-2-(1-ethyl-3-(1-((S)-pyrrolidin-3-yl)piperidin-4-yl)-1H-indazol-5-yl)-5-methylbenzo[d]thiazol-6-yl)acetic acid

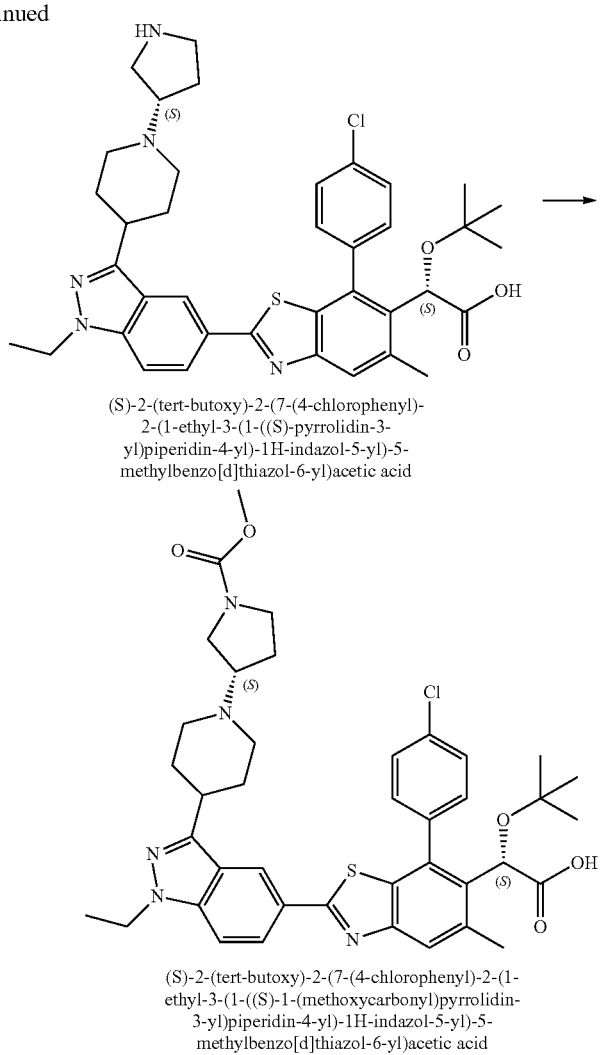

(S)-2-(tert-butoxy)-2-(7-(4-chlorophenyl)-2-(1-ethyl-3-(1-((S)-1-(methoxycarbonyl)pyrrolidin-3-yl)piperidin-4-yl)-1H-indazol-5-yl)-5-methylbenzo[d]thiazol-6-yl)acetic acid Preparation of tert-butyl 3-(4-(5-(6-((S)-1-(tert-butoxy)-2-ethoxy-2-oxoethyl)-7-(4-chlorophenyl)-5-methylbenzo[d]thiazol-2-yl)-1H-indazol-3-yl)piperidin-1-yl)pyrrolidine-1-carboxylate: A solution of ethyl (S)-2-(tert-butoxy)-2-(7-(4-chlorophenyl)-5-methyl-2-(3-(piperidin-4-yl)-1H-indazol-5-yl)benzo[d]thiazol-6-yl)acetate (1.56 g, 2.53 mmol), N-Boc-3-pyrrolidinone (4.68 g, 25.3 mmol), Acetic acid (0.72 ml, 12.6 mmol) Sodium triacetoxyborohydride (2.68 g, 12.6 mmol) in dichloroethane (50 mL) was stirred for 5 hours at room temperature. Reaction was quenched with saturated sodium bicarbonate solution and brine. The mixture was extracted with dichloromethane (2×) and combined organic layer was dried (MgSO$_4$), filtered and concentrated. The residue was purified by CombiFlash (120 g, Gold, 0-20% MeOH/CH$_2$Cl$_2$) to give desired product as two diasteriomers. LCMS-ESI+: calc'd for C$_{43}$H$_{52}$ClN$_5$O$_5$S: 786.43 (M+H)$^+$; found: 786.65 (M+H)$^+$.

Preparation of tert-butyl (S)-3-(4-(5-(6-((S)-1-(tert-butoxy)-2-ethoxy-2-oxoethyl)-7-(4-chlorophenyl)-5-methylbenzo[d]thiazol-2-yl)-1-ethyl-1H-indazol-3-yl)piperidin-1-yl)pyrrolidine-1-carboxylate and tert-butyl (R)-3-(4-(5-(6-((S)-1-(tert-butoxy)-2-ethoxy-2-oxoethyl)-7-(4-chlorophenyl)-5-methylbenzo[d]thiazol-2-yl)-1-ethyl-1H-indazol-3-yl)piperidin-1-yl)pyrrolidine-1-carboxylate: To a solution of tert-butyl 3-(4-(5-(6-((S)-1-(tert-butoxy)-2-ethoxy-2-oxoethyl)-7-(4-chlorophenyl)-5-methylbenzo[d]thiazol-2-yl)-1H-indazol-3-yl)piperidin-1-yl)pyrrolidine-1-carboxylate (995 mg, 1.27 mmol) in anhydrous DMF (10 mL) was added Sodium hydride (60% disp. in oil, 152 mg, 3.80 mmol) and stirred for 20 min at to 0° C. under argon. Iodoethane (610 µl, 7.59 mmol) was added. The reaction mixture was kept at 0° C. for 3 h, then at room temperature for 1 h. Reaction was complete by LCMS analysis. Reaction mixture was neutralized using 1N HCl to pH to 7-8, and extracted with EtOAc. The organic layer was washed with 3% LiCl, dried over MgSO$_4$ and concentrated. The residue was purified by CombiFlash (80 g, Gold, 50-100% EtOAc/Hexane) to give the diastereomeric mixture which was further separated by chiral column separation (AD-H 4.6× 100 mm column, 30% EtOH as co-solvent)

tert-butyl (S)-3-(4-(5-(6-((S)-1-(tert-butoxy)-2-ethoxy-2-oxoethyl)-7-(4-chlorophenyl)-5-methylbenzo[d]thiazol-2-yl)-1-ethyl-1H-indazol-3-yl)piperidin-1-yl)pyrrolidine-1-carboxylate, Rt=1.74 min, (S,S)-diastereomer: $^1$H NMR (400 MHz, Chloroform-d) δ 8.37 (s, 1H), 8.04 (dd, J=9.0, 1.5 Hz, 1H), 7.85 (s, 1H), 7.60-7.45 (m, 4H), 7.39 (d, J=8.8 Hz, 1H), 5.16 (s, 1H), 4.37 (q, J=7.2 Hz, 2H), 4.21 (qq, J=7.2, 3.7 Hz, 2H), 3.84-2.71 (m, 9H), 2.60 (s, 3H), 2.37-

1.95 (m, 7H), 1.83 (s, 1H), 1.62 (s, 3H), 1.48 (d, J=6.0 Hz, 12H), 1.25 (t, J=7.1 Hz, 3H), 0.98 (s, 9H). LCMS-ESI+: calc'd for $C_{45}H_{56}ClN_5O_5S$; 814.5 $(M+H)^+$; found: 814.3 $(M+H)^+$.

tert-butyl (R)-3-(4-(5-(6-((S)-1-(tert-butoxy)-2-ethoxy-2-oxoethyl)-7-(4-chlorophenyl)-5-methylbenzo[d]thiazol-2-yl)-1-ethyl-1H-indazol-3-yl)piperidin-1-yl)pyrrolidine-1-carboxylate, Rt=2.37 min, (R,S)-diastereomer: $^1$H NMR (400 MHz, Chloroform-d) δ 8.37 (s, 1H), 8.04 (d, J=8.8 Hz, 1H), 7.85 (s, 1H), 7.61-7.45 (m, 4H), 7.39 (d, J=8.9 Hz, 1H), 5.16 (s, 1H), 4.37 (q, J=7.2 Hz, 2H), 4.21 (tq, J=7.0, 3.5 Hz, 2H), 3.87-2.71 (m, 9H), 2.60 (s, 3H), 2.40-1.93 (m, 7H), 1.82 (s, 1H), 1.62 (s, 3H), 1.48 (d, J=5.6 Hz, 12H), 1.25 (t, J=7.1 Hz, 3H), 0.98 (s, 9H). LCMS-ESI+: calc'd for $C_{45}H_{56}ClN_5O_5S$; 814.5 $(M+H)^+$; found: 814.4 $(M+H)^+$.

Preparation of ethyl (S)-2-(tert-butoxy)-2-(7-(4-chlorophenyl)-2-(1-ethyl-3-(1-((S)-pyrrolidin-3-yl)piperidin-4-yl)-1H-indazol-5-yl)-5-methylbenzo[d]thiazol-6-yl)acetate: A solution of tert-butyl (S)-3-(4-(5-(6-((S)-1-(tert-butoxy)-2-ethoxy-2-oxoethyl)-7-(4-chlorophenyl)-5-methylbenzo[d]thiazol-2-yl)-1-ethyl-1H-indazol-3-yl)piperidin-1-yl)pyrrolidine-1-carboxylate (339 mg, 0.416 mmol) in 1.25 HCl in isopropanol (20 mL) was stirred at room temperature for 24 h. The solvent was removed by vacuum. The residue was added dichloromethane (50 mL) then evaporated to dryness again. Used as is the next step. LCMS-ESI+: calc'd for $C_{40}H_{48}ClN_5O_3S$: 714.4 $(M+H)^+$; found: 714.4 $(M+H)^+$.

Preparation of (S)-2-(tert-butoxy)-2-(7-(4-chlorophenyl)-2-(1-ethyl-3-(1-((S)-pyrrolidin-3-yl)piperidin-4-yl)-1H-indazol-5-yl)-5-methylbenzo[d]thiazol-6-yl)acetic acid: To the above crude mixture (0.416 mmol) was added THF (10 mL) MeOH (4 mL) and 50% Sodium hydroxide (4 mL) at room temperature. The resulting mixture was stirred at room temperature for 16 h. The reaction mixture was concentrated to remove the organic solvent. Toluene was added and evaporated again to only aqueous layer remained. Used as is for the next step. LCMS-ESI+: calc'd for $C_{38}H_{44}ClN_5O_3S$; 686.3 $(M+H)^+$; found: 686.4 $(M+H)^+$.

Preparation of (S)-2-(tert-butoxy)-2-(7-(4-chlorophenyl)-2-(1-ethyl-3-(1-((S)-1-(methoxycarbonyl)pyrrolidin-3-yl)piperidin-4-yl)-1H-indazol-5-yl)-5-methylbenzo[d]thiazol-6-yl)acetic acid: To above crude mixture containing (S)-2-(tert-butoxy)-2-(7-(4-chlorophenyl)-2-(1-ethyl-3-(1-((S)-pyrrolidin-3-yl)piperidin-4-yl)-1H-indazol-5-yl)-5-methylbenzo[d]thiazol-6-yl)acetic acid (0.416 mmol) were added dichloromethane (80 mL), sat'd sodium bicarbonate (40 mL) and Methyl chloroformate (1000 µl, 1.3 mmol). The mixture was stirred at room temperature for 20 h. The reaction mixture was cooled to 0° C., acidified with 3N HCl to pH=4. The layers were separated and the aqueous phase was extracted with 25% $CH_3Cl/i$-PrOH mixture (2×). The organic phases were combined and concentrated to give crude mixture which was purified by Gilson HPLC (Phenomenex Gemini 250×21.2 10µ C18 column, 40-100% ACN/$H_2O$+0.1% TFA) to give a yellow powder after lyophilization. $^1$H NMR (400 MHz, Chloroform-d) δ 8.71 & 8.30 (s, s, 1H), 8.10-8.03-7.84 (m, 2H), 7.72 (d, J=8.2 Hz, 1H), 7.54 (t, J=10.6 Hz, 3H), 7.47-7.38 (m, 1H), 5.33 (s, 1H), 4.39 (dd, J=12.5, 6.9 Hz, 2H), 3.89 (br, 2H), 3.72 (d, J=10.5 Hz, 6H), 3.50 (d, J=32.3 Hz, 4H), 3.03 (m, 1H), 2.67 (m, 2H), 2.59 (s, 3H), 2.49-2.14 (m, 4H), 1.52 (dt, J=12.7, 7.2 Hz, 3H), 1.25 (br, 5H), 1.01 (s, 9H), 0.92-0.81 (m, 1H). LCMS-ESI+: calc'd for $C_{40}H_{46}ClN_5O_5S$; 744.4 $(M+H)^+$; found: 744.5 $(M+H)^+$.

Example 52. (S)-2-(tert-butoxy)-2-(7-(4-chlorophenyl)-2-(1-ethyl-3-(1-((R)-1-(methoxycarbonyl) pyrrolidin-3-yl)piperidin-4-yl)-1H-indazol-5-yl)-5-methylbenzo[d]thiazol-6-yl)acetic Acid (50)

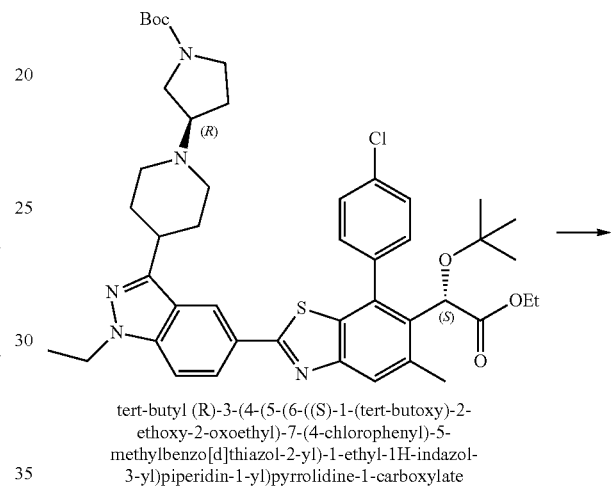

tert-butyl (R)-3-(4-(5-(6-((S)-1-(tert-butoxy)-2-ethoxy-2-oxoethyl)-7-(4-chlorophenyl)-5-methylbenzo[d]thiazol-2-yl)-1-ethyl-1H-indazol-3-yl)piperidin-1-yl)pyrrolidine-1-carboxylate

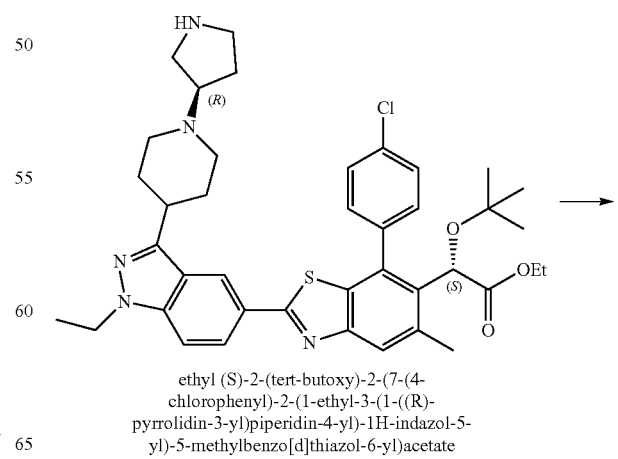

ethyl (S)-2-(tert-butoxy)-2-(7-(4-chlorophenyl)-2-(1-ethyl-3-(1-((R)-pyrrolidin-3-yl)piperidin-4-yl)-1H-indazol-5-yl)-5-methylbenzo[d]thiazol-6-yl)acetate 217
-continued

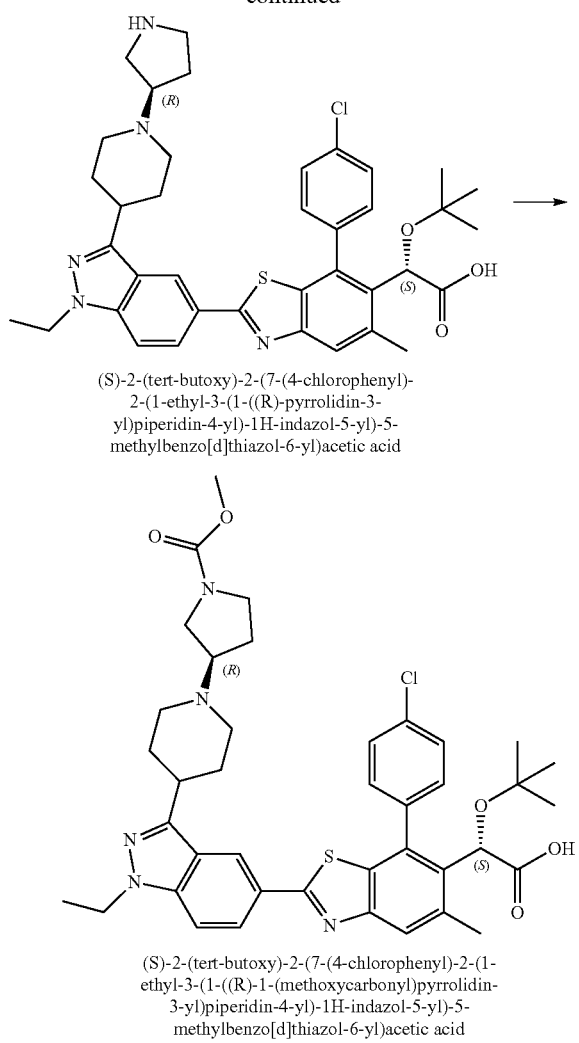

(S)-2-(tert-butoxy)-2-(7-(4-chlorophenyl)-
2-(1-ethyl-3-(1-((R)-pyrrolidin-3-
yl)piperidin-4-yl)-1H-indazol-5-yl)-5-
methylbenzo[d]thiazol-6-yl)acetic acid (S)-2-(tert-butoxy)-2-(7-(4-chlorophenyl)-2-(1-
ethyl-3-(1-((R)-1-(methoxycarbonyl)pyrrolidin-
3-yl)piperidin-4-yl)-1H-indazol-5-yl)-5-
methylbenzo[d]thiazol-6-yl)acetic acid Preparation of (S)-2-(tert-butoxy)-2-(7-(4-chlorophenyl)-2-(i-ethyl-3-(1-((R)-1-(methoxycarbonyl)pyrrolidin-3-yl)piperidin-4-yl)-1H-indazol-5-yl)-5-methylbenzo[d]thiazol-6-yl)acetic acid: Prepared using similar procedures as for (S)-2-(2-(3-(1-(1-acetylazetidin-3-yl)piperidin-4-yl)-1-(difluoromethyl)-1H-indazol-5-yl)-7-(4-chlorophenyl)-5-methylbenzo[d]thiazol-6-yl)-2-(tert-butoxy)acetic acid. Starting from tert-butyl (R)-3-(4-(5-(6-((S)-1-(tert-butoxy)-2-ethoxy-2-oxoethyl)-7-(4-chlorophenyl)-5-methylbenzo[d]thiazol-2-yl)-1-ethyl-1H-indazol-3-yl)piperidin-1-yl)pyrrolidine-1-carboxylate, it was de-Boc in 1.25 HCl in isopropanol and then saponification with 50% Sodium hydroxide followed by the reaction with Methyl chloroformate. The crude mixture was purified by Gilson HPLC (Phenomenex Gemini 250×21.2 10µ C18 column, 40-100% ACN/H$_2$O+0.1% TFA) to give a yellow powder after lyophilization. $^1$H NMR (400 MHz, Chloroform-d) δ 8.49 (d, J=145.1 Hz, 1H), 8.14-7.65 (m, 3H), 7.65-7.38 (m, 4H), 5.33 (s, 1H), 4.39 (dd, J=11.4, 7.6 Hz, 2H), 3.90 (br s, 2H), 3.72 (d, J=12.1 Hz, 5H), 3.48 (d, J=37.2 Hz, 2H), 3.12-2.62 (m, 3H), 2.59 (d, J=3.4 Hz, 3H), 2.47-2.14 (m, 2H), 1.52 (dt, J=11.7, 7.2 Hz, 3H), 1.25 (s, 5H), 1.01 (d, J=2.3 Hz, 9H), 0.91-0.81 (m, 1H). LCMS-ESI$^+$: calc'd for C$_{40}$H$_{46}$ClN$_5$O$_5$S; 744.4 (M+H)$^+$; found: 744.5 (M+H)$^+$.

218

Example 53. Preparation of (S)-2-(tert-butoxy)-2-(7-(4-chlorophenyl)-2-(3-(2,5-dihydrofuran-3-yl)-1-methyl-1H-indazol-5-yl)-5-methylbenzo[d]thiazol-6-yl)acetic Acid (51)

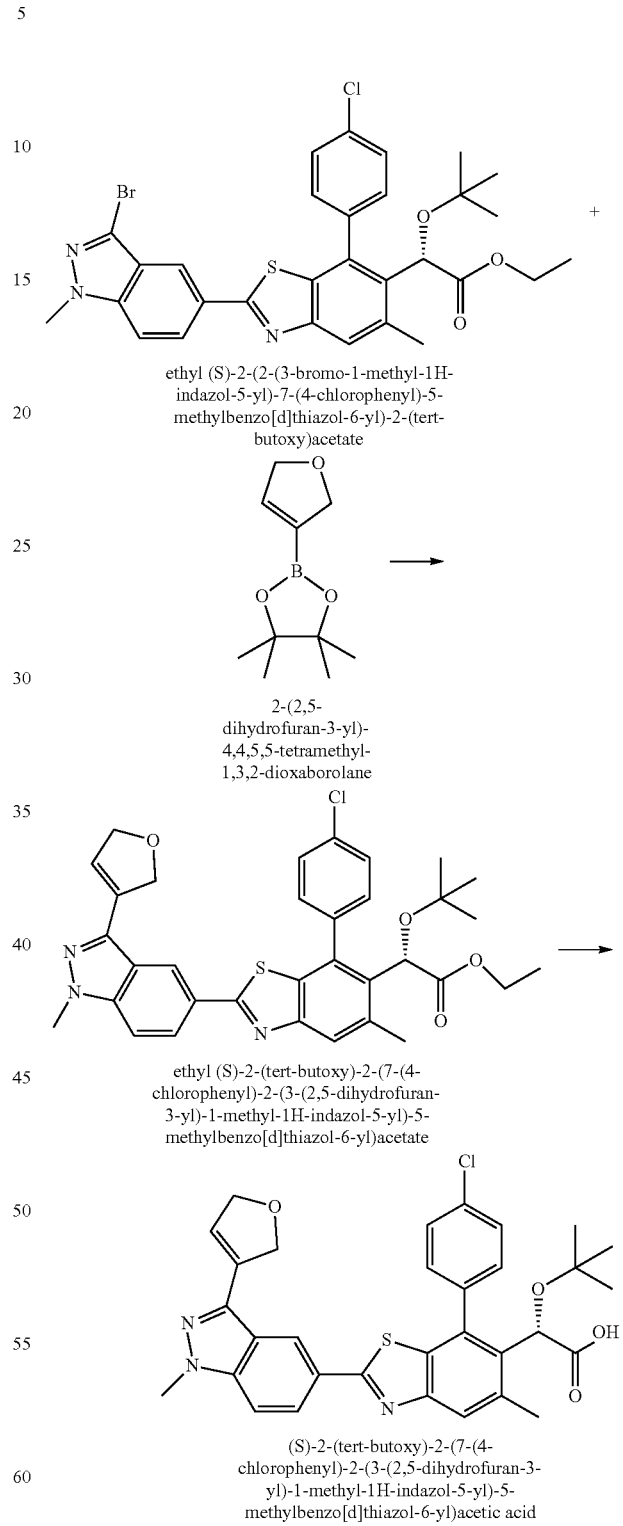

ethyl (S)-2-(2-(3-bromo-1-methyl-1H-indazol-5-yl)-7-(4-chlorophenyl)-5-methylbenzo[d]thiazol-6-yl)-2-(tert-butoxy)acetate 2-(2,5-dihydrofuran-3-yl)-4,4,5,5-tetramethyl-1,3,2-dioxaborolane ethyl (S)-2-(tert-butoxy)-2-(7-(4-chlorophenyl)-2-(3-(2,5-dihydrofuran-3-yl)-1-methyl-1H-indazol-5-yl)-5-methylbenzo[d]thiazol-6-yl)acetate (S)-2-(tert-butoxy)-2-(7-(4-chlorophenyl)-2-(3-(2,5-dihydrofuran-3-yl)-1-methyl-1H-indazol-5-yl)-5-methylbenzo[d]thiazol-6-yl)acetic acid Preparation of ethyl (S)-2-(tert-butoxy)-2-(7-(4-chlorophenyl)-2-(3-(2,5-dihydrofuran-3-yl)-1-methyl-1H-indazol-5-yl)-5-methylbenzo[d]thiazol-6-yl)acetate: A mixture of ethyl (S)-2-(2-(3-bromo-1-methyl-1H-indazol-5-yl)-7-(4- chlorophenyl)-5-methylbenzo[d]thiazol-6-yl)-2-(tert-butoxy)acetate (29.6 mg, 0.047 mmol), 2-(2,5-dihydrofuran-3-yl)-4,4,5,5-tetramethyl-1,3,2-dioxaborolane (13.4 mg, 0.068 mmol), tetrakis(triphenylphosphine)palladium(0) (5.4 mg, 0.005 mmol), and potassium carbonate (21.1 mg, 0.152 mmol) in a microwave vial was purged with argon gas for ~3 min and water (0.25 mL) and dioxane (1 mL) were added. The resulting mixture was reacted in a microwave reactor for 30 min at 110° C. After the reaction mixture was diluted with ethyl acetate and washed with water (×2), and the aqueous fractions were extracted with ethyl acetate (×1), the organic fractions were combined, dried (Na$_2$SO$_4$), and concentrated. The residue was purified by Combiflash (12 g, Gold, 0-100% EtOAc/Hex) to get 23.3 mg of impure product, which was further purified by Gilson HPLC (Phenomenex Gemini 250×21.2 10μ C18 column, 60-100% ACN/H$_2$O+0.1% TFA). The collected fraction was neutralized with saturated aqueous NaHCO$_3$ and concentrated to dryness. The residue was dissolved in dichloromethane, washed with water, dried (Na$_2$SO$_4$), and concentrated to obtain the title product. LCMS-ESI$^+$: calc'd for C$_{35}$H$_{37}$ClN$_3$O$_4$S: 616.20 (M+H)$^+$; found: 616.31 (M+H)$^+$.

Preparation of (S)-2-(tert-butoxy)-2-(7-(4-chlorophenyl)-2-(3-(2,5-dihydrofuran-3-yl)-1-methyl-1H-indazol-5-yl)-5-methylbenzo[d]thiazol-6-yl)acetic acid: To a solution of ethyl (S)-2-(tert-butoxy)-2-(7-(4-chlorophenyl)-2-(3-(2,5-dihydrofuran-3-yl)-1-methyl-1H-indazol-5-yl)-5-methylbenzo[d]thiazol-6-yl)acetate (5.0 mg, 0.008 mmol) in THF (0.5 mL) and MeOH (0.5 mL) was added 2 N NaOH (0.15 mL) at room temperature and kept tightly before the mixture was stirred at 70° C. for 1.5 h. The reaction mixture was concentrated to remove organic solvent and acidified with 2 N HCl. The resulting mixture was dissolved with DMF and MeCN (total ~3 mL), filtered through syringe filter, and purified by Gilson HPLC (Phenomenex Gemini, 60-100% ACN/H$_2$O+0.1% TFA) to obtain the title product after lyophilization. $^1$H NMR (400 MHz, Acetonitrile-d$_3$) δ 8.48 (dd, J=1.5, 0.8 Hz, 1H), 8.13 (dd, J=8.9, 1.6 Hz, 1H), 7.86 (d, J=1.0 Hz, 1H), 7.71-7.64 (m, 1H), 7.64-7.54 (m, 4H), 6.67 (p, J=2.0 Hz, 1H), 5.29 (s, 1H), 5.06 (td, J=4.7, 2.1 Hz, 2H), 4.86 (td, J=4.8, 4.3, 1.7 Hz, 2H), 4.03 (s, 3H), 2.59 (d, J=0.8 Hz, 3H), 1.00 (s, 9H). LCMS-ESI$^+$: calc'd for C$_{32}$H$_{31}$ClN$_3$O$_4$S: 588.17 (M+H)$^+$; found: 588.27 (M+H)$^+$.

Example 54. Preparation of (2S)-2-(tert-butoxy)-2-(7-(4-chlorophenyl)-5-methyl-2-(1-methyl-3-(tetrahydrofuran-3-yl)-1H-indazol-5-yl)benzo[d]thiazol-6-yl)acetic Acid (52)

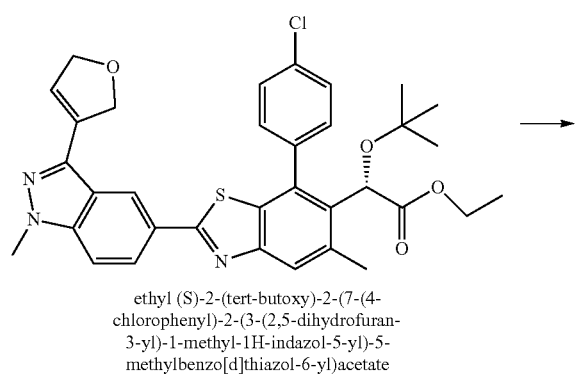

ethyl (S)-2-(tert-butoxy)-2-(7-(4-chlorophenyl)-2-(3-(2,5-dihydrofuran-3-yl)-1-methyl-1H-indazol-5-yl)-5-methylbenzo[d]thiazol-6-yl)acetate

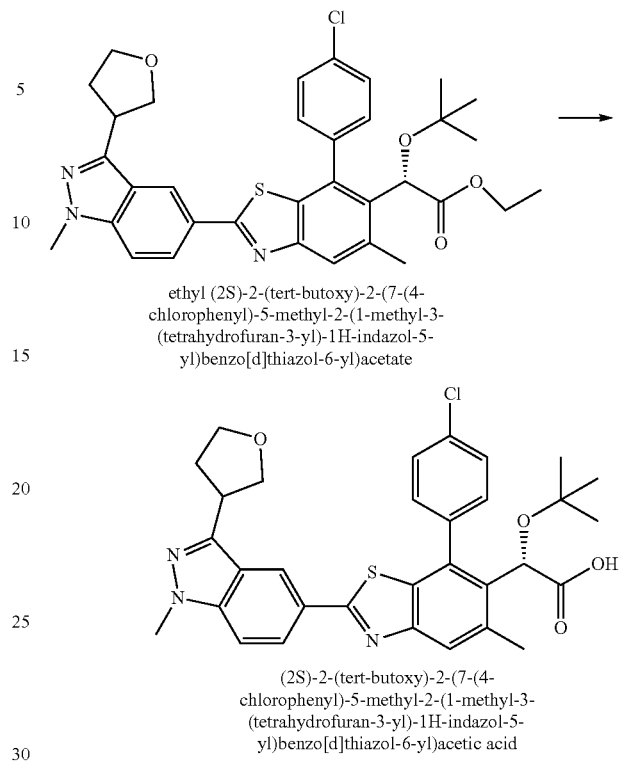

ethyl (2S)-2-(tert-butoxy)-2-(7-(4-chlorophenyl)-5-methyl-2-(1-methyl-3-(tetrahydrofuran-3-yl)-1H-indazol-5-yl)benzo[d]thiazol-6-yl)acetate (2S)-2-(tert-butoxy)-2-(7-(4-chlorophenyl)-5-methyl-2-(1-methyl-3-(tetrahydrofuran-3-yl)-1H-indazol-5-yl)benzo[d]thiazol-6-yl)acetic acid Preparation of ethyl (2S)-2-(tert-butoxy)-2-(7-(4-chlorophenyl)-5-methyl-2-(1-methyl-3-(tetrahydrofuran-3-yl)-1H-indazol-5-yl)benzo[d]thiazol-6-yl)acetate: A mixture of ethyl (S)-2-(tert-butoxy)-2-(7-(4-chlorophenyl)-2-(3-(2,5-dihydrofuran-3-yl)-1-methyl-1H-indazol-5-yl)-5-methylbenzo[d]thiazol-6-yl)acetate (12.0 mg, 0.019 mmol) and 5% Rhodium on alumina (9.7 mg) in ethanol (2 mL) was stirred under H$_2$ atmosphere for 4 h. The reaction mixture was filtered through celite pad and the filtrate was concentrated to dryness to get the crude product. LCMS-ESI$^+$: calc'd for C$_{34}$H$_{37}$ClN$_3$O$_4$S: 618.22 (M+H)$^+$; found: 618.37 (M+H)$^+$.

Preparation of (2S)-2-(tert-butoxy)-2-(7-(4-chlorophenyl)-5-methyl-2-(1-methyl-3-(tetrahydrofuran-3-yl)-1H-indazol-5-yl)benzo[d]thiazol-6-yl)acetic acid: To a solution of the above crude ethyl (2S)-2-(tert-butoxy)-2-(7-(4-chlorophenyl)-5-methyl-2-(1-methyl-3-(tetrahydrofuran-3-yl)-1H-indazol-5-yl)benzo[d]thiazol-6-yl)acetate in THF (0.5 mL) and MeOH (0.5 mL) was added 2 N NaOH (0.2 mL) at room temperature and kept tightly before the mixture was stirred at 70° C. for 1.5 h. The reaction mixture was concentrated to remove organic solvent and acidified with 2 N HCl. The resulting mixture was dissolved with DMF and MeCN (total 6 mL), filtered through syringe filter, and purified by Gilson HPLC (Phenomenex Gemini, 60-100% ACN/H$_2$O+0.1% TFA) to obtain the title product after lyophilization. $^1$H NMR (400 MHz, Acetonitrile-d$_3$) δ 8.41 (two d, J=0.8 Hz, 1H), 8.09-8.06 (m, 0.48H), 8.05 (t, J=1.4 Hz, 0.52H), 7.86 (two s, 1H), 7.67 (two d, J=8.9 Hz, 1H), 7.64-7.57 (m, 3H), 7.55 (two d, J=8.9 Hz, 1H), 5.29 (s, 1H), 4.21-4.12 (m, 1H), 4.05 (two t, J=8.2 Hz, 1H), 3.99 (s, 3H), 4.01-3.85 (m, 3H), 2.58 (d, J=0.8 Hz, 3H), 2.51-2.39 (m, 1H), 2.32-2.20 (m, 1H), 0.99 (s, 9H). LCMS-ESI$^+$: calc'd for C$_{32}$H$_{33}$ClN$_3$O$_4$S: 590.19 (M+H)$^+$; found: 590.29 (M+H)$^+$.

Example 55. (S)-2-(tert-butoxy)-2-(2-(3-(1-(tert-butoxycarbonyl)azetidin-3-yl)-1-methyl-1H-indazol-5-yl)-7-(4-chlorophenyl)-5-methylbenzo[d]thiazol-6-yl)acetic Acid (53)

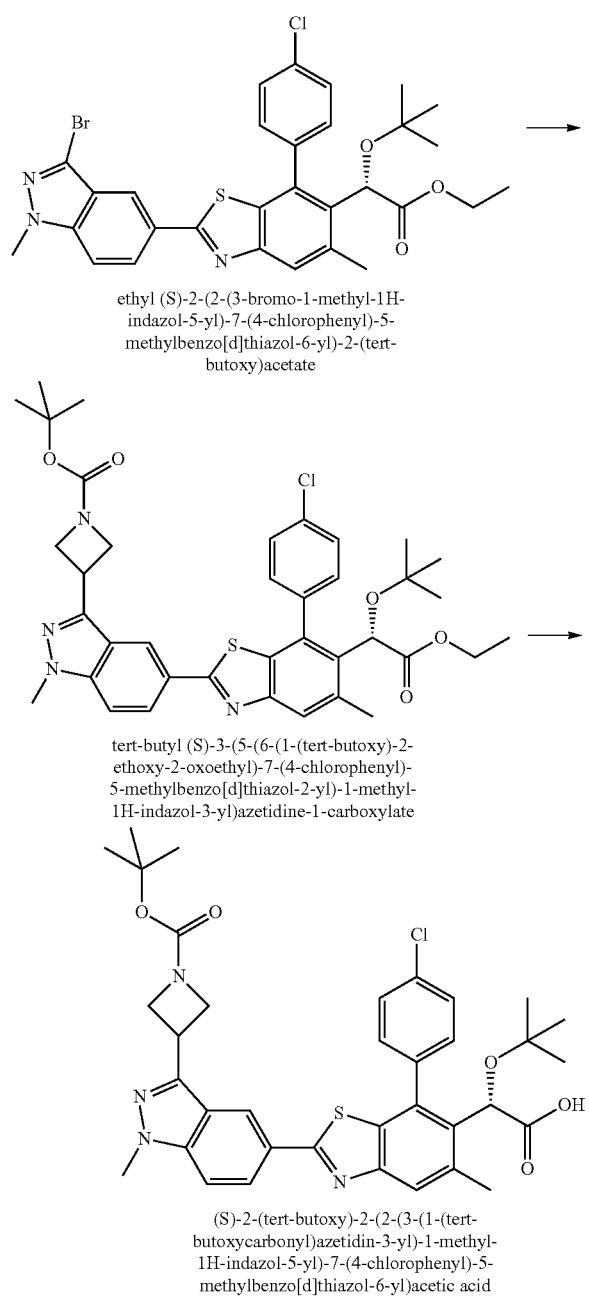

ethyl (S)-2-(2-(3-bromo-1-methyl-1H-indazol-5-yl)-7-(4-chlorophenyl)-5-methylbenzo[d]thiazol-6-yl)-2-(tert-butoxy)acetate tert-butyl (S)-3-(5-(6-(1-(tert-butoxy)-2-ethoxy-2-oxoethyl)-7-(4-chlorophenyl)-5-methylbenzo[d]thiazol-2-yl)-1-methyl-1H-indazol-3-yl)azetidine-1-carboxylate (S)-2-(tert-butoxy)-2-(2-(3-(1-(tert-butoxycarbonyl)azetidin-3-yl)-1-methyl-1H-indazol-5-yl)-7-(4-chlorophenyl)-5-methylbenzo[d]thiazol-6-yl)acetic acid Preparation of tert-butyl (S)-3-(5-(6-(1-(tert-butoxy)-2-ethoxy-2-oxoethyl)-7-(4-chlorophenyl)-5-methylbenzo[d]thiazol-2-yl)-1-methyl-1H-indazol-3-yl)azetidine-1-carboxylate: A mixture of ethyl (S)-2-(2-(3-bromo-1-methyl-1H-indazol-5-yl)-7-(4-chlorophenyl)-5-methylbenzo[d]thiazol-6-yl)-2-(tert-butoxy)acetate (47.1 mg, 0.047 mmol), potassium [1-[(1,1-dimethylethoxy)carbonyl]-3-azetidinyl]trifluoro-borate (29.9 mg, 0.114 mmol), tetrakis(triphenylphosphine)palladium(0) (9.6 mg, 0.008 mmol), and potassium carbonate (32.2 mg, 0.233 mmol), water (0.3 mL), and dioxane (1.2 mL) was placed in a microwave vial and the resulting mixture was reacted in a microwave reactor at 110° C. for 30 min followed by at 150° C. for 2.5 h. The resulting mixture was diluted in methanol, filtered through syringe filter, and purified by Gilson HPLC (Phenomenex Gemini, 700-100% ACN/H$_2$O+0.1% TFA) to obtain the title product after lyophilization. LCMS-ESI$^+$: calc'd for C$_{38}$H$_{44}$ClN$_4$O$_5$S: 703.27 (M+H)$^+$; found: 703.04 (M+H)$^+$.

Preparation of (S)-2-(tert-butoxy)-2-(2-(3-(1-(tert-butoxycarbonyl)azetidin-3-yl)-1-methyl-1H-indazol-5-yl)-7-(4-chlorophenyl)-5-methylbenzo[d]thiazol-6-yl)acetic acid: To a solution of tert-butyl (S)-3-(5-(6-(1-(tert-butoxy)-2-ethoxy-2-oxoethyl)-7-(4-chlorophenyl)-5-methylbenzo[d]thiazol-2-yl)-1-methyl-1H-indazol-3-yl)azetidine-1-carboxylate (4.4 mg, 0.005 mmol) in THF (0.5 mL) and MeOH (0.5 mL) was added 2 N NaOH (0.1 mL) at room temperature and kept tightly before the mixture was stirred at 50° C. for 23.5 h. The reaction mixture was concentrated to remove organic solvent and acidified with 2 N HCl. The resulting mixture was dissolved with DMF and MeCN (total ~3 mL), filtered through syringe filter, and purified by Gilson HPLC (Phenomenex Gemini, 40-100% ACN/H$_2$O+0.1% TFA) to obtain the title product after lyophilization. $^1$H NMR (400 MHz, Acetonitrile-d$_3$) δ 8.41-8.35 (m, 1H), 8.17 (dd, J=8.9, 1.6 Hz, 1H), 7.86 (s, 1H), 7.66 (dd, J=7.8, 2.4 Hz, 1H), 7.63-7.56 (m, 4H), 5.28 (s, 1H), 4.39 (d, J=7.1 Hz, 2H), 4.20 (dd, J=12.7, 5.5 Hz, 3H), 4.04 (s, 3H), 2.58 (s, 3H), 1.44 (s, 9H), 0.99 (s, 9H). LCMS-ESI$^+$: calc'd for C$_{36}$H$_{40}$ClN$_4$O$_5$S: 675.24 (M+H)$^+$; found: 674.98 (M+H)$^+$.

Example 56. Preparation of (S)-2-(tert-butoxy)-2-(7-(4-chlorophenyl)-2-(3-(1-isopropylazetidin-3-yl)-1-methyl-1H-indazol-5-yl)-5-methylbenzo[d]thiazol-6-yl)acetic Acid (54)

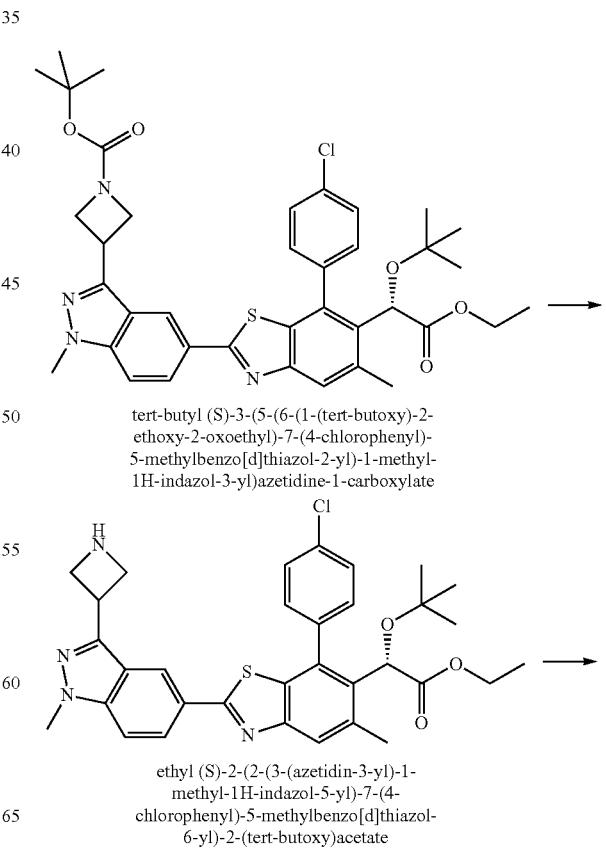

tert-butyl (S)-3-(5-(6-(1-(tert-butoxy)-2-ethoxy-2-oxoethyl)-7-(4-chlorophenyl)-5-methylbenzo[d]thiazol-2-yl)-1-methyl-1H-indazol-3-yl)azetidine-1-carboxylate ethyl (S)-2-(2-(3-(azetidin-3-yl)-1-methyl-1H-indazol-5-yl)-7-(4-chlorophenyl)-5-methylbenzo[d]thiazol-6-yl)-2-(tert-butoxy)acetate

223

-continued

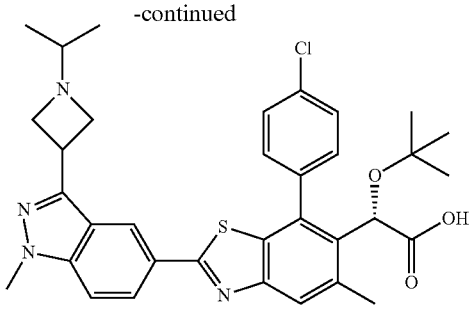

(S)-2-(tert-butoxy)-2-(7-(4-chlorophenyl)-2-(3-(1-isopropylazetidin-3-yl)-1-methyl-1H-indazol-5-yl)-5-methylbenzo[d]thiazol-6-yl)acetic acid Preparation of ethyl (S)-2-(2-(3-(azetidin-3-yl)-1-methyl-1H-indazol-5-yl)-7-(4-chlorophenyl)-5-methylbenzo[d]thiazol-6-yl)-2-(tert-butoxy)acetate: To a flask containing tert-butyl (S)-3-(5-(6-(1-(tert-butoxy)-2-ethoxy-2-oxoethyl)-7-(4-chlorophenyl)-5-methylbenzo[d]thiazol-2-yl)-1-methyl-1H-indazol-3-yl)azetidine-1-carboxylate (16.0 mg, 0.023 mmol) was added 1.25 M HCl in isopropanol (3 mL) and the resulting mixture was stirred at room temperature for 24 h. After the reaction mixture was concentrated, the residue was co-evaporated with acetonitrile (×1) and dried to obtain the crude title product, which was used for the next reaction. LCMS-ESI⁺: calc'd for $C_{33}H_{36}ClN_4O_3S$: 603.22 (M+H)⁺; found: 603.28 (M+H)⁺.

Preparation of (S)-2-(tert-butoxy)-2-(7-(4-chlorophenyl)-2-(3-(1-isopropylazetidin-3-yl)-1-methyl-1H-indazol-5-yl)-5-methylbenzo[d]thiazol-6-yl)acetic acid: A solution of crude ethyl (S)-2-(2-(3-(azetidin-3-yl)-1-methyl-1H-indazol-5-yl)-7-(4-chlorophenyl)-5-methylbenzo[d]thiazol-6-yl)-2-(tert-butoxy)acetate (14.6 mg, 0.023 mmol) in acetonitrile (2 mL) and acetone (0.5 mL) was stirred at 0° C. bath as sodium cyanoborohydride (~30 mg, 0.477 mmol) and acetic acid (2 drops) were added. To the reaction mixture was added. After 30 min, the reaction mixture was quenched with saturated NaHCO₃ solution and the product was extracted with dichloromethane (×2). The combined extracts were dried (Na₂SO₄) and concentrated to get crude isopropylated product with impurities. LCMS-ESI⁺: calc'd for $C_{36}H_{342}ClN_4O_3S$: 645.27 (M+H)⁺; found: 645.32 (M+H)⁺.

The crude isopropylated product was dissolved in THF (0.5 mL) and MeOH (0.5 mL) was added 2 N NaOH (0.2 mL) at room temperature and kept tightly before the mixture was stirred at 70° C. for 1.5 h. The reaction mixture was acidified with 2 N HCl (~0.22 mL) and concentrated to remove organic solvent. The resulting mixture was dissolved with methanol, filtered through syringe filter (total 3 mL), and purified by Gilson HPLC (Phenomenex Gemini, 30-100% ACN/H₂O+0.1% TFA) to obtain the title product after lyophilization. ¹H NMR (400 MHz, Acetonitrile-d₃) δ 11.15 (s, 1H), 8.33 (s, 1H), 8.21-8.13 (m, 1H), 7.86 (s, 1H), 7.67 (dd, J=8.0, 2.1 Hz, 1H), 7.61 (d, J=8.4 Hz, 4H), 5.28 (s, 1H), 4.70-4.50 (m, 2H), 4.24 (m, 2H), 4.08 (s, 3H), 3.44 (hep, J=6.7 Hz, 1H), 2.58 (s, 3H), 1.28 (d, J=6.7 Hz, 6H), 0.99 (s, 9H). LCMS-ESI⁺: calc'd for $C_{34}H_{38}ClN_4O_3S$: 617.24 (M+H)⁺; found: 617.29 (M+H)⁺.

224

Example 57. Preparation of (S)-2-(7-(4-chlorophenyl)-2-(3-(1-isopropylazetidin-3-yl)-1-methyl-1H-indazol-5-yl)-5-methylbenzo[d]thiazol-6-yl)-2-cyclopropoxyacetic Acid (55)

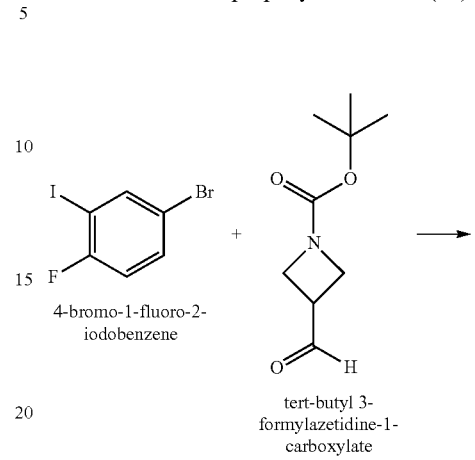

4-bromo-1-fluoro-2-iodobenzene tert-butyl 3-formylazetidine-1-carboxylate

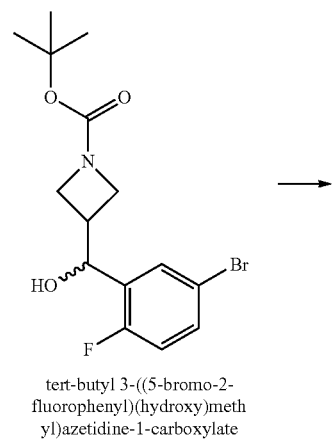

tert-butyl 3-((5-bromo-2-fluorophenyl)(hydroxy)methyl)azetidine-1-carboxylate

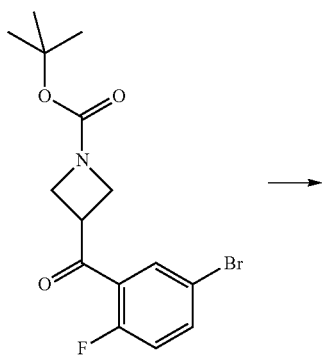

tert-butyl 3-(5-bromo-2-fluorophenyl)azetidine-1-carboxylate

225
-continued

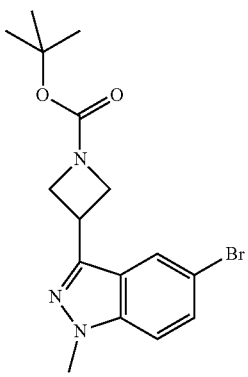

tert-butyl 3-(5-bromo-1-
methyl-1H-indazol-3-
yl)azetidine-1-carboxylate

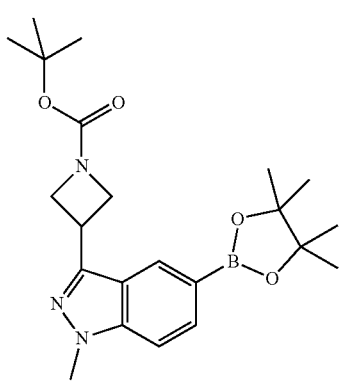

tert-butyl 3-(1-methyl-5-
(4,4,5,5-tetramethyl-
1,3,2-dioxaborolan-2-yl)-
1H-indazol-3-yl)azetidine-
1-carboxylate

+

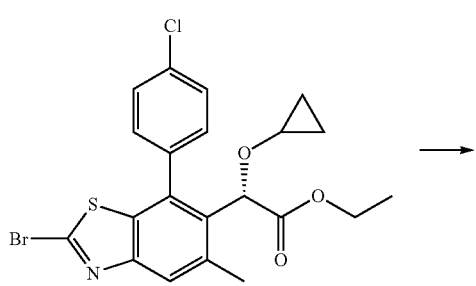

ethyl (S)-2-(2-bromo-7-(4-
chlorophenyl)-5-
methylbenzo[d]thiazol-6-yl)-2-
cyclopropoxyacetate 226
-continued

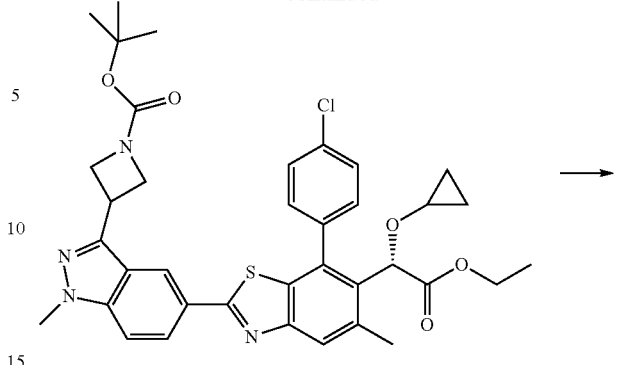

tert-butyl (S)-3-(5-(7-(4-chlorphenyl)-6-
(1-cyclopropoxy-2-ethoxy-2-oxoethyl)-5-
methylbenzo[d]thiazol-2-yl)-1-methyl-1H-
indazol-3-yl)azetidine-1-carboxylate

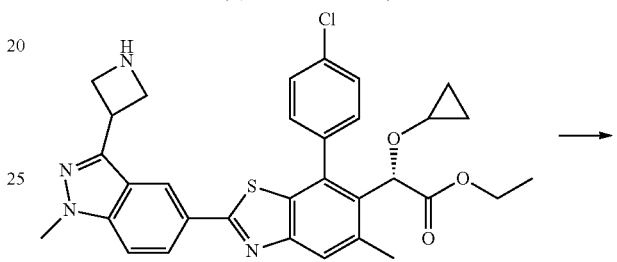

ethyl (S)-2-(2-(3-(azetidin-3-yl)-1-methyl-
1H-indazol-5-yl)-7-(4-chlorophenyl)-5-
methylbenzo[d]thiazol-6-yl)-2-
cyclopropoxyacetate

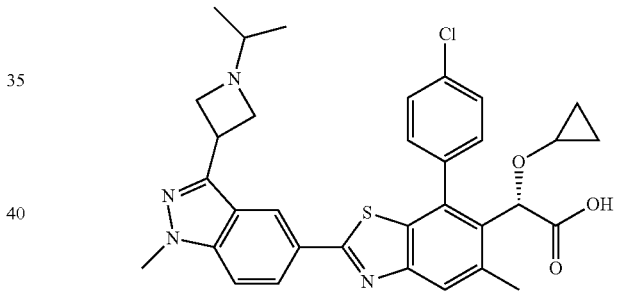

(S)-2-(7-(4-chlorophenyl)-2-(3-(1-
isopropylazetidin-3-yl)-1-methyl-1H-
indazol-5-yl)-5-methylbenzo[d]thiazol-6-
yl)-2-cyclopropoxyacetic acid Preparation of tert-butyl 3-((5-bromo-2-fluorophenyl) (hydroxy)methyl)azetidine-1-carboxylate: A solution of 4-bromo-1-fluoro2-iodobenzene (3.196 g, 10.62 mmol) in 2-Me-THF (22 mL) was stirred in dry ice-acetone bath while 2.5 M n-BuLi in hexane (from Aldrich, 4.25 mL, 10.63 mmol) was added dropwise. After 15 min, A solution of 1-Boc-3-azetidinecarboxaldehyde (1.971 g, 10.64 mmol) in 2-Me-THF (4 mL) was added slowly. After 1 h, the reaction mixture was quenched with saturated aqueous NH$_4$Cl solution at the cold temperature and warmed to rt. The product was extracted with ethyl acetate (~100 mL×2), and the extracts were washed with water (×2) before combining, drying (Na$_2$SO$_4$), and concentration. The concentrated residue was purified by CombiFlash (120 g, Gold, 0-40% EtOAc/Hex) to obtain the title product. LCMS-ESI$^+$: calc'd for $C_{11}H_{12}BrFNO_3$: 304.00 (M+H-C$_4$H$_8$)$^+$; found: 303.87 (M+H-C$_4$H$_8$)$^+$.

Preparation of tert-butyl 3-(5-bromo-2-fluorobenzoyl) azetidine-1-carboxylate: A solution of tert-butyl 3-((5- bromo-2-fluorophenyl)(hydroxy)methyl)azetidine-1-carboxylate (2.499 g, 6.937 mmol) in dichloromethane (50 mL) was stirred at 0° C. as Dess-Martin Periodinane (3.537 g, 8.339 mmol) was added. After 1.5 h, the mixture was filtered through celite pad. The filtrate was washed with saturated aqueous $NaHCO_3$ solution (×1) and water (×1). After the aqueous fractions were extracted with dichloromethane (×1), the organic fractions were combined, dried ($Na_2SO_4$), and concentrated. The residue was purified by CombiFlash (120 g, Gold, 0-40% EtOAc/Hex) to obtain the title product. LCMS-ESI$^+$: calc'd for $C_{11}H_{10}BrFNO_3$: 301.98 (M+H-$C_4H_8$)$^+$; found: 301.90 (M+H-$C_4H_8$)$^+$.

Preparation of tert-butyl 3-(5-bromo-1-methyl-1H-indazol-3-yl)azetidine-1-carboxylate: To a solution of tert-butyl 3-(5-bromo-2-fluorobenzoyl)azetidine-1-carboxylate (1.586 g, 4.428 mmol), p-toluenesulfonic acid hydrate (59 mg, 342.62 umol) in dioxane (16 mL) was added methylhydrazine (1.6 mL, 30.39 mmol) and the mixture was reacted in microwave reactor at 150° C. for 1 h. The reaction mixture was transferred to a RBF and concentrated. The concentrated residue was purified by CombiFlash (120 g, Gold, 0-60% EtOAc/Hex) to obtain the title product. LCMS-ESI$^+$: calc'd for $C_{12}H_{13}BrN_3O_2$: 310.02 (M+H–$C_4H_8$)$^+$; found: 310.01 (M+H–$C_4H_8$)$^+$.

Preparation of tert-butyl 3-(1-methyl-5-(4,4,5,5-tetramethyl-1,3,2-dioxaborolan-2-yl)-1H-indazol-3-yl)azetidine-1-carboxylate: To a flask containing tert-butyl 3-(5-bromo-1-methyl-1H-indazol-3-yl)azetidine-1-carboxylate (604 mg, 1.649 mmol) were added bis(pinacolato)diboron (512.3 mg, 2.017 mmol), dichloro 1,1'-bis(diphenylphosphino)ferrocene palladium (II) dichloromethane (144 mg, 0.176 mmol), and potassium acetate (500.2 mg, 5.097 mmol) and the resulting flask was purged with argon gas. To the flask was added degassed 1,4-dioxane (bubbled with Ar for 1 h, 10 mL) and the resulting mixture was kept tightly and stirred at 95° C. for 1 h and at 100° C. for 30 min. The reaction mixture was diluted with EA, dried ($Na_2SO_4$) and concentrated. The residue was purified by CombiFlash (80 g, Gold, 25-45% EtOAc/Hex) using hexanes-EA as eluents to obtain the title product. LCMS-ESI$^+$: calc'd for $C_{22}H_{33}BN_3O_4$: 414.26 (M+H)+; found: 413.77 (M+H)$^+$.

Preparation of tert-butyl (S)-3-(5-(7-(4-chlorophenyl)-6-(1-cyclopropoxy-2-ethoxy-2-oxoethyl)-5-methylbenzo[d]thiazol-2-yl)-1-methyl-1H-indazol-3-yl)azetidine-1-carboxylate: To a vial containing ethyl (S)-2-(2-bromo-7-(4-chlorophenyl)-5-methylbenzo[d]thiazol-6-yl)-2-cyclopropoxyacetate (35 mg, 0.073 mmol), tert-butyl 3-(1-methyl-5-(4,4,5,5-tetramethyl-1,3,2-dioxaborolan-2-yl)-1H-indazol-3-yl)azetidine-1-carboxylate (32.1 mg, 0.088 mmol), $K_2CO_3$ (34.0 mg, 0.246 mmol), and tetrakis(triphenylphosphine)palladium(0) (9.72 mg, 0.008 mmol) in water (0.25 mL) and 1,4-dioxane (1 mL) was purged with Ar and then kept tightly before heating at 95° C. bath for 45 min. The reaction mixture was diluted with ethyl acetate, dried ($Na_2SO_4$), and concentrated. The residue was purified by CombiFlash (12 g, Gold, 25-70% EtOAc/Hex) to obtain the title product. LCMS-ESI$^+$: calc'd for $C_{37}H_{40}ClN_4O_5S$: 687.24 (M+H)$^+$; found: 687.01 (M+H)$^+$.

Preparation of ethyl (S)-2-(2-(3-(azetidin-3-yl)-1-methyl-1H-indazol-5-yl)-7-(4-chlorophenyl)-5-methylbenzo[d]thiazol-6-yl)-2-cyclopropoxyacetate: To a flask containing tert-butyl (S)-3-(5-(7-(4-chlorophenyl)-6-(1-cyclopropoxy-2-ethoxy-2-oxoethyl)-5-methylbenzo[d]thiazol-2-yl)-1-methyl-1H-indazol-3-yl)azetidine-1-carboxylate (47.4 mg, 0.069 mmol) was added 1.25 M HCl in isopropanol (2 mL, 2.5 mmol) and the resulting solution was stirred at rt. After 20 h, the reaction mixture was concentrated at 20° C. bath and dried in vacuum for 30 min to get crude ethyl (S)-2-(2-(3-(azetidin-3-yl)-1-methyl-1H-indazol-5-yl)-7-(4-chlorophenyl)-5-methylbenzo[d]thiazol-6-yl)-2-cyclopropoxyacetate which contained some isopropanol. LCMS-ESI$^+$: calc'd for $C_{32}H_{32}ClN_4O_3S$: 587.19 (M+H)$^+$; found: 587.26 (M+H)$^+$.

Preparation of (S)-2-(7-(4-chlorophenyl)-2-(3-(1-isopropylazetidin-3-yl)-1-methyl-1H-indazol-5-yl)-5-methylbenzo[d]thiazol-6-yl)-2-cyclopropoxyacetic acid: To a flask containing the above crude ethyl (S)-2-(2-(3-(azetidin-3-yl)-1-methyl-1H-indazol-5-yl)-7-(4-chlorophenyl)-5-methylbenzo[d]thiazol-6-yl)-2-cyclopropoxyacetate were added methanol (3 mL) and acetone (0.15 mL) and stirred at 0° C. bath as sodium cyanoborohydride (50 mg, 0.796 mmol) and AcOH (1 drop) were added. After 1.5 h, the reaction mixture was diluted with saturated $NaHCO_3$, and the product was extracted with ethyl acetate (×3). The extracts were combined dried ($MgSO_4$), concentrated, and dried in vacuum for 30 min. LCMS-ESI: calc'd for $C_{35}H_{38}ClN_4O_3S$: 629.24 (M+H)$^+$; found: 629.33 (M+H)$^+$.

The above residue was dissolved in THF (1 mL) and MeOH (1 mL) before 2 N NaOH (1 mL) was added. The resulting mixture was stirred at 70° C. preheated bath. After 1 h, the reaction mixture was acidified with 2 N HCl (~1.05 mL) and concentrated to almost dryness. The residue was triturated with MeOH (~1.5 mL) and the suspension was filtered through syringe filter. The resulting filtrate was purified by Gilson HPLC (Phenomenex Gemini, 30-50% ACN/$H_2O$+0.1% TFA) to obtain the title product after lyophilization. $^1$H NMR (400 MHz, Acetonitrile-$d_3$) δ 9.08 (br, 1H), 8.32 (dt, J=2.4, 1.2 Hz, 1H), 8.17 (ddd, J=10.4, 9.0, 1.6 Hz, 1H), 7.87 (d, J=6.4 Hz, 1H), 7.66-7.56 (m, 3H), 7.52 (dd, J=8.6, 2.1 Hz, 1H), 7.47 (dd, J=8.5, 2.1 Hz, 1H), 5.17 (s, 1H), 4.68-4.36 (m, 4H), 4.36-4.22 (m, 1H), 4.09 (s, 1.2H), 4.06 (s, 1.8H), 3.66-3.53 (m, 0.4H), 3.48 (dq, J=8.8, 6.4 Hz, 0.6H), 3.26 (tt, J=6.0, 3.0 Hz, 1H), 2.57-2.47 (m, 3H), 1.28 (t, J=6.8 Hz, 6H), 0.48-0.24 (m, 4H). LCMS-ESI$^+$: calc'd for $C_{33}H_{34}ClN_4O_3S$: 601.20 (M+H)$^+$; found: 601.31 (M+H)$^+$.

Example 58. Preparation of (S)-2-(tert-butoxy)-2-(7-(4-chlorophenyl)-2-(3-(1-(2-methoxyethyl)azetidin-3-yl)-1-methyl-1H-indazol-5-yl)-5-methylbenzo[d]thiazol-6-yl)acetic Acid (56)

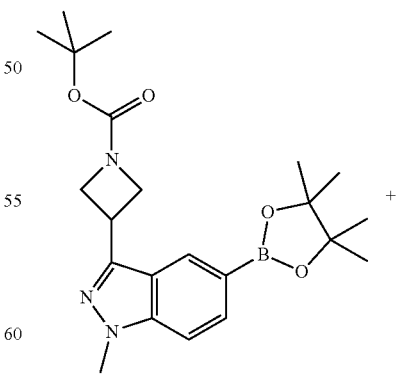

tert-butyl 3-(1-methyl-5-(4,4,5,5-tetramethyl-1,3,2-dioxaborolan-2-yl)-1H-indazol-3-yl)azetidine-1-carboxylate

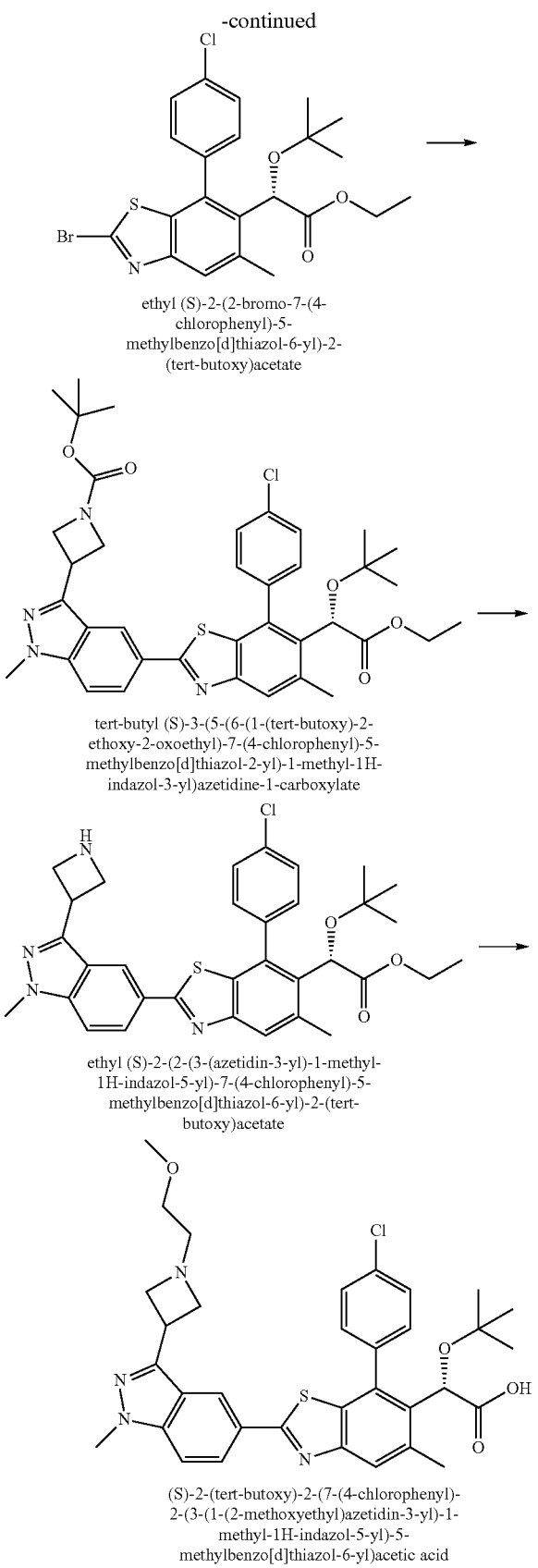

ethyl (S)-2-(2-bromo-7-(4-chlorophenyl)-5-methylbenzo[d]thiazol-6-yl)-2-(tert-butoxy)acetate tert-butyl (S)-3-(5-(6-(1-(tert-butoxy)-2-ethoxy-2-oxoethyl)-7-(4-chlorophenyl)-5-methylbenzo[d]thiazol-2-yl)-1-methyl-1H-indazol-3-yl)azetidine-1-carboxylate ethyl (S)-2-(2-(3-(azetidin-3-yl)-1-methyl-1H-indazol-5-yl)-7-(4-chlorophenyl)-5-methylbenzo[d]thiazol-6-yl)-2-(tert-butoxy)acetate (S)-2-(tert-butoxy)-2-(7-(4-chlorophenyl)-2-(3-(1-(2-methoxyethyl)azetidin-3-yl)-1-methyl-1H-indazol-5-yl)-5-methylbenzo[d]thiazol-6-yl)acetic acid Preparation of tert-butyl (S)-3-(5-(6-(1-(tert-butoxy)-2-ethoxy-2-oxoethyl)-7-(4-chlorophenyl)-5-methylbenzo[d]thiazol-2-yl)-1-methyl-1H-indazol-3-yl)azetidine-1-carboxylate: A microwave reaction vial containing ethyl (S)-2-(2-bromo-7-(4-chlorophenyl)-5-methylbenzo[d]thiazol-6-yl)-2-(tert-butoxy)acetate (98.2 mg, 0.198 mmol), tert-butyl 3-(1-methyl-5-(4,4,5,5-tetramethyl-1,3,2-dioxaborolan-2-yl)-1H-indazol-3-yl)azetidine-1-carboxylate (99.3 mg, 0.240 mmol), potassium carbonate (85.2 mg, 0.616 mmol), and tetrakis(triphenylphosphine)palladium(0) (23.2 mg, 0.020 mmol) in water (0.4 mL) and 1,4-dioxane (1.6 mL) was purged with Ar for 5 min and then kept tightly before heating at 95° C. bath for 5 h. The reaction mixture was diluted with EA, dried ($Na_2SO_4$), and concentrated. The residue was purified by CombiFlash (24 g, Gold, 0-80% EtOAc/Hex) to get impure product. The impure product was purified again by CombiFlash (24 g, Gold, 30-65% EtOAc/Hex) to obtain the title product. LCMS-ESI$^+$: calc'd for $C_{38}H_{44}ClN_4O_5S$: 703.27 (M+H)$^+$; found: 703.03 (M+H)$^+$.

Preparation of ethyl (S)-2-(2-(3-(azetidin-3-yl)-1-methyl-1H-indazol-5-yl)-7-(4-chlorophenyl)-5-methylbenzo[d]thiazol-6-yl)-2-(tert-butoxy)acetate: To a flask containing tert-butyl (S)-3-(5-(6-(1-(tert-butoxy)-2-ethoxy-2-oxoethyl)-7-(4-chlorophenyl)-5-methylbenzo[d]thiazol-2-yl)-1-methyl-1H-indazol-3-yl)azetidine-1-carboxylate (94.7 mg, 0.135 mmol) was added 1.25 M HCl in isopropanol (3.5 mL, 4.375 mmol) and the resulting solution was stirred at rt. After 20 h, the reaction mixture was concentrated and dried in vacuum for 5 h to get crude ethyl (S)-2-(2-(3-(azetidin-3-yl)-1-methyl-1H-indazol-5-yl)-7-(4-chlorophenyl)-5-methylbenzo[d]thiazol-6-yl)-2-(tert-butoxy)acetate. LCMS-ESI$^+$: calc'd for $C_{33}H_{36}ClN_4O_3S$: 603.22 (M+H)$^+$; found: 603.29 (M+H)$^+$.

Preparation of (S)-2-(tert-butoxy)-2-(7-(4-chlorophenyl)-2-(3-(1-(2-methoxyethyl)azetidin-3-yl)-1-methyl-1H-indazol-5-yl)-5-methylbenzo[d]thiazol-6-yl)acetic acid: To a flask containing ¼ of the above crude ethyl (S)-2-(2-(3-(azetidin-3-yl)-1-methyl-1H-indazol-5-yl)-7-(4-chlorophenyl)-5-methylbenzo[d]thiazol-6-yl)-2-(tert-butoxy)acetate were added methanol (2 mL), methoxyacetaldehyde (0.1 mL, 1.357 mmol) and stirred at 0° C. bath as sodium cyanoborohydride (30 mg, 0.477 mmol) and acetic acid (1 drop). After 30 min, the reaction mixture was diluted with saturated aqueous $NaHCO_3$, and the product was extracted with ethyl acetate (×3). The extracts were combined dried ($MgSO_4$), concentrated, and dried in vacuum for 30 min. LCMS-ESI$^+$: calc'd for $C_{36}H_{42}ClN_4O_4S$: 661.26 (M+H)$^+$; found: 661.37 (M+H)$^+$.

The above residue was dissolved in THF (1 mL) and MeOH (1 mL) before 2 N NaOH (1 mL) was added. The resulting mixture was stirred at 70° C. preheated bath for 2 h and the reaction mixture was acidified with 2 N HCl (~1.05 mL) and concentrated to almost dryness. The residue was triturated with MeOH (~1.5 mL) and the suspension was filtered through syringe filter. The resulting filtrate was purified by Gilson HPLC (Phenomenex Gemini, 30-50% ACN/$H_2O$+0.1% TFA) to obtain the title product after lyophilization. $^1$H NMR (400 MHz, Acetonitrile-$d_3$) δ 8.31 (s, 1H), 8.19-8.11 (m, 1H), 7.85 (d, J=2.6 Hz, 1H), 7.67 (dd, J=7.8, 2.4 Hz, 1H), 7.64-7.55 (m, 4H), 5.28 (s, 1H), 4.75 (t, J=9.6 Hz, 1H), 4.60 (m, 2H), 4.47 (m, 1H), 4.35 (br, 1H), 4.07 (two s, 3H), 3.68-3.58 (m, 2H), 3.56-3.50 (m, 1H), 3.47 (m, 1H), 3.36 (two s, 3H), 2.58 (two s, 3H), 0.99 (s, 9H). LCMS-ESI$^+$: calc'd for $C_{34}H_{38}ClN_4O_4S$: 633.23 (M+H)$^+$; found: 633.32 (M+H)$^+$.

Example 59. Preparation of (S)-2-(tert-butoxy)-2-(7-(4-chlorophenyl)-5-methyl-2-(1-methyl-3-(1-methylazetidin-3-yl)-1H-indazol-5-yl)benzo[d]thiazol-6-yl)acetic Acid (57)

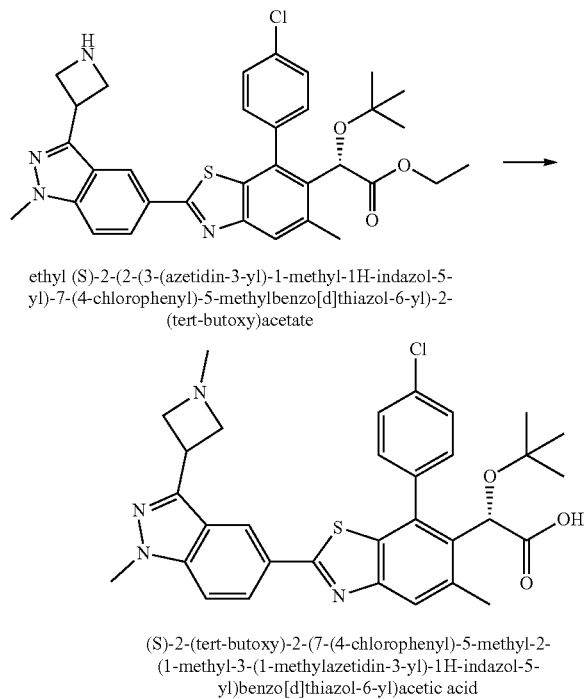

ethyl (S)-2-(2-(3-(azetidin-3-yl)-1-methyl-1H-indazol-5-yl)-7-(4-chlorophenyl)-5-methylbenzo[d]thiazol-6-yl)-2-(tert-butoxy)acetate (S)-2-(tert-butoxy)-2-(7-(4-chlorophenyl)-5-methyl-2-(1-methyl-3-(1-methylazetidin-3-yl)-1H-indazol-5-yl)benzo[d]thiazol-6-yl)acetic acid Preparation of (S)-2-(tert-butoxy)-2-(7-(4-chlorophenyl)-5-methyl-2-(1-methyl-3-(1-methylazetidin-3-yl)-1H-indazol-5-yl)benzo[d]thiazol-6-yl)acetic acid: To a flask containing ⅛ of the above crude ethyl (S)-2-(2-(3-(azetidin-3-yl)-1-methyl-1H-indazol-5-yl)-7-(4-chlorophenyl)-5-methylbenzo[d]thiazol-6-yl)-2-(tert-butoxy)acetate were added methanol (1 mL), 37% formaldehyde (0.1 mL, 1.343 mmol) and stirred at 0° C. bath as sodium cyanoborohydride (30 mg, 0.477 mmol) and acetic acid (1 drop). After 30 min, the reaction mixture was diluted with saturated aqueous NaHCO$_3$, and the product was extracted with ethyl acetate (×3). The extracts were combined dried (MgSO$_4$), concentrated, and dried in vacuum for 30 min. LCMS-ESI$^+$: calc'd for C$_{34}$H$_{38}$ClN$_4$O$_3$S: 617.24 (M+H)$^+$; found: 617.33 (M+H)$^+$.

The above residue was dissolved in THF (1 mL) and MeOH (1 mL) before 2 N NaOH (1 mL) was added. The resulting mixture was stirred at 70° C. preheated bath for 2 h and the reaction mixture was acidified with 2 N HCl (~1.05 mL) and concentrated to almost dryness. The residue was triturated with MeOH (~1.5 mL) and the suspension was filtered through syringe filter. The resulting filtrate was purified by Gilson HPLC (Phenomenex Gemini, 30-60% ACN/H$_2$O+0.1% TFA) to obtain the title product after lyophilization. $^1$H NMR (400 MHz, Acetonitrile-d$_3$) δ 8.30-8.24 (m, 1H), 8.13 (dd, J=8.9, 1.6 Hz, 1H), 7.82 (s, 1H), 7.67 (dd, J=7.8, 2.5 Hz, 1H), 7.64-7.49 (m, 4H), 5.27 (s, 1H), 4.87-4.44 (m, 3H), 4.16 (s, 2H), 4.06 (s, 3H), 2.95 (s, 3H), 2.57 (s, 3H), 0.98 (s, 9H). LCMS-ESI: calc'd for C$_{32}$H$_{34}$ClN$_4$O$_3$S: 589.20 (M+H)$^+$; found: 589.29 (M+H)$^+$.

Example 60. Preparation of (S)-2-(tert-butoxy)-2-(7-(4-chlorophenyl)-2-(3-(1-ethylazetidin-3-yl)-1-methyl-1H-indazol-5-yl)-5-methylbenzo[d]thiazol-6-yl)acetic Acid (58)

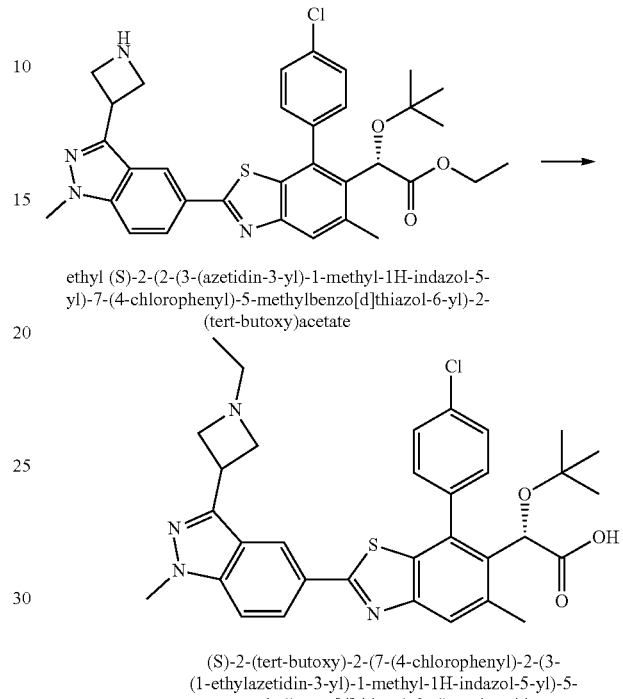

ethyl (S)-2-(2-(3-(azetidin-3-yl)-1-methyl-1H-indazol-5-yl)-7-(4-chlorophenyl)-5-methylbenzo[d]thiazol-6-yl)-2-(tert-butoxy)acetate (S)-2-(tert-butoxy)-2-(7-(4-chlorophenyl)-2-(3-(1-ethylazetidin-3-yl)-1-methyl-1H-indazol-5-yl)-5-methylbenzo[d]thiazol-6-yl)acetic acid Preparation of (S)-2-(tert-butoxy)-2-(7-(4-chlorophenyl)-2-(3-(1-ethylazetidin-3-yl)-1-methyl-1H-indazol-5-yl)-5-methylbenzo[d]thiazol-6-yl)acetic acid: To a flask containing ⅛ of the above crude ethyl (S)-2-(2-(3-(azetidin-3-yl)-1-methyl-1H-indazol-5-yl)-7-(4-chlorophenyl)-5-methylbenzo[d]thiazol-6-yl)-2-(tert-butoxy)acetate were added methanol (1 mL), acetaldehyde (0.015 mL, 0.267 mmol) and stirred at 0° C. bath as sodium cyanoborohydride (30 mg, 0.477 mmol) and acetic acid (1 drop). After 30 min, the reaction mixture was diluted with saturated aqueous NaHCO$_3$, and the product was extracted with ethyl acetate (×3). The extracts were combined dried (MgSO$_4$), concentrated, and dried in vacuum for 30 min. LCMS-ESI$^+$: calc'd for C$_{35}$H$_{40}$ClN$_4$O$_3$S: 631.25 (M+H)$^+$; found: 631.29 (M+H)$^+$.

The above residue was dissolved in THF (1 mL) and MeOH (1 mL) before 2 N NaOH (1 mL) was added. The resulting mixture was stirred at 70° C. preheated bath for 2 h and the reaction mixture was acidified with 2 N HCl (~1.05 mL) and concentrated to almost dryness. The residue was triturated with MeOH (~1.5 mL) and the suspension was filtered through syringe filter. The resulting filtrate was purified by Gilson HPLC (Phenomenex Gemini, 30-60% ACN/H$_2$O+0.1% TFA) to obtain the title product after lyophilization. $^1$H NMR (400 MHz, Acetonitrile-d$_3$) δ 8.27 (s, 1H), 8.13 (dd, J=8.9, 1.6 Hz, 1H), 7.82 (s, 1H), 7.66 (dd, J=7.9, 2.3 Hz, 1H), 7.64-7.53 (m, 4H), 5.27 (s, 1H), 4.65 (m, 3H), 4.36-4.21 (m, 1H), 4.17 (d, J=9.0 Hz, 1H), 4.06 (s, 3H), 3.27 (d, J=8.2 Hz, 2H), 2.57 (d, J=6.5 Hz, 3H), 1.22 (t, J=7.1 Hz, 3H), 0.99 (s, 9H). LCMS-ESI$^+$: calc'd for C$_{33}$H$_{36}$ClN$_4$O$_3$S: 603.22 (M+H)$^+$; found: 603.33 (M+H)$^+$.

Example 61. Preparation of (S)-2-(tert-butoxy)-2-(7-(4-chlorophenyl)-5-methyl-2-(1-methyl-3-(1-(oxetan-3-yl)azetidin-3-yl)-1H-indazol-5-yl)benzo[d]thiazol-6-yl)acetic Acid (59)

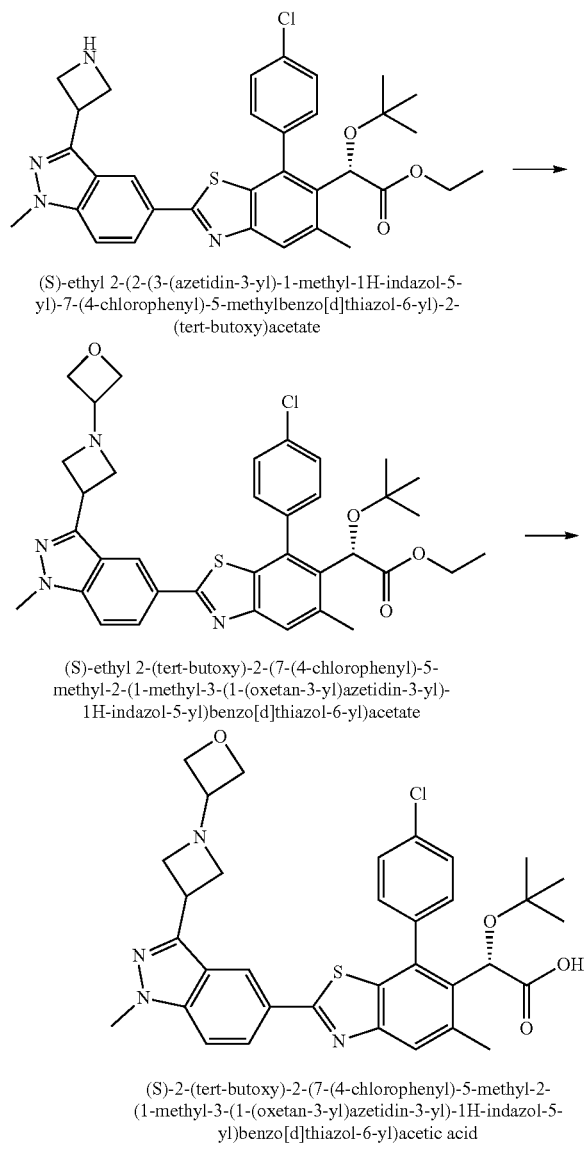

(S)-ethyl 2-(2-(3-(azetidin-3-yl)-1-methyl-1H-indazol-5-yl)-7-(4-chlorophenyl)-5-methylbenzo[d]thiazol-6-yl)-2-(tert-butoxy)acetate (S)-ethyl 2-(tert-butoxy)-2-(7-(4-chlorophenyl)-5-methyl-2-(1-methyl-3-(1-(oxetan-3-yl)azetidin-3-yl)-1H-indazol-5-yl)benzo[d]thiazol-6-yl)acetate (S)-2-(tert-butoxy)-2-(7-(4-chlorophenyl)-5-methyl-2-(1-methyl-3-(1-(oxetan-3-yl)azetidin-3-yl)-1H-indazol-5-yl)benzo[d]thiazol-6-yl)acetic acid Preparation of (S)-ethyl 2-(tert-butoxy)-2-(7-(4-chlorophenyl)-5-methyl-2-(1-methyl-3-(1-(oxetan-3-yl)azetidin-3-yl)-1H-indazol-5-yl)benzo[d]thiazol-6-yl)acetate: In a 50 mL round-bottom flask, ethyl (S)-2-(2-(3-(azetidin-3-yl)-1-methyl-1H-indazol-5-yl)-7-(4-chlorophenyl)-5-methylbenzo[d]thiazol-6-yl)-2-(tert-butoxy)acetate (0.010 g, 0.015 mmol) was dissolved in MeOH (1 mL). Oxetan-3-one (0.011 g, 0.15 mmol) was added to the reaction mixture. NaBH$_3$CN (0.01 g, 0.15 mmol) and one drop of acetic acid were added to the reaction mixture. The reaction mixture was stirred at room temperature for half an hour. After concentration, the residue was dissolved in EtOAc, washed with brine and dried over Na$_2$SO$_4$. After concentration, the crude was used for next step without further purification.

Preparation of (S)-2-(tert-butoxy)-2-(7-(4-chlorophenyl)-5-methyl-2-(1-methyl-3-(1-(oxetan-3-yl)azetidin-3-yl)-1H-indazol-5-yl)benzo[d]thiazol-6-yl)acetic acid: Prepared in a manner similar to (S)-2-(tert-butoxy)-2-(7-(4-chlorophenyl)-5-methyl-2-(1-methyl-3-(2-oxa-6-azaspiro[3.3]heptan-6-yl)-1H-indazol-5-yl)benzo[d]thiazol-6-yl)acetic acid except using (S)-ethyl 2-(tert-butoxy)-2-(7-(4-chlorophenyl)-5-methyl-2-(1-methyl-3-(1-(oxetan-3-yl)azetidin-3-yl)-1H-indazol-5-yl)benzo[d]thiazol-6-yl)acetate instead of (S)-ethyl 2-(tert-butoxy)-2-(7-(4-chlorophenyl)-5-methyl-2-(1-methyl-3-(2-oxa-6-azaspiro[3.3]heptan-6-yl)-1H-indazol-5-yl)benzo[d]thiazol-6-yl)acetate. $^1$H NMR (400 MHz, Chloroform-d) δ 1H NMR (400 MHz, Acetonitrile-d$_3$) δ 8.36 (s, 1H), 8.31-8.10 (m, 1H), 7.88 (d, J=1.0 Hz, 1H), 7.73-7.52 (m, 5H), 5.29 (s, 1H), 5.05-4.36 (m, 4H), 4.17-4.04 (m, 4H), 3.02 (dd, J=8.6, 5.5 Hz, 1H), 2.59 (d, J=0.8 Hz, 4H), 1.00 (s, 9H).

Example 62. Preparation of (S)-2-(2-(3-(1-(tert-butyl)azetidin-3-yl)-1-methyl-1H-indazol-5-yl)-7-(4-chlorophenyl)-5-methylbenzo[d]thiazol-6-yl)-2-cyclopropoxyacetic Acid (60)

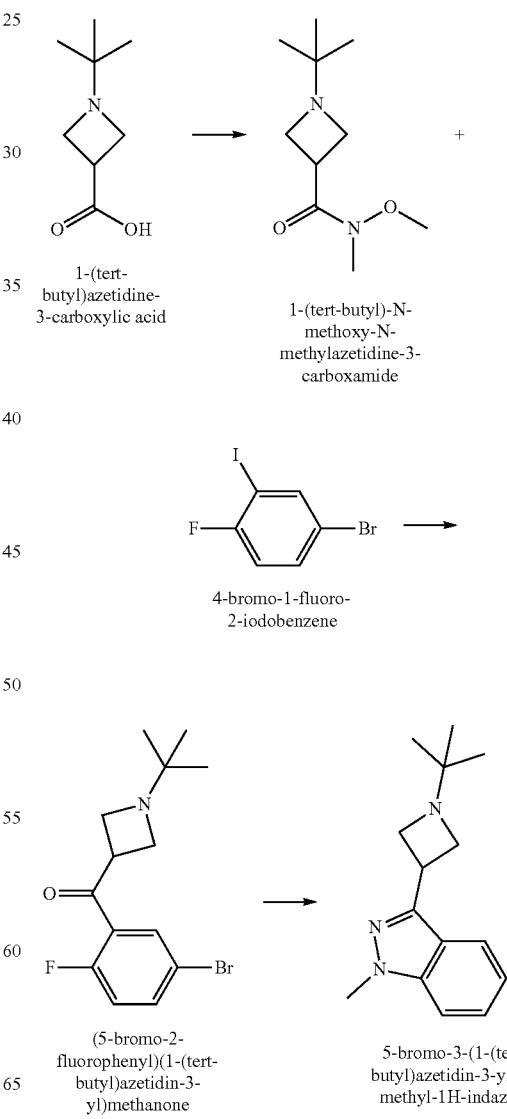

1-(tert-butyl)azetidine-3-carboxylic acid 1-(tert-butyl)-N-methoxy-N-methylazetidine-3-carboxamide 4-bromo-1-fluoro-2-iodobenzene (5-bromo-2-fluorophenyl)(1-(tert-butyl)azetidin-3-yl)methanone 5-bromo-3-(1-(tert-butyl)azetidin-3-yl)-1-methyl-1H-indazole

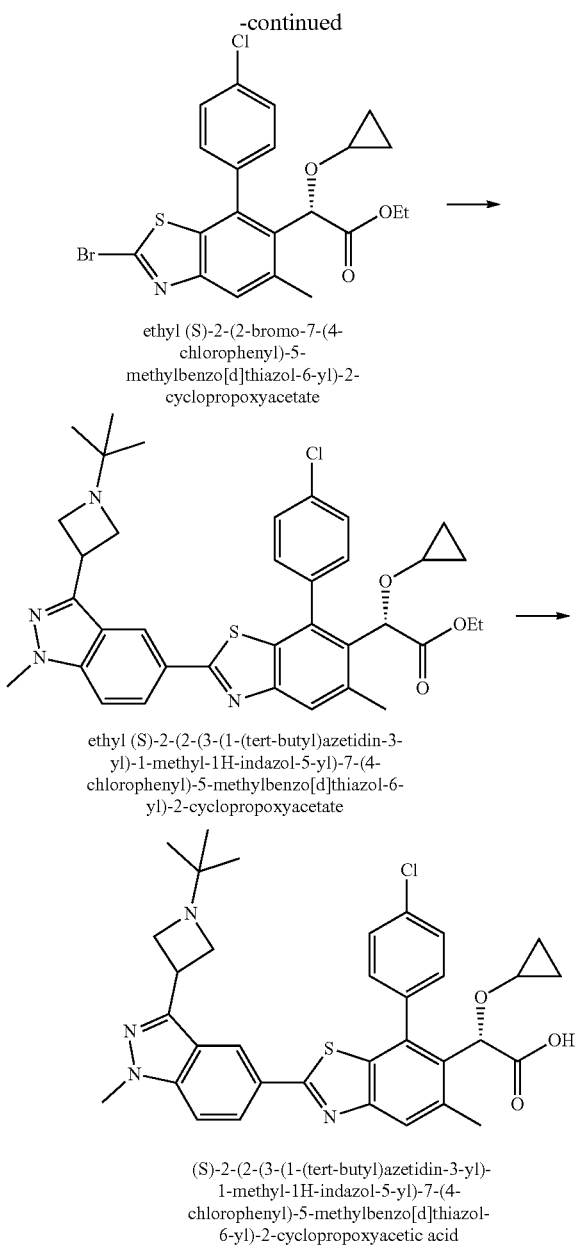

ethyl (S)-2-(2-bromo-7-(4-chlorophenyl)-5-methylbenzo[d]thiazol-6-yl)-2-cyclopropoxyacetate ethyl (S)-2-(2-(3-(1-(tert-butyl)azetidin-3-yl)-1-methyl-1H-indazol-5-yl)-7-(4-chlorophenyl)-5-methylbenzo[d]thiazol-6-yl)-2-cyclopropoxyacetate (S)-2-(2-(3-(1-(tert-butyl)azetidin-3-yl)-1-methyl-1H-indazol-5-yl)-7-(4-chlorophenyl)-5-methylbenzo[d]thiazol-6-yl)-2-cyclopropoxyacetic acid Preparation of 1-(tert-butyl)-N-methoxy-N-methylazetidine-3-carboxamide: 1-(tert-butyl)azetidine-3-carboxylic acid (0.50 g, 3.18 mmol) was dissolved in 2-methyltetrahydrofuran (5 ml) then treated with carbonyl diimidazole (0.618 g, 3.82) and diisopropylethylamine (1.2 ml, 7.0 mmol). The reaction stirred for 30 minutes at room temperature then the N,O-dimethylhydroxylamine hydrochloride (0.213 g, 3.50 mmol) was added. The reaction continued for 15 hours at room temperature. The reaction mixture was concentrated and suspended in ethyl ether and washed with saturated sodium bicarbonate solution. The aqueous layer was back-extracted with ethyl ether (6×), combined organic layer was dried ($MgSO_4$), filtered and concentrated to give desired product with imidazole contamination. $^1$H NMR (400 MHz, Chloroform-d) δ 3.63 (s, 3H), 3.60-3.51 (m, 1H), 3.46 (t, J=7.2 Hz, 2H), 3.38 (t, J=7.6 Hz, 2H), 3.16 (s, 3H), 0.97 (s, 9H).

Preparation of (5-bromo-2-fluorophenyl)(1-(tert-butyl)azetidin-3-yl)methanone: A solution of 4-bromo-1-fluoro-2-iodobenzene (1.50 g, 4.99 mmol) in 2-Me-THF (12 mL) was stirred in dry ice-acetone bath while 1.6 M n-BuLi in hex (3.4 mL, 5.49 mmol) was added dropwise over ~2 min. After 20 min, a solution of 1-(tert-butyl)-N-methoxy-N-methyl-azetidine-3-carboxamide (333 mg, 1.66 mmol) in 2-Me-THF (3 mL) was added slowly. Reaction mixture was stirred at −78° C. for 2 hours. LCMS and TLC show desired product. Reaction was quenched with brine, extracted with ethyl acetate (2×), dried ($MgSO_4$), filtered, concentrated and purified by CombiFlash (40 g Gold, 0-8% $MeOH/CH_2Cl_2$) to give a yellow oil. LCMS-ESI+: calc'd for $C_{14}H_{18}BrFNO$: 314.1 $(M+H)^+$; found: 314.0 $(M+H)^+$.

Preparation of 5-bromo-3-(1-(tert-butyl)azetidin-3-yl)-1-methyl-1H-indazole: To a solution of the (5-bromo-2-fluorophenyl)(1-(tert-butyl)azetidin-3-yl)methanone (279 mg, 0.889 mmol), p-toluenesulfonic acid monohydrate (13 mg, 0.075 mmol) in dioxane (3.3 mL) was added methylhydrazine (0.32 mL, 6.1 mmol) and the reaction mixture was heated in the microwave at 150° C. for 1 hour. Reaction mixture was cooled, concentrated and purified by CombiFlash (24 g Gold, 0-10% $MeOH/CH_2Cl_2$) to give an off-white film. LCMS-ESI$^+$: calc'd for $C_{15}H_{21}BrN_3$: 322.1 $(M+H)^+$; found: 322.1 $(M+H)^+$.

Preparation of ethyl (S)-2-(2-(3-(1-(tert-butyl)azetidin-3-yl)-1-methyl-1H-indazol-5-yl)-7-(4-chlorophenyl)-5-methylbenzo[d]thiazol-6-yl)-2-cyclopropoxyacetate: A 10 mL round bottom flash was charged with 5-bromo-3-(1-(tert-butyl)azetidin-3-yl)-1-methyl-1H-indazole (52 mg, 0.161 mmol), bis(neopentyl glycolato)diboron (47 mg, 0.210 mmol), $PdCl_2(Amphos)_2$ (11 mg, 0.016 mmol) and potassium propionate (812 mg, 0.726 mmol) and flushed with nitrogen. De-gassed dioxane (1.0 mL) was added under a nitrogen atmosphere and reaction mixture was heated to 80° C. for 2 h, then cooled to ~50° C.

To the above reaction mixture, 2M potassium carbonate (0.40 mL, 0.806 mmol) and ethyl (S)-2-(2-bromo-7-(4-chlorophenyl)-5-methylbenzo[d]thiazol-6-yl)-2-cyclopropoxyacetate (25 mg, 0.052 mmol) were added and the reaction heated to 80° C. After 2 h, LCMS showed desired product mass. Reaction was cooled to room temperature, diluted with ethyl acetate, washed with brine, dried ($MgSO_4$), filtered and concentrated. The resulting residue was dissolved in DMF (1.8 mL), filtered through a syringe filter and purified by Gilson HPLC (Gemini, 5-100% ACN/$H_2O$+0.1% TFA). Product was lyophilized overnight to give a yellow powder. LCMS-ESI+: calc'd for $C_{36}H_{40}ClN_4O_3S$: 643.2 $(M+H)^+$; found: 643.3 $(M+H)^+$.

Preparation of (S)-2-(2-(3-(1-(tert-butyl)azetidin-3-yl)-1-methyl-1H-indazol-5-yl)-7-(4-chlorophenyl)-5-methylbenzo[d]thiazol-6-yl)-2-cyclopropoxyacetic acid: A solution of ethyl (S)-2-(2-(3-(1-(tert-butyl)azetidin-3-yl)-1-methyl-1H-indazol-5-yl)-7-(4-chlorophenyl)-5-methylbenzo[d]thiazol-6-yl)-2-cyclopropoxyacetate (5.2 mg, 0.008 mmol), sodium hydroxide (5M, 16 µL, 0.08 mmol) in MeOH (0.2 mL) and THF (1.0 mL) was heated at 45° C. for 2 hours. Reaction mixture was concentrated, dissolved in DMF (1.5 mL), filtered through a syringe filter and purified by Gilson HPLC (Gemini, 5-100% ACN/$H_2O$+0.1% TFA). Product was lyophilized to give an off-white powder. $^1$H NMR (400 MHz, Methanol-$d_4$) δ 8.40 (d, J=13.1 Hz, 1H), 8.21-8.12 (m, 1H), 7.86 (s, 1H), 7.69 (t, J=8.4 Hz, 1H), 7.64-7.48 (m, 4H), 5.17 (s, 1H), 4.75-4.55 (m, 2H), 4.50-4.38 (m, 2H), 4.16-4.09 (m, 3H), 3.27 (m, 1H), 2.57 (s, 3H), 1.45-1.36 (m, 9H), 0.44-0.25 (m, 4H). LCMS-ESI$^+$: calc'd for $C_{34}H_{35}ClN_4O_3S$ $(M+H)^+$: 615.2; found: 615.2 $(M+H)^+$.

Example 63. Preparation of (S)-2-(tert-butoxy)-2-(7-(4-chlorophenyl)-2-(3-(1-(1,3-dimethoxypropan-2-yl)azetidin-3-yl)-1-methyl-1H-indazol-5-yl)-5-methylbenzo[d]thiazol-6-yl)acetic Acid (61)

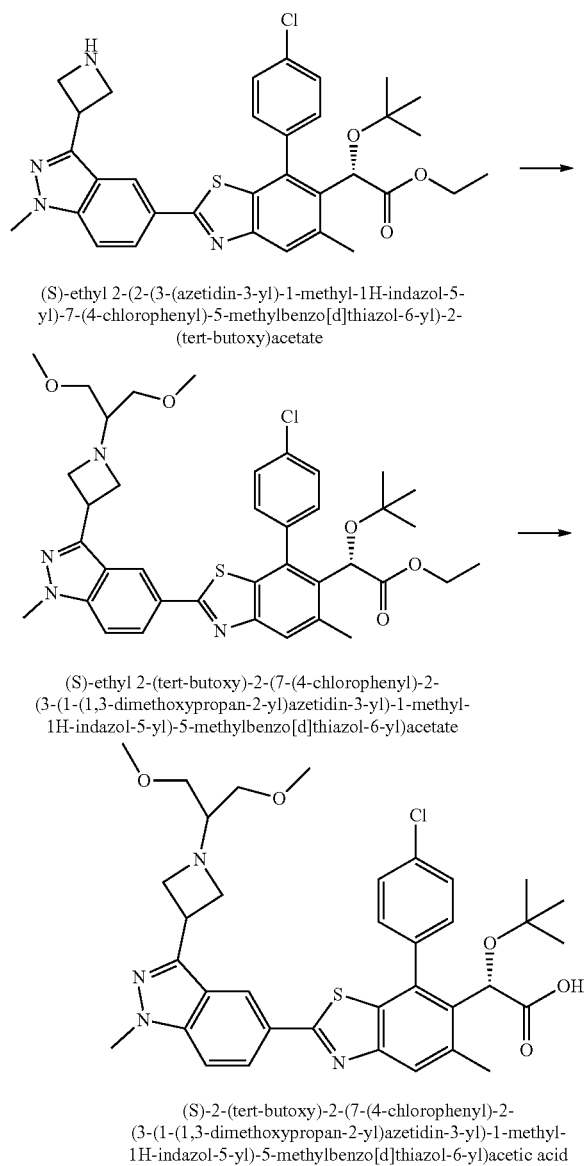

(S)-ethyl 2-(2-(3-(azetidin-3-yl)-1-methyl-1H-indazol-5-yl)-7-(4-chlorophenyl)-5-methylbenzo[d]thiazol-6-yl)-2-(tert-butoxy)acetate (S)-ethyl 2-(tert-butoxy)-2-(7-(4-chlorophenyl)-2-(3-(1-(1,3-dimethoxypropan-2-yl)azetidin-3-yl)-1-methyl-1H-indazol-5-yl)-5-methylbenzo[d]thiazol-6-yl)acetate (S)-2-(tert-butoxy)-2-(7-(4-chlorophenyl)-2-(3-(1-(1,3-dimethoxypropan-2-yl)azetidin-3-yl)-1-methyl-1H-indazol-5-yl)-5-methylbenzo[d]thiazol-6-yl)acetic acid Preparation of (S)-ethyl 2-(tert-butoxy)-2-(7-(4-chlorophenyl)-2-(3-(1-(1,3-dimethoxypropan-2-yl)azetidin-3-yl)-1-methyl-1H-indazol-5-yl)-5-methylbenzo[d]thiazol-6-yl)acetate: In a 50 mL round-bottom flask, (S)-ethyl 2-(2-(3-(azetidin-3-yl)-1-methyl-1H-indazol-5-yl)-7-(4-chlorophenyl)-5-methylbenzo[d]thiazol-6-yl)-2-(tert-butoxy)acetate (0.010 g, 0.015 mmol) was dissolved in MeOH (1 mL). 1,3-Dimethoxypropan-2-one (0.018 g, 0.15 mmol) was added to the reaction mixture. NaBH$_3$CN (0.01 g, 0.15 mmol) and one drop of acetic acid were added to the reaction mixture. The reaction mixture was stirred at room temperature for half an hour. After concentration, the residue was dissolved in EtOAc, washed with brine and dried over Na$_2$SO$_4$. After concentration, the crude was used for next step without further purification.

Preparation of (S)-2-(tert-butoxy)-2-(7-(4-chlorophenyl)-2-(3-(1-(1,3-dimethoxypropan-2-yl)azetidin-3-yl)-1-methyl-1H-indazol-5-yl)-5-methylbenzo[d]thiazol-6-yl)acetic acid: Prepared in a manner similar to (S)-2-(tert-butoxy)-2-(7-(4-chlorophenyl)-5-methyl-2-(1-methyl-3-(2-oxa-6-azaspiro[3.3]heptan-6-yl)-1H-indazol-5-yl)benzo[d]thiazol-6-yl)acetic acid except using (S)-ethyl 2-(tert-butoxy)-2-(7-(4-chlorophenyl)-2-(3-(1-(1,3-dimethoxypropan-2-yl)azetidin-3-yl)-1-methyl-1H-indazol-5-yl)-5-methylbenzo[d]thiazol-6-yl)acetate instead of (S)-ethyl 2-(tert-butoxy)-2-(7-(4-chlorophenyl)-5-methyl-2-(1-methyl-3-(2-oxa-6-azaspiro[3.3]heptan-6-yl)-1H-indazol-5-yl)benzo[d]thiazol-6-yl)acetate. $^1$H NMR (400 MHz, Acetonitrile-d3) δ 8.33 (s, 1H), 8.17 (d, J=8.7 Hz, 1H), 7.87 (d, J=1.0 Hz, 1H), 7.75-7.55 (m, 5H), 5.29 (s, 1H), 4.62 (d, J=23.4 Hz, 4H), 4.08 (s, 3H), 3.65 (s, 5H), 3.36 (d, J=1.1 Hz, 6H), 3.01 (s, 2H), 2.59 (s, 3H), 1.00 (s, 9H).

Example 64. (2S)-2-(tert-butoxy)-2-(2-(3-(1-(tert-butoxycarbonyl)pyrrolidin-3-yl)-1-methyl-1H-indazol-5-yl)-7-(4-chlorophenyl)-5-methylbenzo[d]thiazol-6-yl)acetic Acid (62)

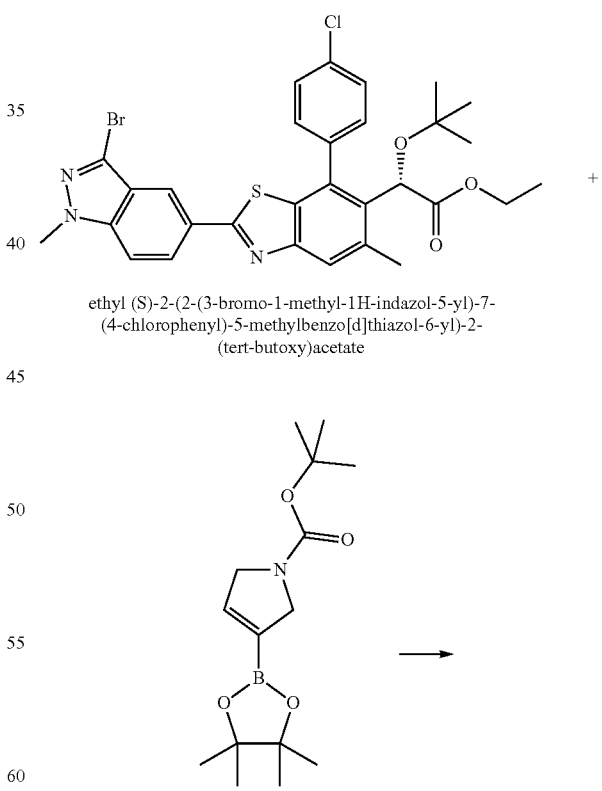

ethyl (S)-2-(2-(3-bromo-1-methyl-1H-indazol-5-yl)-7-(4-chlorophenyl)-5-methylbenzo[d]thiazol-6-yl)-2-(tert-butoxy)acetate tert-butyl 3-(4,4,5,5-tetramethyl-1,3,2-dioxaborolan-2-yl)-2,5-dihydro-1H-pyrrole-1-carboxylate

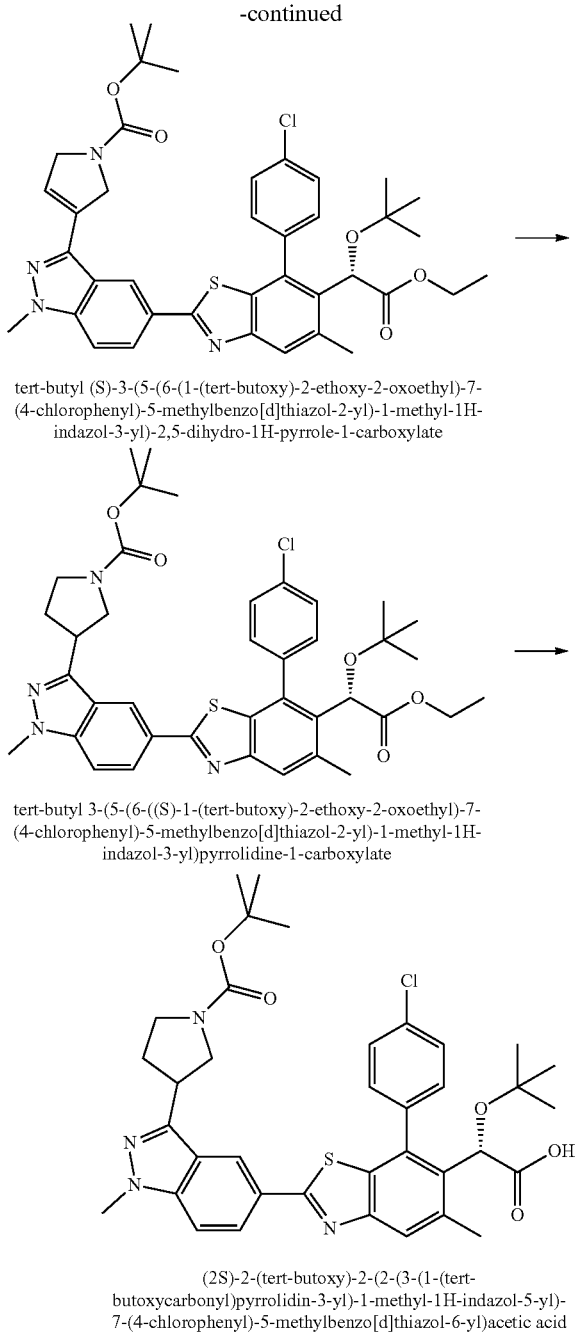

tert-butyl (S)-3-(5-(6-(1-(tert-butoxy)-2-ethoxy-2-oxoethyl)-7-(4-chlorophenyl)-5-methylbenzo[d]thiazol-2-yl)-1-methyl-1H-indazol-3-yl)-2,5-dihydro-1H-pyrrole-1-carboxylate tert-butyl 3-(5-(6-((S)-1-(tert-butoxy)-2-ethoxy-2-oxoethyl)-7-(4-chlorophenyl)-5-methylbenzo[d]thiazol-2-yl)-1-methyl-1H-indazol-3-yl)pyrrolidine-1-carboxylate (2S)-2-(tert-butoxy)-2-(2-(3-(1-(tert-butoxycarbonyl)pyrrolidin-3-yl)-1-methyl-1H-indazol-5-yl)-7-(4-chlorophenyl)-5-methylbenzo[d]thiazol-6-yl)acetic acid Preparation of tert-butyl (S)-3-(5-(6-(1-(tert-butoxy)-2-ethoxy-2-oxoethyl)-7-(4-chlorophenyl)-5-methylbenzo[d]thiazol-2-yl)-1-methyl-1H-indazol-3-yl)-2,5-dihydro-1H-pyrrole-1-carboxylate: A mixture of ethyl (S)-2-(2-(3-bromo-1-methyl-1H-indazol-5-yl)-7-(4-chlorophenyl)-5-methylbenzo[d]thiazol-6-yl)-2-(tert-butoxy)acetate (203.7 mg, 0.325 mmol), tert-butyl 3-(4,4,5,5-tetramethyl-1,3,2-dioxaborolan-2-yl)-2,5-dihydro-1H-pyrrole-1-carboxylate (155.9 mg, 0.528 mmol), tetrakis(triphenylphosphine)palladium(0) (38.6 mg, 0.033 mmol), and potassium carbonate (135.3 mg, 0.979 mmol), water (1 mL), and dioxane (4 mL) was placed in a microwave vial and the resulting mixture was reacted in a microwave reactor at 110° C. for 30 min After the reaction mixture was diluted with ethyl acetate and washed with water (×2), and the aqueous fractions were extracted with ethyl acetate (×1), the organic fractions were combined, dried ($Na_2SO_4$), and concentrated. The residue was purified by Combiflash (40 g, Gold, 0-80% EtOAc/Hex) to obtain the title product. LCMS-ESI: calc'd for $C_{39}H_{44}ClN_4O_5S$: 715.27 $(M+H)^+$; found: 715.06 $(M+H)^+$.

Preparation of tert-butyl 3-(5-(6-((S)-1-(tert-butoxy)-2-ethoxy-2-oxoethyl)-7-(4-chlorophenyl)-5-methylbenzo[d]thiazol-2-yl)-1-methyl-1H-indazol-3-yl)pyrrolidine-1-carboxylate: A mixture of tert-butyl (S)-3-(5-(6-(1-(tert-butoxy)-2-ethoxy-2-oxoethyl)-7-(4-chlorophenyl)-5-methylbenzo[d]thiazol-2-yl)-1-methyl-1H-indazol-3-yl)-2,5-dihydro-1H-pyrrole-1-carboxylate (213.8 mg, 0.299 mmol) and 5% Rhodium on alumina (43.7 mg) in ethanol (10 mL) was stirred under $H_2$ atmosphere for 3 h. The reaction mixture was filtered through celite pad and the filtrate was concentrated to dryness. The residue and 5% Rhodium on alumina (103 mg) in ethanol (10 mL) was again stirred under $H_2$ atmosphere for 18 h. The reaction mixture was filtered through celite pad and the filtrate was concentrated to dryness to obtain the crude title product, which was used for the next reaction. LCMS-ESI: calc'd for $C_{39}H_{46}ClN_4O_5S$: 717.29 $(M+H)^+$; found: 717.08 $(M+H)^+$.

Preparation of (2S)-2-(tert-butoxy)-2-(2-(3-(1-(tert-butoxycarbonyl)pyrrolidin-3-yl)-1-methyl-1H-indazol-5-yl)-7-(4-chlorophenyl)-5-methylbenzo[d]thiazol-6-yl)acetic acid: To a solution of crude tert-butyl 3-(5-(6-((S)-1-(tert-butoxy)-2-ethoxy-2-oxoethyl)-7-(4-chlorophenyl)-5-methylbenzo[d]thiazol-2-yl)-1-methyl-1H-indazol-3-yl)pyrrolidine-1-carboxylate (10.2 mg, 0.014 mmol) in THF (0.5 mL) and MeOH (0.5 mL) was added 2 N NaOH (0.2 mL) at room temperature and kept tightly before the mixture was stirred at 50° C. for 30 h. The reaction mixture was concentrated to remove organic solvent and acidified with 2 N HCl. The resulting mixture was dissolved with DMF and MeCN (total ~3 mL), filtered through syringe filter, and purified by Gilson HPLC (Phenomenex Gemini, 60-100% ACN/$H_2O$+ 0.1% TFA) to obtain the title product after lyophilization. $^1H$ NMR (400 MHz, Acetonitrile-$d_3$) δ 8.39 (s, 1H), 8.14 (d, J=9.0 Hz, 1H), 7.87 (s, 1H), 7.67 (d, J=8.4 Hz, 1H), 7.64-7.54 (m, 4H), 5.28 (s, 1H), 4.02 (s, 3H), 3.84 (m, 1H), 3.72-3.48 (m, 3H), 3.43 (m, 1H), 2.59 (s, 3H), 2.40 (s, 1H), 2.26 (d, J=7.6 Hz, 1H), 1.50-1.41 (m, 9H), 0.99 (s, 9H). LCMS-ESI: calc'd for $C_{37}H_{42}ClN_4O_5S$: 689.26 $(M+H)^+$; found: 689.02 $(M+H)^+$.

Example 65. Preparation of (2S)-2-(tert-butoxy)-2-(7-(4-chlorophenyl)-5-methyl-2-(1-methyl-3-(1-methylpyrrolidin-3-yl)-1H-indazol-5-yl)benzo[d]thiazol-6-yl)acetic Acid (63)

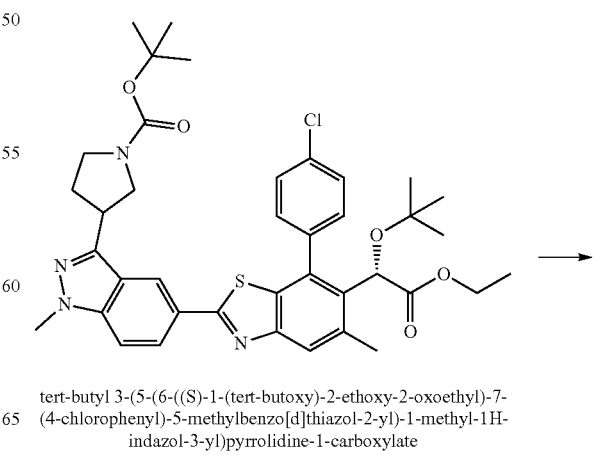

tert-butyl 3-(5-(6-((S)-1-(tert-butoxy)-2-ethoxy-2-oxoethyl)-7-(4-chlorophenyl)-5-methylbenzo[d]thiazol-2-yl)-1-methyl-1H-indazol-3-yl)pyrrolidine-1-carboxylate

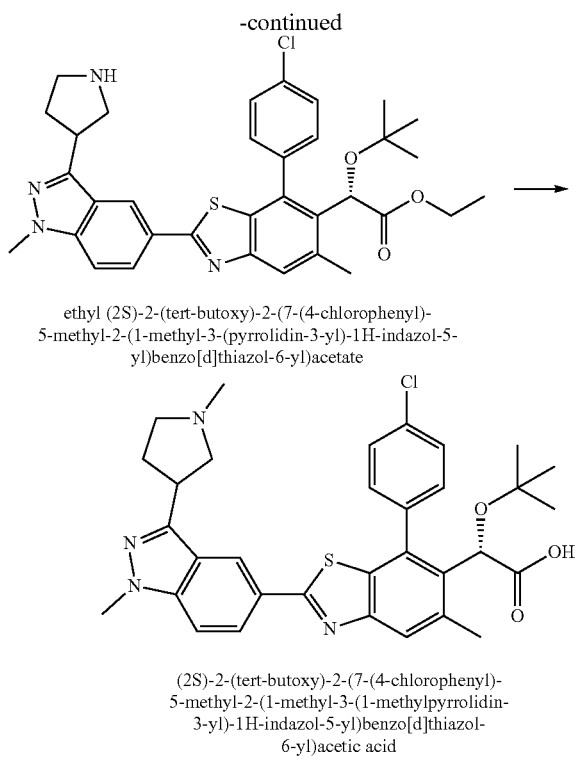

ethyl (2S)-2-(tert-butoxy)-2-(7-(4-chlorophenyl)-
5-methyl-2-(1-methyl-3-(pyrrolidin-3-yl)-1H-indazol-5-
yl)benzo[d]thiazol-6-yl)acetate (2S)-2-(tert-butoxy)-2-(7-(4-chlorophenyl)-
5-methyl-2-(1-methyl-3-(1-methylpyrrolidin-
3-yl)-1H-indazol-5-yl)benzo[d]thiazol-
6-yl)acetic acid Preparation of ethyl (2S)-2-(tert-butoxy)-2-(7-(4-chlorophenyl)-5-methyl-2-(1-methyl-3-(pyrrolidin-3-yl)-1H-indazol-5-yl)benzo[d]thiazol-6-yl)acetate: To a flask containing crude tert-butyl 3-(5-(6-((S)-1-(tert-butoxy)-2-ethoxy-2-oxoethyl)-7-(4-chlorophenyl)-5-methylbenzo[d]thiazol-2-yl)-1-methyl-1H-indazol-3-yl)pyrrolidine-1-carboxylate (202.6 mg, 0.282 mmol) was added 1.25 M HCl in isopropanol (15 mL) and the resulting mixture was stirred at room temperature for 24 h. The reaction mixture was concentrated and dried to obtain the crude title product, which was used for the next reaction. LCMS-ESI⁺: calc'd for $C_{34}H_{38}ClN_4O_3S$: 617.24 (M+H)⁺; found: 617.39 (M+H)⁺.

Preparation of (2S)-2-(tert-butoxy)-2-(7-(4-chlorophenyl)-5-methyl-2-(1-methyl-3-(1-methylpyrrolidin-3-yl)-1H-indazol-5-yl)benzo[d]thiazol-6-yl)acetic acid: A solution of crude ethyl (2S)-2-(tert-butoxy)-2-(7-(4-chlorophenyl)-5-methyl-2-(1-methyl-3-(pyrrolidin-3-yl)-1H-indazol-5-yl)benzo[d]thiazol-6-yl)acetate (30.5 mg, 0.047 mmol) in acetonitrile (2 mL) was stirred at 0° C. bath as 37% formaldehyde (0.1 mL, 1.343 mmol), and sodium cyanoborohydride (~30 mg, 0.477 mmol) were added. To the reaction mixture was added ~2 drops of acetic acid. After 1 h, the reaction mixture was quenched with saturated NaHCO₃ solution and the product was extracted with dichloromethane (×2). The combined extracts were dried (Na₂SO₄) and concentrated to get crude methylated product with impurities. LCMS-ESI: calc'd for $C_{35}H_{40}ClN_4O_3S$: 631.25 (M+H)+; found: 631.40 (M+H)⁺.

The crude methylated product was dissolved in THF (0.5 mL) and MeOH (0.5 mL) was added 2 N NaOH (0.2 mL) at room temperature and kept tightly before the mixture was stirred at 70° C. for 2 h. The reaction mixture was concentrated to remove organic solvent and acidified with 2 N HCl. The resulting mixture was dissolved with DMF and MeCN (total 3 mL), filtered through syringe filter, and purified by Gilson HPLC (Phenomenex Gemini, 60-100% ACN/H₂O+ 0.1% TFA) to give a mixture of two diastereomers of (2S)-2-(tert-butoxy)-2-(7-(4-chlorophenyl)-5-methyl-2-(1-methyl-3-(1-methylpyrrolidin-3-yl)-1H-indazol-5-yl)benzo[d]thiazol-6-yl)acetic acid after lyophilization. ¹H NMR (400 MHz, Acetonitrile-d₃) δ 10.28 (s, 0.5H), 9.29-9.02 (m, 0.5H), 8.37 and 8.31 (two s, 1H), 8.19-8.05 (m, 1H), 7.84 and 7.82 (two s, 1H), 7.72-7.64 (m, 1H), 7.64-7.51 (m, 4H), 5.28 (s, 1H), 4.25 (q, J=6.2 Hz, 0.5H), 4.14 (m, 1H), 4.01 and 4.00 (two s, 3H), 3.97 (m, 0.5H), 3.93-3.74 (m, 1H), 3.46 (m, 1H), 3.25 (m, 1H), 2.99 and 2.97 (two s, 3H), 2.67 (m, 1H), 2.58 and 2.57 (two s, 3H), 2.45-2.23 (m, 1H), 0.99 (s, 9H). LCMS-ESI⁺: calc'd for $C_{33}H_{36}ClN_4O_3S$: 590.19 (M+H)⁺; found: 603.32 (M+H)⁺.

Example 66. Preparation of (2S)-2-(tert-butoxy)-2-(7-(4-chlorophenyl)-2-(3-(1-ethylpyrrolidin-3-yl)-1-methyl-1H-indazol-5-yl)-5-methylbenzo[d]thiazol-6-yl)acetic Acid (64)

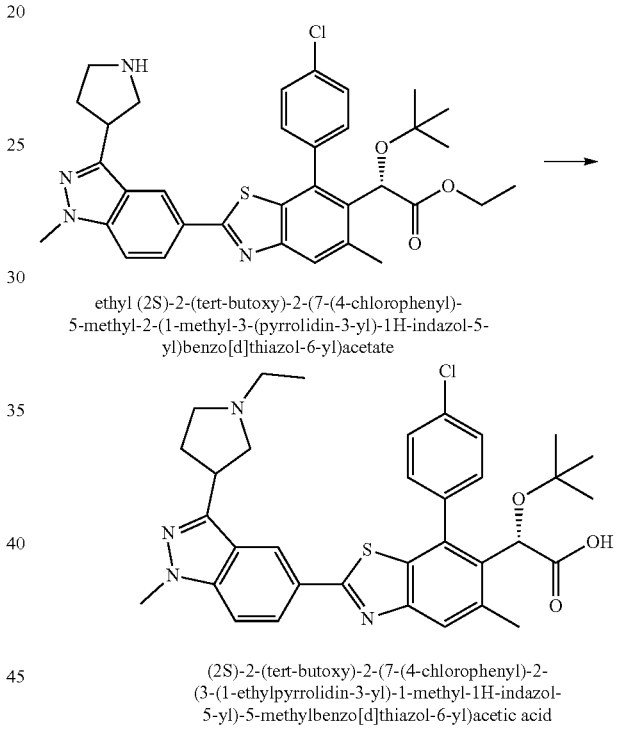

ethyl (2S)-2-(tert-butoxy)-2-(7-(4-chlorophenyl)-
5-methyl-2-(1-methyl-3-(pyrrolidin-3-yl)-1H-indazol-5-
yl)benzo[d]thiazol-6-yl)acetate (2S)-2-(tert-butoxy)-2-(7-(4-chlorophenyl)-2-
(3-(1-ethylpyrrolidin-3-yl)-1-methyl-1H-indazol-
5-yl)-5-methylbenzo[d]thiazol-6-yl)acetic acid Preparation of (2S)-2-(tert-butoxy)-2-(7-(4-chlorophenyl)-2-(3-(1-ethylpyrrolidin-3-yl)-1-methyl-1H-indazol-5-yl)-5-methylbenzo[d]thiazol-6-yl)acetic acid: A solution of crude ethyl (2S)-2-(tert-butoxy)-2-(7-(4-chlorophenyl)-5-methyl-2-(1-methyl-3-(pyrrolidin-3-yl)-1H-indazol-5-yl)benzo[d]thiazol-6-yl)acetate (30.1 mg, 0.046 mmol) in acetonitrile (2 mL) was stirred at 0° C. bath as acetaldehyde (0.05 mL, 0.89 mmol), and sodium cyanoborohydride (~30 mg, 0.477 mmol) were added. To the reaction mixture was added ~2 drops of acetic acid. After 15 min, the reaction mixture was quenched with saturated NaHCO₃ solution and the product was extracted with dichloromethane (×2). The combined extracts were dried (Na₂SO₄) and concentrated to get crude ethylated product with impurities. LCMS-ESI: calc'd for $C_{36}H_{42}ClN_4O_3S$: 645.27 (M+H)⁺; found: 645.42 (M+H)⁺.

The crude ethylated product was dissolved in THF (0.5 mL) and MeOH (0.5 mL) was added 2 N NaOH (0.2 mL) at room temperature and kept tightly before the mixture was stirred at 70° C. for 2 h. The reaction mixture was acidified with 2 N HCl (~0.25 mL), and concentrated to remove organic solvent. The resulting mixture was dissolved with methanol, filtered through syringe filter (total 3 mL), and purified by Gilson HPLC (Phenomenex Gemini, 30-70% ACN/H₂O+0.1% TFA) to give a ~2:3 mixture of two diastereomers of (2S)-2-(tert-butoxy)-2-(7-(4-chlorophenyl)-2-(3-(1-ethylpyrrolidin-3-yl)-1-methyl-1H-indazol-5-yl)-5-methylbenzo[d]thiazol-6-yl)acetic acid after lyophilization. ¹H NMR (400 MHz, Acetonitrile-d₃) δ 8.38 (d, J=11.3 Hz, 1H), 8.16 (dt, J=8.9, 1.7 Hz, 1H), 7.85 (d, J=4.2 Hz, 1H), 7.67 (d, J=8.6 Hz, 1H), 7.59 (m, 4H), 5.28 (s, 1H), 4.50-4.05 (m, 1H), 4.03 (s, 3H), 4.05-3.45 (m, 1H), 3.58-3.13 (m, 5H), 2.70-2.55 (m, 1H), 2.58 (s, 3H), 2.45-2.25 (m, 1H), 1.35 (td, J=7.3, 1.7 Hz, 3H), 0.99 (s, 9H). LCMS-ESI⁺: calc'd for C₃₄H₃₈ClN₄O₃S: 590.19 (M+H)⁺; found: 617.33 (M+H)⁺.

Example 67. Preparation of (2S)-2-(tert-butoxy)-2-(7-(4-chlorophenyl)-2-(3-(1-(2-methoxyethyl)pyrrolidin-3-yl)-1-methyl-1H-indazol-5-yl)-5-methylbenzo[d]thiazol-6-yl)acetic Acid (65)

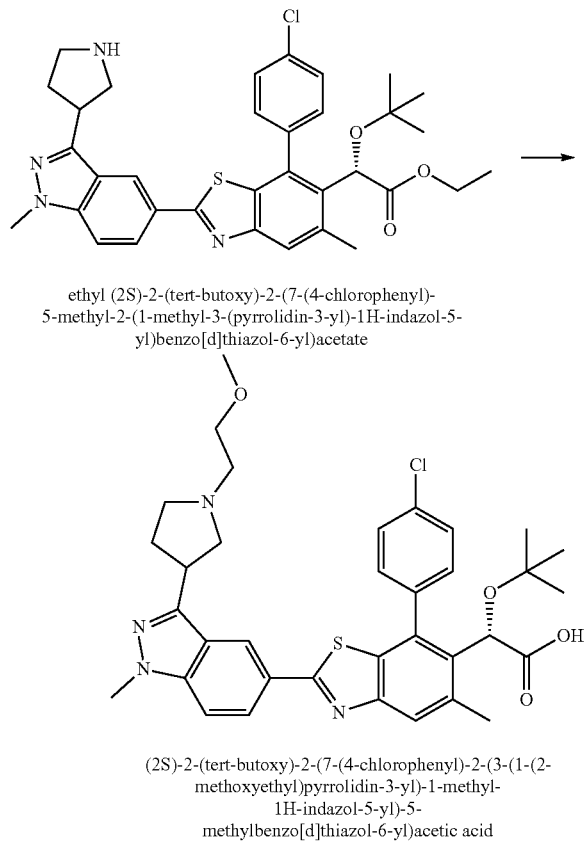

ethyl (2S)-2-(tert-butoxy)-2-(7-(4-chlorophenyl)-5-methyl-2-(1-methyl-3-(pyrrolidin-3-yl)-1H-indazol-5-yl)benzo[d]thiazol-6-yl)acetate (2S)-2-(tert-butoxy)-2-(7-(4-chlorophenyl)-2-(3-(1-(2-methoxyethyl)pyrrolidin-3-yl)-1-methyl-1H-indazol-5-yl)-5-methylbenzo[d]thiazol-6-yl)acetic acid Preparation of (2S)-2-(tert-butoxy)-2-(7-(4-chlorophenyl)-2-(3-(1-(2-methoxyethyl)pyrrolidin-3-yl)-1-methyl-1H-indazol-5-yl)-5-methylbenzo[d]thiazol-6-yl)acetic acid: A solution of crude ethyl (2S)-2-(tert-butoxy)-2-(7-(4-chlorophenyl)-5-methyl-2-(1-methyl-3-(pyrrolidin-3-yl)-1H-indazol-5-yl)benzo[d]thiazol-6-yl)acetate (30.7 mg, 0.049 mmol) in acetonitrile (2 mL) was stirred at 0° C. bath as 2-methoxyacetaldehyde (55 mg, 0.742 mmol), and sodium cyanoborohydride (~30 mg, 0.477 mmol) were added. To the reaction mixture was added ~2 drops of acetic acid. After 25 min, the reaction mixture was quenched with saturated NaHCO₃ solution and the product was extracted with dichloromethane (x2). The combined extracts were dried (Na₂SO₄) and concentrated to get crude methoxyethylated product with impurities. LCMS-ESI⁺: calc'd for C₃₇H₄₄ClN₄O₄S: 675.28 (M+H)⁺; found: 675.47 (M+H)⁺.

The crude methoxyethylated product was dissolved in THF (0.5 mL) and MeOH (0.5 mL) was added 2 N NaOH (0.2 mL) at room temperature and kept tightly before the mixture was stirred at 70° C. for 2 h. The reaction mixture acidified with acetic acid (4-5 drops), and concentrated to remove organic solvent. The resulting mixture was dissolved with methanol, filtered through syringe filter (total 3 mL), and purified by Gilson HPLC (Phenomenex Gemini, 30-70% ACN/H₂O+0.1% TFA) to give a ~2:3 mixture of two diastereomers of (2S)-2-(tert-butoxy)-2-(7-(4-chlorophenyl)-2-(3-(1-(2-methoxyethyl)pyrrolidin-3-yl)-1-methyl-1H-indazol-5-yl)-5-methylbenzo[d]thiazol-6-yl)acetic acid after lyophilization. ¹H NMR (400 MHz, Acetonitrile-d₃) δ 9.18 (s, 0.6H), 8.64 (s, 0.4H), 8.36 (d, J=18.0 Hz, 1H), 8.14 (t, J=8.6 Hz, 1H), 7.84 (d, J=6.6 Hz, 1H), 7.67 (dd, J=7.9, 2.4 Hz, 1H), 7.59 (d, J=7.3 Hz, 4H), 5.28 (s, 1H), 4.31-3.96 (m, 2H), 4.02 (two s, 3H), 3.93-3.77 (m, 1H), 3.75-3.67 (m, 2H), 3.65-3.54 (s, 1H), 3.53-3.43 (m, 3H), 3.40 (two s, 3H), 3.34 (m, 1H), 2.58 (two s, 3H), 2.48-2.19 (m, 1H), 0.99 (s, 9H). LCMS-ESI⁺: calc'd for C₃₅H₄₀ClN₄O₄S: 647.25 (M+H)⁺; found: 647.35 (M+H)⁺.

Example 68. Preparation of (S)-ethyl 2-(tert-butoxy)-2-(7-(4-chlorophenyl)-5-methyl-2-(1-methyl-3-((S)-pyrrolidin-3-yl)-1H-indazol-5-yl)benzo[d]thiazol-6-yl)acetate (66) and (S)-ethyl 2-(tert-butoxy)-2-(7-(4-chlorophenyl)-5-methyl-2-(1-methyl-3-((R)-pyrrolidin-3-yl)-1H-indazol-5-yl)benzo[d]thiazol-6-yl)acetate (67)

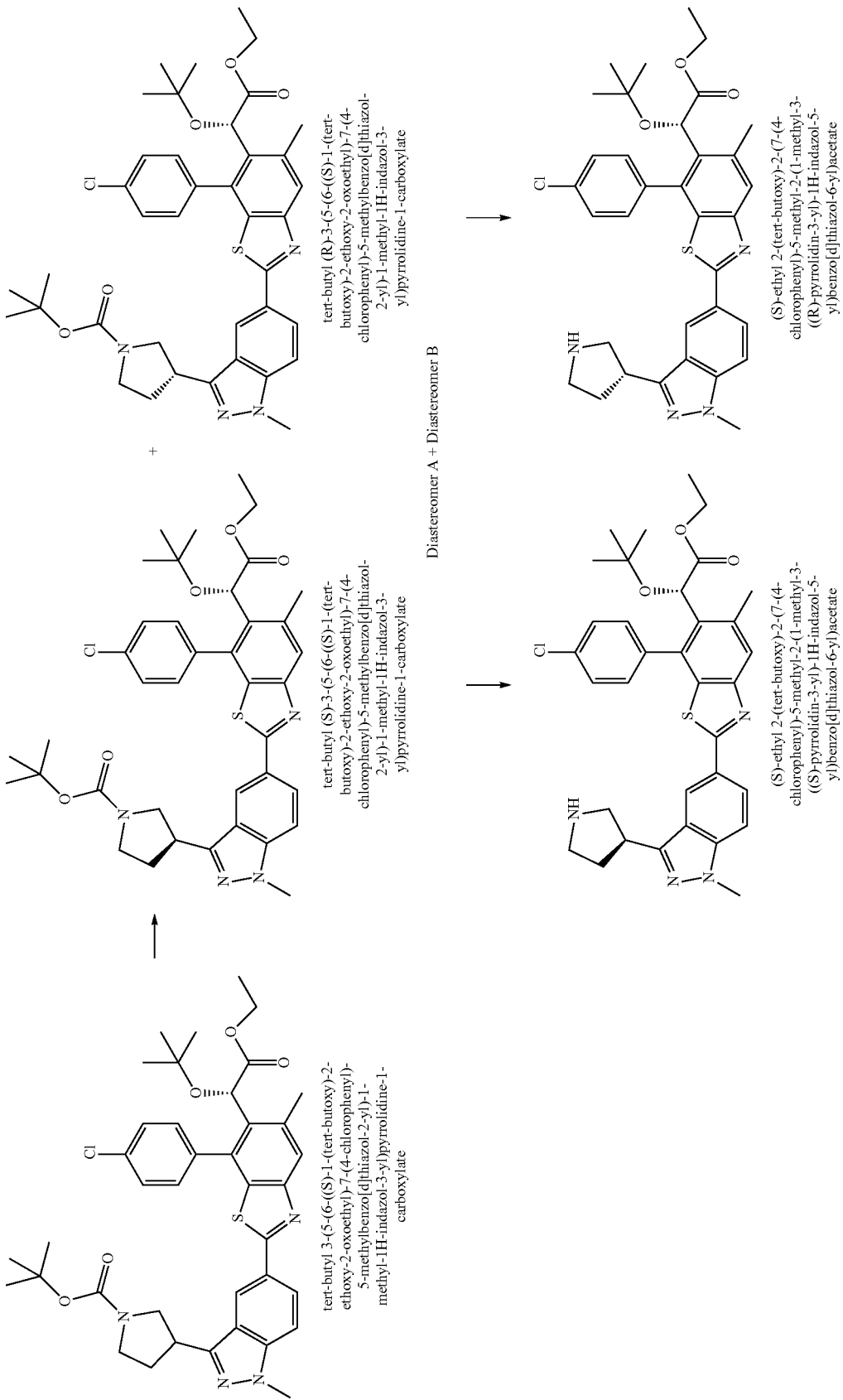

Resolution of tert-butyl (S)-3-(5-(6-((S)-1-(tert-butoxy)-2-ethoxy-2-oxoethyl)-7-(4-chlorophenyl)-5-methylbenzo[d]thiazol-2-yl)-1-methyl-1H-indazol-3-yl)pyrrolidine-1-carboxylate and tert-butyl (R)-3-(5-(6-((S)-1-(tert-butoxy)-2-ethoxy-2-oxoethyl)-7-(4-chlorophenyl)-5-methylbenzo[d]thiazol-2-yl)-1-methyl-1H-indazol-3-yl)pyrrolidine-1-carboxylate: The crude tert-butyl 3-(5-(6-((S)-1-(tert-butoxy)-2-ethoxy-2-oxoethyl)-7-(4-chlorophenyl)-5-methylbenzo[d]thiazol-2-yl)-1-methyl-1H-indazol-3-yl)pyrrolidine-1-carboxylate (908.7 mg, 1.270 mmol) was purified by Combiflash (120 g, Gold, 20-50% EtOAc/Hex) to get 760.1 mg (83%) of purified tert-butyl 3-(5-(6-((S)-1-(tert-butoxy)-2-ethoxy-2-oxoethyl)-7-(4-chlorophenyl)-5-methylbenzo[d]thiazol-2-yl)-1-methyl-1H-indazol-3-yl)pyrrolidine-1-carboxylate. tert-butyl 3-(5-(6-((S)-1-(tert-butoxy)-2-ethoxy-2-oxoethyl)-7-(4-chlorophenyl)-5-methylbenzo[d]thiazol-2-yl)-1-methyl-1H-indazol-3-yl)pyrrolidine-1-carboxylate (200 mg) was separated on chiral HPLC purification (Chiralpak ID, 150×4.6 mm, 5 micron; eluent: heptane/iPA (70/30), flow rate=1 mL/min for 15 min) to obtain diasteromer A (Rt=6.87 min) and diastereomer B (Rt=9.12 min). Stereochemistry was arbitrarily assigned. Diastereomer A assigned as tert-butyl (S)-3-(5-(6-((S)-1-(tert-butoxy)-2-ethoxy-2-oxoethyl)-7-(4-chlorophenyl)-5-methylbenzo[d]thiazol-2-yl)-1-methyl-1H-indazol-3-yl)pyrrolidine-1-carboxylate and tert-butyl (S)-3-(5-(6-((S)-1-(tert-butoxy)-2-ethoxy-2-oxoethyl)-7-(4-chlorophenyl)-5-methylbenzo[d]thiazol-2-yl)-1-methyl-1H-indazol-3-yl)pyrrolidine-1-carboxylate diastereomer B assigned as tert-butyl (R)-3-(5-(6-((S)-1-(tert-butoxy)-2-ethoxy-2-oxoethyl)-7-(4-chlorophenyl)-5-methylbenzo[d]thiazol-2-yl)-1-methyl-1H-indazol-3-yl)pyrrolidine-1-carboxylate. Diastereomer A: LCMS-ESI$^+$: calc'd for $C_{39}H_{46}ClN_4O_5S$: 717.29 (M+H)$^+$; found: 717.10 (M+H)$^+$. Diastereomer B: LCMS-ESI$^+$: calc'd for $C_{39}H_{46}ClN_4O_5S$: 717.29 (M+H)$^+$; found: 717.10 (M+H)$^+$.

Preparation of (S)-ethyl 2-(tert-butoxy)-2-(7-(4-chlorophenyl)-5-methyl-2-(1-methyl-3-((S)-pyrrolidin-3-yl)-1H-indazol-5-yl)benzo[d]thiazol-6-yl)acetate and (S)-ethyl 2-(tert-butoxy)-2-(7-(4-chlorophenyl)-5-methyl-2-(1-methyl-3-((R)-pyrrolidin-3-yl)-1H-indazol-5-yl)benzo[d]thiazol-6-yl)acetate: Separately, diastereomer A (92.0 mg, 0.128 mmol) and diastereomer B (87.8 mg, 0.122 mmol) were each dissolved in 1.25 M hydrochloric acid in isopropanol (6.5 mL and 6.0 mL, respectively) and stirred at rt for 21 h. The reaction mixtures were separately concentrated to get the crude products that were used without further purification. Stereochemistry was arbitrarily assigned. Diastereomer A assigned as (S)-ethyl 2-(tert-butoxy)-2-(7-(4-chlorophenyl)-5-methyl-2-(1-methyl-3-((S)-pyrrolidin-3-yl)-1H-indazol-5-yl)benzo[d]thiazol-6-yl)acetate and diastereomer B assigned as (S)-ethyl 2-(tert-butoxy)-2-(7-(4-chlorophenyl)-5-methyl-2-(1-methyl-3-((R)-pyrrolidin-3-yl)-1H-indazol-5-yl)benzo[d]thiazol-6-yl)acetate, respectively. Diastereomer A: LCMS-ESI$^+$: calc'd for $C_{34}H_{38}ClN_4O_3S$: 617.24 (M+H)$^+$; found: 617.37 (M+H)$^+$. Diastereomer B: LCMS-ESI$^+$: calc'd for $C_{34}H_{38}ClN_4O_3S$: 617.24 (M+H)$^+$; found: 617.38 (M+H)$^+$.

Example 69. Preparation of (S)-2-(tert-butoxy)-2-(7-(4-chlorophenyl)-2-(3-((S)-1-(2-methoxyethyl)pyrrolidin-3-yl)-1-methyl-1H-indazol-5-yl)-5-methylbenzo[d]thiazol-6-yl)acetic Acid (68)

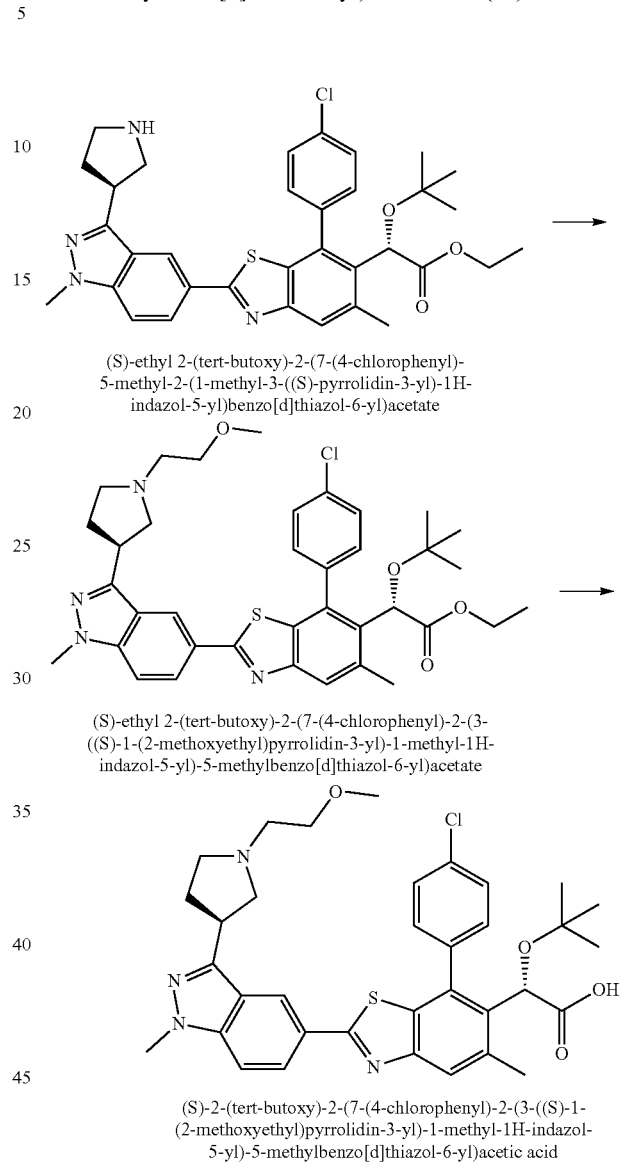

(S)-ethyl 2-(tert-butoxy)-2-(7-(4-chlorophenyl)-5-methyl-2-(1-methyl-3-((S)-pyrrolidin-3-yl)-1H-indazol-5-yl)benzo[d]thiazol-6-yl)acetate (S)-ethyl 2-(tert-butoxy)-2-(7-(4-chlorophenyl)-2-(3-((S)-1-(2-methoxyethyl)pyrrolidin-3-yl)-1-methyl-1H-indazol-5-yl)-5-methylbenzo[d]thiazol-6-yl)acetate (S)-2-(tert-butoxy)-2-(7-(4-chlorophenyl)-2-(3-((S)-1-(2-methoxyethyl)pyrrolidin-3-yl)-1-methyl-1H-indazol-5-yl)-5-methylbenzo[d]thiazol-6-yl)acetic acid Preparation of (S)-ethyl 2-(tert-butoxy)-2-(7-(4-chlorophenyl)-2-(3-((S)-1-(2-methoxyethyl)pyrrolidin-3-yl)-1-methyl-1H-indazol-5-yl)-5-methylbenzo[d]thiazol-6-yl)acetate: Prepared in a manner similar to (2S)-ethyl 2-(tert-butoxy)-2-(7-(4-chlorophenyl)-5-methyl-2-(1-methyl-3-(1-(oxetan-3-yl)pyrrolidin-3-yl)-1H-indazol-5-yl)benzo[d]thiazol-6-yl)acetate except using (S)-ethyl 2-(tert-butoxy)-2-(7-(4-chlorophenyl)-5-methyl-2-(1-methyl-3-((S)-pyrrolidin-3-yl)-1H-indazol-5-yl)benzo[d]thiazol-6-yl)acetate and 2-methoxyacetaldehyde instead of (2S)-ethyl 2-(tert-butoxy)-2-(7-(4-chlorophenyl)-5-methyl-2-(1-methyl-3-(pyrrolidin-3-yl)-1H-indazol-5-yl)benzo[d]thiazol-6-yl)acetate and oxetan-3-one.

Preparation of (S)-2-(tert-butoxy)-2-(7-(4-chlorophenyl)-2-(3-((S)-1-(2-methoxyethyl)pyrrolidin-3-yl)-1-methyl-1H-indazol-5-yl)-5-methylbenzo[d]thiazol-6-yl)acetic acid: Prepared in a manner similar to (S)-2-(tert-butoxy)-2-(7-(4- chlorophenyl)-5-methyl-2-(1-methyl-3-(2-oxa-6-azaspiro[3.3]heptan-6-yl)-1H-indazol-5-yl)benzo[d]thiazol-6-yl)acetic acid except using (S)-ethyl 2-(tert-butoxy)-2-(7-(4-chlorophenyl)-2-(3-((S)-1-(2-methoxyethyl)pyrrolidin-3-yl)-1-methyl-1H-indazol-5-yl)-5-methylbenzo[d]thiazol-6-yl)acetate instead of (S)-ethyl 2-(tert-butoxy)-2-(7-(4-chlorophenyl)-5-methyl-2-(1-methyl-3-(2-oxa-6-azaspiro[3.3]heptan-6-yl)-1H-indazol-5-yl)benzo[d]thiazol-6-yl)acetate. ¹H NMR (400 MHz, Chloroform-d) δ 1H NMR (400 MHz, Acetonitrile-d3) δ 8.39 (d, J=12.0 Hz, 1H), 8.17 (d, J=9.0 Hz, 1H), 7.86 (s, 1H), 7.67 (dd, J=8.0, 2.2 Hz, 1H), 7.60 (d, J=8.5 Hz, 4H), 5.28 (s, 1H), 4.39-4.10 (m, 2H), 4.04 (s, 3H), 3.96-3.79 (m, 1H), 3.72 (t, J=5.0 Hz, 2H), 3.48 (s, 3H), 3.43-3.35 (m, 3H), 3.34 (s, 1H), 2.59 (s, 4H), 2.37 (s, 1H), 1.00 (s, 9H).

Example 70. Preparation of (S)-2-(tert-butoxy)-2-(7-(4-chlorophenyl)-2-(3-((R)-1-(2-methoxyethyl)pyrrolidin-3-yl)-1-methyl-1H-indazol-5-yl)-5-methylbenzo[d]thiazol-6-yl)acetic Acid (69)

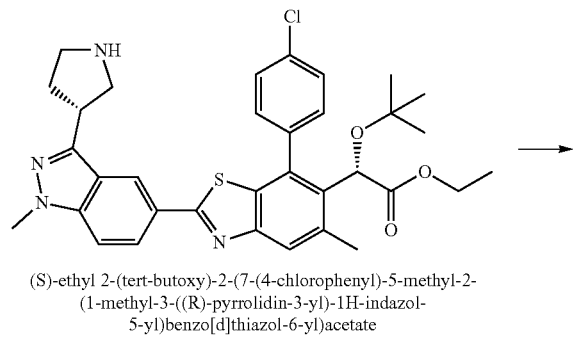

(S)-ethyl 2-(tert-butoxy)-2-(7-(4-chlorophenyl)-5-methyl-2-(1-methyl-3-((R)-pyrrolidin-3-yl)-1H-indazol-5-yl)benzo[d]thiazol-6-yl)acetate

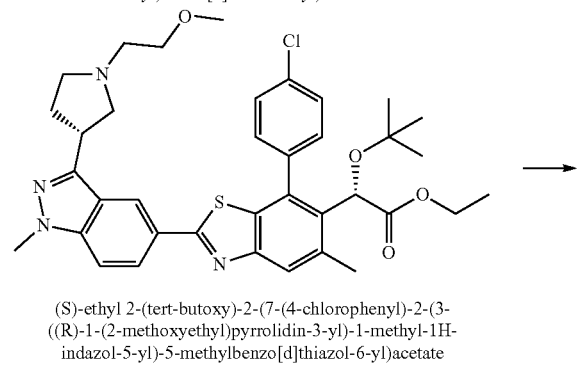

(S)-ethyl 2-(tert-butoxy)-2-(7-(4-chlorophenyl)-2-(3-((R)-1-(2-methoxyethyl)pyrrolidin-3-yl)-1-methyl-1H-indazol-5-yl)-5-methylbenzo[d]thiazol-6-yl)acetate

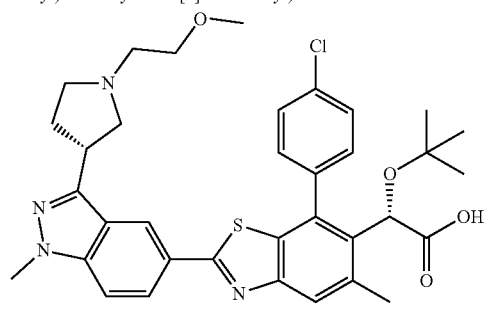

(S)-ethyl 2-(tert-butoxy)-2-(7-(4-chlorophenyl)-2-(3-((R)-1-(2-methoxyethyl)pyrrolidin-3-yl)-1-methyl-1H-indazol-5-yl)-5-methylbenzo[d]thiazol-6-yl)acetate Preparation of (S)-ethyl 2-(tert-butoxy)-2-(7-(4-chlorophenyl)-2-(3-((R)-1-(2-methoxyethyl)pyrrolidin-3-yl)-1-methyl-1H-indazol-5-yl)-5-methylbenzo[d]thiazol-6-yl)acetate: Prepared in a manner similar to (2S)-ethyl 2-(tert-butoxy)-2-(7-(4-chlorophenyl)-5-methyl-2-(1-methyl-3-(1-(oxetan-3-yl)pyrrolidin-3-yl)-1H-indazol-5-yl)benzo[d]thiazol-6-yl)acetate except using (S)-ethyl 2-(tert-butoxy)-2-(7-(4-chlorophenyl)-5-methyl-2-(1-methyl-3-((R)-pyrrolidin-3-yl)-1H-indazol-5-yl)benzo[d]thiazol-6-yl)acetate and 2-methoxyacetaldehyde instead of (2S)-ethyl 2-(tert-butoxy)-2-(7-(4-chlorophenyl)-5-methyl-2-(1-methyl-3-(pyrrolidin-3-yl)-1H-indazol-5-yl)benzo[d]thiazol-6-yl)acetate and oxetan-3-one.

Preparation of (S)-2-(tert-butoxy)-2-(7-(4-chlorophenyl)-2-(3-((R)-1-(2-methoxyethyl)pyrrolidin-3-yl)-1-methyl-1H-indazol-5-yl)-5-methylbenzo[d]thiazol-6-yl)acetic acid: Prepared in a manner similar to (S)-2-(tert-butoxy)-2-(7-(4-chlorophenyl)-5-methyl-2-(1-methyl-3-(2-oxa-6-azaspiro[3.3]heptan-6-yl)-1H-indazol-5-yl)benzo[d]thiazol-6-yl)acetic acid except using (S)-ethyl 2-(tert-butoxy)-2-(7-(4-chlorophenyl)-2-(3-((R)-1-(2-methoxyethyl)pyrrolidin-3-yl)-1-methyl-1H-indazol-5-yl)-5-methylbenzo[d]thiazol-6-yl)acetate instead of (S)-ethyl 2-(tert-butoxy)-2-(7-(4-chlorophenyl)-5-methyl-2-(1-methyl-3-(2-oxa-6-azaspiro[3.3]heptan-6-yl)-1H-indazol-5-yl)benzo[d]thiazol-6-yl)acetate. ¹H NMR (400 MHz, Acetonitrile-d3) δ 8.38 (d, J=5.9 Hz, 1H), 8.17 (d, J=8.9 Hz, 1H), 7.87 (s, 1H), 7.74-7.52 (m, 5H), 5.28 (s, 1H), 4.17 (s, 1H), 4.04 (s, 3H), 3.85 (s, 3H), 3.78-3.65 (m, 4H), 3.63-3.23 (m, 4H), 2.59 (s, 3H), 2.34 (d, J=19.2 Hz, 2H), 1.00 (s, 9H).

Example 71. Preparation of (2S)-2-(tert-butoxy)-2-(7-(4-chlorophenyl)-5-methyl-2-(1-methyl-3-(1-(oxetan-3-yl)pyrrolidin-3-yl)-1H-indazol-5-yl)benzo[d]thiazol-6-yl)acetic Acid (70)

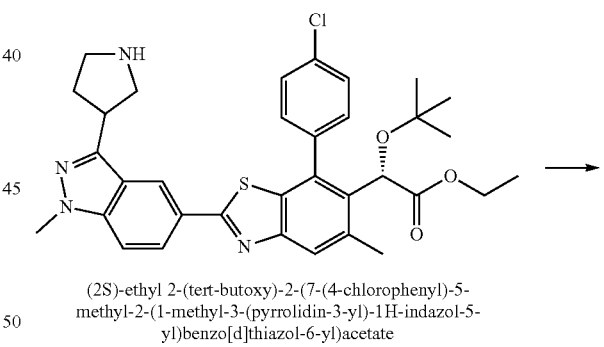

(2S)-ethyl 2-(tert-butoxy)-2-(7-(4-chlorophenyl)-5-methyl-2-(1-methyl-3-(pyrrolidin-3-yl)-1H-indazol-5-yl)benzo[d]thiazol-6-yl)acetate

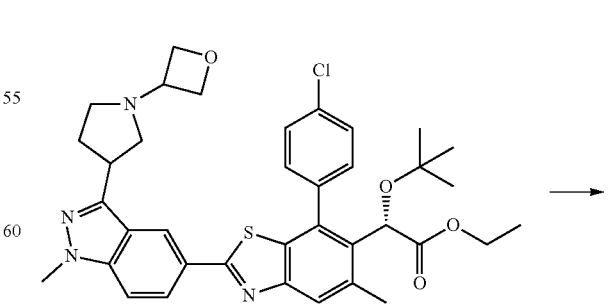

(2S)-ethyl 2-(tert-butoxy)-2-(7-(4-chlorophenyl)-5-methyl-2-(1-methyl-3-(oxetan-3-yl)pyrrolidin-3-yl)-1H-indazol-5-yl)benzo[d]thiazol-6-yl)acetate

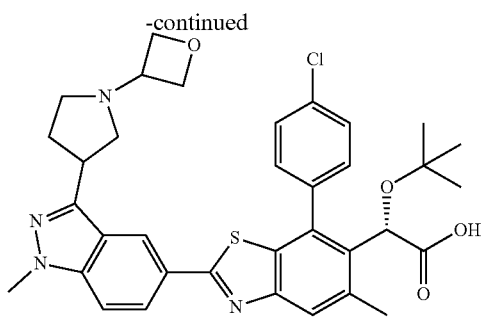

(2S)-2-(tert-butoxy)-2-(7-(4-chlorophenyl)-5-methyl-2-(1-methyl-3-(1-oxetan-3-yl)pyrrolidin-3-yl)-1H-indazol-5-yl)benzo[d]thiazol-6-yl)acetic acid Preparation of (2S)-ethyl 2-(tert-butoxy)-2-(7-(4-chlorophenyl)-5-methyl-2-(1-methyl-3-(1-(oxetan-3-yl)pyrrolidin-3-yl)-1H-indazol-5-yl)benzo[d]thiazol-6-yl)acetate: In a 50 mL round-bottom flask, (2S)-ethyl 2-(tert-butoxy)-2-(7-(4-chlorophenyl)-5-methyl-2-(1-methyl-3-(pyrrolidin-3-yl)-1H-indazol-5-yl)benzo[d]thiazol-6-yl)acetate (0.010 g, 0.015 mmol) was dissolved in MeOH (1 mL). Oxetan-3-one (0.011 g, 0.15 mmol) was added to the reaction mixture. NaBH$_3$CN (0.01 g, 0.15 mmol) and one drop of acetic acid were added to the reaction mixture. The reaction mixture was stirred at room temperature for half an hour. After concentration, the residue was dissolved in EtOAc, washed with brine and dried over Na$_2$SO$_4$. After concentration, the crude was used for next step without further purification.

Preparation of (2S)-2-(tert-butoxy)-2-(7-(4-chlorophenyl)-5-methyl-2-(1-methyl-3-(1-(oxetan-3-yl)pyrrolidin-3-yl)-1H-indazol-5-yl)benzo[d]thiazol-6-yl)acetic acid: Prepared in a manner similar to (S)-2-(tert-butoxy)-2-(7-(4-chlorophenyl)-5-methyl-2-(1-methyl-3-(2-oxa-6-azaspiro[3.3]heptan-6-yl)-1H-indazol-5-yl)benzo[d]thiazol-6-yl)acetic acid except using (2S)-ethyl 2-(tert-butoxy)-2-(7-(4-chlorophenyl)-5-methyl-2-(1-methyl-3-(1-(oxetan-3-yl)pyrrolidin-3-yl)-1H-indazol-5-yl)benzo[d]thiazol-6-yl)acetate instead of (S)-ethyl 2-(tert-butoxy)-2-(7-(4-chlorophenyl)-5-methyl-2-(1-methyl-3-(2-oxa-6-azaspiro[3.3]heptan-6-yl)-1H-indazol-5-yl)benzo[d]thiazol-6-yl)acetate. $^1$H NMR (400 MHz, Acetonitrile-d3) δ 8.42 (s, 1H), 8.18 (dt, J=9.0, 1.8 Hz, 1H), 7.87 (s, 1H), 7.77-7.50 (m, 5H), 5.29 (s, 1H), 5.01-4.82 (m, 2H), 4.76 (d, J=11.0 Hz, 2H), 4.62 (s, 1H), 4.26 (s, 1H), 4.05 (d, J=5.6 Hz, 3H), 3.25 (m, 5H), 2.68 (d, J=12.8 Hz, 1H), 2.59 (s, 3H), 2.39 (dt, J=14.1, 7.3 Hz, 1H), 1.39-1.11 (m, 1H), 1.00 (s, 9H).

Example 72. Preparation of (2S)-2-(tert-butoxy)-2-(7-(4-chlorophenyl)-2-(3-(1-cyclobutylpyrrolidine-3-yl)-1-methyl-1H-indazol-5-yl)-5-methylbenzo[d]thiazol-6-yl)acetic Acid (71)

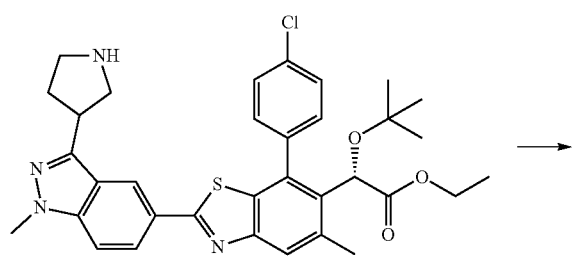

(2S)-ethyl 2-(tert-butoxy)-2-(7-(4-chlorophenyl)-5-methyl-2-(1-methyl-3-(pyrrolidin-3-yl)-1H-indazol-5-yl)benzo[d]thiazol-6-yl)acetate

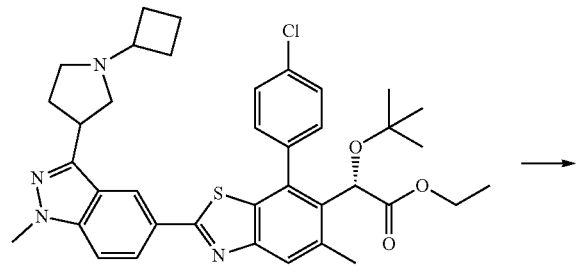

(2S)-ethyl 2-(tert-butoxy)-2-(7-(4-chlorophenyl)-2-(3-(1-cyclobutylpyrrolidin-3-yl)-1-methyl-1H-indazol-5-yl)-5-methylbenzo[d]thiazol-6-yl)acetate

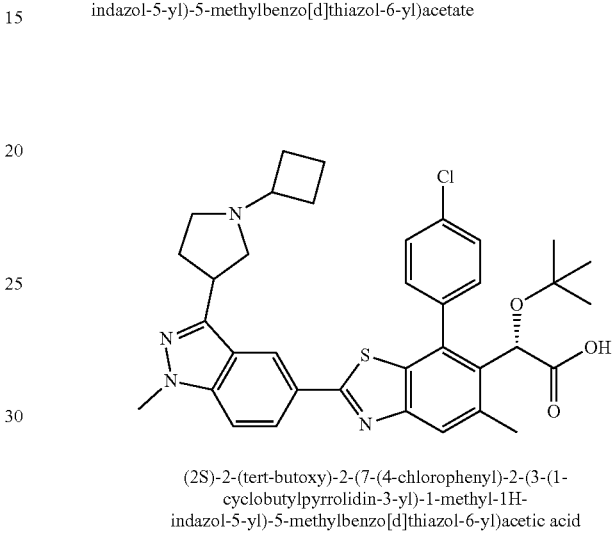

(2S)-2-(tert-butoxy)-2-(7-(4-chlorophenyl)-2-(3-(1-cyclobutylpyrrolidin-3-yl)-1-methyl-1H-indazol-5-yl)-5-methylbenzo[d]thiazol-6-yl)acetic acid Preparation of (2S)-ethyl 2-(tert-butoxy)-2-(7-(4-chlorophenyl)-2-(3-(1-cyclobutylpyrrolidine-3-yl)-1-methyl-1H-indazol-5-yl)-5-methylbenzo[d]thiazol-6-yl)acetate: Prepared in a manner similar to (2S)-ethyl 2-(tert-butoxy)-2-(7-(4-chlorophenyl)-5-methyl-2-(1-methyl-3-(1-(oxetan-3-yl)pyrrolidin-3-yl)-1H-indazol-5-yl)benzo[d]thiazol-6-yl)acetate except using cyclobutanone instead of Oxetan-3-one.

Preparation of (2S)-2-(tert-butoxy)-2-(7-(4-chlorophenyl)-2-(3-(1-cyclobutylpyrrolidine-3-yl)-1-methyl-1H-indazol-5-yl)-5-methylbenzo[d]thiazol-6-yl)acetic acid: Prepared in a manner similar to (S)-2-(tert-butoxy)-2-(7-(4-chlorophenyl)-5-methyl-2-(1-methyl-3-(2-oxa-6-azaspiro[3.3]heptan-6-yl)-1H-indazol-5-yl)benzo[d]thiazol-6-yl)acetic acid except using (2S)-ethyl 2-(tert-butoxy)-2-(7-(4-chlorophenyl)-2-(3-(1-cyclobutylpyrrolidine-3-yl)-1-methyl-1H-indazol-5-yl)-5-methylbenzo[d]thiazol-6-yl)acetate instead of (S)-ethyl 2-(tert-butoxy)-2-(7-(4-chlorophenyl)-5-methyl-2-(1-methyl-3-(2-oxa-6-azaspiro[3.3]heptan-6-yl)-1H-indazol-5-yl)benzo[d]thiazol-6-yl)acetate. $^1$H NMR (400 MHz, Acetonitrile-d3) δ 8.40 (dd, J=11.8, 1.6 Hz, 1H), 8.18 (ddt, J=8.9, 4.0, 1.6 Hz, 1H), 7.98-7.78 (m, 1H), 7.73-7.52 (m, 5H), 5.29 (s, 1H), 4.28-4.07 (m, 1H), 4.05 (d, J=3.1 Hz, 3H), 3.91 (p, J=9.4, 8.7 Hz, 1H), 3.70 (s, 1H), 3.56-3.33 (m, 1H), 3.24-3.13 (m, 1H), 2.91 (m, 5H), 2.59 (s, 3H), 2.34 (dq, J=8.1, 4.5, 3.2 Hz, 5H), 1.00 (s, 9H).

Example 73. Preparation of (2S)-2-(tert-butoxy)-2-(7-(4-chlorophenyl)-2-(3-(1-(methoxycarbonyl)pyrrolidin-3-yl)-1-methyl-1H-indazol-5-yl)-5-methyl-benzo[d]thiazol-6-yl)acetic Acid (72)

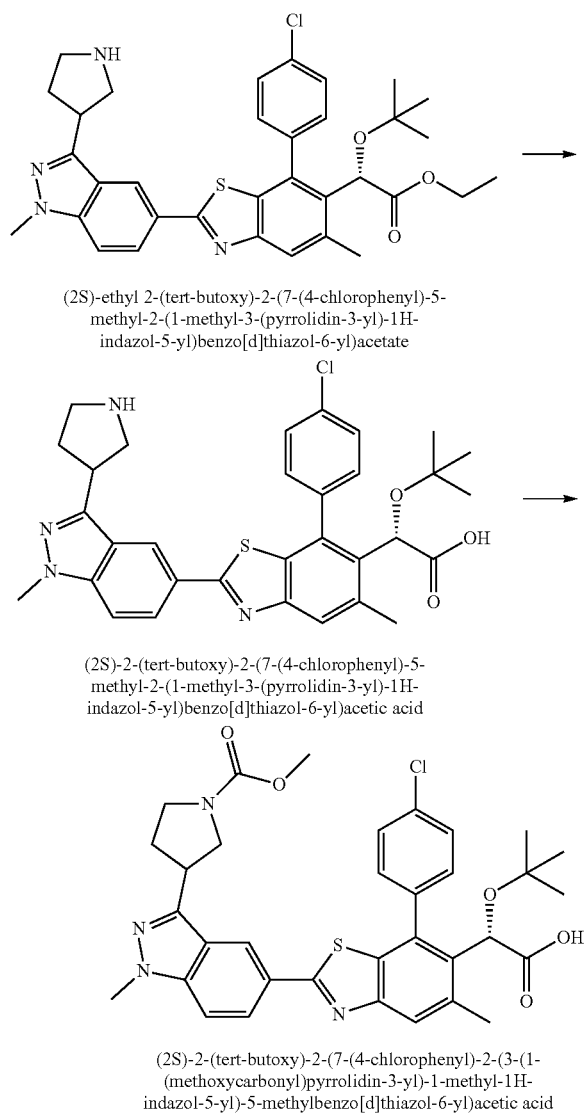

(2S)-ethyl 2-(tert-butoxy)-2-(7-(4-chlorophenyl)-5-methyl-2-(1-methyl-3-(pyrrolidin-3-yl)-1H-indazol-5-yl)benzo[d]thiazol-6-yl)acetate (2S)-2-(tert-butoxy)-2-(7-(4-chlorophenyl)-5-methyl-2-(1-methyl-3-(pyrrolidin-3-yl)-1H-indazol-5-yl)benzo[d]thiazol-6-yl)acetic acid (2S)-2-(tert-butoxy)-2-(7-(4-chlorophenyl)-2-(3-(1-(methoxycarbonyl)pyrrolidin-3-yl)-1-methyl-1H-indazol-5-yl)-5-methylbenzo[d]thiazol-6-yl)acetic acid Preparation of (2S)-2-(tert-butoxy)-2-(7-(4-chlorophenyl)-5-methyl-2-(1-methyl-3-(pyrrolidin-3-yl)-1H-indazol-5-yl)benzo[d]thiazol-6-yl)acetic acid Prepared in a manner similar to (S)-2-(tert-butoxy)-2-(7-(4-chlorophenyl)-5-methyl-2-(1-methyl-3-(2-oxa-6-azaspiro[3.3]heptan-6-yl)-1H-indazol-5-yl)benzo[d]thiazol-6-yl)acetic acid except using (2S)-ethyl 2-(tert-butoxy)-2-(7-(4-chlorophenyl)-5-methyl-2-(1-methyl-3-(pyrrolidin-3-yl)-1H-indazol-5-yl)benzo[d]thiazol-6-yl)acetate instead of (S)-ethyl 2-(tert-butoxy)-2-(7-(4-chlorophenyl)-5-methyl-2-(1-methyl-3-(2-oxa-6-azaspiro[3.3]heptan-6-yl)-1H-indazol-5-yl)benzo[d]thiazol-6-yl)acetate.

Preparation of (2S)-2-(tert-butoxy)-2-(7-(4-chlorophenyl)-2-(3-(1-(methoxycarbonyl)pyrrolidin-3-yl)-1-methyl-1H-indazol-5-yl)-5-methylbenzo[d]thiazol-6-yl)acetic acid: in a 50 mL round-bottom flask, (2S)-2-(tert-butoxy)-2-(7-(4-chlorophenyl)-5-methyl-2-(1-methyl-3-(pyrrolidin-3-yl)-1H-indazol-5-yl)benzo[d]thiazol-6-yl)acetic acid (0.02 g, 0.034 mmol) was dissolved in THF (0.5 mL). 2 N NaOH (0.5 mL) was added to reaction mixture followed by methyl chloroformate (0.004 g, 0.037 mmol). The reaction mixture was stirred at room temperature for 1 hour. The solution was concentrated and the residue was purified by HPLC to give of desired product. $^1$H NMR (400 MHz, Acetonitrile-d3) δ 8.38 (s, 1H), 8.13 (dd, J=8.9, 1.6 Hz, 1H), 7.93-7.76 (m, 1H), 7.74-7.42 (m, 4H), 5.29 (s, 1H), 4.01 (s, 3H), 3.89 (d, J=9.7 Hz, 2H), 3.65 (s, 4H), 3.60-3.53 (m, 1H), 3.48 (dt, J=10.4, 7.6 Hz, 1H), 2.59 (d, J=0.9 Hz, 3H), 2.41 (d, J=10.3 Hz, 1H), 2.33-2.11 (m, 1H), 1.00 (s, 9H).

Example 74. Preparation of (2S)-2-(tert-butoxy)-2-(7-(4-chlorophenyl)-2-(3-(1-((2-methoxyethoxy)carbonyl)pyrrolidin-3-yl)-1-methyl-1H-indazol-5-yl)-5-methylbenzo[d]thiazol-6-yl)acetic Acid (73)

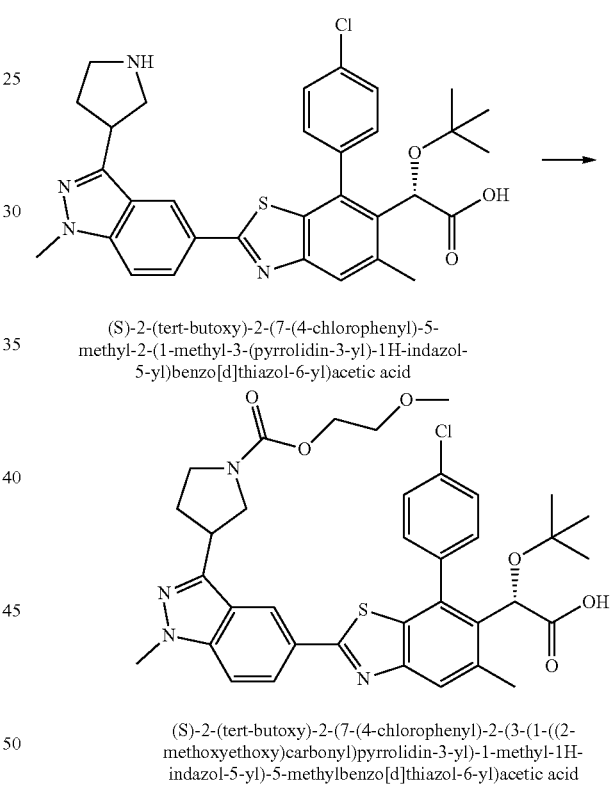

(S)-2-(tert-butoxy)-2-(7-(4-chlorophenyl)-5-methyl-2-(1-methyl-3-(pyrrolidin-3-yl)-1H-indazol-5-yl)benzo[d]thiazol-6-yl)acetic acid (S)-2-(tert-butoxy)-2-(7-(4-chlorophenyl)-2-(3-(1-((2-methoxyethoxy)carbonyl)pyrrolidin-3-yl)-1-methyl-1H-indazol-5-yl)-5-methylbenzo[d]thiazol-6-yl)acetic acid Preparation of (2S)-2-(tert-butoxy)-2-(7-(4-chlorophenyl)-2-(3-(1-((2-methoxyethoxy)carbonyl)pyrrolidin-3-yl)-1-methyl-1H-indazol-5-yl)-5-methylbenzo[d]thiazol-6-yl)acetic acid: Prepared in a manner similar to (2S)-2-(tert-butoxy)-2-(7-(4-chlorophenyl)-2-(3-(1-(methoxycarbonyl)pyrrolidin-3-yl)-1-methyl-1H-indazol-5-yl)-5-methylbenzo[d]thiazol-6-yl)acetic acid except using 2-methoxyethyl carbonochloridate instead of methyl chloroformate. $^1$H NMR (400 MHz, Acetonitrile-d3) δ 8.37 (dd, J=1.7, 0.8 Hz, 1H), 8.13 (dd, J=8.9, 1.6 Hz, 1H), 7.86 (d, J=1.0 Hz, 1H), 7.73-7.50 (m, 5H), 5.29 (s, 1H), 4.27-4.07 (m, 2H), 4.01 (s, 3H), 3.99-3.79 (m, 2H), 3.76-3.43 (m, 5H), 3.37-3.22 (m, 3H), 2.97 (s, 1H), 2.59 (d, J=0.9 Hz, 3H), 2.42 (s, 1H), 2.24 (s, 1H), 1.00 (s, 9H).

Example 75. Preparation of (2S)-2-(2-(3-(1-acetylpyrrolidin-3-yl)-1-methyl-1H-indazol-5-yl)-7-(4-chlorophenyl)-5-methylbenzo[d]thiazol-6-yl)-2-(tert-butoxy)acetic Acid (74)

Example 76 and 77. Preparation of (S)-2-(tert-butoxy)-2-(7-(4-chlorophenyl)-2-(3-((R)-1-(2-methoxyacetyl)pyrrolidin-3-yl)-1-methyl-1H-indazol-5-yl)-5-methylbenzo[d]thiazol-6-yl)acetic Acid (75) and (S)-2-(tert-butoxy)-2-(7-(4-chlorophenyl)-2-(3-((S)-1-(2-methoxyacetyl)pyrrolidin-3-yl)-1-methyl-1H-indazol-5-yl)-5-methylbenzo[d]thiazol-6-yl)acetic Acid (76)

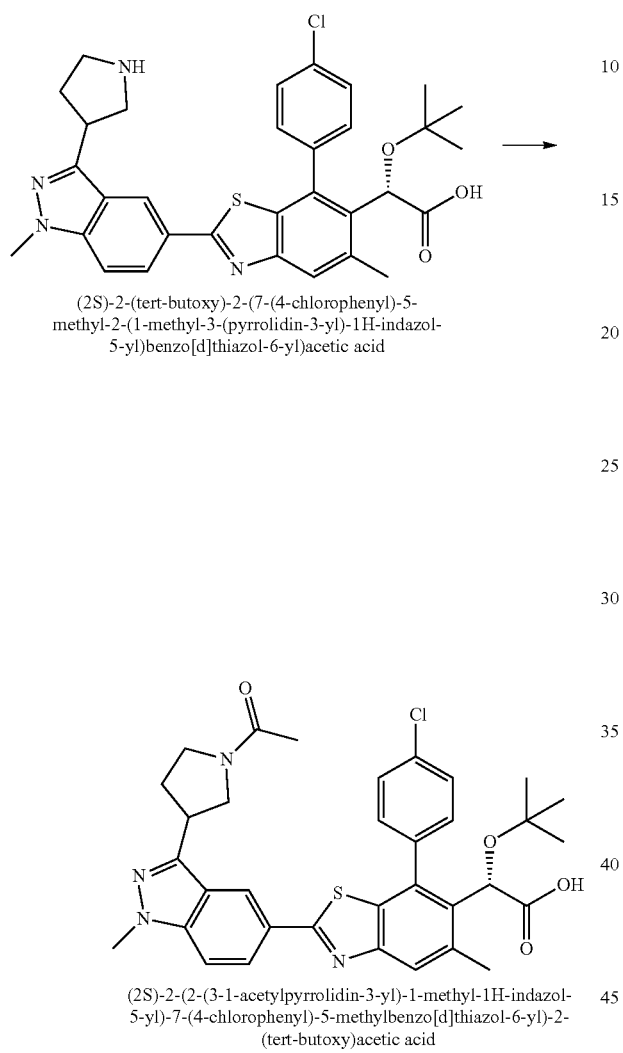

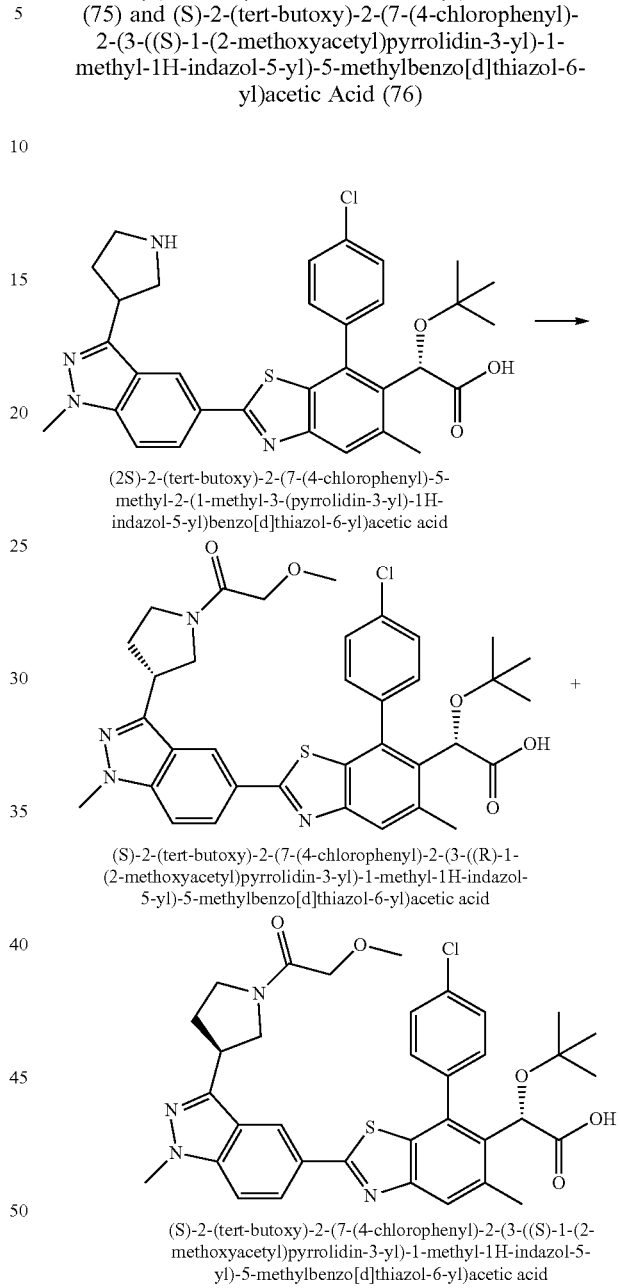

Preparation of (2S)-2-(2-(3-(1-acetylpyrrolidin-3-yl)-1-methyl-1H-indazol-5-yl)-7-(4-chlorophenyl)-5-methylbenzo[d]thiazol-6-yl)-2-(tert-butoxy)acetic acid: Prepared in a manner similar to (2S)-2-(tert-butoxy)-2-(7-(4-chlorophenyl)-2-(3-(1-(methoxycarbonyl)pyrrolidin-3-yl)-1-methyl-1H-indazol-5-yl)-5-methylbenzo[d]thiazol-6-yl) acetic acid except using acetyl chloride instead of methyl chloroformate. ¹H NMR (400 MHz, Acetonitrile-d3) δ 8.53-8.28 (m, 1H), 8.23-8.00 (m, 1H), 7.92-7.79 (m, 1H), 7.72-7.47 (m, 5H), 5.39-5.22 (m, 1H), 3.99 (d, J=4.5 Hz, 4H), 3.94-3.43 (m, 4H), 2.71-2.52 (m, 3H), 2.53-2.19 (m, 2H), 2.19-2.08 (m, 3H), 1.13-0.87 (m, 9H).

Preparation of (S)-2-(tert-butoxy)-2-(7-(4-chlorophenyl)-2-(3-((R)-1-(2-methoxyacetyl)pyrrolidin-3-yl)-1-methyl-1H-indazol-5-yl)-5-methylbenzo[d]thiazol-6-yl)acetic acid & (S)-2-(tert-butoxy)-2-(7-(4-chlorophenyl)-2-(3-((S)-1-(2-methoxyacetyl)pyrrolidin-3-yl)-1-methyl-1H-indazol-5-yl)-5-methylbenzo[d]thiazol-6-yl)acetic acid: Prepared in a manner similar to (2S)-2-(tert-butoxy)-2-(7-(4-chlorophenyl)-2-(3-(1-(methoxycarbonyl)pyrrolidin-3-yl)-1-methyl-1H-indazol-5-yl)-5-methylbenzo[d]thiazol-6-yl)acetic acid except using 2-methoxyacetyl chloride instead of methyl chloroformate. The two diastereoisomers were separated by prep HPLC. (S)-2-(tert-butoxy)-2-(7-(4-chlorophenyl)-2-(3-((R)-1-(2-methoxyacetyl)pyrrolidin-3-yl)-1-methyl-1H-indazol-5-yl)-5-methylbenzo[d]thiazol-6-yl)acetic acid: ¹H NMR (400 MHz, Acetonitrile-d3) δ 8.51-8.28 (m, 1H), 8.22-7.98 (m, 1H), 7.98-7.80 (m, 1H), 7.71-7.47 (m, 5H), 5.28 (s, 1H), 4.15-4.03 (m, 2H), 4.03-3.95 (m, 4H), 3.96-3.46 (m, 5H), 3.45-3.27 (m, 3H), 2.72-2.52 (m, 3H), 2.47-2.09 (m, 2H), 0.99 (d, J=0.9 Hz, 9H). (S)-2-(tert-butoxy)-2-(7-(4-chlorophenyl)-2-(3-((S)-1-(2-methoxyacetyl)pyrrolidin-3-yl)-1-methyl-1H-indazol-5-yl)-5-methylbenzo[d]thiazol-6-yl)acetic acid: ¹H NMR (400 MHz, Acetonitrile-d3) δ 8.47-8.25 (m, 1H), 8.17-8.00 (m, 1H), 7.85 (d, J=5.6 Hz, 1H), 7.72-7.46 (m, 6H), 5.28 (s, 1H), 4.22-4.04 (m, 2H), 4.03-3.93 (m, 4H), 3.78-3.57 (m, 2H), 3.54 (dt, J=17.6, 8.8 Hz, 1H), 3.48-3.29 (m, 3H), 2.70-2.56 (m, 3H), 2.51-2.15 (m, 1H), 1.23 (d, J=6.9 Hz, 1H), 0.99 (d, J=1.1 Hz, 9H).

Example 78. Preparation of (2S)-2-(tert-butoxy)-2-(7-(4-chlorophenyl)-2-(3-(1-(2-methoxyethyl)piperidin-3-yl)-1-methyl-1H-indazol-5-yl)-5-methylbenzo[d]thiazol-6-yl)acetic Acid (77)

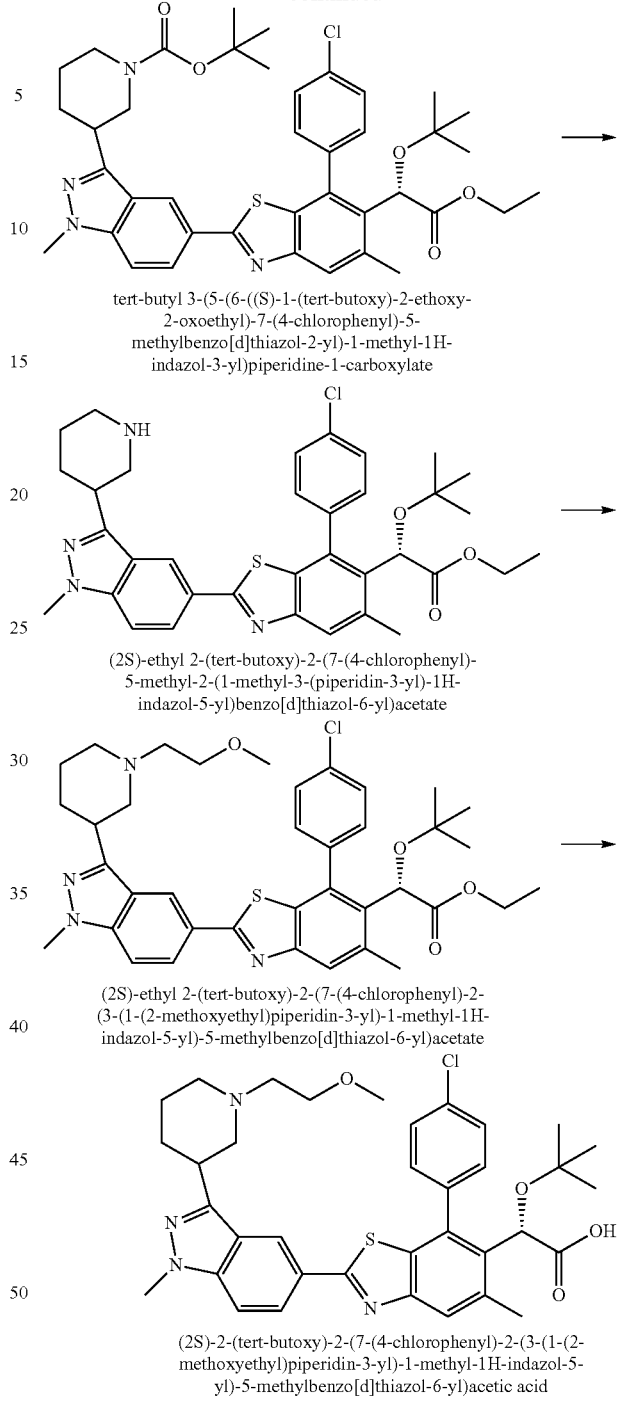

(S)-ethyl 2-(2-(3-bromo-1-methyl-1H-indazol-5-yl)-7-(4-chlorophenyl)-5-methylbenzo[d]thiazol-6-yl)-2-(tert-butoxy)acetate

+ tert-butyl 3-(4,4,5,5-tetramethyl-1,3,2-dioxaborolan-2-yl)-5,6-dihydropyridine-1(2H)-carboxylate

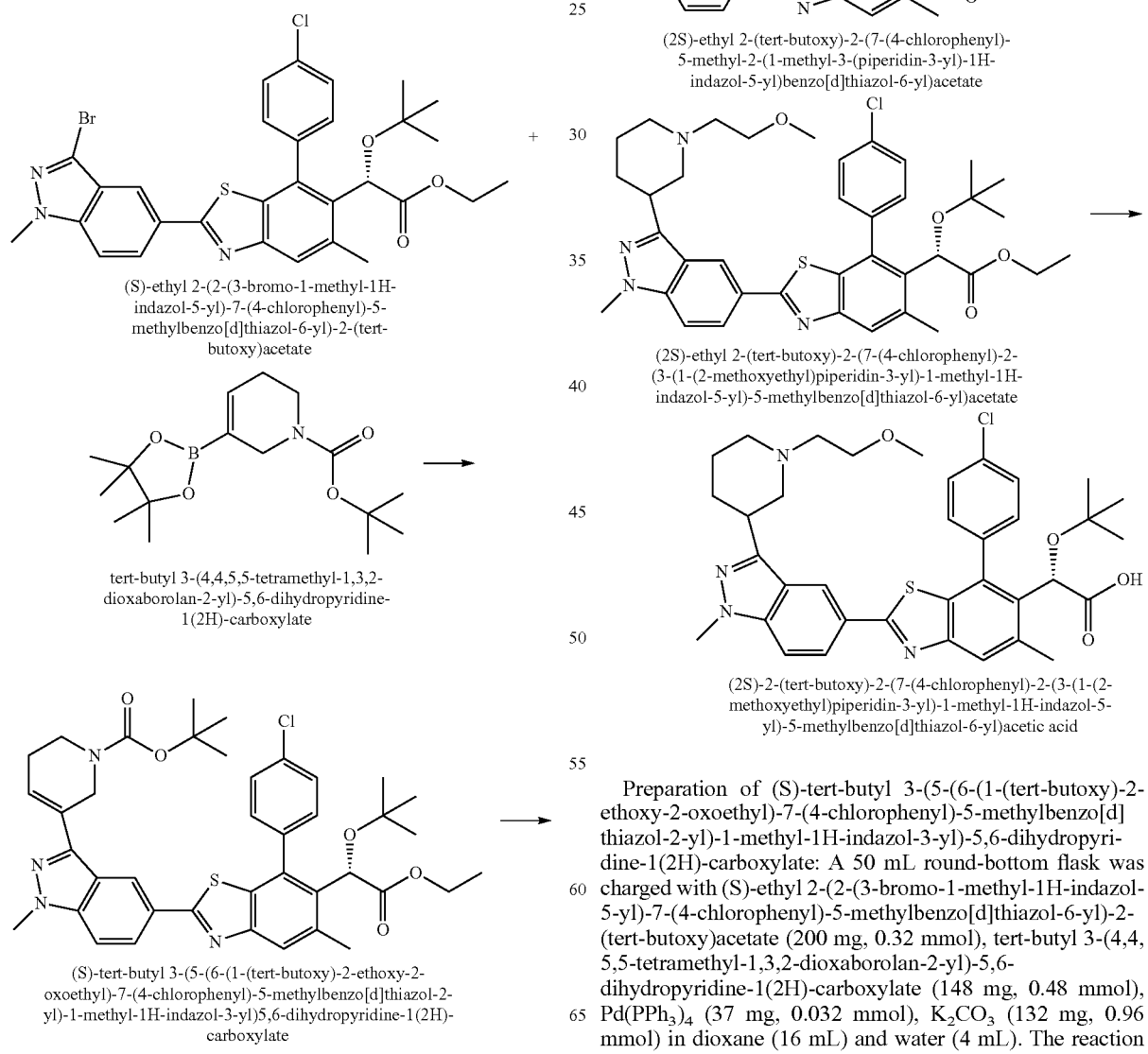

(S)-tert-butyl 3-(5-(6-(1-(tert-butoxy)-2-ethoxy-2-oxoethyl)-7-(4-chlorophenyl)-5-methylbenzo[d]thiazol-2-yl)-1-methyl-1H-indazol-3-yl)5,6-dihydropyridine-1(2H)-carboxylate tert-butyl 3-(5-(6-((S)-1-(tert-butoxy)-2-ethoxy-2-oxoethyl)-7-(4-chlorophenyl)-5-methylbenzo[d]thiazol-2-yl)-1-methyl-1H-indazol-3-yl)piperidine-1-carboxylate (2S)-ethyl 2-(tert-butoxy)-2-(7-(4-chlorophenyl)-5-methyl-2-(1-methyl-3-(piperidin-3-yl)-1H-indazol-5-yl)benzo[d]thiazol-6-yl)acetate (2S)-ethyl 2-(tert-butoxy)-2-(7-(4-chlorophenyl)-2-(3-(1-(2-methoxyethyl)piperidin-3-yl)-1-methyl-1H-indazol-5-yl)-5-methylbenzo[d]thiazol-6-yl)acetate (2S)-2-(tert-butoxy)-2-(7-(4-chlorophenyl)-2-(3-(1-(2-methoxyethyl)piperidin-3-yl)-1-methyl-1H-indazol-5-yl)-5-methylbenzo[d]thiazol-6-yl)acetic acid Preparation of (S)-tert-butyl 3-(5-(6-(1-(tert-butoxy)-2-ethoxy-2-oxoethyl)-7-(4-chlorophenyl)-5-methylbenzo[d]thiazol-2-yl)-1-methyl-1H-indazol-3-yl)-5,6-dihydropyridine-1(2H)-carboxylate: A 50 mL round-bottom flask was charged with (S)-ethyl 2-(2-(3-bromo-1-methyl-1H-indazol-5-yl)-7-(4-chlorophenyl)-5-methylbenzo[d]thiazol-6-yl)-2-(tert-butoxy)acetate (200 mg, 0.32 mmol), tert-butyl 3-(4,4,5,5-tetramethyl-1,3,2-dioxaborolan-2-yl)-5,6-dihydropyridine-1(2H)-carboxylate (148 mg, 0.48 mmol), Pd(PPh₃)₄ (37 mg, 0.032 mmol), K₂CO₃ (132 mg, 0.96 mmol) in dioxane (16 mL) and water (4 mL). The reaction mixture was heated to 100° C. for 1 h. The reaction was cooled to room temperature and diluted with ethyl acetate (50 mL), washed with 1N HCl and dried over Na$_2$SO$_4$. After concentration, the crude was purified by column chromatography on silica gel with hexane-EtOAc to obtain desired product.

Preparation of tert-butyl 3-(5-(6-((S)-1-(tert-butoxy)-2-ethoxy-2-oxoethyl)-7-(4-chlorophenyl)-5-methylbenzo[d]thiazol-2-yl)-1-methyl-1H-indazol-3-yl)piperidine-1-carboxylate: A flask was charged with 5% w/w Rh/Al$_2$O$_3$ (93 mg, 0.045 mmol), (S)-tert-butyl 3-(5-(6-(1-(tert-butoxy)-2-ethoxy-2-oxoethyl)-7-(4-chlorophenyl)-5-methylbenzo[d]thiazol-2-yl)-1-methyl-1H-indazol-3-yl)-5,6-dihydropyridine-1(2H)-carboxylate (220 mg), and EtOH (absolute, 10 mL). The reaction was evacuated (vacuum) and backfilled from a balloon of H$_2$, then stirred vigorously at 23° C. for 2.5 h. The reaction mixture was filtered through celite, and the filtrate was concentrated. The residue was purified by CombiFlash (40 g column) using hexane-ethyl acetate as eluents to give desired product.

Preparation of (2S)-ethyl 2-(tert-butoxy)-2-(7-(4-chlorophenyl)-5-methyl-2-(1-methyl-3-(piperidin-3-yl)-1H-indazol-5-yl)benzo[d]thiazol-6-yl)acetate: tert-butyl 3-(5-(6-((S)-1-(tert-butoxy)-2-ethoxy-2-oxoethyl)-7-(4-chlorophenyl)-5-methylbenzo[d]thiazol-2-yl)-1-methyl-1H-indazol-3-yl)piperidine-1-carboxylate (220 mg, 0.30 mmol) was dissolved in 1.25 M HCl in 2-propanol (15 mL) in a 50 ml round-bottom flask. The reaction mixture was stirred at room temperature for overnight. After concentration, the HCl salt of desired product was obtained.

Preparation of (2S)-ethyl 2-(tert-butoxy)-2-(7-(4-chlorophenyl)-2-(3-(1-(2-methoxyethyl)piperidin-3-yl)-1-methyl-1H-indazol-5-yl)-5-methylbenzo[d]thiazol-6-yl)acetate: In a 50 mL round-bottom flask, (2S)-ethyl 2-(tert-butoxy)-2-(7-(4-chlorophenyl)-5-methyl-2-(1-methyl-3-(piperidin-3-yl)-1H-indazol-5-yl)benzo[d]thiazol-6-yl)acetate (0.010 g, 0.016 mmol) was dissolved in MeOH (1 mL). 2-methoxyacetaldehyde (0.012 g, 0.16 mmol) was added to the reaction mixture. NaBH$_3$CN (0.01 g, 0.15 mmol) and one drop of acetic acid were added to the reaction mixture. The reaction mixture was stirred at room temperature for half an hour. After concentration, the residue was dissolved in EtOAc, washed with brine and dried over Na$_2$SO$_4$. After concentration, the crude was used for next step without further purification.

Preparation of (2S)-2-(tert-butoxy)-2-(7-(4-chlorophenyl)-2-(3-(1-(2-methoxyethyl)piperidin-3-yl)-1-methyl-1H-indazol-5-yl)-5-methylbenzo[d]thiazol-6-yl)acetic acid: Prepared in a manner similar to (S)-2-(tert-butoxy)-2-(7-(4-chlorophenyl)-5-methyl-2-(1-methyl-3-(2-oxa-6-azaspiro[3.3]heptan-6-yl)-1H-indazol-5-yl)benzo[d]thiazol-6-yl) acetic acid except using (2S)-ethyl 2-(tert-butoxy)-2-(7-(4-chlorophenyl)-2-(3-(1-(2-methoxyethyl)piperidin-3-yl)-1-methyl-1H-indazol-5-yl)-5-methylbenzo[d]thiazol-6-yl) acetate instead of (S)-ethyl 2-(tert-butoxy)-2-(7-(4-chlorophenyl)-5-methyl-2-(1-methyl-3-(2-oxa-6-azaspiro[3.3]heptan-6-yl)-1H-indazol-5-yl)benzo[d]thiazol-6-yl) acetate. $^1$H NMR (400 MHz, Acetonitrile-d3) δ 8.43 (dd, J=6.5, 1.5 Hz, 1H), 8.21 (t, J=10.2 Hz, 1H), 7.94-7.75 (m, 1H), 7.78-7.48 (m, 5H), 5.28 (s, 1H), 4.09 (s, 3H), 4.03 (s, 3H), 3.92-3.52 (m, 6H), 3.46 (d, J=1.4 Hz, 1H), 3.34 (d, J=7.8 Hz, 2H), 2.65-2.48 (m, 3H), 2.15 (d, J=56.1 Hz, 2H), 1.84-1.71 (m, 1H), 0.99 (d, J=1.7 Hz, 9H).

Example 79. Preparation of (S)-2-(tert-butoxy)-2-(7-(4-chlorophenyl)-5-methyl-2-(1-methyl-3-(2-oxoimidazolidin-1-yl)-1H-indazol-5-yl) benzo[d]thiazol-6-yl) acetic Acid (78)

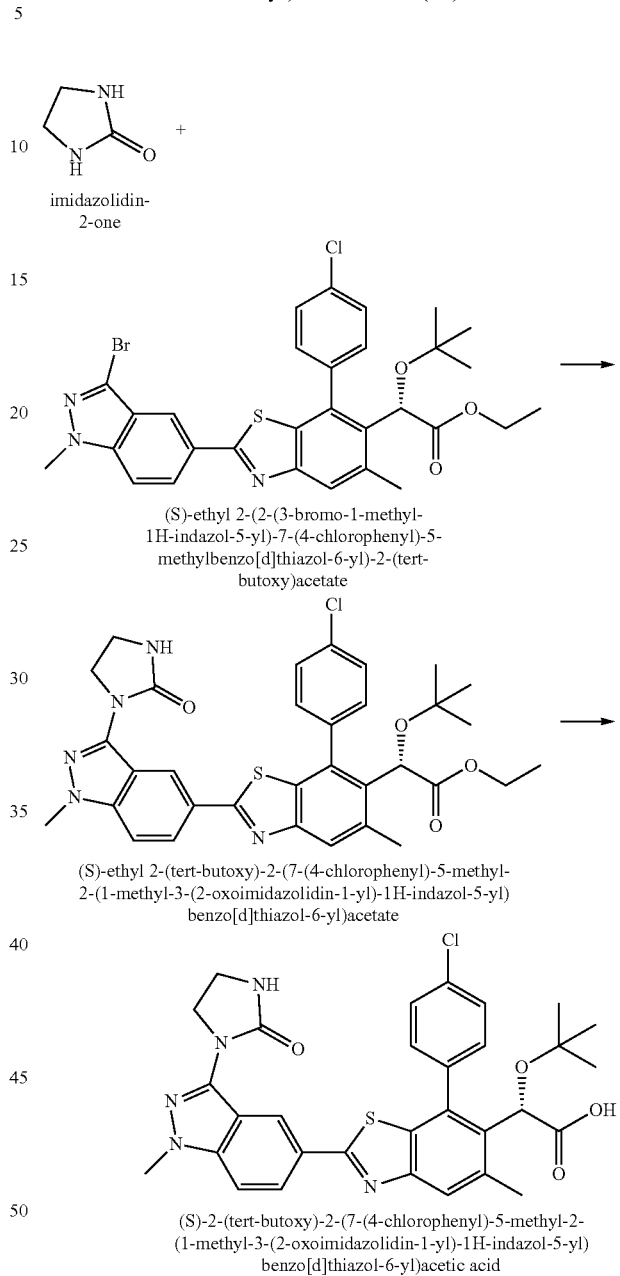

Preparation of (S)-ethyl 2-(tert-butoxy)-2-(7-(4-chlorophenyl)-5-methy-2-(1-methyl-3-(2oxoimidazolidin-1-yl)-1H-indazol-5-yl)benzo[d]thiazol-6-yl)acetate: In a 5 mL microwave vial, (S)-ethyl 2-(2-(3-bromo-1-methyl-1H-indazol-5-yl)-7-(4-chlorophenyl)-5-methylbenzo[d]thiazol-6-yl)-2-(tert-butoxy)acetate (0.025 g, 0.29 mmol), imidazolidin-2-one (0.10 g, 0.15 mmol), CuI (0.015 g, 0.079 mmol), and N,N-dimethyl cyclohexane (0.011 g, 0.079 mmol) in dioxane (1 mL) was heated to 100° C. under MW for one hour. The reaction mixture was diluted with ethyl acetate (50 mL), washed with 1N HCl and dried over Na$_2$SO$_4$. After concentration, the crude was purified by column chromatography on silica gel with hexane-EtOAc to obtain (S)- ethyl 2-(tert-butoxy)-2-(7-(4-chlorophenyl)-5-methyl-2-(1-methyl-3-(2oxoimidazolidin-1-yl)-1H-indazol-5-yl)benzo[d]thiazol-6-yl)acetate.

Preparation of (S)-2-(tert-butoxy)-2-(7-(4-chlorophenyl)-5-methyl-2-(1-methyl-3-(2-oxoimidazolidin-1-yl)-1H-indazol-5-yl)benzo[d]thiazol-6-yl)acetic acid: In a 5 mL microwave vial, (S)-ethyl 2-(tert-butoxy)-2-(7-(4-chlorophenyl)-5-methyl-2-(1-methyl-3-(2oxoimidazolidin-1-yl)-1H-indazol-5-yl)benzo[d]thiazol-6-yl)acetate (0.017 g, 0.027 mmol), lithium iodide (0.08 g, 0.60 mmol) in pyridine (0.5 mL) was heated to 170° C. under MW for two hours. The solution was concentrated and the residue was purified by HPLC to give desired product. $^1$H NMR (400 MHz, Chloroform-d) δ 9.00-8.79 (m, 1H), 8.11 (dd, J=9.0, 1.6 Hz, 1H), 7.77 (s, 1H), 7.75-7.63 (m, 1H), 7.64-7.54 (m, 3H), 7.48 (d, J=9.0 Hz, 1H), 5.24 (s, 1H), 4.26-4.02 (m, 2H), 3.94 (s, 3H), 3.64 (t, J=8.0 Hz, 2H), 2.60 (s, 3H), 0.97 (s, 9H).

Example 80. Preparation of (S)-2-(tert-butoxy)-2-(7-(4-chlorophenyl)-2-(3-(3-(2-methoxyethyl)-2-oxoimidazolidin-1-yl)-1-methyl-1H-indazol-5-yl)-5-methylbenzo[d]thiazol-6-yl)acetic Acid (79)

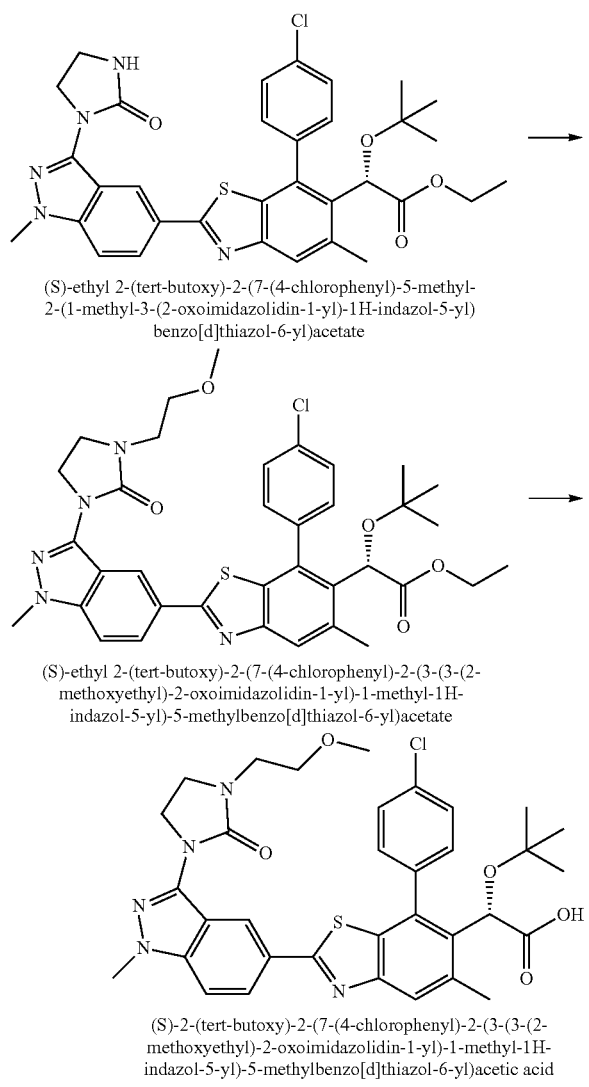

(S)-ethyl 2-(tert-butoxy)-2-(7-(4-chlorophenyl)-5-methyl-2-(1-methyl-3-(2-oxoimidazolidin-1-yl)-1H-indazol-5-yl)benzo[d]thiazol-6-yl)acetate (S)-ethyl 2-(tert-butoxy)-2-(7-(4-chlorophenyl)-2-(3-(3-(2-methoxyethyl)-2-oxoimidazolidin-1-yl)-1-methyl-1H-indazol-5-yl)-5-methylbenzo[d]thiazol-6-yl)acetate (S)-2-(tert-butoxy)-2-(7-(4-chlorophenyl)-2-(3-(3-(2-methoxyethyl)-2-oxoimidazolidin-1-yl)-1-methyl-1H-indazol-5-yl)-5-methylbenzo[d]thiazol-6-yl)acetic acid Preparation of (S)-ethyl 2-(tert-butoxy)-2-(7-(4-chlorophenyl)-2-(3-(3-(2-methoxyethyl)-2-oxoimidazolidin-1-yl)-1-methyl-1H-indazol-5-yl)-5-methylbenzo[d]thiazol-6-yl)acetate: A 50-mL 1-neck round-bottom flask was charged with reactant (S)-ethyl 2-(tert-butoxy)-2-(7-(4-chlorophenyl)-5-methyl-2-(1-methyl-3-(2-oxoimidazolidin-1-yl)-1H-indazol-5-yl)benzo[d]thiazol-6-yl)acetate (0.015 g, 0.024 mmol) in DMF (2 ml). Sodium hydride (60%, 0.003 g, 0.075 mmol) was added to the reaction mixture at room temperature. 2-bromoethyl methyl ether (0.014 g, 0.048 mmol) was added in. The reaction mixture was stirred at room temperature for 1 hour. Two drops of water were added to quench the reaction. The reaction mixture was diluted with MeOH (2 mL) and purified by HPLC to afford desired product.

Preparation of (S)-2-(tert-butoxy)-2-(7-(4-chlorophenyl)-2-(3-(3-(2-methoxyethyl)-2-oxoimidazolidin-1-yl)-1-methyl-1H-indazol-5-yl)-5-methylbenzo[d]thiazol-6-yl)acetic acid: In a 5 mL microwave vial, (S)-ethyl 2-(tert-butoxy)-2-(7-(4-chlorophenyl)-2-(3-(3-(2-methoxyethyl)-2-oxoimidazolidin-1-yl)-1-methyl-1H-indazol-5-yl)-5-methylbenzo[d]thiazol-6-yl)acetate (0.014 g, 0.020 mmol), lithium iodide (0.08 g, 0.60 mmol) in pyridine (0.5 mL) was heated to 170° C. under MW for two hours. The solution was concentrated and the residue was purified by HPLC to give desired product. $^1$H NMR (400 MHz, Chloroform-d) δ 8.88 (d, J=1.7 Hz, 1H), 8.10 (dd, J=8.9, 1.8 Hz, 1H), 7.76 (s, 1H), 7.71-7.59 (m, 1H), 7.55 (dt, J=4.9, 2.5 Hz, 4H), 7.49 (d, J=9.0 Hz, 1H), 5.20 (s, 1H), 4.06-3.87 (m, 6H), 3.69 (dd, J=9.2, 6.8 Hz, 2H), 3.57 (t, J=5.0 Hz, 2H), 3.47 (t, J=5.1 Hz, 2H), 3.35 (d, J=2.6 Hz, 3H), 2.56 (s, 2H), 0.94 (d, J=2.4 Hz, 9H).

Example 81. Preparation of (S)-2-(tert-butoxy)-2-(7-(4-chlorophenyl)-5-methyl-2-(1-methyl-3-(3-methyl-2-oxoimidazolidin-1-yl)-1H-indazol-5-yl)benzo[d]thiazol-6-yl)acetic Acid (80)

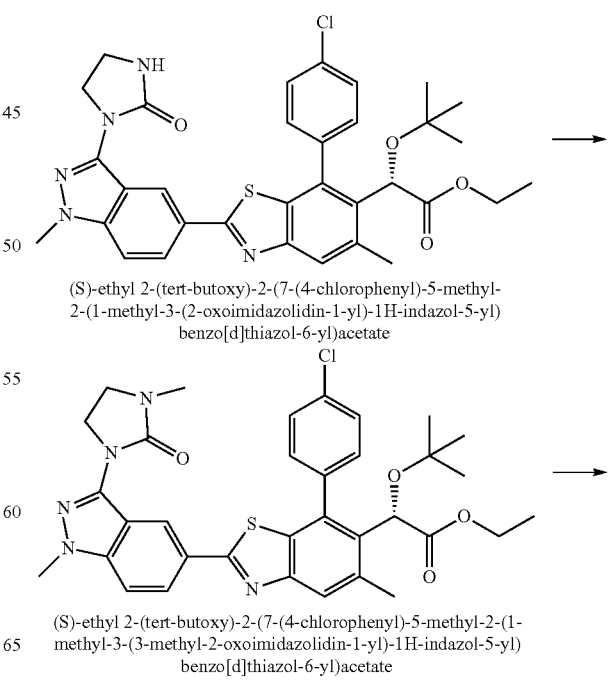

(S)-ethyl 2-(tert-butoxy)-2-(7-(4-chlorophenyl)-5-methyl-2-(1-methyl-3-(2-oxoimidazolidin-1-yl)-1H-indazol-5-yl)benzo[d]thiazol-6-yl)acetate (S)-ethyl 2-(tert-butoxy)-2-(7-(4-chlorophenyl)-5-methyl-2-(1-methyl-3-(3-methyl-2-oxoimidazolidin-1-yl)-1H-indazol-5-yl)benzo[d]thiazol-6-yl)acetate

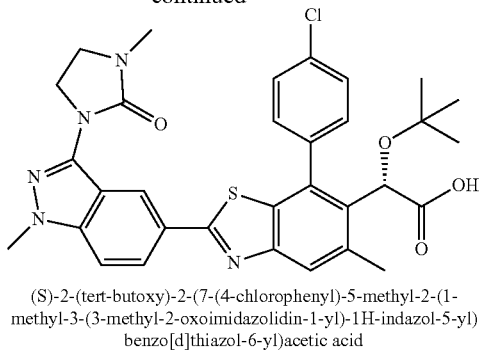

(S)-2-(tert-butoxy)-2-(7-(4-chlorophenyl)-5-methyl-2-(1-methyl-3-(3-methyl-2-oxoimidazolidin-1-yl)-1H-indazol-5-yl)benzo[d]thiazol-6-yl)acetic acid Preparation of (S)-ethyl 2-(tert-butoxy)-2-(7-(4-chlorophenyl)-5-methyl-2-(1-methyl-3-(3-methyl-2-oxoimidazolidin-1-yl)-1H-indazol-5-yl)benzo[d]thiazol-6-yl)acetate: Prepared in a manner similar to (S)-ethyl 2-(tert-butoxy)-2-(7-(4-chlorophenyl)-2-(3-(3-(2-methoxyethyl)-2-oxoimidazolidin-1-yl)-1-methyl-1H-indazol-5-yl)-5-methylbenzo[d]thiazol-6-yl)acetate except using methyl iodide instead of 2-bromoethyl methyl ether.

Preparation of (S)-2-(tert-butoxy)-2-(7-(4-chlorophenyl)-5-methyl-2-(1-methyl-3-(3-methyl-2-oxoimidazolidin-1-yl)-1H-indazol-5-yl) benzo[d]thiazol-6-yl)acetic acid: Prepared in a manner similar to (S)-2-(tert-butoxy)-2-(7-(4-chlorophenyl)-2-(3-(3-(2-methoxyethyl)-2-oxoimidazolidin-1-yl)-1-methyl-1H-indazol-5-yl)-5-methylbenzo[d]thiazol-6-yl)acetic acid except using (S)-ethyl 2-(tert-butoxy)-2-(7-(4-chlorophenyl)-5-methyl-2-(1-methyl-3-(3-methyl-2-oxoimidazolidin-1-yl)-1H-indazol-5-yl)benzo[d]thiazol-6-yl)acetate instead of (S)-ethyl 2-(tert-butoxy)-2-(7-(4-chlorophenyl)-2-(3-(3-(2-methoxyethyl)-2-oxoimidazolidin-1-yl)-1-methyl-1H-indazol-5-yl)-5-methylbenzo[d]thiazol-6-yl)acetate. $^1$H NMR (400 MHz, Chloroform-d) δ 9.01-8.79 (m, 1H), 8.07 (dd, J=8.9, 1.7 Hz, 1H), 7.77 (s, 1H), 7.69 (dd, J=8.6, 2.0 Hz, 1H), 7.58 (dt, J=5.8, 2.2 Hz, 3H), 7.45 (d, J=9.0 Hz, 1H), 5.24 (s, 1H), 4.10-3.83 (m, 6H), 3.59 (dd, J=9.1, 7.0 Hz, 2H), 2.89 (s, 3H), 2.60 (s, 3H), 0.97 (s, 9H).

Example 82. Preparation of (S)-2-(2-(3-(3-((1,3-dioxolan-2-yl)methyl)-2-oxoimidazolidin-1-yl)-1-methyl-1H-indazol-5-yl)-7-(4-chlorophenyl)-5-methylbenzo[d]thiazol-6-yl)-2-(tert-butoxy)acetic Acid (81)

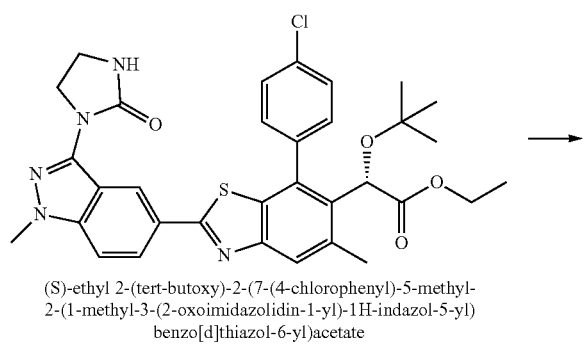

(S)-ethyl 2-(tert-butoxy)-2-(7-(4-chlorophenyl)-5-methyl-2-(1-methyl-3-(2-oxoimidazolidin-1-yl)-1H-indazol-5-yl)benzo[d]thiazol-6-yl)acetate

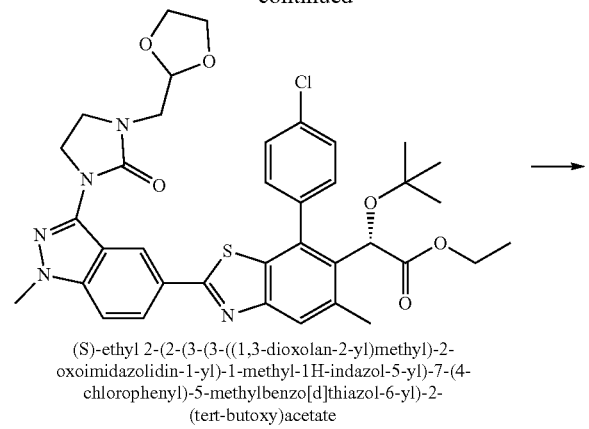

(S)-ethyl 2-(2-(3-(3-((1,3-dioxolan-2-yl)methyl)-2-oxoimidazolidin-1-yl)-1-methyl-1H-indazol-5-yl)-7-(4-chlorophenyl)-5-methylbenzo[d]thiazol-6-yl)-2-(tert-butoxy)acetate (S)-2-(2-(3-(3-((1,3-dioxolan-2-yl)methyl)-2-oxoimidazolidin-1-yl)-1-methyl-1H-indazol-5-yl)-7-(4-chlorophenyl)-5-methylbenzo[d]thiazol-6-yl)-2-(tert-butoxy)acetic acid Preparation of (S)-ethyl 2-(2-(3-(3-((1,3-dioxolan-2-yl)methyl)-2-oxoimidazolidin-1-yl)-1-methyl-1H-indazol-5-yl)-7-(4-chlorophenyl)-5-methylbenzo[d]thiazol-6-yl)-2-(tert-butoxy)acetate: Prepared in a manner similar to (S)-ethyl 2-(tert-butoxy)-2-(7-(4-chlorophenyl)-2-(3-(3-(2-methoxyethyl)-2-oxoimidazolidin-1-yl)-1-methyl-1H-indazol-5-yl)-5-methylbenzo[d]thiazol-6-yl)acetate except using 2-Bromomethyl-1,3-dioxolane instead of 2-bromoethyl methyl ether.

Preparation of (S)-2-(2-(3-(3-((1,3-dioxolan-2-yl)methyl)-2-oxoimidazolidin-1-yl)-1-methyl-1H-indazol-5-yl)-7-(4-chlorophenyl)-5-methylbenzo[d]thiazol-6-yl)-2-(tert-butoxy)acetic acid: Prepared in a manner similar to (S)-2-(tert-butoxy)-2-(7-(4-chlorophenyl)-2-(3-(3-(2-methoxyethyl)-2-oxoimidazolidin-1-yl)-1-methyl-1H-indazol-5-yl)-5-methylbenzo[d]thiazol-6-yl)acetic acid except using (S)-ethyl 2-(2-(3-(3-((1,3-dioxolan-2-yl)methyl)-2-oxoimidazolidin-1-yl)-1-methyl-1H-indazol-5-yl)-7-(4-chlorophenyl)-5-methylbenzo[d]thiazol-6-yl)-2-(tert-butoxy)acetate instead of (S)-ethyl 2-(tert-butoxy)-2-(7-(4-chlorophenyl)-2-(3-(3-(2-methoxyethyl)-2-oxoimidazolidin-1-yl)-1-methyl-1H-indazol-5-yl)-5-methylbenzo[d]thiazol-6-yl)acetate. $^1$H NMR (400 MHz, Chloroform-d) δ 9.09-8.84 (m, 1H), 8.19-8.04 (m, 1H), 7.79 (d, J=2.7 Hz, 1H), 7.68 (dd, J=8.4, 1.9 Hz, 1H), 7.62-7.54 (m, 4H), 7.52 (dd, J=8.9, 1.1 Hz, 1H), 5.25 (d, J=6.7 Hz, 1H), 5.05 (s, 1H), 4.20-4.05 (m, 2H), 4.04-3.99 (m, 2H), 3.97 (d, J=2.7 Hz, 3H), 3.95-3.84 (m, 1H), 3.84-3.69 (m, 3H), 3.48 (d, J=4.2 Hz, 1H), 2.60 (d, J=0.9 Hz, 2H), 0.97 (s, 9H).

Example 83. Preparation of (S)-2-(tert-butoxy)-2-(7-(4-chlorophenyl)-2-(3-(3-ethyl-2-oxoimidazolidin-1-yl)-1-methyl-1H-indazol-5-yl)-5-methylbenzo[d]thiazol-6-yl)acetic Acid (82)

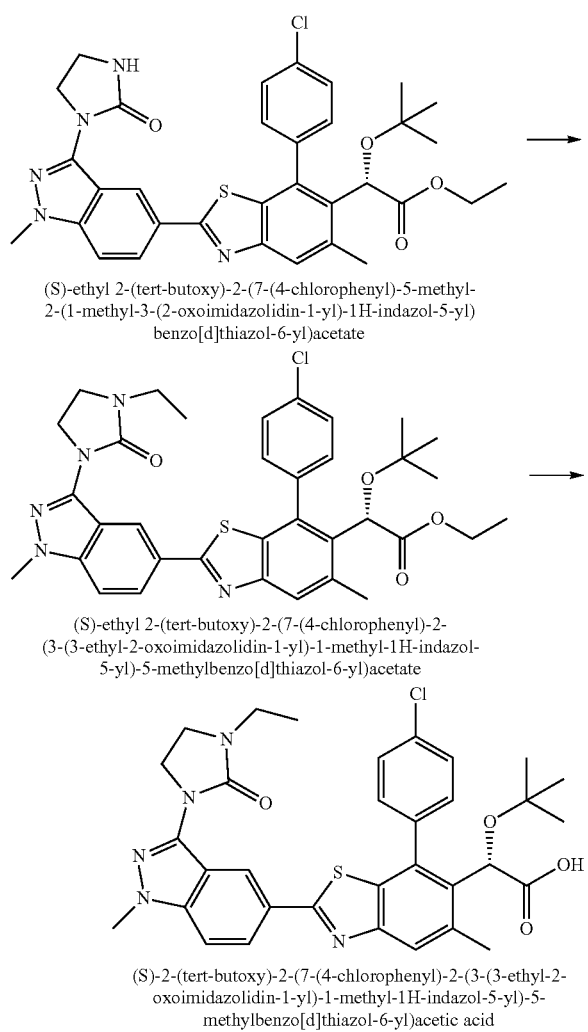

Preparation of (S)-ethyl 2-(tert-butoxy)-2-(7-(4-chlorophenyl)-2-(3-(3-ethyl-2-oxoimidazolidin-1-yl)-1-methyl-1H-indazol-5-yl)-5-methylbenzo[d]thiazol-6-yl)acetate: Prepared in a manner similar to (S)-ethyl 2-(tert-butoxy)-2-(7-(4-chlorophenyl)-2-(3-(3-(2-methoxyethyl)-2-oxoimidazolidin-1-yl)-1-methyl-1H-indazol-5-yl)-5-methylbenzo[d]thiazol-6-yl)acetate except using ethyl iodide instead of 2-bromoethyl methyl ether.

Preparation of (S)-2-(tert-butoxy)-2-(7-(4-chlorophenyl)-2-(3-(3-ethyl-2-oxoimidazolidin-1-yl)-1-methyl-1H-indazol-5-yl)-5-methylbenzo[d]thiazol-6-yl)acetic acid: Prepared in a manner similar to (S)-2-(tert-butoxy)-2-(7-(4-chlorophenyl)-2-(3-(3-(2-methoxyethyl)-2-oxoimidazolidin-1-yl)-1-methyl-1H-indazol-5-yl)-5-methylbenzo[d]thiazol-6-yl)acetic acid except using (S)-ethyl 2-(tert-butoxy)-2-(7-(4-chlorophenyl)-2-(3-(3-ethyl-2-oxoimidazolidin-1-yl)-1-methyl-1H-indazol-5-yl)-5-methylbenzo[d]thiazol-6-yl)acetate instead of (S)-ethyl 2-(tert-butoxy)-2-(7-(4-chlorophenyl)-2-(3-(3-(2-methoxyethyl)-2-oxoimidazolidin-1-yl)-1-methyl-1H-indazol-5-yl)-5-methylbenzo[d]thiazol-6-yl)acetate. $^{1}$H NMR (400 MHz, Chloroform-d) δ 8.92 (dd, J=1.7, 0.7 Hz, 1H), 8.09 (dd, J=9.0, 1.7 Hz, 1H), 7.78 (d, J=0.9 Hz, 1H), 7.72-7.62 (m, 1H), 7.62-7.53 (m, 3H), 7.48 (dd, J=9.0, 0.7 Hz, 1H), 5.24 (s, 1H), 4.06-3.96 (m, 2H), 3.94 (s, 3H), 3.63 (dd, J=8.8, 7.3 Hz, 2H), 3.37 (q, J=7.2 Hz, 3H), 2.60 (d, J=0.8 Hz, 3H), 1.21 (t, J=7.2 Hz, 3H), 0.97 (s, 9H).

Example 84. Preparation of (S)-2-(tert-butoxy)-2-(7-(4-chlorophenyl)-5-methyl-2-(1-methyl-3-(3-(2-morpholinoethyl)-2-oxoimidazolidin-1-yl)-1H-indazol-5-yl)benzo[d]thiazol-6-yl)acetic Acid (83)

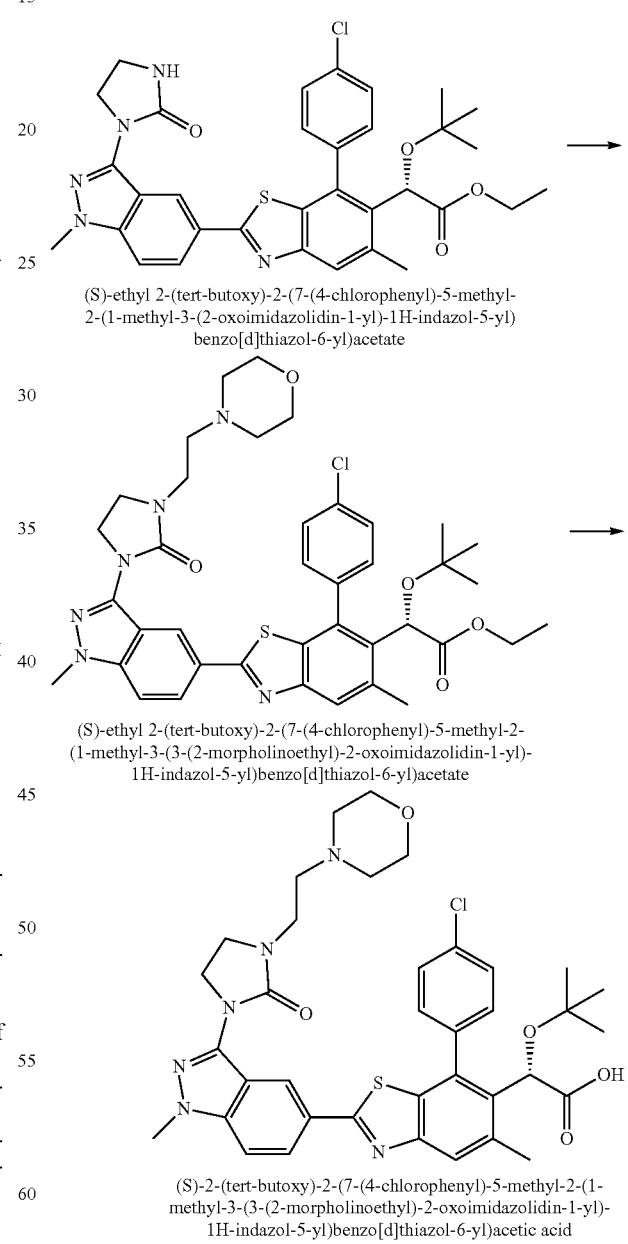

Preparation of (S)-ethyl 2-(tert-butoxy)-2-(7-(4-chlorophenyl)-5-methyl-2-(1-methyl-3-(3-(2-morpholinoethyl)-2-oxoimidazolidin-1-yl)-1H-indazol-5-yl)benzo[d]thiazol-6-yl)acetate: Prepared in a manner similar to (S)-ethyl 2-(tert-butoxy)-2-(7-(4-chlorophenyl)-2-(3-(3-(2-methoxyethyl)-2-oxoimidazolidin-1-yl)-1-methyl-1H-indazol-5-yl)-5-methylbenzo[d]thiazol-6-yl)acetate except using 4-(2-bromoethyl) morpholine instead of 2-bromoethyl methyl ether.

Preparation of (S)-2-(tert-butoxy)-2-(7-(4-chlorophenyl)-5-methyl-2-(1-methyl-3-(3-(2-morpholinoethyl)-2-oxoimidazolidin-1-yl)-1H-indazol-5-yl)benzo[d]thiazol-6-yl)acetic acid: Prepared in a manner similar to (S)-2-(tert-butoxy)-2-(7-(4-chlorophenyl)-2-(3-(3-(2-methoxyethyl)-2-oxoimidazolidin-1-yl)-1-methyl-1H-indazol-5-yl)-5-methylbenzo[d]thiazol-6-yl)acetic acid except using (S)-ethyl 2-(tert-butoxy)-2-(7-(4-chlorophenyl)-5-methyl-2-(1-methyl-3-(3-(2-morpholinoethyl)-2-oxoimidazolidin-1-yl)-1H-indazol-5-yl)benzo[d]thiazol-6-yl)acetate instead of (S)-ethyl 2-(tert-butoxy)-2-(7-(4-chlorophenyl)-2-(3-(3-(2-methoxyethyl)-2-oxoimidazolidin-1-yl)-1-methyl-1H-indazol-5-yl)-5-methylbenzo[d]thiazol-6-yl)acetate. $^1$H NMR (400 MHz, Acetonitrile-d3) δ 9.04 (s, 1H), 8.85-8.70 (m, 2H), 8.60-8.46 (m, 2H), 8.14 (dd, J=8.9, 1.7 Hz, 1H), 8.01 (dd, J=7.9, 6.1 Hz, 2H), 7.86 (d, J=1.0 Hz, 1H), 7.73-7.60 (m, 4H), 7.52 (d, J=9.0 Hz, 1H), 5.27 (s, 1H), 4.07 (dd, J=9.1, 7.0 Hz, 2H), 3.97 (s, 3H), 3.84-3.59 (m, 4H), 3.35 (t, J=5.2 Hz, 2H), 3.12 (s, 2H), 2.58 (s, 3H), 0.99 (s, 9H). LCMS-ESI$^+$: calc'd for $C_{37}H_{41}ClN_6O_5S$: 716.2, 718.2 (M+H$^+$); Found: 716.2, 718.2 (M+H$^+$).

Example 85. Preparation of (S)-2-(tert-butoxy)-2-(7-(4-chlorophenyl)-2-(3-(4-ethyl-3-oxopiperazin-1-yl)-1-methyl-1H-indazol-5-yl)-5-methylbenzo[d]thiazol-6-yl)acetic Acid (84)

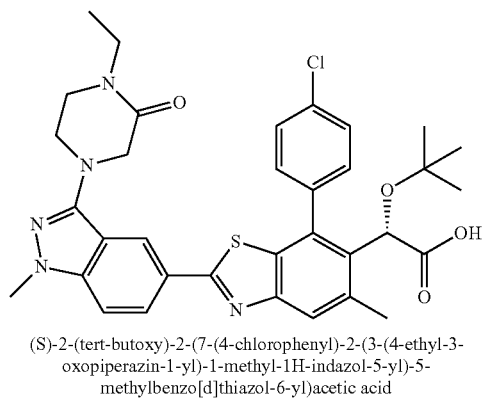 [SMILES: CCN1CCN(c2nn(C)c3ccc(-c4nc5cc(C)c([C@H](OC(C)(C)C)C(=O)O)c(-c6ccc(Cl)cc6)c5s4)cc23)CC1=O]

(S)-2-(tert-butoxy)-2-(7-(4-chlorophenyl)-2-(3-(4-ethyl-3-oxopiperazin-1-yl)-1-methyl-1H-indazol-5-yl)-5-methylbenzo[d]thiazol-6-yl)acetic acid Preparation of (S)-2-(tert-butoxy)-2-(7-(4-chlorophenyl)-2-(3-(4-ethyl-3-oxopiperazin-1-yl)-1-methyl-1H-indazol-5-yl)-5-methylbenzo[d]thiazol-6-yl)acetic acid: (S)-2-(tert-butoxy)-2-(7-(4-chlorophenyl)-2-(3-(4-ethyl-3-oxopiperazin-1-yl)-1-methyl-1H-indazol-5-yl)-5-methylbenzo[d]thiazol-6-yl)acetic acid was prepared in a similar manner as (S)-2-(tert-butoxy)-2-(7-(4-chlorophenyl)-2-(3-(3-(2-methoxyethyl)-2-oxoimidazolidin-1-yl)-1-methyl-1H-indazol-5-yl)-5-methylbenzo[d]thiazol-6-yl)acetic acid. $^1$H NMR (400 MHz, Methanol-d4) δ 8.46-8.39 (m, 1H), 8.07-7.97 (m, 1H), 7.79 (s, 1H), 7.72-7.65 (m, 1H), 7.58 (m, 3H), 7.49 (t, J=9.0 Hz, 1H), 5.24 (s, 1H), 4.07 (m, 1H), 3.91 (m, 4H), 3.76 (m, 2H), 3.63-3.47 (m, 4H), 2.61 (s, 3H), 1.19 (td, J=7.2, 3.0 Hz, 3H), 0.97 (s, 9H); LCMS-ESI+: calc'd for $C_{34}H_{37}ClN_5O_4S$: 646.22 (M+H+); Found: 646.3 (M+H+).

Example 86. Preparation of (S)-2-(tert-butoxy)-2-(7-(4-chlorophenyl)-5-methyl-2-(1-methyl-3-(4-methyl-3-oxopiperazin-1-yl)-1H-indazol-5-yl)benzo[d]thiazol-6-yl)acetic Acid (85)

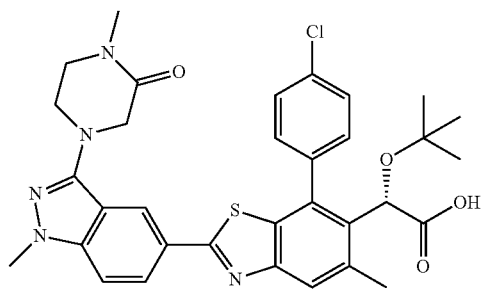

(S)-2-(tert-butoxy)-2-(7-(4-chlorophenyl)-5-methyl-2-(1-methyl-3-(4-methyl-3-oxopiperazin-1-yl)-1H-indazol-5-yl)benzo[d]thiazol-6-yl)acetic acid Preparation of (S)-2-(tert-butoxy)-2-(7-(4-chlorophenyl)-5-methyl-2-(1-methyl-3-(4-methyl-3-oxopiperazin-1-yl)-1H-indazol-5-yl)benzo[d]thiazol-6-yl)acetic acid: (S)-2-(tert-butoxy)-2-(7-(4-chlorophenyl)-5-methyl-2-(1-methyl-3-(4-methyl-3-oxopiperazin-1-yl)-1H-indazol-5-yl)benzo[d]thiazol-6-yl)acetic acid was prepared in a similar manner as (S)-2-(tert-butoxy)-2-(7-(4-chlorophenyl)-2-(3-(3-(2-methoxyethyl)-2-oxoimidazolidin-1-yl)-1-methyl-1H-indazol-5-yl)-5-methylbenzo[d]thiazol-6-yl)acetic acid. $^1$H NMR (400 MHz, Methanol-d4) δ 8.37 (s, 1H), 8.03-7.96 (m, 1H), 7.80-7.76 (m, 1H), 7.74-7.64 (m, 2H), 7.59 (m, 1H), 7.54-7.40 (m, 2H), 5.24 (s, 1H), 4.07 (s, 2H), 3.90 (d, J=8.4 Hz, 3H), 3.76 (s, 2H), 3.58 (t, J=5.4 Hz, 2H), 3.03 (s, 3H), 2.60 (s, 3H), 0.97 (s, 9H); LCMS-ESI+: calc'd for $C_{33}H_{35}ClN_5O_4S$: 632.20 (M+H+); Found: 632.3 (M+H+).

Example 87. Preparation of (S)-2-(tert-butoxy)-2-(7-(4-chlorophenyl)-2-(3-(4-ethyl-2-oxopiperazin-1-yl)-1-methyl-1H-indazol-5-yl)-5-methylbenzo[d]thiazol-6-yl)acetic Acid (86)

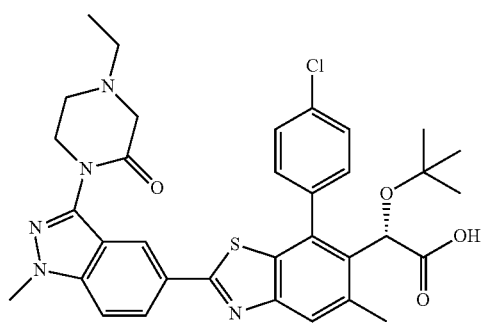

(S)-2-(tert-butoxy)-2-(7-(4-chlorophenyl)-2-(3-(4-ethyl-2-oxopiperazin-1-yl)-1-methyl-1H-indazol-5-yl)-5-methylbenzo[d]thiazol-6-yl)acetic acid Preparation of (S)-2-(tert-butoxy)-2-(7-(4-chlorophenyl)-2-(3-(4-ethyl-2-oxopiperazin-1-yl)-1-methyl-1H-indazol-5-yl)-5-methylbenzo[d]thiazol-6-yl)acetic acid: (S)-2-(tert-butoxy)-2-(7-(4-chlorophenyl)-2-(3-(4-ethyl-2-oxopiperazin-1-yl)-1-methyl-1H-indazol-5-yl)-5-methylbenzo[d]thiazol-6-yl)acetic acid was prepared in a similar manner as (S)-2-(tert-butoxy)-2-(7-(4-chlorophenyl)-2-(3-(3-(2-methoxyethyl)-2-oxoimidazolidin-1-yl)-1-methyl-1H-indazol-5-yl)-5-methylbenzo[d]thiazol-6-yl)acetic acid. $^1$H NMR (400 MHz, Methanol-d4) δ 8.34 (s, 1H), 8.19 (d, J=9.0, 1H), 7.81 (d, J=0.9 Hz, 1H), 7.72-7.64 (m, 2H), 7.63-7.52 (m, 3H), 5.24 (s, 1H), 4.29-4.20 (m, 4H), 4.08 (s, 3H), 3.82 (t, J=5.6 Hz, 2H), 3.43 (q, J=7.3 Hz, 2H), 2.61 (s, 3H), 1.45 (t, J=7.3 Hz, 3H), 0.97 (s, 9H); LCMS-ESI+: calc'd for $C_{34}H_{37}ClN_5O_4S$: 646.22 (M+H+); Found: 646.3 (M+H+).

Example 88. Preparation (S)-2-(tert-butoxy)-2-(7-(4-chlorophenyl)-5-methyl-2-(1-methyl-3-(4-methyl-2-oxopiperazin-1-yl)-1H-indazol-5-yl)benzo[d]thiazol-6-yl)acetic Acid (87)

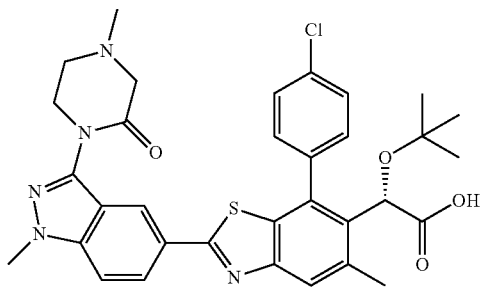

(S)-2-(tert-butoxy)-2-(7-(4-chlorophenyl)-5-methyl-2-(1-methyl-3-(4-methyl-2-oxopiperazin-1-yl)-1H-indazol-5-yl)benzo[d]thiazol-6-yl)acetic acid Preparation of (S)-2-(tert-butoxy)-2-(7-(4-chlorophenyl)-5-methyl-2-(1-methyl-3-(4-methyl-2-oxopiperazin-1-yl)-1H-indazol-5-yl)benzo[d]thiazol-6-yl)acetic acid: (S)-2-(tert-butoxy)-2-(7-(4-chlorophenyl)-5-methyl-2-(1-methyl-3-(4-methyl-2-oxopiperazin-1-yl)-1H-indazol-5-yl)benzo[d]thiazol-6-yl)acetic acid was prepared in a similar manner as (S)-2-(tert-butoxy)-2-(7-(4-chlorophenyl)-2-(3-(3-(2-methoxyethyl)-2-oxoimidazolidin-1-yl)-1-methyl-1H-indazol-5-yl)-5-methylbenzo[d]thiazol-6-yl)acetic acid. $^1$H NMR (400 MHz, CD3OD) δ 8.33 (dd, J=1.7, 0.8 Hz, 1H), 8.18 (dd, J=9.0, 1.7 Hz, 1H), 7.81 (d, J=0.9 Hz, 1H), 7.72-7.64 (m, 2H), 7.63-7.52 (m, 3H), 5.25 (s, 1H), 4.24 (d, J=2.3 Hz, 4H), 4.07 (s, 3H), 3.80 (t, J=5.6 Hz, 2H), 3.11 (s, 3H), 2.61 (d, J=0.8 Hz, 3H), 0.97 (s, 9H); LCMS-ESI+: calc'd for $C_{33}H_{35}ClN_5O_4S$: 632.20 (M+H+); Found: 632.3 (M+H+).

Example 89. Preparation of (S)-2-(tert-butoxy)-2-(7-(4-chlorophenyl)-5-methyl-2-(1-methyl-3-(3-morpholinoazetidin-1-yl)-1H-indazol-5-yl)benzo[d]thiazol-6-yl)acetic Acid (88)

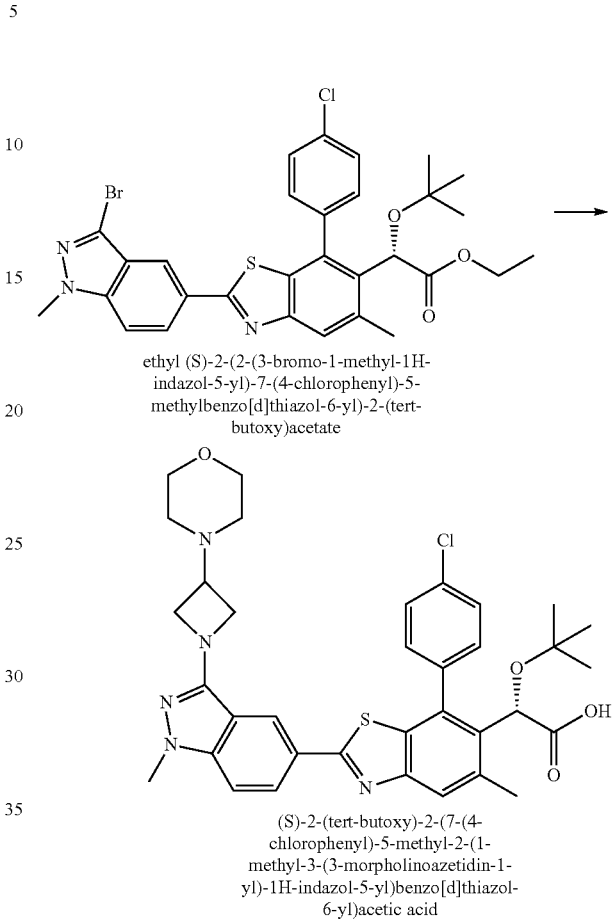

ethyl (S)-2-(2-(3-bromo-1-methyl-1H-indazol-5-yl)-7-(4-chlorophenyl)-5-methylbenzo[d]thiazol-6-yl)-2-(tert-butoxy)acetate (S)-2-(tert-butoxy)-2-(7-(4-chlorophenyl)-5-methyl-2-(1-methyl-3-(3-morpholinoazetidin-1-yl)-1H-indazol-5-yl)benzo[d]thiazol-6-yl)acetic acid Preparation of (S)-2-(tert-butoxy)-2-(7-(4-chlorophenyl)-5-methyl-2-(1-methyl-3-(3-morpholinoazetidin-1-yl)-1H-indazol-5-yl)benzo[d]thiazol-6-yl)acetic acid: A mixture of ethyl (S)-2-(2-(3-bromo-1-methyl-1H-indazol-5-yl)-7-(4-chlorophenyl)-5-methylbenzo[d]thiazol-6-yl)-2-(tert-butoxy)acetate (51.1 mg, 0.081 mmol), 4-(azetidin-3-yl)morpholine dihydrochloride (52.6 mg, 0.244 mmol), SPhos Pd G2 (11.9 mg, 0.017 mmol), and potassium t-butoxide (77.0 mg, 0.686 mmol) in 1,2-dimethoxyethane (1.5 mL) was placed in a microwave vial and reacted in a microwave reactor at 110° C. for 1 h. The resulting mixture was diluted in methanol, acidified with acetic acid (7-8 drops), filtered, and concentrated. The residue was dissolved in methanol (3 mL), filtered through syringe filter, and purified by Gilson HPLC (Phenomenex Gemini, 30-70% ACN/H$_2$O+0.1% TFA) to obtain the title product after lyophilization. $^1$H NMR (400 MHz, Acetonitrile-d$_3$) δ 8.16-8.10 (m, 1H), 8.07 (dd, J=9.0, 1.6 Hz, 1H), 7.83 (s, 1H), 7.66 (dd, J=7.8, 2.0 Hz, 1H), 7.63-7.56 (m, 3H), 7.42 (dd, J=9.0, 0.6 Hz, 1H), 5.27 (s, 1H), 4.50-4.36 (m, 4H), 4.08 (d, J=7.2 Hz, 1H), 3.92 (br, 4H), 3.86 (s, 3H), 3.16 (br, 4H), 2.58 (s, 3H), 0.99 (s, 9H). LCMS-ESI$^+$: calc'd for $C_{35}H_{39}ClN_5O_4S$: 660.24 (M+H)$^+$; found: 660.34 (M+H)$^+$.

Example 90. Preparation of (S)-2-(tert-butoxy)-2-(7-(4-chlorophenyl)-5-methyl-2-(1-methyl-3-(6-methyl-2,6-diazaspiro[3.3]heptan-2-yl)-1H-indazol-5-yl)benzo[d]thiazol-6-yl)acetic Acid (89)

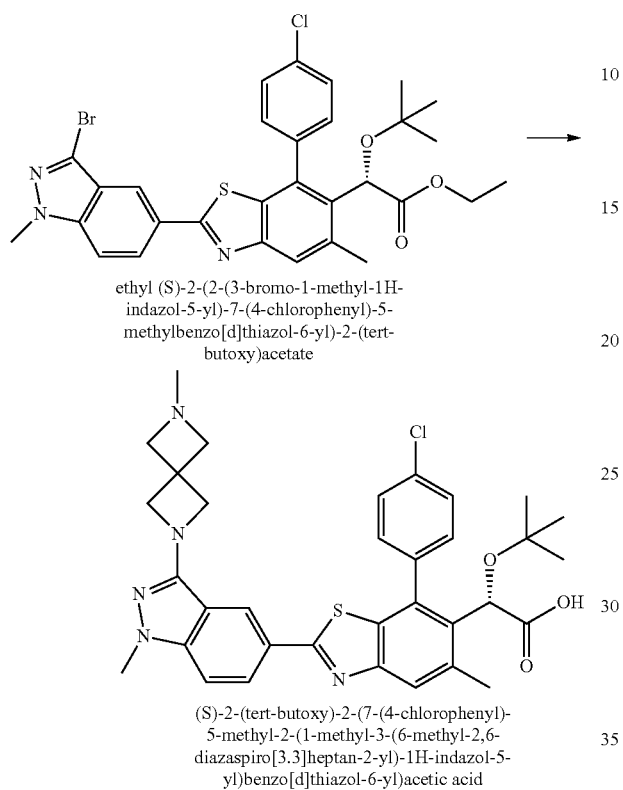

ethyl (S)-2-(2-(3-bromo-1-methyl-1H-indazol-5-yl)-7-(4-chlorophenyl)-5-methylbenzo[d]thiazol-6-yl)-2-(tert-butoxy)acetate (S)-2-(tert-butoxy)-2-(7-(4-chlorophenyl)-5-methyl-2-(1-methyl-3-(6-methyl-2,6-diazaspiro[3.3]heptan-2-yl)-1H-indazol-5-yl)benzo[d]thiazol-6-yl)acetic acid Preparation of (S)-2-(tert-butoxy)-2-(7-(4-chlorophenyl)-5-methyl-2-(1-methyl-3-(6-methyl-2,6-diazaspiro[3.3]heptan-2-yl)-1H-indazol-5-yl)benzo[d]thiazol-6-yl)acetic acid: A mixture of ethyl (S)-2-(2-(3-bromo-1-methyl-1H-indazol-5-yl)-7-(4-chlorophenyl)-5-methylbenzo[d]thiazol-6-yl)-2-(tert-butoxy)acetate (101.9 mg, 0.162 mmol), 2-methyl-2,6-diazaspiro[3.3]heptane (55.2 mg, 0.492 mmol), SPhos Pd G2 (24.9 mg, 0.035 mmol), and potassium t-butoxide (36.6 mg, 0.326 mmol) in 1,2-dimethoxyethane (3 mL) was placed in a microwave vial and reacted in a microwave reactor at 110° C. for 1 h. The resulting mixture was diluted in methanol, acidified with acetic acid (0.05 mL), filtered, and concentrated. The residue was dissolved in methanol-water mixture (9 mL), filtered through syringe filter, and purified by Gilson HPLC (Phenomenex Gemini, 40-55% ACN/H$_2$O+0.1% TFA). The collected fractions were neutralized with 2 N NaOH, and concentrated and lyophilized. The residue was dissolved in methanol-water mixture, filtered through syringe filter, and purified again by Waters HPLC (Phenomenex Gemini-NX, 10-100% ACN) to obtain the title product after lyophilization. $^1$H NMR (400 MHz, DMSO-d$_6$) δ 8.10 (d, J=1.6 Hz, 1H), 8.00 (dd, J=8.9, 1.6 Hz, 1H), 7.83 (s, 1H), 7.73 (d, J=8.2 Hz, 1H), 7.70-7.64 (m, 2H), 7.61 (d, J=7.3 Hz, 1H), 7.53 (d, J=9.0 Hz, 1H), 5.00 (s, 1H), 4.19 (s, 4H), 3.84 (s, 3H), 3.41 (s, 4H), 2.54 (s, 3H), 2.25 (s, 3H), 0.88 (s, 9H). LCMS-ESI$^+$: calc'd for C$_{34}$H$_{37}$ClN$_5$O$_3$S: 630.23 (M+H)$^+$; found: 630.25 (M+H)$^+$.

Example 91. (S)-2-(tert-butoxy)-2-(7-(4-chlorophenyl)-2-(3-(3-(dimethylamino)azetidin-1-yl)-1-methyl-1H-indazol-5-yl)-5-methylbenzo[d]thiazol-6-yl)acetic Acid (90)

ethyl (S)-2-(2-(3-bromo-1-methyl-1H-indazol-5-yl)-7-(4-chlorophenyl)-5-methylbenzo[d]thiazol-6-yl)-2-(tert-butoxy)acetate (S)-2-(tert-butoxy)-2-(7-(4-chlorophenyl)-2-(3-(3-(dimethylamino)azetidin-1-yl)-1-methyl-1H-indazol-5-yl)-5-methylbenzo[d]thiazol-6-yl)acetic acid Preparation of (2S)-2-(tert-butoxy)-2-(7-(4-chlorophenyl)-5-methyl-2-(1-methyl-3-(tetrahydrofuran-3-yl)-1H-indazol-5-yl)benzo[d]thiazol-6-yl)acetic acid: A mixture of ethyl (S)-2-(2-(3-bromo-1-methyl-1H-indazol-5-yl)-7-(4-chlorophenyl)-5-methylbenzo[d]thiazol-6-yl)-2-(tert-butoxy)acetate (49.5 mg, 0.079 mmol), N,N-dimethylazetidin-3-amine dihydrochloride (41.3 mg, 0.239 mmol), SPhos Pd G2 (11.4 mg, 0.016 mmol), and potassium t-butoxide (72.4 mg, 0.646 mmol) in 1,2-dimethoxyethane (1.5 mL) was placed in a microwave vial and reacted in a microwave reactor at 110° C. for 2.5 h. The resulting mixture was diluted in methanol, filtered through syringe filter, and purified by Gilson HPLC (Phenomenex Gemini, 50-100% ACN/H$_2$O+0.1% TFA) to obtain the title product after lyophilization. $^1$H NMR (400 MHz, Acetonitrile-d$_3$) δ 8.15-8.10 (m, 1H), 8.06 (dd, J=9.0, 1.6 Hz, 1H), 7.82 (s, 1H), 7.66 (dd, J=7.8, 2.2 Hz, 1H), 7.59 (d, J=7.9 Hz, 3H), 7.41 (d, J=8.9 Hz, 1H), 5.27 (s, 1H), 4.49-4.29 (m, 4H), 4.17 (dq, J=12.9, 6.0 Hz, 1H), 3.86 (s, 3H), 2.84 (s, 6H), 2.57 (s, 3H), 0.99 (s, 9H). LCMS-ESI$^+$: calc'd for C$_{33}$H$_{37}$ClN$_5$O$_3$S: 618.23 (M+H)$^+$; found: 618.24 (M+H)$^+$.

Example 92. Preparation of (S)-2-(tert-butoxy)-2-(7-(4-chlorophenyl)-5-methyl-2-(1-methyl-3-(2-oxa-6-azaspiro[3.3]heptan-6-yl)-1H-indazol-5-yl)benzo[d]thiazol-6-yl)acetic Acid (91)

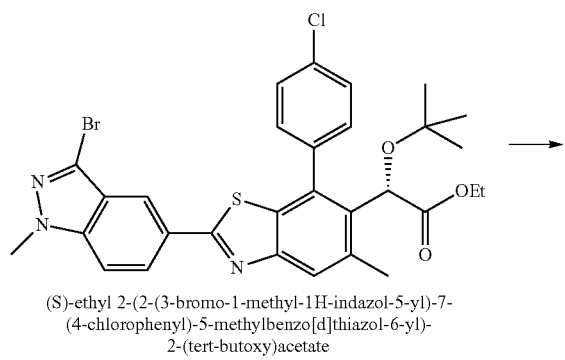

(S)-ethyl 2-(2-(3-bromo-1-methyl-1H-indazol-5-yl)-7-(4-chlorophenyl)-5-methylbenzo[d]thiazol-6-yl)-2-(tert-butoxy)acetate

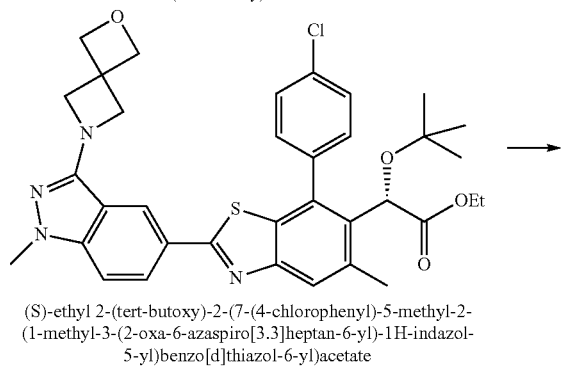

(S)-ethyl 2-(tert-butoxy)-2-(7-(4-chlorophenyl)-5-methyl-2-(1-methyl-3-(2-oxa-6-azaspiro[3.3]heptan-6-yl)-1H-indazol-5-yl)benzo[d]thiazol-6-yl)acetate

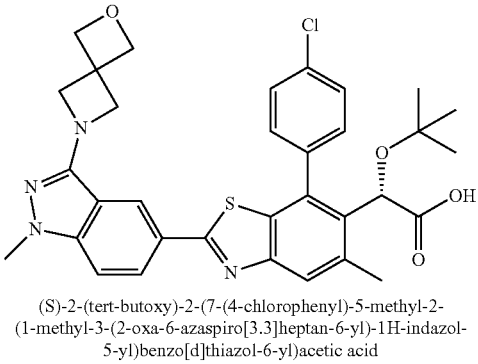

(S)-2-(tert-butoxy)-2-(7-(4-chlorophenyl)-5-methyl-2-(1-methyl-3-(2-oxa-6-azaspiro[3.3]heptan-6-yl)-1H-indazol-5-yl)benzo[d]thiazol-6-yl)acetic acid Preparation of (S)-ethyl 2-(tert-butoxy)-2-(7-(4-chlorophenyl)-5-methyl-2-(1-methyl-3-(2-oxa-6-azaspiro[3.3]heptan-6-yl)-1H-indazol-5-yl)benzo[d]thiazol-6-yl)acetate: In a 5 mL microwave vial, (S)-ethyl 2-(2-(3-bromo-1-methyl-1H-indazol-5-yl)-7-(4-chlorophenyl)-5-methylbenzo[d]thiazol-6-yl)-2-(tert-butoxy)acetate (0.020 g, 0.032 mmol), 2-oxa-6-azaspiro[3.3]heptane (0.01 g, 0.096 mmol), $Pd_2(dba)_3$ (0.004 g, 0.0044 mmol), 2-(Dicyclohexylphosphino)-2',4',6'-triisopropylbiphenyl (0.002 g, 0.0048 mmol) and $Cs_2CO_3$ (0.052 g, 0.16 mmol) in dioxane (1 mL) was heated to 100° C. under MW for one hour. The reaction mixture was diluted with ethyl acetate (50 mL), washed with 1N HCl and dried over $Na_2SO_4$. After concentration, the crude was purified by column chromatography on silica gel with hexane-EtOAc to obtain desired product.

Preparation of (S)-2-(tert-butoxy)-2-(7-(4-chlorophenyl)-5-methyl-2-(1-methyl-3-(2-oxa-6-azaspiro[3.3]heptan-6-yl)-1H-indazol-5-yl)benzo[d]thiazol-6-yl)acetic acid: In a 50 mL round-bottom flask, (S)-ethyl 2-(tert-butoxy)-2-(7-(4-chlorophenyl)-5-methyl-2-(1-methyl-3-(2-oxa-6-azaspiro[3.3]heptan-6-yl)-1H-indazol-5-yl)benzo[d]thiazol-6-yl)acetate (0.014 g, 0.022 mmol) was treated with THF (1 mL), and 5 M aq NaOH (1 mL), then heated to 100° C. for 30 min. The reaction was cooled to 23° C., and filtered (0.45 micron teflon syringe filter). The filtrate was purified by reverse phase HPLC, eluting by 5-100% acetonitrile in $H_2O$ with 0.1% TFA to give desired product. $^1H$ NMR (400 MHz, Acetonitrile-d3) δ 8.16 (dd, J=1.6, 0.8 Hz, 1H), 8.02 (d, J=8.8 Hz, 1H), 7.82 (s, 1H), 7.74-7.62 (m, 1H), 7.62-7.52 (m, 3H), 5.28 (s, 1H), 4.80 (s, 4H), 3.88-3.52 (m, 8H), 2.57 (d, J=0.8 Hz, 3H), 0.99 (s, 9H).

Example 93. Preparation of (S)-2-(tert-butoxy)-2-(7-(4-chlorophenyl)-2-(3-((R)-3-(dimethylamino)pyrrolidin-1-yl)-1-methyl-1H-indazol-5-yl)-5-methylbenzo[d]thiazol-6-yl)acetic Acid (92)

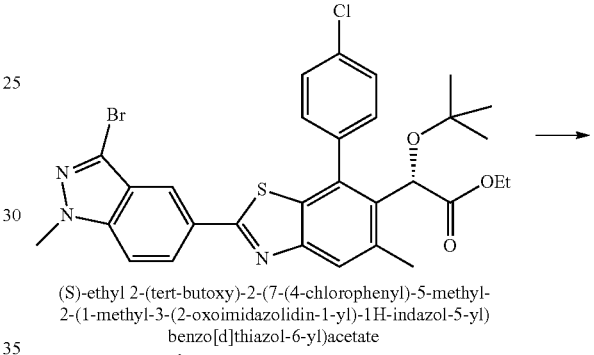

(S)-ethyl 2-(tert-butoxy)-2-(7-(4-chlorophenyl)-5-methyl-2-(1-methyl-3-(2-oxoimidazolidin-1-yl)-1H-indazol-5-yl)benzo[d]thiazol-6-yl)acetate

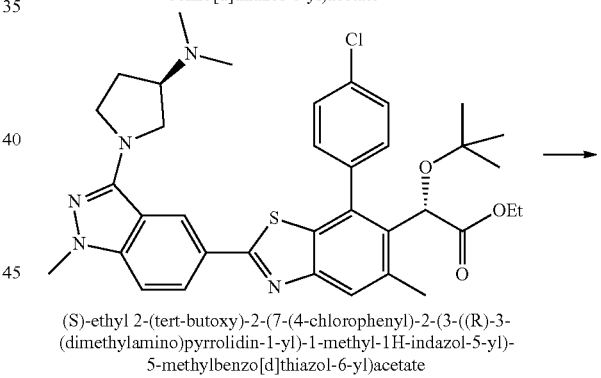

(S)-ethyl 2-(tert-butoxy)-2-(7-(4-chlorophenyl)-2-(3-((R)-3-(dimethylamino)pyrrolidin-1-yl)-1-methyl-1H-indazol-5-yl)-5-methylbenzo[d]thiazol-6-yl)acetate

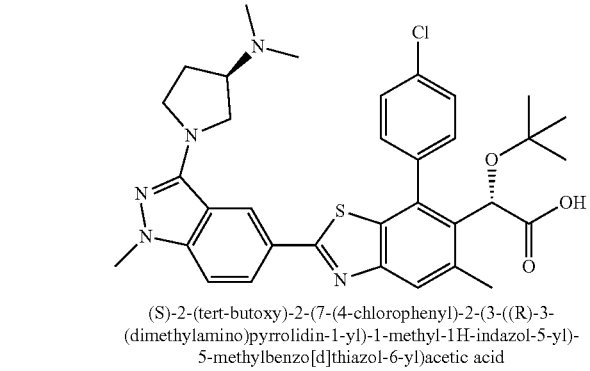

(S)-2-(tert-butoxy)-2-(7-(4-chlorophenyl)-2-(3-((R)-3-(dimethylamino)pyrrolidin-1-yl)-1-methyl-1H-indazol-5-yl)-5-methylbenzo[d]thiazol-6-yl)acetic acid Preparation of (S)-ethyl 2-(tert-butoxy)-2-(7-(4-chlorophenyl)-2-(3-((R)-3-(dimethylamino)pyrrolidin-1-yl)-1-methyl-1H-indazol-5-yl)-5-methylbenzo[d]thiazol-6-yl)acetate: Prepared in a manner similar to (S)-ethyl 2-(tert-butoxy)-2-(7-(4-chlorophenyl)-5-methyl-2-(1-methyl-3-(2-oxa-6-azaspiro[3.3]heptan-6-yl)-1H-indazol-5-yl)benzo[d]thiazol-6-yl)acetate except using (R)—N,N-dimethylpyrrolidin-3-amine and tripotassium phosphate instead of 2-oxa-6-azaspiro[3.3]heptane and Cs₂CO₃.

Preparation of (S)-2-(tert-butoxy)-2-(7-(4-chlorophenyl)-2-(3-((R)-3-(dimethylamino)pyrrolidin-1-yl)-1-methyl-1H-indazol-5-yl)-5-methylbenzo[d]thiazol-6-yl)acetic acid: Prepared in a manner similar to (S)-2-(tert-butoxy)-2-(7-(4-chlorophenyl)-5-methyl-2-(1-methyl-3-(2-oxa-6-azaspiro[3.3]heptan-6-yl)-1H-indazol-5-yl)benzo[d]thiazol-6-yl) acetic acid except using (S)-ethyl 2-(tert-butoxy)-2-(7-(4-chlorophenyl)-2-(3-((R)-3-(dimethylamino)pyrrolidin-1-yl)-1-methyl-1H-indazol-5-yl)-5-methylbenzo[d]thiazol-6-yl)acetate instead of (S)-ethyl 2-(tert-butoxy)-2-(7-(4-chlorophenyl)-5-methyl-2-(1-methyl-3-(2-oxa-6-azaspiro[3.3]heptan-6-yl)-1H-indazol-5-yl)benzo[d]thiazol-6-yl)acetate. ¹H NMR (400 MHz, Acetonitrile-d3) δ 8.50-8.37 (m, 1H), 8.02 (dd, J=9.0, 1.6 Hz, 1H), 7.85 (s, 1H), 7.67 (dd, J=8.7, 1.8 Hz, 1H), 7.61 (q, J=3.8, 2.9 Hz, 3H), 7.41 (d, J=9.0 Hz, 1H), 5.28 (s, 1H), 4.80 (s, 3H), 4.08-3.91 (m, 2H), 3.87 (d, J=6.7 Hz, 2H), 3.67 (td, J=8.5, 7.0 Hz, 1H), 2.92 (s, 3H), 2.59 (d, J=0.8 Hz, 3H), 2.58-2.45 (m, 3H), 2.35 (dq, J=14.4, 7.3 Hz, 3H), 0.99 (s, 9H).

Example 94. Preparation of (S)-2-(tert-butoxy)-2-(7-(4-chlorophenyl)-2-(3-((S)-3-(dimethylamino)pyrrolidin-1-yl)-methyl-1H-indazol-5-yl)-5-methylbenzo[d]thiazol-6-yl)acetic Acid (93)

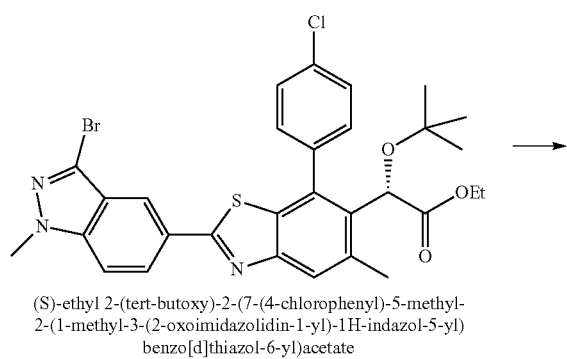

(S)-ethyl 2-(tert-butoxy)-2-(7-(4-chlorophenyl)-5-methyl-2-(1-methyl-3-(2-oxoimidazolidin-1-yl)-1H-indazol-5-yl)benzo[d]thiazol-6-yl)acetate

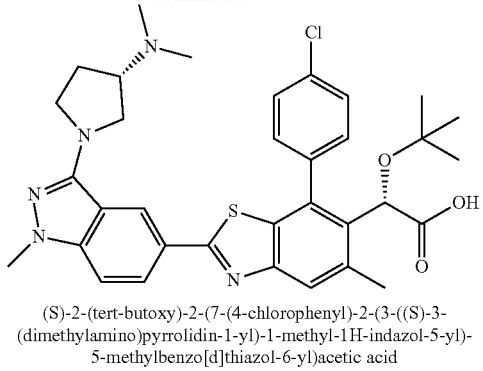

(S)-2-(tert-butoxy)-2-(7-(4-chlorophenyl)-2-(3-((S)-3-(dimethylamino)pyrrolidin-1-yl)-1-methyl-1H-indazol-5-yl)-5-methylbenzo[d]thiazol-6-yl)acetic acid Preparation of (S)-ethyl 2-(tert-butoxy)-2-(7-(4-chlorophenyl)-2-(3-((S)-3-(dimethylamino)pyrrolidin-1-yl)-1-methyl-1H-indazol-5-yl)-5-methylbenzo[d]thiazol-6-yl)acetate: Prepared in a manner similar to (S)-ethyl 2-(tert-butoxy)-2-(7-(4-chlorophenyl)-5-methyl-2-(1-methyl-3-(2-oxa-6-azaspiro[3.3]heptan-6-yl)-1H-indazol-5-yl)benzo[d]thiazol-6-yl)acetate except using (S)—N,N-dimethylpyrrolidin-3-amine and tripotassium phosphate instead of 2-oxa-6-azaspiro[3.3]heptane and Cs₂CO₃.

Preparation of (S)-2-(tert-butoxy)-2-(7-(4-chlorophenyl)-2-(3-((S)-3-(dimethylamino)pyrrolidin-1-yl)-1-methyl-1H-indazol-5-yl)-5-methylbenzo[d]thiazol-6-yl)acetic acid: Prepared in a manner similar to (S)-2-(tert-butoxy)-2-(7-(4-chlorophenyl)-5-methyl-2-(1-methyl-3-(2-oxa-6-azaspiro[3.3]heptan-6-yl)-1H-indazol-5-yl)benzo[d]thiazol-6-yl) acetic acid except using (S)-ethyl 2-(tert-butoxy)-2-(7-(4-chlorophenyl)-2-(3-((S)-3-(dimethylamino)pyrrolidin-1-yl)-1-methyl-1H-indazol-5-yl)-5-methylbenzo[d]thiazol-6-yl) acetate instead of (S)-ethyl 2-(tert-butoxy)-2-(7-(4-chlorophenyl)-5-methyl-2-(1-methyl-3-(2-oxa-6-azaspiro[3.3]heptan-6-yl)-1H-indazol-5-yl)benzo[d]thiazol-6-yl) acetate. ¹H NMR (400 MHz, Acetonitrile-d3) δ 8.37 (dd, J=1.6, 0.7 Hz, 1H), 8.01 (dd, J=8.9, 1.6 Hz, 1H), 7.83 (d, J=0.9 Hz, 1H), 7.75-7.64 (m, 1H), 7.60 (d, J=8.3 Hz, 2H), 7.45-7.31 (m, 1H), 5.27 (s, 1H), 4.08 (q, J=7.1 Hz, 1H), 4.04-3.89 (m, 2H), 3.90-3.74 (m, 5H), 3.67 (d, J=8.5 Hz, 1H), 3.49 (d, J=11.1 Hz, 1H), 3.27-3.03 (m, 4H), 2.86 (s, 3H), 2.58 (d, J=0.8 Hz, 4H), 0.99 (s, 9H).

Example 95. Preparation of (S)-2-(tert-butoxy)-2-(7-(4-chlorophenyl)-2-(3-((S)-3-(dimethylamino)pyrrolidin-1-yl)-1-methyl-1H-indazol-5-yl)-5-methylbenzo[d]thiazol-6-yl)acetic Acid (94)

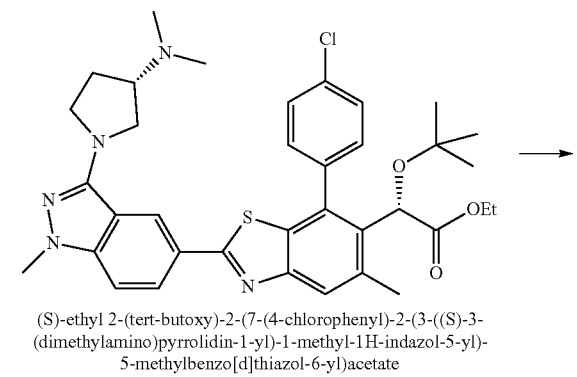

(S)-ethyl 2-(tert-butoxy)-2-(7-(4-chlorophenyl)-2-(3-((S)-3-(dimethylamino)pyrrolidin-1-yl)-1-methyl-1H-indazol-5-yl)-5-methylbenzo[d]thiazol-6-yl)acetate

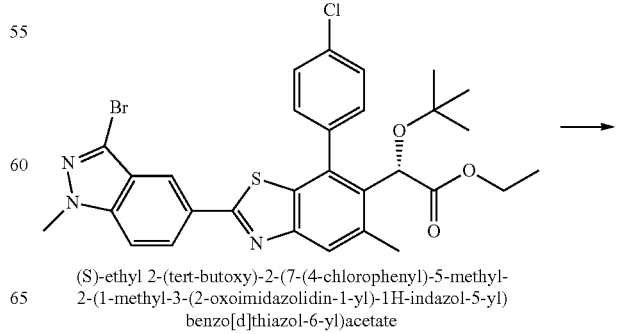

(S)-ethyl 2-(tert-butoxy)-2-(7-(4-chlorophenyl)-5-methyl-2-(1-methyl-3-(2-oxoimidazolidin-1-yl)-1H-indazol-5-yl)benzo[d]thiazol-6-yl)acetate

277

-continued

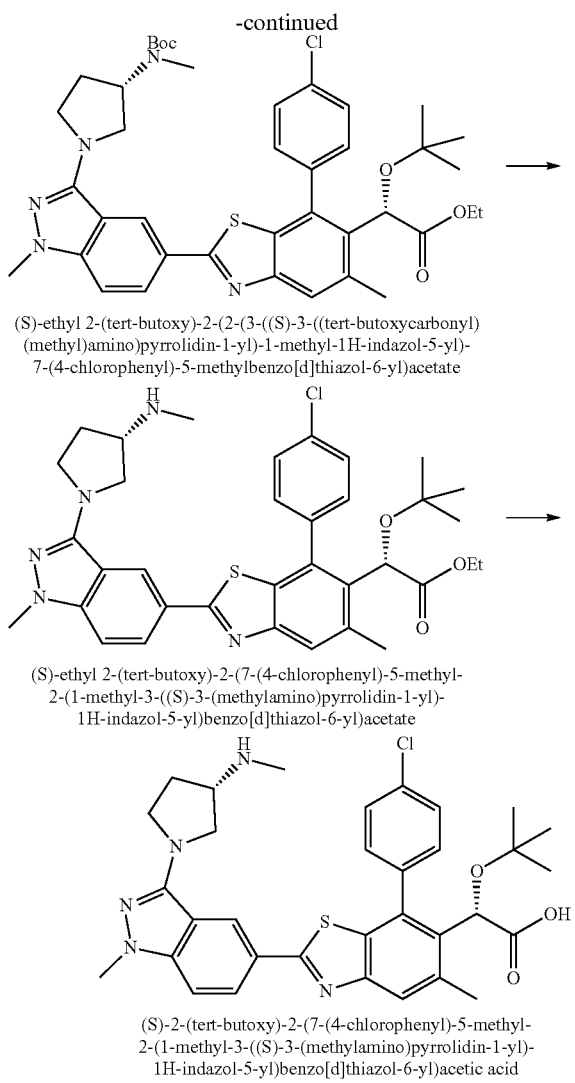

(S)-ethyl 2-(tert-butoxy)-2-(2-(3-((S)-3-((tert-butoxycarbonyl)(methyl)amino)pyrrolidin-1-yl)-1-methyl-1H-indazol-5-yl)-7-(4-chlorophenyl)-5-methylbenzo[d]thiazol-6-yl)acetate (S)-ethyl 2-(tert-butoxy)-2-(7-(4-chlorophenyl)-5-methyl-2-(1-methyl-3-((S)-3-(methylamino)pyrrolidin-1-yl)-1H-indazol-5-yl)benzo[d]thiazol-6-yl)acetate (S)-2-(tert-butoxy)-2-(7-(4-chlorophenyl)-5-methyl-2-(1-methyl-3-((S)-3-(methylamino)pyrrolidin-1-yl)-1H-indazol-5-yl)benzo[d]thiazol-6-yl)acetic acid Preparation of (S)-ethyl 2-(tert-butoxy)-2-(2-(3-((S)-3-((tert-butoxycarbonyl) (methyl)amino)pyrrolidin-1-yl)-1-methyl-1H-indazol-5-yl)-7-(4-chlorophenyl)-5-methylbenzo[d]thiazol-6-yl)acetate: Prepared in a manner similar to (S)-ethyl 2-(tert-butoxy)-2-(7-(4-chlorophenyl)-5-methyl-2-(1-methyl-3-(2-oxa-6-azaspiro[3.3]heptan-6-yl)-1H-indazol-5-yl)benzo[d]thiazol-6-yl)acetate except using (S)-tert-butyl methyl(pyrrolidin-3-yl)carbamate, 2-(Di-t-butylphosphino)biphenyl and tripotassium phosphate instead of 2-oxa-6-azaspiro[3.3]heptane, 2-(Dicyclohexylphosphino)-2',4',6'-triisopropylbiphenyl and $Cs_2CO_3$.

Preparation of (S)-ethyl 2-(tert-butoxy)-2-(7-(4-chlorophenyl)-5-methyl-2-(1-methyl-3-((S)-3-(methylamino)pyrrolidin-1-yl)-1H-indazol-5-yl)benzo[d]thiazol-6-yl)acetate: (S)-ethyl 2-(tert-butoxy)-2-(2-(3-((S)-3-((tert-butoxycarbonyl) (methyl)amino)pyrrolidin-1-yl)-1-methyl-1H-indazol-5-yl)-7-(4-chlorophenyl)-5-methylbenzo[d]thiazol-6-yl)acetate (14 mg, 0.018 mmol) was dissolved in 1.25 M HCl in 2-propanol (3 mL) in a 50 ml round-bottom flask. The reaction mixture was stirred at room temperature for overnight. After concentration, the HCl salt of the desired product was obtained.

Preparation of (S)-2-(tert-butoxy)-2-(7-(4-chlorophenyl)-5-methyl-2-(1-methyl-3-((S)-3-(methylamino)pyrrolidin-1-

278 yl)-1H-indazol-5-yl)benzo[d]thiazol-6-yl)acetic acid: Prepared in a manner similar to (S)-2-(tert-butoxy)-2-(7-(4-chlorophenyl)-5-methyl-2-(1-methyl-3-(2-oxa-6-azaspiro[3.3]heptan-6-yl)-1H-indazol-5-yl)benzo[d]thiazol-6-yl) acetic acid except using (S)-ethyl 2-(tert-butoxy)-2-(7-(4-chlorophenyl)-5-methyl-2-(1-methyl-3-((S)-3-(methylamino)pyrrolidin-1-yl)-1H-indazol-5-yl)benzo[d]thiazol-6-yl)acetate instead of (S)-ethyl 2-(tert-butoxy)-2-(7-(4-chlorophenyl)-5-methyl-2-(1-methyl-3-(2-oxa-6-azaspiro[3.3]heptan-6-yl)-1H-indazol-5-yl)benzo[d]thiazol-6-yl)acetate. $^1$H NMR (400 MHz, Acetonitrile-d3) δ 8.38 (d, J=1.6 Hz, 1H), 8.00 (dd, J=9.0, 1.6 Hz, 1H), 7.82 (s, 1H), 7.72-7.45 (m, 3H), 7.38 (d, J=8.9 Hz, 1H), 5.28 (s, 1H), 3.92 (dd, J=9.0, 6.5 Hz, 2H), 3.85 (s, 4H), 3.76 (dd, J=11.6, 5.9 Hz, 1H), 3.63 (td, J=9.2, 5.3 Hz, 1H), 3.44 (s, 3H), 2.76 (s, 3H), 2.58 (s, 3H), 2.56-2.37 (m, 1H), 2.30 (dt, J=9.8, 4.4 Hz, 1H), 0.99 (s, 9H).

Example 96. Preparation of (S)-2-(tert-butoxy)-2-(7-(4-chlorophenyl)-2-(3-((R)-3-(dimethylamino) pyrrolidin-1-yl)-1-methyl-1H-indazol-5-yl)-5-methylbenzo[d]thiazol-6-yl)acetic Acid (95)

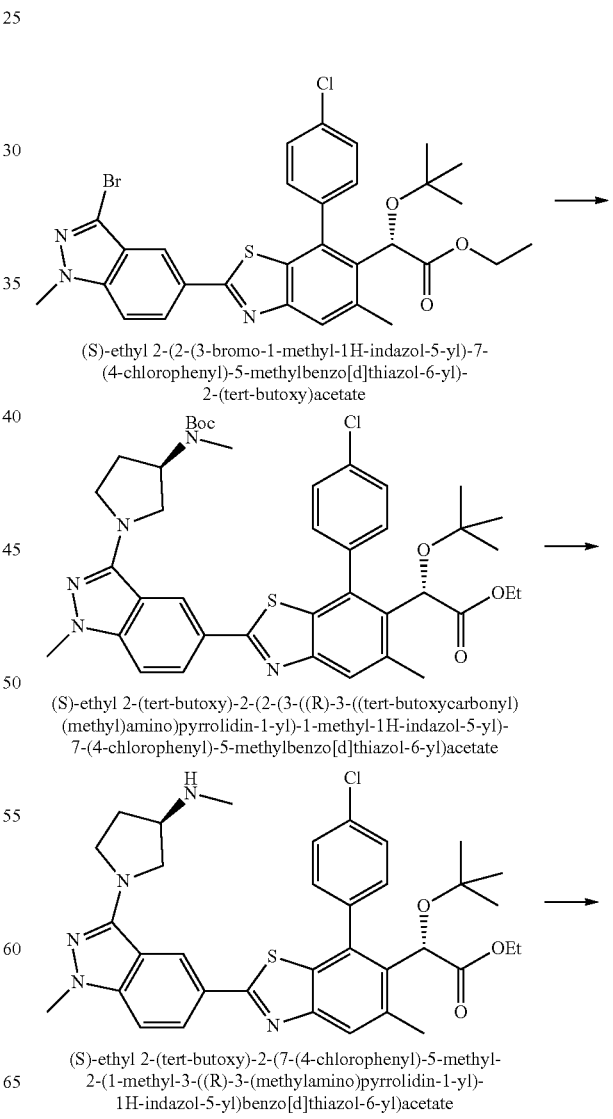

(S)-ethyl 2-(2-(3-bromo-1-methyl-1H-indazol-5-yl)-7-(4-chlorophenyl)-5-methylbenzo[d]thiazol-6-yl)-2-(tert-butoxy)acetate (S)-ethyl 2-(tert-butoxy)-2-(2-(3-((R)-3-((tert-butoxycarbonyl) (methyl)amino)pyrrolidin-1-yl)-1-methyl-1H-indazol-5-yl)-7-(4-chlorophenyl)-5-methylbenzo[d]thiazol-6-yl)acetate (S)-ethyl 2-(tert-butoxy)-2-(7-(4-chlorophenyl)-5-methyl-2-(1-methyl-3-((R)-3-(methylamino)pyrrolidin-1-yl)-1H-indazol-5-yl)benzo[d]thiazol-6-yl)acetate -continued

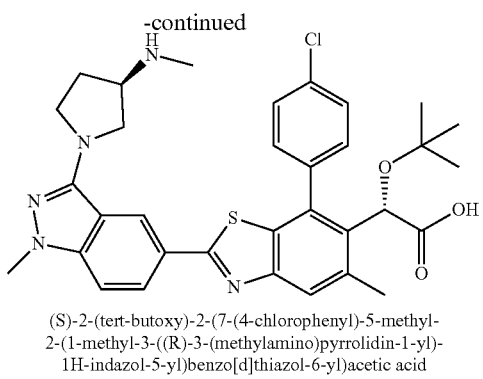

(S)-2-(tert-butoxy)-2-(7-(4-chlorophenyl)-5-methyl-
2-(1-methyl-3-((R)-3-(methylamino)pyrrolidin-1-yl)-
1H-indazol-5-yl)benzo[d]thiazol-6-yl)acetic acid Preparation of (S)-ethyl 2-(tert-butoxy)-2-(2-(3-((R)-3-((tert-butoxycarbonyl) (methyl)amino)pyrrolidin-1-yl)-1-methyl-1H-indazol-5-yl)-7-(4-chlorophenyl)-5-methyl-benzo[d]thiazol-6-yl)acetate: Prepared in a manner similar to (S)-ethyl 2-(tert-butoxy)-2-(7-(4-chlorophenyl)-5-methyl-2-(1-methyl-3-(2-oxa-6-azaspiro[3.3]heptan-6-yl)-1H-indazol-5-yl)benzo[d]thiazol-6-yl)acetate except using (R)-tert-butyl methyl(pyrrolidin-3-yl)carbamate, 2-(Di-t-butylphosphino)biphenyl and tripotassium phosphate instead of 2-oxa-6-azaspiro[3.3]heptane, 2-(Dicyclohexylphosphino)-2',4',6'-triisopropylbiphenyl and Cs$_2$CO$_3$.

Preparation of (S)-ethyl 2-(tert-butoxy)-2-(7-(4-chlorophenyl)-5-methyl-2-(1-methyl-3-((R)-3-(methylamino)pyrrolidin-1-yl)-1H-indazol-5-yl)benzo[d]thiazol-6-yl)acetate: (S)-ethyl 2-(tert-butoxy)-2-(2-(3-((R)-3-((tert-butoxycarbonyl) (methyl)amino)pyrrolidin-1-yl)-1-methyl-1H-indazol-5-yl)-7-(4-chlorophenyl)-5-methylbenzo[d]thiazol-6-yl)acetate (14 mg, 0.018 mmol) was dissolved in 1.25 M HCl in 2-propanol (3 mL) in a 50 ml round-bottom flask. The reaction mixture was stirred at room temperature for overnight. After concentration, the HCl salt of the desired product was obtained.

Preparation of (S)-2-(tert-butoxy)-2-(7-(4-chlorophenyl)-5-methyl-2-(1-methyl-3-((R)-3-(methylamino)pyrrolidin-1-yl)-1H-indazol-5-yl)benzo[d]thiazol-6-yl)acetic acid: Prepared in a manner similar to (S)-2-(tert-butoxy)-2-(7-(4-chlorophenyl)-5-methyl-2-(1-methyl-3-(2-oxa-6-azaspiro[3.3]heptan-6-yl)-1H-indazol-5-yl)benzo[d]thiazol-6-yl) acetic acid except using (S)-ethyl 2-(tert-butoxy)-2-(7-(4-chlorophenyl)-5-methyl-2-(1-methyl-3-((R)-3-(methylamino)pyrrolidin-1-yl)-1H-indazol-5-yl)benzo[d]thiazol-6-yl)acetate instead of (S)-ethyl 2-(tert-butoxy)-2-(7-(4-chlorophenyl)-5-methyl-2-(1-methyl-3-(2-oxa-6-azaspiro[3.3]heptan-6-yl)-1H-indazol-5-yl)benzo[d]thiazol-6-yl)acetate. $^1$H NMR (400 MHz, Chloroform-d) 1H NMR (400 MHz, Acetonitrile-d3) δ 8.48-8.22 (m, 1H), 8.12-7.90 (m, 2H), 7.79 (s, 1H), 7.66 (dd, J=7.8, 2.0 Hz, 1H), 7.58 (d, J=8.2 Hz, 3H), 7.35 (d, J=9.0 Hz, 1H), 5.27 (s, 1H), 4.13 (s, 3H), 3.87 (d, J=24.9 Hz, 3H), 3.62 (s, 1H), 2.75 (d, J=2.9 Hz, 3H), 2.64-2.53 (m, 3H), 2.52-2.34 (m, 1H), 2.33-2.18 (m, 1H), 0.99 (s, 9H).

Example 97. Preparation of (S)-2-(tert-butoxy)-2-(7-(4-chlorophenyl)-5-methyl-2-(1-methyl-3-(2-azaspiro[3.4]octan-2-yl)-1H-indazol-5-yl)benzo[d]thiazol-6-yl)acetic Acid (96)

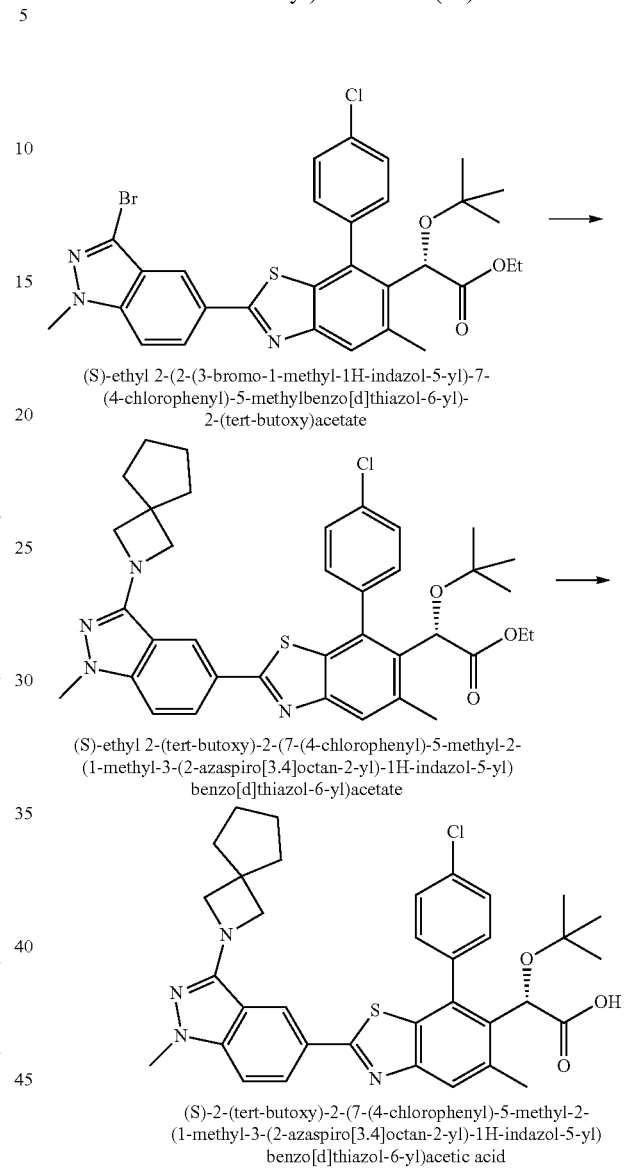

Preparation of (S)-ethyl 2-(tert-butoxy)-2-(7-(4-chlorophenyl)-5-methyl-2-(1-methyl-3-(2-azaspiro[3.4]octan-2-yl)-1H-indazol-5-yl)benzo[d]thiazol-6-yl)acetate: Prepared in a manner similar to (S)-ethyl 2-(tert-butoxy)-2-(7-(4-chlorophenyl)-5-methyl-2-(1-methyl-3-(2-oxa-6-azaspiro[3.3]heptan-6-yl)-1H-indazol-5-yl)benzo[d]thiazol-6-yl)acetate except using 2-azaspiro[3.4]octane instead of 2-oxa-6-azaspiro[3.3]heptane.

Preparation of (S)-2-(tert-butoxy)-2-(7-(4-chlorophenyl)-5-methyl-2-(1-methyl-3-(2-azaspiro[3.4]octan-2-yl)-1H-indazol-5-yl)benzo[d]thiazol-6-yl)acetic acid: Prepared in a manner similar to (S)-2-(tert-butoxy)-2-(7-(4-chlorophenyl)-5-methyl-2-(1-methyl-3-(2-oxa-6-azaspiro[3.3]heptan-6-yl)-1H-indazol-5-yl)benzo[d]thiazol-6-yl)acetic acid except using (S)-ethyl 2-(tert-butoxy)-2-(7-(4-chlorophenyl)-5-methyl-2-(1-methyl-3-(2-azaspiro[3.4]octan-2-yl)-1H-indazol-5-yl)benzo[d]thiazol-6-yl)acetate instead of (S)- ethyl 2-(tert-butoxy)-2-(7-(4-chlorophenyl)-5-methyl-2-(1-methyl-3-(2-oxa-6-azaspiro[3.3]heptan-6-yl)-1H-indazol-5-yl)benzo[d]thiazol-6-yl)acetate. ¹H NMR (400 MHz, Acetonitrile-d3) δ 8.33-8.18 (m, 1H), 8.12 (s, 1H), 7.82 (s, 1H), 7.72-7.62 (m, 1H), 7.60 (dtd, J=5.7, 2.7, 1.1 Hz, 3H), 5.24 (m, 10H), 2.56 (d, J=0.8 Hz, 3H), 1.78-1.61 (m, 4H), 0.98 (s, 9H).

Example 98. Preparation of (S)-2-(tert-butoxy)-2-(7-(4-chlorophenyl)-5-methyl-2-(1-methyl-3-(2-azaspiro[3.5]nonan-2-yl)-1H-indazol-5-yl)benzo[d]thiazol-6-yl)acetic Acid (97)

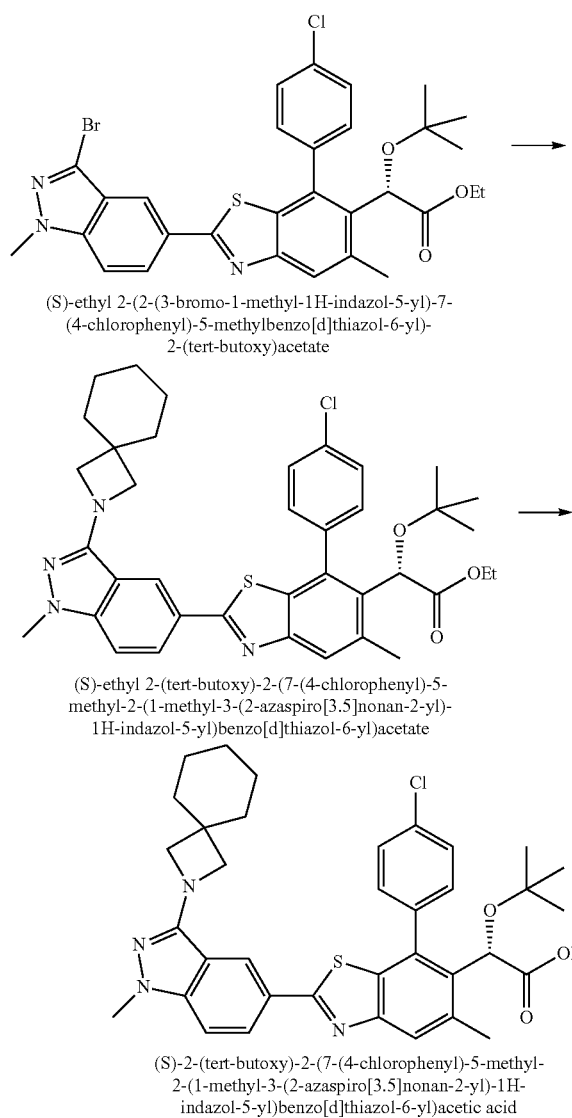

(S)-ethyl 2-(2-(3-bromo-1-methyl-1H-indazol-5-yl)-7-(4-chlorophenyl)-5-methylbenzo[d]thiazol-6-yl)-2-(tert-butoxy)acetate (S)-ethyl 2-(tert-butoxy)-2-(7-(4-chlorophenyl)-5-methyl-2-(1-methyl-3-(2-azaspiro[3.5]nonan-2-yl)-1H-indazol-5-yl)benzo[d]thiazol-6-yl)acetate (S)-2-(tert-butoxy)-2-(7-(4-chlorophenyl)-5-methyl-2-(1-methyl-3-(2-azaspiro[3.5]nonan-2-yl)-1H-indazol-5-yl)benzo[d]thiazol-6-yl)acetic acid Preparation of (S)-ethyl 2-(tert-butoxy)-2-(7-(4-chlorophenyl)-5-methyl-2-(1-methyl-3-(2-azaspiro[3.5]nonan-2-yl)-1H-indazol-5-yl)benzo[d]thiazol-6-yl)acetate: Prepared in a manner similar to (S)-ethyl 2-(tert-butoxy)-2-(7-(4-chlorophenyl)-5-methyl-2-(1-methyl-3-(2-oxa-6-azaspiro[3.3]heptan-6-yl)-1H-indazol-5-yl)benzo[d]thiazol-6-yl)acetate except using 2-azaspiro[3.5]nonane instead of 2-oxa-6-azaspiro[3.3]heptane.

Preparation of (S)-2-(tert-butoxy)-2-(7-(4-chlorophenyl)-5-methyl-2-(1-methyl-3-(2-azaspiro[3.5]nonan-2-yl)-1H-indazol-5-yl)benzo[d]thiazol-6-yl)acetic acid: Prepared in a manner similar to (S)-2-(tert-butoxy)-2-(7-(4-chlorophenyl)-5-methyl-2-(1-methyl-3-(2-oxa-6-azaspiro[3.3]heptan-6-yl)-1H-indazol-5-yl)benzo[d]thiazol-6-yl)acetic acid except using (S)-ethyl 2-(tert-butoxy)-2-(7-(4-chlorophenyl)-5-methyl-2-(1-methyl-3-(2-azaspiro[3.5]nonan-2-yl)-1H-indazol-5-yl)benzo[d]thiazol-6-yl)acetate instead of (S)-ethyl 2-(tert-butoxy)-2-(7-(4-chlorophenyl)-5-methyl-2-(1-methyl-3-(2-oxa-6-azaspiro[3.3]heptan-6-yl)-1H-indazol-5-yl)benzo[d]thiazol-6-yl)acetate. ¹H NMR (400 MHz, Acetonitrile-d3) δ 8.23 (d, J=1.6 Hz, 1H), 8.13 (s, 1H), 7.82 (s, 1H), 7.66 (dd, J=8.9, 2.2 Hz, 1H), 7.59 (q, J=3.6, 2.9 Hz, 3H), 7.03 (s, 1H), 5.28 (s, 1H), 5.00 (m, 8H), 2.57 (s, 3H), 2.06-1.86 (m, 2H), 1.79 (t, J=5.7 Hz, 2H), 1.64-1.37 (m, 2H), 1.34-1.17 (m, 4H), 0.99 (s, 9H).

Example 99. Preparation of (S)-2-(tert-butoxy)-2-(7-(4-chlorophenyl)-2-(3-(4-(2-methoxyethyl)piperazin-1-yl)-1-methyl-1H-indazol-5-yl)-5-methylbenzo[d]thiazol-6-yl)acetic Acid (98)

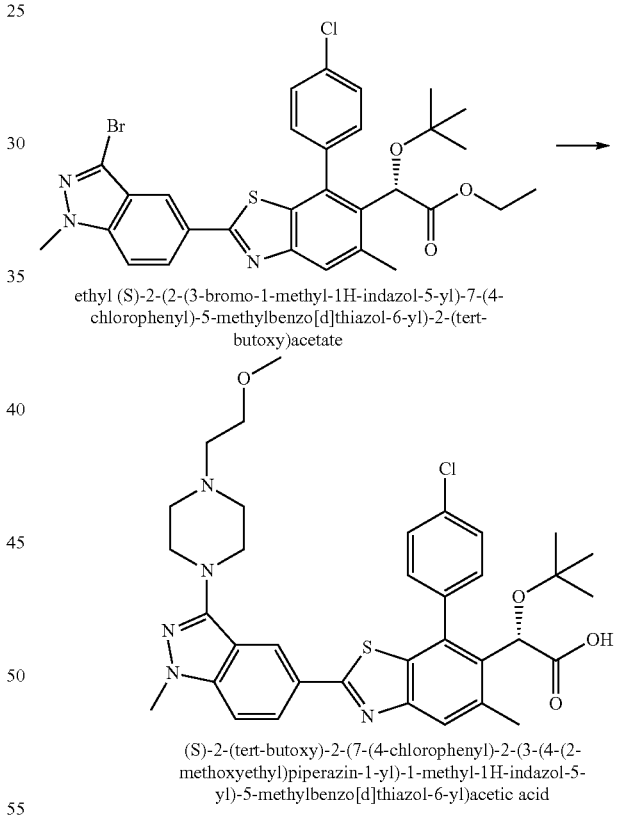

ethyl (S)-2-(2-(3-bromo-1-methyl-1H-indazol-5-yl)-7-(4-chlorophenyl)-5-methylbenzo[d]thiazol-6-yl)-2-(tert-butoxy)acetate (S)-2-(tert-butoxy)-2-(7-(4-chlorophenyl)-2-(3-(4-(2-methoxyethyl)piperazin-1-yl)-1-methyl-1H-indazol-5-yl)-5-methylbenzo[d]thiazol-6-yl)acetic acid Preparation of (S)-2-(tert-butoxy)-2-(7-(4-chlorophenyl)-2-(3-(4-(2-methoxyethyl)piperazin-1-yl)-1-methyl-1H-indazol-5-yl)-5-methylbenzo[d]thiazol-6-yl)acetic acid: A mixture of ethyl (S)-2-(2-(3-bromo-1-methyl-1H-indazol-5-yl)-7-(4-chlorophenyl)-5-methylbenzo[d]thiazol-6-yl)-2-(tert-butoxy)acetate (50.4 mg, 0.080 mmol), 1-(2-methoxyethyl)piperazine (36.0 mg, 0.250 mmol), SPhos Pd G2 (11.8 mg, 0.016 mmol), and potassium t-butoxide (18.3 mg, 0.163 mmol) in 1,2-dimethoxyethane (1.5 mL) was placed in a microwave vial and reacted in a microwave reactor at 110° C. for 2 h. The resulting mixture was diluted in methanol, filtered, and concentrated. The residue was dissolved in THF (0.5 mL), methanol (0.5 mL), and 2 N NaOH (0.2 mL) at room temperature and kept tightly before the mixture was stirred at 70° C. for 3 h. The reaction mixture was acidified with acetic acid (0.05 mL) and concentrated to remove organic solvent. The resulting mixture was dissolved in methanol (3 mL), filtered through syringe filter, and purified by Gilson HPLC (Phenomenex Gemini, 30-70% ACN/H$_2$O+0.1% TFA) to obtain the title product after lyophilization. $^1$H NMR (400 MHz, Acetonitrile-d$_3$) δ 8.33-8.26 (m, 1H), 8.10 (dd, J=9.0, 1.5 Hz, 1H), 7.83 (s, 1H), 7.71-7.63 (m, 1H), 7.63-7.54 (m, 3H), 7.47 (d, J=8.9 Hz, 1H), 5.27 (s, 1H), 3.89 (s, 3H), 3.81-3.73 (m, 2H), 3.73-3.57 (m, 4H), 3.55-3.39 (m, 4H), 3.36 (s, 3H), 3.30 (t, J=5.0 Hz, 2H), 2.58 (s, 3H), 0.99 (s, 9H). LCMS-ESI$^+$: calc'd for C$_{35}$H$_{41}$CN$_5$O$_4$S: 662.26 (M+H)$^+$; found: 662.32 (M+H)$^+$.

Example 100. Preparation of (S)-2-(tert-butoxy)-2-(7-(4-chlorophenyl)-2-(3-(4-(2-ethoxyethyl)piperazin-1-yl)-1-methyl-1H-indazol-5-yl)-5-methylbenzo[d]thiazol-6-yl)acetic Acid (99)

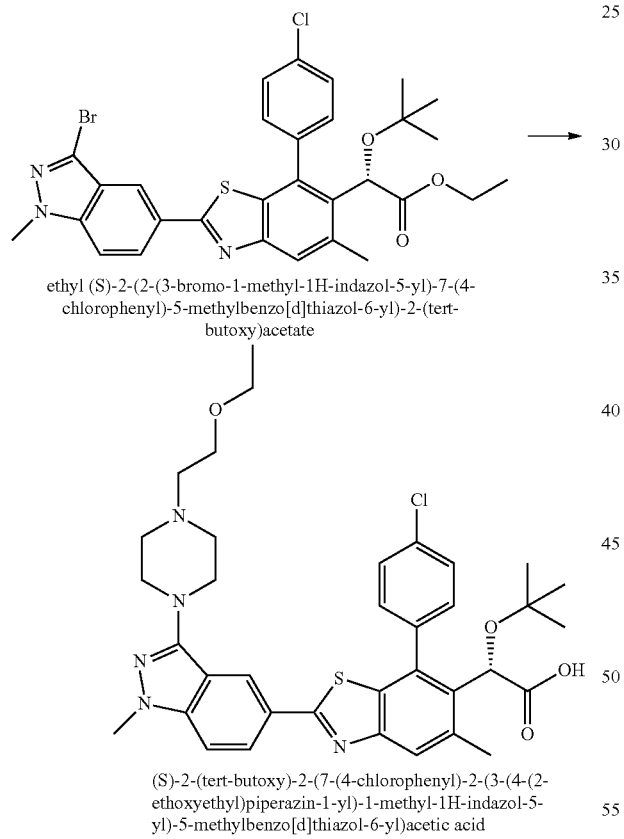

ethyl (S)-2-(2-(3-bromo-1-methyl-1H-indazol-5-yl)-7-(4-chlorophenyl)-5-methylbenzo[d]thiazol-6-yl)-2-(tert-butoxy)acetate (S)-2-(tert-butoxy)-2-(7-(4-chlorophenyl)-2-(3-(4-(2-ethoxyethyl)piperazin-1-yl)-1-methyl-1H-indazol-5-yl)-5-methylbenzo[d]thiazol-6-yl)acetic acid Preparation of (S)-2-(tert-butoxy)-2-(7-(4-chlorophenyl)-2-(3-(4-(2-ethoxyethyl)piperazin-1-yl)-1-methyl-1H-indazol-f5-yl)-5-methylbenzo[d]thiazol-6-yl)acetic acid: A mixture of ethyl (S)-2-(2-(3-bromo-1-methyl-1H-indazol-5-yl)-7-(4-chlorophenyl)-5-methylbenzo[d]thiazol-6-yl)-2-(tert-butoxy)acetate (102.2 mg, 0.163 mmol), 1-(2-ethoxyethyl)piperazine (78.2 mg, 0.494 mmol), SPhos Pd G2 (24.2 mg, 0.034 mmol), and potassium t-butoxide (37.5 mg, 0.334 mmol) in 1,2-dimethoxyethane (3 mL) was placed in a microwave vial and reacted in a microwave reactor at 110° C. for 2 h. The resulting mixture was diluted in methanol, filtered, and concentrated. The residue was dissolved in THF (1 mL), methanol (1 mL), and 2 N NaOH (0.4 mL) at room temperature and kept tightly before the mixture was stirred at 70° C. for 3 h. The reaction mixture was acidified with acetic acid (0.10 mL) and concentrated to remove organic solvent. The resulting mixture was dissolved in methanol (6 mL), filtered through syringe filter, and purified by Gilson HPLC (Phenomenex Gemini, 40-75% ACN/H$_2$O+0.1% TFA) to obtain the title product after lyophilization. $^1$H NMR (400 MHz, Acetonitrile-d$_3$) δ 8.33 (dd, J=1.6, 0.8 Hz, 1H), 8.13 (dd, J=9.0, 1.6 Hz, 1H), 7.85 (d, J=0.8 Hz, 1H), 7.67 (dd, J=8.0, 2.2 Hz, 1H), 7.60 (d, J=8.3 Hz, 3H), 7.50 (dd, J=8.9, 0.8 Hz, 1H), 5.28 (s, 1H), 4.01 (d, J=11.4 Hz, 2H), 3.91 (s, 3H), 3.81-3.74 (m, 2H), 3.68 (d, J=10.0 Hz, 2H), 3.58 (q, J=7.0 Hz, 2H), 3.48-3.29 (m, 6H), 2.58 (d, J=0.8 Hz, 3H), 1.23 (t, J=7.0 Hz, 3H), 0.99 (s, 9H). LCMS-ESI$^+$: calc'd for C$_{36}$H$_{43}$ClN$_5$O$_4$S: 676.27 (M+H)$^+$; found: 676.41 (M+H)$^+$.

Example 101. Preparation of (S)-2-(tert-butoxy)-2-(7-(4-chlorophenyl)-2-(3-(4-(cyclopropylmethyl)piperazin-1-yl)-1-methyl-1H-indazol-5-yl)-5-methylbenzo[d]thiazol-6-yl)acetic Acid (100)

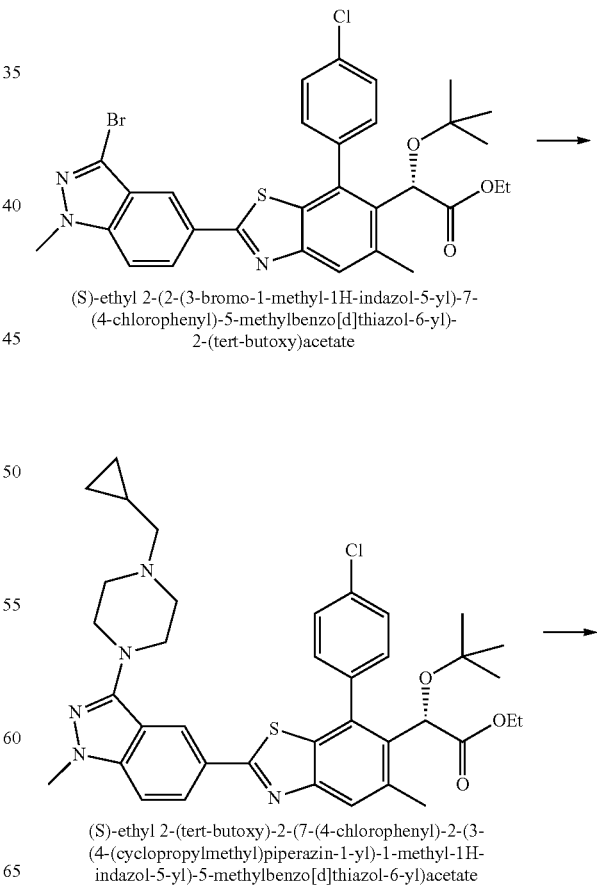

(S)-ethyl 2-(2-(3-bromo-1-methyl-1H-indazol-5-yl)-7-(4-chlorophenyl)-5-methylbenzo[d]thiazol-6-yl)-2-(tert-butoxy)acetate (S)-ethyl 2-(tert-butoxy)-2-(7-(4-chlorophenyl)-2-(3-(4-(cyclopropylmethyl)piperazin-1-yl)-1-methyl-1H-indazol-5-yl)-5-methylbenzo[d]thiazol-6-yl)acetate

285
-continued

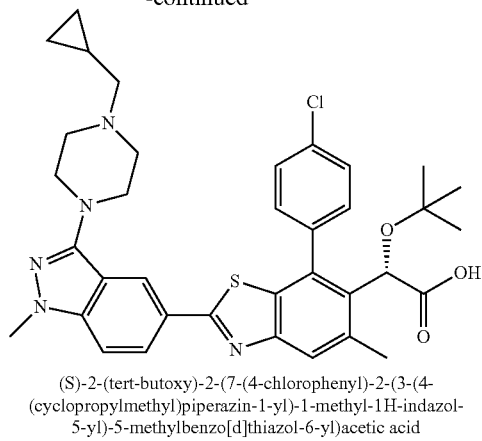

(S)-2-(tert-butoxy)-2-(7-(4-chlorophenyl)-2-(3-(4-(cyclopropylmethyl)piperazin-1-yl)-1-methyl-1H-indazol-5-yl)-5-methylbenzo[d]thiazol-6-yl)acetic acid Preparation of (S)-ethyl 2-(tert-butoxy)-2-(7-(4-chlorophenyl)-2-(3-(4-(cyclopropylmethyl)piperazin-1-yl)-1-methyl-1H-indazol-5-yl)-5-methylbenzo[d]thiazol-6-yl)acetate: Prepared in a manner similar to (S)-ethyl 2-(tert-butoxy)-2-(7-(4-chlorophenyl)-5-methyl-2-(1-methyl-3-(2-oxa-6-azaspiro[3.3]heptan-6-yl)-1H-indazol-5-yl)benzo[d]thiazol-6-yl)acetate except using 1-(cyclopropylmethyl)piperazine HBr salt, SPhos Pd G2 and potassium tert-butoxide instead of 2-oxa-6-azaspiro[3.3]heptane, $Pd_2(dba)_3$, 2-(Dicyclohexylphosphino)-2',4',6'-triisopropylbiphenyl and $Cs_2CO_3$.

Preparation of (S)-2-(tert-butoxy)-2-(7-(4-chlorophenyl)-2-(3-(4-(cyclopropylmethyl)piperazin-1-yl)-1-methyl-1H-indazol-5-yl)-5-methylbenzo[d]thiazol-6-yl)acetic acid: Prepared in a manner similar to (S)-2-(tert-butoxy)-2-(7-(4-chlorophenyl)-5-methyl-2-(1-methyl-3-(2-oxa-6-azaspiro[3.3]heptan-6-yl)-1H-indazol-5-yl)benzo[d]thiazol-6-yl)acetic acid except using (S)-ethyl 2-(tert-butoxy)-2-(7-(4-chlorophenyl)-2-(3-(4-(cyclopropylmethyl)piperazin-1-yl)-1-methyl-1H-indazol-5-yl)-5-methylbenzo[d]thiazol-6-yl)acetate instead of (S)-ethyl 2-(tert-butoxy)-2-(7-(4-chlorophenyl)-5-methyl-2-(1-methyl-3-(2-oxa-6-azaspiro[3.3]heptan-6-yl)-1H-indazol-5-yl)benzo[d]thiazol-6-yl)acetate. $^1H$ NMR (400 MHz, Acetonitrile-d3) δ 8.43-8.28 (m, 1H), 8.14 (dd, J=8.9, 1.6 Hz, 1H), 7.85 (s, 1H), 7.69-7.64 (m, 1H), 7.61 (d, J=8.0 Hz, 3H), 7.50 (dd, J=8.9, 0.7 Hz, 1H), 5.28 (s, 1H), 4.09 (s, 1H), 4.01 (d, J=13.6 Hz, 2H), 3.92 (s, 3H), 3.72 (d, J=7.3 Hz, 2H), 3.40 (d, J=12.3 Hz, 1H), 3.34-3.18 (m, 3H), 3.06 (d, J=7.1 Hz, 3H), 2.69-2.34 (m, 2H), 0.99 (s, 9H), 0.95 (s, 1H), 0.83-0.67 (m, 2H), 0.45 (dt, J=6.3, 4.6 Hz, 2H).

Example 102. Preparation of (2S)-2-(tert-butoxy)-2-(7-(4-chlorophenyl)-5-methyl-2-(1-methyl-3-(6-methyl-3,6-diazabicyclo[3.1.1]heptan-3-yl)-1H-indazol-5-yl)benzo[d]thiazol-6-yl)acetic Acid (101)

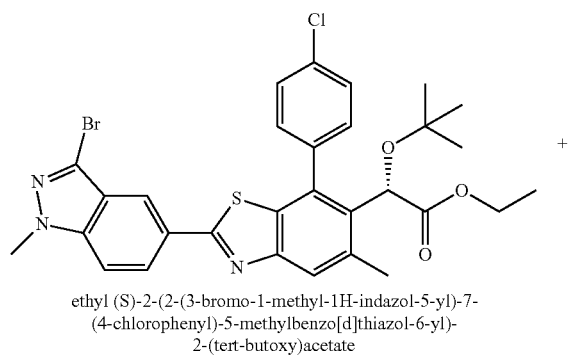

ethyl (S)-2-(2-(3-bromo-1-methyl-1H-indazol-5-yl)-7-(4-chlorophenyl)-5-methylbenzo[d]thiazol-6-yl)-2-(tert-butoxy)acetate

286
-continued

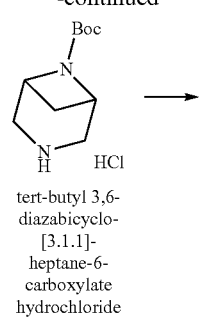

tert-butyl 3,6-diazabicyclo-[3.1.1]-heptane-6-carboxylate hydrochloride

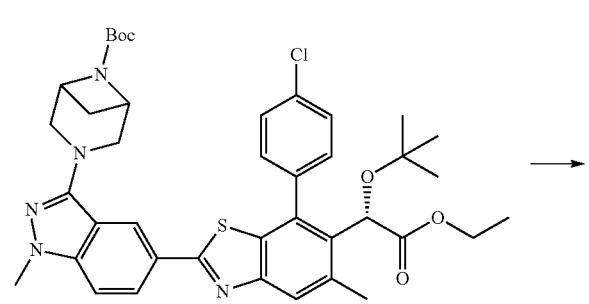

tert-butyl 3-(5-(6-((S)-1-(tert-butoxy)-2-ethoxy-2-oxoethyl)-7-(4-chlorophenyl)-5-methylbenzo[d]thiazol-2-yl)-1-methyl-1H-indazol-3-yl)-3,6-diazabicyclo[3.1.1]heptane-6-carboxylate

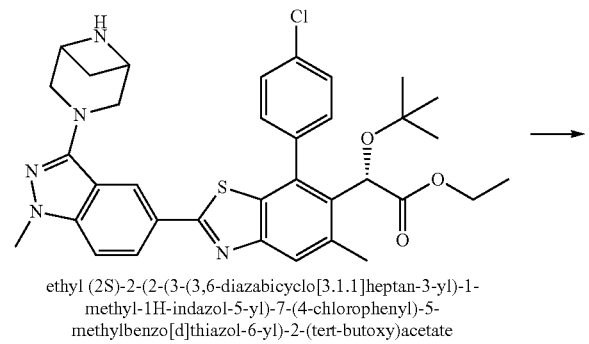

ethyl (2S)-2-(2-(3-(3,6-diazabicyclo[3.1.1]heptan-3-yl)-1-methyl-1H-indazol-5-yl)-7-(4-chlorophenyl)-5-methylbenzo[d]thiazol-6-yl)-2-(tert-butoxy)acetate

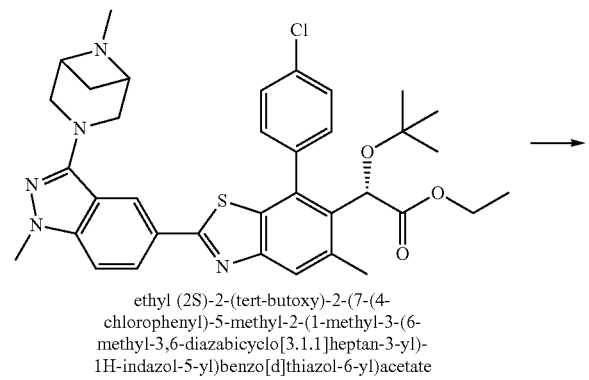

ethyl (2S)-2-(tert-butoxy)-2-(7-(4-chlorophenyl)-5-methyl-2-(1-methyl-3-(6-methyl-3,6-diazabicyclo[3.1.1]heptan-3-yl)-1H-indazol-5-yl)benzo[d]thiazol-6-yl)acetate -continued

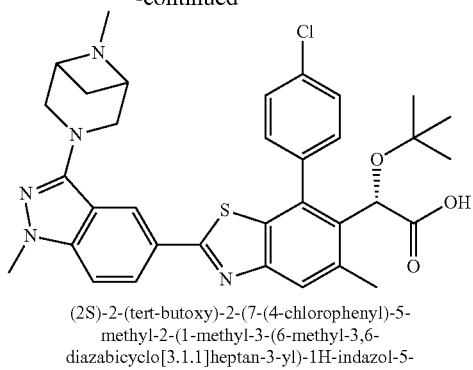

(2S)-2-(tert-butoxy)-2-(7-(4-chlorophenyl)-5-
methyl-2-(1-methyl-3-(6-methyl-3,6-
diazabicyclo[3.1.1]heptan-3-yl)-1H-indazol-5-
yl)benzo[d]thiazol-6-yl)acetic acid Preparation of tert-butyl 3-(5-(6-((S)-1-(tert-butoxy)-2-ethoxy-2-oxoethyl)-7-(4-chlorophenyl)-5-methylbenzo[d]thiazol-2-yl)-1-methyl-1H-indazol-3-yl)-3,6-diazabicyclo[3.1.1]heptane-6-carboxylate: A microwave vial containing Tris(dibenzylideneacetone) dipalladium (0) (14.6 mg, 16 µmol), 2-(Dicyclohexylphosphino)-2',4',6'-triisopropylbiphenyl (7.6 mg, 16 µmol) and cesium carbonate (130 mg, 400 µmol) in 1,4-dioxane (1 mL) was purged with Argon for 5 min. Ethyl (S)-2-(2-(3-bromo-1-methyl-1H-indazol-5-yl)-7-(4-chlorophenyl)-5-methylbenzo[d]thiazol-6-yl)-2-(tert-butoxy)acetate (50 mg, 80 µmol) and tert-butyl 3,6-diazabicyclo[3.1.1]heptane-6-carboxylate hydrochloride (56 mg, 240 µmol) were added and reaction mixture was sealed and heated in a microwave reactor at 100° C. After 1.5 h, half of the Ethyl (S)-2-(2-(3-bromo-1-methyl-1H-indazol-5-yl)-7-(4-chlorophenyl)-5-methylbenzo[d]thiazol-6-yl)-2-(tert-butoxy)acetate remained. Reaction mixture was re-subjected to microwave at 100° C. for 1.5 h, resulting in a third of the ethyl (S)-2-(2-(3-bromo-1-methyl-1H-indazol-5-yl)-7-(4-chlorophenyl)-5-methylbenzo[d]thiazol-6-yl)-2-(tert-butoxy)acetate remaining. The reaction mixture was transferred into a new reaction vial with the same amount of reagents and repeated above procedure. After cooling to room temperature, the resulting mixture was diluted ethyl acetate. The mixture was washed with brine. The organic phase was dried (Na$_2$SO$_4$) and concentrated. The residue was purified by CombiFlash (40 g, Gold, 0-50% EtOAc/Hex plus 0.1% TEA) to give desired product. LCMS-ESI+: calc'd for: C$_{40}$H$_{46}$ClN$_5$O$_5$S; 744.4 (M+H)$^+$; found: 744.2 (M+H)$^+$.

Preparation of ethyl (2S)-2-(2-(3-(3,6-diazabicyclo[3.1.1]heptan-3-yl)-1-methyl-1H-indazol-5-yl)-7-(4-chlorophenyl)-5-methylbenzo[d]thiazol-6-yl)-2-(tert-butoxy)acetate: A solution tert-butyl 3-(5-(6-((S)-1-(tert-butoxy)-2-ethoxy-2-oxoethyl)-7-(4-chlorophenyl)-5-methylbenzo[d]thiazol-2-yl)-1-methyl-1H-indazol-3-yl)-3,6-diazabicyclo[3.1.1]heptane-6-carboxylate (20 mg, 0.027 mmol) in 1.25 HCl in isopropanol (4.0 mL) was stirred for 22 h at room temperature. Reaction mixture was quenched with saturated sodium bicarbonate solution carefully and extracted with ethyl acetate (2×). Combined organic layer was dried (MgSO$_4$), filtered and concentrated to give crude desired product that was used in the next step without further purification. LCMS-ESI+: calc'd for C$_{35}$H$_{38}$ClN$_5$O$_3$S; 644.2 (M+H)$^+$; found: 644.4 (M+H)$^+$.

Preparation of ethyl (2S)-2-(tert-butoxy)-2-(7-(4-chlorophenyl)-5-methyl-2-(1-methyl-3-(6-methyl-3,6-diazabicyclo[3.1.1]heptan-3-yl)-1H-indazol-5-yl)benzo[d]thiazol-6-yl)acetate: A solution of ethyl (2S)-2-(2-(3-(3,6-diazabicyclo[3.1.1]heptan-3-yl)-1-methyl-1H-indazol-5-yl)-7-(4-chlorophenyl)-5-methylbenzo[d]thiazol-6-yl)-2-(tert-butoxy)acetate (from above reaction, 0.027 mmol) in acetonitrile (2 mL) was stirred at 0° C. bath as 37% formaldehyde (0.08 mL, 0.8 mmol), and sodium cyanoborohydride (20 mg, 0.3 mmol) were added. To the reaction mixture was added ~2 drops of acetic acid. After 1 h, the reaction was completed and carried to the next step directly. LCMS-ESI+: calc'd for: C$_{36}$H$_{40}$ClN$_5$O$_3$S; 658.3 (M+H)$^+$; found: 658.3 (M+H)$^+$.

Preparation of (2S)-2-(tert-butoxy)-2-(7-(4-chlorophenyl)-5-methyl-2-(1-methyl-3-(6-methyl-3,6-diazabicyclo[3.1.1]heptan-3-yl)-1H-indazol-5-yl)benzo[d]thiazol-6-yl)acetic acid: Above reaction mixture containing ethyl (2S)-2-(tert-butoxy)-2-(7-(4-chlorophenyl)-5-methyl-2-(1-methyl-3-(6-methyl-3,6-diazabicyclo[3.1.1]heptan-3-yl)-1H-indazol-5-yl)benzo[d]thiazol-6-yl)acetate (0.027 mmol) was added THF (2 mL), MeOH (0.5 mL) and 50% aqueous sodium hydroxide (0.5 mL) at room temperature. The mixture was stirred at 60° C. for 2 h. The reaction mixture was cooled by ice and acidified with 3 N HCl. The resulting mixture was extracted with ethyl acetate (2×). Combined organic layer was dried (MgSO$_4$), filtered and concentrated to give crude mixture which was purified by Gilson HPLC (Phenomenex Gemini 250×21.2 10µ C18 column, 40-100% ACN/H$_2$O+0.1% TFA) to give a yellow powder after lyophilization. $^1$H NMR (400 MHz, Chloroform-d) δ 8.51 (s, 1H), 7.96 (d, J=8.9 Hz, 1H), 7.78 (d, J=28.3 Hz, 2H), 7.51 (d, J=5.0 Hz, 4H), 7.22 (s, 1H), 5.27 (s, 1H), 4.20-3.75 (m, 9H), 2.91 (s, 1H), 2.59 (s, 3H), 2.38 (s, 3H), 1.64-1.35 (m, 2H), 0.99 (s, 9H). LCMS-ESI+: calc'd for C$_{34}$H$_{36}$ClN$_5$O$_3$S; 630.2 (M+H)$^+$; found: 630.4 (M+H)$^+$.

Example 103. Preparation of (S)-2-(tert-butoxy)-2-(7-(4-chlorophenyl)-2-(3-(3-((methoxycarbonyl)(methyl)amino)azetidin-1-yl)-1-methyl-1H-indazol-5-yl)-5-methylbenzo[d]thiazol-6-yl)acetic Acid (102)

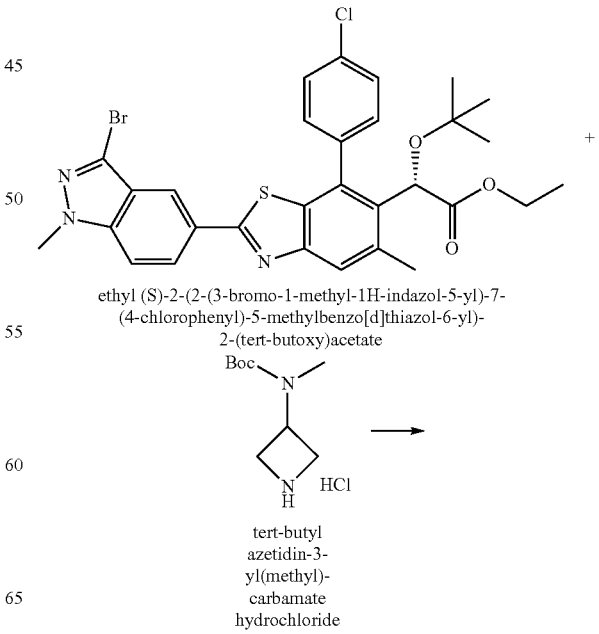

ethyl (S)-2-(2-(3-bromo-1-methyl-1H-indazol-5-yl)-7-(4-chlorophenyl)-5-methylbenzo[d]thiazol-6-yl)-2-(tert-butoxy)acetate tert-butyl
azetidin-3-
yl(methyl)-
carbamate
hydrochloride

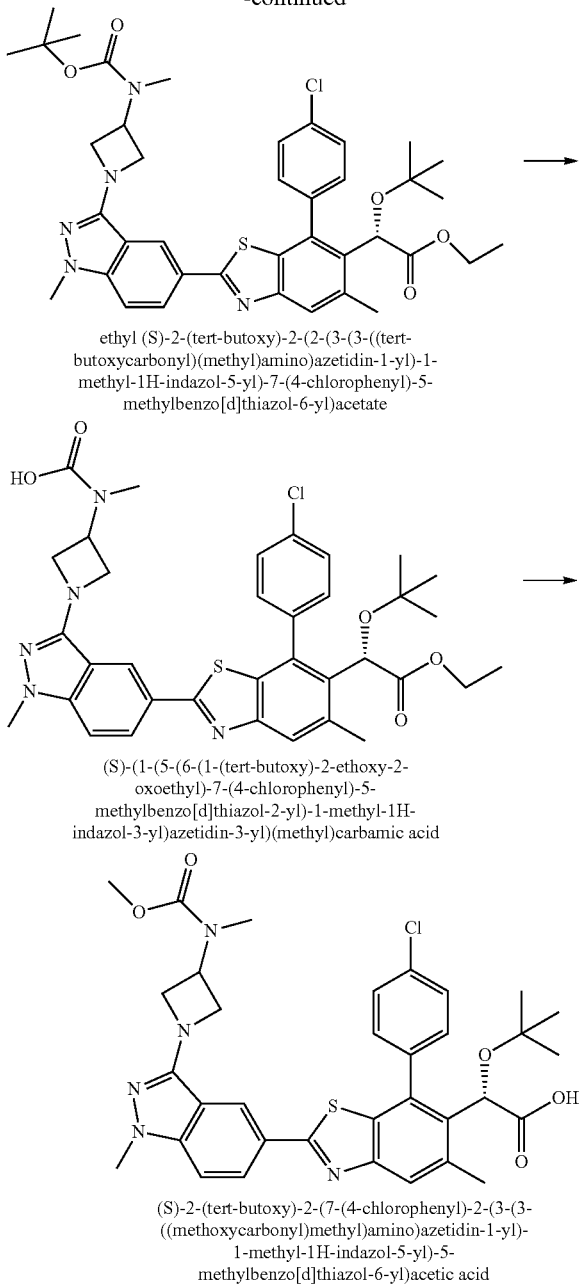

ethyl (S)-2-(tert-butoxy)-2-(2-(3-(3-((tert-butoxycarbonyl)(methyl)amino)azetidin-1-yl)-1-methyl-1H-indazol-5-yl)-7-(4-chlorophenyl)-5-methylbenzo[d]thiazol-6-yl)acetate (S)-(1-(5-(6-(1-(tert-butoxy)-2-ethoxy-2-oxoethyl)-7-(4-chlorophenyl)-5-methylbenzo[d]thiazol-2-yl)-1-methyl-1H-indazol-3-yl)azetidin-3-yl)(methyl)carbamic acid (S)-2-(tert-butoxy)-2-(7-(4-chlorophenyl)-2-(3-(3-((methoxycarbonyl)methyl)amino)azetidin-1-yl)-1-methyl-1H-indazol-5-yl)-5-methylbenzo[d]thiazol-6-yl)acetic acid Preparation of ethyl (S)-2-(tert-butoxy)-2-(2-(3-(3-((tert-butoxycarbonyl)(methyl)amino)azetidin-1-yl)-1-methyl-1H-indazol-5-yl)-7-(4-chlorophenyl)-5-methylbenzo[d]thiazol-6-yl)acetate: A microwave vial containing Tris (dibenzylideneacetone) dipalladium (0) (14.6 mg, 16 μmol), 2-(Dicyclohexylphosphino)-2',4',6'-triisopropylbiphenyl (7.6 mg, 16 μmol) and potassium phosphate tribasic (84.6 mg, 399 μmol) in 1,4-dioxane (1 mL) was purged with Argon for 5 min. Ethyl (S)-2-(2-(3-bromo-1-methyl-1H-indazol-5-yl)-7-(4-chlorophenyl)-5-methylbenzo[d]thiazol-6-yl)-2-(tert-butoxy)acetate (50 mg, 80 μmol) and tert-butyl azetidin-3-yl(methyl)carbamate hydrochloride (53 mg, 240 μmol). The mixture was sealed and reacted in a microwave reactor at 110° C. for 1 h. After cooling to room temperature, the resulting mixture was diluted ethyl acetate. The mixture was washed with brine. The organic phase was dried (Na$_2$SO$_4$) and concentrated. The residue was purified by CombiFlash (40 g, Gold, 0-50% EtOAc/Hex plus 0.1% TEA) to give desired product. LCMS-ESI+: calc'd for: C$_{39}$H$_{46}$ClN$_5$S; 732.3 (M+H)$^+$; found: 732.0 (M+H)$^+$.

Preparation of (S)-(1-(5-(6-(1-(tert-butoxy)-2-ethoxy-2-oxoethyl)-7-(4-chlorophenyl)-5-methylbenzo[d]thiazol-2-yl)-1-methyl-1H-indazol-3-yl)azetidin-3-yl)(methyl)carbamic acid: A solution ethyl (S)-2-(tert-butoxy)-2-(2-(3-(3-((tert-butoxycarbonyl)(methyl)amino)azetidin-1-yl)-1-methyl-1H-indazol-5-yl)-7-(4-chlorophenyl)-5-methylbenzo[d]thiazol-6-yl)acetate (20 mg, 0.027 mmol) in 1.25 HCl in isopropanol (4.0 mL) was stirred for 2 h at room temperature. Reaction mixture was quenched with saturated sodium bicarbonate solution carefully and extracted with ethyl acetate (2×). Combined organic layer was dried (MgSO$_4$), filtered and concentrated to give crude desired product that was used in the next step without further purification. LCMS-ESI+: calc'd for C$_{35}$H$_{38}$ClN$_5$O$_5$S; 676.2 (M+H)$^+$; found: 676.3 (M+H)$^+$.

Preparation of (S)-2-(tert-butoxy)-2-(7-(4-chlorophenyl)-2-(3-(3-((methoxycarbonyl)(methyl)amino)azetidin-1-yl)-1-methyl-1H-indazol-5-yl)-5-methylbenzo[d]thiazol-6-yl)acetic acid: A solution of (S)-(1-(5-(6-(1-(tert-butoxy)-2-ethoxy-2-oxoethyl)-7-(4-chlorophenyl)-5-methylbenzo[d]thiazol-2-yl)-1-methyl-1H-indazol-3-yl)azetidin-3-yl)(methyl)carbamic acid (from above reaction, 0.029 mmol) in DMF (1 mL) was stirred at 0° C. bath as NaH (60%, 3.6 mg, 0.09 mmol), and iodomethane (13 mg, 0.09 mmol) were added. The reaction mixture was stirred at room temperature for 18 h. The reaction mixture was cooled by ice and acidified with 3 N HCl. The resulting mixture was extracted with ethyl acetate (2×). Combined organic layer was dried (MgSO$_4$), filtered and concentrated to give crude mixture which was purified by Gilson HPLC (Phenomenex Gemini 250×21.2 10μ C18 column, 40-100% ACN/H$_2$O+0.1% TFA) to give a yellow powder after lyophilization. $^1$H NMR (400 MHz, Chloroform-d) δ 8.49 (d, J=1.7 Hz, 1H), 7.97-7.85 (m, 2H), 7.72 (d, J=8.1 Hz, 1H), 7.53 (td, J=7.4, 5.7 Hz, 3H), 7.26 (m, 1H), 5.32 (s, 1H), 4.40 (t, J=8.6 Hz, 1H), 4.24-4.06 (m, 2H), 3.88 (s, 3H), 3.86-3.78 (m, 1H), 3.52 (dt, J=13.0, 6.0 Hz, 2H), 3.32 (d, J=1.0 Hz, 3H), 2.99 (s, 3H), 2.59 (s, 3H), 1.26 (s, 1H), 1.01 (s, 9H). LCMS-ESI+: calc'd for C$_{34}$H$_{36}$ClN$_5$O$_5$S; 662.2 (M+H)$^+$; found: 662.3 (M+H)$^+$.

Example 104. (S)-2-(7-(4-chlorophenyl)-5-methyl-2-(1-methyl-3-(4-methylpiperazin-1. yl)-1H-indazol-5-yl)benzo[d]thiazol-6-yl)-2-cyclopropoxyacetic Acid (103)

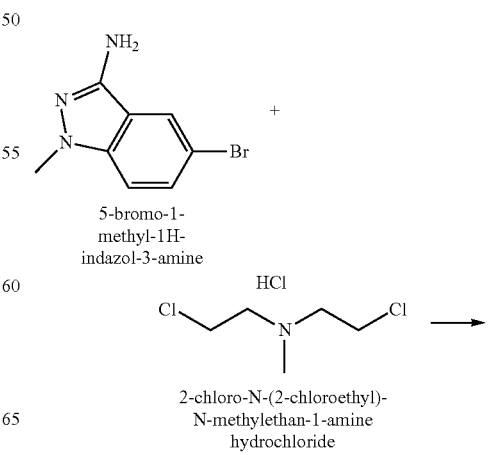

5-bromo-1-methyl-1H-indazol-3-amine 2-chloro-N-(2-chloroethyl)-N-methylethan-1-amine hydrochloride -continued

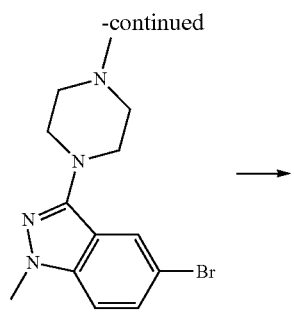

5-bromo-1-methyl-3-(4-methylpiperazin-1-yl)-1H-indazole

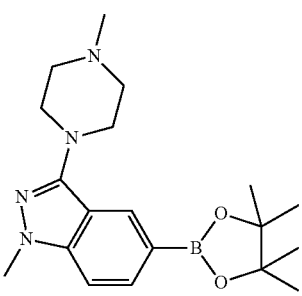

1-methyl-3-(4-methylpiperazin-1-yl)-5-(4,4,5,5-tetramethyl-1,3,2-dioxaborolan-2-yl)-1H-indazole

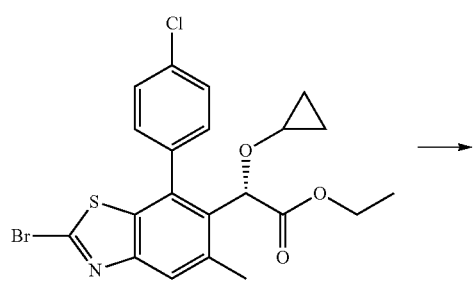

ethyl (S)-2-(2-bromo-7-(4-chlorophenyl)-5-methylbenzo[d]thiazol-6-yl)-2-cyclopropoxyacetate

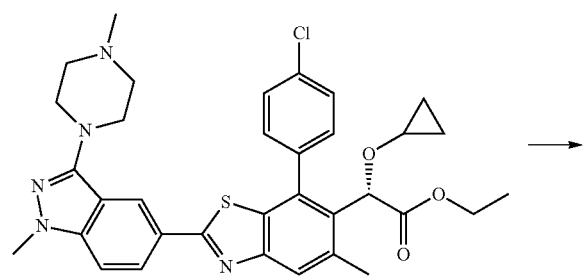

ethyl (S)-2-(7-(4-chlorophenyl)-5-methyl-2-(1-methyl-3-(4-methylpiperazin-1-yl)-1H-indazol-5-yl)benzo[d]thiazol-6-yl)-2-cyclopropoxyacetate -continued

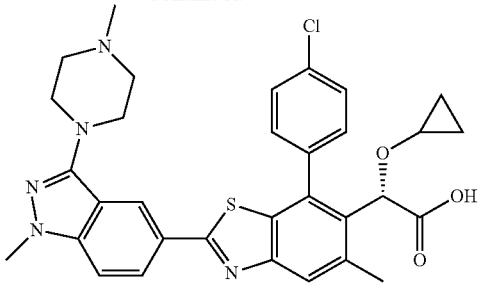

(S)-2-(7-(4-chlorophenyl)-5-methyl-2-(1-methyl-3-(4-methylpiperazin-1-yl)-1H-indazol-5-yl)benzo[d]thiazol-6-yl)-2-cyclopropoxyacetic acid Preparation of 5-bromo-1-methyl-3-(4-methylpiperazin-1-yl)-1H-indazole: A microwave vial containing 5-bromo-1-methyl-1H-indazol-3-amine (700 mg, 3.1 mmol), 2-chloro-N-(2-chloroethyl)-N-methylethan-1-amine hydrochloride (655.7 mg, 3.41 mmol), tetrabutylammonium iodide (114.37 mg, 0.31 mmol) and N-Ethyldiisopropylamine (1780 µl, 10.22 mmol) in anhydrous DMF (3 mL) was sealed and heated in a microwave reactor at 200° C. for 1 h. After cooling to room temperature, the resulting mixture was diluted ethyl acetate. The mixture was washed with 3% v LiCl aq. Solution. The organic phase was dried ($Na_2SO_4$) and concentrated. The residue was purified by CombiFlash (40 g, Gold, 0-20% MeOH/DCM.) to give desired product. $^1$H NMR (400 MHz, Methanol-d4) δ 7.84 (dd, J=1.9, 0.7 Hz, 1H), 7.41 (dd, J=9.0, 1.8 Hz, 1H), 7.28 (dd, J=9.0, 0.7 Hz, 1H), 3.84 (s, 3H), 3.46-3.33 (m, 4H), 2.73-2.62 (m, 4H), 2.38 (s, 3H). LCMS-ESI+: calc'd for: $C_{13}H_{17}BrN_4$; 309.2 $(M+H)^+$; found: 309.2 $(M+H)^+$.

Preparation of ethyl (S)-2-(7-(4-chlorophenyl)-5-methyl-2-(1-methyl-3-(4-methylpiperazin-1-yl)-1H-indazol-5-yl)benzo[d]thiazol-6-yl)-2-cyclopropoxyacetate: A microwave tube containing 5-bromo-1-methyl-3-(4-methylpiperazin-1-yl)-1H-indazole (40 mg, 129 µmol), Bis (Pinacolato) Diboron (36 mg, 142 µmol), potassium acetate (56 mg, 569 µmol), and PdCl2(dppf)-DCM (10.6 mg, 13 µmol) in 1,4-dioxane (2 mL) was added a drop of AcOH. The mixture was purged with Argon gas for 5 min, then sealed and reacted in a microwave reactor at 100° C. for 1.5 h. LCMS showed full conversion to the boronate ester. LCMS-ESI+: calc'd for: $C_{19}H_{29}BN_4O_2$; 257.3 $(M+H)^+$; found: 357.34 $(M+H)^+$.

After cooling to room temperature, ethyl (S)-2-(2-bromo-7-(4-chlorophenyl)-5-methylbenzo[d]thiazol-6-yl)-2-cyclopropoxyacetate (15 mg, 31.2 µmol), tetrakis(triphenylphosphine)nickel (3.61 mg, 3.12 µmol) and 2M aq $K_2CO_3$ (1 ml) were added. The mixture was purged with Argon gas for 5 min, then sealed and heated in a microwave reactor at 100° C. for 1 h. LCMS showed the reaction was completed. The reaction mixture was cooled to room temperature, diluted ethyl acetate, washed with sat'd $NaHCO_3$, and brine. The organic phase was dried ($Na_2SO_4$) and concentrated. The residue was purified by CombiFlash (40 g, Gold, 0-20% MeOH/DCM) to give the product. LCMS-ESI+: calc'd for: $C_{34}H_{36}ClN_5O_3S$; 630.2 $(M+H)^+$; found: 630.4 $(M+H)^+$.

Preparation of (S)-2-(7-(4-chlorophenyl)-5-methyl-2-(1-methyl-3-(4-methylpiperazin-1-yl)-1H-indazol-5-yl)benzo[d]thiazol-6-yl)-2-cyclopropoxyacetic acid: To ethyl (S)-2-(7-(4-chlorophenyl)-5-methyl-2-(1-methyl-3-(4-methylpiperazin-1-yl)-1H-indazol-5-yl)benzo[d]thiazol-6-yl)-2-cyclopropoxyacetate (20 mg) was added THF (1.5 mL), MeOH (0.2 mL) and 50% aqueous sodium hydroxide (0.4 mL) at room temperature. The mixture was stirred at 60° C. for 2 h. The reaction mixture was cooled by ice and acidified with 3 N HCl. The resulting mixture was extracted with ethyl acetate (2×) and combined organic layer was dried (MgSO₄), filtered and concentrated to give crude mixture which was purified by Gilson HPLC (Phenomenex Gemini 250×21.2 10μ C18 column, 40-100% ACN/H₂O+ 0.1% TFA) to give a yellow powder after lyophilization. ¹H NMR (400 MHz, Chloroform-d) δ 8.32 (d, J=1.6 Hz, 1H), 7.98 (dd, J=8.9, 1.5 Hz, 1H), 7.91-7.84 (m, 1H), 7.55-7.46 (m, 3H), 7.43 (dd, J=8.2, 1.9 Hz, 1H), 7.35-7.28 (m, 1H), 5.22 (s, 1H), 4.02 (d, J=13.9 Hz, 1H), 3.92 (s, 3H), 3.77-3.51 (m, 4H), 3.27-3.09 (m, 4H), 2.90 (s, 3H), 2.68, 2.55 (s, 3H), 0.57-0.16 (m, 4H). LCMS-ESI+: calc'd for C₃₂H₃₂ClN₅O₃S; 602.2 (M+H)⁺; found: 602.4 (M+H)⁺.

Example 105. (S)-2-(tert-butoxy)-2-(7-(4-chlorophenyl)-5-methyl-2-(1-methyl-3-(4-(oxetan-3-yl)piperazin-1-yl)-1H-indazol-5-yl)benzo[d]thiazol-6-yl) acetic Acid (104)

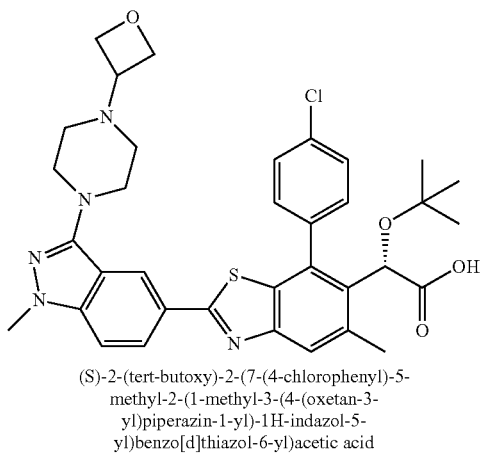 [SMILES: Cc1cc2nc(-c3ccc4c(c3)c(N3CCN(C5COC5)CC3)nn4C)sc2c(-c2ccc(Cl)cc2)c1[C@H](OC(C)(C)C)C(=O)O]

(S)-2-(tert-butoxy)-2-(7-(4-chlorophenyl)-5-methyl-2-(1-methyl-3-(4-(oxetan-3-yl)piperazin-1-yl)-1H-indazol-5-yl)benzo[d]thiazol-6-yl)acetic acid Preparation of (S)-2-(tert-butoxy)-2-(7-(4-chlorophenyl)-5-methyl-2-(1-methyl-3-(4-(oxetan-3-yl)piperazin-1-yl)-1H-indazol-5-yl)benzo[d]thiazol-6-yl)acetic acid: Prepared in a manner similar to (S)-2-(7-(4-chlorophenyl)-5-methyl-2-(1-methyl-3-(4-methylpiperazin-1-yl)-1H-indazol-5-yl)benzo[d]thiazol-6-yl)-2-cyclopropoxyacetic acid. ¹H NMR (400 MHz, Chloroform-d) δ 8.33 (d, J=1.6 Hz, 1H), 7.96 (dd, J=8.8, 1.4 Hz, 1H), 7.85 (s, 1H), 7.71 (d, J=8.8 Hz, 1H), 7.58-7.45 (m, 3H), 7.32 (d, J=8.9 Hz, 1H), 5.30 (s, 1H), 5.09 (dd, J=7.9, 6.1 Hz, 2H), 4.82 (t, J=7.6 Hz, 2H), 4.25 (t, J=6.7 Hz, 1H), 3.92 (s, 3H), 3.89-3.67 (m, 4H), 3.35 (s, 4H), 2.57 (s, 3H), 1.01 (s, 9H); LCMS-ESI+: calc'd for C₃₅H₃₉ClN₅O₄S; 660.2 (M+H)⁺; found: 660.4 (M+H)⁺.

Example 106A and 106B. Preparation of (S)-2-(tert-butoxy)-2-(7-(4-chlorophenyl)-5-methyl-2-(1-methyl-3-(1-methyl-1,2,3,6-tetrahydropyridin-4-yl)-1H-pyrrolo[2,3-b]pyridin-5-yl)benzo[d]thiazol-6-yl) acetic Acid (105) and (S)-2-(tert-butoxy)-2-(7-(4-chlorophenyl)-5-methyl-2-(1-methyl-3-(1-methylpiperidin-4-yl)-1H-pyrrolo[2,3-b]pyridin-5-yl)benzodithiazol-6-yl)acetic Acid (106)

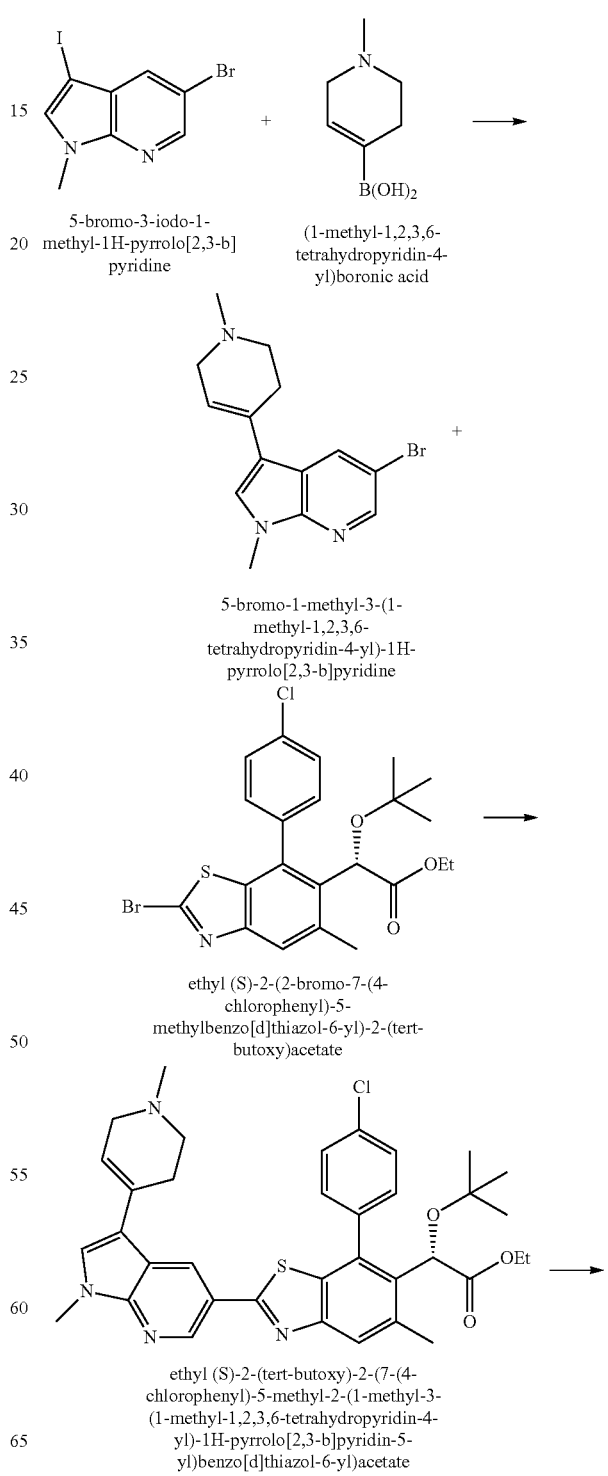

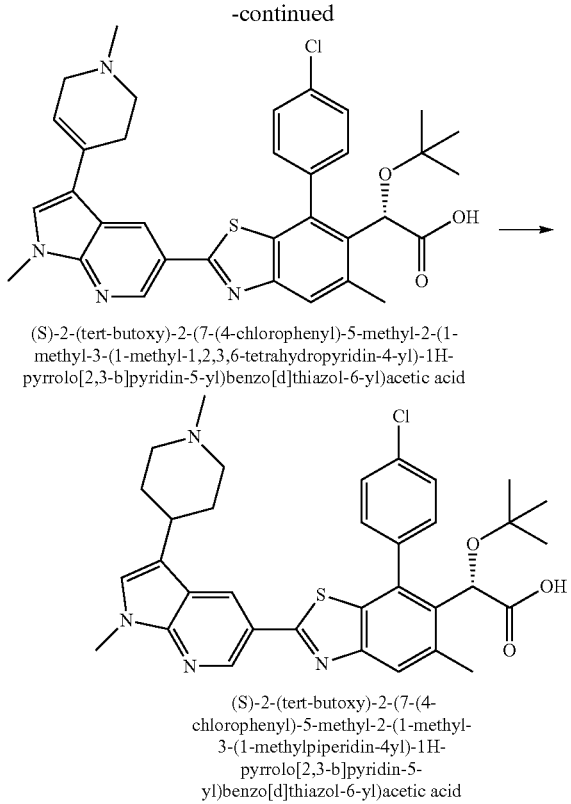

(S)-2-(tert-butoxy)-2-(7-(4-chlorophenyl)-5-methyl-2-(1-methyl-3-(1-methyl-1,2,3,6-tetrahydropyridin-4-yl)-1H-pyrrolo[2,3-b]pyridin-5-yl)benzo[d]thiazol-6-yl)acetic acid (S)-2-(tert-butoxy)-2-(7-(4-chlorophenyl)-5-methyl-2-(1-methyl-3-(1-methylpiperidin-4yl)-1H-pyrrolo[2,3-b]pyridin-5-yl)benzo[d]thiazol-6-yl)acetic acid Preparation of 5-bromo-1-methyl-3-(1-methyl-1,2,3,6-tetrahydropyridin-4-yl)-1H-pyrrolo-[2,3-b]pyridine: To a solution of 5-bromo-3-iodo-1-methyl-1H-pyrrolo[2,3-b]pyridine (180 mg, 0.534 mmol) and 1-methyl-1,2,3,6-tetrahydropyridin-4-boronic acid (155 mg, 0.694 mmol) in dioxane (5.4 mL, degassed) was added tetrakis(triphenylphosphine)palladium(0) (75 mg, 0.064 mmol), $K_2CO_3$ (369 mg, 2.67 mmol) and water (1.8 mL, degassed). The reaction mixture was heated at 40° C. for 15 h, cooled and partitioned between ethyl acetate and brine. The organic layer was separated, dried over $Na_2SO_4$, filtered and concentrated to give crude which was purified by chromatographic column to afford the desired product (106 mg, 65%). LCMS-ESI+: calc'd for $C_{14}H_{17}BrN_3$: 306.1 (M+H+); Found: 306.2 (M+H+).

Preparation of ethyl (S)-2-(tert-butoxy)-2-(7-(4-chlorophenyl)-5-methyl-2-(1-methyl-3-(1-methyl-1,2,3,6-tetrahydropyridin-4-yl)-1H-pyrrolo[2,3-b]pyridin-5-yl)benzo[d]thiazol-6-yl)acetate: The title compound was synthesized in a manner analogous for tert-butyl (S)-4-(5-(6-(1-(tert-butoxy)-2-ethoxy-2-oxoethyl)-7-(4-chlorophenyl)-5-methyl-benzo[d]thiazol-2-yl)-1-methyl-1H-pyrrolo[2,3-b]pyridin-3-yl)piperidine-1-carboxylate, using 5-bromo-1-methyl-3-(1-methyl-1,2,3,6-tetrahydropyridin-4-yl)-1H-pyrrolo-[2,3-b]pyridine instead of tert-butyl 4-(5-bromo-1-methyl-1H-pyrrolo[2,3-b]pyridin-3-yl)piperidine-1-carboxylate. LCMS-ESI+: calc'd for $C_{36}H_{40}ClN_4O_3S$: 643.2 (M+H+); Found: 643.2 (M+H+).

Preparation of (S)-2-(tert-butoxy)-2-(7-(4-chlorophenyl)-5-methyl-2-(1-methyl-3-(1-methyl-1,2,3,6-tetrahydropyridin-4-yl)-1H-pyrrolo[2,3-b]pyridin-5-yl)benzo[d]thiazol-6-yl)acetic acid: To a solution of ethyl (S)-2-(tert-butoxy)-2-(7-(4-chlorophenyl)-5-methyl-2-(1-methyl-3-(1-methyl-1,2,3,6-tetrahydropyridin-4-yl)-1H-pyrrolo[2,3-b]pyridin-5-yl)benzo[d]thiazol-6-yl)acetate: (25 mg, 0.039 mmol) in THF/$CH_3OH$ (1.0 ml/1.0 ml) was added 2N NaOH (0.2 ml, 0.39 mmol). The reaction mixture was heated at 50° C. for 2 h and the crude was purified by reverse phase HPLC, eluting by 0-100% acetonitrile in $H_2O$ with 0.1% TFA to give the product as TFA salt. $^1H$ NMR (400 MHz, $CD_3OD$) δ 8.97-8.84 (m, 2H), 7.85 (s, 1H), 7.71-7.60 (m, 5H), 6.31 (s, 1H), 5.25 (s, 1H), 4.11-3.74 (m, 6H), 3.13-2.95 (m, 6H), 2.62 (s, 3H), 0.98 (s, 9H). LCMS-ESI+: calc'd for $C_{34}H_{36}ClN_4O_3S$: 615.2 (M+H+); Found 615.2 (M+H+).

Preparation of (S)-2-(tert-butoxy)-2-(7-(4-chlorophenyl)-5-methyl-2-(1-methyl-3-(1-methylpiperidin-4-yl)-1H-pyrrolo[2,3-b]pyridin-5-yl)benzo[d]thiazol-6-yl)acetic acid: A mixture of (S)-2-(tert-butoxy)-2-(7-(4-chlorophenyl)-5-methyl-2-(1-methyl-3-(1-methyl-1,2,3,6-tetrahydropyridin-4-yl)-1H-pyrrolo[2,3-b]pyridin-5-yl)benzo[d]thiazol-6-yl)acetic acid (5.2 mg, 0.008 mmol), rhodium on alumina (8 mg, 0.004 mmol) in ethanol (1.5 mL) under hydrogen atmosphere. After stirring for 8 hours, Celite was added and the mixture was filtered through a pad of Celite. Concentration and purification by Gilson HPLC (Gemini, 5-100% ACN/$H_2O$+0.1% TFA) gave a white powder after lyophilization. $^1H$ NMR (400 MHz, Methanol-$d_4$) δ 8.94 (d, J=2.0 Hz, 1H), 8.64 (d, J=2.1 Hz, 1H), 7.83 (s, 1H), 7.73-7.66 (m, 1H), 7.60 (d, J=6.5 Hz, 3H), 7.35 (s, 1H), 5.26 (s, 1H), 3.86 (s, 3H), 3.64 (d, J=12.7 Hz, 2H), 3.22 (t, J=12.3 Hz, 3H), 2.95 (s, 3H), 2.62 (s, 3H), 2.33 (d, J=14.5 Hz, 2H), 2.09-1.94 (m, 2H), 0.98 (s, 9H). LCMS-ESI+: calc'd for $C_{34}H_{38}ClN_4O_3S$: 617.2 (M+H)$^+$; found: 617.5 (M+H)$^+$.

Example 107. Preparation of (S)-2-(tert-butoxy)-2-(7-(4-chlorophenyl)-5-methyl-2-(1-methyl-3-(4-methylpiperazin-1-yl)-1H-pyrrolo[2,3-b]pyridin-5-yl)benzo[d]thiazol-6-yl)acetic Acid (107)

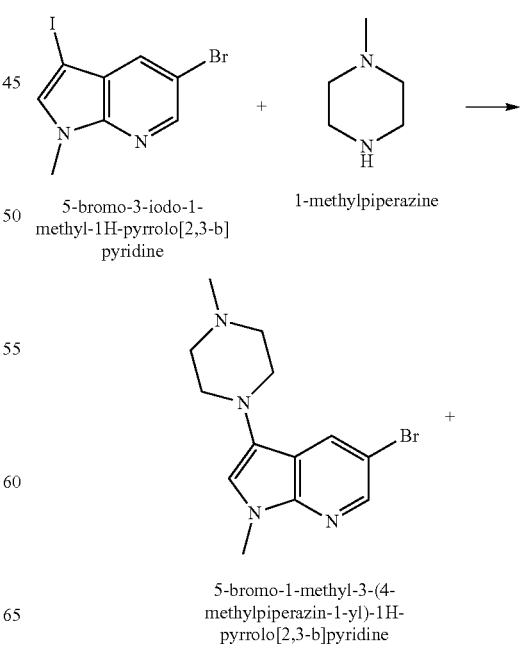

5-bromo-3-iodo-1-methyl-1H-pyrrolo[2,3-b]pyridine 1-methylpiperazine 5-bromo-1-methyl-3-(4-methylpiperazin-1-yl)-1H-pyrrolo[2,3-b]pyridine

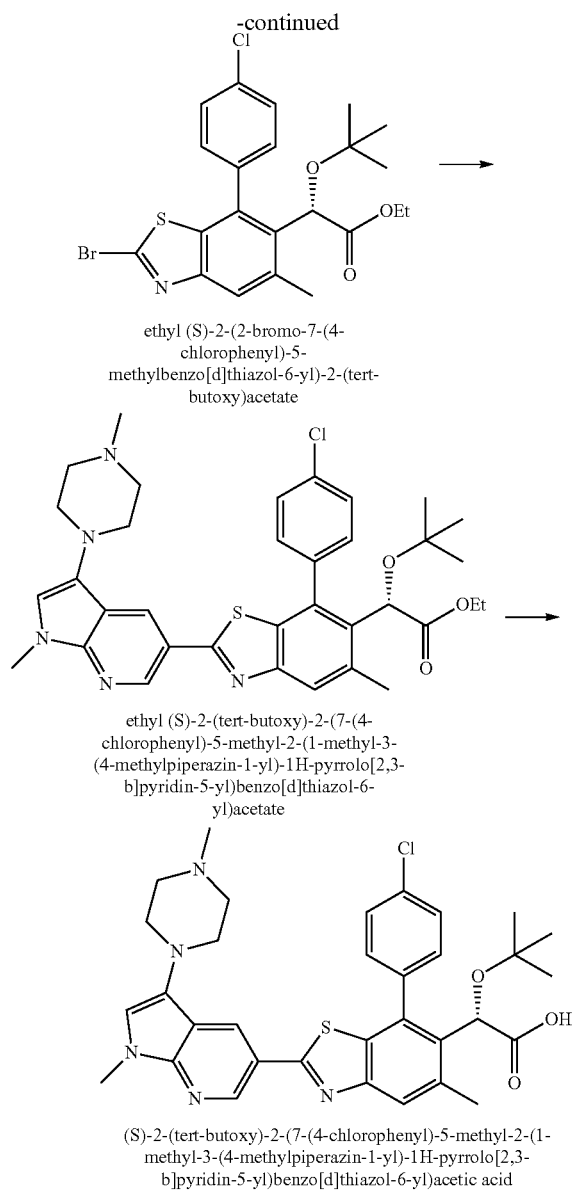

Preparation of 5-bromo-1-methyl-3-(4-methylpiperazin-1-yl)-1H-pyrrolo[2,3-b]pyridine: A solution of 5-bromo-3-iodo-1-methyl-1H-pyrrolo[2,3-b]pyridine (150 mg, 0.445 mmol), 1-methylpiperazine (356.7 mg, 3.56 mmol), copper (I) iodide (84.8 mg, 0.445 mmol), K$_3$PO$_4$ (378 mg, 1.78 mmol), 1,2-ethanediol (138 mg, 2.23 mmol) in isopropyl alcohol (5 ml) in a sealed tubes was heated at 70° C. for 2 days. After cooling to room temperature, the reaction mixture was filtered through Celite. The filtrate was concentrated in vacuo. The residue was taken up in EtOAc and the solution was washed with saturated NaHCO$_3$, dried (Na$_2$SO$_4$) and concentrated. Purification by flash chromatography afforded title compound. LCMS-ESI+: calc'd for C$_{13}$H$_{18}$BrN$_4$: 309.1 (M+H+); Found: 309.1 (M+H+).

Preparation of ethyl (S)-2-(tert-butoxy)-2-(7-(4-chlorophenyl)-5-methyl-2-(1-methyl-3-(4-methylpiperazin-1-yl)-1H-pyrrolo[2,3-b]pyridin-5-yl)benzo[d]thiazol-6-yl)acetate: The title compound was synthesized in a manner analogous for tert-butyl (S)-4-(5-(6-(1-(tert-butoxy)-2-ethoxy-2-oxoethyl)-7-(4-chlorophenyl)-5-methylbenzo[d]thiazol-2-yl)-1-methyl-1H-pyrrolo[2,3-b]pyridin-3-yl)piperidine-1-carboxylate, using 5-bromo-1-methyl-3-(4-methylpiperazin-1-yl)-1H-pyrrolo[2,3-b]pyridine instead of tert-butyl 4-(5-bromo-1-methyl-1H-pyrrolo[2,3-b]pyridin-3-yl)piperidine-1-carboxylate. LCMS-ESI+: calc'd for C$_{35}$H$_{41}$ClN$_5$O$_3$S: 646.3 (M+H+); Found: 646.3 (M+H+).

Preparation of (S)-2-(tert-butoxy)-2-(7-(4-chlorophenyl)-5-methyl-2-(1-methyl-3-(4-methylpiperazin-1-yl)-1H-pyrrolo[2,3-b]pyridin-5-yl)benzo[d]thiazol-6-yl)acetic acid: To a solution of ethyl (S)-2-(tert-butoxy)-2-(7-(4-chlorophenyl)-5-methyl-2-(1-methyl-3-(4-methylpiperazin-1-yl)-1H-pyrrolo[2,3-b]pyridin-5-yl)benzo[d]thiazol-6-yl)acetate (57 mg, 0.088 mmol) in THF/CH$_3$OH (1.0 ml/1.0 ml) was added 2N NaOH (0.44 ml, 0.88 mmol). The reaction mixture was heated at 50° C. for 2 h and the crude was purified by reverse phase HPLC, eluting by 0-100% acetonitrile/H$_2$O with 0.1% TFA to give the desired product. $^1$H NMR (400 MHz, CD$_3$OD) δ 8.92 (s, 1H), 8.61 (d, J=2 Hz, 1H), 7.70-7.60 (m, 4H), 7.16 (s, 1H), 5.25 (s, 1H), 3.84 (s, 3H), 3.80-3.10 (m, 8H), 3.01 (s, 3H), 2.62 (s, 3H), 0.98 (s, 9H). LCMS-ESI+: calc'd for C$_{33}$H$_{37}$ClN$_5$O$_3$S: 618.2 (M+H+); Found 618.2 (M+H+).

Example 108. Preparation of (S)-2-(tert-butoxy)-2-(7-(4-chlorophenyl)-5-methyl-2-(1-methyl-3-(1-(oxetan-3-yl)piperidin-4-yl)-1H-pyrrolo[3,2-b]pyridin-5-yl)benzo[d]thiazol-6-yl)acetic Acid (108)

-continued

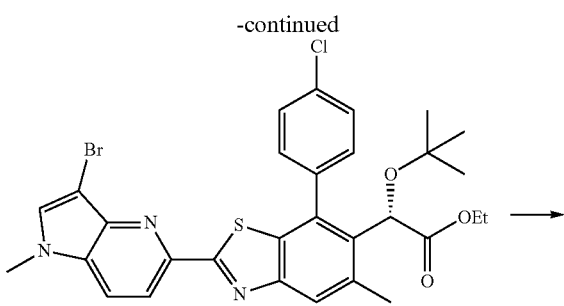

ethyl (S)-2-(2-(3-bromo-1-methyl-1H-pyrrolo[3,2-b]pyridin-5-yl)-7-(4-chlorophenyl)-5-methylbenzo[d]thiazol-6-yl)-2-(tert-butoxy)acetate

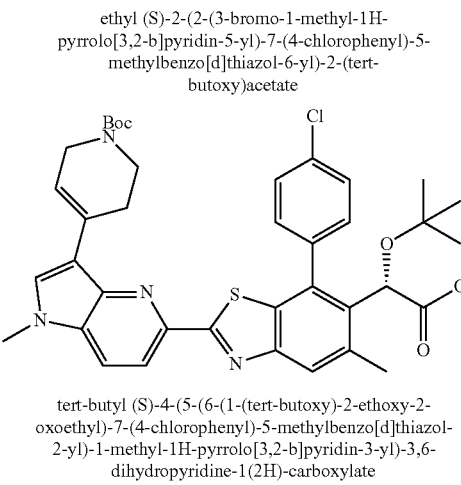

tert-butyl (S)-4-(5-(6-(1-(tert-butoxy)-2-ethoxy-2-oxoethyl)-7-(4-chlorophenyl)-5-methylbenzo[d]thiazol-2-yl)-1-methyl-1H-pyrrolo[3,2-b]pyridin-3-yl)-3,6-dihydropyridine-1(2H)-carboxylate

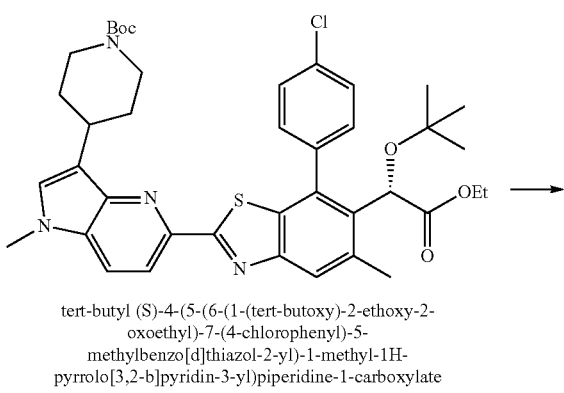

tert-butyl (S)-4-(5-(6-(1-(tert-butoxy)-2-ethoxy-2-oxoethyl)-7-(4-chlorophenyl)-5-methylbenzo[d]thiazol-2-yl)-1-methyl-1H-pyrrolo[3,2-b]pyridin-3-yl)piperidine-1-carboxylate

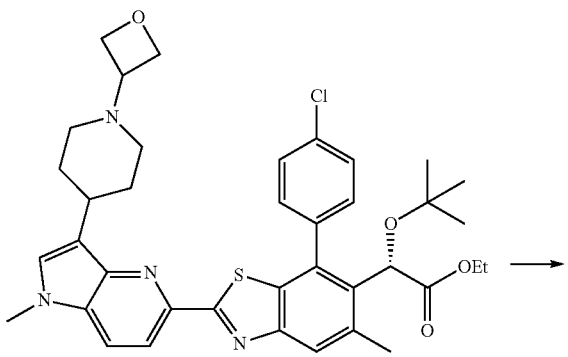

ethyl (S)-2-(tert-butoxy)-2-(7-(4-chlorophenyl)-5-methyl-2-(1-methyl-3-(1-(oxetan-3-yl)piperidin-4-yl)-1H-pyrrolo[3,2-b]pyridin-5-yl)benzo[d]thiazol-6-yl)acetate -continued

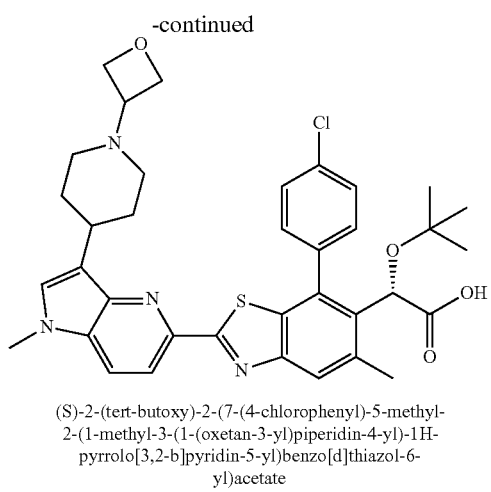

(S)-2-(tert-butoxy)-2-(7-(4-chlorophenyl)-5-methyl-2-(1-methyl-3-(1-(oxetan-3-yl)piperidin-4-yl)-1H-pyrrolo[3,2-b]pyridin-5-yl)benzo[d]thiazol-6-yl)acetate Preparation of 5-bromo-1-methyl-1H-pyrrolo[3,2-b]pyridine: To a solution of 5-bromo-1H-pyrrolo[3,2-b]pyridine (1.02 g, 5.2 mmol) in DMF (10 mL) at 0° C. was added sodium hydride (60%, 0.21 g, 5.2 mmol) and stirred for 10 minutes. Iodomethane (322 µL, 5.2 mmol) was added and reaction mixture was stirred for one hour. Reaction mixture was quenched with saturated sodium bicarbonate solution and extracted with ethyl acetate (3×). Combined organic layer was dried (MgSO$_4$), filtered, concentrated and purified by CombiFlash (ethyl acetate/hexanes) to give desired product. LCMS-ESI+: calc'd for $C_8H_8BrN_2$: 211.0 (M+H+); Found 211.2 (M+H+).

Preparation of ethyl (S)-2-(tert-butoxy)-2-(7-(4-chlorophenyl)-5-methyl-2-(1-methyl-1H-pyrrolo[3,2-b]pyridin-5-yl)benzo[d]thiazol-6-yl)acetate: To a solution of 5-bromo-1-methyl-1H-pyrrolo[3,2-b]pyridine (489 mg, 0.84 mmol), Pd(PPh$_3$)$_4$ (73 mg, 0.063 mmol), copper(I) iodide (40.2 mg, 0.21 mmol), and hexa-n-butylditin (0.425 mL, 0.84 mmol) in toluene (0.5 mL) at 110° C. was added ethyl (S)-2-(2-bromo-7-(4-chlorophenyl)-5-methylbenzo[d]thiazol-6-yl)-2-(tert-butoxy)acetate (0.210 g, 0.42 mmol) in toluene (3 mL) over 30 minutes. Reaction mixture was stirred overnight at 110° C., cooled to room temperature and purified by CombiFlash (ethyl acetate/hexanes) to give desired product. LCMS-ESI+: calc'd for $C_{30}H_{31}ClN_3O_3S$: 548.2 (M+H+); Found 548.2 (M+H+).

Preparation of ethyl (S)-2-(2-(3-bromo-1-methyl-1H-pyrrolo[3,2-b]pyridin-5-yl)-7-(4-chlorophenyl)-5-methylbenzo[d]thiazol-6-yl)-2-(tert-butoxy)acetate: To a solution of ethyl (S)-2-(tert-butoxy)-2-(7-(4-chlorophenyl)-5-methyl-2-(1-methyl-1H-pyrrolo[3,2-b]pyridin-5-yl)benzo[d]thiazol-6-yl)acetate (67 mg, 0.12 mmol) in DMF at 0° C. was added N-bromosuccinimide (22 mg, 0.12 mmol) and reaction mixture was stirred for one hour. Reaction mixture was partitioned between ethyl acetate and saturated sodium bicarbonate solution and organic layer was concentrated and purified by CombiFlash (ethyl acetate/hexanes) to give desired product. LCMS-ESI+: calc'd for $C_{30}H_{30}BrClN_3O_3S$: 626.1 (M+H+); Found 626.1 (M+H+).

Preparation of tert-butyl (S)-4-(5-(6-(1-(tert-butoxy)-2-ethoxy-2-oxoethyl)-7-(4-chlorophenyl)-5-methylbenzo[d]thiazol-2-yl)-1-methyl-1H-pyrrolo[3,2-b]pyridin-3-yl)-3,6-dihydropyridine-1(2H)-carboxylate: A mixture of ethyl (S)-2-(2-(3-bromo-1-methyl-1H-pyrrolo[3,2-b]pyridin-5-yl)-7-(4-chlorophenyl)-5-methylbenzo[d]thiazol-6-yl)-2-(tert-butoxy)acetate (0.047 g, 0.075 mmol), tert-butyl 4-(4,4,5,5-tetramethyl-1,3,2-dioxaborolan-2-yl)-3,6-dihydropyridine-1

(2H)-carboxylate (25 mg, 0.083 mmol), Pd(PPh$_3$)$_4$ (9 mg, 0.008 mmol), and 2M sodium carbonate solution (0.11 mL, 0.22 mmol) in dioxane (1.0 mL) was heated at 90° C. for one hour. LCMS showed reaction was incomplete. Additional tert-butyl 4-(4,4,5,5-tetramethyl-1,3,2-dioxaborolan-2-yl)-3,6-dihydropyridine-1(2H)-carboxylate (25 mg, 0.083 mmol) and Pd(PPh$_3$)$_4$ (9 mg, 0.008 mmol) were added and reaction continued for 0.5 hour. Reaction mixture was portioned between ethyl acetate and saturated sodium bicarbonate solution, organic layer dried (MgSO$_4$), filtered, concentrated and purified by CombiFlash (ethyl acetate/hexanes) to give desired product. LCMS-ESI+: calc'd for C$_{40}$H$_{46}$ClN$_4$O$_5$S: 729.3 (M+H)$^+$; found: 729.1.

Preparation of tert-butyl (S)-4-(5-(6-(1-(tert-butoxy)-2-ethoxy-2-oxoethyl)-7-(4-chlorophenyl)-5-methylbenzo[d]thiazol-2-yl)-1-methyl-1H-pyrrolo[3,2-b]pyridin-3-yl)piperidine-1-carboxylate: A mixture of tert-butyl (S)-4-(5-(6-(1-(tert-butoxy)-2-ethoxy-2-oxoethyl)-7-(4-chlorophenyl)-5-methylbenzo[d]thiazol-2-yl)-1-methyl-1H-pyrrolo[3,2-b]pyridin-3-yl)-3,6-dihydropyridine-1(2H)-carboxylate (22 mg, 0.030 mmol) and 5% rhodium on alumina (22 mg) in ethanol (20 mL) was stirred under hydrogen atmosphere overnight. Reaction mixture was filtered, concentrated and used in the next step without further purification. LCMS-ESI+: calc'd for C$_{40}$H$_{48}$ClN$_4$O$_5$S: 731.3 (M+H)$^+$; found: 731.2.

Preparation of ethyl (S)-2-(tert-butoxy)-2-(7-(4-chlorophenyl)-5-methyl-2-(1-methyl-3-(1-(oxetan-3-yl)piperidin-4-yl)-1H-pyrrolo[3,2-b]pyridin-5-yl)benzo[d]thiazol-6-yl)acetate: To tert-butyl (S)-4-(5-(6-(1-(tert-butoxy)-2-ethoxy-2-oxoethyl)-7-(4-chlorophenyl)-5-methylbenzo[d]thiazol-2-yl)-1-methyl-1H-pyrrolo[3,2-b]pyridin-3-yl)piperidine-1-carboxylate (17 mg, 0.023 mmol) was added 1.25 N hydrochloric acid in isopropanol. Reaction mixture was stirred for 20 hours. The pH was adjusted to pH 8 using 1M sodium hydroxide, extracted with ethyl acetate (2×), 15% methanol in dichloromethane (2×). The combined organic layer was, dried (MgSO$_4$), filtered, concentrated and used in the next step without further purification. LCMS-ESI+: calc'd for C$_{35}$H$_{40}$ClN$_4$O$_3$S: 631.2 (M+H)$^+$; found: 631.3.

A solution of free amine (85 mg, 0.14), oxetan-3-one (10 mg, 0.14 mmol), acetic acid (2 μL, 0.03 mmol) and sodium cyanoborohydride (8.0 mg, 0.14 mmol) in methanol (1.0 mL) was stirred overnight. Reaction mixture was concentrated and used in the next step without further purification. LCMS-ESI+: calc'd for C$_{37}$H$_{43}$ClN$_5$O$_4$S: 688.3 (M+H)$^+$; found: 687.4.

Preparation of (S)-2-(tert-butoxy)-2-(7-(4-chlorophenyl)-5-methyl-2-(1-methyl-3-(1-(oxetan-3-yl)piperidin-4-yl)-1H-pyrrolo[3,2-b]pyridin-5-yl)benzo[d]thiazol-6-yl)acetic acid: A solution of ethyl (S)-2-(tert-butoxy)-2-(7-(4-chlorophenyl)-5-methyl-2-(1-methyl-3-(1-(oxetan-3-yl)piperidin-4-yl)-1H-pyrrolo[3,2-b]pyridin-5-yl)benzo[d]thiazol-6-yl)acetate and 2M sodium hydroxide in THF/Ethanol was stirred at 60° C. for one hour. Reaction mixture was filtered through a syringe filter and purified by Gilson HPLC (Gemini, 5-100% ACN/H$_2$O+0.1% TFA). Product was lyophilized to give an off-white powder. $^1$H NMR (400 MHz, Methanol-d4) δ 8.18 (d, J=8.6 Hz, 1H), 7.90 (d, J=8.6 Hz, 1H), 7.82 s, 1H), 7.72-7.52 (m, 4H), 7.42 (s, 1H), 5.22 (s, 1H), 4.82 (m, 4H), 4.42 (m, 1H), 3.84 (s, 3H), 3.57 (m, 2H), 3.38 (m, 1H), 3.09 (m, 2H), 2.61 (s, 3H), 2.49 (m, 2H), 2.04 (m, 2H), 0.97 (s, 9H); LCMS-ESI+: calc'd for C$_{36}$H$_{40}$ClN$_4$O$_4$S: 659.2 (M+H)$^+$; found: 659.3.

Example 109. Preparation of (S)-2-(tert-butoxy)-2-(7-(4-chlorophenyl)-5-methyl-2-(3-(1-(oxetan-3-yl)piperidin-4-yl)pyrazolo[1,5-a]pyrimidin-5-yl)benzo[d]thiazol-6-yl)acetic Acid (109)

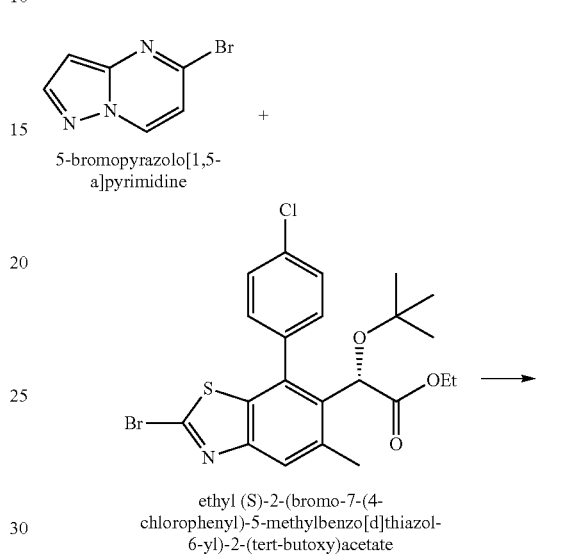

5-bromopyrazolo[1,5-a]pyrimidine ethyl (S)-2-(bromo-7-(4-chlorophenyl)-5-methylbenzo[d]thiazol-6-yl)-2-(tert-butoxy)acetate

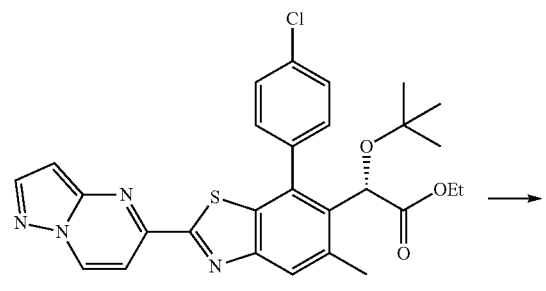

ethyl (S)-2-(tert-butoxy)-2-(7-(4-chlorophenyl)-5-methyl-2-(pyrazolo[1,5-a]pyrimidin-5-yl)benzo[d]thiazol-6-yl)acetate

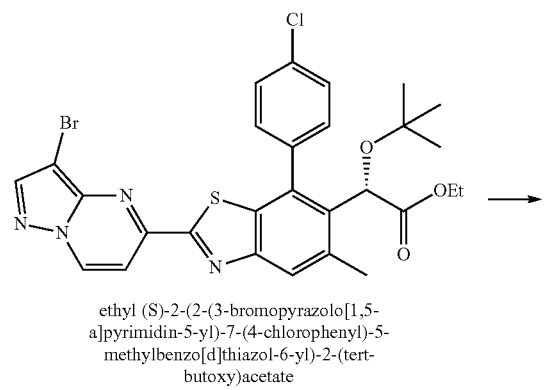

ethyl (S)-2-(2-(3-bromopyrazolo[1,5-a]pyrimidin-5-yl)-7-(4-chlorophenyl)-5-methylbenzo[d]thiazol-6-yl)-2-(tert-butoxy)acetate

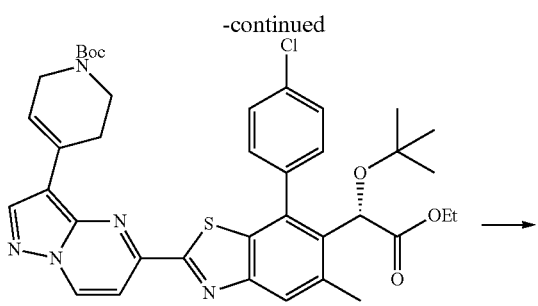

tert-butyl (S)-4-(5-(6-(1-(tert-butoxy)-2-ethoxy-2-oxoethyl)-7-(4-chlorophenyl)-5-methylbenzo[d]thiazol-2-yl)pyrazolo[1,5-a]pyrimidin-3-yl)-3,6-dihydropyridine-1(2H)-carboxylate

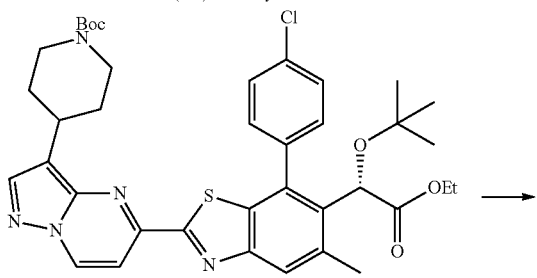

tert-butyl (S)-4-(5-(6-(1-(tert-butoxy)-2-ethoxy-2-oxoethyl)-7-(4-chlorophenyl)-5-methylbenzo[d]thiazol-2-yl)pyrazolo[1,5-a]pyrimidin-3-yl)piperidine-1-carboxylate

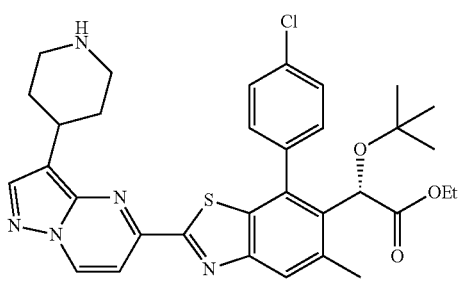

ethyl (S)-2-(tert-butoxy)-2-(7-(4-chlorophenyl)-5-methyl-2-(3-piperidin-4-yl)pyrazolo[1,5-a]pyrimidin-5-yl)benzo[d]thiazol-6-yl)acetate

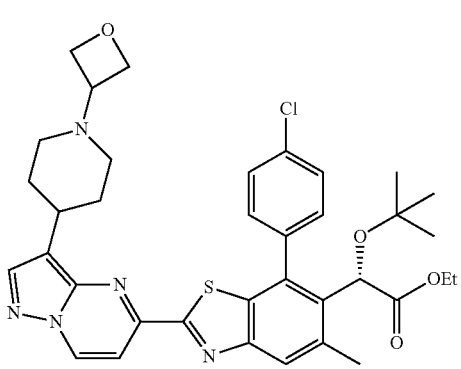

ethyl (S)-2-(tert-butoxy)-2-(7-(4-chlorophenyl)-5-methyl-2-(3-(1-(oxetan-3-yl)piperidin-4-yl)pyrazolo[1,5-a]pyrimidin-5-yl)benzo[d]thiazol-6-yl)acetate

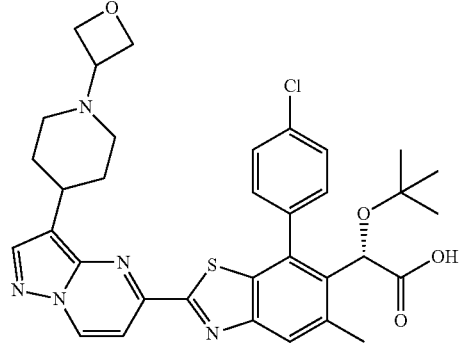

(S)-2-(tert-butoxy)-2-(7-(4-chlorophenyl)-5-methyl-2-(3-(1-(oxetan-3-yl)piperidin-4-yl)pyrazolo[1,5-a]pyrimidin-5-yl)benzo[d]thiazol-6-yl)acetic acid Preparation of ethyl (S)-2-(tert-butoxy)-2-(7-(4-chlorophenyl)-5-methyl-2-(pyrazolo[1,5-a]pyrimidin-5-yl)benzo[d]thiazol-6-yl)acetate: To a solution of 5-bromopyrazolo[1,5-a]pyrimidine (200 mg, 1.00 mmol), Pd(PPh$_3$)$_4$ (117 mg, 0.101 mmol), copper(I) iodide (96 mg, 0.101 mmol), and hexa-n-butylditin (0.51 mL, 1.0 mmol) in toluene (0.5 mL) at 110° C. was added ethyl (S)-2-(2-bromo-7-(4-chlorophenyl)-5-methylbenzo[d]thiazol-6-yl)-2-(tert-butoxy)acetate (0.50 g, 1.0 mmol) in toluene (3 mL) over 30 minutes. Reaction mixture was stirred nine hours at 110° C., cooled to room temperature. Ethyl acetate and lithium chloride were added and stirred over the weekend. Reaction mixture was filtered, concentrated and purified by CombiFlash (ethyl acetate/hexanes) to give desired product. LCMS-ESI+: calc'd for C$_{28}$H$_{28}$ClN$_4$O$_3$S: 535.2 (M+H+); Found 535.2 (M+H+).

Preparation of ethyl (S)-2-(2-(3-bromopyrazolo[1,5-a]pyrimidin-5-yl)-7-(4-chlorophenyl)-5-methylbenzo[d]thiazol-6-yl)-2-(tert-butoxy)acetate: To a solution of ethyl (S)-2-(tert-butoxy)-2-(7-(4-chlorophenyl)-5-methyl-2-(pyrazolo[1,5-a]pyrimidin-5-yl)benzo[d]thiazol-6-yl)acetate (343 mg, 0.641 mmol) in dichloromethane at −78° C. was added N-bromosuccinimide (114 mg, 0.641 mmol) and reaction mixture was stirred for one hour. Reaction mixture was warmed to room temperature and after 0.5 hours, reaction mixture was partitioned between ethyl acetate and saturated sodium bicarbonate solution and organic layer was concentrated and purified by CombiFlash (ethyl acetate/hexanes) to give desired product. LCMS-ESI+: calc'd for C$_{28}$H$_{27}$BrClN$_4$O$_3$S: 613.1 (M+H+); Found 613.1 (M+H+).

Preparation of tert-butyl (S)-4-(5-(6-(1-(tert-butoxy)-2-ethoxy-2-oxoethyl)-7-(4-chlorophenyl)-5-methylbenzo[d]thiazol-2-yl)pyrazolo[1,5-a]pyrimidin-3-yl)-3,6-dihydropyridine-1(2H)-carboxylate: A mixture of ethyl (S)-2-(2-(3-bromopyrazolo[1,5-a]pyrimidin-5-yl)-7-(4-chlorophenyl)-5-methylbenzo[d]thiazol-6-yl)-2-(tert-butoxy)acetate (0.343 g, 0.559 mmol), tert-butyl 4-(4,4,5,5-tetramethyl-1,3,2-dioxaborolan-2-yl)-3,6-dihydropyridine-1(2H)-carboxylate (190 mg, 0.615 mmol), Pd(PPh$_3$)$_4$ (5 mg, 0.048 mmol), and 2M sodium carbonate solution (0.84 mL, 2.0 mmol) in dioxane (10 mL) was heated at 90° C. for four hours. Reaction mixture was portioned between ethyl acetate and saturated sodium bicarbonate solution, organic layer dried (MgSO$_4$), filtered, concentrated and purified by CombiFlash (ethyl acetate/hexanes) to give desired product. LCMS-ESI+: calc'd for C$_{38}$H$_{43}$ClN$_5$O$_5$S: 716.3 (M+H)$^+$; found: 716.0.

Preparation of tert-butyl (S)-4-(5-(6-(1-(tert-butoxy)-2-ethoxy-2-oxoethyl)-7-(4-chlorophenyl)-5-methylbenzo[d]thiazol-2-yl)pyrazolo[1,5-a]pyrimidin-3-yl)piperidine-1-carboxylate: A mixture of tert-butyl (S)-4-(5-(6-(1-(tert-butoxy)-2-ethoxy-2-oxoethyl)-7-(4-chlorophenyl)-5-methylbenzo[d]thiazol-2-yl)pyrazolo[1,5-a]pyrimidin-3-yl)-3,6-dihydropyridine-1(2H)-carboxylate (96 mg, 0.13 mmol) and 10% platinum on carbon (50 mg) in ethanol (10 mL) and ethyl acetate (20 mL) containing a few drops of acetic acid was stirred under hydrogen atmosphere for one day. Additional 10% platinum on carbon (50 mg) was added and reaction stirred for three days. Reaction mixture was filtered, concentrated and used in the next step without further purification. LCMS-ESI+: calc'd for $C_{38}H_{45}ClN_5O_5S$: 717.3 (M+H)$^+$; found: 714.0.

Preparation of ethyl (S)-2-(tert-butoxy)-2-(7-(4-chlorophenyl)-5-methyl-2-(3-(1-(oxetan-3-yl)piperidin-4-yl)pyrazolo[1,5-a]pyrimidin-5-yl)benzo[d]thiazol-6-yl)acetate: To tert-butyl (S)-4-(5-(6-(1-(tert-butoxy)-2-ethoxy-2-oxoethyl)-7-(4-chlorophenyl)-5-methylbenzo[d]thiazol-2-yl)pyrazolo[1,5-a]pyrimidin-3-yl)piperidine-1-carboxylate (18 mg, 0.025 mmol) was added 1.25 N hydrochloric acid in isopropanol (1 mL). Reaction mixture was stirred for 48 hours. The reaction was quenched with saturated sodium bicarbonate solution, pH was adjusted to pH 7 using 2M sodium hydroxide, extracted with ethyl acetate (2×), 10% methanol in ethyl acetate (2×). The combined organic layer was, dried (MgSO$_4$), filtered, concentrated and used in the next step without further purification. LCMS-ESI+: calc'd for $C_{33}H_{37}ClN_5O_3S$: 618.2 (M+H)$^+$; found: 618.3.

A solution of free amine (16 mg, 0.026), oxetan-3-one (19 mg, 0.26 mmol), acetic acid (one drop) and sodium cyanoborohydride (8.0 mg, 0.13 mmol) in methanol (1.0 mL) was stirred overnight. Reaction mixture was concentrated and purified by Gilson HPLC (Gemini, 5-100% ACN/H$_2$O+ 0.1% TFA). Product was lyophilized to give desired product. LCMS-ESI+: calc'd for $C_{36}H_{41}ClN_5O_4S$: 674.3 (M+H)$^+$; found: 674.3.

Preparation of (S)-2-(tert-butoxy)-2-(7-(4-chlorophenyl)-5-methyl-2-(3-(1-(oxetan-3-yl)piperidin-4-yl)pyrazolo[1,5-a]pyrimidin-5-yl)benzo[d]thiazol-6-yl)acetic acid: A solution of ethyl (S)-2-(tert-butoxy)-2-(7-(4-chlorophenyl)-5-methyl-2-(3-(1-(oxetan-3-yl)piperidin-4-yl)pyrazolo[1,5-a]pyrimidin-5-yl)benzo[d]thiazol-6-yl)acetate and 2M sodium hydroxide in THF/Ethanol was stirred at 60° C. for two hours. Reaction mixture was filtered through a syringe filter and purified by Gilson HPLC (Gemini, 5-100% ACN/H$_2$O+ 0.1% TFA). Product was lyophilized to give an off-white powder. $^1$H NMR (400 MHz, Methanol-d4) δ 8.92 (s, 1H), 8.15 (s, 1H), 7.82 (m, 2H), 7.62 (m, 1H), 7.57 (m, 3H), 5.26 (s, 1H), 4.79 (m, 4H), 4.38 (m, 1H), 3.52 (m, 2H), 3.32 (m, 1H), 3.05 (m, 2H), 2.58 (s, 3H), 2.32 (m, 2H), 2.09 (m, 2H), 0.98 (s, 9H); LCMS-ESI+: calc'd for $C_{34}H_{37}ClN_5O_4S$: 646.2 (M+H)$^+$; found: 646.2.

Example 110. Preparation of (S)-2-(tert-butoxy)-2-(7-(4-chlorophenyl)-5-methyl-2-(3-(1-(oxetan-3-yl)piperidin-4-yl)pyrazolo[1,5-a]pyrimidin-5-yl)benzo[d]thiazol-6-yl)acetic Acid (110)

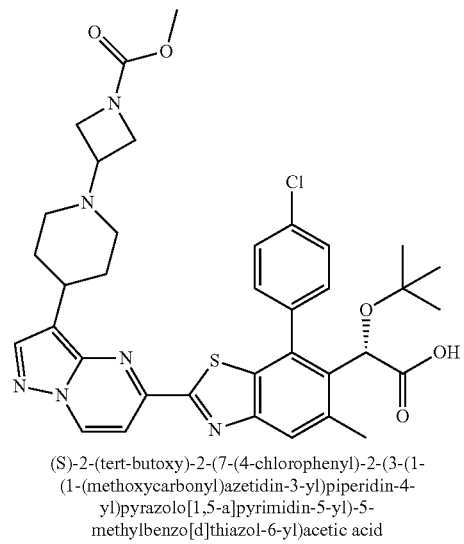 [SMILES: COC(=O)N1CC(N2CCC(c3cnn4ccc(-c5nc6cc(C)c([C@H](OC(C)(C)C)C(=O)O)c(-c7ccc(Cl)cc7)c6s5)nc34)CC2)C1]

(S)-2-(tert-butoxy)-2-(7-(4-chlorophenyl)-2-(3-(1-(1-(methoxycarbonyl)azetidin-3-yl)piperidin-4-yl)pyrazolo[1,5-a]pyrimidin-5-yl)-5-methylbenzo[d]thiazol-6-yl)acetic acid Preparation of (S)-2-(tert-butoxy)-2-(7-(4-chlorophenyl)-2-(3-(1-(1-(methoxycarbonyl)azetidin-3-yl)piperidin-4-yl)pyrazolo[1,5-a]pyrimidin-5-yl)-5-methylbenzo[d]thiazol-6-yl)acetic acid: Prepared in a manner similar to (S)-2-(tert-butoxy)-2-(7-(4-chlorophenyl)-5-methyl-2-(3-(1-(oxetan-3-yl)piperidin-4-yl)pyrazolo[1,5-a]pyrimidin-5-yl)benzo[d]thiazol-6-yl)acetic acid. $^1$H NMR (400 MHz, Methanol-d4) δ 8.91 (dd, J=7.3, 1.3 Hz, 1H), 8.08 (s, 1H), 7.87-7.77 (m, 2H), 7.68 (dd, J=8.5, 2.1 Hz, 1H), 7.64-7.51 (m, 3H), 5.24 (s, 1H), 4.37-4.20 (m, 4H), 4.15-4.06 (m, 1H), 3.71 (s, 3H), 3.62 (s, 1H), 3.13 (s, 1H), 2.61 (s, 3H), 2.35 (d, J=14.1 Hz, 2H), 2.13 (s, 1H), 0.98 (s, 9H); LCMS-ESI+: calc'd for $C_{34}H_{37}ClN_5O_4S$: 703.2 (M+H)$^+$; found: 703.3.

Example 111. Preparation of (S)-2-(tert-butoxy)-2-(7-(4-chlorophenyl)-2-(3-(4-isopropylpiperazin-1-yl)-1-methyl-1H-pyrazolo[3,4-b]pyridin-5-yl)-5-methylbenzo[d]thiazol-6-yl)acetic Acid (111)

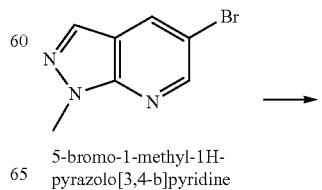

5-bromo-1-methyl-1H-pyrazolo[3,4-b]pyridine

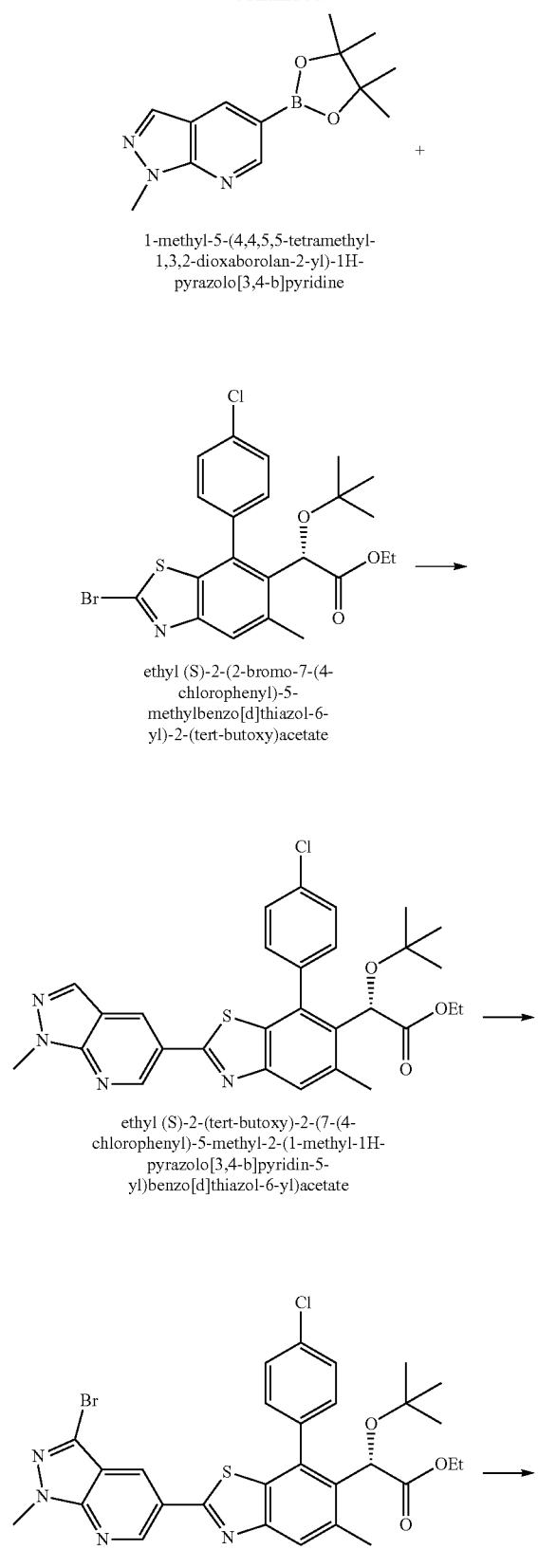

1-methyl-5-(4,4,5,5-tetramethyl-1,3,2-dioxaborolan-2-yl)-1H-pyrazolo[3,4-b]pyridine ethyl (S)-2-(2-bromo-7-(4-chlorophenyl)-5-methylbenzo[d]thiazol-6-yl)-2-(tert-butoxy)acetate ethyl (S)-2-(tert-butoxy)-2-(7-(4-chlorophenyl)-5-methyl-2-(1-methyl-1H-pyrazolo[3,4-b]pyridin-5-yl)benzo[d]thiazol-6-yl)acetate ethyl (S)-2-(2-(3-bromo-1-methyl-1H-pyrazolo[3,4-b]pyridin-5-yl)-7-(4-chlorophenyl)-5-methylbenzo[d]thiazol-6-yl)-2-(tert-butoxy)acetate

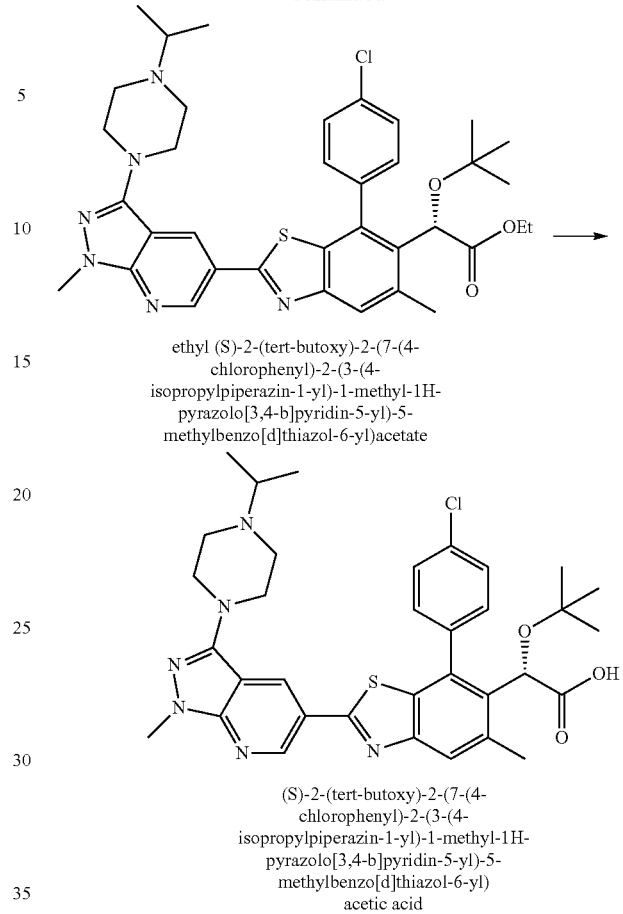

ethyl (S)-2-(tert-butoxy)-2-(7-(4-chlorophenyl)-2-(3-(4-isopropylpiperazin-1-yl)-1-methyl-1H-pyrazolo[3,4-b]pyridin-5-yl)-5-methylbenzo[d]thiazol-6-yl)acetate (S)-2-(tert-butoxy)-2-(7-(4-chlorophenyl)-2-(3-(4-isopropylpiperazin-1-yl)-1-methyl-1H-pyrazolo[3,4-b]pyridin-5-yl)-5-methylbenzo[d]thiazol-6-yl) acetic acid Preparation of 1-methyl-5-(4,4,5,5-tetramethyl-1,3,2-dioxaborolan-2-yl)-1H-pyrazolo[3,4-b]pyridine: A mixture of 5-bromo-1-methyl-1H-pyrazolo[3,4-b]pyridine (3.04 g, 14.0 mmol), bis(pinacolato)diboron (4.37 g, 17.0 mmol), PdCl2(dppf) (0.992 g, 1 mmol), and potassium acetate (3.52 g, 36 mmol) in dioxane was heated at 100° C. for 1 hour. Reaction mixture was portioned between ethyl acetate and saturated sodium bicarbonate solution, organic layer dried (MgSO$_4$), filtered, concentrated and purified by CombiFlash (ethyl acetate/hexanes) to give desired product. LCMS-ESI+: calc'd for $C_{13}H_{19}BN_3O_2$: 260.2 (M+H)$^+$; found: 260.2 (M+H)$^+$.

Preparation of ethyl (S)-2-(tert-butoxy)-2-(7-(4-chlorophenyl)-5-methyl-2-(1-methyl-1H-pyrazolo[3,4-b]pyridin-5-yl)benzo[d]thiazol-6-yl)acetate: A mixture of ethyl (S)-2-(2-bromo-7-(4-chlorophenyl)-5-methylbenzo[d]thiazol-6-yl)-2-(tert-butoxy)acetate (3.84 g, 8.0 mmol), 1-methyl-5-(4,4,5,5-tetramethyl-1,3,2-dioxaborolan-2-yl)-1H-pyrazolo[3,4-b]pyridine (2.0 g, 8.0 mmol), Pd(PPh$_3$)$_4$ (0.446 g, 0.39 mmol) in 2M potassium carbonate solution (7.72 mL, 15 mmol) and dioxane (40 mL) was heated at 100° C. for 1 hour. Reaction was stopped, reaction mixture was portioned between ethyl acetate and saturated sodium bicarbonate solution, organic layer dried (MgSO$_4$), filtered, concentrated and purified by CombiFlash (ethyl acetate/hexanes) to give desired product. LCMS-ESI+: calc'd for $C_{29}H_{30}ClN_4O_3S$: 549.2 (M+H)$^+$; found: 549.2.

Preparation of ethyl (S)-2-(2-(3-bromo-1-methyl-1H-pyrazolo[3,4-b]pyridin-5-yl)-7-(4-chlorophenyl)-5-methylbenzo[d]thiazol-6-yl)-2-(tert-butoxy)acetate: To a solution of ethyl (S)-2-(tert-butoxy)-2-(7-(4-chlorophenyl)-5- methyl-2-(1-methyl-1H-pyrazolo[3,4-b]pyridin-5-yl)benzo[d]thiazol-6-yl)acetate (450 mg, 0.82 mmol) in acetonitrile (1.0 mL) was added 2,9-lutidine (286 µL, 2.5 mmol), followed by bromine (393 mg, 2.5 mmol). Reaction mixture was stirred overnight, quenched with saturated sodium bicarbonate solution, extracted with ethyl acetate (2×), organic layer dried (MgSO$_4$), filtered, concentrated and purified by CombiFlash (ethyl acetate/hexanes) to give desired product. LCMS-ESI+: calc'd for $C_{29}H_{29}BrClN_4O_3S$: 627.1 (M+H)$^+$; found: 627.12.

Preparation of ethyl (S)-2-(tert-butoxy)-2-(7-(4-chlorophenyl)-2-(3-(4-isopropylpiperazin-1-yl)-1-methyl-1H-pyrazolo[3,4-b]pyridin-5-yl)-5-methylbenzo[d]thiazol-6-yl)acetate: A mixture of ethyl (S)-2-(2-(3-bromo-1-methyl-1H-pyrazolo[3,4-b]pyridin-5-yl)-7-(4-chlorophenyl)-5-methylbenzo[d]thiazol-6-yl)-2-(tert-butoxy)acetate (17 mg, 0.027 mmol), N-isopropylpiperazine (10 mg, 0.078 mmol), Tris(dibenzylideneacetone)dipalladium(0) (2 mg, 0.0027 mmol), 4,5-Bis(diphenylphosphino)-9,9-dimethylxanthene (3 mg, 0.0054 mmol) and cesium carbonate (26 mg, 0.081 mmol) in dioxane (1 mL) was heated at 100° C. overnight. Reaction mixture was portioned between ethyl acetate and saturated sodium bicarbonate solution, organic layer dried (MgSO$_4$), filtered, concentrated and purified by CombiFlash (ethyl acetate/hexanes to 20% methanol in ethyl acetate) to give desired product. LCMS-ESI+: calc'd for $C_{36}H_{44}ClN_6O_3S$: 675.3 (M+H)$^+$; found: 675.3.

Preparation of (S)-2-(tert-butoxy)-2-(7-(4-chlorophenyl)-2-(3-(4-isopropylpiperazin-1-yl)-1-methyl-1H-pyrazolo[3,4-b]pyridin-5-yl)-5-methylbenzo[d]thiazol-6-yl)acetic acid: A solution of ethyl (S)-2-(tert-butoxy)-2-(7-(4-chlorophenyl)-2-(3-(4-isopropylpiperazin-1-yl)-1-methyl-1H-pyrazolo[3,4-b]pyridin-5-yl)-5-methylbenzo[d]thiazol-6-yl)acetate (8 mg, 0.11 mmol) and 2M sodium hydroxide in THF/ethanol (1 mL) was stirred at 60° C. for one hour. Reaction mixture was filtered through a syringe filter and purified by Gilson HPLC (Gemini, 5-100% ACN/H$_2$O+ 0.1% TFA). Product was lyophilized to give an off-white powder. $^1$H NMR (400 MHz, Methanol-d4) δ 9.15 (s, 1H), 8.79 (s, 1H), 7.84 (s, 1H), 7.72-7.65 (m, 1H), 7.63-7.56 (m, 3H), 5.25 (s, 1H), 4.22 (m, 2H), 3.97 (s, 3H), 3.62 (m, 3H), 3.42 (m, 6H), 2.62 (s, 3H), 1.44 (d, J=6.6 Hz, 6H), 0.98 (s, 9H); LCMS-ESI+: calc'd for $C_{34}H_{40}ClN_6O_3S$: 675.3 (M+H)$^+$; found: 647.3.

Example 112. Preparation of (S)-2-(tert-butoxy)-2-(7-(4-chlorophenyl)-5-methyl-2-(1-methyl-3-(4-(oxetan-3-yl)piperazin-1-yl)-1H-pyrazolo[3,4-b]pyridin-5-yl)benzo[d]thiazol-6-yl)acetic Acid (112)

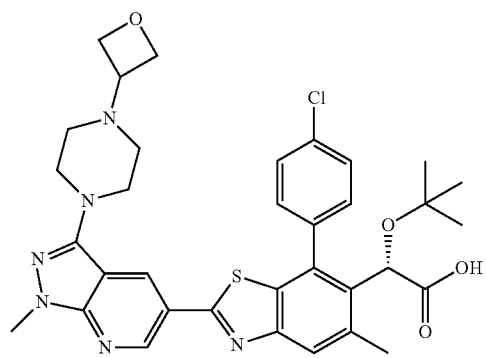

(S)-2-(tert-butoxy)-2-(7-(4-chlorophenyl)-5-methyl-2-(1-methyl-3-(4-(oxetan-3-yl)piperazin-1-yl)-1H-pyrazolo[3,4-b]pyridin-5-yl)benzo[d]thiazol-6-yl)acetic acid Preparation of (S)-2-(tert-butoxy)-2-(7-(4-chlorophenyl)-5-methyl-2-(1-methyl-3-(4-(oxetan-3-yl)piperazin-1-yl)-1H-pyrazolo[3,4-b]pyridin-5-yl)benzo[d]thiazol-6-yl)acetic acid: Prepared in a similar manner as (S)-2-(tert-butoxy)-2-(7-(4-chlorophenyl)-2-(3-(4-isopropylpiperazin-1-yl)-1-methyl-1H-pyrazolo[3,4-b]pyridin-5-yl)-5-methylbenzo[d]thiazol-6-yl)acetic acid. $^1$H NMR (400 MHz, Methanol-d4) δ 9.12 (s, 1H), 8.75 (s, 1H), 7.82 (s, 1H), 7.72-7.64 (m, 1H), 7.62-7.53 (m, 3H), 5.25 (s, 1H), 4.98-4.81 (m, 4H), 4.50-4.40 (m, 1H), 3.96 (s, 3H), 3.78 (m, 4H), 3.40 (m, 4H), 2.61 (s, 3H), 0.97 (s, 9H); LCMS-ESI+: calc'd for $C_{34}H_{38}ClN_6O_4S$: 661.2 (M+H)$^+$; found: 661.2.

Example 113. Preparation of (S)-2-(tert-butoxy)-2-(7-(4-chlorophenyl)-5-methyl-2-(1-methyl-3-(1-(oxetan-3-yl)piperidin-4-yl)-1H-pyrazolo[3,4-b]pyridin-5-yl)benzo[d]thiazol-6-yl)acetic Acid (113)

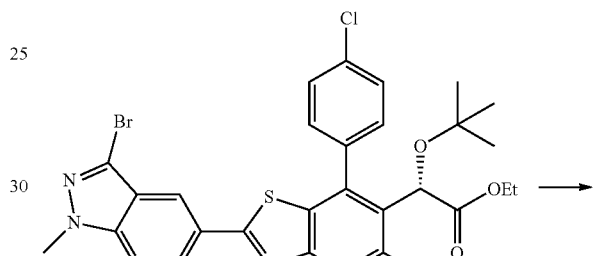

ethyl (S)-2-(2-(3-bromo-1-methyl-1H-pyrazolo[3,4-b]pyridin-5-yl)-7-(4-chlorophenyl)-5-methylbenzo[d]thiazol-6-yl)-2-(tert-butoxy)acetate

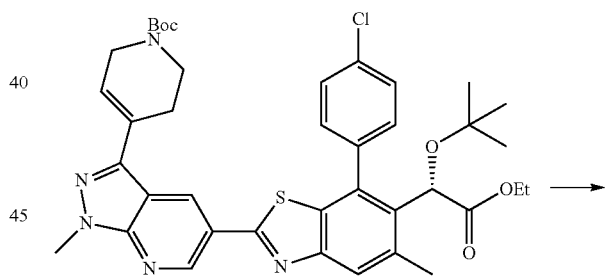

tert-butyl (S)-4-(5-(6-1-(tert-butoxy)-2-ethoxy-2-oxoethyl)-7-(4-chlorophenyl)-5-methylbenzo[d]thiazol-2-yl)-1-methyl-1H-pyrazolo[3,4-b]pyridin-3-yl)-3,6-dihydropyridine-1(2H)-carboxylate

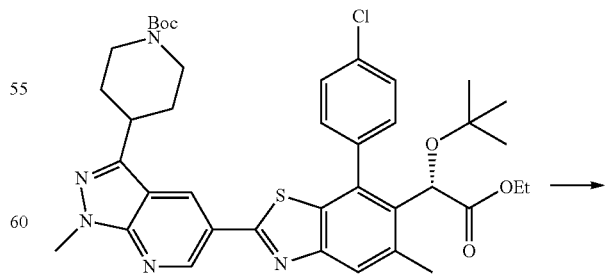

tert-butyl (S)-4-(5-(6-1-(tert-butoxy)-2-ethoxy-2-oxoethyl)-7-(4-chlorophenyl)-5-methylbenzo[d]thiazol-2-yl)-1-methyl-1H-pyrazolo[3,4-b]pyridin-3-yl)piperidine-1-carboxylate

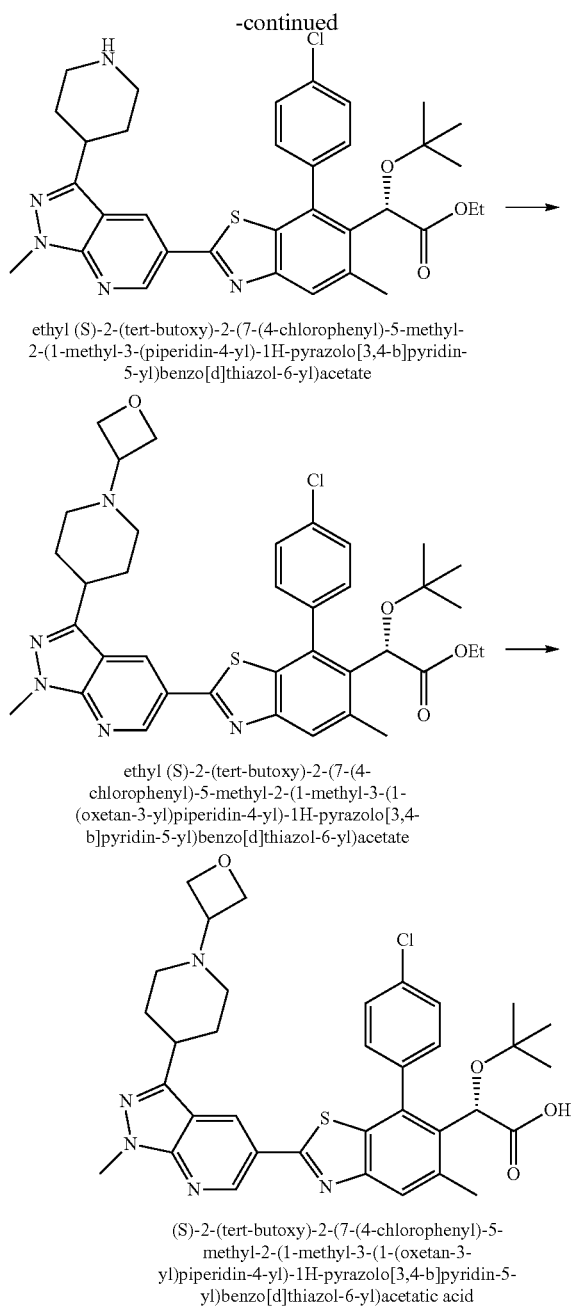

ethyl (S)-2-(tert-butoxy)-2-(7-(4-chlorophenyl)-5-methyl-2-(1-methyl-3-(piperidin-4-yl)-1H-pyrazolo[3,4-b]pyridin-5-yl)benzo[d]thiazol-6-yl)acetate ethyl (S)-2-(tert-butoxy)-2-(7-(4-chlorophenyl)-5-methyl-2-(1-methyl-3-(1-(oxetan-3-yl)piperidin-4-yl)-1H-pyrazolo[3,4-b]pyridin-5-yl)benzo[d]thiazol-6-yl)acetate (S)-2-(tert-butoxy)-2-(7-(4-chlorophenyl)-5-methyl-2-(1-methyl-3-(1-(oxetan-3-yl)piperidin-4-yl)-1H-pyrazolo[3,4-b]pyridin-5-yl)benzo[d]thiazol-6-yl)acetatic acid Preparation of tert-butyl (S)-4-(5-(6-(1-(tert-butoxy)-2-ethoxy-2-oxoethyl)-7-(4-chlorophenyl)-5-methylbenzo[d]thiazol-2-yl)-1-methyl-1H-pyrazolo[3,4-b]pyridin-3-yl)-3,6-dihydropyridine-1(2H)-carboxylate: A mixture of ethyl (S)-2-(2-(3-bromo-1-methyl-1H-pyrazolo[3,4-b]pyridin-5-yl)-7-(4-chlorophenyl)-5-methylbenzo[d]thiazol-6-yl)-2-(tert-butoxy)acetate (0.114 g, 0.18 mmol), tert-butyl 4-(4,4,5,5-tetramethyl-1,3,2-dioxaborolan-2-yl)-3,6-dihydropyridine-1(2H)-carboxylate (67 mg, 0.22 mmol), Pd(PPh$_3$)$_4$ (0.446 g, 0.39 mmol), and 2M sodium carbonate solution (0.27 mL, 0.55 mmol) in dioxane (1.0 mL) was heated at 100° C. for two hours. Reaction mixture was portioned between ethyl acetate and saturated sodium bicarbonate solution, organic layer dried (MgSO$_4$), filtered, concentrated and purified by CombiFlash (ethyl acetate/hexanes) to give desired product. LCMS-ESI+: calc'd for C$_{39}$H$_{45}$ClN$_5$S: 730.3 (M+H)$^+$; found: 730.0.

Preparation of tert-butyl (S)-4-(5-(6-(1-(tert-butoxy)-2-ethoxy-2-oxoethyl)-7-(4-chlorophenyl)-5-methylbenzo[d]thiazol-2-yl)-1-methyl-1H-pyrazolo[3,4-b]pyridin-3-yl)piperidine-1-carboxylate: A mixture of tert-butyl (S)-4-(5-(6-(1-(tert-butoxy)-2-ethoxy-2-oxoethyl)-7-(4-chlorophenyl)-5-methylbenzo[d]thiazol-2-yl)-1-methyl-1H-pyrazolo[3,4-b]pyridin-3-yl)-3,6-dihydropyridine-1(2H)-carboxylate (0.840 g, 1.15 mmol) and 5% rhodium on alumina (400 mg) in ethanol was stirred under hydrogen atmosphere overnight. Additional 5% rhodium on alumina (400 mg) was added and reaction continued for one day. Reaction mixture was filtered, concentrated and used in the next step without further purification. LCMS-ESI+: calc'd for C$_{39}$H$_{47}$ClN$_5$S: 632.2 (M-Boc+H)$^+$; found: 632.3.

Preparation of ethyl (S)-2-(tert-butoxy)-2-(7-(4-chlorophenyl)-5-methyl-2-(1-methyl-3-(piperidin-4-yl)-1H-pyrazolo[3,4-b]pyridin-5-yl)benzo[d]thiazol-6-yl)acetate: To tert-butyl (S)-4-(5-(6-(1-(tert-butoxy)-2-ethoxy-2-oxoethyl)-7-(4-chlorophenyl)-5-methylbenzo[d]thiazol-2-yl)-1-methyl-1H-pyrazolo[3,4-b]pyridin-3-yl)piperidine-1-carboxylate (72 mg, 0.98 mmol) was added 1.25 N hydrochloric acid in isopropanol. Reaction mixture was stirred for 28 hours. The pH was adjusted to pH 7 using 1M sodium hydroxide, extracted with ethyl acetate (2×), 15% methanol in dichloromethane (2×). The combined organic layer was washed with saturated sodium bicarbonate solution, dried (MgSO$_4$), filtered, concentrated and used in the next step without further purification. LCMS-ESI+: calc'd for C$_{39}$H$_{47}$ClN$_5$O$_5$S: 632.2 (M+H)$^+$; found: 632.3.

Preparation of ethyl (S)-2-(tert-butoxy)-2-(7-(4-chlorophenyl)-5-methyl-2-(1-methyl-3-(1-(oxetan-3-yl)piperidin-4-yl)-1H-pyrazolo[3,4-b]pyridin-5-yl)benzo[d]thiazol-6-yl)acetate: A solution of ethyl (S)-2-(tert-butoxy)-2-(7-(4-chlorophenyl)-5-methyl-2-(1-methyl-3-(piperidin-4-yl)-1H-pyrazolo[3,4-b]pyridin-5-yl)benzo[d]thiazol-6-yl)acetate (28 mg, 0.040 mmol), oxetan-3-one (25 mg, 0.40 mmol), acetic acid (5 μL, 0.08 mmol) and sodium cyanoborohydride (12 mg, 0.2 mmol) in methanol (1.0 mL) was stirred overnight. Reaction mixture was quenched with saturated sodium bicarbonate solution and extracted with ethyl acetate (2×), 15% methanol in dichloromethane (2×). The combined organic layer was dried (MgSO$_4$), filtered, concentrated and purified by CombiFlash (ethyl acetate/hexanes to 20% methanol in ethyl acetate) to give desired product. LCMS-ESI+: calc'd for C$_{37}$H$_{43}$ClN$_5$O$_4$S: 688.3 (M+H)$^+$; found: 688.3.

Preparation of (S)-2-(tert-butoxy)-2-(7-(4-chlorophenyl)-5-methyl-2-(1-methyl-3-(1-(oxetan-3-yl)piperidin-4-yl)-1H-pyrazolo[3,4-b]pyridin-5-yl)benzo[d]thiazol-6-yl)acetic acid: A solution of ethyl (S)-2-(tert-butoxy)-2-(7-(4-chlorophenyl)-5-methyl-2-(1-methyl-3-(1-(oxetan-3-yl)piperidin-4-yl)-1H-pyrazolo[3,4-b]pyridin-5-yl)benzo[d]thiazol-6-yl)acetate and 2M sodium hydroxide in THF/Ethanol was stirred at 40° C. overnight. Reaction mixture was filtered through a syringe filter and purified by Gilson HPLC (Gemini, 5-100% ACN/H$_2$O+0.1% TFA). Product was lyophilized to give an off-white powder. $^1$H NMR (400 MHz, Methanol-d4) δ 9.22 (s, 1H), 8.82 (s, 1H), 7.85 (s, 1H), 7.72-7.65 (m, 1H), 7.63-7.54 (m, 3H), 5.26 (s, 1H), 4.93 (m, 2H), 4.84 (m, 2H), 4.48 (m, 1H), 4.09 (s, 3H), 3.64-3.50 (m, 3H), 2.62 (s, 3H), 2.42 (m, 2H), 2.24 (m, 2H), 0.98 (s, 9H); LCMS-ESI+: calc'd for C$_{35}$H$_{39}$ClN$_5$O$_4$S: 660.2 (M+H)$^+$; found: 660.3.

Example 114A and 114B. Preparation of (S)-2-(tert-butoxy)-2-(7-(4-chlorophenyl)-2-(3-(1-(1-(methoxycarbonyl)azetidin-3-yl)piperidin-4-yl)-1-methyl-1H-pyrazolo[3,4-b]pyridin-5-yl)-5-methylbenzo[d]thiazol-6-yl)acetic Acid (114) and (S)-2-(tert-butoxy)-2-(7-(4-chlorophenyl)-2-(3-(1-(1-(ethoxycarbonyl)azetidin-3-yl)piperidin-4-yl)-1-methyl-1H-pyrazolo[3,4-b]pyridin-5-yl)-5-methylbenzo[d]thiazol-6-yl)acetic Acid (115)

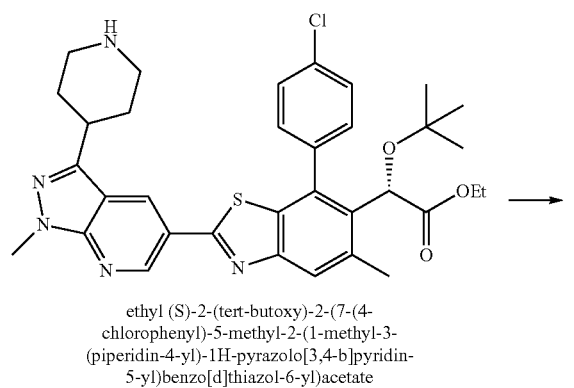

ethyl (S)-2-(tert-butoxy)-2-(7-(4-chlorophenyl)-5-methyl-2-(1-methyl-3-(piperidin-4-yl)-1H-pyrazolo[3,4-b]pyridin-5-yl)benzo[d]thiazol-6-yl)acetate

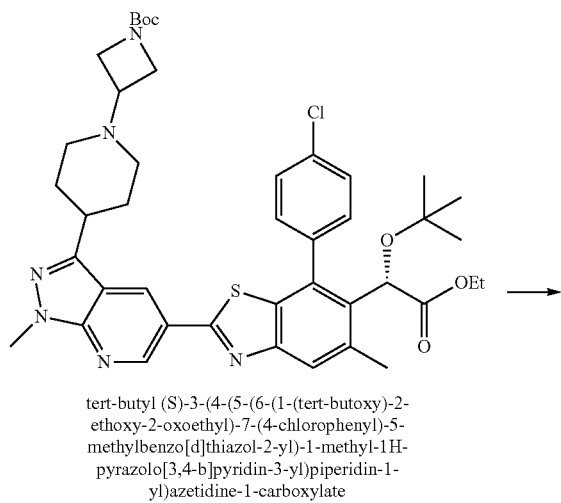

tert-butyl (S)-3-(4-(5-(6-(1-(tert-butoxy)-2-ethoxy-2-oxoethyl)-7-(4-chlorophenyl)-5-methylbenzo[d]thiazol-2-yl)-1-methyl-1H-pyrazolo[3,4-b]pyridin-3-yl)piperidin-1-yl)azetidine-1-carboxylate

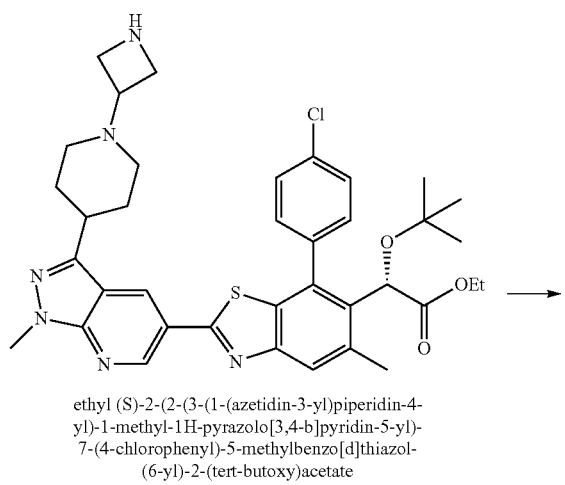

ethyl (S)-2-(2-(3-(1-(azetidin-3-yl)piperidin-4-yl)-1-methyl-1H-pyrazolo[3,4-b]pyridin-5-yl)-7-(4-chlorophenyl)-5-methylbenzo[d]thiazol-(6-yl)-2-(tert-butoxy)acetate -continued

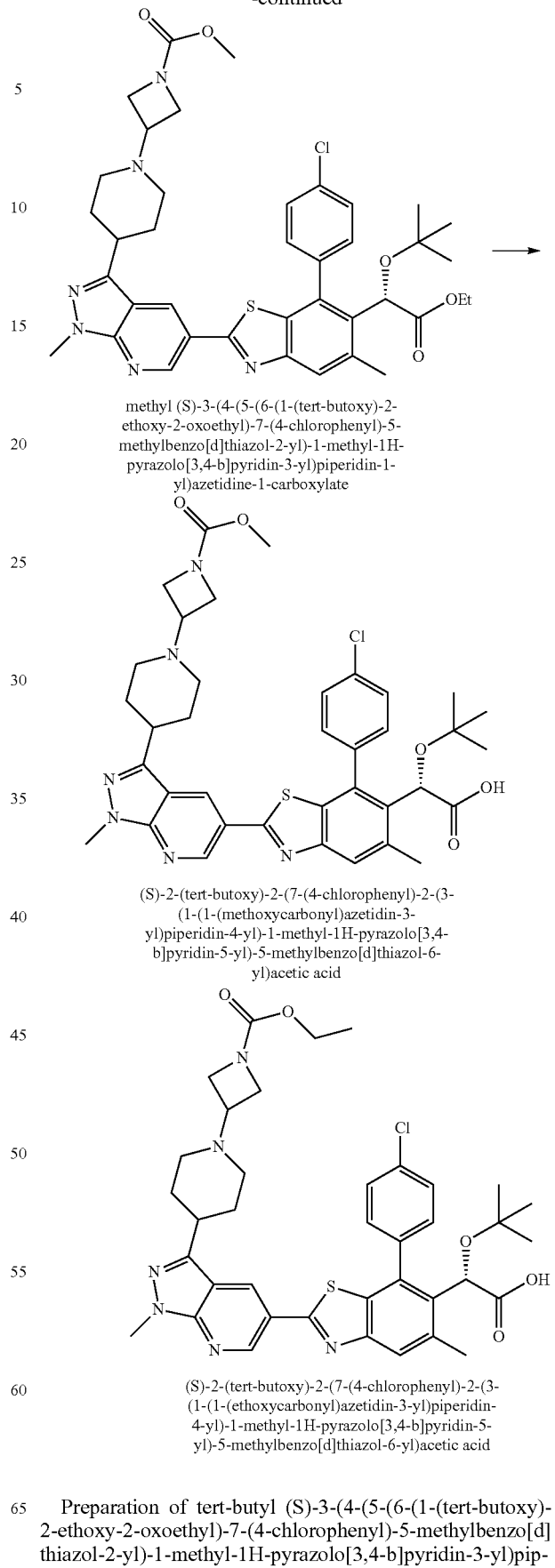

methyl (S)-3-(4-(5-(6-(1-(tert-butoxy)-2-ethoxy-2-oxoethyl)-7-(4-chlorophenyl)-5-methylbenzo[d]thiazol-2-yl)-1-methyl-1H-pyrazolo[3,4-b]pyridin-3-yl)piperidin-1-yl)azetidine-1-carboxylate (S)-2-(tert-butoxy)-2-(7-(4-chlorophenyl)-2-(3-(1-(1-(methoxycarbonyl)azetidin-3-yl)piperidin-4-yl)-1-methyl-1H-pyrazolo[3,4-b]pyridin-5-yl)-5-methylbenzo[d]thiazol-6-yl)acetic acid (S)-2-(tert-butoxy)-2-(7-(4-chlorophenyl)-2-(3-(1-(1-(ethoxycarbonyl)azetidin-3-yl)piperidin-4-yl)-1-methyl-1H-pyrazolo[3,4-b]pyridin-5-yl)-5-methylbenzo[d]thiazol-6-yl)acetic acid Preparation of tert-butyl (S)-3-(4-(5-(6-(1-(tert-butoxy)-2-ethoxy-2-oxoethyl)-7-(4-chlorophenyl)-5-methylbenzo[d]thiazol-2-yl)-1-methyl-1H-pyrazolo[3,4-b]pyridin-3-yl)piperidin-1-yl)azetidine-1-carboxylate: ethyl (S)-2-(tert-butoxy)-2-(7-(4-chlorophenyl)-5-methyl-2-(1-methyl-3-(piperidin-4-yl)-1H-pyrazolo[3,4-b]pyridin-5-yl)benzo[d]thiazol-6-yl)acetate (70 mg, 0.11 mmol), tert-butyl 3-oxoazetidine-1-carboxylate (95 mg, 0.55 mmol), acetic acid (6 μL, 0.11 mmol) and sodium cyanoborohydride (35 mg, 0.55 mmol) in methanol (1.0 mL) was stirred overnight. Reaction mixture was quenched with saturated sodium bicarbonate solution and extracted with ethyl acetate (2×), 15% methanol in dichloromethane (2×). The combined organic layer was dried (MgSO$_4$), filtered, concentrated and used in next step without further purification. LCMS-ESI+: calc'd for $C_{42}H_{52}ClN_6O_5S$: 787.3 (M+H)$^+$; found: 787.1.

Preparation of ethyl (S)-2-(2-(3-(1-(azetidin-3-yl)piperidin-4-yl)-1-methyl-1H-pyrazolo[3,4-b]pyridin-5-yl)-7-(4-chlorophenyl)-5-methylbenzo[d]thiazol-6-yl)-2-(tert-butoxy)acetate: tert-butyl (S)-3-(4-(5-(6-(1-(tert-butoxy)-2-ethoxy-2-oxoethyl)-7-(4-chlorophenyl)-5-methylbenzo[d]thiazol-2-yl)-1-methyl-1H-pyrazolo[3,4-b]pyridin-3-yl)piperidin-1-yl)azetidine-1-carboxylate (47 mg, 0.060 mmol) in 1.25 N hydrochloric acid in isopropanol was stirred for two days. The pH was adjusted to pH 9 with 2M sodium hydroxide. Purification by Gilson HPLC (Gemini, 5-100% ACN/H$_2$O+0.1% TFA) gave desired product. LCMS-ESI+: calc'd for $C_{37}H_{44}ClN_6O_3S$: 687.3 (M+H)$^+$; found: 687.4.

Preparation of methyl (S)-3-(4-(5-(6-(1-(tert-butoxy)-2-ethoxy-2-oxoethyl)-7-(4-chlorophenyl)-5-methylbenzo[d]thiazol-2-yl)-1-methyl-1H-pyrazolo[3,4-b]pyridin-3-yl)piperidin-1-yl)azetidine-1-carboxylate: To a solution of ethyl (S)-2-(2-(3-(1-(azetidin-3-yl)piperidin-4-yl)-1-methyl-1H-pyrazolo[3,4-b]pyridin-5-yl)-7-(4-chlorophenyl)-5-methylbenzo[d]thiazol-6-yl)-2-(tert-butoxy)acetate (15 mg, 0.022 mmol) in dichloromethane (1.0 mL) at ° C. was added NN-diisopropylethylamine (15 μL, 0.088 mmol), followed by methyl chloroformate (3 μL, 0.044 mmol). Reaction mixture was stirred for five minutes, then purified by Gilson HPLC (Gemini, 5-100% ACN/H$_2$O+0.1% TFA) gave desired product. LCMS-ESI+: calc'd for $C_{39}H_{46}ClN_6O_5S$: 745.3 (M+H)$^+$; found: 745.3.

Preparation of (S)-2-(tert-butoxy)-2-(7-(4-chlorophenyl)-2-(3-(1-(1-(methoxycarbonyl)azetidin-3-yl)piperidin-4-yl)-1-methyl-1H-pyrazolo[3,4-b]pyridin-5-yl)-5-methylbenzo[d]thiazol-6-yl)acetic acid and (S)-2-(tert-butoxy)-2-(7-(4-chlorophenyl)-2-(3-(1-(1-(ethoxycarbonyl)azetidin-3-yl)piperidin-4-yl)-1-methyl-1H-pyrazolo[3,4-b]pyridin-5-yl)-5-methylbenzo[d]thiazol-6-yl)acetic acid: A solution of methyl (S)-3-(4-(5-(6-(1-(tert-butoxy)-2-ethoxy-2-oxoethyl)-7-(4-chlorophenyl)-5-methylbenzo[d]thiazol-2-yl)-1-methyl-1H-pyrazolo[3,4-b]pyridin-3-yl)piperidin-1-yl)azetidine-1-carboxylate (10 mg. 0.013 mmol) and 2N sodium hydroxide (67 μL, 0.13 mmol) in THF/EtOH (1.0 mL) was heated at 60° C. for one hour. Reaction mixture was filtered through a syringe filter and purified by Gilson HPLC (Gemini, 5-100% ACN/H$_2$O+0.1% TFA). Product was lyophilized to give an off-white powder.

(S)-2-(tert-butoxy)-2-(7-(4-chlorophenyl)-2-(3-(1-(1-(methoxycarbonyl)azetidin-3-yl)piperidin-4-yl)-1-methyl-1H-pyrazolo[3,4-b]pyridin-5-yl)-5-methylbenzo[d]thiazol-6-yl)acetic acid: $^1$H NMR (400 MHz, Methanol-d4) δ 9.23 (m, 1H), 8.82 (s, 1H), 7.86 (s, 1H), 7.73-7.54 (m, 4H), 5.26 (s, 1H), 4.36 (t, J=9.0 Hz, 2H), 4.27-4.12 (m, 3H), 4.09 (s, 3H), 3.72 (s, 3H), 3.62 (m, 3H), 3.18 (m, 2H), 2.62 (s, 3H), 2.42-2.22 (m, 4H), 0.98 (s, 9H); LCMS-ESI+: calc'd for $C_{37}H_{42}ClN_6O_5S$: 717.3 (M+H)$^+$; found: 717.3.

(S)-2-(tert-butoxy)-2-(7-(4-chlorophenyl)-2-(3-(1-(1-(ethoxycarbonyl)azetidin-3-yl)piperidin-4-yl)-1-methyl-1H-pyrazolo[3,4-b]pyridin-5-yl)-5-methylbenzo[d]thiazol-6-yl)acetic acid: $^1$H NMR (400 MHz, Methanol-d4) δ 9.24 (s, 1H), 8.83 (s, 1H), 7.86 (s, 1H), 7.73-7.57 (m, 4H), 5.26 (s, 1H), 4.37 (m, 2H), 4.25-4.07 (m, 5H), 4.05 (s, 3H), 3.71-3.50 (m, 3H), 3.20 (m, 2H), 2.62 (s, 3H), 2.42 (m, 2H), 2.21 (m, 2H), 1.27 (t, J=7.1 Hz, 3H), 0.98 (s, 9H); LCMS-ESI+: calc'd for $C_{38}H_{44}ClN_6O_5S$: 731.3 (M+H)$^+$; found: 731.3

Example 115. Preparation of (S)-2-(tert-butoxy)-2-(2-(3-(1-(1-(tert-butoxycarbonyl)azetidin-3-yl)piperidin-4-yl)-1-methyl-1H-pyrazolo[3,4-b]pyridin-5-yl)-7-(4-chlorophenyl)-5-methylbenzo[d]thiazol-6-yl)acetic Acid (116)

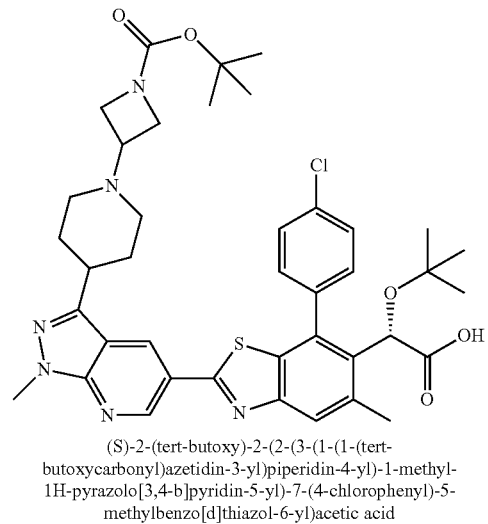 [SMILES: Cc1cc2nc(-c3cnc4c(c3)c(C3CCN(C5CN(C(=O)OC(C)(C)C)C5)CC3)nn4C)sc2c(-c2ccc(Cl)cc2)c1[C@H](OC(C)(C)C)C(=O)O]

(S)-2-(tert-butoxy)-2-(2-(3-(1-(1-(tert-butoxycarbonyl)azetidin-3-yl)piperidin-4-yl)-1-methyl-1H-pyrazolo[3,4-b]pyridin-5-yl)-7-(4-chlorophenyl)-5-methylbenzo[d]thiazol-6-yl)acetic acid Preparation of (S)-2-(tert-butoxy)-2-(2-(3-(1-(1-(tert-butoxycarbonyl)azetidin-3-yl)piperidin-4-yl)-1-methyl-1H-pyrazolo[3,4-b]pyridin-5-yl)-7-(4-chlorophenyl)-5-methylbenzo[d]thiazol-6-yl)acetic acid: Prepared in a similar manner as (S)-2-(tert-butoxy)-2-(7-(4-chlorophenyl)-2-(3-(1-(1-(methoxycarbonyl)azetidin-3-yl)piperidin-4-yl)-1-methyl-1H-pyrazolo[3,4-b]pyridin-5-yl)-5-methylbenzo[d]thiazol-6-yl)acetic acid. $^1$H NMR (400 MHz, Methanol-d4) δ 9.24 (s, 1H), 8.84 (s, 1H), 7.86 (s, 1H), 7.73-7.57 (m, 4H), 5.26 (s, 1H), 4.30 (m, 2H), 4.15 (m, 3H), 4.08 (s, 3H), 3.71 (m, 2H), 3.51 (m, 1H), 3.18 (m, 2H), 2.62 (s, 3H), 2.41 (m, 2H), 2.20 (m, 2H), 1.47 (s, 9H), 1.28 (s, 1H), 0.98 (s, 9H); LCMS-ESI+: calc'd for $C_{40}H_{48}ClN_6O_5S$: 759.3 (M+H)$^+$; found: 759.1.

Example 116. Preparation of (S)-2-(2-(3-(1-(1-acetylazetidin-3-yl)piperidin-4-yl)-1-methyl-1H-pyrazolo[3,4-b]pyridin-5-yl)-7-(4-chlorophenyl)-5-methylbenzo[d]thiazol-6-yl)-2-(tert-butoxy)acetic Acid (117)

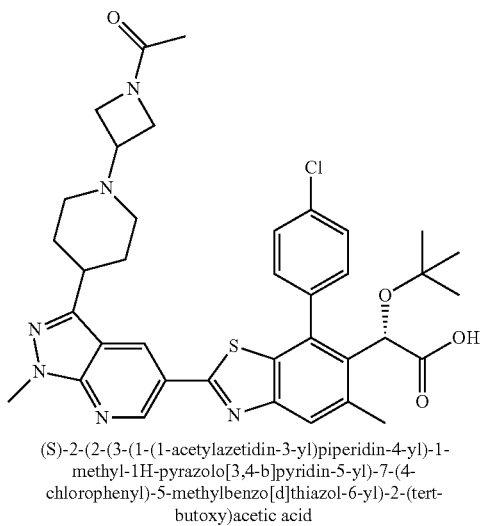 [SMILES: CC(=O)N1CC(N2CCC(c3nn(C)c4ncc(-c5nc6cc(C)c([C@H](OC(C)(C)C)C(=O)O)c(-c7ccc(Cl)cc7)c6s5)cc34)CC2)C1]

(S)-2-(2-(3-(1-(1-acetylazetidin-3-yl)piperidin-4-yl)-1-methyl-1H-pyrazolo[3,4-b]pyridin-5-yl)-7-(4-chlorophenyl)-5-methylbenzo[d]thiazol-6-yl)-2-(tert-butoxy)acetic acid Preparation of (S)-2-(2-(3-(1-(1-acetylazetidin-3-yl)piperidin-4-yl)-1-methyl-1H-pyrazolo[3,4-b]pyridin-5-yl)-7-(4-chlorophenyl)-5-methylbenzo[d]thiazol-6-yl)-2-(tert-butoxy)acetic acid: Prepared in a similar manner as (S)-2-(tert-butoxy)-2-(7-(4-chlorophenyl)-2-(3-(1-(1-(methoxycarbonyl)azetidin-3-yl)piperidin-4-yl)-1-methyl-1H-pyrazolo[3,4-b]pyridin-5-yl)-5-methylbenzo[d]thiazol-6-yl)acetic acid. $^1$H NMR (400 MHz, Methanol-d4) δ 9.23 (d, J=2.0 Hz, 2H), 8.84 (d, J=2.0 Hz, 2H), 7.86 (d, J=0.9 Hz, 2H), 7.73-7.65 (m, 2H), 7.64-7.57 (m, 4H), 5.26 (s, 2H), 4.63-4.54 (m, 3H), 4.45 (dd, J=11.0, 4.2 Hz, 3H), 4.39-4.28 (m, 3H), 4.24-4.15 (m, 3H), 4.10 (s, 4H), 3.70 (s, 2H), 3.56 (s, 1H), 3.19 (s, 2H), 2.62 (s, 4H), 2.44 (d, J=14.6 Hz, 4H), 2.24 (s, 2H), 1.94 (s, 4H), 0.98 (s, 9H); LCMS-ESI+: calc'd for $C_{37}H_{42}ClN_6O_4S$: 701.3 (M+H)$^+$; found: 701.3.

Example 117. Preparation of (S)-2-(tert-butoxy)-2-(7-(4-chlorophenyl)-5-methyl-2-(1-methyl-3-(1-(oxetan-3-yl)piperidin-4-yl)-1H-pyrazolo[3,4-b]pyrazin-5-yl)benzo[d]thiazol-6-yl)acetic Acid (118)

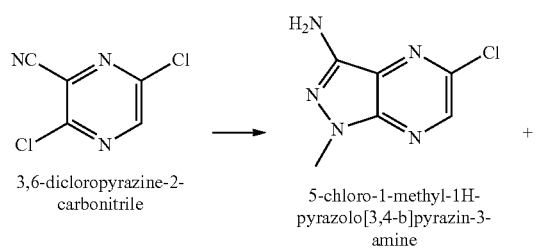

3,6-dicloropyrazine-2-carbonitrile 5-chloro-1-methyl-1H-pyrazolo[3,4-b]pyrazin-3-amine

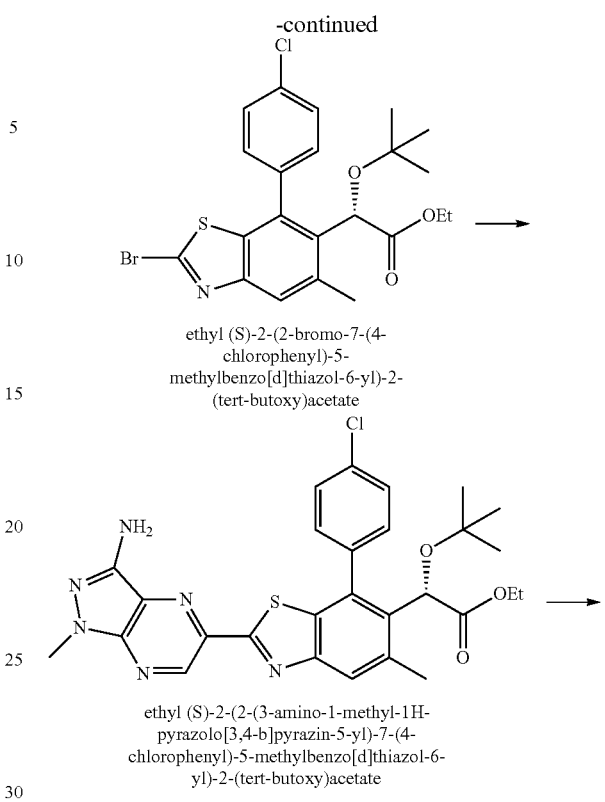

ethyl (S)-2-(2-bromo-7-(4-chlorophenyl)-5-methylbenzo[d]thiazol-6-yl)-2-(tert-butoxy)acetate ethyl (S)-2-(2-(3-amino-1-methyl-1H-pyrazolo[3,4-b]pyrazin-5-yl)-7-(4-chlorophenyl)-5-methylbenzo[d]thiazol-6-yl)-2-(tert-butoxy)acetate

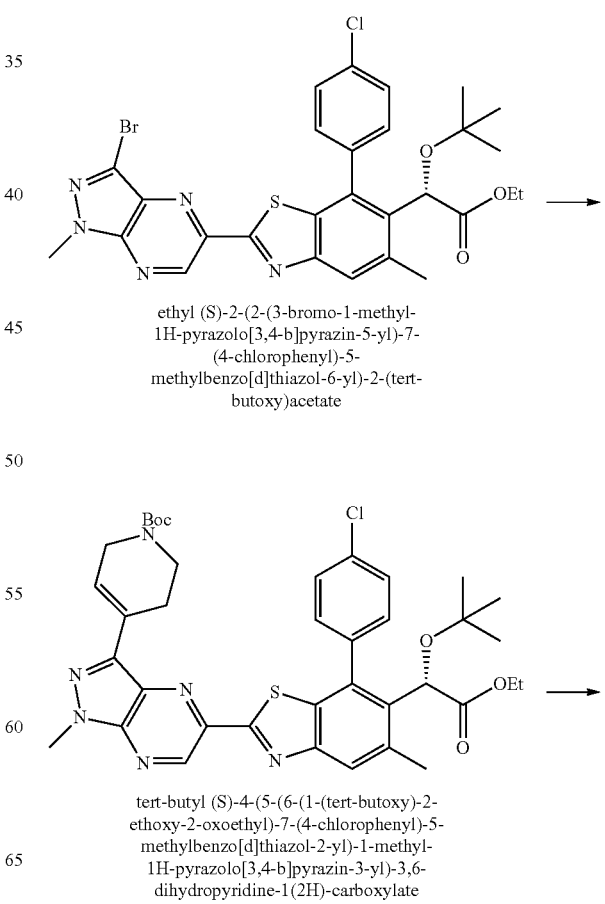

ethyl (S)-2-(2-(3-bromo-1-methyl-1H-pyrazolo[3,4-b]pyrazin-5-yl)-7-(4-chlorophenyl)-5-methylbenzo[d]thiazol-6-yl)-2-(tert-butoxy)acetate tert-butyl (S)-4-(5-(6-(1-(tert-butoxy)-2-ethoxy-2-oxoethyl)-7-(4-chlorophenyl)-5-methylbenzo[d]thiazol-2-yl)-1-methyl-1H-pyrazolo[3,4-b]pyrazin-3-yl)-3,6-dihydropyridine-1(2H)-carboxylate

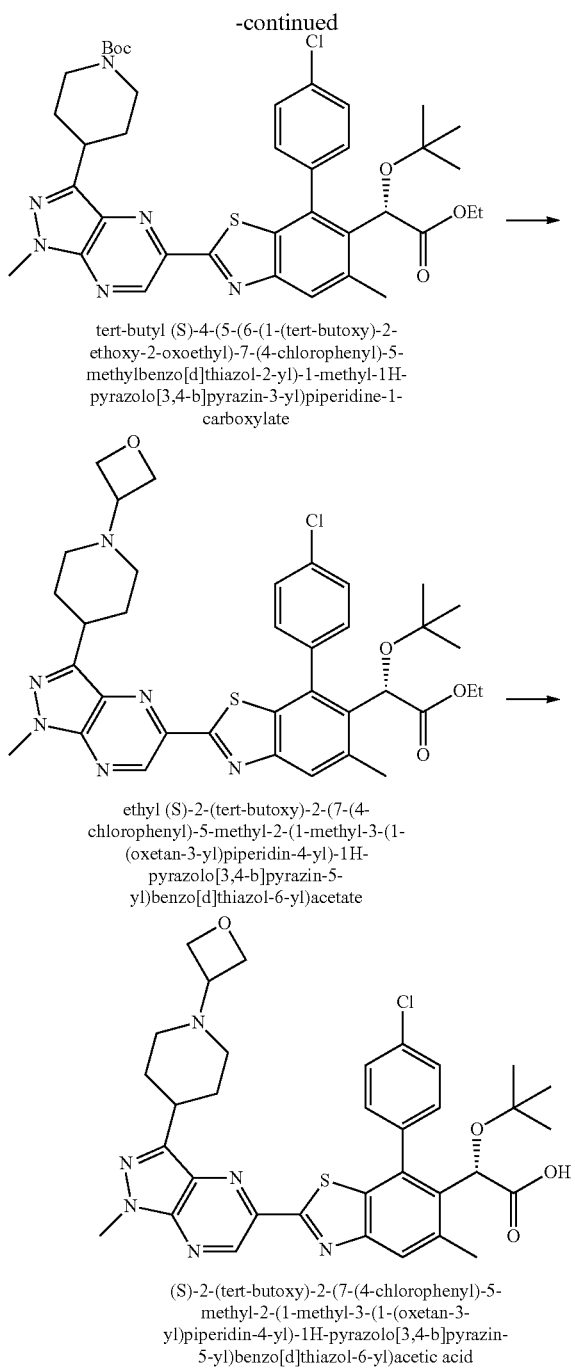

tert-butyl (S)-4-(5-(6-(1-(tert-butoxy)-2-ethoxy-2-oxoethyl)-7-(4-chlorophenyl)-5-methylbenzo[d]thiazol-2-yl)-1-methyl-1H-pyrazolo[3,4-b]pyrazin-3-yl)piperidine-1-carboxylate ethyl (S)-2-(tert-butoxy)-2-(7-(4-chlorophenyl)-5-methyl-2-(1-methyl-3-(1-(oxetan-3-yl)piperidin-4-yl)-1H-pyrazolo[3,4-b]pyrazin-5-yl)benzo[d]thiazol-6-yl)acetate (S)-2-(tert-butoxy)-2-(7-(4-chlorophenyl)-5-methyl-2-(1-methyl-3-(1-(oxetan-3-yl)piperidin-4-yl)-1H-pyrazolo[3,4-b]pyrazin-5-yl)benzo[d]thiazol-6-yl)acetic acid Preparation of 5-chloro-1-methyl-1H-pyrazolo[3,4-b]pyrazin-3-amine: To a solution of 3,6-dichloropyrazine-2-carbonitrile (1.088 g, 6.25 mmol) in toluene (12 mL) at 0° C. was added dropwise methyl hydrazine (362 μL, 6.88 mmol). Reaction mixture was stirred for 3 hours at 0° C. LCMS shows no starting material. Reaction mixture was concentrated and purified by CombiFlash (120 g Gold, 10-45% EtOAc/Hex) to give impure product. Crystallized from hot acetone/hexane to give two crops of 5-chloro-1-methyl-1H-pyrazolo[3,4-b]pyrazin-3-amine. LCMS-ESI+: calc'd for $C_6H_7ClN_5$: 184.0 (M+H)+; found: 184.2 (M+H)+.

Preparation of ethyl (S)-2-(2-(3-amino-1-methyl-1H-pyrazolo[3,4-b]pyrazin-5-yl)-7-(4-chlorophenyl)-5-methyl-benzo[d]thiazol-6-yl)-2-(tert-butoxy)acetate: A 50 mL round bottom flask was charged with 5-chloro-1-methyl-1H-pyrazolo[3,4-b]pyrazin-3-amine (100 mg, 0.545 mmol), bis(pinacolato)diboron (160 mg, 0.708 mmol), PdCl$_2$(Amphos)$_2$ (39 mg, 0.054 mmol) and potassium propionate (274 mg, 2.45 mmol) and flushed with nitrogen. De-gassed dioxane (5.0 mL) was added under a nitrogen atmosphere and reaction mixture was sparged for 5 minutes, then heated to 85° C. for 3 h. LCMS showed desired product mass for 5-(5,5-dimethyl-1,3,2-dioxaborinan-2-yl)-1-methyl-1H-pyrazolo[3,4-b]pyrazin-3-amine. Reaction mixture was cooled to ~50° C.

To the above reaction mixture, 2M potassium carbonate (1.7 mL, 3.36 mmol) and ethyl (S)-2-(2-bromo-7-(4-chlorophenyl)-5-methylbenzo[d]thiazol-6-yl)-2-(tert-butoxy)acetate (222 mg, 0.447 mmol) were added and the reaction heated to 70° C. After 2 h, LCMS showed desired product mass. Reaction was cooled to room temperature and partitioned between EtOAc/brine. Organic layer was dried (MgSO$_4$), filtered, concentrated and purified by CombiFlash (12 g Gold, 0-50% EtOAc/hex) to a yellow film. LCMS-ESI+: calc'd for $C_{28}H_{30}ClN_6O_3S$: 565.2 (M+H)+; found: 565.2 (M+H)+.

Preparation of ethyl (S)-2-(2-(3-bromo-1-methyl-1H-pyrazolo[3,4-b]pyrazin-5-yl)-7-(4-chlorophenyl)-5-methyl-benzo[d]thiazol-6-yl)-2-(tert-butoxy)acetate: To a solution ethyl (S)-2-(2-(3-amino-1-methyl-1H-pyrazolo[3,4-b]pyrazin-5-yl)-7-(4-chlorophenyl)-5-methylbenzo[d]thiazol-6-yl)-2-(tert-butoxy)acetate (136 mg, 0.240 mmol) in acetonitrile (5 mL) was added cupric bromide (64 mg, 0.29 mmol), followed by tert-butyl nitrite (43 μL, 0.36 mmol) at 0° C. Reaction mixture was warmed to room temperature over 3 hours. LCMS shows almost complete conversion. Reaction mixture was diluted with ethyl acetate, washed with brine/sodium sulfite, dried (MgSO$_4$), filtered and concentrated. Residue was purified by CombiFlash (12 Gold, 0-30% EtOAc/Hex) to give a yellow solid. LCMS-ESI+: calc'd for $C_{28}H_{28}BrClN_5O_3S$: 628.1 (M+H)+; found: 628.2 (M+H)+.

Preparation of tert-butyl (S)-4-(5-(6-(1-(tert-butoxy)-2-ethoxy-2-oxoethyl)-7-(4-chlorophenyl)-5-methylbenzo[d]thiazol-2-yl)-1-methyl-1H-pyrazolo[3,4-b]pyrazin-3-yl)-3,6-dihydropyridine-1(2H)-carboxylate: A mixture of ethyl (S)-2-(2-(3-bromo-1-methyl-1H-pyrazolo[3,4-b]pyrazin-5-yl)-7-(4-chlorophenyl)-5-methylbenzo[d]thiazol-6-yl)-2-(tert-butoxy)acetate (110 mg, 0.176 mmol), tert-butyl 4-(4,4,5,5-tetramethyl-1,3,2-dioxaborolan-2-yl)-5,6-dihydropyridine-1(2H)-carboxylate (81 mg, 0.264 mmol) and palladium (0) tetrakis(triphenylphosphine) (30 mg, 0.026 mmol) in 2M potassium carbonate (0.26 mL, 0.53 mmol) and dioxane (2.0 mL) was sparged with nitrogen for 5 minutes, then heated at 80° C. After 4 hours, additional tert-butyl 4-(4,4,5,5-tetramethyl-1,3,2-dioxaborolan-2-yl)-5,6-dihydropyridine-1(2H)-carboxylate (81 mg, 0.264 mmol) and 2M potassium carbonate (0.26 mL, 0.53 mmol) were added and reaction mixture was heated to 100° C. After 1 hour, reaction was complete. Reaction mixture was cooled to room temperature, diluted with ethyl acetate and washed with brine. Organic layer was dried (MgSO$_4$), filtered, concentrated and purified by CombiFlash (12 g, Gold, 0-30% EtOAc/Hex) to give a yellow foam. LCMS-ESI+: calc'd for $C_{38}H_{44}ClN_6O_5S$: 731.3 (M+H)+; found: 731.0 (M+H)+.

Preparation of tert-butyl (S)-4-(5-(6-(1-(tert-butoxy)-2-ethoxy-2-oxoethyl)-7-(4-chlorophenyl)-5-methylbenzo[d]thiazol-2-yl)-1-methyl-1H-pyrazolo[3,4-b]pyrazin-3-yl)piperidine-1-carboxylate: A mixture of tert-butyl (S)-4-(5-(6-(1-(tert-butoxy)-2-ethoxy-2-oxoethyl)-7-(4-chlorophenyl)-

5-methylbenzo[d]thiazol-2-yl)-1-methyl-1H-pyrazolo[3,4-b]pyrazin-3-yl)-3,6-dihydropyridine-1 (2H)-carboxylate (90% purity, 133 mg, 0.164 mmol) and rhodium on alumina (130 mg, 0.063 mmol) in ethanol (5.0 mL) was stirred under hydrogen atmosphere for 8 hours. Reaction mixture was filtered through a pad of Celite, concentrated and purified by CombiFlash (12 g, Gold, 0-30% EtOAc/Hex) to give a yellow film. LCMS-ESI+: calc'd for $C_{38}H_{46}ClN_6O_5S$: 733.3 $(M+H)^+$; found: 733.1 $(M+H)^+$.

Preparation of ethyl (S)-2-(tert-butoxy)-2-(7-(4-chlorophenyl)-5-methyl-2-(1-methyl-3-(1-(oxetan-3-yl)piperidin-4-yl)-1H-pyrazolo[3,4-b]pyrazin-5-yl)benzo[d]thiazol-6-yl)acetate: A solution of tert-butyl (S)-4-(5-(6-(1-(tert-butoxy)-2-ethoxy-2-oxoethyl)-7-(4-chlorophenyl)-5-methylbenzo[d]thiazol-2-yl)-1-methyl-1H-pyrazolo[3,4-b]pyrazin-3-yl)piperidine-1-carboxylate (80 mg, 0.11 mmol) in 1.25 HCl in isopropanol (4.4 mL) was stirred at room temperature for 6 hours. HPLC showed ~50% completion. Reaction mixture was quenched with saturated sodium bicarbonate solution and extracted with ethyl acetate (2×). Combined organic layer was dried ($MgSO_4$), filtered and concentrated to give ethyl (S)-2-(tert-butoxy)-2-(7-(4-chlorophenyl)-5-methyl-2-(1-methyl-3-(1-(oxetan-3-yl)piperidin-4-yl)-1H-pyrazolo[3,4-b]pyrazin-5-yl)benzo[d]thiazol-6-yl)acetate plus tert-butyl (S)-4-(5-(6-(1-(tert-butoxy)-2-ethoxy-2-oxoethyl)-7-(4-chlorophenyl)-5-methylbenzo[d]thiazol-2-yl)-1-methyl-1H-pyrazolo[3,4-b]pyrazin-3-yl)piperidine-1-carboxylate. Mixture was used in next step without further purification.

The above mixture was dissolved in ethanol (1.5 mL), and 3-oxetanone (36 µL, 0.57 mmol), acetic acid (16 µL, 0.28 mmol) and sodium cyanoborohydride (36 mg, 0.57 mmol) were added. Reaction mixture was stirred for 3 hours. LCMS showed nearly complete conversion. Reaction was quenched with saturated sodium bicarbonate solution and brine. The mixture was extracted with ethyl acetate (2×) and combined organic layer was dried ($MgSO_4$), filtered and concentrated. The residue was purified by CombiFlash (4 g, Gold, 0-20% MeOH/EtOAc) to give pure desired product. LCMS-ESI+: calc'd for $C_{36}H_{42}ClN_6O_4S$: 689.3 $(M+H)^+$; found: 689.3 $(M+H)^+$.

Preparation of (S)-2-(tert-butoxy)-2-(7-(4-chlorophenyl)-5-methyl-2-(1-methyl-3-(1-(oxetan-3-yl)piperidin-4-yl)-1H-pyrazolo[3,4-b]pyrazin-5-yl)benzo[d]thiazol-6-yl)acetic acid: A solution of ethyl (S)-2-(tert-butoxy)-2-(7-(4-chlorophenyl)-5-methyl-2-(1-methyl-3-(1-(oxetan-3-yl)piperidin-4-yl)-1H-pyrazolo[3,4-b]pyrazin-5-yl)benzo[d]thiazol-6-yl)acetate (31.7 mg, 0.046 mmol) and 5M sodium hydroxide (92 µL, 0.46 mmol) in tetrahydrofuran (1.2 mL) and methanol (0.2 mL) was stirred at 50° C. for 4 hours. LCMS showed incomplete conversion. Added more 5M sodium hydroxide (92 µL, 0.46 mmol) and stirred for 45 minutes. Reaction mixture was cooled to room temperature, diluted with DMF (0.5 mL) and concentrated to ~0.7 mL. The resulting mixture was diluted with methanol, filtered through a syringe filter and purified by Gilson HPLC (Gemini, 5-100% ACN/$H_2O$+0.1% TFA). Product was lyophilized to give an off-white powder. $^1$H NMR (400 MHz, Methanol-$d_4$) δ 9.56 (s, 1H), 7.96 (s, 1H), 7.79-7.49 (m, 4H), 5.29 (s, 1H), 4.86 (d, J=6.0 Hz, 4H), 4.54-4.40 (m, 1H), 4.17 (s, 3H), 3.77-3.53 (m, 2H), 3.16 (s, 2H), 2.67 (s, 3H), 2.55 (s, 2H), 2.33 (d, J=14.3 Hz, 2H), 1.02 (s, 9H). LCMS-ESI+: calc'd for $C_{34}H_{38}ClN_6O_4S$: 661.2 $(M+H)^+$; found: 661.2 $(M+H)^+$.

Example 118. Preparation of (S)-2-(tert-butoxy)-2-(7-(4-chlorophenyl)-2-(3-(1-(1-(methoxycarbonyl)azetidin-3-yl)piperidin-4-yl)-1-methyl-1H-pyrazolo[3,4-b]pyrazin-5-yl)-5-methylbenzo[d]thiazol-6-yl) acetic Acid (119)

tert-butyl (S)-4-(5-(6-(1-(tert-butoxy)-2-ethoxy-2-oxoethyl)-7-(4-chlorophenyl)-5-methylbenzo[d]thiazol-2-yl)-1-methyl-1H-pyrazolo[3,4-b]pyrazin-3-yl)piperidine-1-carboxylate tert-butyl (S)-3-(4-(5-(6-(1-(tert-butoxy)-2-ethoxy-2-oxoethyl)-7-(4-chlorophenyl)-5-methylbenzo[d]thiazol-2-yl)-1-methyl-1H-pyrazolo[3,4-b]pyrazin-3-yl)piperidin-1-yl)azetidine-1-carboxylate ethyl (S)-2-(2-(3-(1-(azetidin-3-yl)piperidin-4-yl)-1-methyl-1H-pyrazolo[3,4-b]pyrazin-5-yl)-7-(4-chlorophenyl)-5-methylbenzo[d]thiazol-6-yl)-2-(tert-butoxy)acetate

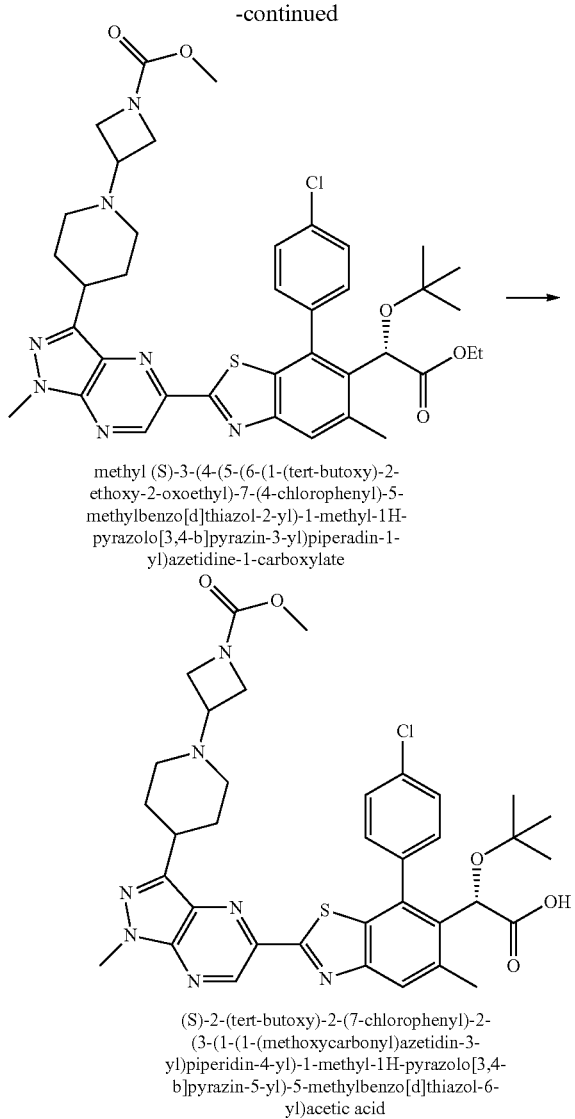

methyl (S)-3-(4-(5-(6-(1-(tert-butoxy)-2-ethoxy-2-oxoethyl)-7-(4-chlorophenyl)-5-methylbenzo[d]thiazol-2-yl)-1-methyl-1H-pyrazolo[3,4-b]pyrazin-3-yl)piperadin-1-yl)azetidine-1-carboxylate (S)-2-(tert-butoxy)-2-(7-chlorophenyl)-2-(3-(1-(1-(methoxycarbonyl)azetidin-3-yl)piperidin-4-yl)-1-methyl-1H-pyrazolo[3,4-b]pyrazin-5-yl)-5-methylbenzo[d]thiazol-6-yl)acetic acid Preparation of tert-butyl (S)-3-(4-(5-(6-(1-(tert-butoxy)-2-ethoxy-2-oxoethyl)-7-(4-chlorophenyl)-5-methylbenzo[d]thiazol-2-yl)-1-methyl-1H-pyrazolo[3,4-b]pyrazin-3-yl)piperidin-1-yl)azetidine-1-carboxylate: A solution of tert-butyl (S)-4-(5-(6-(1-(tert-butoxy)-2-ethoxy-2-oxoethyl)-7-(4-chlorophenyl)-5-methylbenzo[d]thiazol-2-yl)-1-methyl-1H-pyrazolo[3,4-b]pyrazin-3-yl)piperidine-1-carboxylate (47 mg, 0.064 mmol) in 1.25 HCl in isopropanol (2.5 mL) was stirred at room temperature for 2 days. Reaction mixture was quenched with saturated sodium bicarbonate solution and extracted with ethyl acetate (2×). Combined organic layer was dried (MgSO$_4$), filtered and concentrated to give a crude mixture that was used in next step without further purification.

The above mixture was dissolved in ethanol (1.5 mL), and N-Boc 3-oxoazetidine (102 mg, 0.59 mmol), acetic acid (17 µL, 0.297 mmol) and sodium cyanoborohydride (37 mg, 0.59 mmol) were added. Reaction mixture was stirred for 3 hours. LCMS showed nearly complete conversion. Reaction was quenched with saturated sodium bicarbonate solution and brine. The mixture was extracted with ethyl acetate (2×) and combined organic layer was dried (MgSO$_4$), filtered and concentrated. The residue was purified by CombiFlash (4 g, Gold, 0-20% MeOH/EtOAc) to give pure desired product. LCMS-ESI+: calc'd for $C_{41}H_{51}ClN_7O_5S$: 788.3 (M+H)$^+$; found: 788.1 (M+H)$^+$.

Preparation of ethyl (S)-2-(2-(3-(1-(azetidin-3-yl)piperidin-4-yl)-1-methyl-1H-pyrazolo[3,4-b]pyrazin-5-yl)-7-(4-chlorophenyl)-5-methylbenzo[d]thiazol-6-yl)-2-(tert-butoxy)acetate: To a flask containing tert-butyl (S)-3-(4-(5-(6-(1-(tert-butoxy)-2-ethoxy-2-oxoethyl)-7-(4-chlorophenyl)-5-methylbenzo[d]thiazol-2-yl)-1-methyl-1H-pyrazolo[3,4-b]pyrazin-3-yl)piperidin-1-yl)azetidine-1-carboxylate (25 mg, 0.032 mmol) was added 1.25M hydrogen chloride in isopropanol (1.2 mL, 1.5 mmol). Reaction mixture was stirred overnight to give a yellow mixture. LCMS shows~50% completion. Dichloromethane (1.2 mL) was added and reaction mixture was continued for 8 hours. Additional 1.25M hydrogen chloride in isopropanol (1.2 mL, 1.5 mmol) was added and reaction was stirred overnight. HPLC showed ~80% completion. Reaction was quenched with solid sodium bicarbonate and stirred for 5 minutes. Water was added and reaction mixture was partioned between dichloromethane and brine. Aqueous layer was back extracted with dichloromethane (2×) and combined organic layer was dried (MgSO$_4$), filtered, dried under vacuum and used in next step without further purification. LCMS-ESI+: calc'd for $C_{36}H_{43}ClN_7O_3S$: 688.3 (M+H)$^+$; found: 688.3 (M+H)$^+$.

Preparation of methyl (S)-3-(4-(5-(6-(1-(tert-butoxy)-2-ethoxy-2-oxoethyl)-7-(4-chlorophenyl)-5-methylbenzo[d]thiazol-2-yl)-1-methyl-1H-pyrazolo[3,4-b]pyrazin-3-yl)piperidin-1-yl)azetidine-1-carboxylate: To a solution of ethyl (S)-2-(2-(3-(1-(azetidin-3-yl)piperidin-4-yl)-1-methyl-1H-pyrazolo[3,4-b]pyrazin-5-yl)-7-(4-chlorophenyl)-5-methylbenzo[d]thiazol-6-yl)-2-(tert-butoxy)acetate (11 mg, 0.012 mmol) in dichloromethane (1.0 mL) was added diisopropylethylamine (21 µL, 0.12 mmol), followed by methyl chloroformate (5 µL, 0.062 mmol). Reaction mixture was stirred for 1 hour, then quenched with saturated sodium bicarbonate solution. Mixture was extracted with dichloromethane (2×), dried (MgSO$_4$), filtered and concentrated. Residue was purified by CombiFlash (4 g, Gold, 0-40% Hex/(20% MeOH/EtOAc) to give a yellow film, plus an impurity. The mixture was purified by Gilson HPLC (Gemini, 5-100% ACN/H$_2$O+0.1% TFA) and product-containing fractions were concentrated to remove organics, basified with saturated sodium bicarbonate solution and extracted with ethyl acetate (2×). Combined organic layer was dried (MgSO$_4$), filtered and dried to give a colorless film. LCMS-ESI+: calc'd for $C_{38}H_{45}ClN_7O_5S$: 746.3 (M+H)$^+$; found: 746.3 (M+H)$^+$.

Preparation of (S)-2-(tert-butoxy)-2-(7-(4-chlorophenyl)-2-(3-(1-(1-(methoxycarbonyl)azetidin-3-yl)piperidin-4-yl)-1-methyl-1H-pyrazolo[3,4-b]pyrazin-5-yl)-5-methylbenzo[d]thiazol-6-yl)acetic acid: methyl (S)-3-(4-(5-(6-(1-(tert-butoxy)-2-ethoxy-2-oxoethyl)-7-(4-chlorophenyl)-5-methylbenzo[d]thiazol-2-yl)-1-methyl-1H-pyrazolo[3,4-b]pyrazin-3-yl)piperidin-1-yl)azetidine-1-carboxylate (5.9 mg, 0.01 mmol) and 5M sodium hydroxide (10 µL, 0.05 mmol) in THF (1.0 mL) and MeOH (0.1 mL) were stirred at 60° C. for 2.5 hours. Reaction mixture was diluted with DMF (0.5 mL) and concentrated to ~0.5 mL, filtered through a syringe filter and purified by Gilson HPLC (Gemini, 5-100% ACN/H$_2$O+0.1% TFA). Product was lyophilized to give an off-white powder. $^1$H NMR (400 MHz, Methanol-d$_4$) δ 9.53 (s, 1H), 7.93 (s, 1H), 7.72-7.66 (m, 1H), 7.64-7.53 (m, 3H), 5.24 (s, 1H), 4.33 (s, 2H), 4.27-4.16 (m, 2H), 4.14 (s, 4H), 3.72 (s, 4H), 3.59 (br s, 1H), 3.15 (br s, 2H), 2.63 (s, 3H), 2.51 (br s, 2H), 2.29 (br s, 1H), 0.98 (s, 9H). LCMS-ESI+: calc'd for C$_{36}$H$_{41}$ClN$_7$O$_5$S: 718.3 (M+H)$^+$; found: 718.2 (M+H)$^+$.

Example 119. Preparation of (S)-2-(2-(3-(1-(1-acetylazetidin-3-yl)piperidin-4-yl)-1-methyl-1H-pyrazolo[3,4-b]pyrazin-5-yl)-7-(4-chlorophenyl)-5-methylbenzo[d]thiazol-6-yl)-2-(tert-butoxy)acetic Acid (120)

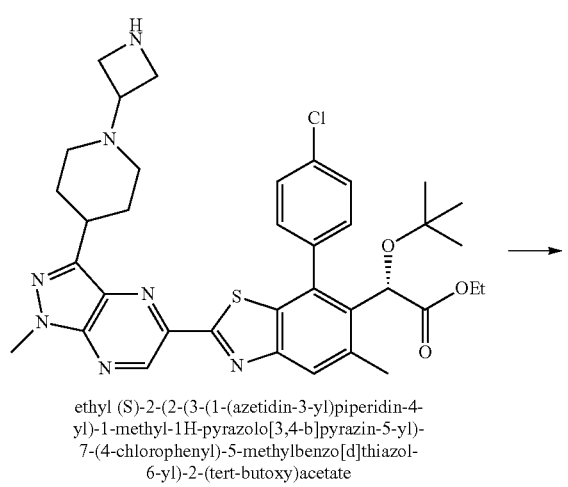

ethyl (S)-2-(2-(3-(1-(azetidin-3-yl)piperidin-4-yl)-1-methyl-1H-pyrazolo[3,4-b]pyrazin-5-yl)-7-(4-chlorophenyl)-5-methylbenzo[d]thiazol-6-yl)-2-(tert-butoxy)acetate

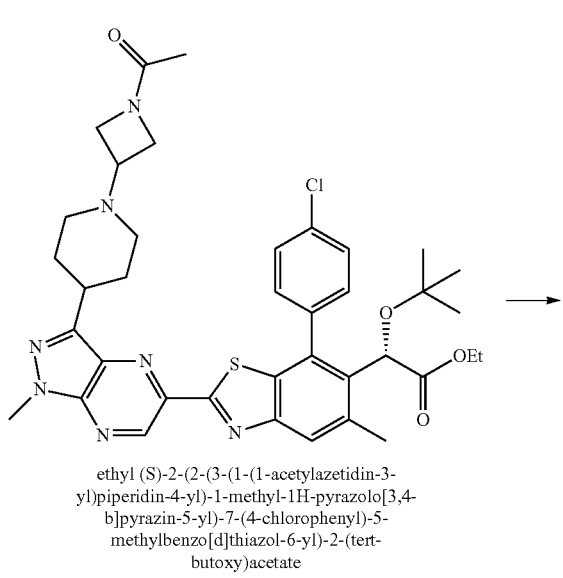

ethyl (S)-2-(2-(3-(1-(1-acetylazetidin-3-yl)piperidin-4-yl)-1-methyl-1H-pyrazolo[3,4-b]pyrazin-5-yl)-7-(4-chlorophenyl)-5-methylbenzo[d]thiazol-6-yl)-2-(tert-butoxy)acetate

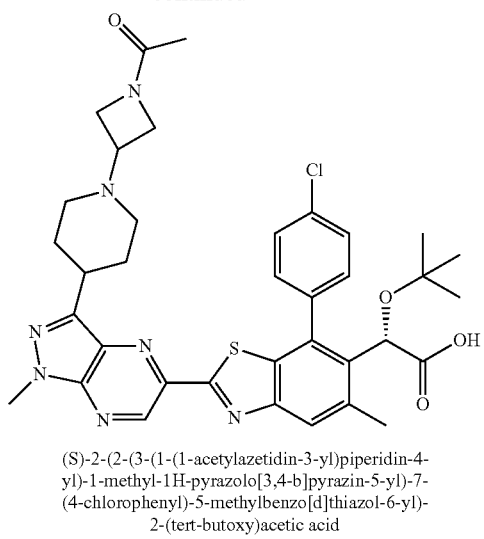

(S)-2-(2-(3-(1-(1-acetylazetidin-3-yl)piperidin-4-yl)-1-methyl-1H-pyrazolo[3,4-b]pyrazin-5-yl)-7-(4-chlorophenyl)-5-methylbenzo[d]thiazol-6-yl)-2-(tert-butoxy)acetic acid Preparation of ethyl (S)-2-(2-(3-(1-(1-acetylazetidin-3-yl)piperidin-4-yl)-1-methyl-1H-pyrazolo[3,4-b]pyrazin-5-yl)-7-(4-chlorophenyl)-5-methylbenzo[d]thiazol-6-yl)-2-(tert-butoxy)acetate: To a solution of ethyl (S)-2-(2-(3-(1-(azetidin-3-yl)piperidin-4-yl)-1-methyl-1H-pyrazolo[3,4-b]pyrazin-5-yl)-7-(4-chlorophenyl)-5-methylbenzo[d]thiazol-6-yl)-2-(tert-butoxy)acetate (11 mg, 0.012 mmol) in dichloromethane (1.0 mL) was added diisopropylethylamine (21 μL, 0.12 mmol), followed by acetyl chloride (4 μL, 0.062 mmol). Reaction mixture was stirred for 1 hour, then quenched with saturated sodium bicarbonate solution. Mixture was extracted with dichloromethane (2×), dried (MgSO$_4$), filtered and concentrated. Residue was purified by CombiFlash (4 g, Gold, 0-40% Hex/(20% MeOH/EtOAc) to give a yellow film. LCMS-ESI+: calc'd for C$_{38}$H$_{45}$ClN$_7$O$_4$S: 730.3 (M+H)$^+$; found: 730.4 (M+H)$^+$.

Preparation of (S)-2-(2-(3-(1-(1-acetylazetidin-3-yl)piperidin-4-yl)-1-methyl-1H-pyrazolo[3,4-b]pyrazin-5-yl)-7-(4-chlorophenyl)-5-methylbenzo[d]thiazol-6-yl)-2-(tert-butoxy)acetic acid: ethyl (S)-2-(2-(3-(1-(1-acetylazetidin-3-yl)piperidin-4-yl)-1-methyl-1H-pyrazolo[3,4-b]pyrazin-5-yl)-7-(4-chlorophenyl)-5-methylbenzo[d]thiazol-6-yl)-2-(tert-butoxy)acetate (7.5 mg, 0.01 mmol) and 5M sodium hydroxide (10 μL, 0.05 mmol) in THF (1.0 mL) and MeOH (0.1 mL) were stirred at 60° C. for 1.5 hours. Reaction mixture was diluted with DMF (0.5 mL) and concentrated to ~0.5 mL, filtered through a syringe filter and purified by Gilson HPLC (Gemini, 5-100% ACN/H$_2$O+0.1% TFA). Product was lyophilized to give an off-white powder. $^1$H NMR (400 MHz, Methanol-d$_4$) δ 9.53 (s, 1H), 7.93 (s, 1H), 7.75-7.65 (m, 1H), 7.65-7.46 (m, 3H), 5.25 (s, 1H), 4.65-4.50 (m, 1H), 4.49-4.39 (m, 1H), 4.38-4.23 (m, 1H), 4.23-4.04 (m, 5H), 3.86-3.50 (m, 3H), 3.20 (s, 2H), 2.63 (s, 3H), 2.52 (br s, 2H), 2.30 (br s, 1H), 1.94 (s, 3H), 0.98 (s, 9H). LCMS-ESI+: calc'd for C$_{36}$H$_{41}$ClN$_7$O$_4$S: 702.3 (M+H)$^+$; found: 702.2 (M+H)$^+$

Example 120. Preparation of (S)-2-(tert-butoxy)-2-(7-(4-chlorophenyl)-2-(3-(4,4-dimethyl-2-oxoimidazolidin-1-yl)-1-methyl-1H-indazol-5-yl)-5-methylbenzo[d]thiazol-6-yl)acetic Acid (121)

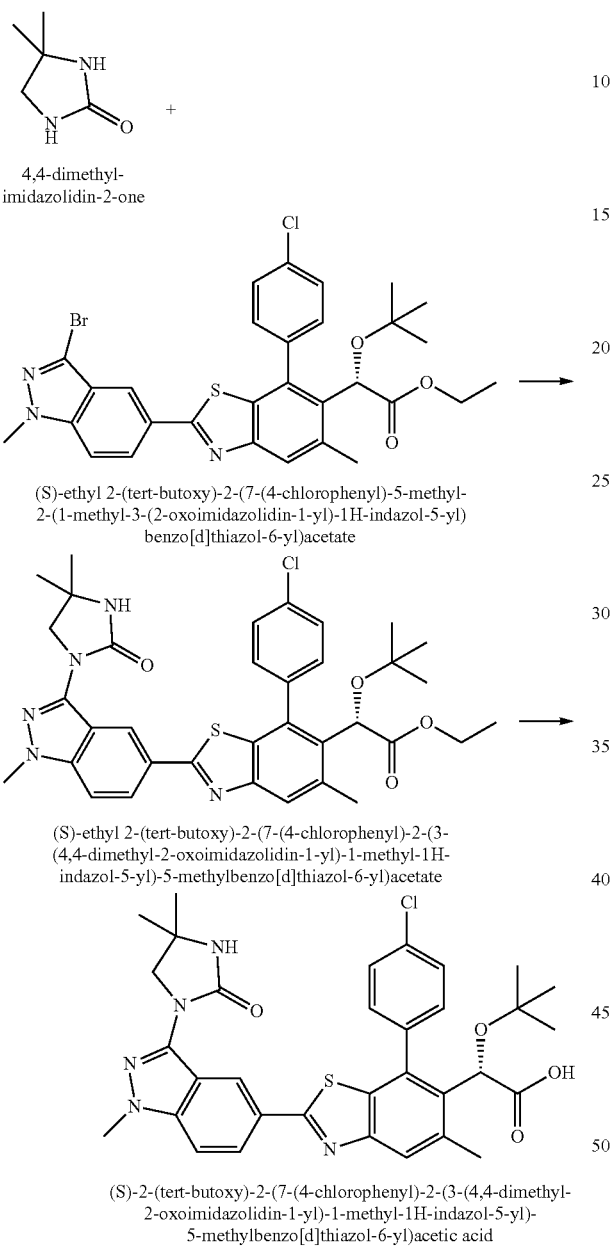

Preparation of (S)-ethyl 2-(tert-butoxy)-2-(7-(4-chlorophenyl)-2-(3-(4,4-dimethyl-2-oxoimidazolidin-1-yl)-1-methyl-1H-indazol-5-yl)-5-methylbenzo[d]thiazol-6-yl)acetate: Prepared in a manner similar to (S)-ethyl 2-(tert-butoxy)-2-(7-(4-chlorophenyl)-5-methyl-2-(1-methyl-3-(2oxoimidazolidin-1-yl)-1H-indazol-5-yl)benzo[d]thiazol-6-yl)acetate except using 4,4-dimethylimidazolidin-2-one instead of imidazolidin-2-one.

Preparation of (S)-2-(tert-butoxy)-2-(7-(4-chlorophenyl)-2-(3-(4,4-dimethyl-2-oxoimidazolidin-1-yl)-1-methyl-1H-indazol-5-yl)-5-methylbenzo[d]thiazol-6-yl)acetic acid: Prepared in a manner similar to (S)-2-(tert-butoxy)-2-(7-(4-chlorophenyl)-5-methyl-2-(1-methyl-3-(2-oxoimidazolidin-1-yl)-1H-indazol-5-yl)benzo[d]thiazol-6-yl)acetic acid except using (S)-ethyl 2-(tert-butoxy)-2-(7-(4-chlorophenyl)-2-(3-(4,4-dimethyl-2-oxoimidazolidin-1-yl)-1-methyl-1H-indazol-5-yl)-5-methylbenzo[d]thiazol-6-yl)acetate instead of (S)-ethyl 2-(tert-butoxy)-2-(7-(4-chlorophenyl)-5-methyl-2-(1-methyl-3-(2oxoimidazolidin-1-yl)-1H-indazol-5-yl)benzo[d]thiazol-6-yl)acetate. $^1$H NMR (400 MHz, Acetonitrile-d3) δ 9.08 (d, J=1.7 Hz, 1H), 8.11 (dd, J=9.0, 1.7 Hz, 1H), 7.85 (s, 1H), 7.74-7.51 (m, 4H), 7.47 (dd, J=8.9, 0.8 Hz, 1H), 5.28 (s, 1H), 3.94 (s, 3H), 3.80 (d, J=1.0 Hz, 2H), 2.79-2.45 (m, 3H), 1.52-1.30 (m, 6H), 0.99 (s, 9H).

Example 121. Preparation of (S)-2-(tert-butoxy)-2-(7-(4-chlorophenyl)-5-methyl-2-(1-methyl-3-(3,4,4-trimethyl-2-oxoimidazolidin-1-yl)-1H-indazol-5-yl)benzo[d]thiazol-6-yl)acetic Acid (122)

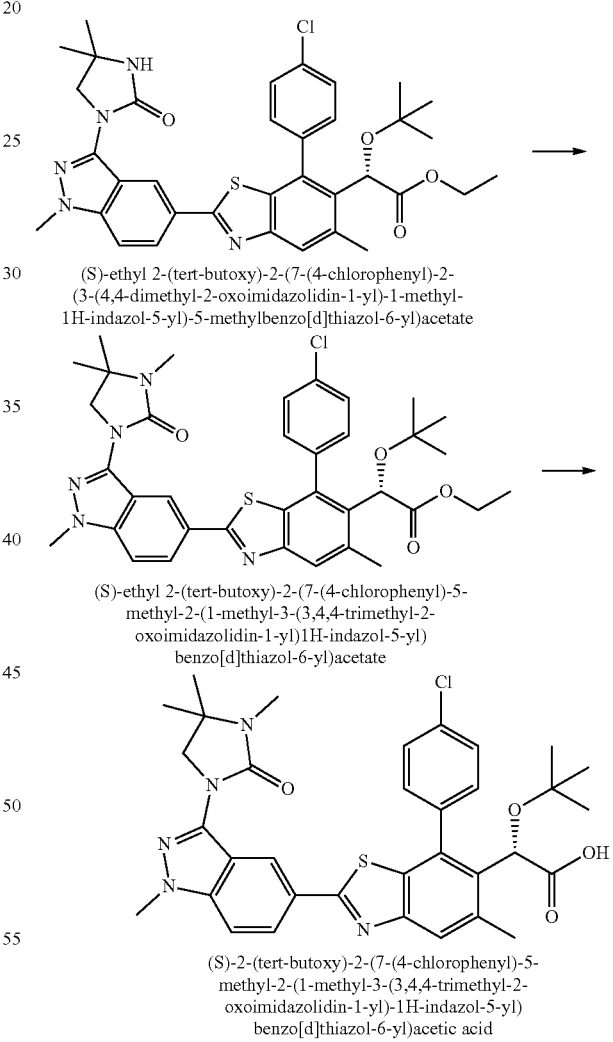

Preparation of (S)-ethyl 2-(tert-butoxy)-2-(7-(4-chlorophenyl)-5-methyl-2-(1-methyl-3-(3,4,4-trimethyl-2-oxoimidazolidin-1-yl)-1H-indazol-5-yl)benzo[d]thiazol-6-yl)acetate: Prepared in a manner similar to (S)-ethyl 2-(tert-butoxy)-2-(7-(4-chlorophenyl)-5-methyl-2-(1-methyl-3-(3-methyl-2-oxoimidazolidin-1-yl)-1H-indazol-5-yl)benzo[d]thiazol-6-yl)acetate except using (S)-ethyl 2-(tert-butoxy)-

2-(7-(4-chlorophenyl)-2-(3-(4,4-dimethyl-2-oxoimidazolidin-1-yl)-1-methyl-1H-indazol-5-yl)-5-methylbenzo[d]thiazol-6-yl)acetate instead of (S)-ethyl 2-(tert-butoxy)-2-(7-(4-chlorophenyl)-5-methyl-2-(1-methyl-3-(2-oxoimidazolidin-1-yl)-1H-indazol-5-yl)benzo[d]thiazol-6-yl)acetate.

Preparation of (S)-2-(tert-butoxy)-2-(7-(4-chlorophenyl)-5-methyl-2-(1-methyl-3-(3,4,4-trimethyl-2-oxoimidazolidin-1-yl)-1H-indazol-5-yl)benzo[d]thiazol-6-yl)acetic acid: Prepared in a manner similar to (S)-2-(tert-butoxy)-2-(7-(4-chlorophenyl)-2-(3-(3-(2-methoxyethyl)-2-oxoimidazolidin-1-yl)-1-methyl-1H-indazol-5-yl)-5-methylbenzo[d]thiazol-6-yl)acetic acid except using (S)-ethyl 2-(tert-butoxy)-2-(7-(4-chlorophenyl)-5-methyl-2-(1-methyl-3-(3,4,4-trimethyl-2-oxoimidazolidin-1-yl)-1H-indazol-5-yl)benzo[d]thiazol-6-yl)acetate instead of (S)-ethyl 2-(tert-butoxy)-2-(7-(4-chlorophenyl)-2-(3-(3-(2-methoxyethyl)-2-oxoimidazolidin-1-yl)-1-methyl-1H-indazol-5-yl)-5-methylbenzo[d]thiazol-6-yl)acetate. $^1$H NMR (400 MHz, Acetonitrile-d3) δ 9.14 (s, 1H), 8.12 (dd, J=9.0, 1.7 Hz, 1H), 7.85 (s, 1H), 7.74-7.55 (m, 3H), 7.51-7.41 (m, 1H), 5.28 (s, 1H), 3.94 (s, 3H), 3.75 (s, 3H), 2.83 (s, 3H), 2.58 (d, J=0.9 Hz, 3H), 1.38 (d, J=1.9 Hz, 6H), 1.00 (s, 9H).

Example 122. Preparation of (S)-2-(tert-butoxy)-2-(7-(4-chlorophenyl)-2-(3-(3-(2-methoxyethyl)-4,4-dimethyl-2-oxoimidazolidin-1-yl)-1-methyl-1H-indazol-5-yl)-5-methylbenzo[d]thiazol-6-yl)acetic Acid (123)

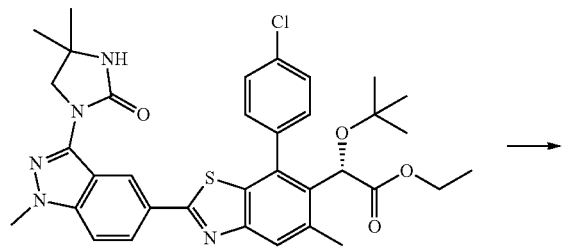

(S)-ethyl 2-(tert-butoxy)-2-(7-(4-chlorophenyl)-2-(3-(4,4-dimethyl-2-oxoimidazolidin-1-yl)-1-methyl-1H-indazol-5-yl)-5-methylbenzo[d]thiazol-6-yl)acetate

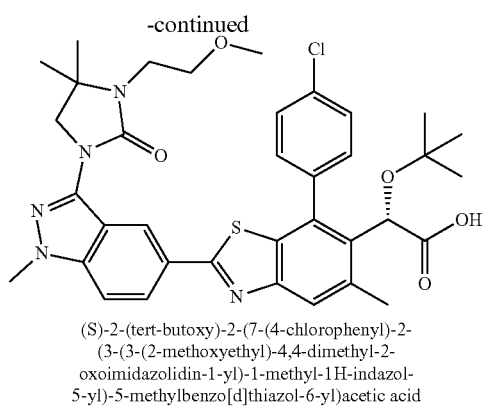

(S)-2-(tert-butoxy)-2-(7-(4-chlorophenyl)-2-(3-(3-(2-methoxyethyl)-4,4-dimethyl-2-oxoimidazolidin-1-yl)-1-methyl-1H-indazol-5-yl)-5-methylbenzo[d]thiazol-6-yl)acetic acid Preparation of (S)-2-(tert-butoxy)-2-(7-(4-chlorophenyl)-2-(3-(3-(2-methoxyethyl)-4,4-dimethyl-2-oxoimidazolidin-1-yl)-1-methyl-1H-indazol-5-yl)-5-methylbenzo[d]thiazol-6-yl)acetic acid: Prepared in a manner similar to (S)-2-(tert-butoxy)-2-(7-(4-chlorophenyl)-2-(3-(3-(2-methoxyethyl)-2-oxoimidazolidin-1-yl)-1-methyl-1H-indazol-5-yl)-5-methylbenzo[d]thiazol-6-yl)acetic acid except using (S)-ethyl 2-(tert-butoxy)-2-(7-(4-chlorophenyl)-2-(3-(4,4-dimethyl-2-oxoimidazolidin-1-yl)-1-methyl-1H-indazol-5-yl)-5-methylbenzo[d]thiazol-6-yl)acetate instead of (S)-ethyl 2-(tert-butoxy)-2-(7-(4-chlorophenyl)-2-(3-(3-(2-methoxyethyl)-2-oxoimidazolidin-1-yl)-1-methyl-1H-indazol-5-yl)-5-methylbenzo[d]thiazol-6-yl)acetate. $^1$H NMR (400 MHz, Acetonitrile-d3) δ 9.08 (dd, J=1.7, 0.8 Hz, 1H), 8.08 (dd, J=9.0, 1.7 Hz, 1H), 7.82 (d, J=1.0 Hz, 1H), 7.71-7.52 (m, 3H), 7.46-7.34 (m, 1H), 5.26 (s, 1H), 3.91 (s, 3H), 3.72 (d, J=1.2 Hz, 2H), 3.53 (d, J=6.2 Hz, 2H), 3.37 (d, J=17.6 Hz, 6H), 2.55 (d, J=0.8 Hz, 3H), 1.38 (d, J=1.9 Hz, 6H), 0.99 (s, 9H).

Example 123. Preparation of (2S)-2-(tert-butoxy)-2-(7-(4-chlorophenyl)-2-(3-(1-(1-methoxypropan-2-yl)azetidin-3-yl)-1-methyl-1H-indazol-5-yl)-5-methylbenzo[d]thiazol-6-yl)acetic Acid (124)

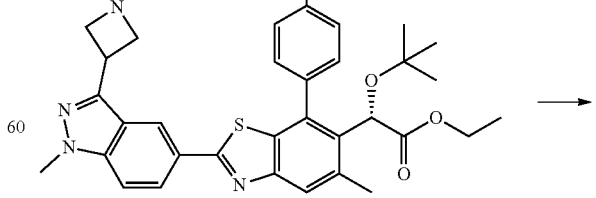

ethyl (S)-2-(2-(3-(azetidin-3-yl)-1-methyl-1H-indazol-5-yl)-7-(4-chlorophenyl)-5-methylbenzo[d]thiazol-6-yl)-2-(tert-butoxy)acetate

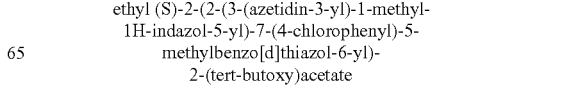

-continued

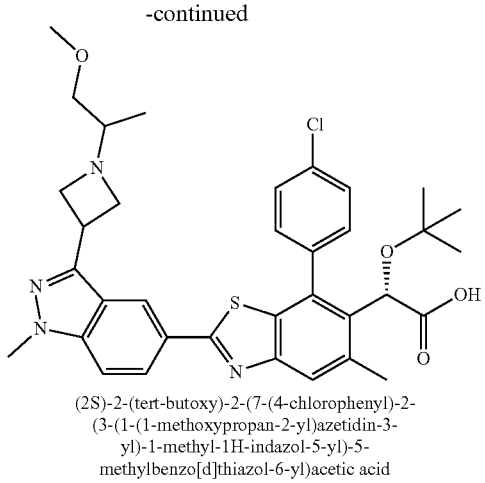

(2S)-2-(tert-butoxy)-2-(7-(4-chlorophenyl)-2-
(3-(1-(1-methoxypropan-2-yl)azetidin-3-
yl)-1-methyl-1H-indazol-5-yl)-5-
methylbenzo[d]thiazol-6-yl)acetic acid Preparation of (2S)-2-(tert-butoxy)-2-(7-(4-chlorophenyl)-2-(3-(1-(1-methoxypropan-2-yl)azetidin-3-yl)-1-methyl-1H-indazol-5-yl)-5-methylbenzo[d]thiazol-6-yl) acetic acid: To a flask containing/4 of the above crude ethyl (S)-2-(2-(3-(azetidin-3-yl)-1-methyl-1H-indazol-5-yl)-7-(4-chlorophenyl)-5-methylbenzo[d]thiazol-6-yl)-2-(tert-butoxy)acetate were added methanol (2 mL), methoxyacetone (0.1 mL, 1.077 mmol) and stirred at 0° C. bath as sodium cyanoborohydride (30 mg, 0.477 mmol) and acetic acid (1 drop). After 30 min, the reaction mixture was diluted with saturated aqueous NaHCO$_3$, and the product was extracted with ethyl acetate (×3). The extracts were combined dried (MgSO$_4$), concentrated, and dried in vacuum for 30 min. LCMS-ESI$^+$: calc'd for C$_{37}$H$_{44}$ClN$_4$O$_4$S: 675.28 (M+H)$^+$; found: 675.39 (M+H)$^+$.

The above residue was dissolved in THF (1 mL) and MeOH (1 mL) before 2 N NaOH (1 mL) was added. The resulting mixture was stirred at 70° C. preheated bath for 2 h and the reaction mixture was acidified with 2 N HCl (~1.05 mL) and concentrated to almost dryness. The residue was triturated with MeOH (~1.5 mL) and the suspension was filtered through syringe filter. The resulting filtrate was purified by Gilson HPLC (Phenomenex Gemini 250×21.2 10u C18 column, 30-60% ACN/H$_2$O+0.1% TFA) to give a diastereomeric mixture of (2S)-2-(tert-butoxy)-2-(7-(4-chlorophenyl)-2-(3-(1-(1-methoxypropan-2-yl)azetidin-3-yl)-1-methyl-1H-indazol-5-yl)-5-methylbenzo[d]thiazol-6-yl) acetic acid after lyophilization. $^1$H NMR (400 MHz, Acetonitrile-d$_3$) δ 9.10 (s, 1H), 8.28 (d, J=1.7 Hz, 1H), 8.19-8.10 (m, 1H), 7.84 (d, J=6.0 Hz, 1H), 7.70-7.64 (m, 1H), 7.64-7.52 (m, 4H), 5.28 (s, 1H), 4.69-4.33 (m, 5H), 4.08 (s, 1H), 4.05 (s, 2H), 3.77-3.42 (m, 3H), 3.37 (four s, 3H), 2.57 (two s, 3H), 1.28 (four d, J=6.7 Hz, 3H), 0.99 (s, 9H). LCMS-ESI$^+$: calc'd for C$_{35}$H$_{40}$ClN$_4$O$_4$S: 647.25 (M+H)$^+$; found: 647.35 (M+H)$^+$.

Example 124. Exemplary Compound Characterization

| Structure | Cmpd# | Chemical Name | ES/MS m/z | 1H HMR | Method |
|---|---|---|---|---|---|
| 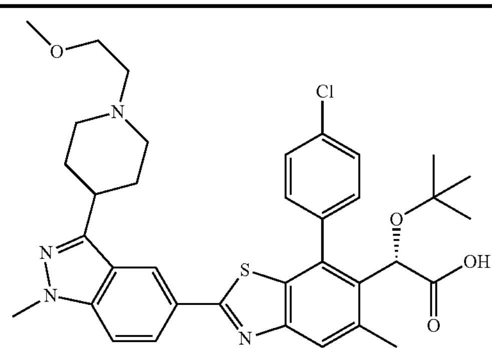 | 125 | (S)-2-(tert-butoxy)-2-(7-(4-chloro-phenyl)-2-(3-(1-(2-methoxyethyl)piperidin-4-yl)-1-methyl-1H-indazol-5-yl)-5-methylbenzo[d]thiazol-6-yl) acetic acid | 661.3 (M + H)+ | 1H NMR (400 MHz, Chloroform-d) d 8.28 (s, 1H), 7.96 (s, 1H), 7.83 (s, 2H), 7.59-7.42 (m, 3H), 7.37 (d, J = 8.8 Hz, 1H), 5.27 (s, 1H), 4.00 (s, 3H), 3.79 (t, J = 4.7 Hz, 2H), 3.48 (s, 0H), 3.36 (s, 3H), 3.23 (s, 2H), 2.60 (s, 3H), 2.48-2.08 (m, 4H), 1.37-1.09 (m, 6H), 0.99 (s, 9H), 0.85 (t, J = 9.5 Hz, 4H). | A |
| 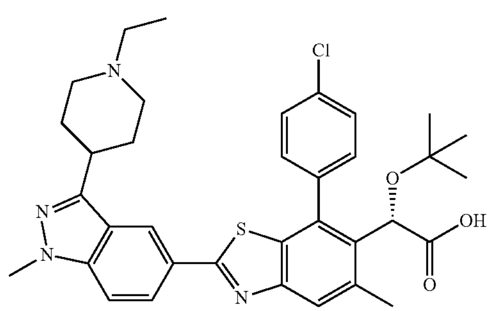 [SMILES: CCN1CCC(c2nn(C)c3ccc(-c4nc5cc(C)c([C@H](OC(C)(C)C)C(=O)O)c(-c6ccc(Cl)cc6)c5s4)cc23)CC1] | 126 | (S)-2-(tert-butoxy)-2-(7-(4-chloro-phenyl)-2-(3-(1-ethylpiperidin-4-yl)-1-methyl-1H-indazol-5-yl)-5-methylbenzo[d]thiazol-6-yl) acetic acid | 631.4 (M + H)+ | 1H NMR (400 MHz, Chloroform-d) d 8.34-8.17 (m, 1H), 8.05-7.90 (m, 1H), 7.80 (s, 1H), 7.64 (d, J = 7.9 Hz, 1H), 7.45 (d, J = 8.2 Hz, 3H), 7.37-7.28 (m, 1H), 5.25 (d, J = 2.7 Hz, 1H), 3.96 (d, J = 8.1 Hz, 3H), 3.83-2.65 (m, 6H), 2.50 (s, 3H), 2.23 (d, J = 16.6 Hz, 4H), 1.34 (dt, J = 15.3, 7.2 Hz, 3H), 0.93 (s, 9H) | A |

-continued

| Structure | Cmpd# | Chemical Name | ES/MS m/z | 1H HMR | Method |
|---|---|---|---|---|---|
| 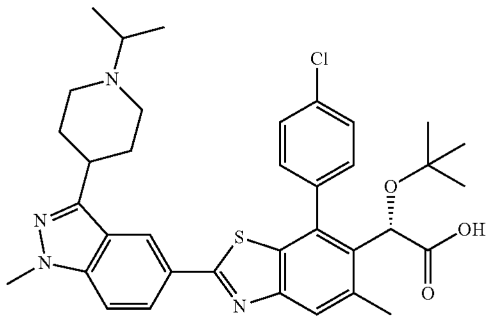 [SMILES: Cc1cc2nc(-c3ccc4c(c3)c(C3CCN(C(C)C)CC3)nn4C)sc2c(-c2ccc(Cl)cc2)c1[C@H](OC(C)(C)C)C(=O)O] | 127 | (S)-2-(tert-butoxy)-2-(7-(4-chlorophenyl)-2-(3-(1-isopropylpiperidin-4-yl)-1-methyl-1H-indazol-5-yl)-5-methylbenzo[d]thiazol-6-yl) acetic acid | 645.4 (M + H)+ | 1H NMR (400 MHz, Chloroform-d) d 11.64 (d, J = 220.5 Hz, 1H), 8.42-8.20 (m, 1H), 8.06 (ddd, J = 30.3, 8.8, 1.5 Hz, 1H), 7.87 (d, J = 1.0 Hz, 1H), 7.72 (d, J = 8.2 Hz, 1H), 7.61-7.46 (m, 3H), 7.46-7.33 (m, 1H), 5.32 (d, J = 3.9 Hz, 1H), 4.04 (d, J = 9.0 Hz, 3H), 3.81-2.85 (m, 6H), 2.79-2.60 (m, 2H), 2.58 (s, 3H), 2.39-2.17 (m, 2H), 2.01 (dd, J = 99.3, 1.3 Hz, 1H), 1.40 (dd, J = 16.3, 6.6 Hz, 6H), 1.26 (s, 2H), 1.01 (s, 9H). | A |
| 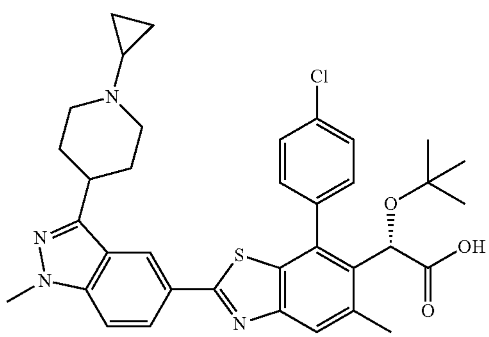 [SMILES: Cc1cc2nc(-c3ccc4c(c3)c(C3CCN(C5CC5)CC3)nn4C)sc2c(-c2ccc(Cl)cc2)c1[C@H](OC(C)(C)C)C(=O)O] | 128 | (S)-2-(tert-butoxy)-2-(7-(4-chlorophenyl)-2-(3-(1-cyclopropylpiperidin-4-yl)-1-methyl-1H-indazol-5-yl)-5-methylbenzo[d]thiazol-6-yl) acetic acid | 643.44 (M + H)+ | $^1$H NMR (400 MHz, Methanol-d$_4$) δ 8.45 (s, 1 H), 8.11 (dd, J = 8.8, 1.6 Hz, 1 H), 7.81 (s, 1 H), 7.74-7.65 (m, 1 H), 7.67-7.52 (m, 4 H), 5.26 (s, 1 H), 4.03 (s, 3 H), 3.81 (d, J = 12.4 Hz, 2 H), 3.42 (t, J = 12.8 Hz, 2 H), 2.90 (dt, J = 12.2, 6.2 Hz, 1 H), 2.61 (s, 3 H), 2.36 (d, J = 14.5 Hz, 2 H), 2.17 (q, J = 12.5 Hz, 2 H), 1.09-0.98 (m, 4 H), 0.98 (s, 9 H) | A |
| 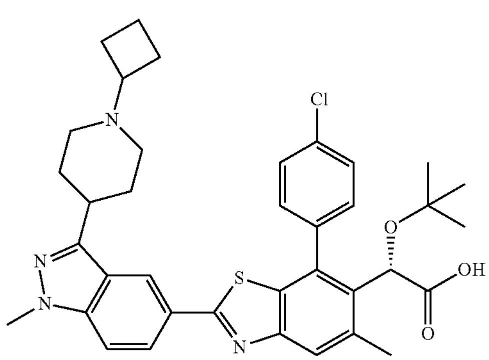 | 129 | (S)-2-(tert-butoxy)-2-(7-(4-chlorophenyl)-2-(3-(1-cyclobutylpiperidin-4-yl)-1-methyl-1H-indazol-5-yl)-5-methylbenzo[d]thiazol-6-yl) acetic acid | 657.49 (M + H)+ | $^1$H NMR (400 MHz, Methanol-d$_4$) δ 8.46 (dd, J = 1.7, 0.8 Hz, 1 H), 8.13 (dd, J = 8.9, 1.6 Hz, 1 H), 7.82 (s, 1 H), 7.72-7.67 (m, 1 H), 7.66-7.58 (m, 4 H), 5.26 (s, 1 H), 4.05 (s, 3 H), 3.74 (p, J = 8.1 Hz, 1 H), 3.64 (d, J = 12.4 Hz, 2 H), 3.56-3.42 (m, 1 H), 3.02 (t, J = 12.8 Hz, 2 H), 2.62 (s, 3 H), 2.47-2.31 (m, 4 H), 2.31-2.07 (m, 4 H), | A |

-continued

| Structure | Cmpd# | Chemical Name | ES/MS m/z | 1H HMR | Method |
|---|---|---|---|---|---|
| | | | | 2.00-1.80 (m, 2 H), 0.98 (d, J = 1.9 Hz, 9 H) | |
| 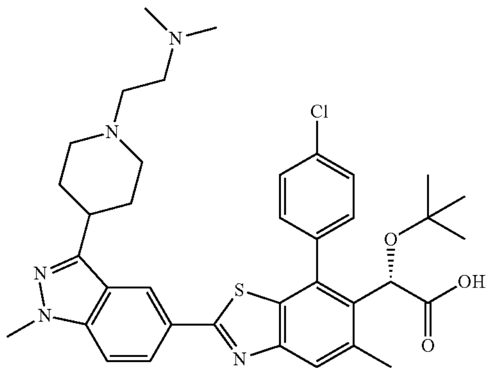 [SMILES: Cc1cc2nc(-c3ccc4c(c3)c(C3CCN(CCN(C)C)CC3)nn4C)sc2c(-c2ccc(Cl)cc2)c1[C@H](OC(C)(C)C)C(=O)O] | 130 | (S)-2-(tert-butoxy)-2-(7-(4-chlorophenyl)-2-(3-(1-(2-(dimethylamino)ethyl)piperidin-4-yl)-1-methyl-1H-indazol-5-yl)-5-methylbenzo[d]thiazol-6-yl)acetic acid | 673.54 (M + H)+ | ¹H NMR (400 MHz, Methanol-d₄) δ 8.47-8.45 (m, 1 H), 8.11 (dd, J = 8.9, 1.6 Hz, 1 H), 7.82 (d, J = 0.9 Hz, 1 H), 7.72-7.66 (m, 1 H), 7.66-7.56 (m, 4 H), 5.26 (s, 1 H), 4.06 (s, 3 H), 3.75 (d, J = 12.0 Hz, 2 H), 3.67 (s, 4 H), 3.63-3.49 (m, 1 H), 3.42-3.31 (m, 2 H), 3.01 (s, 6 H), 2.62 (s, 3 H), 2.46-2.36 (m, 2 H), 2.38-2.22 (m, 2 H), 0.98 (s, 9 H) | A |
| 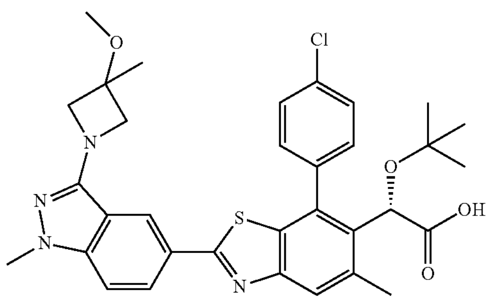 [SMILES: COC1(C)CN(c2nn(C)c3ccc(-c4nc5cc(C)c([C@H](OC(C)(C)C)C(=O)O)c(-c6ccc(Cl)cc6)c5s4)cc23)C1] | 131 | (S)-2-(tert-butoxy)-2-(7-(4-chlorophenyl)-2-(3-(3-methoxy-3-methylazetidin-1-yl)-1-methyl-1H-indazol-5-yl)-5-methylbenzo[d]thiazol-6-yl)acetic acid | 619.3 (M + H)+ | 1H NMR (400 MHz, Chloroform-d) δ 8.28 (d, J = 1.8 Hz, 1H), 8.00 (dd, J = 9.0, 1.8 Hz, 1H), 7.90 (s, 1H), 7.71 (d, J = 7.7 Hz, 1H), 7.61-7.40 (m, 3H), 7.29 (s, 1H), 5.31 (s, 1H), 4.46-4.08 (m, 4H), 3.91 (s, 3H), 3.32 (s, 3H), 2.57 (s, 3H), 1.63 (s, 3H), 1.25 (s, 9H), 1.00 (s, 9H), 0.86 (dt, J = 13.7, 4.1 Hz, 3H) | B |
| 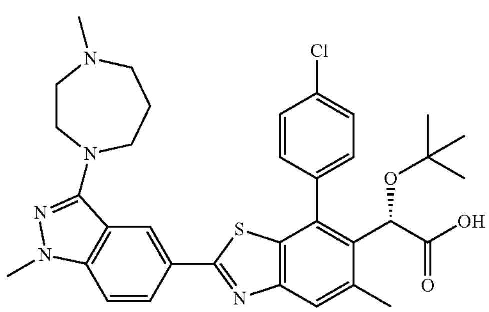 [SMILES: Cc1cc2nc(-c3ccc4c(c3)c(N3CCCN(C)CC3)nn4C)sc2c(-c2ccc(Cl)cc2)c1[C@H](OC(C)(C)C)C(=O)O] | 132 | (S)-2-(tert-butoxy)-2-(7-(4-chlorophenyl)-5-methyl-2-(1-methyl-3-(4-methyl-1,4-diazepan-1-yl)-1H-indazol-5-yl)benzo[d]thiazol-6-yl)acetic acid | 632.2 (M + H)+ | 1H NMR (400 MHz, Chloroform-d) d 8.38 (d, J = 5.3 Hz, 1H), 7.88 (d, J = 6.2 Hz, 2H), 7.72 (d, J = 8.2 Hz, 1H), 7.60-7.45 (m, 3H), 7.24 (s, 1H), 5.31 (s, 1H), 4.20 (d, J = 16.8 Hz, 1H), 3.87 (s, 5H), 3.77 (m, 1H), 3.63 (m, 1H), 3.33 (m, 2H), 3.14 (m, 2H), 2.92 (s, 3H), 2.58 (s, 3H), 2.35 (m, 1H), 1.25 (m, 4H), 1.01 (s, 10H), 0.90 (d, J = 19.8 Hz, 1H). | B |

-continued

| Structure | Cmpd# | Chemical Name | ES/MS m/z | 1H HMR | Method |
|---|---|---|---|---|---|
| 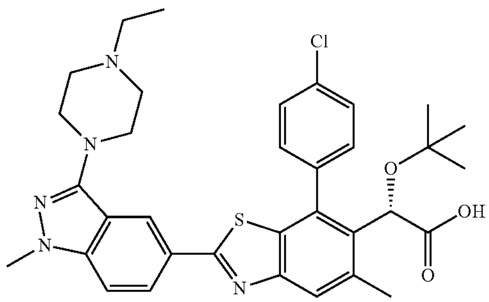 | 133 | (S)-2-(tert-butoxy)-2-(7-(4-chlorophenyl)-2-(3-(4-ethylpiperazin-1-yl)-1-methyl-1H-indazol-5-yl)-5-methylbenzo[d]thiazol-6-yl)acetic acid | 632.2 (M + H+) | 1H NMR (400 MHz, CD3OD) δ 8.42-8.37 (m, 1H), 8.03 (dd, J = 8.9, 1.6 Hz, 1H), 7.79 (d, J = 0.9 Hz, 1H), 7.72-7.64 (m, 1H), 7.63-7.48 (m, 4H), 5.24 (s, 1H), 4.11 (d, J = 11.7 Hz, 2H), 3.92 (s, 3H), 3.68 (s, 1H), 3.37-3.25 (m, 10H), 2.61 (d, J = 0.7 Hz, 3H), 1.41 (t, J = 7.3 Hz, 3H), 0.97 (s, 9H) | B |
| 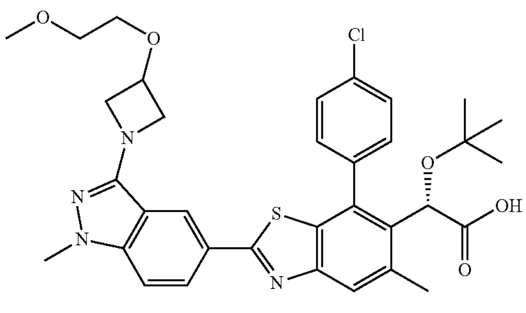 | 134 | (S)-2-(tert-butoxy)-2-(7-(4-chlorophenyl)-2-(3-(3-(2-methoxyethoxy)azetidin-1-yl)-1-methyl-1H-indazol-5-yl)-5-methylbenzo[d]thiazol-6-yl)acetic acid | 649.2 (M + H)+ | 1H NMR (400 MHz, Chloroform-d) δ 8.24 (s, 1H), 8.03 (d, J = 8.7 Hz, 1H), 7.88 (s, 1H), 7.71 (s, 1H), 7.52 (d, J = 7.5 Hz, 5H), 7.22 (s, 2H), 5.31 (d, J = 6.9 Hz, 3H), 4.51 (s, 3H), 4.16 (d, J = 24.0 Hz, 2H), 3.88 (d, J = 9.9 Hz, 5H), 3.68-3.52 (m, 5H), 3.40 (s, 4H), 2.59 (d, J = 17.5 Hz, 6H), 1.14 (s, 3H), 1.01 (s, 16H), 0.86 (d, J = 17.0 Hz, | D |
| 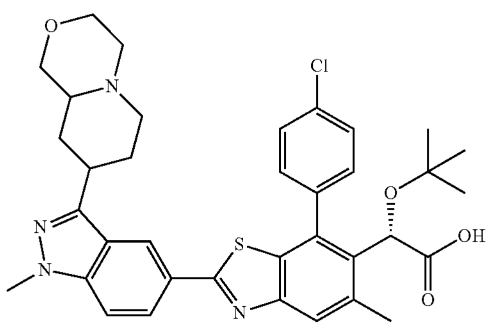 [SMILES: Cc1cc2nc(-c3ccc4c(c3)c(C3CCN5CCOCC5C3)nn4C)sc2c(-c2ccc(Cl)cc2)c1[C@H](OC(C)(C)C)C(=O)O] | 135 | (S)-2-(tert-butoxy)-2-(7-(4-chlorophenyl)-2-(3-((R)-hexahydropyrazino[2,1-c][1,4]oxazin-8(1H)-yl)-1-methyl-1H-indazol-5-yl)-5-methylbenzo[d]thiazol-6-yl)acetic acid | 660.2 (M + H)+ | 1H NMR (400 MHz, Chloroform-d) δ 8.45 (d, J = 1.6 Hz, 1H), 7.94-7.83 (m, 2H), 7.72 (d, J = 8.1 Hz, 1H), 7.60-7.42 (m, 3H), 7.34 (d, J = 8.9 Hz, 1H), 5.32 (s, 1H), 4.05 (dd, J = 12.3, 4.9 Hz, 4H), 3.93 (s + m, 4H), 3.65 (tt, J = 22.1, 12.0 Hz, 4H), 3.49-3.36 (m, 1H), 3.25 (t, J = 12.4 Hz, 1H), 3.04 (dd, J = 12.1, 7.7 Hz, 1H), 2.59 (s, 3H), 1.01 (s, 9H), 0.88 (t, J = 7.3 Hz, 1H). | D |

-continued

| Structure | Cmpd# | Chemical Name | ES/MS m/z | 1H HMR | Method |
|---|---|---|---|---|---|
| 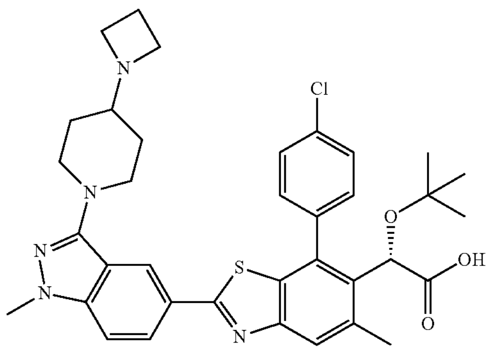 | 136 | (S)-2-(2-(3-(4-(azetidin-1-yl)piperidin-1-yl)-1-methyl-1H-indazol-5-yl)-7-(4-chlorophenyl)-5-methylbenzo[d]thiazol-6-yl)-2-(tert-butoxy)acetic acid | 658.32 (M + H)+ | | D |
| 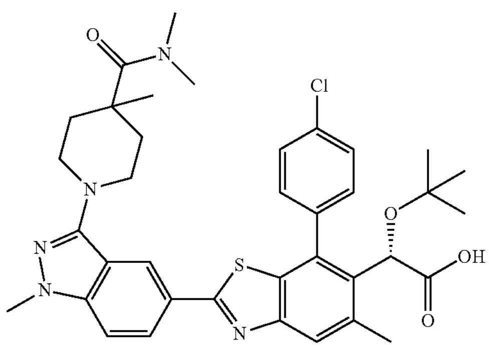 [SMILES: Cc1cc2nc(-c3ccc4c(c3)c(N3CCC(C)(C(=O)N(C)C)CC3)nn4C)sc2c(-c2ccc(Cl)cc2)c1[C@H](OC(C)(C)C)C(=O)O] | 137 | (S)-2-(tert-butoxy)-2-(7-(4-chlorophenyl)-2-(3-(4-(dimethylcarbamoyl)-4-methylpiperidin-1-yl)-1-methyl-1H-indazol-5-yl)-5-methylbenzo[d]thiazol-6-yl)acetic acid | 688.20 (M + H)+ | $^1$H NMR (400 MHz, Methanol-d$_4$) δ 8.43 (d, J = 1.0 Hz, 1 H), 8.11-7.92 (m, 1 H), 7.80 (s, 1 H), 7.73-7.65 (m, 1 H), 7.65-7.51 (m, 4 H), 5.25 (s, 1 H), 4.30-3.37 (m, 7 H), 3.10 (s, 6 H), 2.61 (s, 3 H), 2.52-2.29 (m, 2 H), 1.93-1.66 (m, 2 H), 1.39 (s, 3 H), 0.98 (s, 9 H) | D |
| 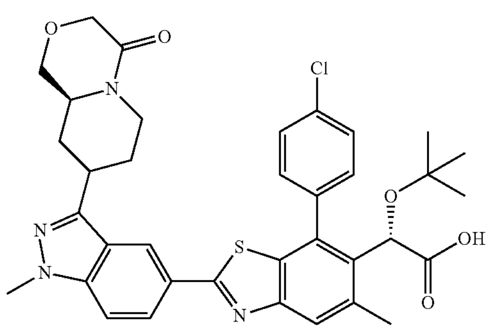 [SMILES: Cc1cc2nc(-c3ccc4c(c3)c(C3CCN5C(=O)COC[C@@H]5C3)nn4C)sc2c(-c2ccc(Cl)cc2)c1[C@H](OC(C)(C)C)C(=O)O] | 138 | (S)-2-(tert-butoxy)-2-(7-(4-chlorophenyl)-5-methyl-2-(1-methyl-3-((S)-4-oxohexahydropyrazino[2,1-c][1,4]oxazin-8(1H)-yl)-1H-indazol-5-yl)benzo[d]thiazol-6-yl)acetic acid | 674.27 (M + H)+ | $^1$H NMR (400 MHz, Methanol-d$_4$) δ 8.44 (s, 1H), 7.98 (d, 1H), 7.80 (s, 1H), 7.72-7.67 (m, 1H), 7.63-7.42 (m, 4H), 5.25 (s, 1H), 4.64 (d, J = 12.9 Hz, 1H), 4.21-4.10 (m, 3H), 4.03-3.84 (m, 6H), 3.71 (dd, J = 12.0, 7.3 Hz, 1H), 3.16-3.05 (m, 1H), 3.05-2.81 (m, 2H), 2.61 (s, 3H), 0.98 (s, 9H) | D |
| 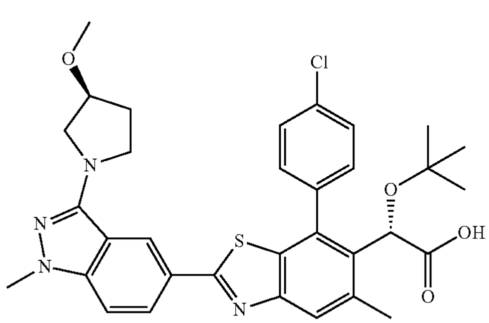 [SMILES: CO[C@H]1CCN(c2nn(C)c3ccc(-c4nc5cc(C)c([C@H](OC(C)(C)C)C(=O)O)c(-c6ccc(Cl)cc6)c5s4)cc23)C1] | 139 | (S)-2-(tert-butoxy)-2-(7-(4-chlorophenyl)-2-(3-((S)-3-methoxypyrrolidin-1-yl)-1-methyl-1H-indazol-5-yl)-5-methylbenzo[d]thiazol-6-yl)acetic acid | 619.2 (M + H)+ | 1H NMR (400 MHz, Acetonitrile-d3) δ 8.42-8.35 (m, 1H), 8.11 (s, 0H), 7.99 (dd, J = 9.0, 1.6 Hz, 1H), 7.81 (s, 1H), 7.70-7.64 (m, 1H), 7.60 (s, 3H), 7.33 (d, J = 8.9 Hz, 1H), 5.26 (s, 1H), 4.19-4.10 (m, 1H), 3.82 (s, 3H), 3.77-3.56 (m, 4H), 3.35 (s, 3H), 2.58 (s, 3H), 2.27 (t, J = 7.4 Hz, 1H), 2.20-2.06 (m, 3H), | D |

-continued

| Structure | Cmpd# | Chemical Name | ES/MS m/z | 1H HMR | Method |
|---|---|---|---|---|---|
| | | | | 1.12 (d, J = 6.1 Hz, 2H), 0.98 (s, 9H), 0.90 (t, J = 6.8 Hz, 2H). | |
| 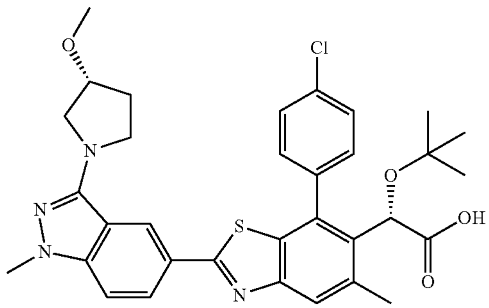 [SMILES: CO[C@@H]1CCN(c2nn(C)c3ccc(-c4nc5cc(C)c([C@H](OC(C)(C)C)C(=O)O)c(-c6ccc(Cl)cc6)c5s4)cc23)C1] | 140 | (S)-2-(tert-butoxy)-2-(7-(4-chlorophenyl)-2-(3-((R)-3-methoxypyrrolidin-1-yl)-1-methyl-1H-indazol-5-yl)-5-methylbenzo[d]thiazol-6-yl) acetic acid | 619.2 (M + H)+ | 1H NMR (400 MHz, Acetonitrile-d3) δ 8.44-8.37 (m, 1H), 8.09 (d, J = 8.3 Hz, 1H), 7.83 (s, 1H), 7.71-7.54 (m, 4H), 5.28 (s, 1H), 4.17 (d, J = 5.6 Hz, 1H), 3.35 (s, 3H), 2.65 (s, 1H), 2.58 (d, J = 0.8 Hz, 3H), 2.27 (t, J = 7.5 Hz, 1H), 2.14 (d, J = 26.3 Hz, 2H), 1.65-1.48 (m, 1H), 0.99 (s, 9H), 0.94-0.81 (m, 3H). | D |
| 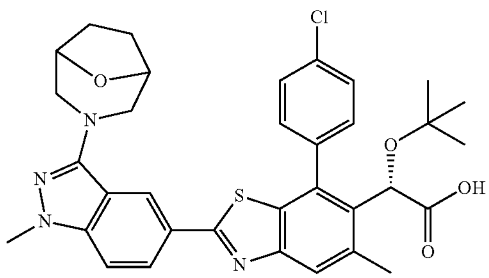 [SMILES: Cc1cc2nc(-c3ccc4c(c3)c(N3CC5CCC(C3)O5)nn4C)sc2c(-c2ccc(Cl)cc2)c1[C@H](OC(C)(C)C)C(=O)O] | 141 | (2S)-2-(2-(3-(8-oxa-3-azabicyclo[3.2.1]octan-3-yl)-1-methyl-1H-indazol-5-yl)-7-(4-chlorophenyl)-5-methylbenzo[d]thiazol-6-yl)-2-(tert-butoxy) acetic acid | 631.3 (M + H)+ | 1H NMR (400 MHz, Chloroform-d) δ 8.02-7.86 (m, 2H), 7.73 (s, 1H), 7.61-7.45 (m, 4H), 7.23 (s, 1H), 5.31 (s, 1H), 4.54 (s, 2H), 3.90 (s, 3H), 3.81-3.69 (m, 3H), 3.37 (d, J = 11.8 Hz, 2H), 2.58 (s, 3H), 2.41-2.26 (m, 2H), 2.18-1.97 (m, 3H), 1.01 (s, 9H), 0.88 (t, J = 6.7 Hz, 2H). | B |
| 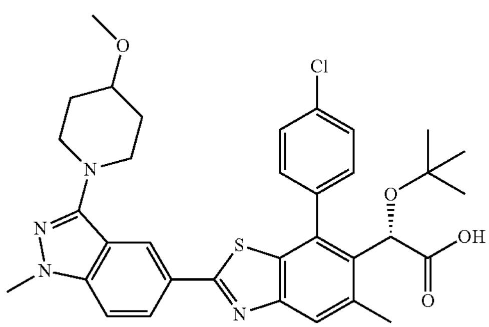 [SMILES: COC1CCN(c2nn(C)c3ccc(-c4nc5cc(C)c([C@H](OC(C)(C)C)C(=O)O)c(-c6ccc(Cl)cc6)c5s4)cc23)CC1] | 142 | (S)-2-(tert-butoxy)-2-(7-(4-chlorophenyl)-2-(3-(4-methoxypiperidin-1-yl)-1-methyl-1H-indazol-5-yl)-5-methylbenzo[d]thiazol-6-yl) acetic acid | 633.3 (M + H)+ | 1H NMR (400 MHz, Chloroform-d) δ 8.37-8.29 (m, 1H), 8.00 (dd, J = 8.9, 1.5 Hz, 1H), 7.84 (s, 1H), 7.72 (d, J = 8.3 Hz, 1H), 7.52 (d, J = 8.4 Hz, 3H), 7.24 (s, 1H), 5.31 (s, 1H), 3.89 (s, 3H), 3.86-3.70 (m, 2H), 3.41 (s, 3H), 3.16 (ddt, J = 13.0, 9.8, 3.5 Hz, 2H), 2.56 (s, 3H), 2.18-1.64 (m, 4H), 1.25 (s, 1H), 1.00 (s, 9H). | B |

-continued

| Structure | Cmpd# | Chemical Name | ES/MS m/z | 1H HMR | Method |
|---|---|---|---|---|---|
| 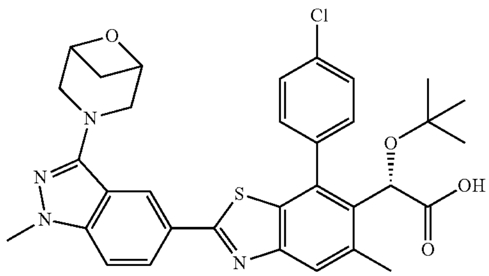 [SMILES: Cc1cc2nc(-c3ccc4c(c3)c(N3CC5CC(C3)O5)nn4C)sc2c(-c2ccc(Cl)cc2)c1[C@H](OC(C)(C)C)C(=O)O] | 143 | (2S)-2-(2-(3-(6-oxa-3-azabicyclo[3.1.1]heptan-3-yl)-1-methyl-1H-indazol-5-yl)-7-(4-chlorophenyl)-5-methylbenzo[d]thiazol-6-yl)-2-(tert-butoxy)acetic acid | 617.3 (M + H)+ | 1H NMR (400 MHz, Chloroform-d) δ 8.66 (s, 1H), 7.97-7.86 (m, 2H), 7.78-7.67 (m, 1H), 7.59-7.41 (m, 3H), 7.23 (s, 1H), 5.30 (s, 1H), 4.84 (d, J = 6.5 Hz, 2H), 4.04 (s, 4H), 3.92 (s, 3H), 3.43-3.24 (m, 1H), 2.58 (s, 4H), 2.16 (d, J = 8.9 Hz, 1H), 1.01 (s, 9H). | B |
| 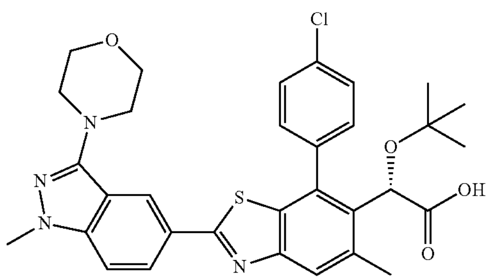 [SMILES: Cc1cc2nc(-c3ccc4c(c3)c(N3CCOCC3)nn4C)sc2c(-c2ccc(Cl)cc2)c1[C@H](OC(C)(C)C)C(=O)O] | 144 | (S)-2-(tert-butoxy)-2-(7-(4-chlorophenyl)-5-methyl-2-(1-methyl-3-morpholino-1H-indazol-5-yl)benzo[d]thiazol-6-yl)acetic acid | 605.3 (M + H)+ | 1H NMR (400 MHz, Chloroform-d) δ 8.53 (d, J = 1.9 Hz, 1H), 7.97-7.86 (m, 2H), 7.72 (d, J = 7.8 Hz, 1H), 7.64-7.52 (m, 2H), 7.51-7.42 (m, 1H), 7.34 (d, J = 8.9 Hz, 1H), 5.31 (s, 1H), 4.06-3.83 (m, 6H), 3.55 (t, J = 3.8 Hz, 4H), 2.59 (s, 3H), 2.01 (s, 1H), 1.01 (s, 9H). | B |
| 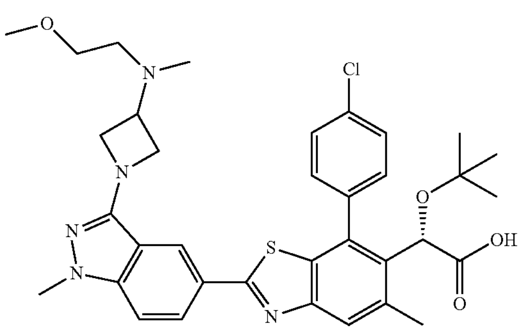 [SMILES: COCCN(C)C1CN(c2nn(C)c3ccc(-c4nc5cc(C)c([C@H](OC(C)(C)C)C(=O)O)c(-c6ccc(Cl)cc6)c5s4)cc23)C1] | 145 | (S)-2-(tert-butoxy)-2-(7-(4-chlorophenyl)-2-(3-(3-((2-methoxyethyl)(methyl)amino)azetidin-1-yl)-1-methyl-1H-indazol-5-yl)-5-methylbenzo[d]thiazol-6-yl)acetic acid | 662.3 (M + H)+ | 1H NMR (400 MHz, Chloroform-d) δ 8.10-8.00 (m, 1H), 7.82 (dd, J = 9.0, 1.6 Hz, 1H), 7.69 (s, 1H), 7.54 (dd, J = 8.7, 2.1 Hz, 1H), 7.45-7.31 (m, 3H), 7.16 (d, J = 8.9 Hz, 1H), 5.11 (s, 1H), 4.40-4.26 (m, 4H), 3.75 (s, 3H), 3.64 (dd, J = 5.6, 3.6 Hz, 2H), 3.28 (s, 3H), 3.26-3.18 (m, 1H), 2.87 (s, 3H), 2.48 (s, 3H), 1.89 (s, 2H), 0.85 (s, 9H). | D |

-continued

| Structure | Cmpd# | Chemical Name | ES/MS m/z | 1H HMR | Method |
|---|---|---|---|---|---|
| 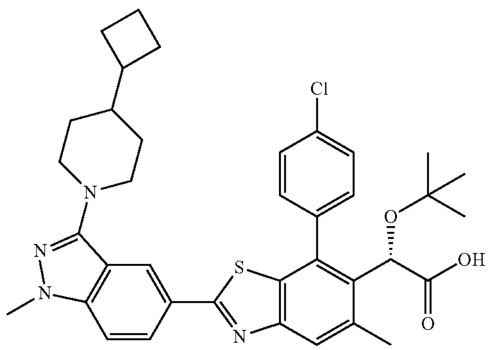 | 146 | (S)-2-(tert-butoxy)-2-(7-(4-chlorophenyl)-5-methyl-2-(1-methyl-3-(4-(oxetan-3-yl)piperidin-1-yl)-1H-indazol-5-yl)benzo[d]thiazol-6-yl)acetic acid | 659.3 (M + H)+ | 1H NMR (400 MHz, Chloroform-d) δ 8.40 (d, J = 1.5 Hz, 1H), 8.04 (dd, J = 8.8, 1.5 Hz, 1H), 7.87 (s, 1H), 7.72 (d, J = 7.9 Hz, 1H), 7.58-7.45 (m, 4H), 7.31 (d, J = 8.9 Hz, 1H), 5.32 (s, 1H), 4.84 (dd, J = 7.9, 6.1 Hz, 2H), 4.56 (t, J = 6.3 Hz, 2H), 4.00 (d, J = 12.2 Hz, 2H), 3.93 (s, 3H), 3.20-2.95 (m, 2H), 2.87 (q, J = 8.0 Hz, 1H), 2.56 (s, 3H), 2.03-1.85 (m, 1H), 1.81 (d, J = 12.5 Hz, 2H), 1.52 (dd, J = 16.3, 9.2 Hz, 2H), 1.00 (s, 9H). | D |
| 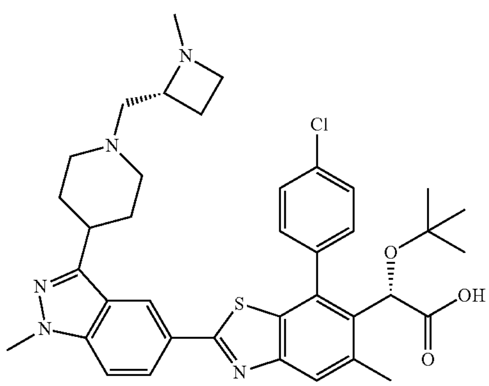 [SMILES: Cc1cc2nc(-c3ccc4c(c3)c(C3CCN(C[C@H]5CCN5C)CC3)nn4C)sc2c(-c2ccc(Cl)cc2)c1[C@H](OC(C)(C)C)C(=O)O] | 147 | (S)-2-(2-(3-(1-(((R)-1-acetylazetidin-2-yl)methyl)piperidin-4-yl)-1-methyl-1H-indazol-5-yl)-7-(4-chlorophenyl)-5-methylbenzo[d]thiazol-6-yl)-2-(tert-butoxy)acetic acid | 686.81 (M + H)+ | $^1$H NMR (400 MHz, Chloroform-d) δ 8.44 (s, 1H), 8.07 (dd, J = 8.9, 1.6 Hz, 1H), 7.81 (s, 1H), 7.74-7.68 (m, 1H), 7.66-7.53 (m, 4H), 5.25 (s, 1H), 4.29-4.15 (m, 1H), 4.04 (s, 4H), 3.75-3.36 (m, 5H), 3.18-2.96 (m, 5H), 2.77-2.66 (m, 1H), 2.62 (s, 3H), 2.59-2.45 (m, 1H), 2.26 (dp, J = 23.5, 11.9 Hz, 5H), 0.98 (s, 9H) | E |
| 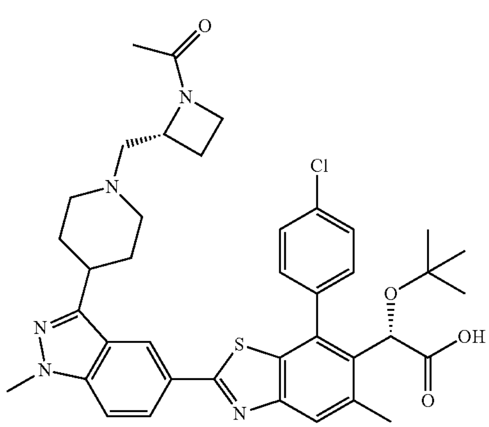 [SMILES: CC(=O)N1CC[C@@H]1CN1CCC(c2nn(C)c3ccc(-c4nc5cc(C)c([C@H](OC(C)(C)C)C(=O)O)c(-c6ccc(Cl)cc6)c5s4)cc23)CC1] | 148 | (S)-2-(2-(3-(1-(((R)-1-acetylazetidin-2-yl)methyl)piperidin-4-yl)-1-methyl-1H-indazol-5-yl)-7-(4-chlorophenyl)-5-methylbenzo[d]thiazol-6-yl)-2-(tert-butoxy)acetic acid | 714.66 (M + H)+ | $^1$H NMR (400 MHz, Methanol-d$_4$) δ 8.47-8.42 (m, 1H), 8.12 (d, J = 8.8, 1.6 Hz, 1H), 7.82 (s, 1H), 7.69 (d, J = 8.6, 2.1 Hz, 1H), 7.67-7.56 (m, 4H), 5.25 (s, 1H), 5.07-4.95 (m, 2H), 4.31-4.15 (m, 2H), 4.14-4.00 (m, 4H), 3.85-3.34 (m, 5H), 3.22-3.11 (m, 1H), 2.62 (s, 3H), 2.58-2.10 (m, 5H), | E |

-continued

| Structure | Cmpd# | Chemical Name | ES/MS m/z | 1H HMR | Method |
|---|---|---|---|---|---|
| | | | | 1.97-1.89 (m, 3H), 0.98 (s, 9H) | |
| 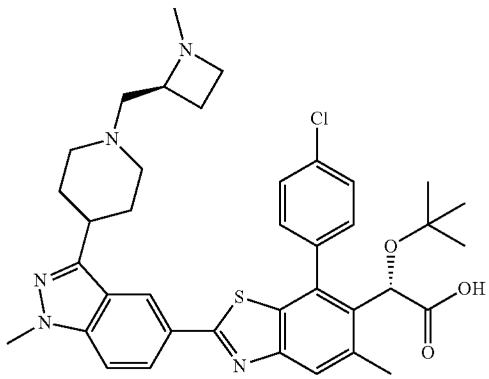 [SMILES: Cc1cc2nc(-c3ccc4c(c3)c(C3CCN(C[C@@H]5CCN5C)CC3)nn4C)sc2c(-c2ccc(Cl)cc2)c1[C@H](OC(C)(C)C)C(=O)O] | 149 | (S)-2-(tert-butoxy)-2-(7-(4-chlorophenyl)-5-methyl-2-(1-methyl-3-(((S)-1-methylazetidin-2-yl)methyl)piperidin-4-yl)-1H-indazol-5-yl)benzo[d]thiazol-6-yl)acetic acid | 686.43 (M + H)+ | ¹H NMR (400 MHz, Methanol-d₄) δ 8.45 (s, 1H), 8.10 (d, J = 8.9, 1.6 Hz, 1H), 7.82 (s, 1H), 7.72-7.57 (m, 5H), 5.26 (s, 1H), 4.24 (s, 1H), 4.05 (s, 3H), 3.74 (dd, 1H), 3.63-3.40 (m, 5H), 3.25-3.05 (m, 2H), 3.02 (s, 3H), 2.73 (tt, 1H), 2.62 (s, 3H), 2.55 (t, J = 10.4 Hz, 1H), 2.38-2.17 (m, 5H), 0.98 (s, 9H) | E |
| 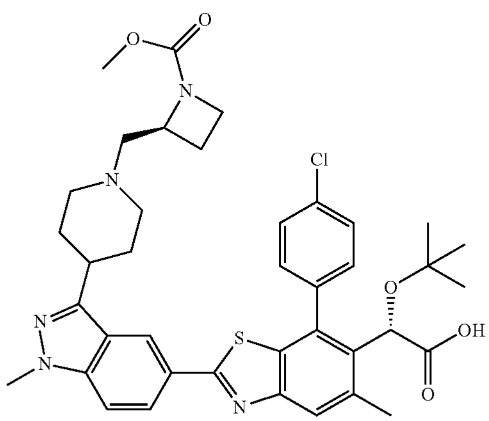 [SMILES: COC(=O)N1CC[C@H]1CN1CCC(c2nn(C)c3ccc(-c4nc5cc(C)c([C@H](OC(C)(C)C)C(=O)O)c(-c6ccc(Cl)cc6)c5s4)cc23)CC1] | 150 | (S)-2-(tert-butoxy)-2-(7-(4-chlorophenyl)-2-(3-(1-(((S)-1-(methoxycarbonyl)azetidin-2-yl)methyl)piperidin-4-yl)-1-methyl-1H-indazol-5-yl)-5-methylbenzo[d]thiazol-6-yl)acetic acid | 730.68 (M + H)+ | ¹H NMR (400 MHz, Methanol-d₄) δ 8.46 (s, 1H), 8.12 (d, 1H), 7.82 (s, 1H), 7.72-7.56 (m, 5H), 5.26 (s, 1H), 4.06 (s, 3H), 3.97 (tt, J = 8.0, 7.4 Hz, 1H), 3.75 (s, 3H), 3.72-3.36 (m, 6H), 3.17 (dd, J = 22.9, 10.7 Hz, 1H), 2.62 (s, 3H), 2.57-2.47 (m, 2H), 2.40 (t, J = 15.3 Hz, 2H), 2.33-2.06 (m, 4H), 0.98 (s, 9H) | E |
| 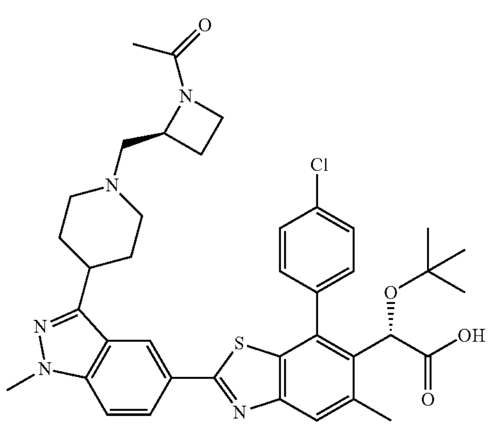 [SMILES: CC(=O)N1CC[C@H]1CN1CCC(c2nn(C)c3ccc(-c4nc5cc(C)c([C@H](OC(C)(C)C)C(=O)O)c(-c6ccc(Cl)cc6)c5s4)cc23)CC1] | 151 | (S)-2-(2-(3-(1-(((S)-1-acetylazetidin-2-yl)methyl)piperidin-4-yl)-1-methyl-1H-indazol-5-yl)-7-(4-chlorophenyl)-5-methylbenzo[d]thiazol-6-yl)-2-(tert-butoxy)acetic acid | 714.68 (M + H)+ | ¹H NMR (400 MHz, Methanol-d₄) δ 8.45 (s, 1H), 8.13 (d, J = 8.9, 1.6 Hz, 1H), 7.82 (s, 1H), 7.69 (d, 1H), 7.66-7.56 (m, 4H), 5.25 (s, 1H), 5.00 (q, J = 9.0 Hz, 1H), 4.30-4.14 (m, 2H), 4.06 (d, J = 12.5 Hz, 3H), 3.73-3.35 (m, 4H), 3.16 (t, 1H), 2.62 (s, 3H), 2.59-2.46 (m, 1H), 2.48-2.31 (m, 3H), 2.31-2.08 (m, 4H), 1.94 (d, J = 11.4 Hz, 3H), 0.98 (s, 9H) | E |

| Structure | Cmpd# | Chemical Name | ES/MS m/z | 1H HMR | Method |
|---|---|---|---|---|---|
| 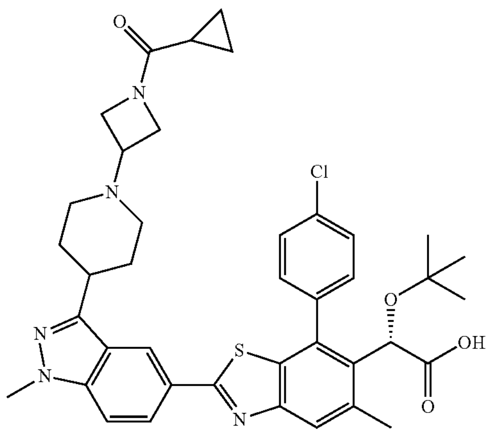 [SMILES: Cc1cc2nc(-c3ccc4c(c3)c(C3CCN(C5CN(C(=O)C6CC6)C5)CC3)nn4C)sc2c(-c2ccc(Cl)cc2)c1[C@H](OC(C)(C)C)C(=O)O] | 152 | (S)-2-(tert-butoxy)-2-(7-(4-chlorophenyl)-2-(3-(1-(1-(cyclopropanecarbonyl)azetidin-3-yl)piperidin-4-yl)-1-methyl-1H-indazol-5-yl)-5-methylbenzo[d]thiazol-6-yl)acetic acid | 726.68 (M + H)+ | ¹H NMR (400 MHz, Methanol-d₄) δ 8.47 (s, 1H), 8.13 (d, 1H), 7.82 (s, 1H), 7.72-7.56 (m, 5H), 5.26 (s, 1H), 4.78-4.68 (m, 1H), 4.64-4.54 (m, 1H), 4.40-4.29 (m, 1H), 4.29-4.15 (m, 2H), 4.06 (s, 3H), 3.83-3.47 (m, 3H), 3.26-3.10 (m, 2H), 2.62 (s, 3H), 2.48-2.36 (m, 2H), 2.34-2.15 (m, 2H), 1.67-1.56 (m, 1H), 0.99 (s, 9H), 0.95-0.86 (m, 4H) | F |
| 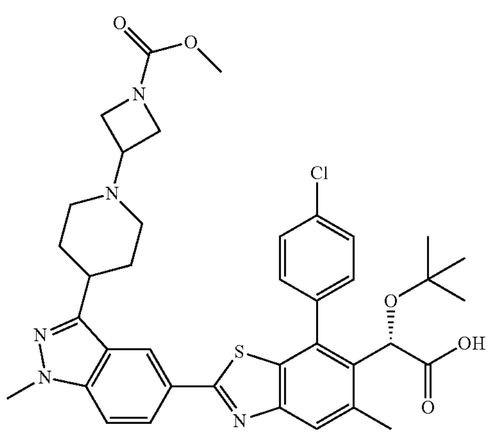 [SMILES: COC(=O)N1CC(N2CCC(c3nn(C)c4ccc(-c5nc6cc(C)c([C@H](OC(C)(C)C)C(=O)O)c(-c7ccc(Cl)cc7)c6s5)cc34)CC2)C1] | 153 | (S)-2-(tert-butoxy)-2-(7-(4-chlorophenyl)-2-(3-(1-(1-(methoxycarbonyl)azetidin-3-yl)piperidin-4-yl)-1-methyl-1H-indazol-5-yl)-5-methylbenzo[d]thiazol-6-yl)acetic acid | 716.52 (M + H)+ | ¹H NMR (400 MHz, Methanol-d₄) δ 8.46 (s, 1H), 8.13 (d, J = 8.9 Hz, 1H), 7.82 (s, 1H), 7.73-7.53 (m, 5H), 5.25 (s, 1H), 4.46-4.11 (m, 6H), 4.06 (s, 3H), 3.73 (s, 4H), 3.60-3.45 (m, 1H), 3.22-3.06 (m, 2H), 2.62 (s, 3H), 2.48-2.33 (m, 2H), 2.31-2.11 (m, 2H), 0.98 (s, 9H) | F |
| 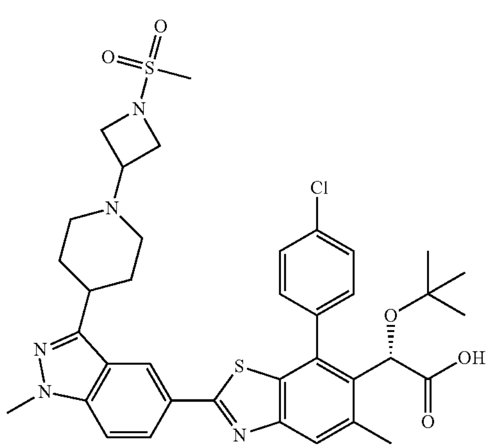 [SMILES: Cc1cc2nc(-c3ccc4c(c3)c(C3CCN(C5CN(S(C)(=O)=O)C5)CC3)nn4C)sc2c(-c2ccc(Cl)cc2)c1[C@H](OC(C)(C)C)C(=O)O] | 154 | (S)-2-(tert-butoxy)-2-(7-(4-chlorophenyl)-5-methyl-2-(2-methyl-3-(1-(1-(methylsulfonyl)azetidin-3-yl)piperidin-4-yl)-1H-indazol-5-yl)benzo[d]thiazol-6-yl)acetic acid | 736.56 (M + H)+ | ¹H NMR (400 MHz, Methanol-d₄) δ 8.47-8.44 (m, 1H), 8.11 (dd, J = 8.9, 1.6 Hz, 1H), 7.82 (d, J = 0.8 Hz, 1H), 7.72-7.66 (m, 1H), 7.65-7.57 (m, 4H), 5.26 (s, 1H), 4.29-4.19 (m, 5H), 4.05 (s, 3H), 3.76-3.45 (m, 4H), 3.30-3.11 (m, 1H), 3.03 (s, 3H), 2.62 (s, 3H), 2.46-2.18 (m, 4H), 0.98 (s, 9H) | F |

-continued

| Structure | Cmpd# | Chemical Name | ES/MS m/z | 1H HMR | Method |
|---|---|---|---|---|---|
| 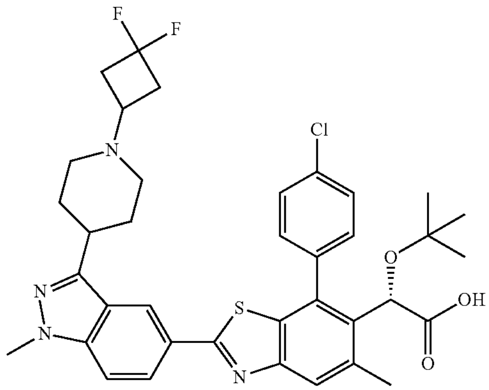 [SMILES: Cc1cc2nc(-c3ccc4c(c3)c(C3CCN(C5CC(F)(F)C5)CC3)nn4C)sc2c(-c2ccc(Cl)cc2)c1[C@H](OC(C)(C)C)C(=O)O] | 155 | (S)-2-(tert-butoxy)-2-(7-(4-chloro-phenyl)-2-(3-(1-(3,3-difluorocyclo-butyl)piperidin-4-yl)-1-methyl-1H-indazol-5-yl)-5-methylbenzo[d]thiazol-6-yl) acetic acid | 693.7 (M + H)+ | $^{1}$H NMR (400 MHz, Methanol-$d_4$) δ 8.45 (s, 1H), 8.11 (dd, J = 8.9, 1.6 Hz, 1H), 7.82 (s, 1H), 7.72-7.66 (m, 1H), 7.66-7.52 (m, 4H), 5.26 (s, 1H), 4.05 (s, 3H), 3.91-3.62 (m, 3H), 3.62-3.43 (m, 1H), 3.26-2.89 (m, 6H), 2.62 (s, 3H), 2.45-2.33 (m, 2H), 2.28-2.12 (m, 2H), 0.98 (s, 9H) | G |
| 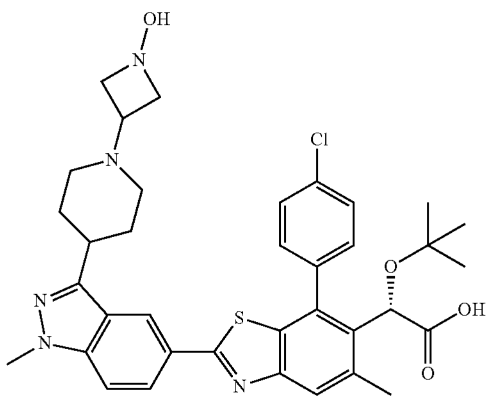 [SMILES: Cc1cc2nc(-c3ccc4c(c3)c(C3CCN(C5CN(O)C5)CC3)nn4C)sc2c(-c2ccc(Cl)cc2)c1[C@H](OC(C)(C)C)C(=O)O] | 156 | (S)-2-(tert-butoxy)-2-(7-(4-chloro-phenyl)-2-(3-(1-((1s,3s)-3-hydroxy-cyclobutyl)piperidin-4-yl)-1-methyl-1H-indazol-5-yl)-5-methylbenzo[d]thiazol-6-yl) acetic acid | 673.95 (M + H)+ | $^{1}$H NMR (400 MHz, Methanol-$d_4$) δ 8.39 (s, 1H), 8.07 (dd, J = 8.9, 1.6 Hz, 1H), 7.79 (s, 1H), 7.71-7.67 (m, 1H), 7.61-7.56 (m, 4H), 5.25 (s, 1H), 4.11 (p, J = 7.2 Hz, 1H), 4.00 (s, 3H), 3.96-3.69 (m, 1H), 3.64 (d, J = 12.2 Hz, 2H), 3.45 (ddt, J = 12.3, 8.5, 4.0 Hz, 1H), 3.39-3.21 (m, 2H), 3.09-2.95 (m, 2H), 2.87-2.70 (m, 1H), 2.60 (s, 3H), 2.42-2.05 (m, 6H), 0.98 (s, 9H) | G |
| 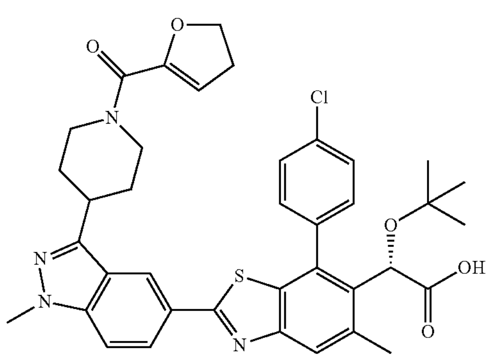 [SMILES: Cc1cc2nc(-c3ccc4c(c3)c(C3CCN(C(=O)C5=CCCO5)CC3)nn4C)sc2c(-c2ccc(Cl)cc2)c1[C@H](OC(C)(C)C)C(=O)O] | 157 | (S)-2-(tert-butoxy)-2-(7-(4-chloro-phenyl)-5-methyl-2-(1-methyl-3-(1-((S)-tetrahydrofuran-2-carbonyl)piperidin-4-yl)-1H-indazol-5-yl)benzo[d]thiazol-6-yl)acetic acid | 701.33 (M + H)+ | $^{1}$H NMR (400 MHz, Methanol-$d_4$) δ 8.38 (s, 1H), 8.04 (dd, J = 8.9, 1.6 Hz, 1H), 7.79 (s, 1H), 7.72-7.66 (m, 1H), 7.61-7.52 (m, 5H), 5.25 (s, 1H), 4.79 (t, J = 7.8, 5.9 Hz, 1H), 4.64-4.54 (m, 1H), 4.24-4.06 (m, 1H), 3.98 (s, 3H), 3.97-3.80 (m, 2H), 3.49-3.35 (m, 1H), 3.36-3.21 (m, 1H), 3.00-2.84 (m, 1H), 2.61 (s, 3H), 2.30-1.75 (m, 7H), 0.98 (s, 9H) | G |

-continued

| Structure | Cmpd# | Chemical Name | ES/MS m/z | 1H HMR | Method |
|---|---|---|---|---|---|
| 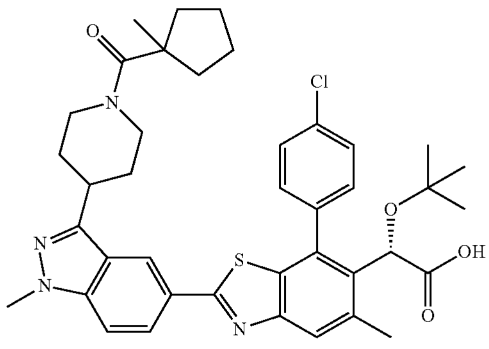 [SMILES: Cc1cc2nc(-c3ccc4c(c3)c(C3CCN(C(=O)C5(C)CCCC5)CC3)nn4C)sc2c(-c2ccc(Cl)cc2)c1[C@H](OC(C)(C)C)C(=O)O] | 158 | (2S)-2-(tert-butoxy)-2-(7-(4-chlorophenyl)-5-methyl-2-(1-methyl-3-(1-(2-methyltetrahydrofuran-2-carbonyl)piperidin-4-yl)-1H-indazol-5-yl)benzo[d]thiazol-6-yl)acetic acid | 715.18 (M + H)+ | $^1$H NMR (400 MHz, Methanol-$d_4$) δ 8.35 (s, 1H), 8.08-8.01 (m, 1H), 7.78 (s, 1H), 7.73-7.66 (m, 1H), 7.61-7.51 (m, 4H), 5.25 (s, 1H), 4.61 (s, 1H), 4.00-3.90 (m, 4H), 3.90-3.73 (m, 1H), 3.46-3.33 (m, 1H), 3.25-3.08 (m, 1H), 3.01-2.64 (m, 2H), 2.61 (s, 3H), 2.12-1.61 (m, 8H), 1.49 (d, J = 1.5 Hz, 3H), 0.98 (s, 9H). | H |
| 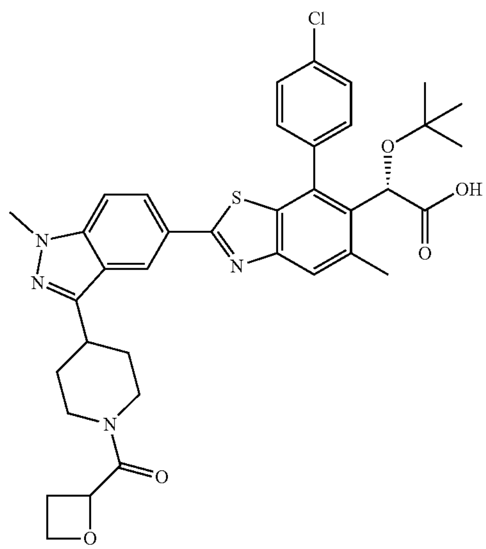 [SMILES: Cc1cc2nc(-c3ccc4c(c3)c(C3CCN(C(=O)C5CCO5)CC3)nn4C)sc2c(-c2ccc(Cl)cc2)c1[C@H](OC(C)(C)C)C(=O)O] | 159 | (2S)-2-(tert-butoxy)-2-(7-(4-chlorophenyl)-5-methyl-2-(1-methyl-3-(1-(oxetane-2-carbonyl)piperidin-4-yl)-1H-indazol-5-yl)benzo[d]thiazol-6-yl)acetic acid | 687.27 (M + H)+ | $^1$H NMR (400 MHz, Methanol-$d_4$) δ 8.47-8.41 (m, 1H), 8.11-8.04 (m, 1H), 7.81 (s, 1H), 7.71-7.65 (m, 1H), 7.63-7.52 (m, 5H), 5.54 (dt, 1H), 5.26 (s, 1H), 4.77-4.46 (m, 3H), 4.05-4.00 (m, 4H), 3.84-3.70 (m, 1H), 3.50-3.36 (m, 1H), 3.05-2.82 (m, 3H), 2.61 (s, 3H), 2.21-1.79 (m, 3H), 0.98 (s, 9H) | H |
| 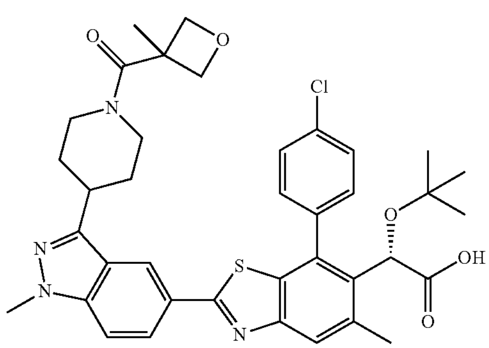 [SMILES: Cc1cc2nc(-c3ccc4c(c3)c(C3CCN(C(=O)C5(C)COC5)CC3)nn4C)sc2c(-c2ccc(Cl)cc2)c1[C@H](OC(C)(C)C)C(=O)O] | 160 | (S)-2-(tert-butoxy)-2-(7-(4-chlorophenyl)-5-methyl-2-(1-methyl-3-(1-(3-methyloxetane-3-carbonyl)piperidin-4-yl)-1H-indazol-5-yl)benzo[d]thiazol-6-yl)acetic acid | 701.29 (M + H)+ | $^1$H NMR (400 MHz, Methanol-$d_4$) δ 8.37 (s, 1H), 8.01 (d, 1H), 7.78 (s, 1H), 7.72-7.66 (m, 1H), 7.60-7.50 (m, 4H), 5.25 (s, 1H), 4.98 (t, J = 5.5 Hz, 2H), 4.63-4.53 (m, 1H), 4.38 (d, J = 5.9 Hz, 2H), 3.97 (s, 3H), 3.45-3.34 (m, 1H), 3.27-3.16 (m, 2H), 2.96-2.85 (m, 1H), 2.60 (s, 3H), 2.13-2.04 (m, 3H), 1.96-1.74 (m, 1H), 1.69 | H |

-continued

| Structure | Cmpd# | Chemical Name | ES/MS m/z | 1H HMR | Method |
|---|---|---|---|---|---|
| | | | | (s, 3H), 0.97 (s, 9H) | |
| 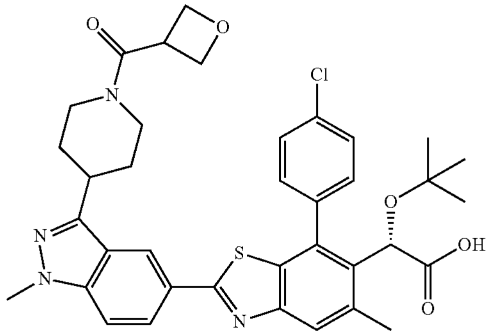 [SMILES: Cc1cc2nc(-c3ccc4c(c3)c(C3CCN(C(=O)C5COC5)CC3)nn4C)sc2c(-c2ccc(Cl)cc2)c1[C@H](OC(C)(C)C)C(=O)O] | 161 | (S)-2-(tert-butoxy)-2-(7-(4-chlorophenyl)-5-methyl-2-(1-methyl-3-(1-(oxetane-3-carbonyl)piperidin-4-yl)-1H-indazol-5-yl)benzo[d]thiazol-6-yl)acetic acid | 687.28 (M + H)+ | $^1$H NMR (400 MHz, Methanol-d$_4$) δ 8.43 (s, 1H), 8.05 (dt, J = 8.9, 1.6 Hz, 1H), 7.81 (s, 1H), 7.72-7.66 (m, 1H), 7.64-7.54 (m, 4H), 5.26 (s, 1H), 4.93-4.89 (m, 2H), 4.86-4.83 (m, 2H), 4.67-4.57 (m, 1H), 4.31-4.20 (m, 1H), 4.01 (s, 3H), 3.62 (d, J = 13.8 Hz, 1H), 3.50-3.37 (m, 1H), 3.29-3.19 (m, 1H), 3.01-2.90 (m, 1H), 2.61 (s, 3H), 2.15-2.04 (m, 2H), 1.92-1.78 (m, 2H), 0.98 (s, 9H) | H |
| 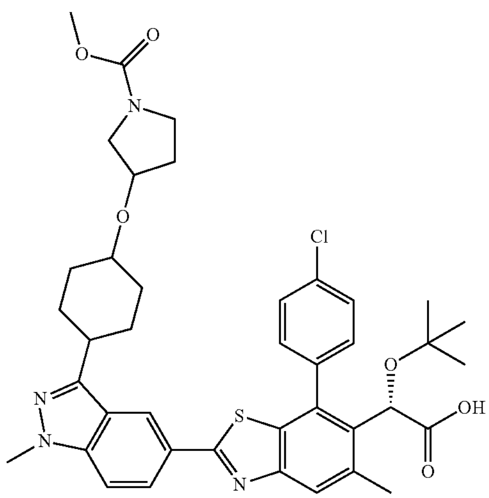 | 162 | (S)-2-(tert-butoxy)-2-(7-(4-chlorophenyl)-2-(3-(1-((S)-1-(methoxycarbonyl)pyrrolidin-3-yl)piperidin-4-yl)-1-methyl-1H-indazol-5-yl)-5-methylbenzo[d]thiazol-6-yl)acetic acid | 730.36 (M + H)+ | $^1$H NMR (400 MHz, Methanol-d$_4$) δ 8.46 (s, 1H), 8.13 (d, J = 8.9 Hz, 1H), 7.82 (s, 1H), 7.73-7.52 (m, 5H), 5.26 (s, 1H), 4.08-3.92 (m, 5H), 3.86-3.34 (m, 10H), 2.65-2.07 (m, 10H), 0.99 (s, 9H). | I |
| 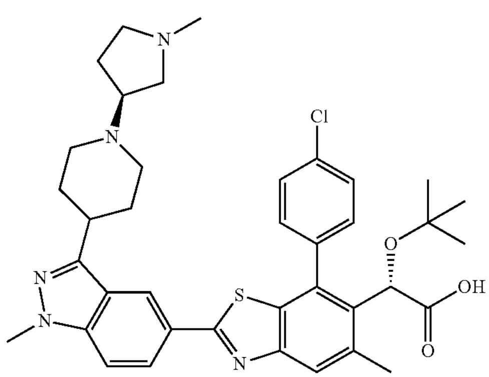 [SMILES: Cc1cc2nc(-c3ccc4c(c3)c(C3CCN([C@H]5CCN(C)C5)CC3)nn4C)sc2c(-c2ccc(Cl)cc2)c1[C@H](OC(C)(C)C)C(=O)O] | 163 | (S)-2-(tert-butoxy)-2-(7-(4-chlorophenyl)-5-methyl-2-(1-methyl-3-(1-((S)-1-methylpyrrolidin-3-yl)piperidin-4-yl)-1H-indazol-5-yl)benzo[d]thiazol-6-yl)acetic acid | 686.59 (M + H)+ | $^1$H NMR (400 MHz, Methanol-d$_4$) δ 8.45 (d, 1H), 8.13-8.04 (m, 1H), 7.82 (d, J = 3.1 Hz, 1H), 7.75-7.68 (m, 1H), 7.67-7.55 (m, 4H), 7.23 (dq, J = 10.4, 5.9, 5.3 Hz, 1H), 6.92-6.83 (m, 1H), 5.26 (s, 1H), 4.18-4.08 (m, 1H), 4.05 (d, J = 6.1 Hz, 3H), 3.97-3.37 (m, 4H), 3.27-3.16 (m, 2H), 3.02 (s, 3H), 2.68-2.60 (m, | I |

| Structure | Cmpd# | Chemical Name | ES/MS m/z | 1H HMR | Method |
|---|---|---|---|---|---|
| | | | | 4H), 2.48-2.20 (m, 5H), 1.89-1.79 (m, 1H), 0.98 (s, 9H) | |
| 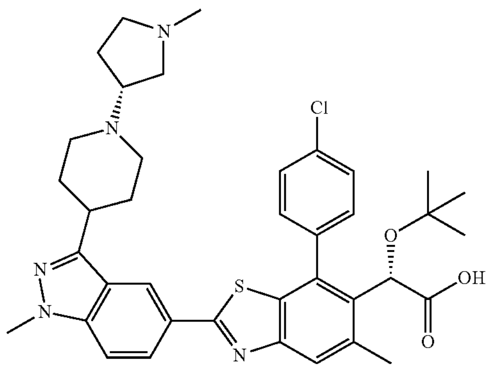 [SMILES: Cc1cc2nc(-c3ccc4c(c3)c(C3CCN([C@@H]5CCN(C)C5)CC3)nn4C)sc2c(-c2ccc(Cl)cc2)c1[C@H](OC(C)(C)C)C(=O)O] | 164 | (S)-2-(tert-butoxy)-2-(7-(4-chlorophenyl)-5-methyl-2-(1-methyl-3-(1-((R)-1-methylpyrrolidin-3-yl)piperidin-4-yl)-1H-indazol-5-yl)benzo[d]thiazol-6-yl)acetic acid | 686.59 (M + H)+ | ¹H NMR (400 MHz, Methanol-d₄) δ 8.44 (t, J = 2.2 Hz, 1H), 8.09 (ddd, J = 8.8, 7.1, 1.6 Hz, 1H), 7.84-7.79 (m, 1H), 7.74-7.67 (m, 1H), 7.66-7.54 (m, 5H), 7.27-7.16 (m, 1H), 6.91-6.81 (m, 1H), 5.26 (s, 1H), 4.23 (p, J = 7.9 Hz, 1H), 4.05 (d, J = 3.1 Hz, 3H), 4.00-3.33 (m, 5H), 3.04 (s, 3H), 2.76-2.64 (m, 1H), 2.62 (d, J = 0.7 Hz, 3H), 2.53-2.19 (m, 5H), 1.88-1.77 (m, 1H), 0.98 (s, 9H) | J |
| 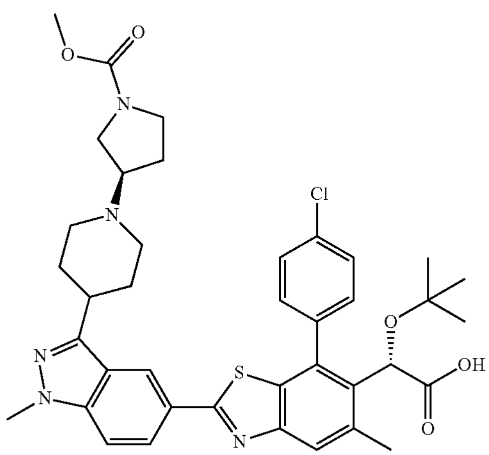 [SMILES: COC(=O)N1CC[C@@H](N2CCC(c3nn(C)c4ccc(-c5nc6cc(C)c([C@H](OC(C)(C)C)C(=O)O)c(-c7ccc(Cl)cc7)c6s5)cc34)CC2)C1] | 165 | (S)-2-(tert-butoxy)-2-(7-(4-chlorophenyl)-2-(3-(1-((R)-1-(methoxycarbonyl)pyrrolidin-3-yl)piperidin-4-yl)-1-methyl-1H-indazol-5-yl)-5-methylbenzo[d]thiazol-6-yl)acetic acid | 730.74 (M + H)+ | ¹H NMR (400 MHz, Methanol-d₄) δ 8.46 (s, 1H), 8.13 (d, J = 8.9 Hz, 1H), 7.82 (s, 1H), 7.73-7.52 (m, 5H), 5.26 (s, 1H), 4.15-3.91 (m, 6H), 3.74 (s, 9H), 2.62 (s, 3H), 2.59-2.05 (m, 7H), 0.99 (s, 9H). | J |
| 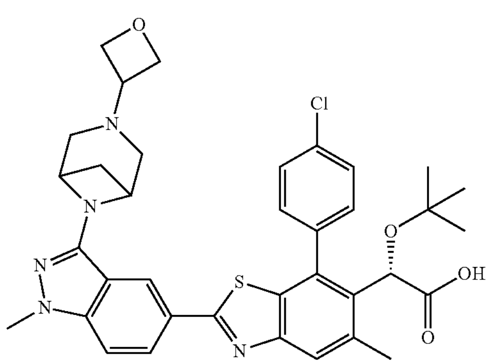 [SMILES: Cc1cc2nc(-c3ccc4c(c3)c(N3C5CC3CN(C3COC3)C5)nn4C)sc2c(-c2ccc(Cl)cc2)c1[C@H](OC(C)(C)C)C(=O)O] | 166 | (2S)-2-(tert-butoxy)-2-(7-(4-chlorophenyl)-5-methyl-2-(2-methyl-3-(3-(oxetan-3-yl)-3,6-diazabicyclo[3.1.1]heptan-6-yl)-1H-indazol-5-yl)benzo[d]thiazol-6-yl)acetic acid | 672.42 (M + H)+ | ¹H NMR (400 MHz, Methanol-d₄) δ 8.24 (s, 1H), 8.05 (dd, J = 9.0, 1.6 Hz, 1H), 7.80 (s, 1H), 7.70-7.65 (m, 1H), 7.63-7.54 (m, 4H), 5.24 (s, 1H), 4.76 (t, J = 7.7 Hz, 2H), 4.71 (d, J = 6.2 Hz, 2H), 4.61-4.51 (m, 2H), 4.34-4.21 (m, 1H), 3.97 (s, 3H), 3.95-3.68 (m, 4H), 3.25-3.16 (m, 1H), 2.61 (s, 3H), 2.15 (d, J = 10.0 | K |

-continued

| Structure | Cmpd# | Chemical Name | ES/MS m/z | 1H HMR | Method |
|---|---|---|---|---|---|
| | | | | Hz, 1H), 0.98 (s, 9H) | |
| 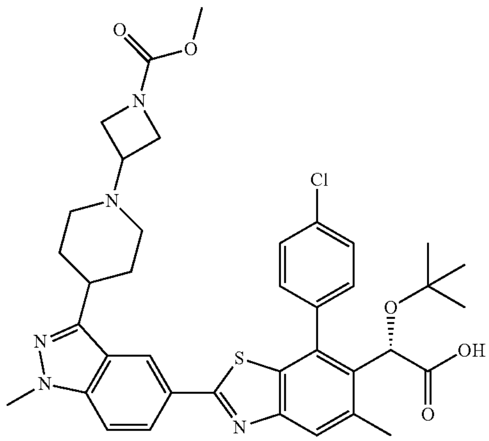 [SMILES: COC(=O)N1CC(N2CCC(c3nn(C)c4ccc(-c5nc6cc(C)c([C@H](OC(C)(C)C)C(=O)O)c(-c7ccc(Cl)cc7)c6s5)cc34)CC2)C1] | 167 | (S)-2-(tert-butoxy)-2-(7-(4-chlorophenyl)-2-(3-(1-(1-(methoxycarbonyl)azetidin-3-yl)piperidin-4-yl)-1-methyl-1H-pyrazolo[4,3-b]pyridin-5-yl)-5-methylbenzo[d]thiazol-6-yl)acetic acid | 717.55 (M + H)+ | $^1$H NMR (400 MHz, Methanol-$d_4$) δ 8.41 (d, J = 8.9 Hz, 1 H), 8.13 (d, J = 8.9 Hz, 1 H), 7.88 (d, J = 0.9 Hz, 1 H), 7.73-7.65 (m, 1 H), 7.65-7.48 (m, 3 H), 5.24 (s, 1 H), 4.43-4.26 (m, 2 H), 4.28-4.16 (m, 3 H), 4.13 (td, J = 7.4, 4.7 Hz, 1 H), 4.09 (s, 3 H), 3.72 (s, 3 H), 3.70-3.51 (m, 2 H), 3.28-3.06 (m, 2 H), 2.62 (s, 3 H), 2.59-2.38 (m, 2 H), 2.35-2.13 (m, 2 H), 0.98 (s, 9 H) | L |
| 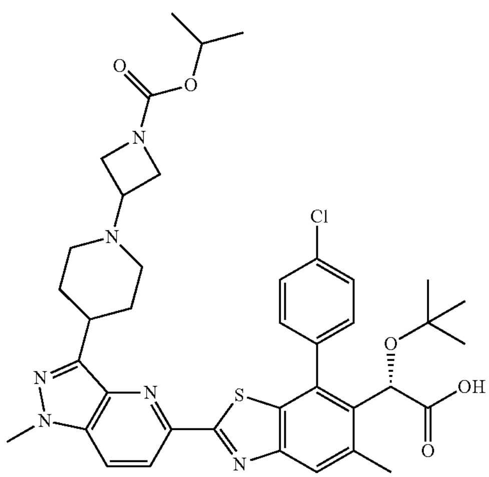 [SMILES: Cc1cc2nc(-c3ccc4c(n3)c(C3CCN(C5CN(C(=O)OC(C)C)C5)CC3)nn4C)sc2c(-c2ccc(Cl)cc2)c1[C@H](OC(C)(C)C)C(=O)O] | 168 | (S)-2-(tert-butoxy)-2-(7-(4-chlorophenyl)-2-(3-(1-(1-(isopropoxycarbonyl)azetidin-3-yl)piperidin-4-yl)-1-methyl-1H-pyrazolo[4,3-b]pyridin-5-yl)-5-methylbenzo[d]thiazol-6-yl)acetic acid | 745.55 (M + H)+ | $^1$H NMR (400 MHz, Methanol-$d_4$) δ 8.41 (d, J = 8.9 Hz, 1 H), 8.14 (d, J = 9.0 Hz, 1 H), 7.88 (s, 1 H), 7.69 (dd, J = 8.7, 2.1 Hz, 1 H), 7.66-7.51 (m, 3 H), 5.24 (s, 1 H), 4.40-4.25 (m, 2 H), 4.25-4.15 (m, 2 H), 4.15-4.01 (m, 5 H), 3.79-3.54 (m, 2 H), 3.24-3.06 (m, 1 H), 2.62 (s, 3 H), 2.58-2.44 (m, 2 H), 2.35-2.14 (m, 2 H), 1.27 (d, J = 6.3 Hz, 6 H), 0.98 (s, 9 H) | L |
| 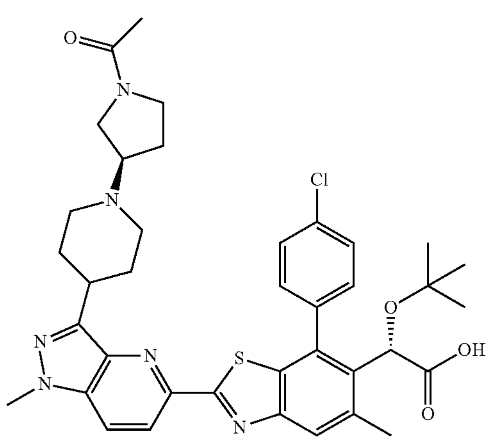 [SMILES: CC(=O)N1CC[C@@H](N2CCC(c3nn(C)c4ccc(-c5nc6cc(C)c([C@H](OC(C)(C)C)C(=O)O)c(-c7ccc(Cl)cc7)c6s5)nc34)CC2)C1] | 169 | (S)-2-(2-(3-(1-((R)-1-acetylpyrrolidin-3-yl)piperidin-4-yl)-1-methyl-1H-pyrazolo[4,3-b]pyridin-5-yl)-7-(4-chlorophenyl)-5-methylbenzo[d]thiazol-6-yl)-2-(tert-butoxy)acetic acid | 715.69 (M + H)+ | $^1$H NMR (400 MHz, Methanol-$d_4$) δ 8.27 (dd, J = 8.9, 3.0 Hz, 1 H), 7.99 (dd, J = 8.9, 3.3 Hz, 1 H), 7.81 (s, 1 H), 7.73-7.66 (m, 1 H), 7.64-7.51 (m, 3 H), 5.24 (s, 1 H), 4.18-3.89 (m, 3 H), 3.91-3.46 (m, 5 H), 3.48-3.31 (m, 3 H), 2.62 (s, 3 H), 2.56-2.37 (m, 3 H), 2.38-2.15 (m, 5 H), 2.16-1.98 (m, 3 H), 0.98 (s, 9 H) | L |

| Structure | Cmpd# | Chemical Name | ES/MS m/z | 1H HMR | Method |
|---|---|---|---|---|---|
| 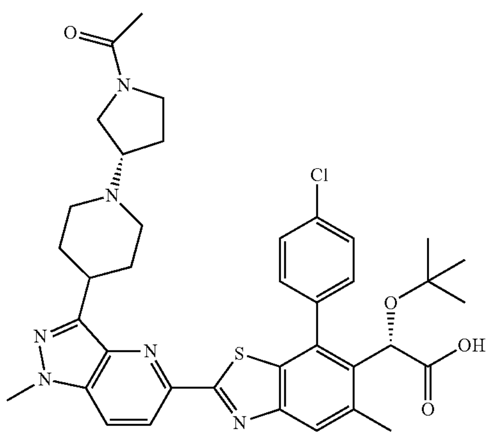 [SMILES: CC(=O)N1CC[C@H](N2CCC(c3nn(C)c4ccc(-c5nc6cc(C)c([C@H](OC(C)(C)C)C(=O)O)c(-c7ccc(Cl)cc7)c6s5)nc34)CC2)C1] | 170 | (S)-2-(2-(3-(1-((S)-1-acetyl-pyrrolidin-3-yl) piperidin-4-yl)-1-methyl-1H-pyrazolo[4,3-b] pyridin-5-yl)-7-(4-chlorophenyl)-5-methylbenzo [d]thiazol-6-yl)-2-(tert-butoxy) acetic acid | 715.63 (M + H)+ | $^1$H NMR (400 MHz, Methanol-d$_4$) δ 8.41 (dd, J = 9.0, 1.1 Hz, 1 H), 8.14 (d, J = 9.0 Hz, 1 H), 7.88 (s, 1 H), 7.70 (dd, J = 8.8, 2.1 Hz, 1 H), 7.65-7.54 (m, 3 H), 5.24 (s, 1 H), 4.09 (s, 3 H), 4.06-3.90 (m, 2 H), 3.89-3.74 (m, 2 H), 3.74-3.34 (m, 5 H), 2.62 (s, 3 H), 2.58-2.45 (m, 3 H), 2.33-2.17 (m, 3 H), 2.17-1.99 (m, 4 H), 0.98 (s, 9 H) | L |
| 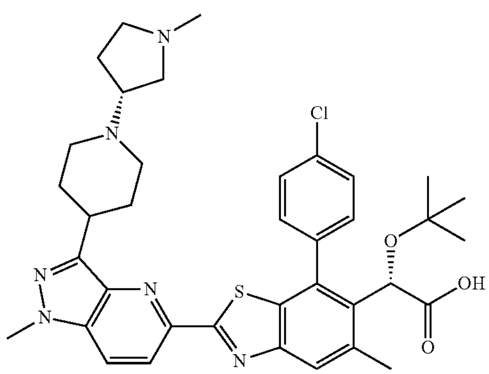 [SMILES: Cc1cc2nc(-c3ccc4c(n3)c(C3CCN([C@@H]5CCN(C)C5)CC3)nn4C)sc2c(-c2ccc(Cl)cc2)c1[C@H](OC(C)(C)C)C(=O)O] | 171 | (S)-2-(tert-butoxy)-2-(7-(4-chloro-phenyl)-5-methyl-2-(1-methyl-3-(1-((R)-1-methyl-pyrrolidin-3-yl) piperidin-4-yl)-1H-pyrazolo[4,3-b] pyridin-5-yl) benzo[d]thiazol-6-yl)acetic acid | 687.29 (M + H)+ | $^1$H NMR (400 MHz, Methanol-d$_4$) δ 8.42 (d, J = 8.9 Hz, 1 H), 8.15 (d, J = 9.0 Hz, 1 H), 7.89 (s, 1 H), 7.75-7.66 (m, 1 H), 7.66-7.50 (m, 3 H), 5.24 (s, 1 H), 4.27-4.12 (m, 1 H), 4.10 (s, 3 H), 3.94-3.76 (m, 2 H), 3.76-3.58 (m, 5 H), 3.03 (s, 3 H), 2.71-2.64 (m, 1 H), 2.63 (s, 3 H), 2.60-2.15 (m, 7 H), 0.98 (s, 9 H) | L |
| 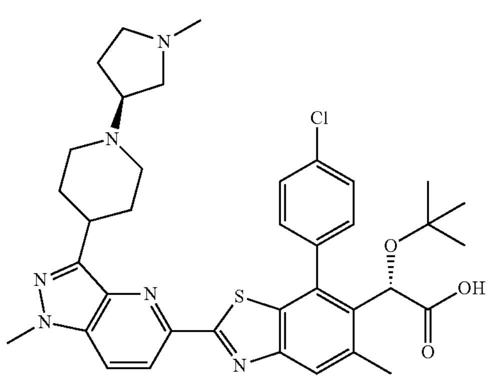 [SMILES: Cc1cc2nc(-c3ccc4c(n3)c(C3CCN([C@H]5CCN(C)C5)CC3)nn4C)sc2c(-c2ccc(Cl)cc2)c1[C@H](OC(C)(C)C)C(=O)O] | 172 | (S)-2-(tert-butoxy)-2-(7-(4-chloro-phenyl)-5-methyl-2-(1-methyl-3-(1-((S)-1-methyl-pyrrolidin-3-yl) piperidin-4-yl)-1H-pyrazolo[4,3-b] pyridin-5-yl) benzo[d]thiazol-6-yl)acetic acid | 687.59 (M + H)+ | $^1$H NMR (400 MHz, Methanol-d$_4$) δ 8.41 (d, J = 8.9 Hz, 1 H), 8.13 (d, J = 8.9 Hz, 1 H), 7.88 (s, 1 H), 7.74-7.65 (m, 1 H), 7.65-7.49 (m, 3 H), 5.25 (s, 1 H), 4.30-4.15 (m, 1 H), 4.09 (s, 3 H), 4.01-3.55 (m, 7 H), 3.53-3.32 (m, 2 H), 3.02 (s, 3 H), 2.74-2.63 (m, 1 H), 2.62 (s, 3 H), 2.61-2.31 (m, 5 H), 0.98 (s, 9 H) | L |

| Structure | Cmpd# | Chemical Name | ES/MS m/z | 1H HMR | Method |
|---|---|---|---|---|---|
| 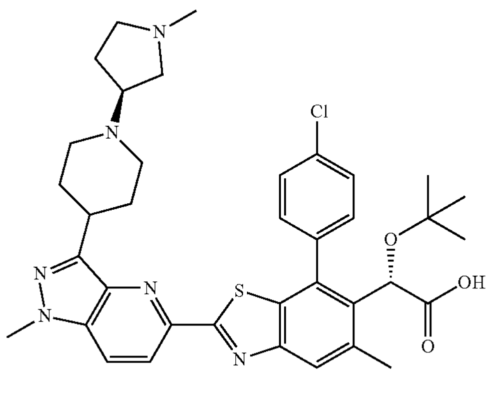 | 173 | (S)-2-(tert-butoxy)-2-(7-(4-chlorophenyl)-2-(3-(1-(2-(dimethylamino)ethyl)piperidin-4-yl)-1-methyl-1H-pyrazolo[4,3-b]pyridin-5-yl)-5-methylbenzo[d]thiazol-6-yl)acetic acid | 675.29 (M + H)+ | $^1$H NMR (400 MHz, Methanol-d$_4$) δ 8.41 (d, J = 8.9 Hz, 1 H), 8.13 (d, J = 9.0 Hz, 1 H), 7.88 (s, 1 H), 7.77-7.66 (m, 1 H), 7.66-7.45 (m, 3 H), 5.24 (s, 1 H), 4.09 (s, 3 H), 3.76-3.46 (m, 9 H), 2.98 (s, 6 H), 2.63 (s, 3 H), 2.56-2.37 (m, 2 H), 2.43-2.25 (m, 2 H), 0.98 (s, 9 H) | L |
| 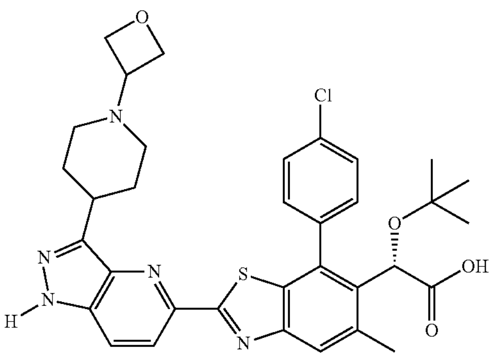 [SMILES: Cc1cc2nc(-c3ccc4[nH]nc(C5CCN(C6COC6)CC5)c4n3)sc2c(-c2ccc(Cl)cc2)c1[C@H](OC(C)(C)C)C(=O)O] | 174 | (S)-2-(tert-butoxy)-2-(7-(4-chlorophenyl)-5-methyl-2-(3-(1-(oxetan-3-yl)piperidin-4-yl)-1H-pyrazolo[4,3-b]pyridin-5-yl)benzo[d]thiazol-6-yl)acetic acid | 646.67 (M + H)+ | $^1$H NMR (400 MHz, Methanol-d$_4$) δ 8.40 (d, J = 8.8 Hz, 1 H), 8.08 (d, J = 8.8 Hz, 1 H), 7.87 (s, 1 H), 7.74-7.65 (m, 1 H), 7.66-7.48 (m, 3 H), 5.24 (s, 1 H), 4.86-4.73 (m, 4 H), 4.45 (dt, J = 13.4, 6.9 Hz, 1 H), 3.74-3.52 (m, 3 H), 3.23-3.01 (m, 2 H), 2.62 (s, 3 H), 2.59-2.41 (m, 2 H), 2.41-2.11 (m, 2 H), 0.98 (s, 9 H) | L |
| 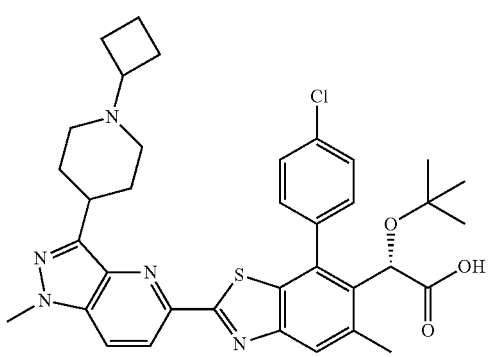 [SMILES: Cc1cc2nc(-c3ccc4c(n3)c(C3CCN(C5CCC5)CC3)nn4C)sc2c(-c2ccc(Cl)cc2)c1[C@H](OC(C)(C)C)C(=O)O] | 175 | (S)-2-(tert-butoxy)-2-(7-(4-chlorophenyl)-5-methyl-2-(1-methyl-3-(1-(oxetan-3-yl)piperidin-4-yl)-1H-pyrazolo[4,3-b]pyridin-5-yl)benzo[d]thiazol-6-yl)acetic acid | 660.53 (M + H)+ | $^1$H NMR (400 MHz, Methanol-d$_4$) δ 8.37 (d, J = 8.9 Hz, 1 H), 8.10 (d, J = 8.9 Hz, 1 H), 7.86 (d, J = 0.9 Hz, 1 H), 7.69 (dt, J = 7.4, 1.9 Hz, 1 H), 7.65-7.48 (m, 3 H), 5.24 (s, 1 H), 4.88-4.67 (m, 4 H), 4.45 (p, J = 6.4 Hz, 1 H), 4.06 (s, 3 H), 3.72-3.50 (m, 3 H), 3.21-2.98 (m, 2 H), 2.62 (d, J = 0.8 Hz, 3 H), 2.58-2.38 (m, 2 H), 2.36-2.12 (m, 2 H), 0.98 (s, 9 H). | L |

| Structure | Cmpd# | Chemical Name | ES/MS m/z | 1H HMR | Method |
|---|---|---|---|---|---|
| 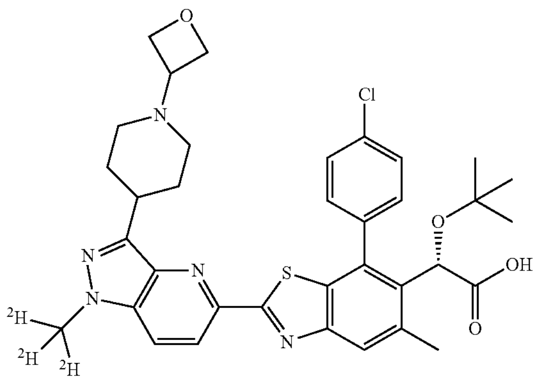 [SMILES: [2H]C([2H])([2H])n1nc(C2CCN(C3COC3)CC2)c2nc(-c3nc4cc(C)c([C@H](OC(C)(C)C)C(=O)O)c(-c5ccc(Cl)cc5)c4s3)ccc21] | 176 | (S)-2-(tert-butoxy)-2-(7-(4-chloro-phenyl)-5-methyl-2-(1-(methyl-d3)-3-(1-(oxetan-3-yl)piperidin-4-yl)-1H-pyrazolo[4,3-b]pyridin-5-yl)benzo[d]thiazol-6-yl)acetic acid | 663.73 (M + H)+ | $^1$H NMR (400 MHz, Methanol-$d_4$) δ 8.36 (d, J = 8.9 Hz, 1 H), 8.10 (d, J = 8.9 Hz, 1 H), 7.85 (s, 1 H), 7.69 (dt, J = 7.7, 1.9 Hz, 1 H), 7.66-7.50 (m, 3 H), 5.24 (s, 1 H), 4.88-4.66 (m, 4 H), 4.45 (p, J = 6.5 Hz, 1 H), 3.76-3.47 (m, 3 H), 3.23-3.01 (m, 2 H), 2.62 (s, 3 H), 2.56-2.38 (m, 2 H), 2.38-2.13 (m, 2 H), 0.98 (s, 9 H). | L |
| 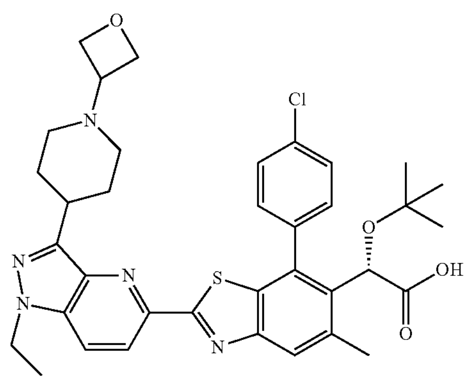 [SMILES: CCn1nc(C2CCN(C3COC3)CC2)c2nc(-c3nc4cc(C)c([C@H](OC(C)(C)C)C(=O)O)c(-c5ccc(Cl)cc5)c4s3)ccc21] | 177 | (S)-2-(tert-butoxy)-2-(7-(4-chloro-phenyl)-2-(1-ethyl-3-(1-(oxetan-3-yl)piperidin-4-yl)-1H-pyrazolo[4,3-b]pyridin-5-yl)-5-methylbenzo[d]thiazol-6-yl)acetic acid | 674.68 (M + H)+ | $^1$H NMR (400 MHz, Methanol-$d_4$) δ 8.35 (d, J = 8.9 Hz, 1 H), 8.12 (d, J = 8.9 Hz, 1 H), 7.85 (s, 1 H), 7.73-7.65 (m, 1 H), 7.65-7.49 (m, 3 H), 5.24 (s, 1 H), 4.88-4.77 (m, 4 H), 4.51-4.37 (m, 4 H), 3.71-3.51 (m, 2 H), 3.21-3.03 (m, 2 H), 2.62 (s, 3 H), 2.56-2.39 (m, 2 H), 2.37-2.14 (m, 2 H), 1.49 (t, J = 7.2 Hz, 3 H), 0.97 (s, 9 H) | L |
| 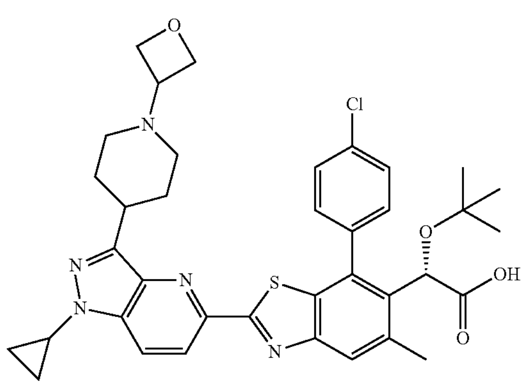 | 178 | (S)-2-(tert-butoxy)-2-(7-(4-chloro-phenyl)-2-(1-cyclo-propyl-3-(1-(oxetan-3-yl)piperidin-4-yl)-1H-pyrazolo[4,3-b]pyridin-5-yl)-5-methylbenzo[d]thiazol-6-yl)acetic acid | 686.50 (M + H)+ | $^1$H NMR (400 MHz, Methanol-$d_4$) δ 8.37 (dt, J = 8.9, 1.7 Hz, 1 H), 8.19 (dt, J = 8.7, 1.6 Hz, 1 H), 7.86 (s, 1 H), 7.75-7.64 (m, 1 H), 7.64-7.48 (m, 3 H), 5.24 (s, 1 H), 4.89-4.73 (m, 4 H), 4.53-4.35 (m, 1 H), 3.80-3.43 (m, 4 H), 3.24-2.98 (m, 2 H), 2.62 (s, 3 H), 2.56-2.35 (m, 2 H), 2.37-2.15 (m, 2 H), 1.26-1.14 (m, 4 H), 0.98 (s, 9 H) | L |

-continued

| Structure | Cmpd# | Chemical Name | ES/MS m/z | 1H HMR | Method |
|---|---|---|---|---|---|
| 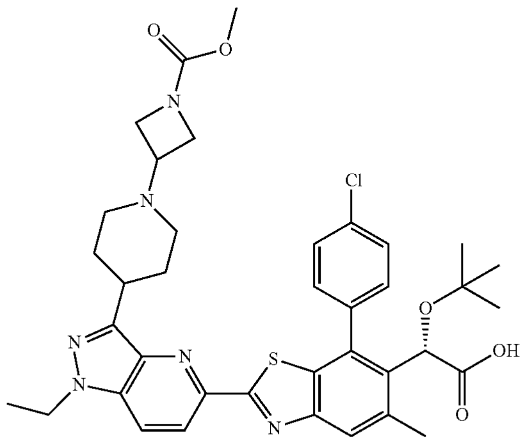 [SMILES: CCn1nc(C2CCN(C3CN(C(=O)OC)C3)CC2)c2nc(-c3nc4cc(C)c([C@H](OC(C)(C)C)C(=O)O)c(-c5ccc(Cl)cc5)c4s3)ccc21] | 179 | (S)-2-(tert-butoxy)-2-(7-(4-chlorophenyl)-2-(1-ethyl-3-(1-(1-(methoxycarbonyl)azetidin-3-yl)piperidin-4-yl)-1H-pyrazolo[4,3-b]pyridin-5-yl)-5-methylbenzo[d]thiazol-6-yl)acetic acid | 731.60 (M + H)+ | $^1$H NMR (400 MHz, Methanol-$d_4$) δ 8.41 (d, J = 8.9 Hz, 1 H), 8.18 (d, J = 8.9 Hz, 1 H), 7.88 (s, 1 H), 7.75-7.65 (m, 1 H), 7.65-7.47 (m, 3 H), 5.24 (s, 1 H), 4.48 (q, J = 7.2 Hz, 2 H), 4.42-4.27 (m, 2 H), 4.28-4.13 (m, 2 H), 4.17-4.06 (m, 1 H), 3.77-3.66 (m, 4 H), 3.66-3.54 (m, 2 H), 3.24-3.06 (m, 2 H), 2.62 (s, 3 H), 2.61-2.41 (m, 2 H), 2.39-2.09 (m, 2 H), 1.50 (t, J = 7.2 Hz, 3 H), 0.98 (s, 9 H) | L |
| 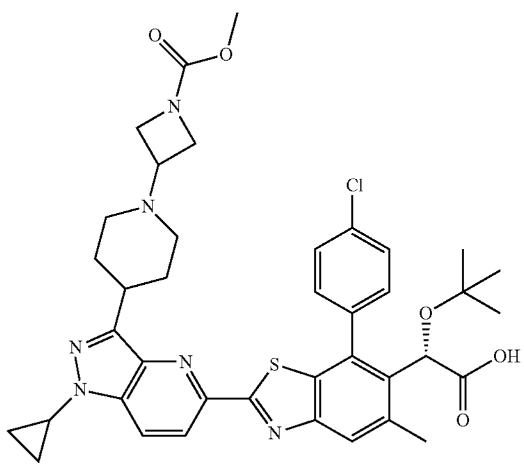 | 180 | (S)-2-(tert-butoxy)-2-(7-(4-chlorophenyl)-2-(1-cyclopropyl-3-(1-(1-(methoxycarbonyl)azetidin-3-yl)piperidin-4-yl)-1H-pyrazolo[4,3-b]pyridin-5-yl)-5-methylbenzo[d]thiazol-6-yl)acetic acid | 744.04 (M + H)+ | $^1$H NMR (400 MHz, Methanol-$d_4$) δ 8.44 (d, J = 8.8 Hz, 1 H), 8.26 (d, J = 8.9 Hz, 1 H), 7.89 (s, 1 H), 7.75-7.65 (m, 1 H), 7.65-7.52 (m, 3 H), 5.24 (s, 1 H), 4.46-4.28 (m, 2 H), 4.28-4.08 (m, 2 H), 4.17-4.03 (m, 2 H), 1.29-1.11 (m, 5 H), 3.65-3.55 (m, 1 H), 3.25-3.07 (m, 2 H), 2.63 (s, 3 H), 2.57-2.41 (m, 2 H), 2.33-2.14 (m, 2 H), 1.29-1.11 (m, 4 H), 0.98 (s, 9 H) | L |
| 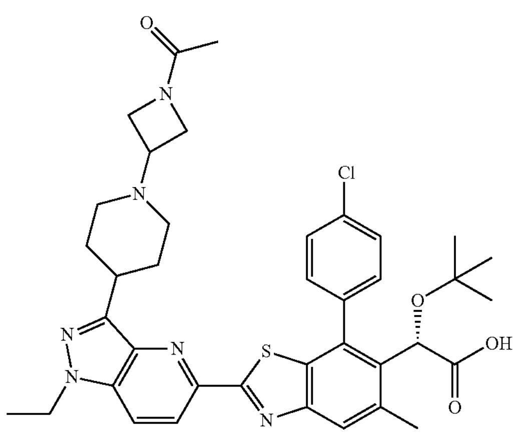 [SMILES: CCn1nc(C2CCN(C3CN(C(C)=O)C3)CC2)c2nc(-c3nc4cc(C)c([C@H](OC(C)(C)C)C(=O)O)c(-c5ccc(Cl)cc5)c4s3)ccc21] | 181 | (S)-2-(2-(3-(1-(1-acetylazetidin-3-yl)piperidin-4-yl)-1-ethyl-1H-pyrazolo[4,3-b]pyridin-5-yl)-7-(4-chlorophenyl)-5-methylbenzo[d]thiazol-6-yl)-2-(tert-butoxy)acetic acid | 715.57 (M + H)+ | $^1$H NMR (400 MHz, Methanol-$d_4$) δ 8.40 (dt, J = 8.9, 1.5 Hz, 1 H), 8.17 (d, J = 9.1 Hz, 1 H), 7.88 (s, 1 H), 7.76-7.66 (m, 1 H), 7.66-7.43 (m, 3 H), 5.24 (s, 1 H), 4.63-4.52 (m, 1 H), 4.47 (q, J = 7.3 Hz, 2 H), 4.38-4.26 (m, 1 H), 4.24-4.07 (m, 3 H), 3.82-3.49 (m, 3 H), 3.28-3.05 (m, 2 H), 2.62 (s, 3 H), 2.61-2.44 (m, 2 H), | L |

| Structure | Cmpd# | Chemical Name | ES/MS m/z | 1H HMR | Method |
|---|---|---|---|---|---|
| | | | | 2.38-2.13 (m, 2 H), 1.94 (s, 3 H), 1.50 (t, J = 7.2 Hz, 3 H), 0.98 (s, 9 H) | |
| 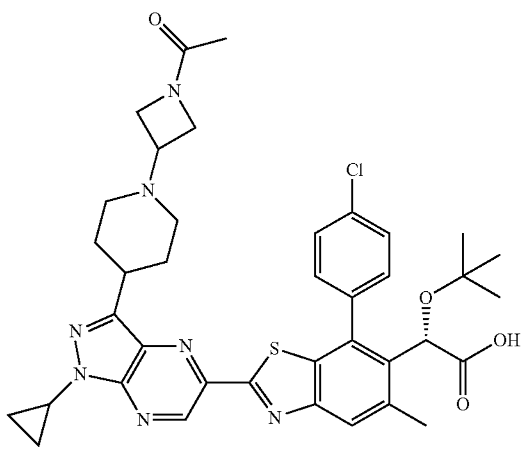 | 182 | (S)-2-(2-(3-(1-(1-acetylazetidin-3-yl)piperidin-4-yl)-1-cyclopropyl-1H-pyrazolo[4,3-b]pyridin-5-yl)-7-(4-chlorophenyl)-5-methylbenzo[d]thiazol-6-yl)-2-(tert-butoxy) acetic acid | 727.59 (M + H)+ | $^1$H NMR (400 MHz, Methanol-d$_4$) δ 8.44 (d, J = 8.9 Hz, 1 H), 8.25 (d, J = 8.8 Hz, 1 H), 7.88 (s, 1 H), 7.69 (d, J = 8.1 Hz, 1 H), 7.65-7.48 (m, 3 H), 5.23 (s, 1 H), 4.65-4.51 (m, 1 H), 4.51-4.34 (m, 1 H), 4.38-4.23 (m, 1 H), 4.24-4.07 (m, 3 H), 3.80-3.67 (m, 3 H), 3.26-3.07 (m, 2 H), 2.62 (s, 3 H), 2.59-2.37 (m, 2 H), 2.38-2.11 (m, 2 H), 1.94 (s, 3 H), 1.25-1.17 (m, 4 H), 0.97 (s, 9 H) | L |
| 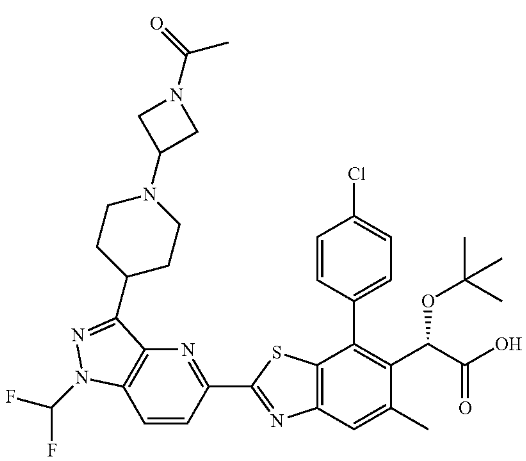 [SMILES: CC(=O)N1CC(N2CCC(c3nn(C(F)F)c4ccc(-c5nc6cc(C)c([C@H](OC(C)(C)C)C(=O)O)c(-c7ccc(Cl)cc7)c6s5)nc34)CC2)C1] | 183 | (S)-2-(2-(3-(1-(1-acetylazetidin-3-yl)piperidin-4-yl)-1-(difluoromethyl)-1H-pyrazolo[4,3-b]pyridin-5-yl)-7-(4-chlorophenyl)-5-methylbenzo[d]thiazol-6-yl)-2-(tert-butoxy) acetic acid | 737.52 (M + H)+ | $^1$H NMR (400 MHz, Methanol-d$_4$) δ 8.57 (dd, J = 8.9, 1.1 Hz, 1 H), 8.37 (d, J = 8.8 Hz, 1 H), 7.98-7.64 (m, 3 H), 7.64-7.53 (m, 3 H), 5.24 (s, 1 H), 4.63-4.50 (m, 1 H), 4.50-4.38 (m, 1 H), 4.37-4.23 (m, 1 H), 4.24-4.06 (m, 2 H), 3.84-3.56 (m, 3 H), 3.27-3.06 (m, 2 H), 2.62 (s, 3 H), 2.59-2.41 (m, 2 H), 2.39-2.11 (m, 2 H), 1.93 (s, 3 H), 0.98 (s, 9 H) | L |
| 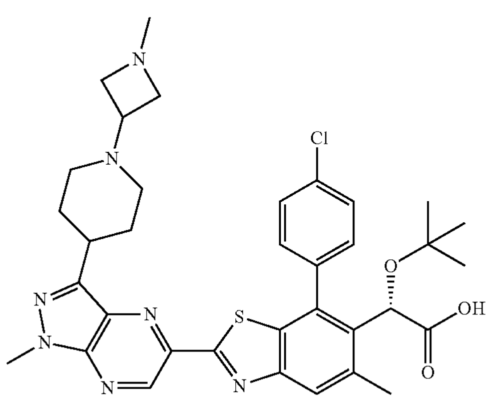 [SMILES: Cc1cc2nc(-c3cnc4c(n3)c(C3CCN(C5CN(C)C5)CC3)nn4C)sc2c(-c2ccc(Cl)cc2)c1[C@H](OC(C)(C)C)C(=O)O] | 184 | (S)-2-(tert-butoxy)-2-(7-(4-chlorophenyl)-5-methyl-2-(1-methyl-3-(1-(1-methylazetidin-3-yl)piperidin-4-yl)-1H-pyrazolo[4,3-b]pyridin-5-yl)benzo[d]thiazol-6-yl) acetic acid | 673.54 (M + H)+ | $^1$H NMR (400 MHz, Methanol-d$_4$) δ 8.40 (d, J = 8.9 Hz, 1 H), 8.12 (d, J = 8.9 Hz, 1 H), 7.88 (s, 1 H), 7.70 (dd, J = 9.3, 2.0 Hz, 1 H), 7.65-7.53 (m, 3 H), 5.25 (s, 1 H), 4.48-4.27 (m, 5 H), 4.09 (s, 3 H), 4.02-3.84 (m, 1 H), 3.58-3.43 (m, 1 H), 3.02 (s, 3 H), 2.85-2.66 (m, | L |

-continued

| Structure | Cmpd# | Chemical Name | ES/MS m/z | 1H HMR | Method |
|---|---|---|---|---|---|
| | | | | 2 H), 2.62 (s, 3 H), 2.46-2.29 (m, 2 H), 2.33-2.16 (m, 3 H), 0.98 (s, 9 H) | |
| 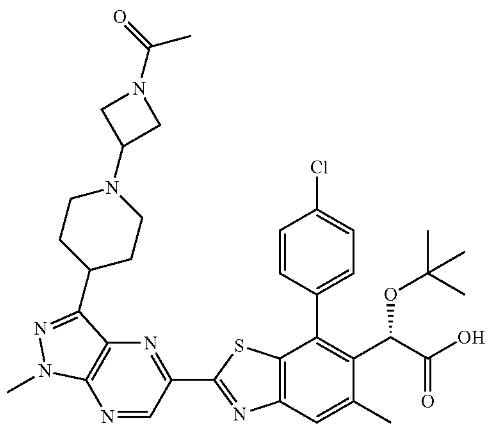 | 185 | (S)-2-(2-(3-(1-(1-acetylazetidin-3-yl)piperidin-4-yl)-1-methyl-1H-pyrazolo[4,3-b]pyridin-5-yl)-7-(4-chlorophenyl)-5-methylbenzo[d]thiazol-6-yl)-2-(tert-butoxy)acetic acid | 701.50 (M + H)+ | ¹H NMR (400 MHz, Methanol-d₄) δ 8.42 (d, J = 8.9 Hz, 1 H), 8.15 (d, J = 8.9 Hz, 1 H), 7.88 (s, 1 H), 7.77-7.66 (m, 1 H), 7.66-7.49 (m, 3 H), 5.24 (s, 1 H), 4.65-4.50 (m, 1 H), 4.51-4.38 (m, 1 H), 4.40-4.20 (m, 2 H), 4.22-4.10 (m, 2 H), 4.10 (s, 3 H), 3.84-3.52 (m, 2 H), 3.30-3.08 (m, 2 H), 2.62 (s, 3 H), 2.61-2.42 (m, 2 H), 2.34-2.16 (m, 2 H), 1.94 (s, 3 H), 0.98 (s, 9 H) | L |
| 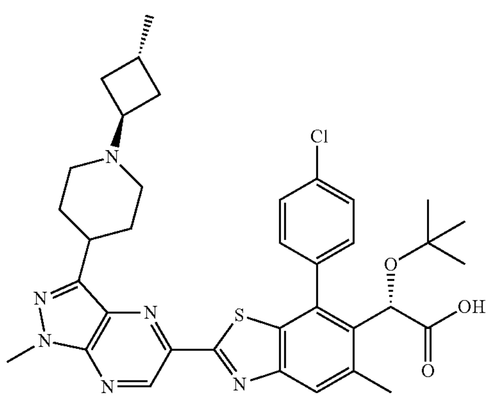 [SMILES: Cc1cc2nc(-c3cnc4c(n3)c(C3CCN([C@H]5C[C@H](C)C5)CC3)nn4C)sc2c(-c2ccc(Cl)cc2)c1[C@H](OC(C)(C)C)C(=O)O] | 186 | (S)-2-(tert-butoxy)-2-(7-(4-chlorophenyl)-2-(3-(1-((1r,3r)-3-hydroxycyclobutyl)piperidin-4-yl)-1-methyl-1H-pyrazolo[4,3-b]pyridin-5-yl)-5-methylbenzo[d]thiazol-6-yl)acetic acid | 674.50 (M + H)+ | ¹H NMR (400 MHz, Methanol-d₄) δ 8.42 (d, J = 8.9 Hz, 1 H), 8.22-8.07 (m, 1 H), 7.88 (s, 1 H), 7.72-7.66 (m, 1 H), 7.66-7.50 (m, 3 H), 5.25 (s, 1 H), 4.49-4.33 (m, 1 H), 4.09 (s, 3 H), 4.01-3.86 (m, 2 H), 3.72-3.50 (m, 4 H), 3.14-3.01 (m, 2 H), 2.63 (s, 3 H), 2.60-2.43 (m, 3 H), 2.43-2.12 (m, 3 H), 0.98 (s, 9 H) | L |
| 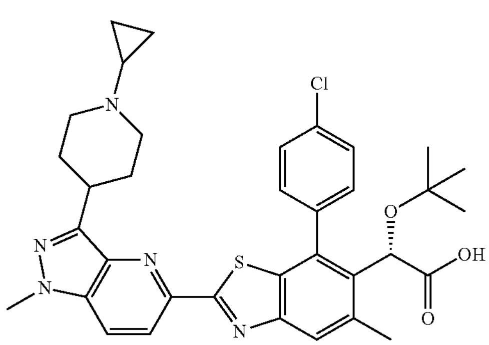 | 187 | (S)-2-(tert-butoxy)-2-(7-(4-chlorophenyl)-2-(3-(1-cyclopropylpiperidin-4-yl)-1-methyl-1H-pyrazolo[4,3-b]pyridin-5-yl)-5-methylbenzo[d]thiazol-6-yl)acetic acid | 644.45 (M + H)+ | ¹H NMR (400 MHz, Methanol-d₄) δ 8.39 (d, J = 8.9 Hz, 1 H), 8.12 (d, J = 9.0 Hz, 1 H), 7.87 (s, 1 H), 7.70 (d, J = 8.3 Hz, 1 H), 7.65-7.47 (m, 3 H), 5.24 (s, 1 H), 4.07 (s, 3 H), 3.87-3.69 (m, 2 H), 3.67-3.49 (m, 2 H), 3.53-3.36 (m, 1 H), 2.94-2.73 (m, 1 H), 2.62 (s, 3 H), 2.55-2.39 (m, 2 H), 2.35-2.05 (m, 2 H), 1.07-0.98 (m, 4 H), 0.98 (s, 9 H) | L |

| Structure | Cmpd# | Chemical Name | ES/MS m/z | 1H HMR | Method |
|---|---|---|---|---|---|
| 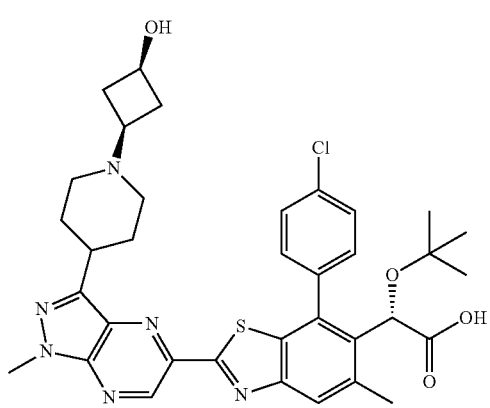 [SMILES: Cc1cc2nc(-c3cnc4c(n3)c(C3CCN([C@H]5C[C@@H](O)C5)CC3)nn4C)sc2c(-c2ccc(Cl)cc2)c1[C@H](OC(C)(C)C)C(=O)O] | 188 | (S)-2-(tert-butoxy)-2-(7-(4-chlorophenyl)-2-(3-(1-((1s,3s)-3-hydroxycyclobutyl)piperidin-4-yl)-1-methyl-1H-pyrazolo[4,3-b]pyrazin-5-yl)-5-methylbenzo[d]thiazol-6-yl)acetic acid | 674.63 (M + H)+ | $^1$H NMR (400 MHz, Methanol-d$_4$) δ 8.39 (d, J = 8.9 Hz, 1 H), 8.11 (d, J = 8.9 Hz, 1 H), 7.87 (d, J = 0.9 Hz, 1 H), 7.69 (dt, J = 7.5, 1.9 Hz, 1 H), 7.65-7.50 (m, 3 H), 5.24 (s, 1 H), 4.15-4.01 (m, 4 H), 3.69-3.50 (m, 2 H), 3.29-3.12 (m, 2 H), 3.06 (ddd, J = 17.0, 12.6, 2.9 Hz, 2 H), 2.84-2.67 (m, 2 H), 2.62 (s, 3 H), 2.47 (d, J = 14.4 Hz, 2 H), 2.40-1.98 (m, 4 H), 0.98 (s, 9 H) | L |
| 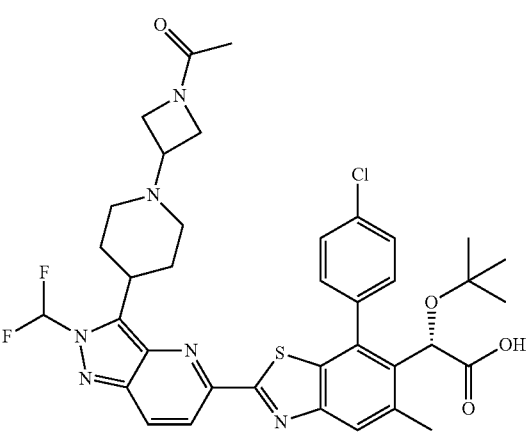 [SMILES: CC(=O)N1CC(N2CCC(c3c4nc(-c5nc6cc(C)c([C@H](OC(C)(C)C)C(=O)O)c(-c7ccc(Cl)cc7)c6s5)ccc4nn3C(F)F)CC2)C1] | 189 | (S)-2-(2-(3-(1-(1-acetylazetidin-3-yl)piperidin-4-yl)-2-(difluoromethyl)-2H-pyrazolo[4,3-b]pyridin-5-yl)-7-(4-chlorophenyl)-5-methylbenzo[d]thiazol-6-yl)-2-(tert-butoxy)acetic acid | 737.82 (M + H)+ | $^1$H NMR (400 MHz, Methanol-d$_4$) δ 8.46 (d, J = 9.4 Hz, 1 H), 8.27 (d, J = 9.3 Hz, 1 H), 8.15-7.77 (m, 2 H), 7.77-7.66 (m, 1 H), 7.61 (d, J = 11.3 Hz, 3 H), 5.21 (s, 1 H), 4.67-4.50 (m, 1 H), 4.50-4.37 (m, 1 H), 4.38-4.24 (m, 1 H), 4.24-4.09 (m, 2 H), 3.98-3.83 (m, 1 H), 3.78 (dd, J = 29.3, 12.6 Hz, 2 H), 3.28-3.09 (m, 2 H), 3.06-2.65 (m, 2 H), 2.64 (s, 3 H), 2.43-2.25 (m, 2 H), 2.04-1.91 (m, 3 H), 0.98 (d, J = 1.4 Hz, 9 H) | L |

| Structure | Cmpd# | Chemical Name | ES/MS m/z | 1H HMR | Method |
|---|---|---|---|---|---|
| 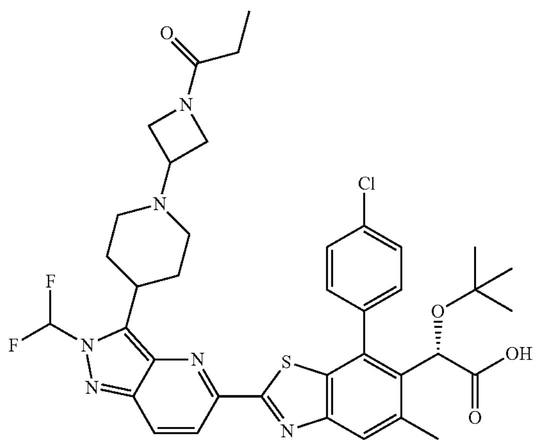 [SMILES: CCC(=O)N1CC(N2CCC(c3c4nc(-c5nc6cc(C)c([C@H](OC(C)(C)C)C(=O)O)c(-c7ccc(Cl)cc7)c6s5)ccc4nn3C(F)F)CC2)C1] | 190 | (S)-2-(tert-butoxy)-2-(7-(4-chlorophenyl)-2-(2-(difluoromethyl)-3-(1-(1-(methoxycarbonyl)azetidin-3-yl)piperidin-4-yl)-2H-pyrazolo[4,3-b]pyridin-5-yl)-5-methylbenzo[d]thiazol-6-yl)acetic acid | 753.57 (M + H)+ | $^1$H NMR (400 MHz, Methanol-$d_4$) δ 8.46 (d, J = 9.2 Hz, 1 H), 8.26 (d, J = 9.3 Hz, 1 H), 8.16-7.77 (m, 2 H), 7.77-7.67 (m, 1 H), 7.67-7.49 (m, 3 H), 5.21 (s, 1 H), 4.43-4.27 (m, 2 H), 4.28-4.07 (m, 2 H), 3.98-3.79 (m, 2 H), 3.83-3.68 (m, 5 H), 3.25-3.08 (m, 2 H), 3.00-2.83 (m, 1 H), 2.83-2.64 (m, 1 H), 2.64 (s, 3 H), 2.42-2.24 (m, 2 H), 0.98 (s, 9 H) | L |
| 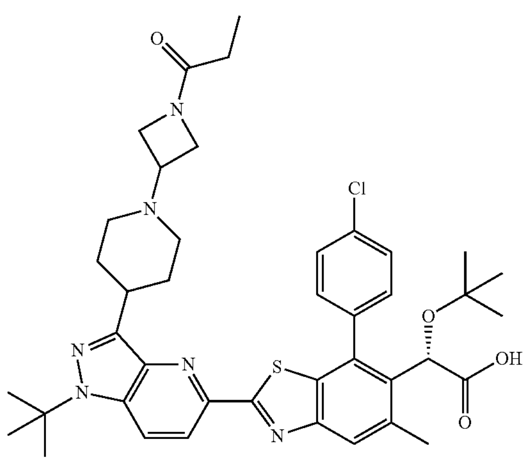 | 191 | (S)-2-(tert-butoxy)-2-(7-(4-chlorophenyl)-2-(3-(1-(1-(methoxycarbonyl)azetidin-3-yl)piperidin-4-yl)-1-(methyl-d3)-1H-pyrazolo[4,3-b]pyridin-5-yl)-5-methylbenzo[d]thiazol-6-yl)acetic acid | 720.56 (M + H)+ | 1H NMR (400 MHz, Chloroform-d) δ 8.62 (d, J = 8.9 Hz, 1H), 7.97 (s, 1H), 7.93 (d, J = 8.9 Hz, 1H), 7.62-7.43 (m, 4H), 5.18 (s, 1H), 4.33-4.15 (m, 5H), 3.97-3.93 (m, 1H), 3.77-3.63 (m, 3H), 3.44 (t, J = 5.5 Hz, 1H), 2.86-2.75 (m, 3H), 2.62 (s, 3H), 2.28-2.18 (m, 1H), 2.05 (s, 3H), 0.98 (s, 9H). | L |
| 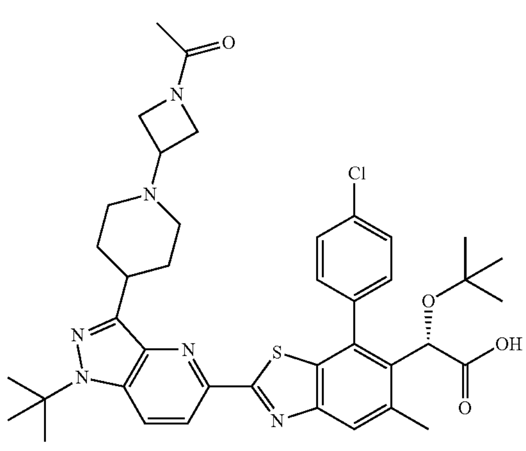 | 192 | (S)-2-(2-(3-(1-(1-acetylazetidin-3-yl)piperidin-4-yl)-1-(methyl-d3)-1H-pyrazolo[4,3-b]pyridin-5-yl)-7-(4-chlorophenyl)-5-methylbenzo[d]thiazol-6-yl)-2-(tert-butoxy)acetic acid | 704.60 (M + H)+ | $^1$H NMR (400 MHz, Methanol-$d_4$) δ 8.43 (d, J = 8.4 Hz, 1H), 8.15 (d, J = 8.8 Hz, 1H), 7.89 (s, 1H), 7.71-7.66 (m, 1H), 7.65-7.53 (m, 3H), 5.24 (s, 1H), 4.62-4.23 (m, 3H), 4.21-4.07 (m, 3H), 3.80-3.55 (m, 3H), 2.63 (s, 3H), 2.58-2.13 (m, 5H), 1.94 (s, 3H), 0.98 (s, 9H). | L |

-continued

| Structure | Cmpd# | Chemical Name | ES/MS m/z | 1H HMR | Method |
|---|---|---|---|---|---|
| 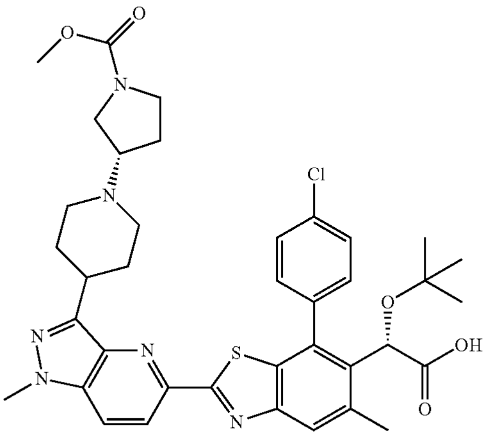 [SMILES: COC(=O)N1CC[C@H](N2CCC(c3nn(C)c4ccc(-c5nc6cc(C)c([C@H](OC(C)(C)C)C(=O)O)c(-c7ccc(Cl)cc7)c6s5)nc34)CC2)C1] | 193 | (S)-2-(tert-butoxy)-2-(7-(4-chlorophenyl)-2-(3-(1-((S)-1-(methoxycarbonyl)pyrrolidin-3-yl)piperidin-4-yl)-1-methyl-1H-pyrazolo[4,3-b]pyridin-5-yl)-5-methylbenzo[d]thiazol-6-yl) acetic acid | 731.58 (M + H)+ | $^1$H NMR (400 MHz, Methanol-d$_4$) δ 8.19 (d, J = 8.9 Hz, 1H), 7.91 (d, J = 8.9 Hz, 1H), 7.77 (s, 1H), 7.73-7.67 (m, 1H), 7.63-7.51 (m, 3H), 5.24 (s, 1H), 4.03-3.83 (m, 5H), 3.81-3.39 (m, 10H), 3.39-3.18 (m, 1H), 2.61 (s, 3H), 2.56-2.06 (m, 6H), 0.97 (s, 9H). | L |
| 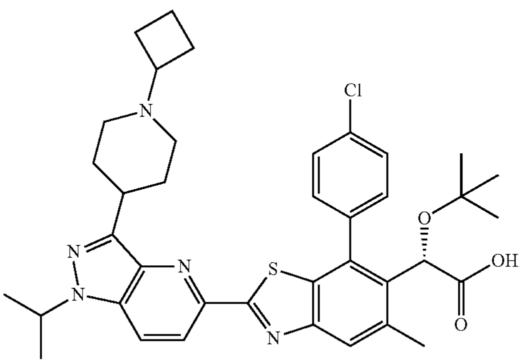 | 194 | (S)-2-(tert-butoxy)-2-(7-(4-chlorophenyl)-2-(1-(difluoromethyl)-3-(1-(oxetan-3-yl)piperidin-4-yl)-1H-pyrazolo[4,3-b]pyridin-5-yl)-5-methylbenzo[d]thiazol-6-yl) acetic acid | 696.43 (M + H)+ | $^1$H NMR (400 MHz, Methanol-d$_4$) δ 8.58 (d, J = 8.9, 0.9 Hz, 1H), 8.38 (d, J = 8.9 Hz, 1H), 7.99-7.82 (m, 2H), 7.73-7.55 (m, 4H), 5.25 (s, 1H), 4.85-4.73 (m, 3H), 4.52-4.38 (m, 1H), 3.80-3.58 (m, 4H), 3.24-3.08 (m, 3H), 2.67-2.51 (m, 4H), 2.35-2.15 (m, 2H), 0.98 (s, 9H). | L |
| 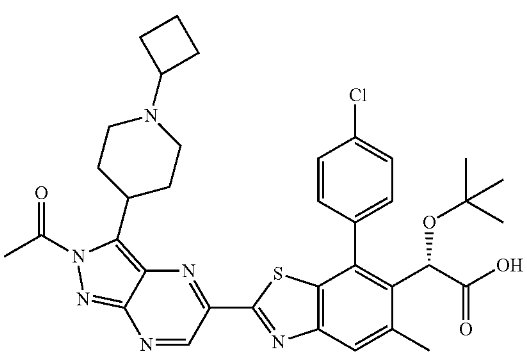 | 195 | (S)-2-(tert-butoxy)-2-(7-(4-chlorophenyl)-2-(2-(difluoromethyl)-3-(1-(oxetan-3-yl)piperidin-4-yl)-2H-pyrazolo[4,3-b]pyridin-5-yl)-5-methylbenzo[d]thiazol-6-yl) acetic acid | 696.43 (M + H)+ | $^1$H NMR (400 MHz, Methanol-d$_4$) δ 8.46 (d, J = 9.3 Hz, 1H), 8.27 (d, J = 9.4 Hz, 1H), 8.14-7.80 (m, 2H), 7.74-7.57 (m, 4H), 5.23 (s, 1H), 4.84-4.75 (m, 1H), 4.53-4.35 (m, 1H), 3.96-3.81 (m, 2H), 3.69 (dd, J = 27.4, 12.4 Hz, 3H), 3.22-2.67 (m, 4H), 2.64 (s, 3H), 2.41-2.20 (m, 3H), 0.99 (d, J = 0.9 Hz, 9H). | L |

| Structure | Cmpd# | Chemical Name | ES/MS m/z | 1H HMR | Method |
|---|---|---|---|---|---|
| 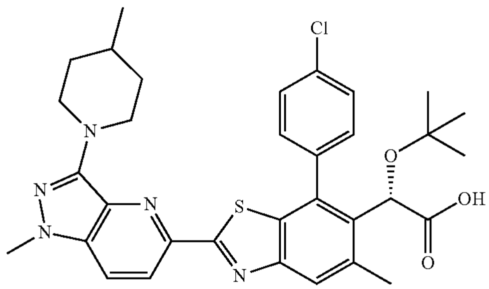 [SMILES: Cc1cc2nc(-c3ccc4c(n3)c(N3CCC(C)CC3)nn4C)sc2c(-c2ccc(Cl)cc2)c1[C@H](OC(C)(C)C)C(=O)O] | 196 | (S)-2-(tert-butoxy)-2-(7-(4-chlorophenyl)-5-methyl-2-(1-methyl-3-(4-methylpiperazin-1-yl)-1H-pyrazolo[4,3-b]pyridin-5-yl)benzo[d]thiazol-6-yl)acetic acid | 619.3 (M + H)+ | 1H NMR (400 MHz, Methanol-d4) δ 8.34 (d, J = 9.0 Hz, 1H), 7.98 (d, J = 9.0 Hz, 1H), 7.85 (s, 1H), 7.72-7.65 (m, 1H), 7.62-7.52 (m, 3H), 5.22 (s, 1H), 4.74 (s, 2H), 3.92 (s, 3H), 3.60 (s, 2H), 3.33 (s, 2H), 2.94 (s, 3H), 2.61 (s, 3H), 0.96 (s, 9H). | M |
| 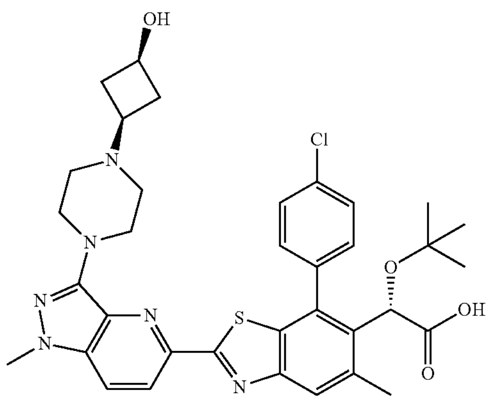 [SMILES: Cc1cc2nc(-c3ccc4c(n3)c(N3CCN([C@H]5C[C@@H](O)C5)CC3)nn4C)sc2c(-c2ccc(Cl)cc2)c1[C@H](OC(C)(C)C)C(=O)O] | 197 | (S)-2-(tert-butoxy)-2-(7-(4-chlorophenyl)-2-(3-(4-((1s,3s)-3-hydroxycyclobutyl)piperazin-1-yl)-1-methyl-1H-pyrazolo[4,3-b]pyridin-5-yl)-5-methylbenzo[d]thiazol-6-yl)acetic acid | 676.37 (M + H)+ | $^1$H NMR (400 MHz, Methanol-d$_4$) δ 8.36 (d, J = 9.0 Hz, 1 H), 8.00 (d, J = 9.0 Hz, 1 H), 7.86 (s, 1 H), 7.68 (dd, J = 8.6, 2.2 Hz, 1 H), 7.64-7.50 (m, 3 H), 5.22 (s, 1 H), 4.84-4.66 (m, 3 H), 4.14-3.99 (m, 1 H), 3.94 (s, 3 H), 3.68-3.52 (m, 2 H), 3.41-3.33 (m, 2 H), 3.23-3.02 (m, 2 H), 2.86-2.67 (m, 2 H), 2.61 (s, 3 H), 2.16-1.99 (m, 2 H), 0.96 (s, 9 H) | M |
| 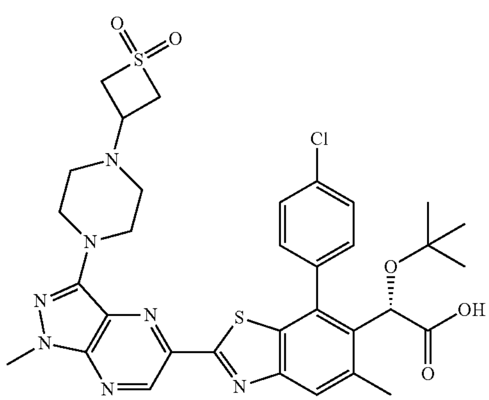 [SMILES: Cc1cc2nc(-c3cnc4c(n3)c(N3CCN(C5CS(=O)(=O)C5)CC3)nn4C)sc2c(-c2ccc(Cl)cc2)c1[C@H](OC(C)(C)C)C(=O)O] | 198 | (S)-2-(tert-butoxy)-2-(7-(4-chlorophenyl)-2-(3-(4-(1,1-dioxidothietan-3-yl)piperazin-1-yl)-1-methyl-1H-pyrazolo[4,3-b]pyridin-5-yl)-5-methylbenzo[d]thiazol-6-yl)acetic acid | 709.10 (M + H)+ | $^1$H NMR (400 MHz, Methanol-d$_4$) δ 8.33 (d, J = 9.0 Hz, 1 H), 7.95 (d, J = 9.0 Hz, 1 H), 7.85 (s, 1 H), 7.77-7.63 (m, 1 H), 7.64-7.44 (m, 3 H), 5.22 (s, 1 H), 4.43-4.12 (m, 4 H), 3.91 (s, 3 H), 3.92-3.83 (m, 4 H), 3.62-3.45 (m, 1 H), 2.95-2.81 (m, 4 H), 2.61 (s, 3 H), 0.96 (s, 9 H) | M |

| Structure | Cmpd# | Chemical Name | ES/MS m/z | 1H HMR | Method |
|---|---|---|---|---|---|
| 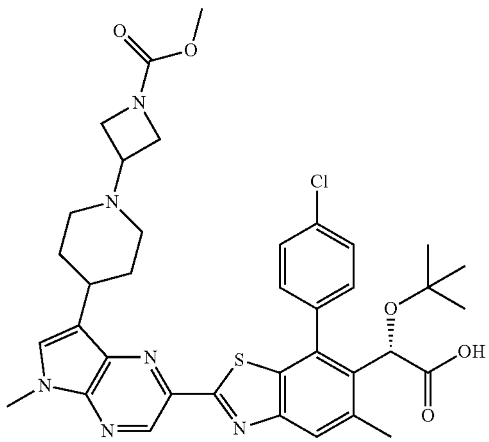 [SMILES: COC(=O)N1CC(N2CCC(c3cn(C)c4ncc(-c5nc6cc(C)c([C@H](OC(C)(C)C)C(=O)O)c(-c7ccc(Cl)cc7)c6s5)nc34)CC2)C1] | 199 | (S)-2-(tert-butoxy)-2-(7-(4-chlorophenyl)-2-(7-(1-(1-(methoxycarbonyl)azetidin-3-yl)piperidin-4-yl)-5-methyl-5H-pyrrolo[2,3-b]pyrazin-2-yl)-5-methylbenzo[d]thiazol-6-yl)acetic acid | 717.57 (M + H)+ | $^1$H NMR (400 MHz, Methanol-d$_4$) δ 9.21 (s, 1 H), 7.86 (s, 1 H), 7.74-7.63 (m, 2 H), 7.64-7.53 (m, 3 H), 5.24 (s, 1 H), 4.40-4.25 (m, 3 H), 4.26-4.17 (m, 2 H), 4.18-4.07 (m, 1 H), 3.87 (s, 3 H), 3.73 (s, 3 H), 3.70-3.58 (m, 2 H), 3.21-3.00 (m, 2 H), 2.63 (s, 3 H), 2.54-2.33 (m, 2 H), 2.22-2.00 (m, 2 H), 0.98 (s, 9 H) | N |
| 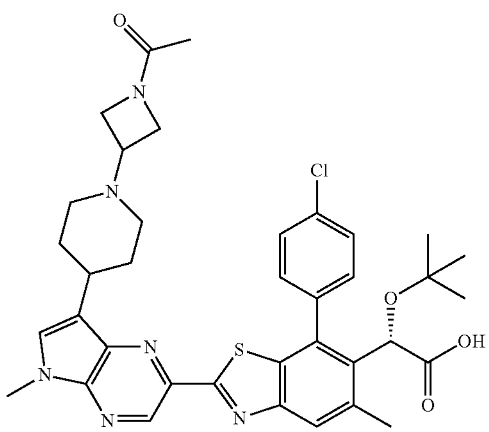 [SMILES: CC(=O)N1CC(N2CCC(c3cn(C)c4ncc(-c5nc6cc(C)c([C@H](OC(C)(C)C)C(=O)O)c(-c7ccc(Cl)cc7)c6s5)nc34)CC2)C1] | 200 | (S)-2-(2-(7-(1-(1-acetylazetidin-3-yl)piperidin-4-yl)-5-methyl-5H-pyrrolo[2,3-b]pyrazin-2-yl)-7-(4-chlorophenyl)-5-methylbenzo[d]thiazol-6-yl)-2-(tert-butoxy)acetic acid | 701.46 (M + H)+ | $^1$H NMR (400 MHz, Methanol-d$_4$) δ 9.24 (s, 1 H), 7.88 (s, 1 H), 7.69 (d, J = 8.9 Hz, 2 H), 7.60 (t, J = 8.0 Hz, 3 H), 5.24 (s, 1 H), 4.64-4.50 (m, 1 H), 4.50-4.38 (m, 1 H), 4.38-4.24 (m, 1 H), 4.22-4.07 (m, 2 H), 3.90 (s, 3 H), 3.77-3.59 (m, 2 H), 3.43-3.34 (m, 1 H), 3.26-3.04 (m, 2 H), 2.63 (s, 3 H), 2.55-2.37 (m, 2 H), 2.24-2.00 (m, 2 H), 1.94 (s, 3 H), 0.98 (s, 9 H) | N |
| 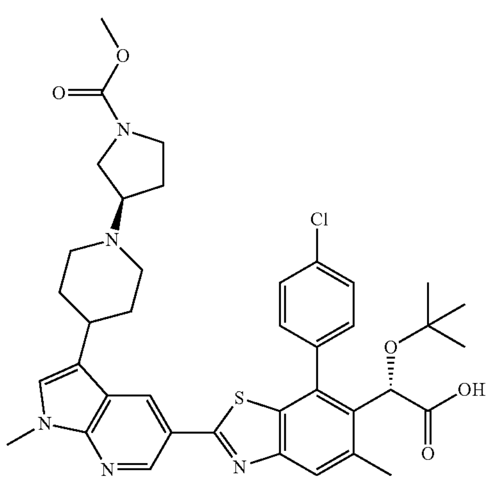 | 201 | (S)-2-(tert-butoxy)-2-(7-(4-chlorophenyl)-2-(3-(1-((R)-1-(methoxycarbonyl)pyrrolidin-3-yl)piperidin-4-yl)-1-methyl-1H-pyrrolo[2,3-b]pyridin-5-yl)-5-methylbenzo[d]thiazol-6-yl)acetic acid | 703.3 (M + H)+ | 1H NMR (400 MHz, Methanol-d4) δ 8.75 (d, J = 1.7 Hz, 1H), 8.43-8.36 (m, 1H), 7.75-7.65 (m, 2H), 7.55 (d, J = 9.5 Hz, 3H), 7.18 (s, 1H), 5.25 (s, 1H), 3.95 (s, 2H), 3.72 (s, 3H), 3.69 (s, 3H), 3.59 (d, J = 10.5 Hz, 3H), 3.44 (q, J = 9.7 Hz, 1H), 3.29-3.02 (m, 3H), 2.57 (s, 3H), 2.48 (s, 1H), 2.21 (dd, J = 26.8, 14.4 Hz, 3H), 2.00 (d, J = 15.2 Hz, 2H), 0.95 (s, 9H). | O |

| Structure | Cmpd# | Chemical Name | ES/MS m/z | 1H HMR | Method |
|---|---|---|---|---|---|
| 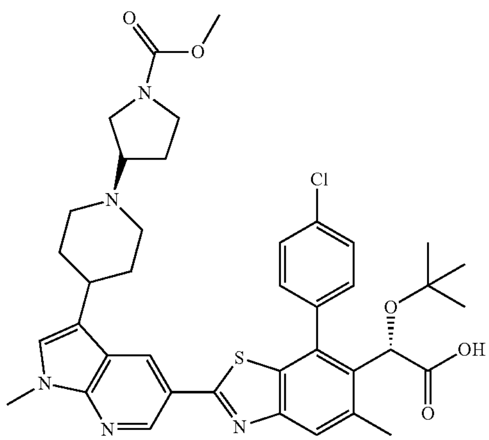 | 202 | (S)-2-(tert-butoxy)-2-(7-(4-chlorophenyl)-2-(3-(1-((S)-1-(methoxycarbonyl)pyrrolidin-3-yl)piperidin-4-yl)-1-methyl-1H-pyrrolo[2,3-b]pyridin-5-yl)-5-methylbenzo[d]thiazol-6-yl)acetic acid | 703.3 (M + H)+ | 1H NMR (400 MHz, Methanol-d4) δ 8.87 (d, J = 1.8 Hz, 1H), 8.58-8.51 (m, 1H), 7.79 (s, 1H), 7.72-7.66 (m, 1H), 7.59 (d, J = 1.6 Hz, 1H), 7.57 (s, 2H), 7.30 (s, 1H), 5.26 (s, 1H), 3.97 (s, 2H), 3.84-3.52 (m, 10H), 3.52-3.40 (m, 1H), 3.28-3.11 (m, 2H), 2.60 (s, 3H), 2.51 (s, 1H), 2.40-1.92 (m, 5H), 0.97 (s, 9H). | O |
| 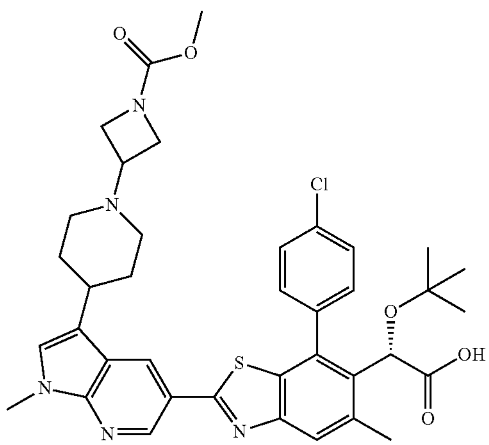 | 203 | (S)-2-(tert-butoxy)-2-(7-(4-chlorophenyl)-2-(3-(1-(1-(methoxycarbonyl)azetidin-3-yl)piperidin-4-yl)-1-methyl-1H-pyrrolo[2,3-b]pyridin-5-yl)-5-methylbenzo[d]thiazol-6-yl)acetic acid | 716.3 (M + H)+ | 1H NMR (400 MHz, Methanol-d4) δ 8.92 (d, J = 1.9 Hz, 1H), 8.60 (d, J = 2.0 Hz, 1H), 7.82 (s, 1H), 7.73-7.65 (m, 1H), 7.59 (d, J = 6.5 Hz, 3H), 7.35 (s, 1H), 5.25 (s, 1H), 4.45-4.07 (m, 6H), 3.85 (s, 3H), 3.72 (s, 3H), 3.67 (d, J = 6.8 Hz, 2H), 3.27-3.03 (m, 3H), 2.61 (s, 3H), 2.35 (d, J = 15.0 Hz, 2H), 2.16-1.97 (m, 2H), 0.98 (s, 9H). | O |
| 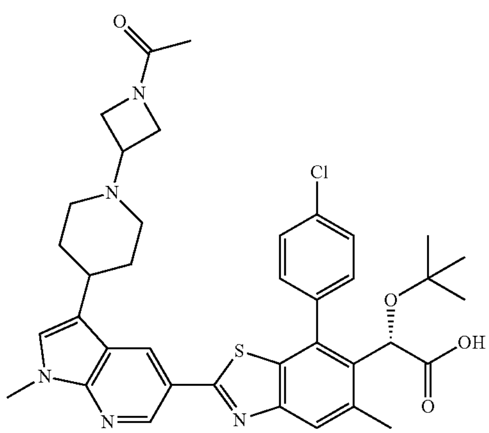 | 204 | (S)-2-(2-(3-(1-(1-acetylazetidin-3-yl)piperidin-4-yl)-1-methyl-1H-pyrrolo[2,3-b]pyridin-5-yl)-7-(4-chlorophenyl)-5-methylbenzo[d]thiazol-6-yl)-2-(tert-butoxy)acetic acid | 700.2 (M + H)+ | 1H NMR (400 MHz, Methanol-d4) δ 8.92 (s, 1H), 8.61 (s, 1H), 7.82 (s, 1H), 7.72 (m, 1H), 7.59 (m, 3H), 7.35 (s, 1H), 5.26 (s, 1H), 4.59 (t, J = 8.9 Hz, 1H), 4.48 (dd, J = 10.5, 4.5 Hz, 1H), 4.34 (dd, J = 11.3, 7.8 Hz, 1H), 4.19 (m, 2H), 3.85 (s, 3H), 3.69 (m, 3H), 3.30 (s, 3H), 3.24 (m, 1H), 3.18 (m, 2H), 2.61 (s, 3H), 2.36 (d, J = 14.8 Hz, 2H), 2.09 (t, J = 13.1 Hz, | O |

-continued

| Structure | Cmpd# | Chemical Name | ES/MS m/z | 1H HMR | Method |
|---|---|---|---|---|---|
| | | | | 2H), 1.94 (s, 3H), 0.98 (s, 9H). | |
| 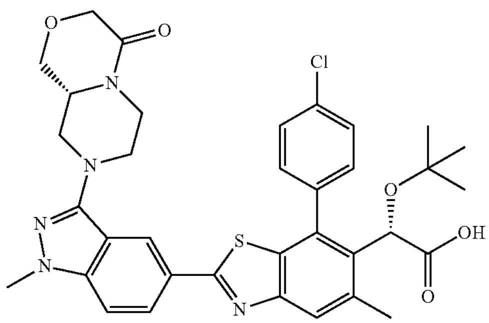 [SMILES: Cc1cc2nc(-c3ccc4c(c3)c(N3CCN5C(=O)COC[C@H]5C3)nn4C)sc2c(-c2ccc(Cl)cc2)c1[C@H](OC(C)(C)C)C(=O)O] | 205 | (S)-2-(tert-butoxy)-2-(7-(4-chlorophenyl)-5-methyl-2-(1-methyl-3-((R)-4-oxohexahydropyrazino[2,1-c][1,4]oxazin-8(1H)-yl)-1H-indazol-5-yl)benzo[d]thiazol-6-yl)acetic acid | 674.25 (M + H)+ | ¹H NMR (400 MHz, Methanol-d₄) δ 8.46 (s, 1H), 7.99 (dd, J = 8.9, 1.6 Hz, 1H), 7.81 (s, 1H), 7.72-7.67 (m, 1H), 7.63-7.46 (m, 4H), 5.25 (s, 1H), 4.64 (d, J = 13.1 Hz, 1H), 4.19-4.12 (m, 3H), 4.03-3.87 (m, 6H), 3.71 (dd, J = 12.0, 7.3 Hz, 1H), 3.18-3.06 (m, 1H), 3.05-2.83 (m, 2H), 2.61 (d, J = 0.8 Hz, 3H), 0.98 (s, 9H). | D |
| 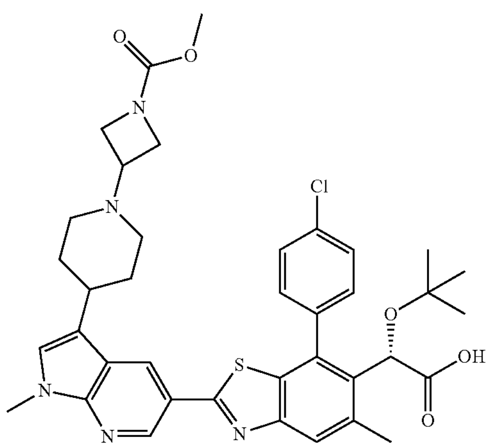 | 206 | (S)-2-(tert-butoxy)-2-(7-(4-chlorophenyl)-2-(3-(4-((1s,3s)-3-hydroxycyclobutyl)piperazin-1-yl)-1-methyl-1H-indazol-5-yl)-5-methylbenzo[d]thiazol-6-yl)acetic acid | 674.95 (M + H)+ | ¹H NMR (400 MHz, Methanol-d₄) δ 8.42 (s, 1H), 8.06 (dd, J = 8.9, 1.6 Hz, 1H), 7.81 (s, 1H), 7.71-7.67 (m, 1H), 7.63-7.53 (m, 4H), 5.25 (s, 1H), 4.23-4.03 (m, 3H), 3.94 (s, 3H), 3.75-3.50 (m, 4H), 3.31 (s, 5H), 2.87-2.75 (m, 2H), 2.61 (s, 3H), 2.19-2.06 (m, 2H), 0.98 (s, 9H). | D |
| 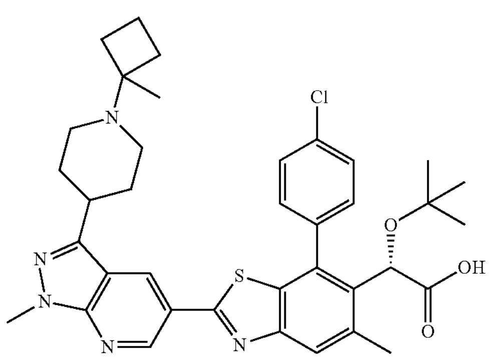 [SMILES: Cc1cc2nc(-c3cnc4c(c3)c(C3CCN(C5(C)CCC5)CC3)nn4C)sc2c(-c2ccc(Cl)cc2)c1[C@H](OC(C)(C)C)C(=O)O] | 207 | (S)-2-(tert-butoxy)-2-(7-(4-chlorophenyl)-5-methyl-2-(1-methyl-3-(4-(3-methyloxetan-3-yl)piperazin-1-yl)-1H-indazol-5-yl)benzo[d]thiazol-6-yl)acetic acid | 674.32 (M + H)+ | ¹H NMR (400 MHz, Methanol-d₄) δ 8.42 (s, 1H), 8.07 (dd, J = 8.9, 1.6 Hz, 1H), 7.80 (s, 1H), 7.71-7.66 (m, 1H), 7.62-7.53 (m, 4H), 5.25 (s, 1H), 4.93 (d, J = 7.9 Hz, 2H), 4.57 (d, J = 7.9 Hz, 2H), 3.95 (s, 3H), 3.90-3.56 (m, 4H), 3.52-3.45 (m, 4H), 2.61 (s, 3H), 1.81 (s, 3H), 0.98 (s, 9H). | D |

| Structure | Cmpd# | Chemical Name | ES/MS m/z | 1H HMR | Method |
|---|---|---|---|---|---|
| 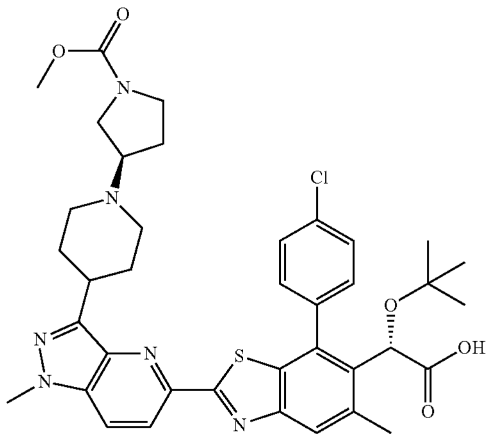 [SMILES: COC(=O)N1CC[C@@H](N2CCC(c3nn(C)c4ccc(-c5nc6cc(C)c([C@H](OC(C)(C)C)C(=O)O)c(-c7ccc(Cl)cc7)c6s5)nc34)CC2)C1] | 208 | (S)-2-(tert-butoxy)-2-(7-(4-chloro-phenyl)-2-(3-(1-((R)-1-(methoxy-carbonyl)pyrrolidin-3-yl)piperidin-4-yl)-1-methyl-1H-pyrazolo[4,3-b]pyridin-5-yl)-5-methylbenzo[d]thiazol-6-yl)acetic acid | 731.58 (M + H)+ | $^1$H NMR (400 MHz, Methanol-$d_4$) δ 8.38 (d, J = 8.9 Hz, 1H), 8.11 (d, J = 8.9 Hz, 1H), 7.86 (s, 1H), 7.72-7.66 (m, 1H), 7.64-7.54 (m, 3H), 5.24 (s, 1H), 4.07 (s, 3H), 4.02-3.91 (m, 2H), 3.82-3.34 (m, 11H), 2.62 (s, 3H), 2.57-1.99 (m, 6H), 0.98 (s, 9H). | L |

Example 125: Compound Assays

Antiviral Assay in MT4 Cells

For the antiviral assay, 0.4 μL of 189X test concentration of 3-fold serially diluted compound in DMSO was added to 40 μL of cell growth medium (RPMI 1640, 10% FBS, 1% Penicillin-Streptomycin, 1% L-Glutamine, 1% HEPES) in each well of 384-well plate (10 concentrations) in quadruplicate.

1 mL Aliquots of MT4 cells were pre-infected for 3 hours at 37° C. with 25 μL of cell growth medium (mock-infected) or a fresh 1:250 dilution of an HIV-IIIb (wildtype, IN T174I BT, or IN T174I DE) concentrated ABI stock (0.004 m.o.i.). IN T174I BT virus was derived from viral breakthrough (BT) assay as described in Mulato, A.; Hansen, D.; Thielen, A.; Porter, D.; Stepan, G.; White, K.; Daeumer, M.; Cihlar, T.; Yant, S. R. AIDS Research and Human Retroviruses, July 2016, ahead of print. doi:10.1089/aid.2016.0071. IN T174I DE virus was derived from serial passaging with dose escalation (DE) of test compound. Infected and uninfected cells were diluted in cell growth media and 35 μL (2000 cells) was added to each well of the assay plates.

Assay plates were then maintained in a humidified, 5% $CO_2$ incubator at 37° C. After 5 days of incubation, 25 μl of 2× concentrated CellTiter-Glo™ Reagent (catalog # G7573, Promega Biosciences, Inc., Madison, Wis.) was added to each well of the assay plate. Cell lysis was carried out by incubating at room temperature for 10 minutes and then chemiluminescence was read using an Envision plate reader (PerkinElmer). $EC_{50}$ values were calculated as the compound concentration that caused a 50% decrease in luminescence signal, a measure of HIV-1 replication.

| Structure | Compound # | WT EC50 (nM) | T174I BT EC50 (nM) | T174I DE EC50 (nM) | Hum MS stability t½ (min) |
|---|---|---|---|---|---|
| 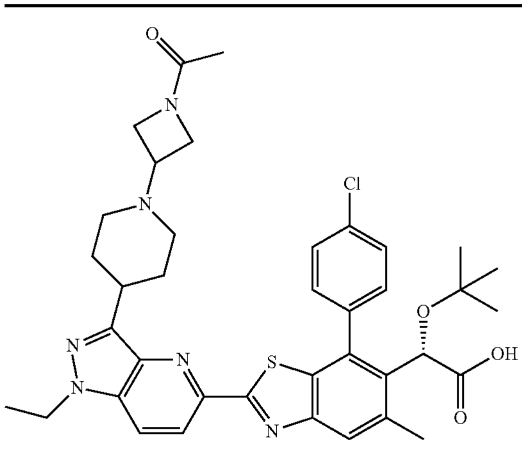 | 181 | 1 | 12 | 34 | |

-continued

| Structure | Compound # | WT EC50 (nM) | T174I BT EC50 (nM) | T174I DE EC50 (nM) | Hum MS stability t½ (min) |
|---|---|---|---|---|---|
| 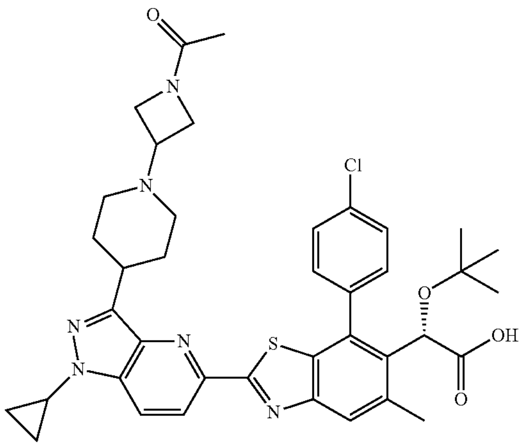 | 182 | 2 | 27 | 59 | |
| 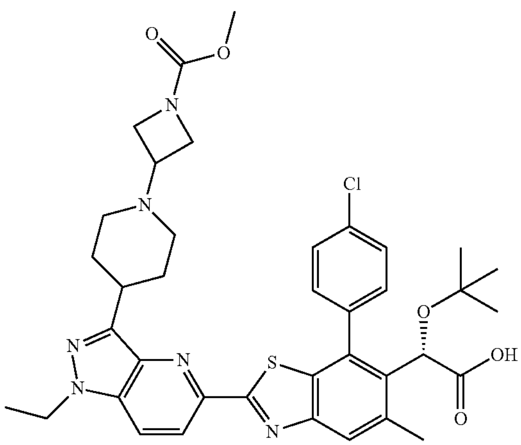 [SMILES: CCn1nc(C2CCN(C3CN(C(=O)OC)C3)CC2)c2nc(-c3nc4cc(C)c([C@H](OC(C)(C)C)C(=O)O)c(-c5ccc(Cl)cc5)c4s3)ccc21] | 179 | 3 | 28 | 108 | |
| 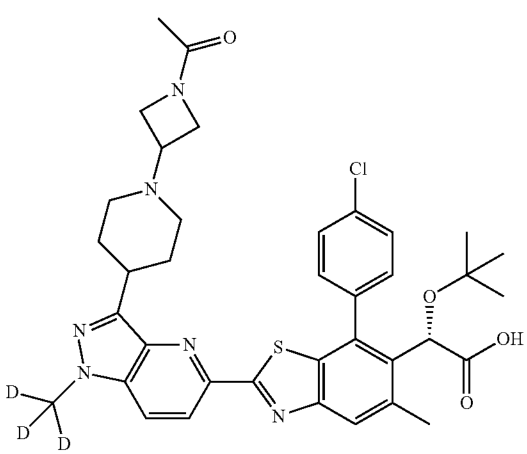 [SMILES: [2H]C([2H])([2H])n1nc(C2CCN(C3CN(C(C)=O)C3)CC2)c2nc(-c3nc4cc(C)c([C@H](OC(C)(C)C)C(=O)O)c(-c5ccc(Cl)cc5)c4s3)ccc21] | 192 | 1 | 28 | 55 | |

-continued

| Structure | Compound # | WT EC50 (nM) | T174I BT EC50 (nM) | T174I DE EC50 (nM) | Hum MS stability t½ (min) |
|---|---|---|---|---|---|
| 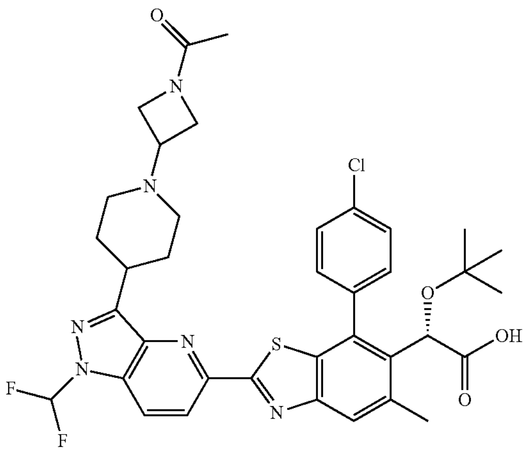 [SMILES: CC(=O)N1CC(N2CCC(c3nn(C(F)F)c4ccc(-c5nc6cc(C)c([C@H](OC(C)(C)C)C(=O)O)c(-c7ccc(Cl)cc7)c6s5)nc34)CC2)C1] | 183 | 2 | 29 | 69 | |
| 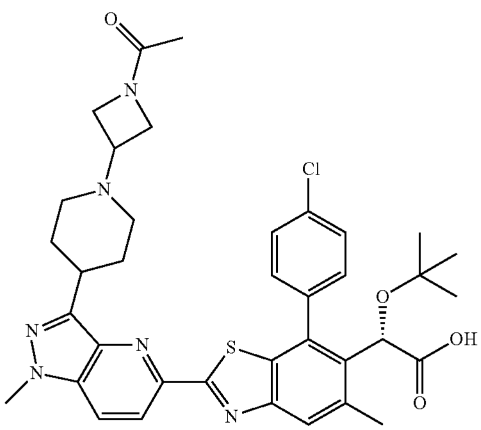 [SMILES: CC(=O)N1CC(N2CCC(c3nn(C)c4ccc(-c5nc6cc(C)c([C@H](OC(C)(C)C)C(=O)O)c(-c7ccc(Cl)cc7)c6s5)nc34)CC2)C1] | 185 | 1 | 35 | 66 | 36 |
| 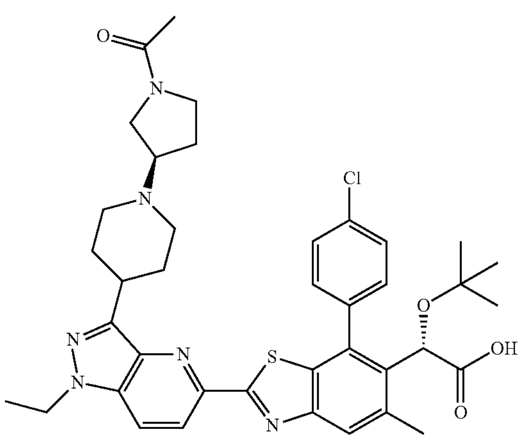 [SMILES: CCn1nc(C2CCN([C@@H]3CCN(C(C)=O)C3)CC2)c2nc(-c3nc4cc(C)c([C@H](OC(C)(C)C)C(=O)O)c(-c5ccc(Cl)cc5)c4s3)ccc21] | 169 | 2 | 36 | 86 | 30 |

-continued
| Structure | Compound # | WT EC50 (nM) | T174I BT EC50 (nM) | T174I DE EC50 (nM) | Hum MS stability t½ (min) |
|---|---|---|---|---|---|
| 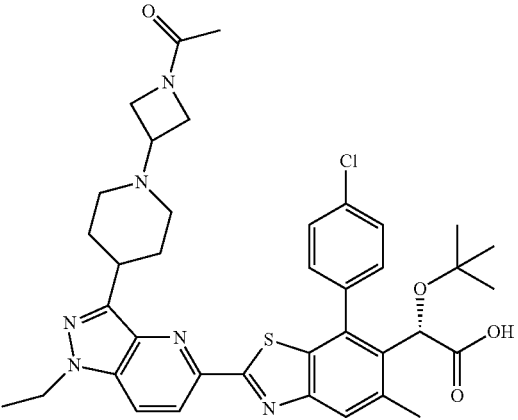 [SMILES: CCn1nc(C2CCN(C3CN(C(C)=O)C3)CC2)c2nc(-c3nc4cc(C)c([C@H](OC(C)(C)C)C(=O)O)c(-c5ccc(Cl)cc5)c4s3)ccc21] | 47 | 7 | 38 | 67 | |
| 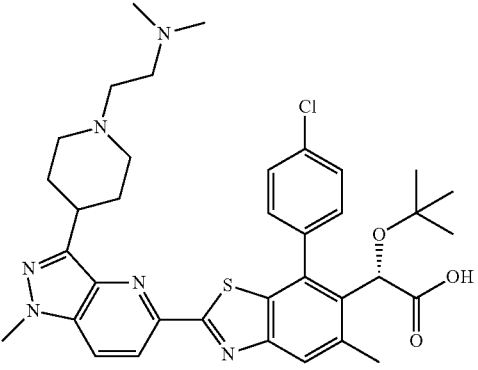 [SMILES: Cc1cc2nc(-c3ccc4c(n3)c(C3CCN(CCN(C)C)CC3)nn4C)sc2c(-c2ccc(Cl)cc2)c1[C@H](OC(C)(C)C)C(=O)O] | 173 | 2 | 45 | 89 | 72 |
| 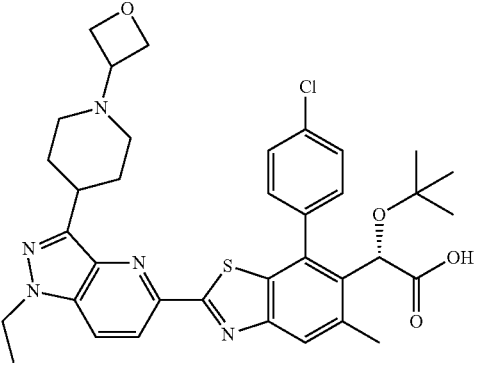 [SMILES: CCn1nc(C2CCN(C3COC3)CC2)c2nc(-c3nc4cc(C)c([C@H](OC(C)(C)C)C(=O)O)c(-c5ccc(Cl)cc5)c4s3)ccc21] | 177 | 3 | 47 | 185 | |
| 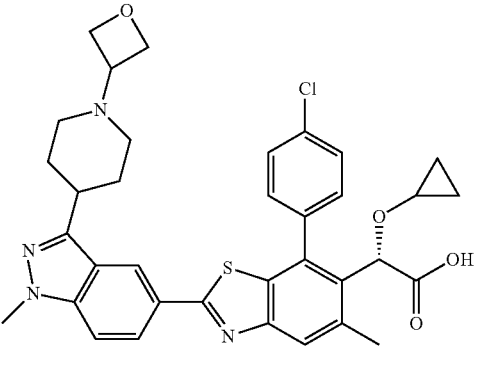 [SMILES: Cc1cc2nc(-c3ccc4c(c3)c(C3CCN(C5COC5)CC3)nn4C)sc2c(-c2ccc(Cl)cc2)c1[C@H](OC1CC1)C(=O)O] | 22 | 23 | 48 | 108 | |

-continued

| Structure | Compound # | WT EC50 (nM) | T174I BT EC50 (nM) | T174I DE EC50 (nM) | Hum MS stability t½ (min) |
|---|---|---|---|---|---|
| 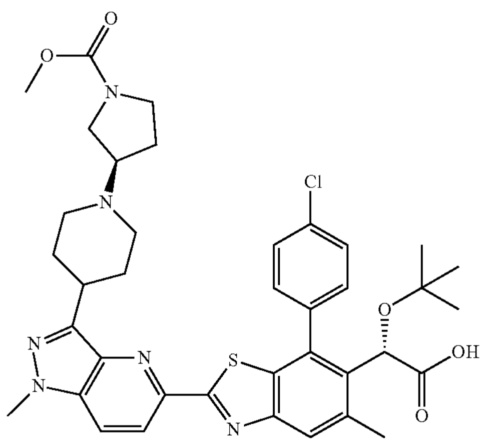 [SMILES: COC(=O)N1CC[C@@H](N2CCC(c3nn(C)c4ccc(-c5nc6cc(C)c([C@H](OC(C)(C)C)C(=O)O)c(-c7ccc(Cl)cc7)c6s5)nc34)CC2)C1] | 208 | 2 | 54 | 206 | |
| 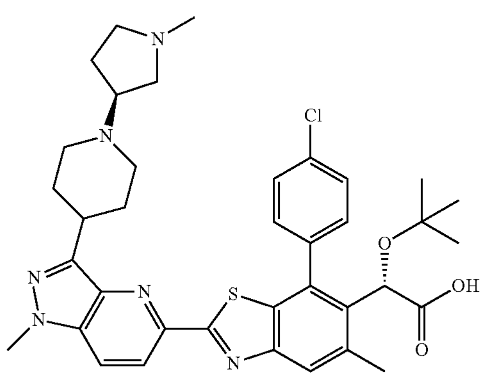 [SMILES: Cc1cc2nc(-c3ccc4c(n3)c(C3CCN([C@H]5CCN(C)C5)CC3)nn4C)sc2c(-c2ccc(Cl)cc2)c1[C@H](OC(C)(C)C)C(=O)O] | 172 | 5 | 54 | 118 | 56 |
| 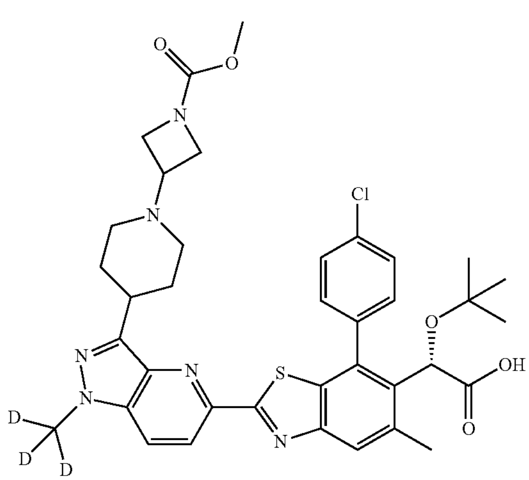 | 191 | 2 | 55 | 108 | |

-continued

| Structure | Compound # | WT EC50 (nM) | T174I BT EC50 (nM) | T174I DE EC50 (nM) | Hum MS stability t½ (min) |
|---|---|---|---|---|---|
| 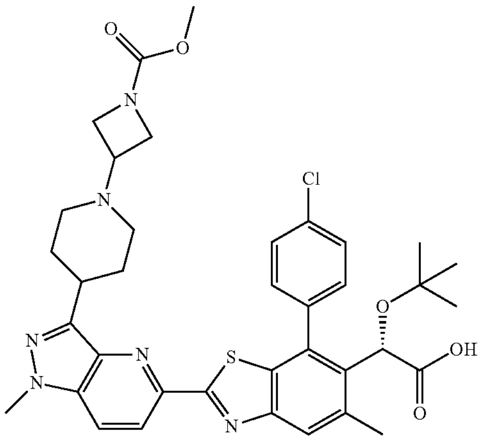 | 167 | 3 | 57 | 138 | 395 |
| 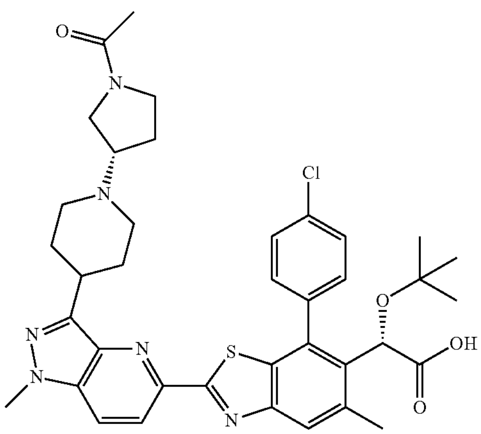 [SMILES: CC(=O)N1CC[C@H](N2CCC(c3nn(C)c4ccc(-c5nc6cc(C)c([C@H](OC(C)(C)C)C(=O)O)c(-c7ccc(Cl)cc7)c6s5)nc34)CC2)C1] | 170 | 2 | 57 | 112 | 32 |
| 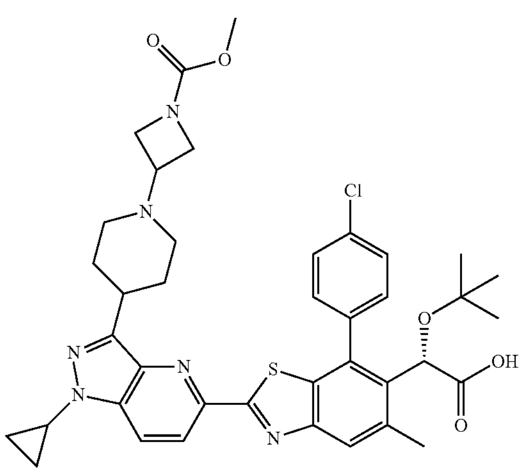 | 180 | 4 | 64 | 212 | |

-continued

| Structure | Compound # | WT EC50 (nM) | T174I BT EC50 (nM) | T174I DE EC50 (nM) | Hum MS stability t½ (min) |
|---|---|---|---|---|---|
| 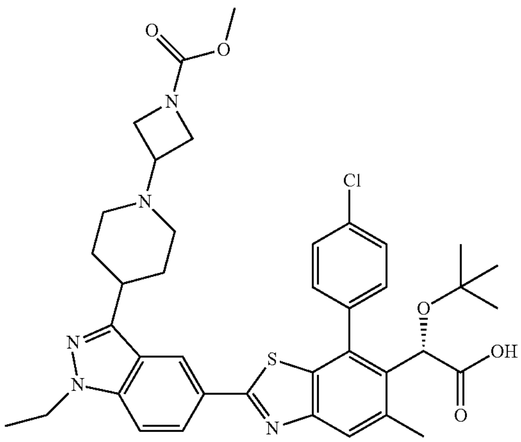 [SMILES: CCn1nc(C2CCN(C3CN(C(=O)OC)C3)CC2)c2cc(-c3nc4cc(C)c([C@H](OC(C)(C)C)C(=O)O)c(-c5ccc(Cl)cc5)c4s3)ccc21] | 48 | 8 | 70 | 165 | |
| 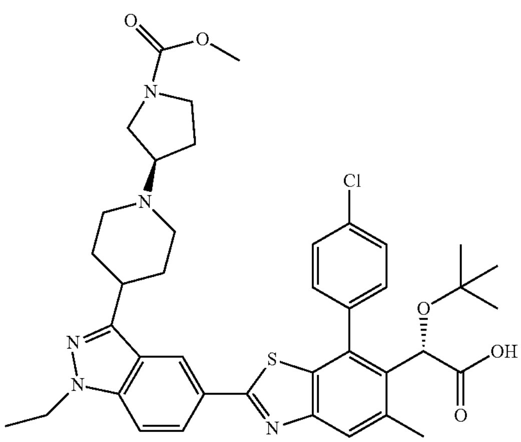 [SMILES: CCn1nc(C2CCN([C@@H]3CCN(C(=O)OC)C3)CC2)c2cc(-c3nc4cc(C)c([C@H](OC(C)(C)C)C(=O)O)c(-c5ccc(Cl)cc5)c4s3)ccc21] | 50 | 4 | 74 | 276 | |
| 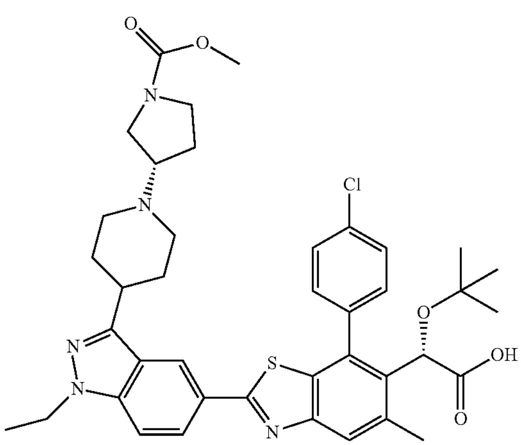 [SMILES: CCn1nc(C2CCN([C@H]3CCN(C(=O)OC)C3)CC2)c2cc(-c3nc4cc(C)c([C@H](OC(C)(C)C)C(=O)O)c(-c5ccc(Cl)cc5)c4s3)ccc21] | 49 | 4 | 79 | 286 | |

-continued

| Structure | Compound # | WT EC50 (nM) | T174I BT EC50 (nM) | T174I DE EC50 (nM) | Hum MS stability t½ (min) |
|---|---|---|---|---|---|
| 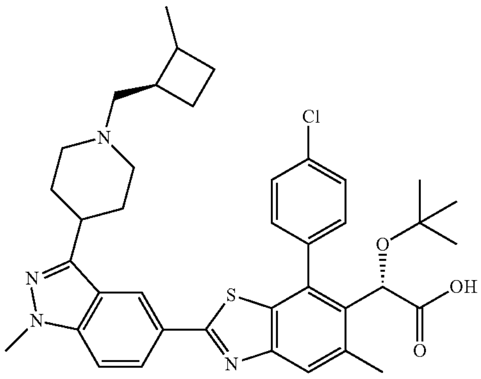 [SMILES: Cc1cc2nc(-c3ccc4c(c3)c(C3CCN(C[C@@H]5CCC5C)CC3)nn4C)sc2c(-c2ccc(Cl)cc2)c1[C@H](OC(C)(C)C)C(=O)O] | 149 | 11 | 80 | 98 | |
| 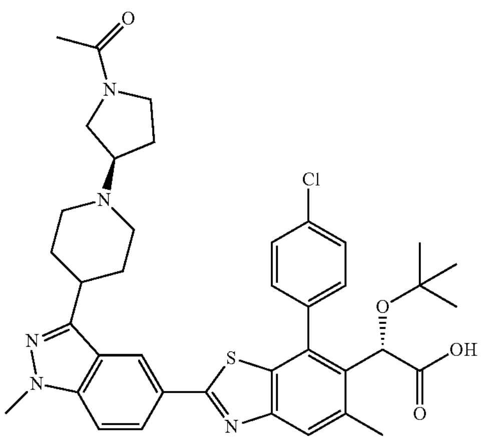 [SMILES: CC(=O)N1CC[C@@H](N2CCC(c3nn(C)c4ccc(-c5nc6cc(C)c([C@H](OC(C)(C)C)C(=O)O)c(-c7ccc(Cl)cc7)c6s5)cc34)CC2)C1] | 12 | 10 | 81 | 138 | 395 |
| 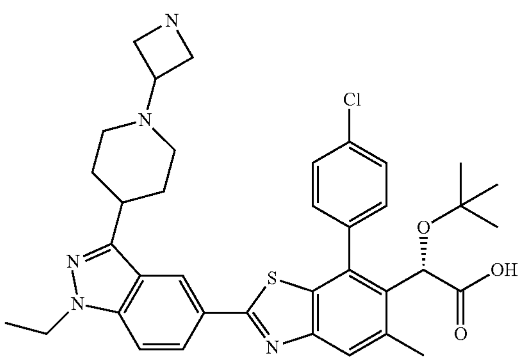 [SMILES: CCn1nc(C2CCN(C3CNC3)CC2)c2cc(-c3nc4cc(C)c([C@H](OC(C)(C)C)C(=O)O)c(-c5ccc(Cl)cc5)c4s3)ccc21] | 35 | 4 | 84 | 238 | |
| 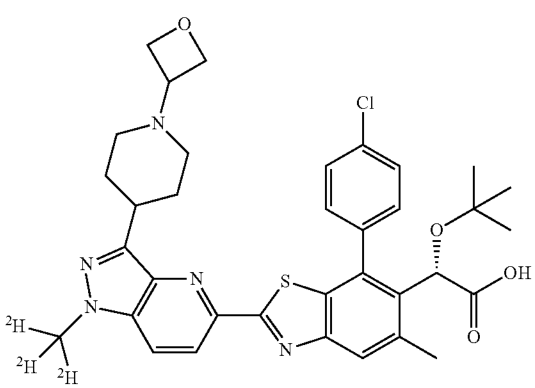 [SMILES: [2H]C([2H])([2H])n1nc(C2CCN(C3COC3)CC2)c2nc(-c3nc4cc(C)c([C@H](OC(C)(C)C)C(=O)O)c(-c5ccc(Cl)cc5)c4s3)ccc21] | 176 | 3 | 85 | 214 | |

-continued
| Structure | Compound # | WT EC50 (nM) | T174I BT EC50 (nM) | T174I DE EC50 (nM) | Hum MS stability t½ (min) |
|---|---|---|---|---|---|
| 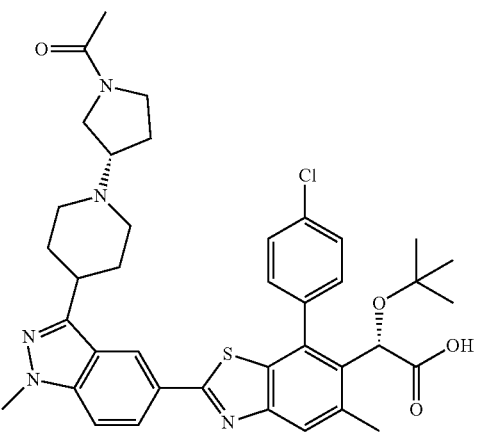 [SMILES: CC(=O)N1CC[C@H](N2CCC(c3nn(C)c4ccc(-c5nc6cc(C)c([C@H](OC(C)(C)C)C(=O)O)c(-c7ccc(Cl)cc7)c6s5)cc34)CC2)C1] | 11 | 8 | 85 | 166 | 395 |
| 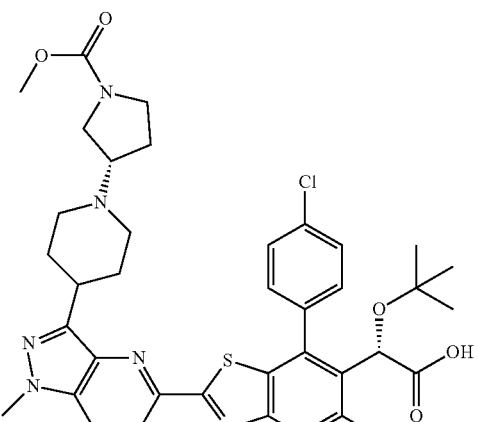 | 193 | 3 | 87 | 265 | |
| 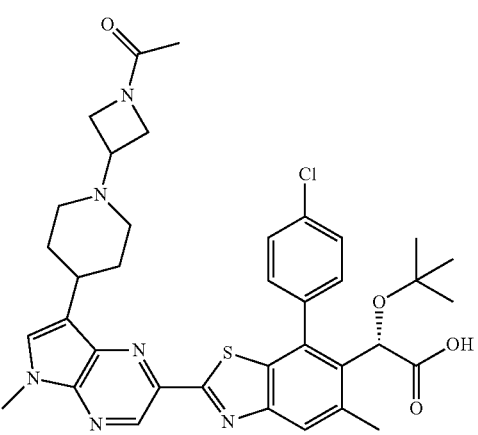 | 200 | 1 | 90 | 241 | |

-continued

| Structure | Compound # | WT EC50 (nM) | T174I BT EC50 (nM) | T174I DE EC50 (nM) | Hum MS stability t½ (min) |
|---|---|---|---|---|---|
| 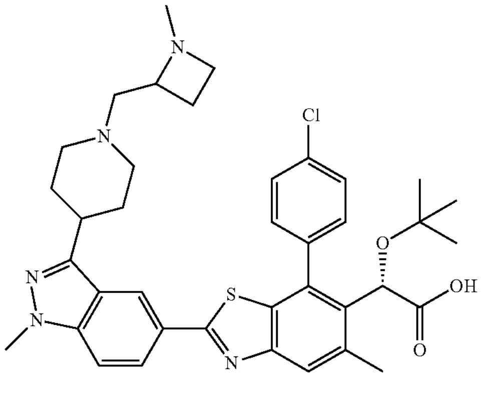 [SMILES: Cc1cc2nc(-c3ccc4c(c3)c(C3CCN(CC5CCN5C)CC3)nn4C)sc2c(-c2ccc(Cl)cc2)c1[C@H](OC(C)(C)C)C(=O)O] | 147 | 11 | 91 | 167 | |
| 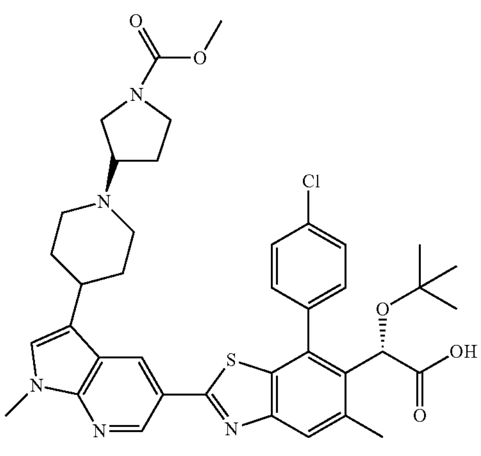 | 201 | 7 | 92 | 530 | |
| 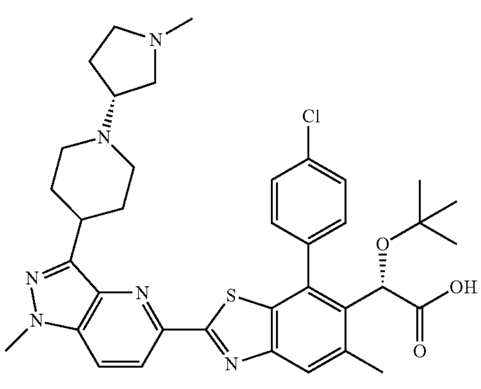 [SMILES: Cc1cc2nc(-c3ccc4c(n3)c(C3CCN([C@@H]5CCN(C)C5)CC3)nn4C)sc2c(-c2ccc(Cl)cc2)c1[C@H](OC(C)(C)C)C(=O)O] | 171 | 5 | 98 | 239 | |

-continued

| Structure | Compound # | WT EC50 (nM) | T174I BT EC50 (nM) | T174I DE EC50 (nM) | Hum MS stability t½ (min) |
|---|---|---|---|---|---|
| 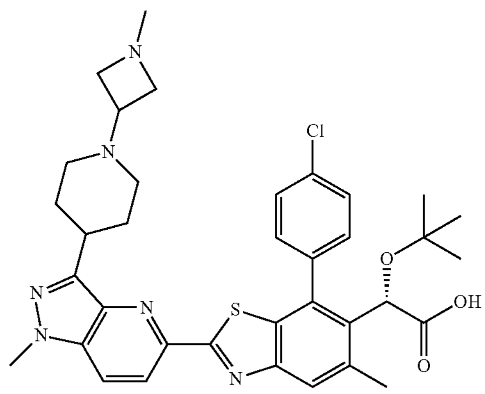 | 184 | 4 | 103 | 218 | 46 |
| 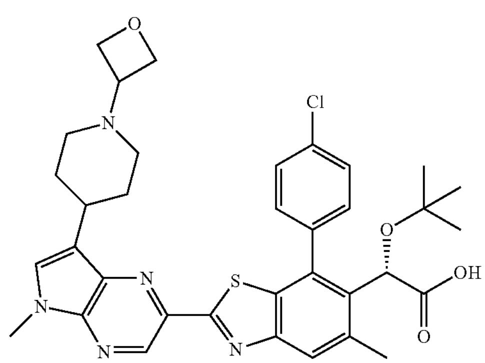 [SMILES: Cc1cc2nc(-c3cnc4c(n3)c(C3CCN(C5COC5)CC3)cn4C)sc2c(-c2ccc(Cl)cc2)c1[C@H](OC(C)(C)C)C(=O)O] | 16 | 2 | 104 | 603 | |
| 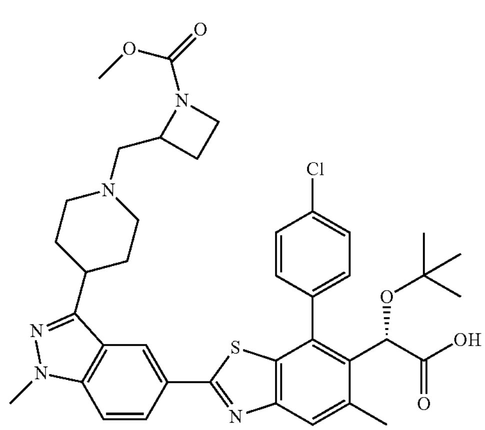 [SMILES: COC(=O)N1CCC1CN1CCC(c2nn(C)c3ccc(-c4nc5cc(C)c([C@H](OC(C)(C)C)C(=O)O)c(-c6ccc(Cl)cc6)c5s4)cc23)CC1] | 5 | 3 | 106 | 169 | |

-continued
| Structure | Compound # | WT EC50 (nM) | T174I BT EC50 (nM) | T174I DE EC50 (nM) | Hum MS stability t½ (min) |
|---|---|---|---|---|---|
| 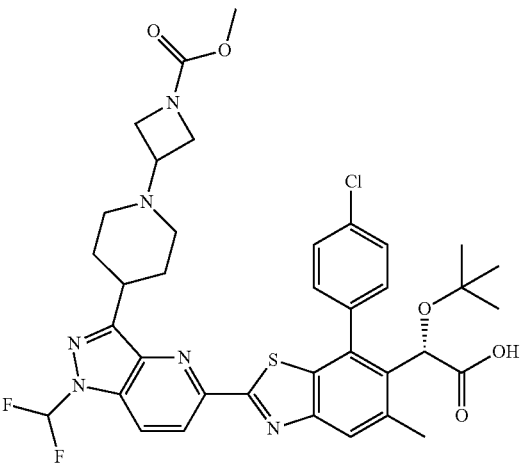 [SMILES: COC(=O)N1CC(N2CCC(c3nn(C(F)F)c4ccc(-c5nc6cc(C)c([C@H](OC(C)(C)C)C(=O)O)c(-c7ccc(Cl)cc7)c6s5)nc34)CC2)C1] | 14 | 5 | 109 | 304 | |
| 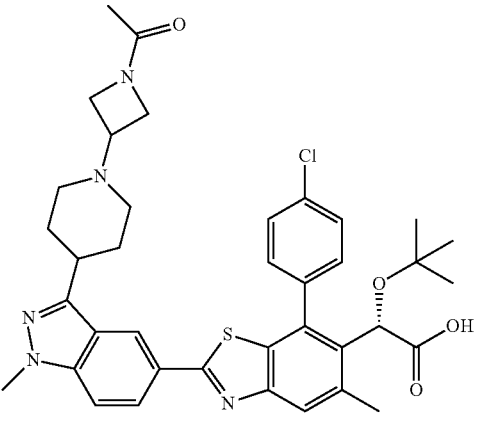 [SMILES: CC(=O)N1CC(N2CCC(c3nn(C)c4ccc(-c5nc6cc(C)c([C@H](OC(C)(C)C)C(=O)O)c(-c7ccc(Cl)cc7)c6s5)cc34)CC2)C1] | 30 | 12 | 111 | 187 | 395 |
| 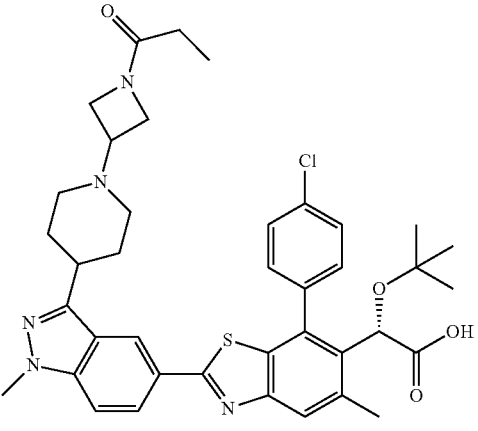 [SMILES: CCC(=O)N1CC(N2CCC(c3nn(C)c4ccc(-c5nc6cc(C)c([C@H](OC(C)(C)C)C(=O)O)c(-c7ccc(Cl)cc7)c6s5)cc34)CC2)C1] | 7 | 14 | 114 | 138 | |

-continued

| Structure | Compound # | WT EC50 (nM) | T174I BT EC50 (nM) | T174I DE EC50 (nM) | Hum MS stability t½ (min) |
|---|---|---|---|---|---|
| 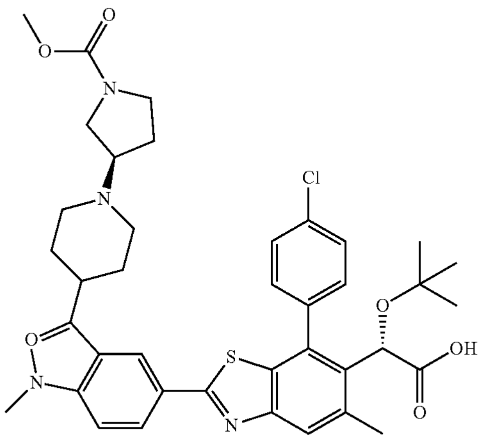 | 165 | 5 | 118 | 182 | |
| 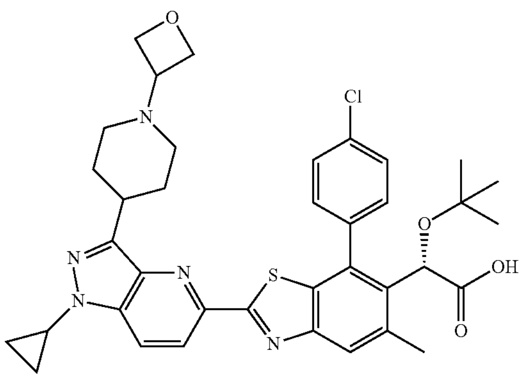 | 178 | 4 | 121 | 317 | |
| 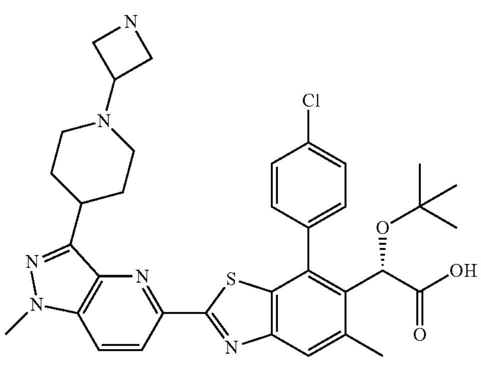 [SMILES: Cc1cc2nc(-c3ccc4c(n3)c(C3CCN(C5CNC5)CC3)nn4C)sc2c(-c2ccc(Cl)cc2)c1[C@H](OC(C)(C)C)C(=O)O] | 175 | 3 | 122 | 252 | 357 |
| 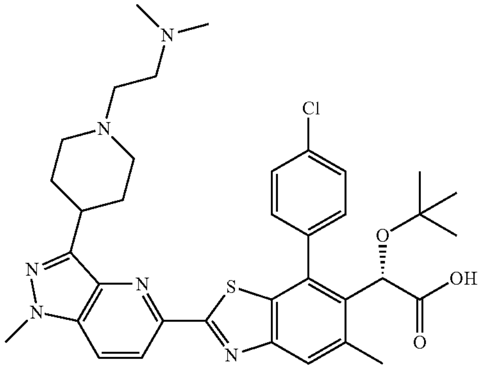 [SMILES: Cc1cc2nc(-c3ccc4c(n3)c(C3CCN(CCN(C)C)CC3)nn4C)sc2c(-c2ccc(Cl)cc2)c1[C@H](OC(C)(C)C)C(=O)O] | 130 | 12 | 122 | 232 | 395 |

-continued
| Structure | Compound # | WT EC50 (nM) | T174I BT EC50 (nM) | T174I DE EC50 (nM) | Hum MS stability t½ (min) |
|---|---|---|---|---|---|
| 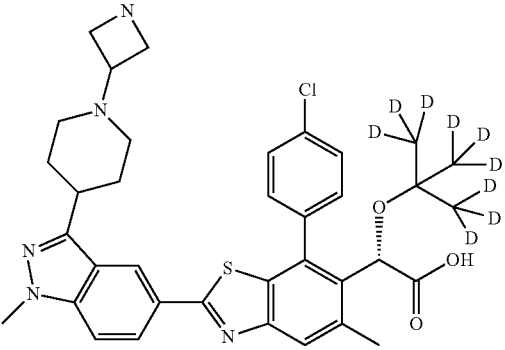 [SMILES: [2H]C([2H])([2H])C(O[C@H](C(=O)O)c1c(C)cc2nc(-c3ccc4c(c3)c(C3CCN(C5CNC5)CC3)nn4C)sc2c1-c1ccc(Cl)cc1)(C([2H])([2H])[2H])C([2H])([2H])[2H]] | 21 | 4 | 124 | 239 | 198 |
| 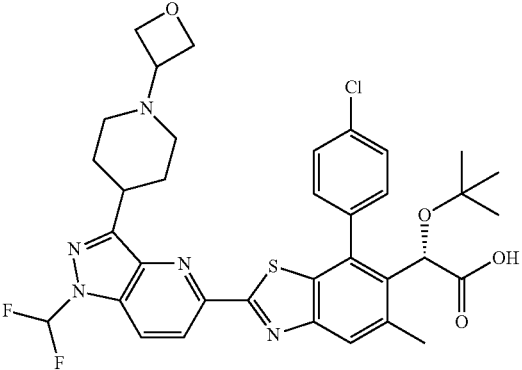 [SMILES: Cc1cc2nc(-c3ccc4c(n3)c(C3CCN(C5COC5)CC3)nn4C(F)F)sc2c(-c2ccc(Cl)cc2)c1[C@H](OC(C)(C)C)C(=O)O] | 194 | 4 | 126 | 300 | |
| 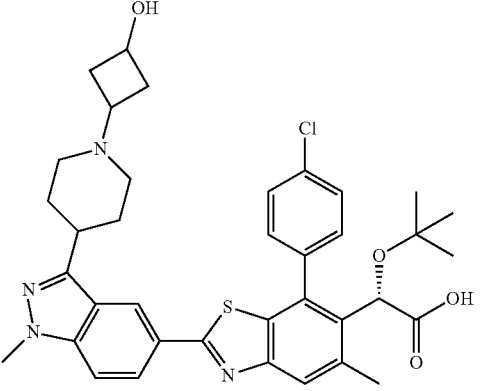 [SMILES: Cc1cc2nc(-c3ccc4c(c3)c(C3CCN(C5CC(O)C5)CC3)nn4C)sc2c(-c2ccc(Cl)cc2)c1[C@H](OC(C)(C)C)C(=O)O] | 156 | 11 | 126 | 197 | 297 |
| 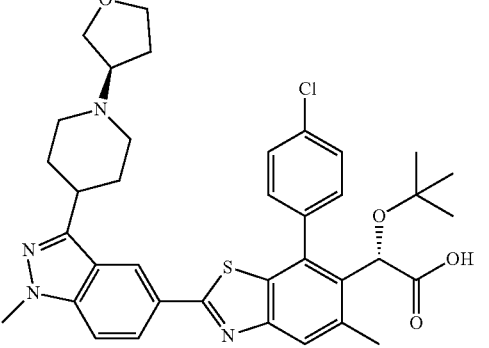 | 26 | 4 | 129 | 270 | 281 |

-continued
| Structure | Compound # | WT EC50 (nM) | T174I BT EC50 (nM) | T174I DE EC50 (nM) | Hum MS stability t½ (min) |
|---|---|---|---|---|---|
| 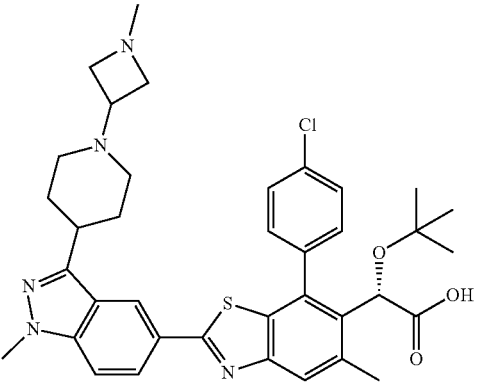 [SMILES: Cc1cc2nc(-c3ccc4c(c3)c(C3CCN(C5CN(C)C5)CC3)nn4C)sc2c(-c2ccc(Cl)cc2)c1[C@H](OC(C)(C)C)C(=O)O] | 31 | 12 | 138 | 236 | 395 |
| 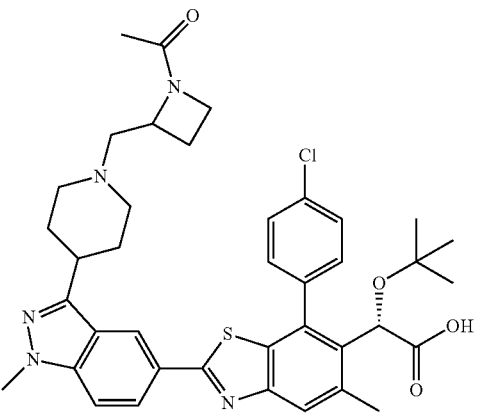 [SMILES: CC(=O)N1CCC1CN1CCC(c2nn(C)c3ccc(-c4nc5cc(C)c([C@H](OC(C)(C)C)C(=O)O)c(-c6ccc(Cl)cc6)c5s4)cc23)CC1] | 148 | 12 | 143 | 199 | |
| 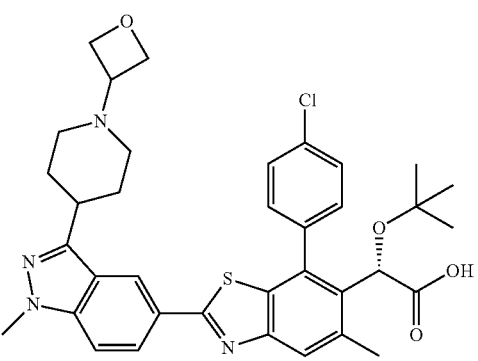 | 1 | 5 | 143 | 315 | 350 |

-continued

| Structure | Compound # | WT EC50 (nM) | T174I BT EC50 (nM) | T174I DE EC50 (nM) | Hum MS stability t½ (min) |
|---|---|---|---|---|---|
| 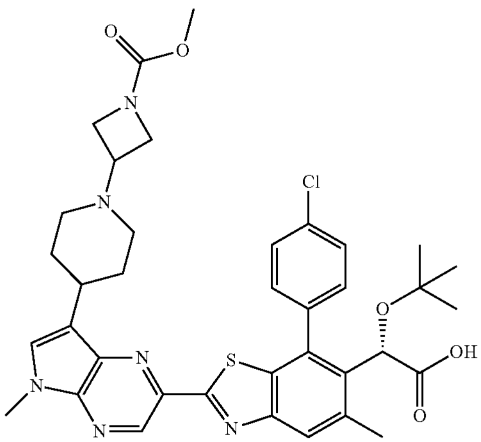 [SMILES: COC(=O)N1CC(N2CCC(c3cn(C)c4ncc(-c5nc6cc(C)c([C@H](OC(C)(C)C)C(=O)O)c(-c7ccc(Cl)cc7)c6s5)nc34)CC2)C1] | 199 | 4 | 149 | 770 | |
| 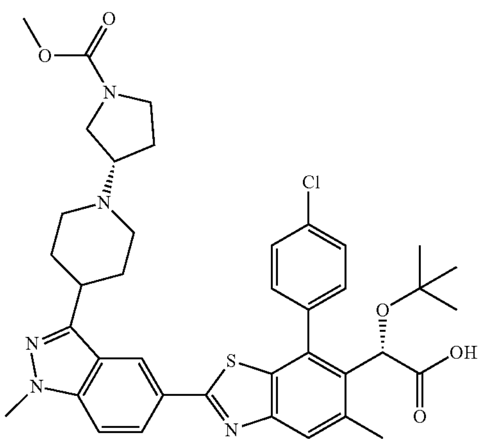 [SMILES: COC(=O)N1CC[C@H](N2CCC(c3nn(C)c4ccc(-c5nc6cc(C)c([C@H](OC(C)(C)C)C(=O)O)c(-c7ccc(Cl)cc7)c6s5)cc34)CC2)C1] | 162 | 5 | 149 | 272 | |
| 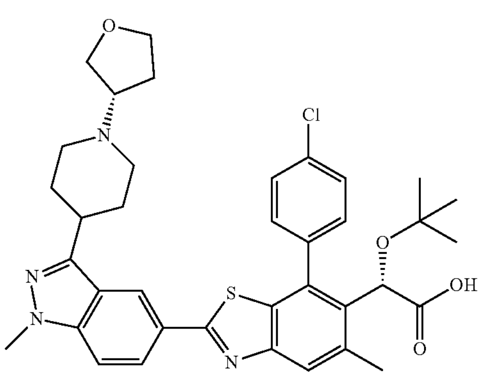 [SMILES: Cc1cc2nc(-c3ccc4c(c3)c(C3CCN([C@H]5CCOC5)CC3)nn4C)sc2c(-c2ccc(Cl)cc2)c1[C@H](OC(C)(C)C)C(=O)O] | 27 | 4 | 154 | 245 | 250 |

-continued
| Structure | Compound # | WT EC50 (nM) | T174I BT EC50 (nM) | T174I DE EC50 (nM) | Hum MS stability t½ (min) |
|---|---|---|---|---|---|
| 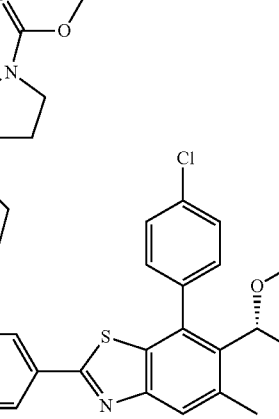 | 202 | 7 | 157 | 680 | |
| 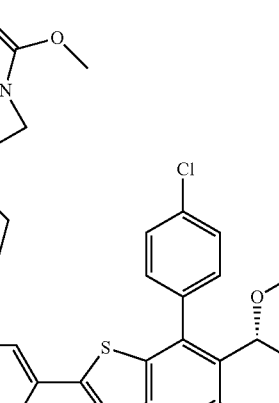 | 153 | 11 | 159 | 217 | |
| 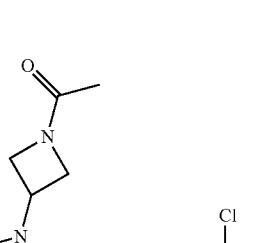 | 45 | 17 | 174 | 287 | |

-continued

| Structure | Compound # | WT EC50 (nM) | T174I BT EC50 (nM) | T174I DE EC50 (nM) | Hum MS stability t½ (min) |
|---|---|---|---|---|---|
| 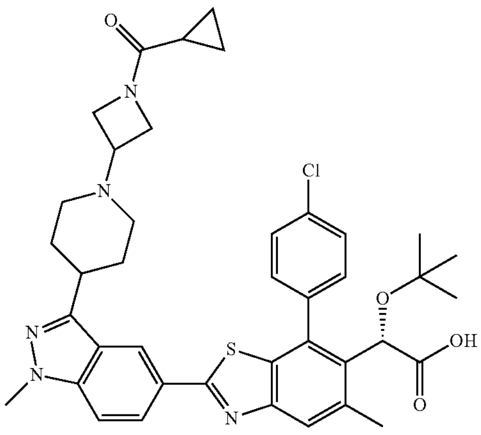 [SMILES: Cc1cc2nc(-c3ccc4c(c3)c(C3CCN(C5CN(C(=O)C6CC6)C5)CC3)nn4C)sc2c(-c2ccc(Cl)cc2)c1[C@H](OC(C)(C)C)C(=O)O] | 152 | 23 | 175 | 210 | |
| 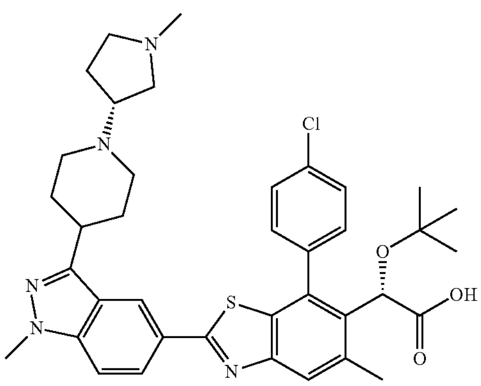 [SMILES: Cc1cc2nc(-c3ccc4c(c3)c(C3CCN([C@@H]5CCN(C)C5)CC3)nn4C)sc2c(-c2ccc(Cl)cc2)c1[C@H](OC(C)(C)C)C(=O)O] | 164 | 15 | 184 | 183 | |
| 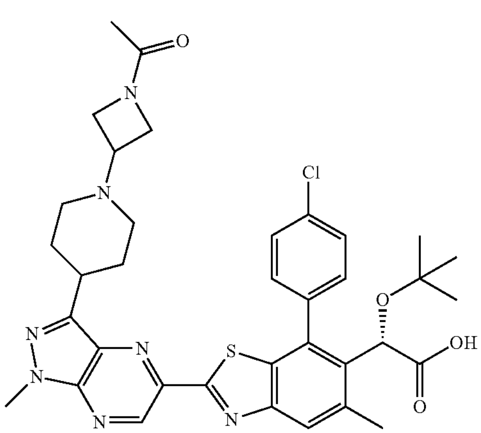 [SMILES: CC(=O)N1CC(N2CCC(c3nn(C)c4ncc(-c5nc6cc(C)c([C@H](OC(C)(C)C)C(=O)O)c(-c7ccc(Cl)cc7)c6s5)nc34)CC2)C1] | 120 | 3 | 185 | 217 | |

-continued

| Structure | Compound # | WT EC50 (nM) | T174I BT EC50 (nM) | T174I DE EC50 (nM) | Hum MS stability t½ (min) |
|---|---|---|---|---|---|
| 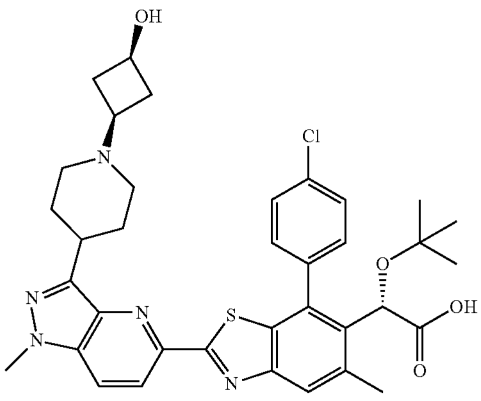 [SMILES: Cc1cc2nc(-c3ccc4c(n3)c(C3CCN([C@H]5C[C@@H](O)C5)CC3)nn4C)sc2c(-c2ccc(Cl)cc2)c1[C@H](OC(C)(C)C)C(=O)O] | 188 | 11 | 196 | 391 | 152 |
| 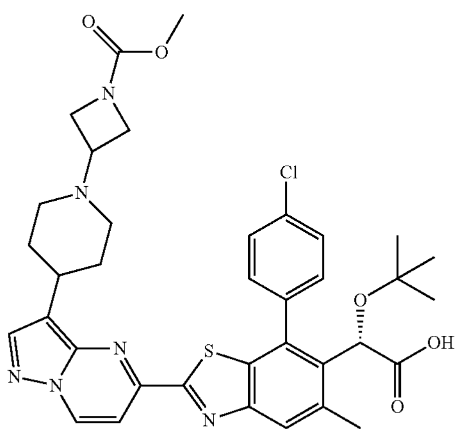 [SMILES: COC(=O)N1CC(N2CCC(c3cnn4ccc(-c5nc6cc(C)c([C@H](OC(C)(C)C)C(=O)O)c(-c7ccc(Cl)cc7)c6s5)nc34)CC2)C1] | 110 | 2 | 198 | 559 | |
| 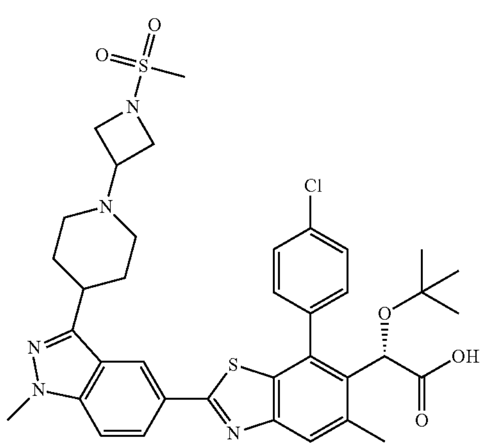 [SMILES: Cc1cc2nc(-c3ccc4c(c3)c(C3CCN(C5CN(S(C)(=O)=O)C5)CC3)nn4C)sc2c(-c2ccc(Cl)cc2)c1[C@H](OC(C)(C)C)C(=O)O] | 154 | 13 | 201 | 321 | 348 |

-continued

| Structure | Compound # | WT EC50 (nM) | T174I BT EC50 (nM) | T174I DE EC50 (nM) | Hum MS stability t½ (min) |
|---|---|---|---|---|---|
| 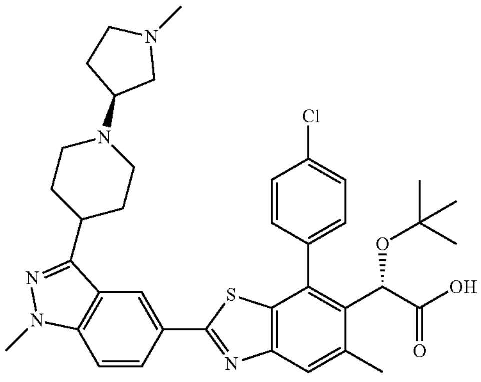 [SMILES: Cc1cc2nc(-c3ccc4c(c3)c(C3CCN([C@H]5CCN(C)C5)CC3)nn4C)sc2c(-c2ccc(Cl)cc2)c1[C@H](OC(C)(C)C)C(=O)O] | 163 | 20 | 204 | 324 | 127 |
| 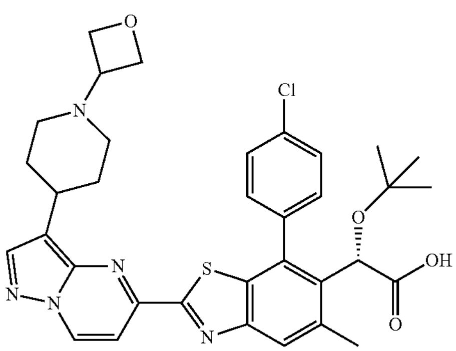 [SMILES: Cc1cc2nc(-c3ccn4ncc(C5CCN(C6COC6)CC5)c4n3)sc2c(-c2ccc(Cl)cc2)c1[C@H](OC(C)(C)C)C(=O)O] | 109 | 3 | 205 | 614 | |
| 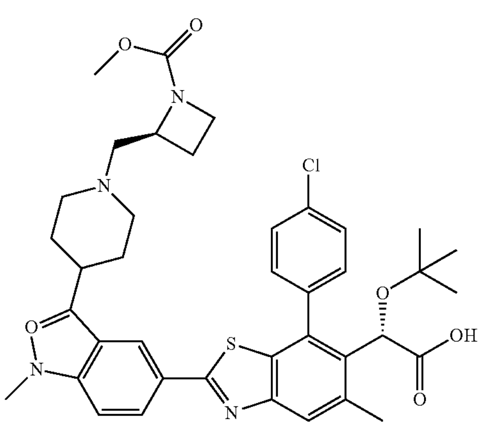 | 150 | 4 | 214 | 182 | |

-continued
| Structure | Compound # | WT EC50 (nM) | T174I BT EC50 (nM) | T174I DE EC50 (nM) | Hum MS stability t½ (min) |
|---|---|---|---|---|---|
| 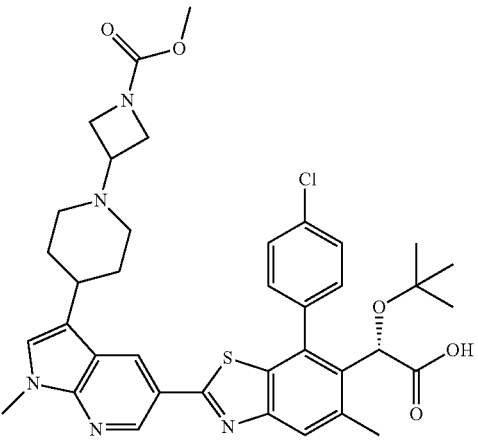 | 203 | 11 | 215 | 702 | |
| 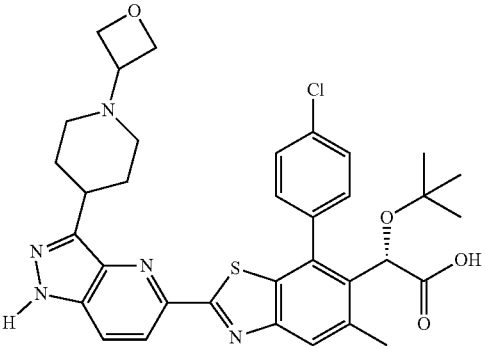 | 174 | 11 | 219 | 587 | |
| 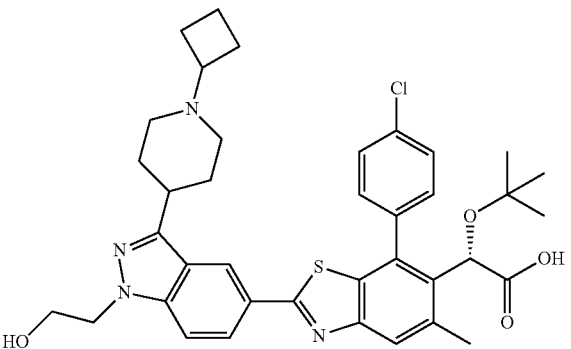 [SMILES: Cc1cc2nc(-c3ccc4c(c3)c(C3CCN(C5CCC5)CC3)nn4CCO)sc2c(-c2ccc(Cl)cc2)c1[C@H](OC(C)(C)C)C(=O)O] | 37 | 22 | 223 | 405 | |

-continued
| Structure | Compound # | WT EC50 (nM) | T174I BT EC50 (nM) | T174I DE EC50 (nM) | Hum MS stability t½ (min) |
|---|---|---|---|---|---|
| 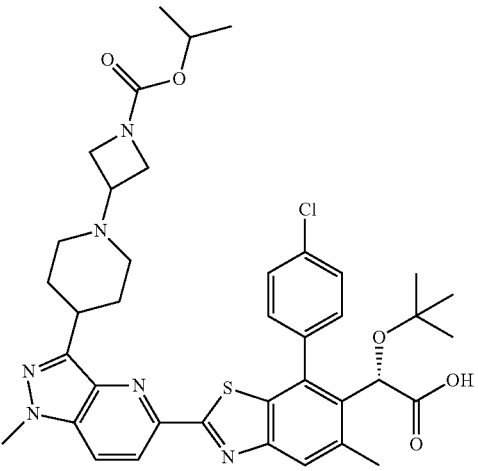 [SMILES: Cc1cc2nc(-c3ccc4c(n3)c(C3CCN(C5CN(C(=O)OC(C)C)C5)CC3)nn4C)sc2c(-c2ccc(Cl)cc2)c1[C@H](OC(C)(C)C)C(=O)O] | 168 | 11 | 230 | 456 | 395 |
| 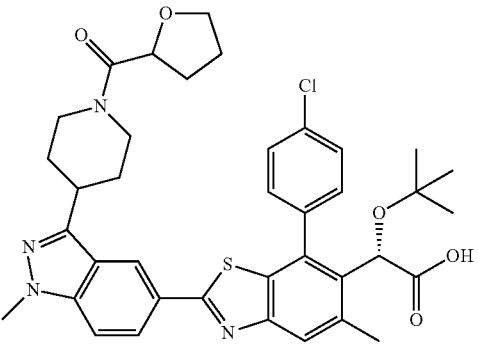 [SMILES: Cc1cc2nc(-c3ccc4c(c3)c(C3CCN(C(=O)C5CCCO5)CC3)nn4C)sc2c(-c2ccc(Cl)cc2)c1[C@H](OC(C)(C)C)C(=O)O] | 9 | 9 | 237 | 511 | 250 |
| 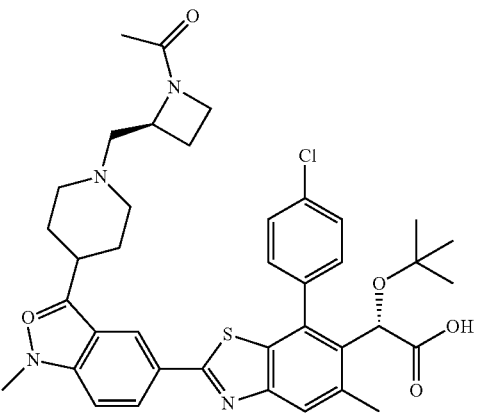 | 151 | 16 | 237 | 231 | |

-continued

| Structure | Compound # | WT EC50 (nM) | T174I BT EC50 (nM) | T174I DE EC50 (nM) | Hum MS stability t½ (min) |
|---|---|---|---|---|---|
| 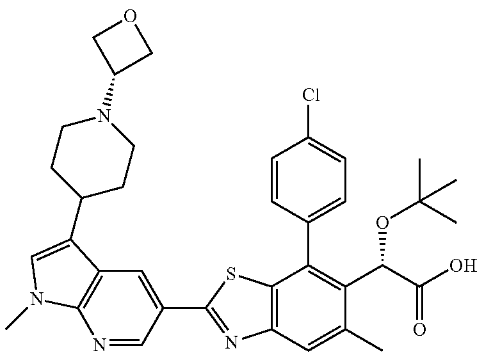 | 17 | 8 | 238 | 786 | 282 |
| 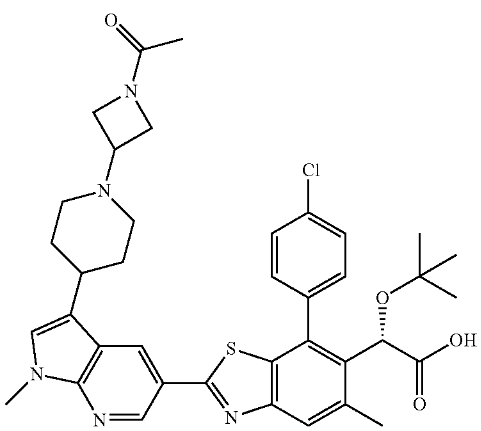 | 204 | 15 | 255 | 636 | |
| 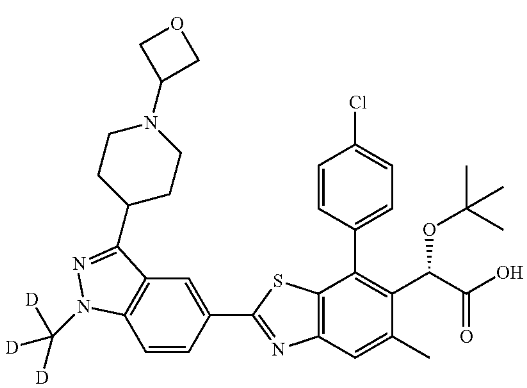 | 40 | 10 | 257 | 518 | |
| 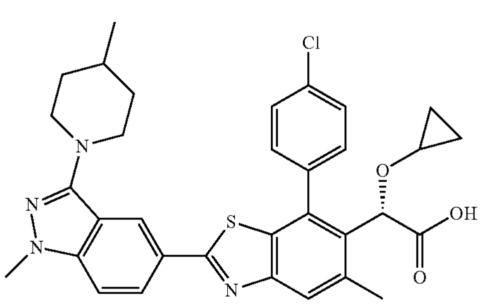 [SMILES: Cc1cc2nc(-c3ccc4c(c3)c(N3CCC(C)CC3)nn4C)sc2c(-c2ccc(Cl)cc2)c1[C@H](OC1CC1)C(=O)O] | 103 | 32 | 267 | 367 | 148 |

-continued

| Structure | Compound # | WT EC50 (nM) | T174I BT EC50 (nM) | T174I DE EC50 (nM) | Hum MS stability t½ (min) |
|---|---|---|---|---|---|
| 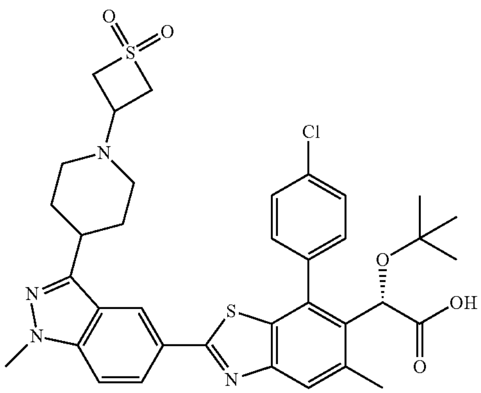 [SMILES: Cc1cc2nc(-c3ccc4c(c3)c(C3CCN(C5CS(=O)(=O)C5)CC3)nn4C)sc2c(-c2ccc(Cl)cc2)c1[C@H](OC(C)(C)C)C(=O)O] | 10 | 10 | 275 | 303 | 215 |
| 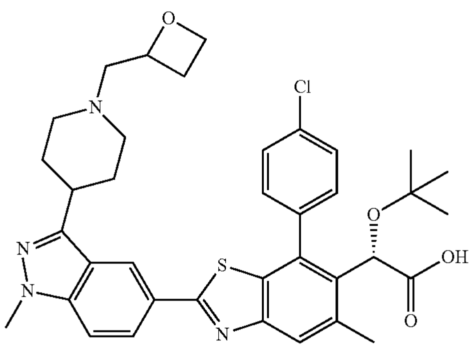 [SMILES: Cc1cc2nc(-c3ccc4c(c3)c(C3CCN(CC5CCO5)CC3)nn4C)sc2c(-c2ccc(Cl)cc2)c1[C@H](OC(C)(C)C)C(=O)O] | 6 | 4 | 283 | 577 | 395 |
| 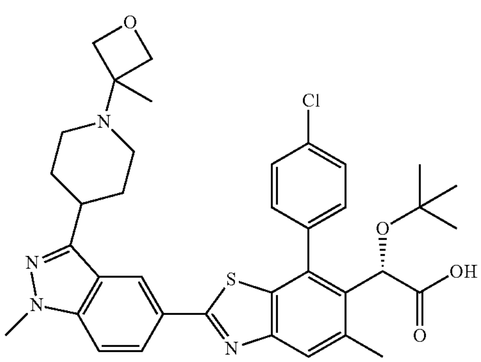 [SMILES: Cc1cc2nc(-c3ccc4c(c3)c(C3CCN(C5(C)COC5)CC3)nn4C)sc2c(-c2ccc(Cl)cc2)c1[C@H](OC(C)(C)C)C(=O)O] | 20 | 7 | 287 | 542 | |
| 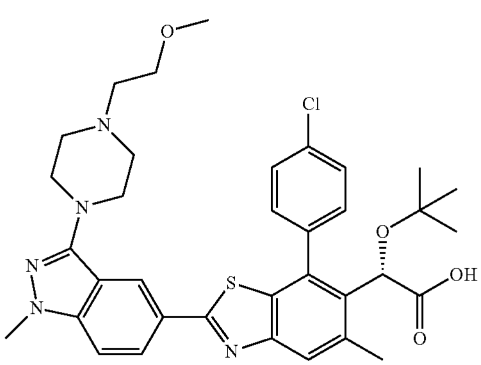 [SMILES: COCCN1CCN(c2nn(C)c3ccc(-c4nc5cc(C)c([C@H](OC(C)(C)C)C(=O)O)c(-c6ccc(Cl)cc6)c5s4)cc23)CC1] | 98 | 4 | 290 | 516 | 190 |

-continued
| Structure | Compound # | WT EC50 (nM) | T174I BT EC50 (nM) | T174I DE EC50 (nM) | Hum MS stability t½ (min) |
|---|---|---|---|---|---|
| 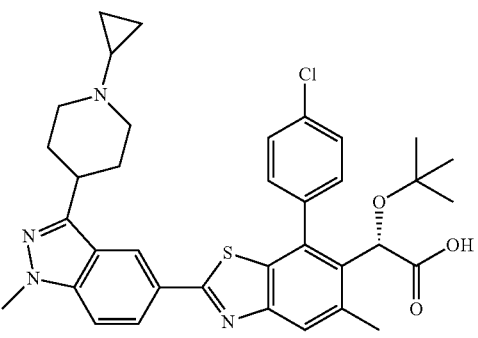 [SMILES: Cc1cc2nc(-c3ccc4c(c3)c(C3CCN(C5CC5)CC3)nn4C)sc2c(-c2ccc(Cl)cc2)c1[C@H](OC(C)(C)C)C(=O)O] | 128 | 4 | 292 | 511 | 242 |
| 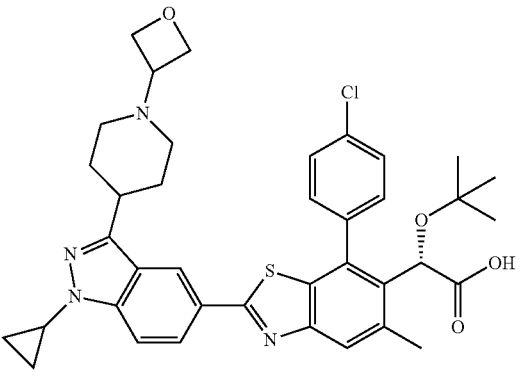 [SMILES: Cc1cc2nc(-c3ccc4c(c3)c(C3CCN(C5COC5)CC3)nn4C3CC3)sc2c(-c2ccc(Cl)cc2)c1[C@H](OC(C)(C)C)C(=O)O] | 38 | 8 | 293 | 349 | |
| 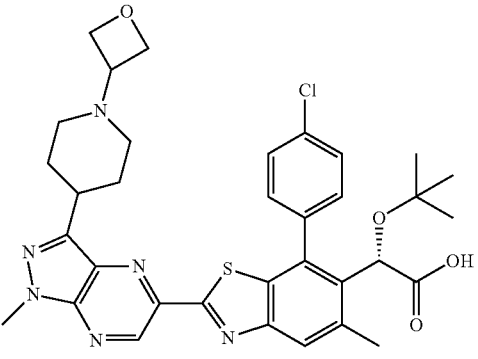 [SMILES: Cc1cc2nc(-c3cnc4c(n3)c(C3CCN(C5COC5)CC3)nn4C)sc2c(-c2ccc(Cl)cc2)c1[C@H](OC(C)(C)C)C(=O)O] | 118 | 4 | 298 | 737 | |
| 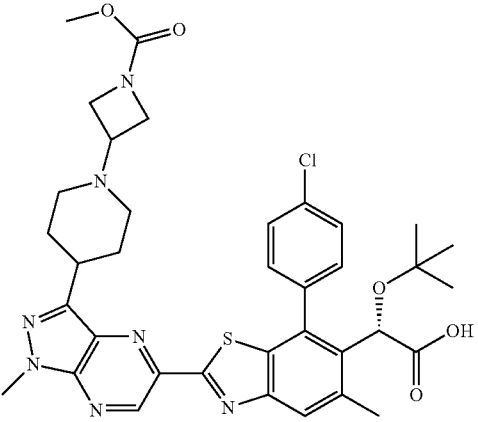 [SMILES: COC(=O)N1CC(N2CCC(c3nn(C)c4ncc(-c5nc6cc(C)c([C@H](OC(C)(C)C)C(=O)O)c(-c7ccc(Cl)cc7)c6s5)nc34)CC2)C1] | 119 | 8 | 310 | 332 | |

-continued

| Structure | Compound # | WT EC50 (nM) | T174I BT EC50 (nM) | T174I DE EC50 (nM) | Hum MS stability t½ (min) |
|---|---|---|---|---|---|
| 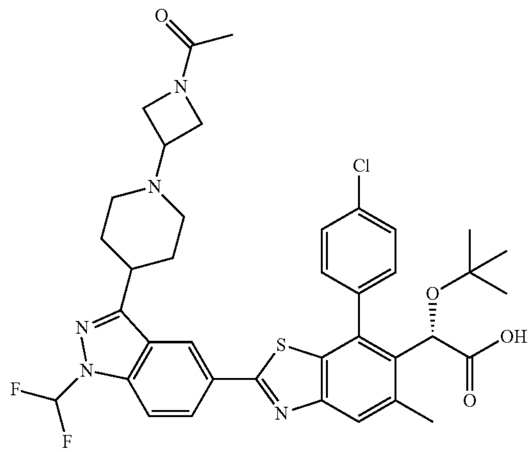 | 43 | 26 | 313 | 409 | |
| 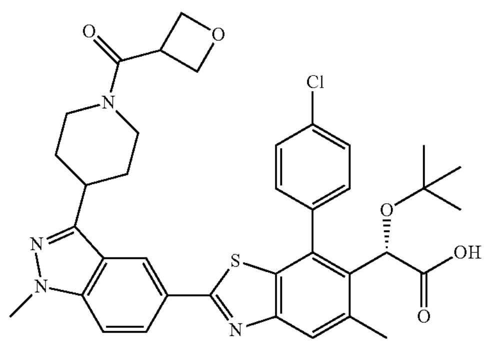 [SMILES: Cc1cc2nc(-c3ccc4c(c3)c(C3CCN(C(=O)C5COC5)CC3)nn4C)sc2c(-c2ccc(Cl)cc2)c1[C@H](OC(C)(C)C)C(=O)O] | 161 | 18 | 316 | 600 | |
| 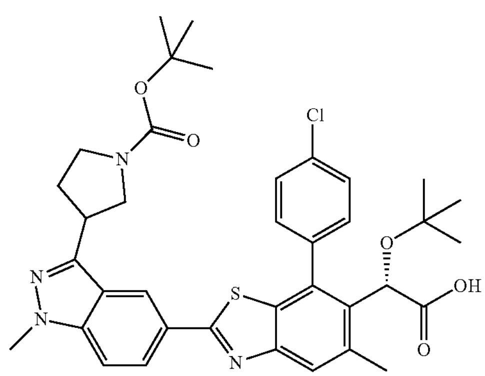 [SMILES: Cc1cc2nc(-c3ccc4c(c3)c(C3CCN(C(=O)OC(C)(C)C)C3)nn4C)sc2c(-c2ccc(Cl)cc2)c1[C@H](OC(C)(C)C)C(=O)O] | 62 | 108 | 331 | 514 | |
| 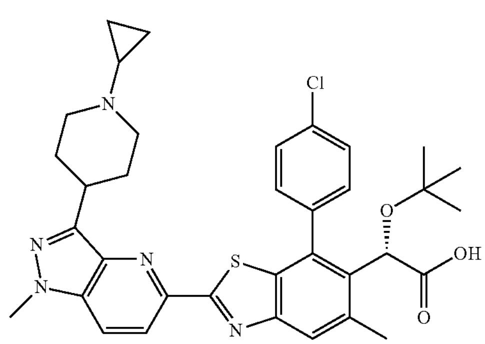 [SMILES: Cc1cc2nc(-c3ccc4c(n3)c(C3CCN(C5CC5)CC3)nn4C)sc2c(-c2ccc(Cl)cc2)c1[C@H](OC(C)(C)C)C(=O)O] | 187 | 4 | 339 | 844 | |

-continued

| Structure | Compound # | WT EC50 (nM) | T174I BT EC50 (nM) | T174I DE EC50 (nM) | Hum MS stability t½ (min) |
|---|---|---|---|---|---|
| 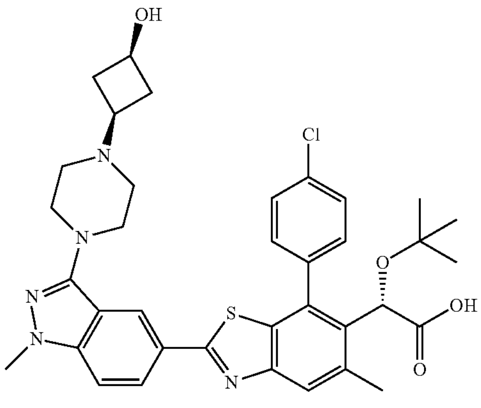 | 206 | 21 | 340 | 539 | |
| 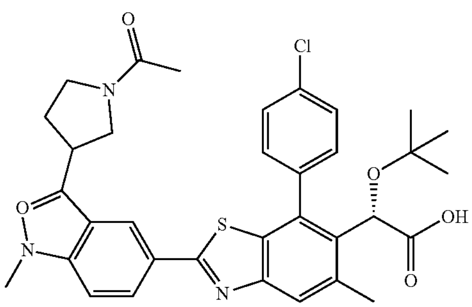 | 74 | 10 | 349 | 587 | 199 |
| 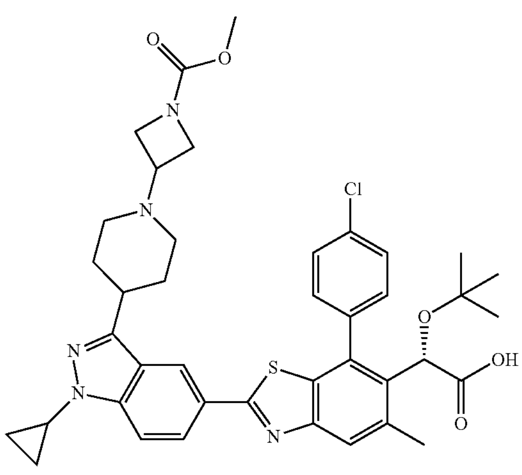 [SMILES: COC(=O)N1CC(N2CCC(c3nn(C4CC4)c4ccc(-c5nc6cc(C)c([C@H](OC(C)(C)C)C(=O)O)c(-c7ccc(Cl)cc7)c6s5)cc34)CC2)C1] | 46 | 17 | 352 | 716 | |

-continued
| Structure | Compound # | WT EC50 (nM) | T174I BT EC50 (nM) | T174I DE EC50 (nM) | Hum MS stability t½ (min) |
|---|---|---|---|---|---|
| 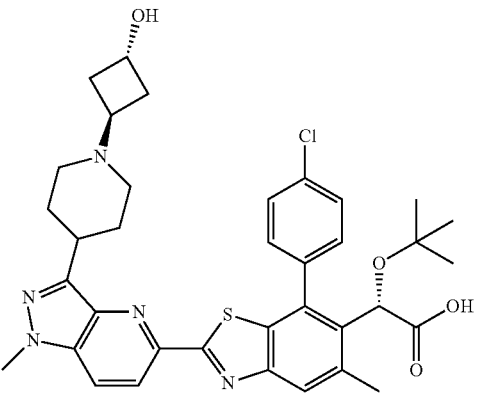 [SMILES: Cc1cc2nc(-c3ccc4c(n3)c(C3CCN([C@H]5C[C@H](O)C5)CC3)nn4C)sc2c(-c2ccc(Cl)cc2)c1[C@H](OC(C)(C)C)C(=O)O] | 186 | 29 | 367 | 784 | |
| 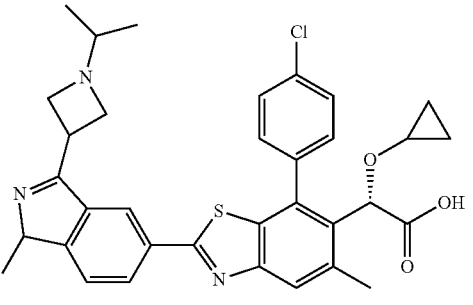 [SMILES: Cc1cc2nc(-c3ccc4c(c3)C(C3CN(C(C)C)C3)=NC4C)sc2c(-c2ccc(Cl)cc2)c1[C@H](OC1CC1)C(=O)O] | 55 | 36 | 372 | 1070 | 395 |
| 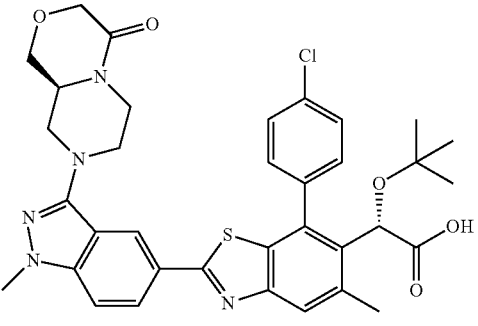 [SMILES: Cc1cc2nc(-c3ccc4c(c3)c(N3CCN5C(=O)COC[C@@H]5C3)nn4C)sc2c(-c2ccc(Cl)cc2)c1[C@H](OC(C)(C)C)C(=O)O] | 138 | 7 | 373 | 678 | 395 |
| 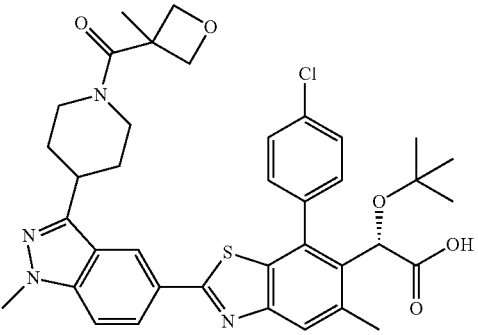 [SMILES: Cc1cc2nc(-c3ccc4c(c3)c(C3CCN(C(=O)C5(C)COC5)CC3)nn4C)sc2c(-c2ccc(Cl)cc2)c1[C@H](OC(C)(C)C)C(=O)O] | 160 | 15 | 375 | 756 | |

-continued

| Structure | Compound # | WT EC50 (nM) | T174I BT EC50 (nM) | T174I DE EC50 (nM) | Hum MS stability t½ (min) |
|---|---|---|---|---|---|
| 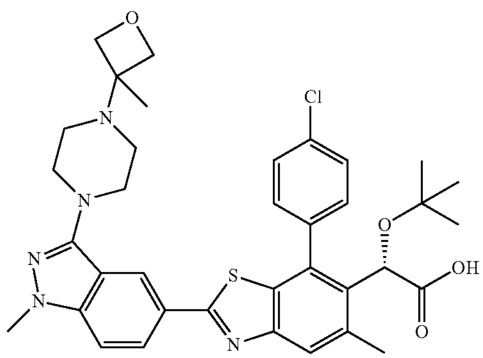 | 207 | 4 | 380 | 693 | 395 |
| 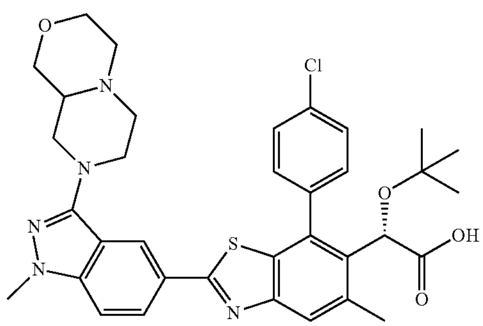 [SMILES: Cc1cc2nc(-c3ccc4c(c3)c(N3CCN5CCOCC5C3)nn4C)sc2c(-c2ccc(Cl)cc2)c1[C@H](OC(C)(C)C)C(=O)O] | 135 | 10 | 399 | 1059 | 165 |
| 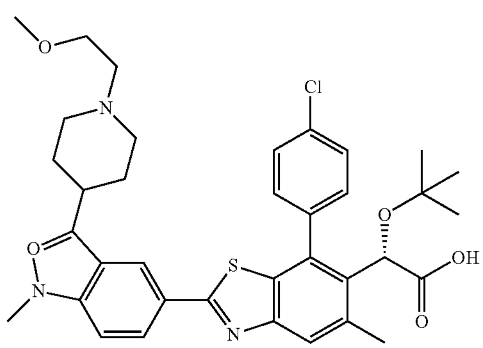 | 125 | 8 | 400 | 715 | 263 |
| 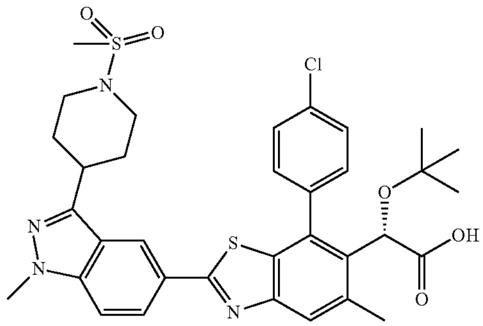 [SMILES: Cc1cc2nc(-c3ccc4c(c3)c(C3CCN(S(C)(=O)=O)CC3)nn4C)sc2c(-c2ccc(Cl)cc2)c1[C@H](OC(C)(C)C)C(=O)O] | 25 | 10 | 404 | 806 | 255 |

-continued
| Structure | Compound # | WT EC50 (nM) | T174I BT EC50 (nM) | T174I DE EC50 (nM) | Hum MS stability t½ (min) |
|---|---|---|---|---|---|
| 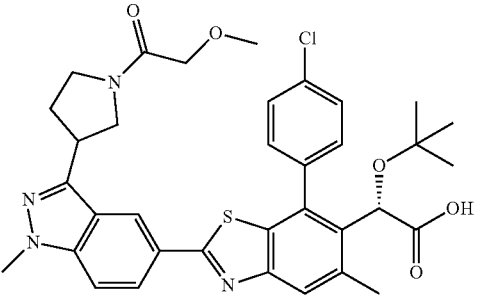 [SMILES: COCC(=O)N1CCC(c2nn(C)c3ccc(-c4nc5cc(C)c([C@H](OC(C)(C)C)C(=O)O)c(-c6ccc(Cl)cc6)c5s4)cc23)C1] | 75 | 16 | 423 | 496 | |
| 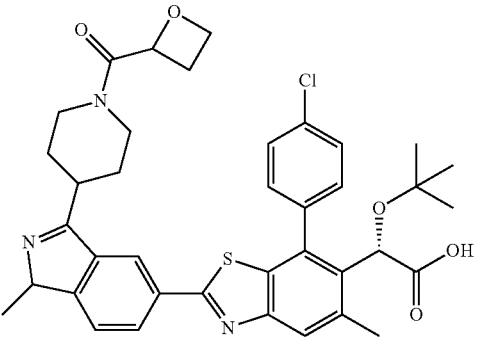 [SMILES: Cc1cc2nc(-c3ccc4c(c3)C(C3CCN(C(=O)C5CCO5)CC3)=NC4C)sc2c(-c2ccc(Cl)cc2)c1[C@H](OC(C)(C)C)C(=O)O] | 159 | 11 | 430 | 583 | |
| 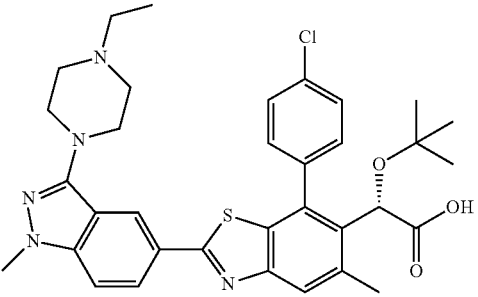 | 133 | 3 | 434 | 439 | 349 |
| 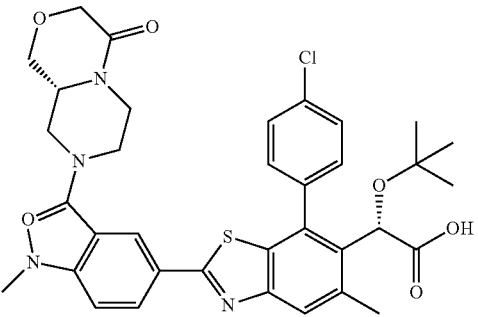 | 205 | 7 | 457 | 736 | |

-continued
| Structure | Compound # | WT EC50 (nM) | T174I BT EC50 (nM) | T174I DE EC50 (nM) | Hum MS stability t½ (min) |
|---|---|---|---|---|---|
| 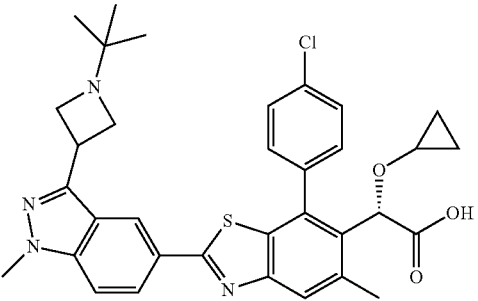 [SMILES: Cc1cc2nc(-c3ccc4c(c3)c(C3CN(C(C)(C)C)C3)nn4C)sc2c(-c2ccc(Cl)cc2)c1[C@H](OC1CC1)C(=O)O] | 60 | 31 | 477 | 692 | |
| 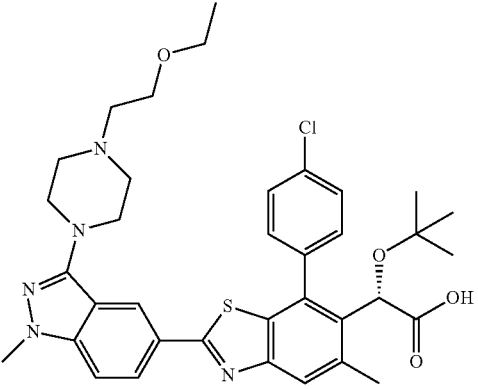 [SMILES: CCOCCN1CCN(c2nn(C)c3ccc(-c4nc5cc(C)c([C@H](OC(C)(C)C)C(=O)O)c(-c6ccc(Cl)cc6)c5s4)cc23)CC1] | 99 | 6 | 485 | 759 | 260 |
| 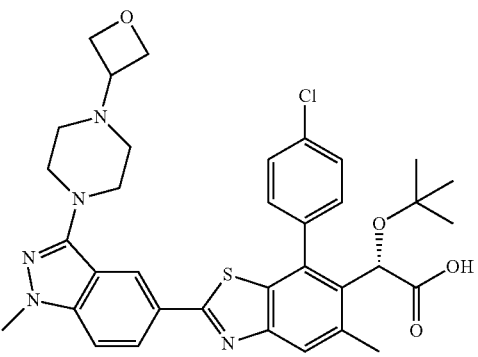 [SMILES: Cc1cc2nc(-c3ccc4c(c3)c(N3CCN(C5COC5)CC3)nn4C)sc2c(-c2ccc(Cl)cc2)c1[C@H](OC(C)(C)C)C(=O)O] | 104 | 11 | 491 | 904 | 395 |
| 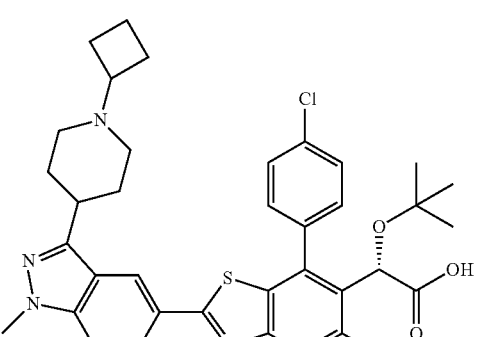 | 129 | 5 | 509 | 696 | |

-continued

| Structure | Compound # | WT EC50 (nM) | T174I BT EC50 (nM) | T174I DE EC50 (nM) | Hum MS stability t½ (min) |
|---|---|---|---|---|---|
| 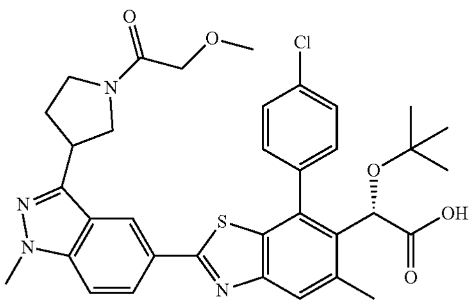 [SMILES: COCC(=O)N1CCC(c2nn(C)c3ccc(-c4nc5cc(C)c([C@H](OC(C)(C)C)C(=O)O)c(-c6ccc(Cl)cc6)c5s4)cc23)C1] | 76 | 16 | 510 | 906 | |
| 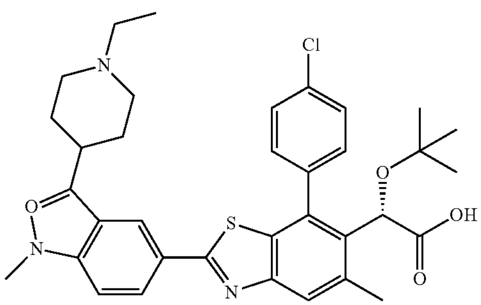 | 126 | 8 | 551 | 540 | 395 |
| 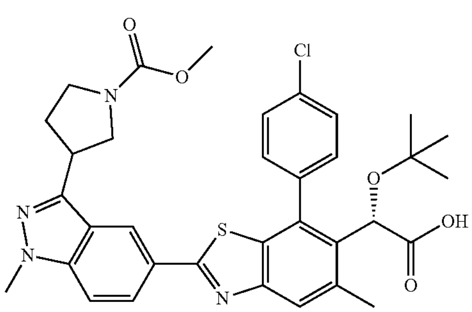 [SMILES: COC(=O)N1CCC(c2nn(C)c3ccc(-c4nc5cc(C)c([C@H](OC(C)(C)C)C(=O)O)c(-c6ccc(Cl)cc6)c5s4)cc23)C1] | 72 | 7 | 553 | 1034 | 395 |
| 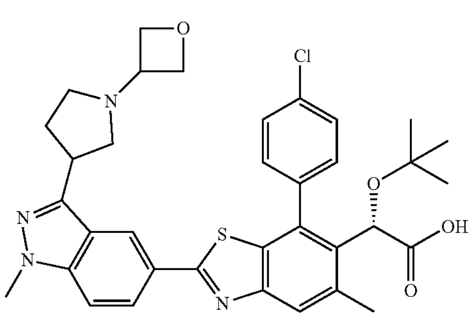 [SMILES: Cc1cc2nc(-c3ccc4c(c3)c(C3CCN(C5COC5)C3)nn4C)sc2c(-c2ccc(Cl)cc2)c1[C@H](OC(C)(C)C)C(=O)O] | 70 | 7 | 587 | 942 | 352 |

-continued

| Structure | Compound # | WT EC50 (nM) | T174I BT EC50 (nM) | T174I DE EC50 (nM) | Hum MS stability t½ (min) |
|---|---|---|---|---|---|
| 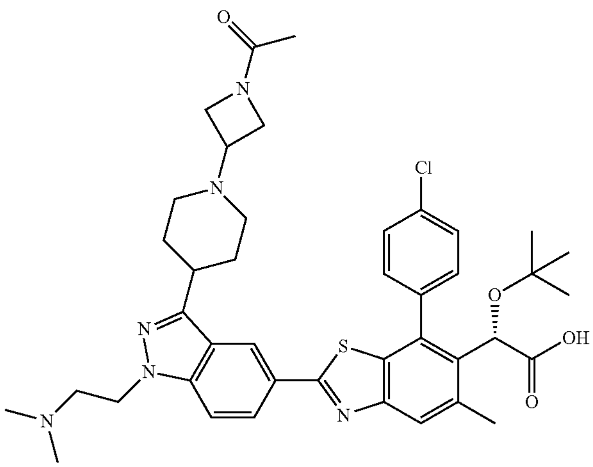 [SMILES: CC(=O)N1CC(N2CCC(c3nn(CCN(C)C)c4ccc(-c5nc6cc(C)c([C@H](OC(C)(C)C)C(=O)O)c(-c7ccc(Cl)cc7)c6s5)cc34)CC2)C1] | 33 | 5 | 587 | 1016 | |
| 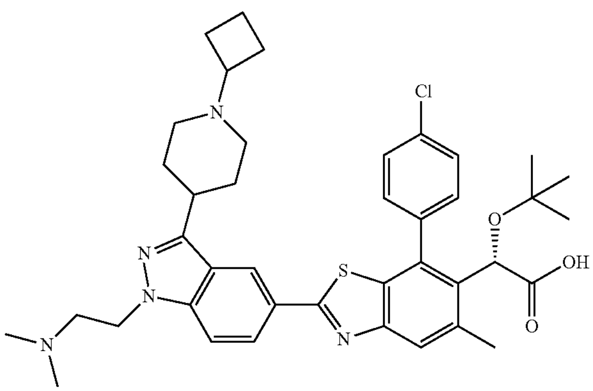 [SMILES: Cc1cc2nc(-c3ccc4c(c3)c(C3CCN(C5CCC5)CC3)nn4CCN(C)C)sc2c(-c2ccc(Cl)cc2)c1[C@H](OC(C)(C)C)C(=O)O] | 32 | 11 | 591 | 1601 | 90 |
| 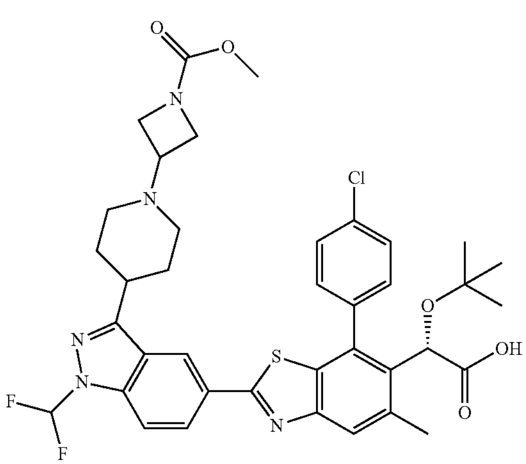 [SMILES: COC(=O)N1CC(N2CCC(c3nn(C(F)F)c4ccc(-c5nc6cc(C)c([C@H](OC(C)(C)C)C(=O)O)c(-c7ccc(Cl)cc7)c6s5)cc34)CC2)C1] | 44 | 30 | 600 | 776 | |

-continued
| Structure | Compound # | WT EC50 (nM) | T174I BT EC50 (nM) | T174I DE EC50 (nM) | Hum MS stability t½ (min) |
|---|---|---|---|---|---|
| 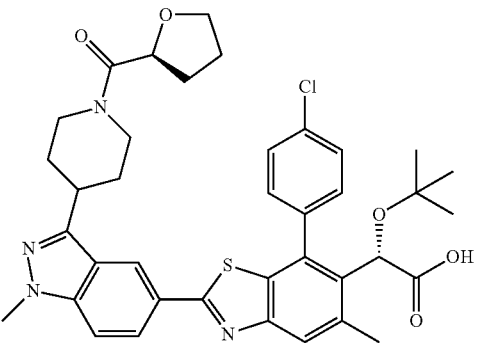 [SMILES: Cc1cc2nc(-c3ccc4c(c3)c(C3CCN(C(=O)[C@@H]5CCCO5)CC3)nn4C)sc2c(-c2ccc(Cl)cc2)c1[C@H](OC(C)(C)C)C(=O)O] | 157 | 11 | 620 | 789 | |
| 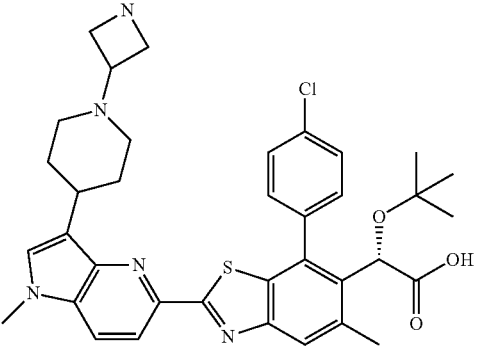 | 108 | 6 | 630 | 1229 | 395 |
| 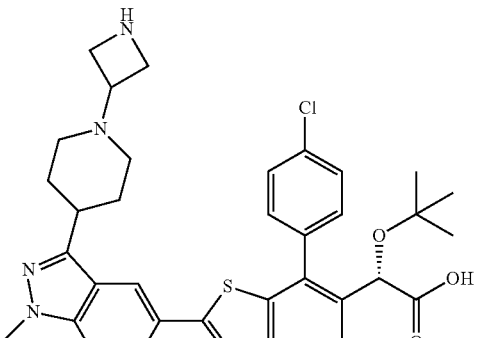 | 29 | 52 | 646 | 823 | |
| 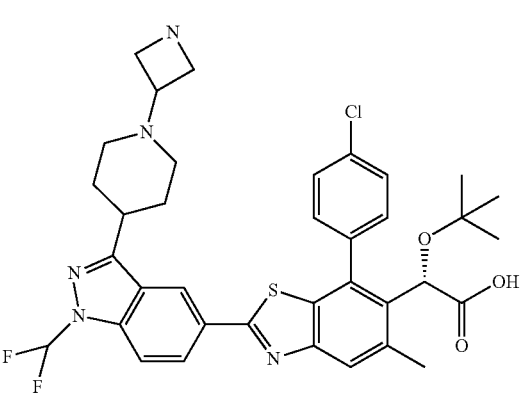 [SMILES: Cc1cc2nc(-c3ccc4c(c3)c(C3CCN(C5CNC5)CC3)nn4C(F)F)sc2c(-c2ccc(Cl)cc2)c1[C@H](OC(C)(C)C)C(=O)O] | 39 | 13 | 651 | 1149 | |

-continued
| Structure | Compound # | WT EC50 (nM) | T174I BT EC50 (nM) | T174I DE EC50 (nM) | Hum MS stability t½ (min) |
|---|---|---|---|---|---|
| 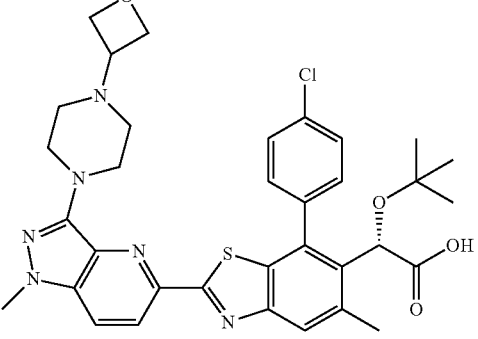 | 15 | 4 | 657 | 3071 | 170 |
| 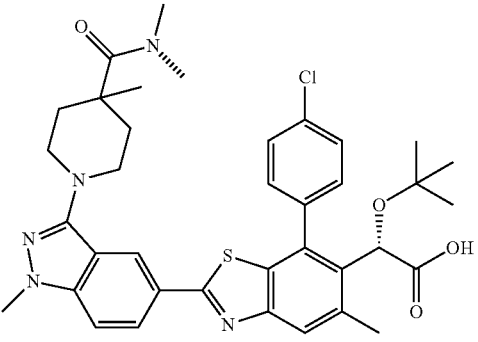 | 137 | 10 | 697 | 962 | |
| 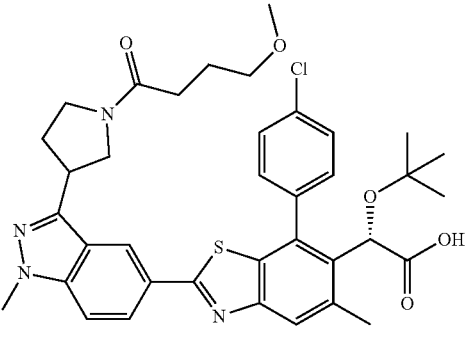 [SMILES: COCCCC(=O)N1CCC(c2nn(C)c3ccc(-c4nc5cc(C)c([C@H](OC(C)(C)C)C(=O)O)c(-c6ccc(Cl)cc6)c5s4)cc23)C1] | 73 | 6 | 720 | 823 | 183 |
| 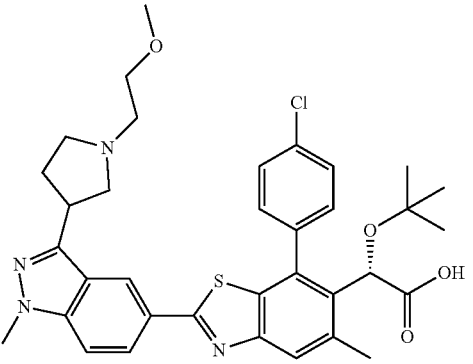 [SMILES: COCCN1CCC(c2nn(C)c3ccc(-c4nc5cc(C)c([C@H](OC(C)(C)C)C(=O)O)c(-c6ccc(Cl)cc6)c5s4)cc23)C1] | 65 | 4 | 752 | 2117 | 395 |

-continued

| Structure | Compound # | WT EC50 (nM) | T174I BT EC50 (nM) | T174I DE EC50 (nM) | Hum MS stability t½ (min) |
|---|---|---|---|---|---|
| 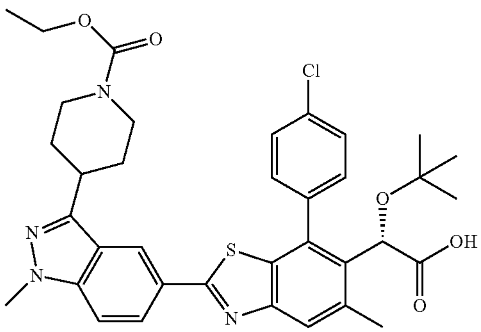 [SMILES: CCOC(=O)N1CCC(c2nn(C)c3ccc(-c4nc5cc(C)c([C@H](OC(C)(C)C)C(=O)O)c(-c6ccc(Cl)cc6)c5s4)cc23)CC1] | 24 | 16 | 769 | 1094 | |
| 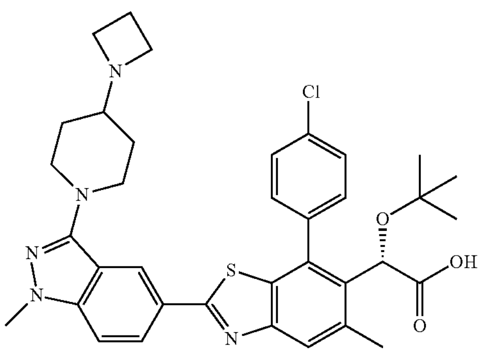 [SMILES: Cc1cc2nc(-c3ccc4c(c3)c(N3CCC(N5CCC5)CC3)nn4C)sc2c(-c2ccc(Cl)cc2)c1[C@H](OC(C)(C)C)C(=O)O] | 136 | 14 | 857 | 1698 | |
| 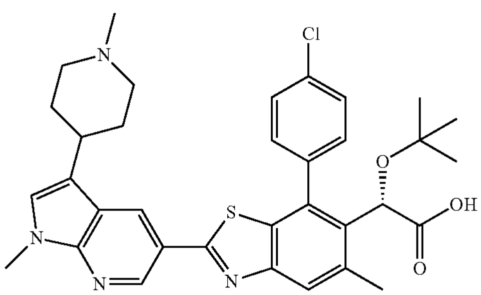 [SMILES: Cc1cc2nc(-c3cnc4c(c3)c(C3CCN(C)CC3)cn4C)sc2c(-c2ccc(Cl)cc2)c1[C@H](OC(C)(C)C)C(=O)O] | 106 | 29 | 864 | 3077 | 395 |
| 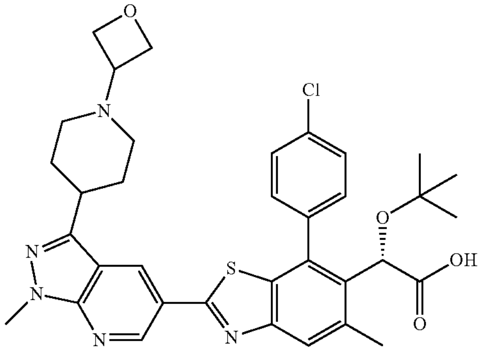 | 113 | 5 | 871 | 1523 | |

-continued

| Structure | Compound # | WT EC50 (nM) | T174I BT EC50 (nM) | T174I DE EC50 (nM) | Hum MS stability t½ (min) |
|---|---|---|---|---|---|
| 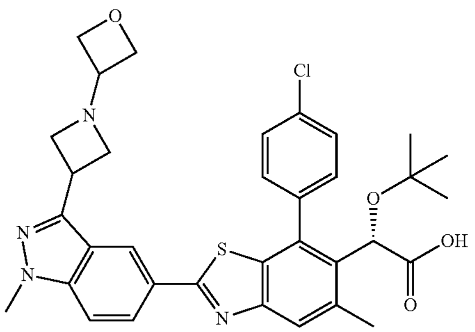 [SMILES: Cc1cc2nc(-c3ccc4c(c3)c(C3CN(C5COC5)C3)nn4C)sc2c(-c2ccc(Cl)cc2)c1[C@H](OC(C)(C)C)C(=O)O] | 59 | 8 | 883 | 1734 | 395 |
| 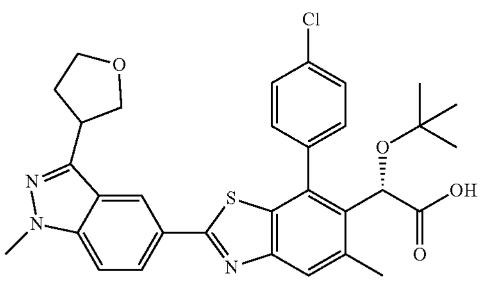 [SMILES: Cc1cc2nc(-c3ccc4c(c3)c(C3CCOC3)nn4C)sc2c(-c2ccc(Cl)cc2)c1[C@H](OC(C)(C)C)C(=O)O] | 52 | 8 | 905 | 946 | 223 |
| 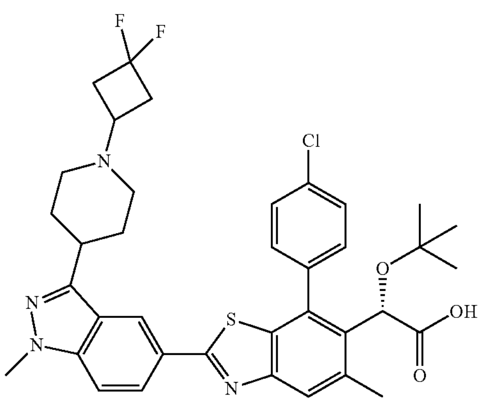 [SMILES: Cc1cc2nc(-c3ccc4c(c3)c(C3CCN(C5CC(F)(F)C5)CC3)nn4C)sc2c(-c2ccc(Cl)cc2)c1[C@H](OC(C)(C)C)C(=O)O] | 155 | 13 | 922 | 1919 | |
| 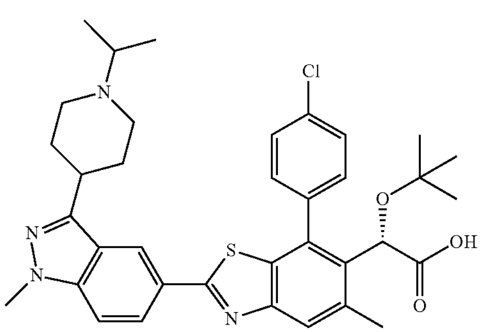 [SMILES: Cc1cc2nc(-c3ccc4c(c3)c(C3CCN(C(C)C)CC3)nn4C)sc2c(-c2ccc(Cl)cc2)c1[C@H](OC(C)(C)C)C(=O)O] | 127 | 8 | 932 | 1702 | |

| Structure | Compound # | WT EC50 (nM) | T174I BT EC50 (nM) | T174I DE EC50 (nM) | Hum MS stability t½ (min) |
|---|---|---|---|---|---|
| 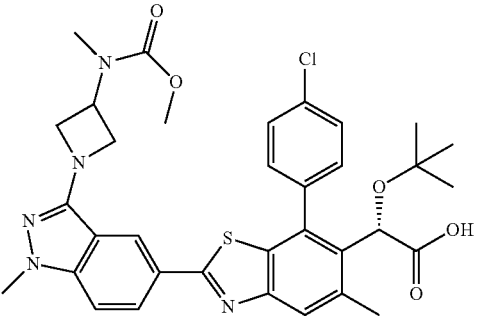 [SMILES: COC(=O)N(C)C1CN(c2nn(C)c3ccc(-c4nc5cc(C)c([C@H](OC(C)(C)C)C(=O)O)c(-c6ccc(Cl)cc6)c5s4)cc23)C1] | 102 | 13 | 934 | 1271 | |
| 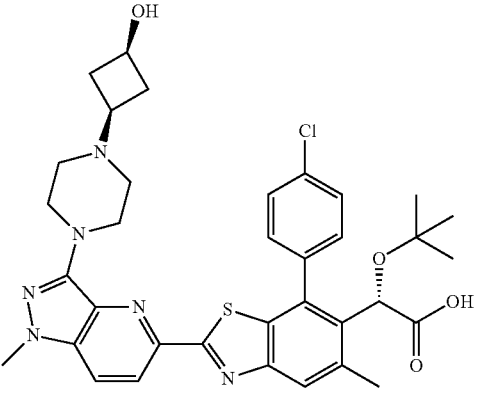 | 197 | 18 | 936 | 2679 | 168 |
| 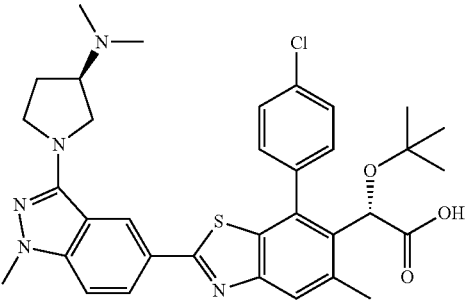 | 92 | 14 | 938 | 1945 | 363 |
| 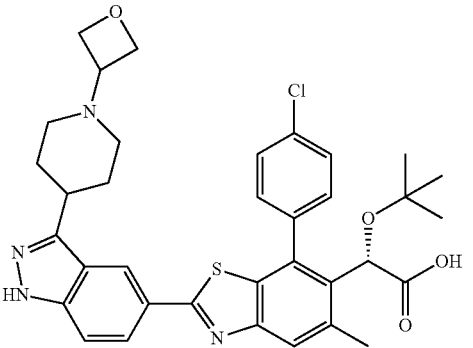 [SMILES: Cc1cc2nc(-c3ccc4[nH]nc(C5CCN(C6COC6)CC5)c4c3)sc2c(-c2ccc(Cl)cc2)c1[C@H](OC(C)(C)C)C(=O)O] | 34 | 31 | 968 | 1173 | |

-continued

| Structure | Compound # | WT EC50 (nM) | T174I BT EC50 (nM) | T174I DE EC50 (nM) | Hum MS stability t½ (min) |
|---|---|---|---|---|---|
| 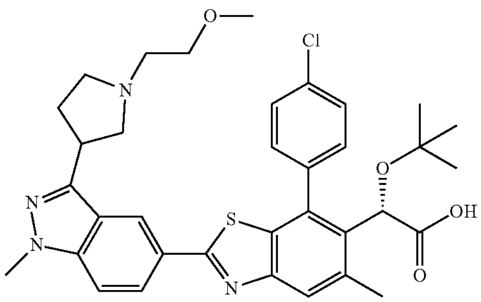 [SMILES: COCCN1CCC(c2nn(C)c3ccc(-c4nc5cc(C)c([C@H](OC(C)(C)C)C(=O)O)c(-c6ccc(Cl)cc6)c5s4)cc23)C1] | 69 | 5 | 972 | 1154 | 343 |
| 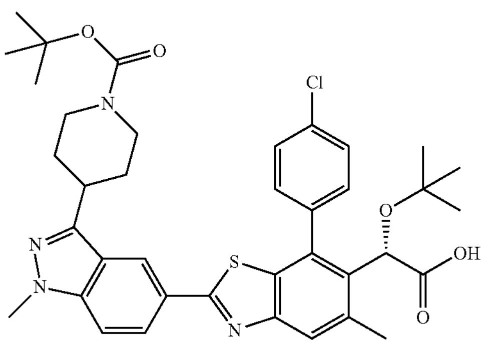 [SMILES: Cc1cc2nc(-c3ccc4c(c3)c(C3CCN(C(=O)OC(C)(C)C)CC3)nn4C)sc2c(-c2ccc(Cl)cc2)c1[C@H](OC(C)(C)C)C(=O)O] | 23 | 99 | 987 | 356 | |
| 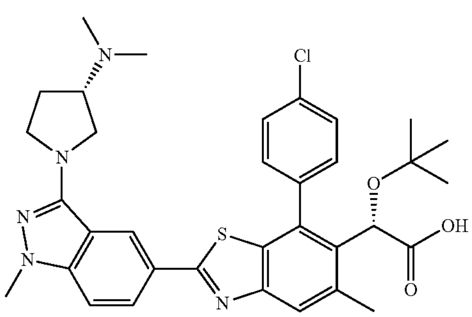 [SMILES: Cc1cc2nc(-c3ccc4c(c3)c(N3CC[C@H](N(C)C)C3)nn4C)sc2c(-c2ccc(Cl)cc2)c1[C@H](OC(C)(C)C)C(=O)O] | 93 | 13 | 1008 | 3451 | 395 |
| 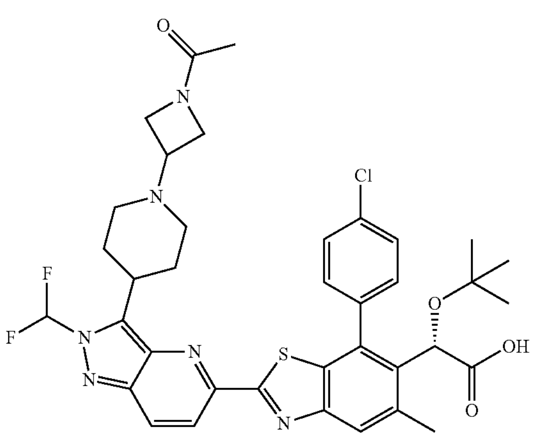 [SMILES: CC(=O)N1CC(N2CCC(c3c4nc(-c5nc6cc(C)c([C@H](OC(C)(C)C)C(=O)O)c(-c7ccc(Cl)cc7)c6s5)ccc4nn3C(F)F)CC2)C1] | 189 | 12 | 1023 | 1403 | |

-continued

| Structure | Compound # | WT EC50 (nM) | T174I BT EC50 (nM) | T174I DE EC50 (nM) | Hum MS stability t½ (min) |
|---|---|---|---|---|---|
| 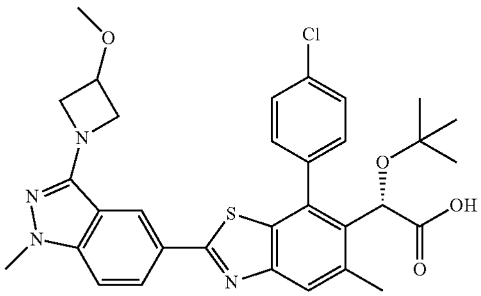 [SMILES: COC1CN(c2nn(C)c3ccc(-c4nc5cc(C)c([C@H](OC(C)(C)C)C(=O)O)c(-c6ccc(Cl)cc6)c5s4)cc23)C1] | 2 | 7 | 1024 | 2583 | 109 |
| 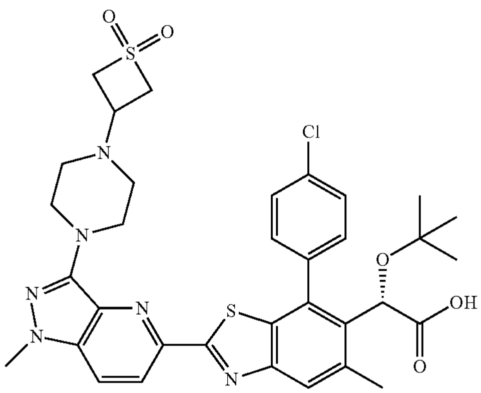 | 198 | 9 | 1044 | 4618 | |
| 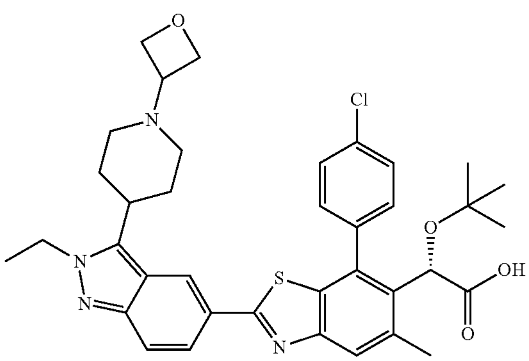 [SMILES: CCn1nc2ccc(-c3nc4cc(C)c([C@H](OC(C)(C)C)C(=O)O)c(-c5ccc(Cl)cc5)c4s3)cc2c1C1CCN(C2COC2)CC1] | 36 | 14 | 1078 | 3575 | |
| 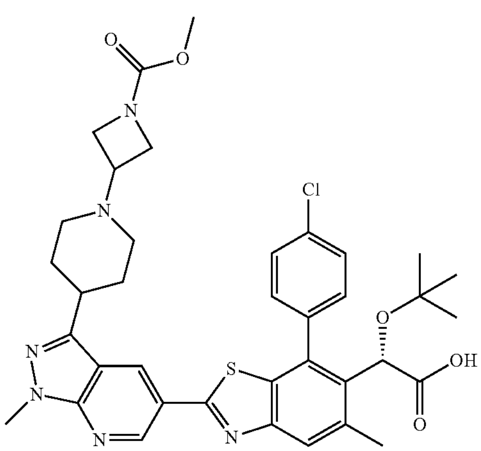 [SMILES: COC(=O)N1CC(N2CCC(c3nn(C)c4ncc(-c5nc6cc(C)c([C@H](OC(C)(C)C)C(=O)O)c(-c7ccc(Cl)cc7)c6s5)cc34)CC2)C1] | 114 | 12 | 1085 | 2203 | |

-continued

| Structure | Compound # | WT EC50 (nM) | T174I BT EC50 (nM) | T174I DE EC50 (nM) | Hum MS stability t½ (min) |
|---|---|---|---|---|---|
| 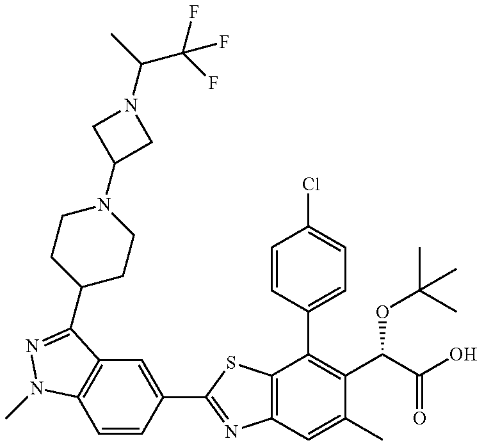 [SMILES: Cc1cc2nc(-c3ccc4c(c3)c(C3CCN(C5CN(C(C)C(F)(F)F)C5)CC3)nn4C)sc2c(-c2ccc(Cl)cc2)c1[C@H](OC(C)(C)C)C(=O)O] | 8 | 13 | 1091 | 1334 | |
| 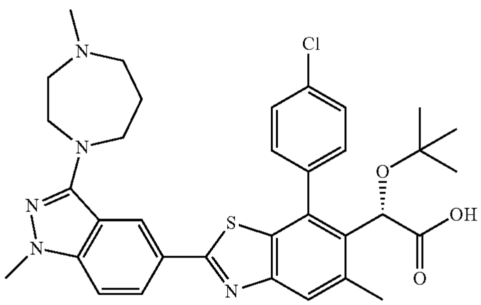 [SMILES: Cc1cc2nc(-c3ccc4c(c3)c(N3CCCN(C)CC3)nn4C)sc2c(-c2ccc(Cl)cc2)c1[C@H](OC(C)(C)C)C(=O)O] | 132 | 25 | 1100 | 1684 | 395 |
| 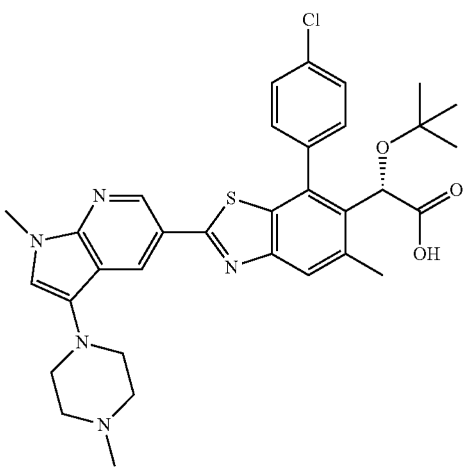 [SMILES: Cc1cc2nc(-c3cnc4c(c3)c(N3CCN(C)CC3)cn4C)sc2c(-c2ccc(Cl)cc2)c1[C@H](OC(C)(C)C)C(=O)O] | 107 | 23 | 1113 | 2365 | |
| 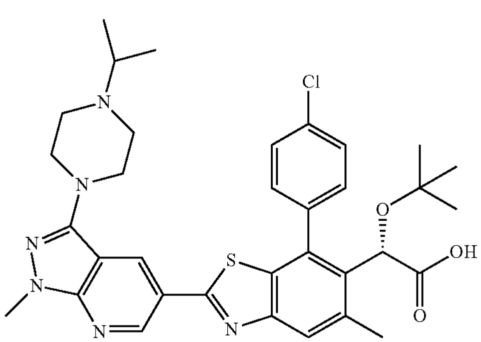 [SMILES: Cc1cc2nc(-c3cnc4c(c3)c(N3CCN(C(C)C)CC3)nn4C)sc2c(-c2ccc(Cl)cc2)c1[C@H](OC(C)(C)C)C(=O)O] | 111 | 5 | 1151 | 2876 | |

-continued

| Structure | Compound # | WT EC50 (nM) | T174I BT EC50 (nM) | T174I DE EC50 (nM) | Hum MS stability t½ (min) |
|---|---|---|---|---|---|
| 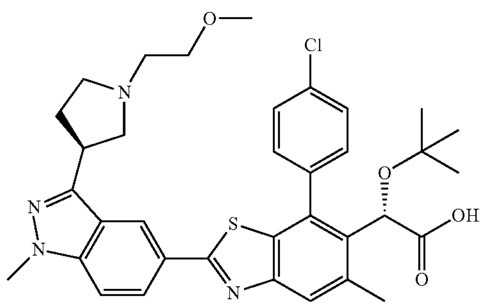 [SMILES: COCCN1CC[C@H](c2nn(C)c3ccc(-c4nc5cc(C)c([C@H](OC(C)(C)C)C(=O)O)c(-c6ccc(Cl)cc6)c5s4)cc23)C1] | 68 | 5 | 1155 | 1602 | 395 |
| 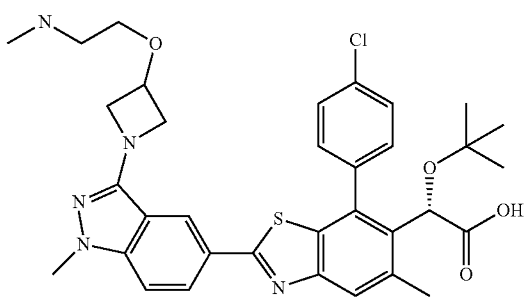 [SMILES: CNCCOC1CN(c2nn(C)c3ccc(-c4nc5cc(C)c([C@H](OC(C)(C)C)C(=O)O)c(-c6ccc(Cl)cc6)c5s4)cc23)C1] | 134 | 13 | 1164 | 2244 | 89 |
| 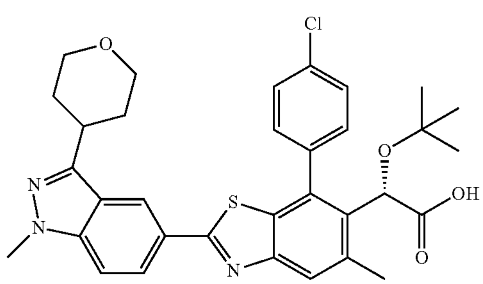 [SMILES: Cc1cc2nc(-c3ccc4c(c3)c(C3CCOCC3)nn4C)sc2c(-c2ccc(Cl)cc2)c1[C@H](OC(C)(C)C)C(=O)O] | 19 | 12 | 1166 | 2780 | 249 |
| 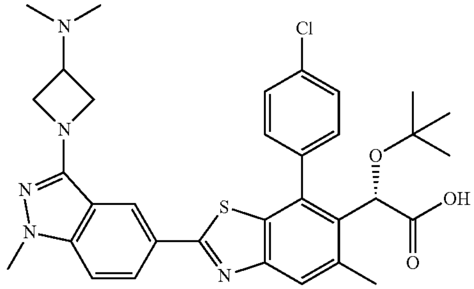 [SMILES: Cc1cc2nc(-c3ccc4c(c3)c(N3CC(N(C)C)C3)nn4C)sc2c(-c2ccc(Cl)cc2)c1[C@H](OC(C)(C)C)C(=O)O] | 90 | 8 | 1178 | 1354 | 395 |

-continued
| Structure | Compound # | WT EC50 (nM) | T174I BT EC50 (nM) | T174I DE EC50 (nM) | Hum MS stability t½ (min) |
|---|---|---|---|---|---|
| 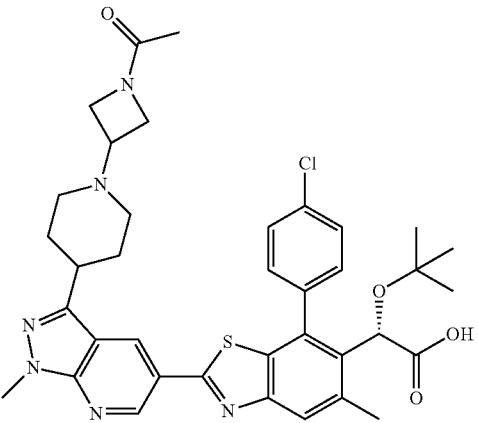 | 117 | 27 | 1179 | 1686 | |
| 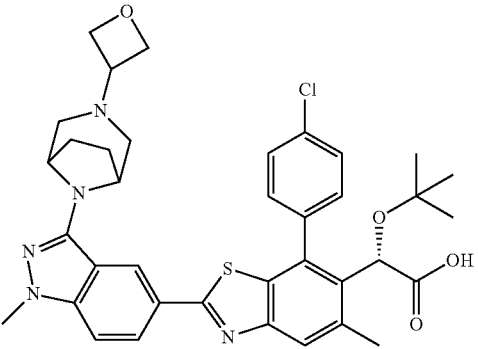 [SMILES: Cc1cc2nc(-c3ccc4c(c3)c(N3C5CCC3CN(C3COC3)C5)nn4C)sc2c(-c2ccc(Cl)cc2)c1[C@H](OC(C)(C)C)C(=O)O] | 13 | 10 | 1227 | 3128 | |
| 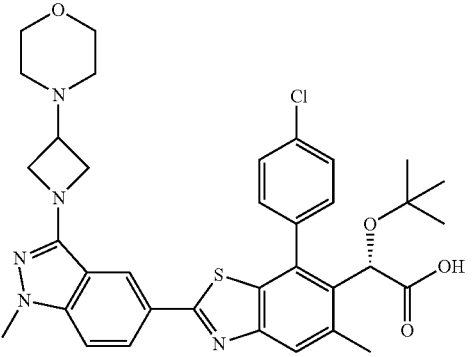 [SMILES: Cc1cc2nc(-c3ccc4c(c3)c(N3CC(N5CCOCC5)C3)nn4C)sc2c(-c2ccc(Cl)cc2)c1[C@H](OC(C)(C)C)C(=O)O] | 88 | 10 | 1242 | 1696 | 395 |
| 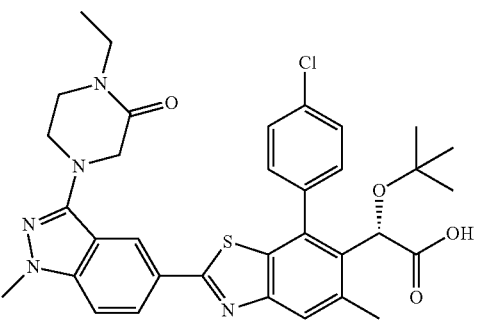 [SMILES: CCN1CCN(c2nn(C)c3ccc(-c4nc5cc(C)c([C@H](OC(C)(C)C)C(=O)O)c(-c6ccc(Cl)cc6)c5s4)cc23)CC1=O] | 84 | 48 | 1250 | 1872 | |

-continued
| Structure | Compound # | WT EC50 (nM) | T174I BT EC50 (nM) | T174I DE EC50 (nM) | Hum MS stability t½ (min) |
|---|---|---|---|---|---|
| 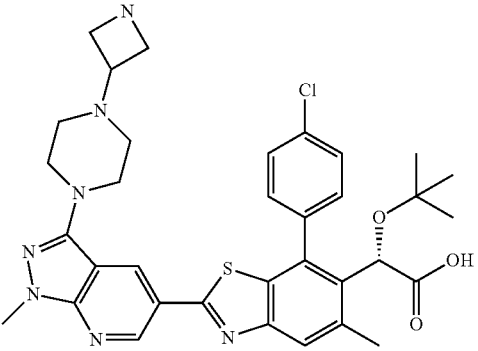 | 112 | 10 | 1250 | 2112 | |
| 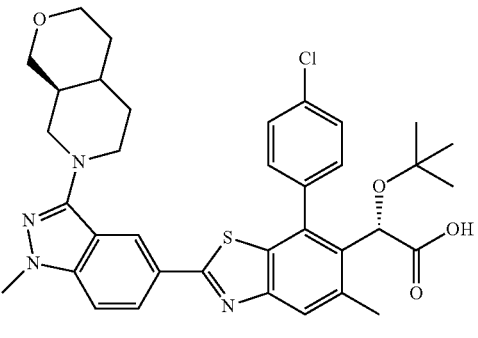 | 4 | 10 | 1268 | 1744 | 395 |
| 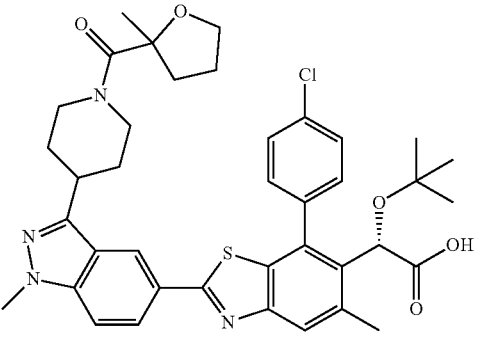 [SMILES: Cc1cc2nc(-c3ccc4c(c3)c(C3CCN(C(=O)C5(C)CCCO5)CC3)nn4C)sc2c(-c2ccc(Cl)cc2)c1[C@H](OC(C)(C)C)C(=O)O] | 158 | 11 | 1301 | 1670 | |
| 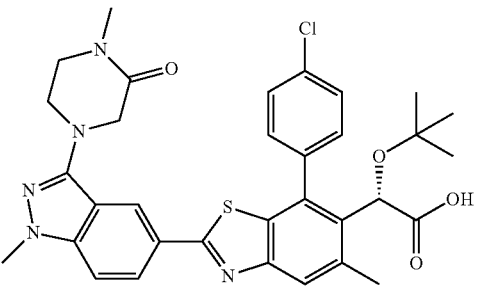 [SMILES: Cc1cc2nc(-c3ccc4c(c3)c(N3CCN(C)C(=O)C3)nn4C)sc2c(-c2ccc(Cl)cc2)c1[C@H](OC(C)(C)C)C(=O)O] | 85 | 57 | 1349 | 1166 | |

-continued

| Structure | Compound # | WT EC50 (nM) | T174I BT EC50 (nM) | T174I DE EC50 (nM) | Hum MS stability t½ (min) |
|---|---|---|---|---|---|
| 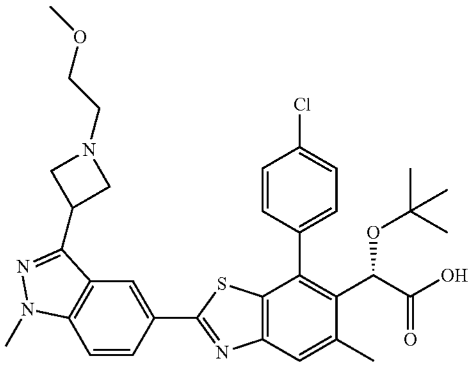 [SMILES: COCCN1CC(c2nn(C)c3ccc(-c4nc5cc(C)c([C@H](OC(C)(C)C)C(=O)O)c(-c6ccc(Cl)cc6)c5s4)cc23)C1] | 56 | 4 | 1386 | 2071 | 395 |
| 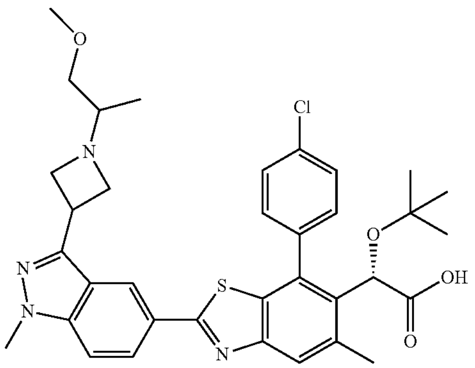 [SMILES: COCC(C)N1CC(c2nn(C)c3ccc(-c4nc5cc(C)c([C@H](OC(C)(C)C)C(=O)O)c(-c6ccc(Cl)cc6)c5s4)cc23)C1] | 124 | 4 | 1440 | 3443 | 395 |
| 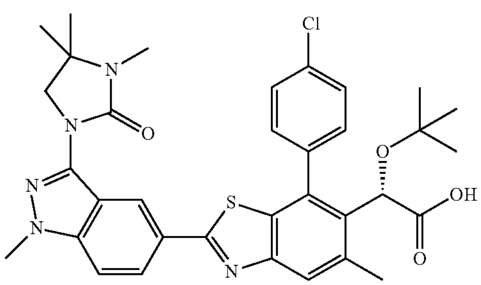 [SMILES: Cc1cc2nc(-c3ccc4c(c3)c(N3CC(C)(C)N(C)C3=O)nn4C)sc2c(-c2ccc(Cl)cc2)c1[C@H](OC(C)(C)C)C(=O)O] | 122 | 14 | 1443 | 3813 | 269 |
| 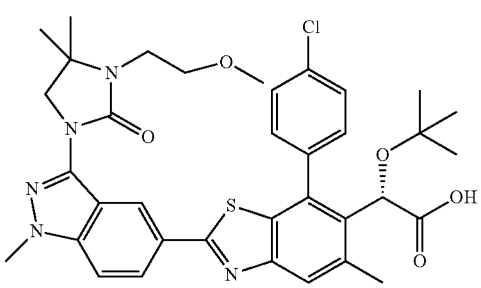 [SMILES: COCCN1C(=O)N(c2nn(C)c3ccc(-c4nc5cc(C)c([C@H](OC(C)(C)C)C(=O)O)c(-c6ccc(Cl)cc6)c5s4)cc23)CC1(C)C] | 123 | 11 | 1446 | 7088 | 96 |

-continued

| Structure | Compound # | WT EC50 (nM) | T174I BT EC50 (nM) | T174I DE EC50 (nM) | Hum MS stability t½ (min) |
|---|---|---|---|---|---|
| 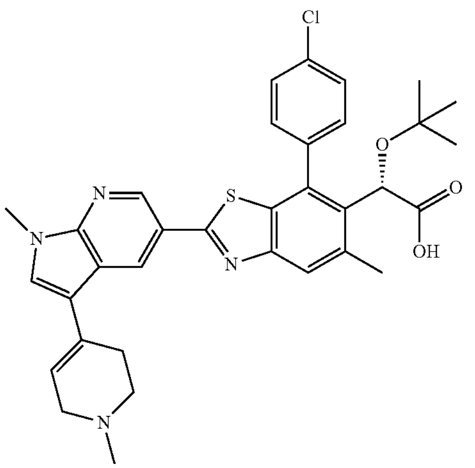 [SMILES: Cc1cc2nc(-c3cnc4c(c3)c(C3=CCN(C)CC3)cn4C)sc2c(-c2ccc(Cl)cc2)c1[C@H](OC(C)(C)C)C(=O)O] | 105 | 35 | 1464 | 2292 | |
| 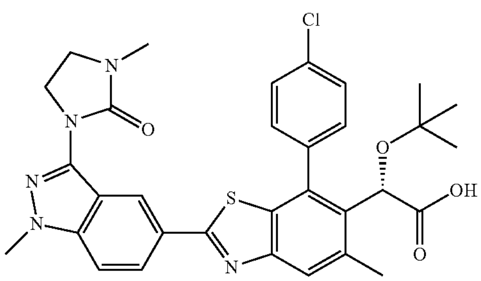 [SMILES: Cc1cc2nc(-c3ccc4c(c3)c(N3CCN(C)C3=O)nn4C)sc2c(-c2ccc(Cl)cc2)c1[C@H](OC(C)(C)C)C(=O)O] | 80 | 13 | 1512 | 2278 | 325 |
| 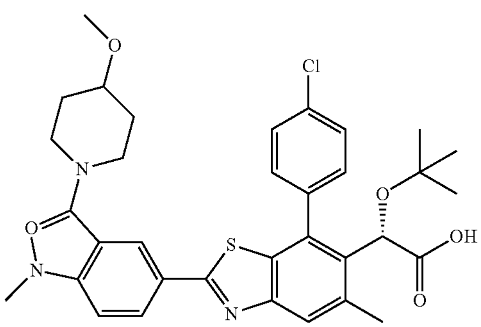 | 142 | 12 | 1565 | 2331 | |
| 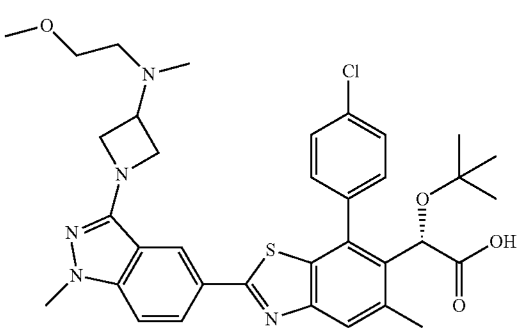 [SMILES: COCCN(C)C1CN(c2nn(C)c3ccc(-c4nc5cc(C)c([C@H](OC(C)(C)C)C(=O)O)c(-c6ccc(Cl)cc6)c5s4)cc23)C1] | 145 | 12 | 1592 | 2168 | 129 |

-continued

| Structure | Compound # | WT EC50 (nM) | T174I BT EC50 (nM) | T174I DE EC50 (nM) | Hum MS stability t½ (min) |
|---|---|---|---|---|---|
| 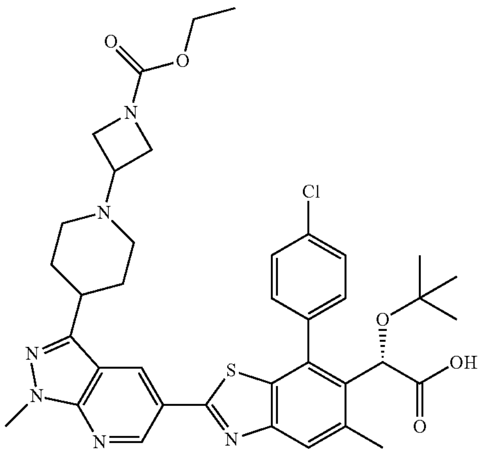 [SMILES: CCOC(=O)N1CC(N2CCC(c3nn(C)c4ncc(-c5nc6cc(C)c([C@H](OC(C)(C)C)C(=O)O)c(-c7ccc(Cl)cc7)c6s5)cc34)CC2)C1] | 115 | 14 | 1599 | 2449 | |
| 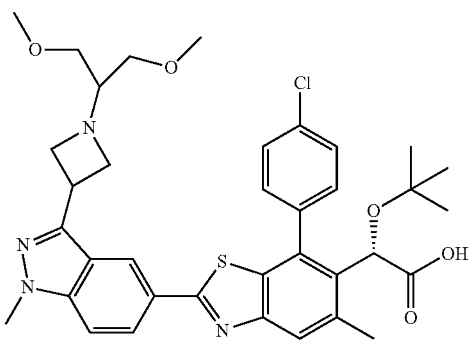 [SMILES: COCC(COC)N1CC(c2nn(C)c3ccc(-c4nc5cc(C)c([C@H](OC(C)(C)C)C(=O)O)c(-c6ccc(Cl)cc6)c5s4)cc23)C1] | 61 | 7 | 1607 | 2703 | 217 |
| 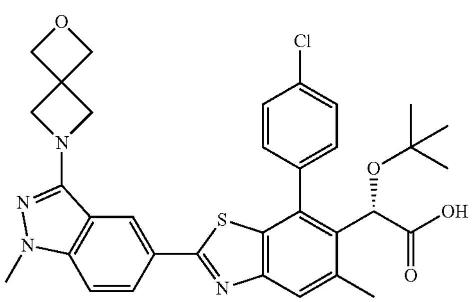 [SMILES: Cc1cc2nc(-c3ccc4c(c3)c(N3CC5(COC5)C3)nn4C)sc2c(-c2ccc(Cl)cc2)c1[C@H](OC(C)(C)C)C(=O)O] | 91 | 11 | 1722 | 2440 | |
| 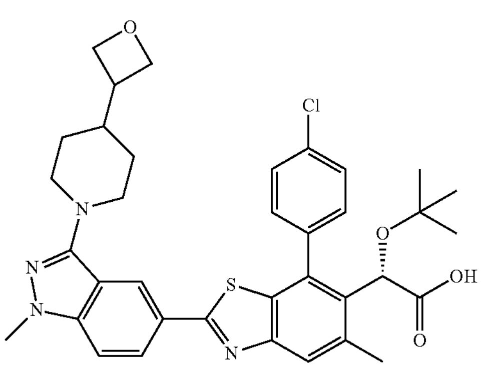 | 146 | 31 | 1745 | 2215 | |

-continued
| Structure | Compound # | WT EC50 (nM) | T174I BT EC50 (nM) | T174I DE EC50 (nM) | Hum MS stability t½ (min) |
|---|---|---|---|---|---|
| 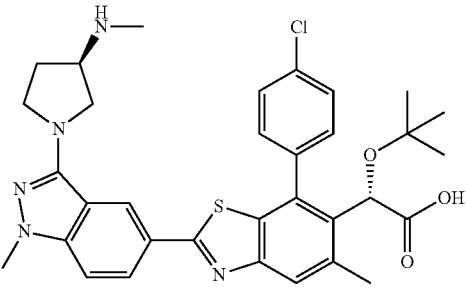 [SMILES: CN[C@@H]1CCN(c2nn(C)c3ccc(-c4nc5cc(C)c([C@H](OC(C)(C)C)C(=O)O)c(-c6ccc(Cl)cc6)c5s4)cc23)C1] | 95 | 41 | 1748 | 11505 | |
| 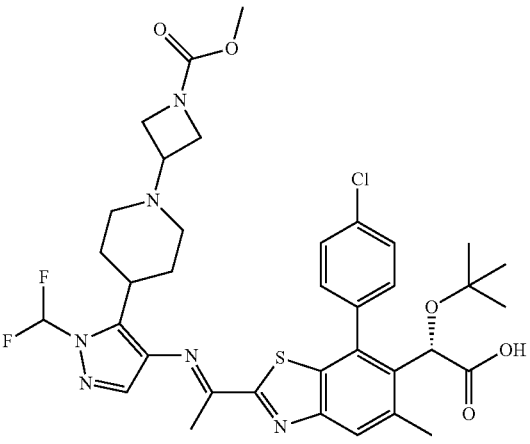 [SMILES: COC(=O)N1CC(N2CCC(c3c(/N=C(\C)c4nc5cc(C)c([C@H](OC(C)(C)C)C(=O)O)c(-c6ccc(Cl)cc6)c5s4)cnn3C(F)F)CC2)C1] | 190 | 6 | 1765 | 2748 | |
| 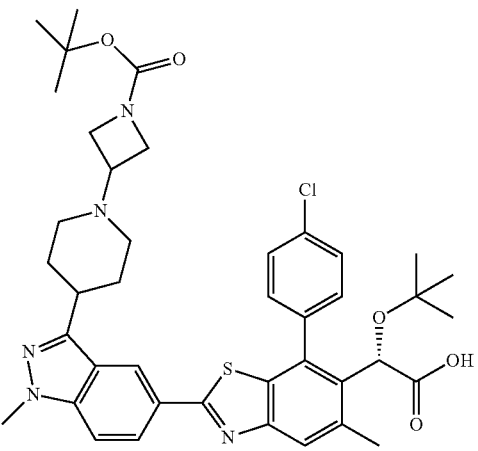 [SMILES: Cc1cc2nc(-c3ccc4c(c3)c(C3CCN(C5CN(C(=O)OC(C)(C)C)C5)CC3)nn4C)sc2c(-c2ccc(Cl)cc2)c1[C@H](OC(C)(C)C)C(=O)O] | 28 | 73 | 1801 | 2258 | |
| 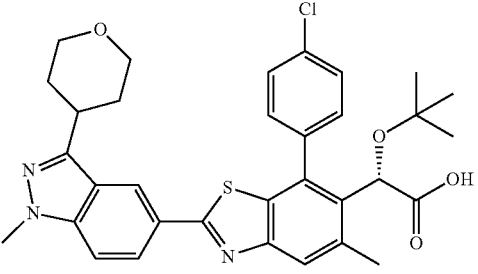 [SMILES: Cc1cc2nc(-c3ccc4c(c3)c(C3CCOCC3)nn4C)sc2c(-c2ccc(Cl)cc2)c1[C@H](OC(C)(C)C)C(=O)O] | 144 | 10 | 1809 | 3273 | |

-continued
| Structure | Compound # | WT EC50 (nM) | T174I BT EC50 (nM) | T174I DE EC50 (nM) | Hum MS stability t½ (min) |
|---|---|---|---|---|---|
| 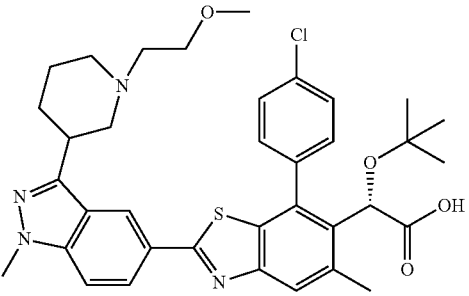 [SMILES: COCCN1CCCC(c2nn(C)c3ccc(-c4nc5cc(C)c([C@H](OC(C)(C)C)C(=O)O)c(-c6ccc(Cl)cc6)c5s4)cc23)C1] | 77 | 9 | 1810 | 3273 | 130 |
| 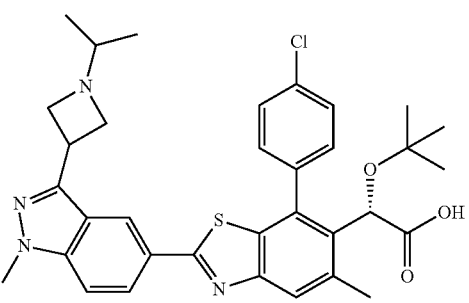 [SMILES: Cc1cc2nc(-c3ccc4c(c3)c(C3CN(C(C)C)C3)nn4C)sc2c(-c2ccc(Cl)cc2)c1[C@H](OC(C)(C)C)C(=O)O] | 54 | 6 | 1829 | 3294 | 395 |
| 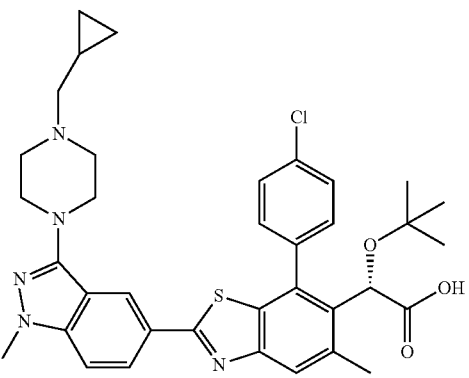 [SMILES: Cc1cc2nc(-c3ccc4c(c3)c(N3CCN(CC5CC5)CC3)nn4C)sc2c(-c2ccc(Cl)cc2)c1[C@H](OC(C)(C)C)C(=O)O] | 100 | 10 | 1883 | 3587 | 194 |
| 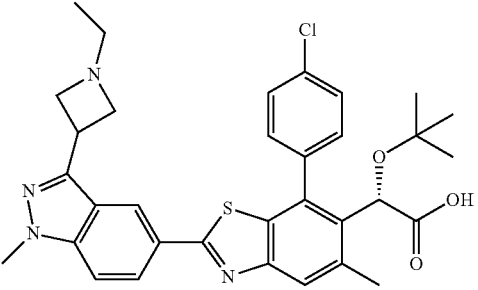 [SMILES: CCN1CC(c2nn(C)c3ccc(-c4nc5cc(C)c([C@H](OC(C)(C)C)C(=O)O)c(-c6ccc(Cl)cc6)c5s4)cc23)C1] | 58 | 9 | 1930 | 3092 | 395 |

-continued

| Structure | Compound # | WT EC50 (nM) | T174I BT EC50 (nM) | T174I DE EC50 (nM) | Hum MS stability t½ (min) |
|---|---|---|---|---|---|
| 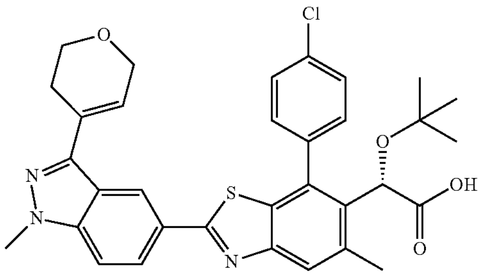 [SMILES: Cc1cc2nc(-c3ccc4c(c3)c(C3=CCOCC3)nn4C)sc2c(-c2ccc(Cl)cc2)c1[C@H](OC(C)(C)C)C(=O)O] | 18 | 14 | 2154 | 4502 | |
| 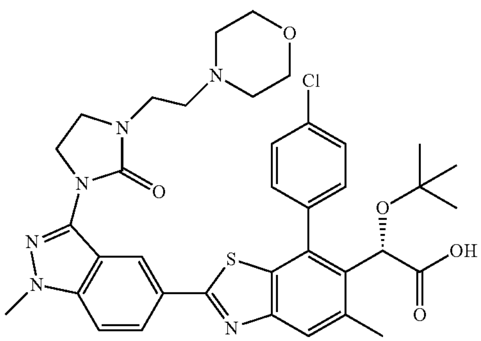 [SMILES: Cc1cc2nc(-c3ccc4c(c3)c(N3CCN(CCN5CCOCC5)C3=O)nn4C)sc2c(-c2ccc(Cl)cc2)c1[C@H](OC(C)(C)C)C(=O)O] | 83 | 17 | 2231 | 2813 | |
| 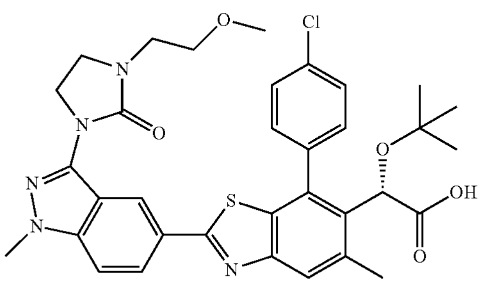 [SMILES: COCCN1CCN(c2nn(C)c3ccc(-c4nc5cc(C)c([C@H](OC(C)(C)C)C(=O)O)c(-c6ccc(Cl)cc6)c5s4)cc23)C1=O] | 79 | 7 | 2325 | 2183 | 395 |
| 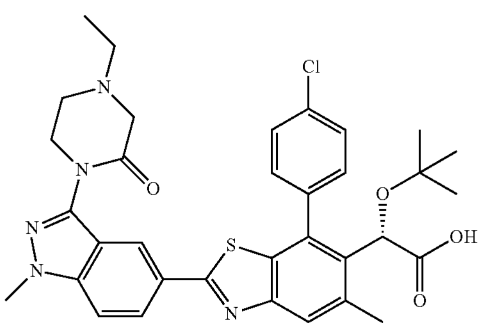 [SMILES: CCN1CCN(c2nn(C)c3ccc(-c4nc5cc(C)c([C@H](OC(C)(C)C)C(=O)O)c(-c6ccc(Cl)cc6)c5s4)cc23)C(=O)C1] | 86 | 15 | 2334 | 1995 | |
| 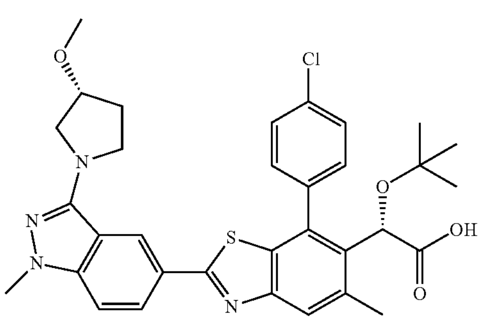 [SMILES: CO[C@@H]1CCN(c2nn(C)c3ccc(-c4nc5cc(C)c([C@H](OC(C)(C)C)C(=O)O)c(-c6ccc(Cl)cc6)c5s4)cc23)C1] | 140 | 29 | 2369 | 2630 | |

-continued
| Structure | Compound # | WT EC50 (nM) | T174I BT EC50 (nM) | T174I DE EC50 (nM) | Hum MS stability t½ (min) |
|---|---|---|---|---|---|
| 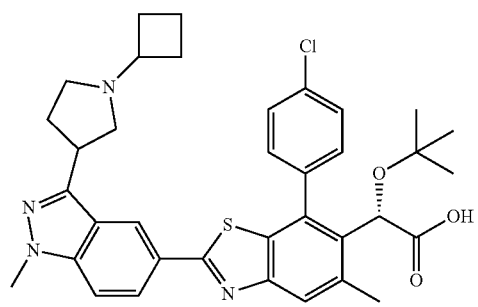 [SMILES: Cc1cc2nc(-c3ccc4c(c3)c(C3CCN(C5CCC5)C3)nn4C)sc2c(-c2ccc(Cl)cc2)c1[C@H](OC(C)(C)C)C(=O)O] | 71 | 5 | 2469 | 2239 | 395 |
| 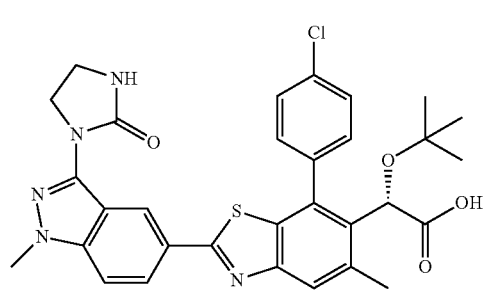 [SMILES: Cc1cc2nc(-c3ccc4c(c3)c(N3CCNC3=O)nn4C)sc2c(-c2ccc(Cl)cc2)c1[C@H](OC(C)(C)C)C(=O)O] | 78 | 32 | 2693 | 3194 | |
| 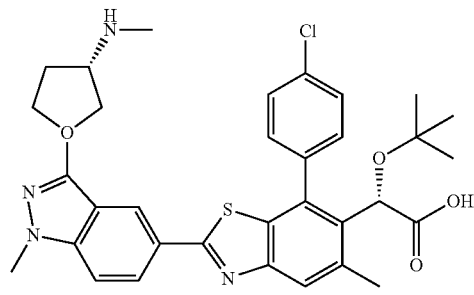 | 94 | 38 | 2717 | 2519 | |
| 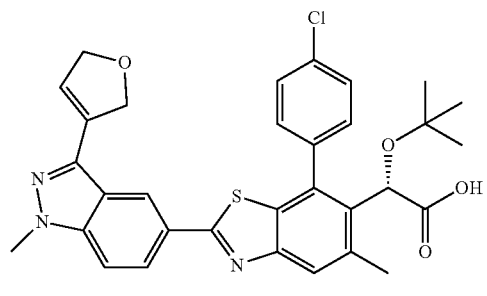 [SMILES: Cc1cc2nc(-c3ccc4c(c3)c(C3=CCOC3)nn4C)sc2c(-c2ccc(Cl)cc2)c1[C@H](OC(C)(C)C)C(=O)O] | 51 | 15 | 2725 | 3591 | |
| 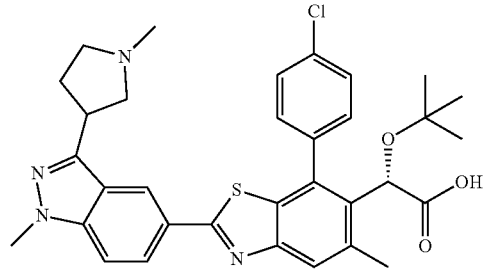 [SMILES: Cc1cc2nc(-c3ccc4c(c3)c(C3CCN(C)C3)nn4C)sc2c(-c2ccc(Cl)cc2)c1[C@H](OC(C)(C)C)C(=O)O] | 63 | 10 | 2796 | 13152 | 395 |

-continued
| Structure | Compound # | WT EC50 (nM) | T174I BT EC50 (nM) | T174I DE EC50 (nM) | Hum MS stability t½ (min) |
|---|---|---|---|---|---|
| 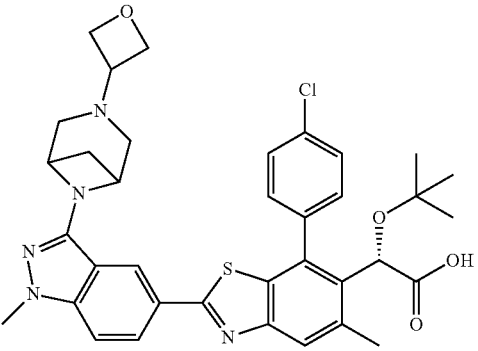 [SMILES: Cc1cc2nc(-c3ccc4c(c3)c(N3C5CC3CN(C3COC3)C5)nn4C)sc2c(-c2ccc(Cl)cc2)c1[C@H](OC(C)(C)C)C(=O)O] | 166 | 11 | 2835 | 2141 | |
| 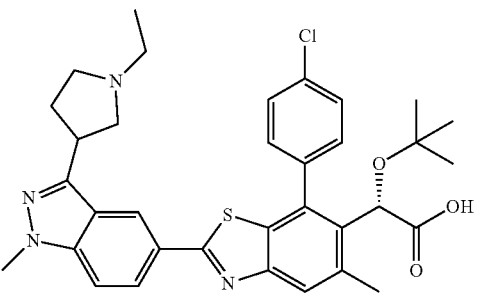 [SMILES: CCN1CCC(c2nn(C)c3ccc(-c4nc5cc(C)c([C@H](OC(C)(C)C)C(=O)O)c(-c6ccc(Cl)cc6)c5s4)cc23)C1] | 64 | 11 | 2842 | 2624 | 395 |
| 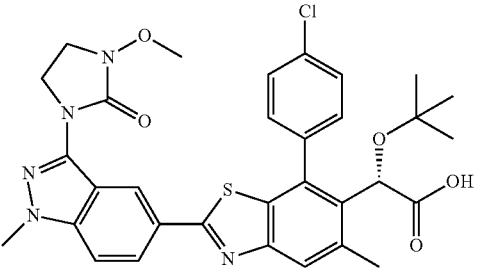 [SMILES: CON1CCN(c2nn(C)c3ccc(-c4nc5cc(C)c([C@H](OC(C)(C)C)C(=O)O)c(-c6ccc(Cl)cc6)c5s4)cc23)C1=O] | 82 | 14 | 3088 | 3866 | 395 |
| 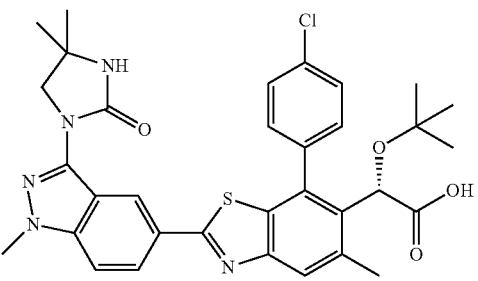 [SMILES: Cc1cc2nc(-c3ccc4c(c3)c(N3CC(C)(C)NC3=O)nn4C)sc2c(-c2ccc(Cl)cc2)c1[C@H](OC(C)(C)C)C(=O)O] | 121 | 39 | 3481 | 2692 | |
| 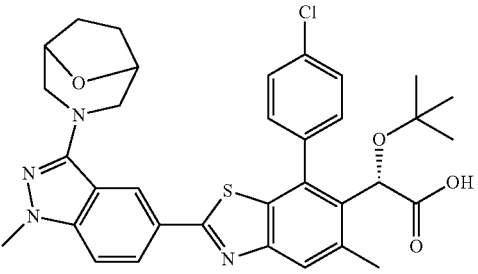 [SMILES: Cc1cc2nc(-c3ccc4c(c3)c(N3CC5CCC(C3)O5)nn4C)sc2c(-c2ccc(Cl)cc2)c1[C@H](OC(C)(C)C)C(=O)O] | 141 | 24 | 3557 | 3930 | |

-continued

| Structure | Compound # | WT EC50 (nM) | T174I BT EC50 (nM) | T174I DE EC50 (nM) | Hum MS stability t½ (min) |
|---|---|---|---|---|---|
| 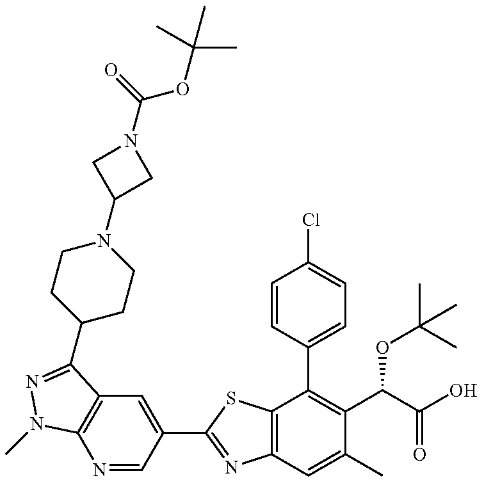 [SMILES: Cc1cc2nc(-c3cnc4c(c3)c(C3CCN(C5CN(C(=O)OC(C)(C)C)C5)CC3)nn4C)sc2c(-c2ccc(Cl)cc2)c1[C@H](OC(C)(C)C)C(=O)O] | 116 | 40 | 3812 | 5192 | |
| 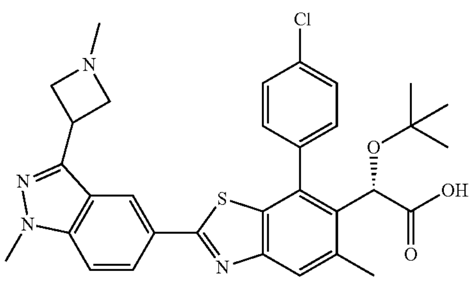 [SMILES: Cc1cc2nc(-c3ccc4c(c3)c(C3CN(C)C3)nn4C)sc2c(-c2ccc(Cl)cc2)c1[C@H](OC(C)(C)C)C(=O)O] | 57 | 13 | 4263 | 4136 | 395 |
| 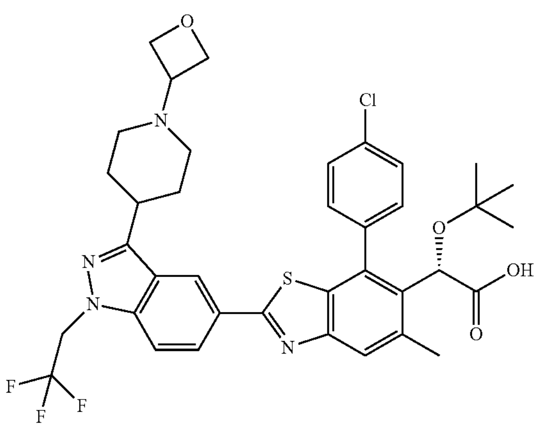 [SMILES: Cc1cc2nc(-c3ccc4c(c3)c(C3CCN(C5COC5)CC3)nn4CC(F)(F)F)sc2c(-c2ccc(Cl)cc2)c1[C@H](OC(C)(C)C)C(=O)O] | 41 | 3828 | 4976 | 5308 | |
| 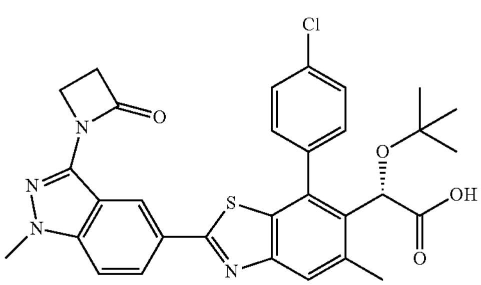 [SMILES: Cc1cc2nc(-c3ccc4c(c3)c(N3CCC3=O)nn4C)sc2c(-c2ccc(Cl)cc2)c1[C@H](OC(C)(C)C)C(=O)O] | 3 | 43 | 5714 | 5714 | |

-continued

| Structure | Compound # | WT EC50 (nM) | T174I BT EC50 (nM) | T174I DE EC50 (nM) | Hum MS stability t½ (min) |
|---|---|---|---|---|---|
| 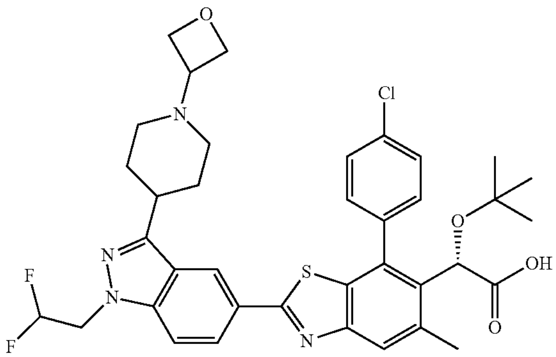 [SMILES: Cc1cc2nc(-c3ccc4c(c3)c(C3CCN(C5COC5)CC3)nn4CC(F)F)sc2c(-c2ccc(Cl)cc2)c1[C@H](OC(C)(C)C)C(=O)O] | 42 | 5039 | 5714 | 5714 | |
| 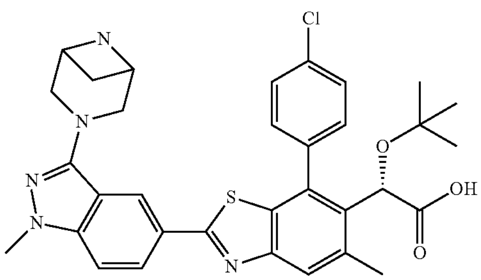 [SMILES: Cc1cc2nc(-c3ccc4c(c3)c(N3CC5CC(C3)N5)nn4C)sc2c(-c2ccc(Cl)cc2)c1[C@H](OC(C)(C)C)C(=O)O] | 143 | 27 | 5775 | 5610 | |
| 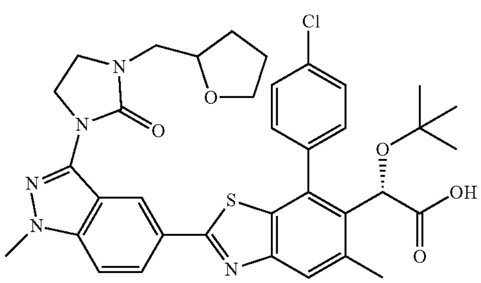 [SMILES: Cc1cc2nc(-c3ccc4c(c3)c(N3CCN(CC5CCCO5)C3=O)nn4C)sc2c(-c2ccc(Cl)cc2)c1[C@H](OC(C)(C)C)C(=O)O] | 81 | 13 | 6593 | 6973 | |
| 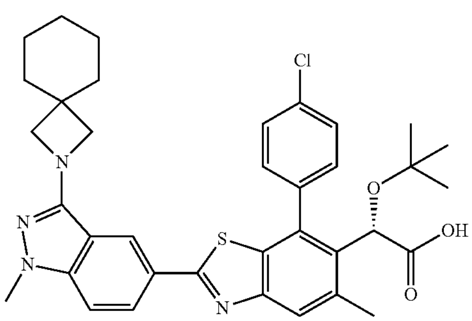 [SMILES: Cc1cc2nc(-c3ccc4c(c3)c(N3CC5(CCCCC5)C3)nn4C)sc2c(-c2ccc(Cl)cc2)c1[C@H](OC(C)(C)C)C(=O)O] | 97 | 150 | 6809 | 9186 | |
| 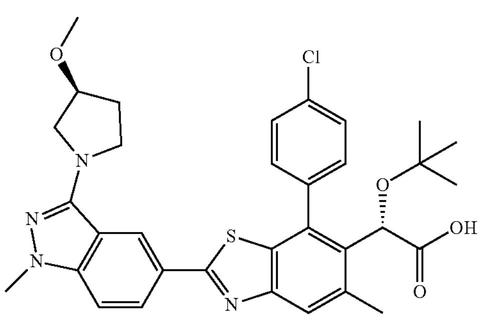 [SMILES: CO[C@H]1CCN(c2nn(C)c3ccc(-c4nc5cc(C)c([C@H](OC(C)(C)C)C(=O)O)c(-c6ccc(Cl)cc6)c5s4)cc23)C1] | 139 | 88 | 7810 | 5777 | |

-continued

| Structure | Compound # | WT EC50 (nM) | T174I BT EC50 (nM) | T174I DE EC50 (nM) | Hum MS stability t½ (min) |
|---|---|---|---|---|---|
| 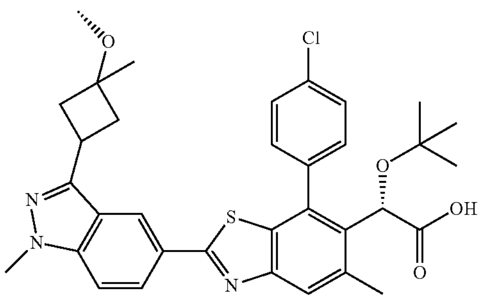 | 131 | 10 | 7946 | 3743 | 249 |
| 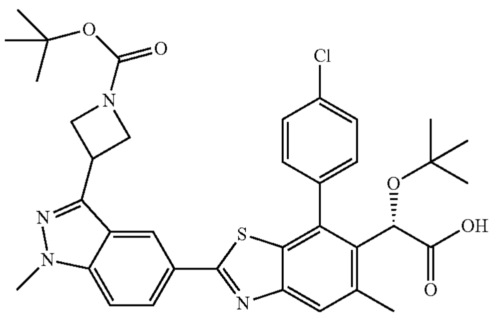 [SMILES: Cc1cc2nc(-c3ccc4c(c3)c(C3CN(C(=O)OC(C)(C)C)C3)nn4C)sc2c(-c2ccc(Cl)cc2)c1[C@H](OC(C)(C)C)C(=O)O] | 53 | 45 | 8909 | 57000 | |
| 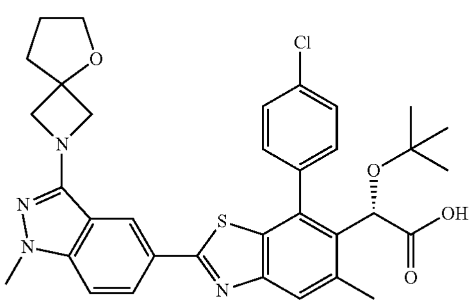 [SMILES: Cc1cc2nc(-c3ccc4c(c3)c(N3CC5(CCCO5)C3)nn4C)sc2c(-c2ccc(Cl)cc2)c1[C@H](OC(C)(C)C)C(=O)O] | 96 | 61 | 10259 | 9207 | |
| 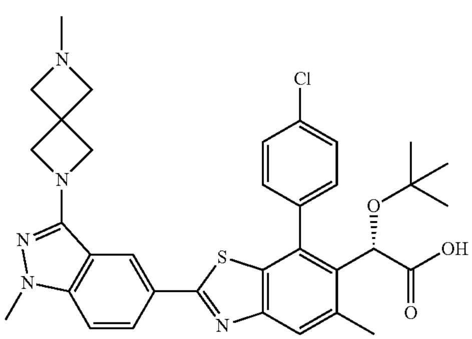 [SMILES: Cc1cc2nc(-c3ccc4c(c3)c(N3CC5(CN(C)C5)C3)nn4C)sc2c(-c2ccc(Cl)cc2)c1[C@H](OC(C)(C)C)C(=O)O] | 89 | 107 | 57000 | 57000 | |

| Structure | Compound # | WT EC50 (nM) | T174I BT EC50 (nM) | T174I DE EC50 (nM) | Hum MS stability t½ (min) |
|---|---|---|---|---|---|
| 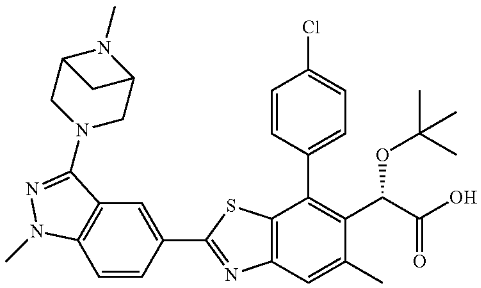 [SMILES: Cc1cc2nc(-c3ccc4c(c3)c(N3CC5CC(C3)N5C)nn4C)sc2c(-c2ccc(Cl)cc2)c1[C@H](OC(C)(C)C)C(=O)O] | 101 | 58 | 57000 | 57000 | |
| 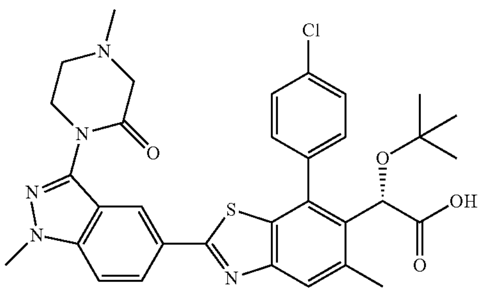 [SMILES: Cc1cc2nc(-c3ccc4c(c3)c(N3CCN(C)CC3=O)nn4C)sc2c(-c2ccc(Cl)cc2)c1[C@H](OC(C)(C)C)C(=O)O] | 87 | 13 | | | 395 |
| 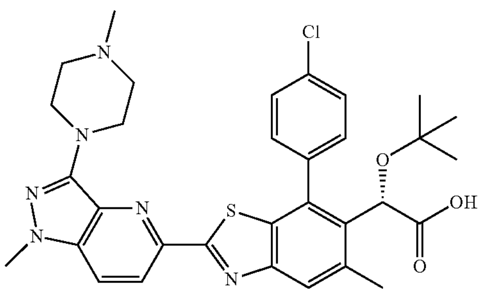 [SMILES: Cc1cc2nc(-c3ccc4c(n3)c(N3CCN(C)CC3)nn4C)sc2c(-c2ccc(Cl)cc2)c1[C@H](OC(C)(C)C)C(=O)O] | 196 | 4 | | | 395 |
| 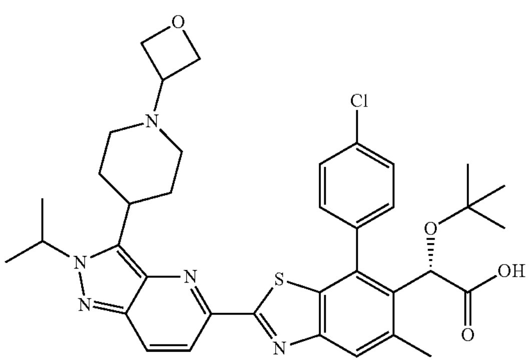 [SMILES: Cc1cc2nc(-c3ccc4nn(C(C)C)c(C5CCN(C6COC6)CC5)c4n3)sc2c(-c2ccc(Cl)cc2)c1[C@H](OC(C)(C)C)C(=O)O] | 195 | | | | |

All references, including publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

The use of the terms "a" and "an" and "the" and similar references in the context of this disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., such as, preferred, preferably) provided herein, is intended merely to further illustrate the content of the disclosure and does not pose a limitation on the scope of the claims. No language in the specification should be construed as indicating any non-claimed element as essential to the practice of the present disclosure.

Alternative embodiments of the claimed disclosure are described herein, including the best mode known to the inventors for practicing the claimed invention. Of these, variations of the disclosed embodiments will become apparent to those of ordinary skill in the art upon reading the foregoing disclosure. The inventors expect skilled artisans to employ such variations as appropriate (e.g., altering or combining features or embodiments), and the inventors intend for the invention to be practiced otherwise than as specifically described herein.

Accordingly, this invention includes all modifications and equivalents of the subject matter recited in the claims appended hereto as permitted by applicable law. Moreover, any combination of the above described elements in all possible variations thereof is encompassed by the invention unless otherwise indicated herein or otherwise clearly contradicted by context.

The use of individual numerical values is stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value or range. Thus, as a general matter, "about" or "approximately" broaden the numerical value. Also, the disclosure of ranges is intended as a continuous range including every value between the minimum and maximum values plus the broadening of the range afforded by the use of the term "about" or "approximately." Thus, recitation of ranges of values herein are merely intended to serve as a shorthand method of referring individually to each separate value falling within the range, unless otherwise indicated herein, and each separate value is incorporated into the specification as if it were individually recited herein.

It is to be understood that any ranges, ratios and ranges of ratios that can be formed by, or derived from, any of the data disclosed herein represent further embodiments of the present disclosure and are included as part of the disclosure as though they were explicitly set forth. This includes ranges that can be formed that do or do not include a finite upper and/or lower boundary. Accordingly, a person of ordinary skill in the art most closely related to a particular range, ratio or range of ratios will appreciate that such values are unambiguously derivable from the data presented herein.

What is claimed is:

1. A compound of Formula I:

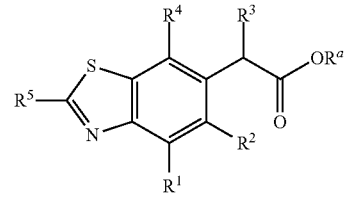

I or a pharmaceutically acceptable salt thereof, wherein:
  $R^1$ is H or $(C_1-C_6)$alkyl;
  $R^2$ is H or $(C_1-C_6)$alkyl;
  $R^a$ is H or $(C_1-C_6)$alkyl;
  $R^3$ is $O(C_1-C_6)$alkyl or $O(C_1-C_6)$cycloalkyl;
  $R^4$ is a 3-8 membered saturated, partially unsaturated, or aryl monocyclic ring containing 0-4 heteroatoms independently selected from nitrogen, oxygen, or sulfur, or an 8-13 membered saturated, partially unsaturated, or aryl bicyclic or tricyclic ring containing 0-4 heteroatoms independently selected from nitrogen, oxygen, or sulfur, and wherein $R^4$ is optionally substituted with 1-10 $R^f$;
  each $R^f$ is independently halo, $R^X$, $OR^X$, $SR^X$, CN, S(O)$R^X$, $SO_2R^X$, $OSO_2R^X$, $N(R^X)_2$, $NO_2$, $NR^XC(O)R^X$, $NR^XC(O)(CO)R^X$, $NR^XC(O)N(R^X)_2$, $NR^XC(O)OR^X$, $N(R^X)S(O)R^X$, $N(R^X)SO_2R^X$, $N(R^X)SO_2OR^X$, $C(O)R^X$, $C(O)OR^X$, $OC(O)R^X$, $OC(O)OR^X$, $C(O)N(R^X)_2$, $OC(O)N(R^X)_2$, or a 3-8 membered saturated, partially unsaturated, or aryl monocyclic ring containing 0-4 heteroatoms independently selected from nitrogen, oxygen, or sulfur, or two $R^f$ on the same carbon are taken together to form an oxo group;
  each $R^X$ is independently H, halo, $N(R^Y)_2$, $C(O)OR^Y$, $C_{1-8}$ aliphatic, $C_{1-8}$ heteroaliphatic, $(C_3-C_6)$cycloalkyl, 3-8 membered heterocycloalkyl containing 1-3 heteroatoms independently selected from nitrogen, oxygen, or sulfur, optionally substituted phenyl, or two $R^X$ on the same nitrogen are taken together to form a 5-6 membered saturated, partially saturated, or heteroaryl ring having 1-3 heteroatoms independently selected from nitrogen, oxygen, and sulfur, or two $R^X$ on the same carbon or on adjacent carbons are optionally taken together to form a $(C_3-C_6)$cycloalkyl, or a 3-6 membered saturated fused monocyclic ring containing 0-2 heteroatoms independently selected from nitrogen, oxygen, and sulfur, or two $R^X$ on the same carbon are taken together to form an oxo group;
    wherein the $C_{1-8}$ aliphatic, $C_{1-8}$ heteroaliphatic, $(C_3-C_6)$cycloalkyl, 3-8 membered heterocycloalkyl, or phenyl is optionally substituted with 1-5 $R^z$;
  each $R^z$ is independently halo, $C_{1-8}$ aliphatic, or $C_{1-8}$ heteroaliphatic;
  each $R^Y$ is independently H or $(C_1-C_6)$alkyl;
  $R^5$ is

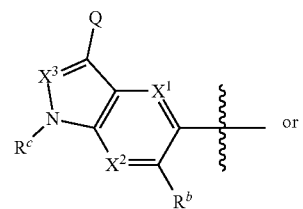

or

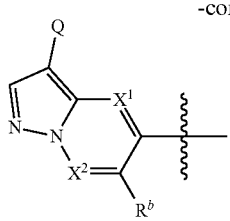

$R^b$ is H or $(C_1$-$C_6)$alkyl;

$R^c$ is H, $(C_1$-$C_6)$alkyl or $(C_3$-$C_6)$cycloalkyl, wherein $R^c$ is optionally substituted with 1-5 groups independently selected from halo, D, $OR^X$, and $N(R^X)_2$;

Q is a 3-10 membered saturated or partially unsaturated monocyclic or bicyclic heterocycloalkyl containing 1-3 heteroatoms independently selected from nitrogen, oxygen, or sulfur, optionally substituted with 1-5 $R^e$;

each $R^e$ is independently H, $(C_1$-$C_6)$alkyl, $N(R^X)_2$, $C(O)R^X$, $C(O)OR^X$, $S(O)_2R^X$, $(C_3$-$C_6)$cycloalkyl or 3-6 membered heterocycloalkyl containing 1-2 heteroatoms independently selected from nitrogen, oxygen, or sulfur, or two $R^e$ wherein $R^e$ on the same carbon are taken together to form an oxo group, or two $R^e$ wherein $R^e$ on the same carbon are taken together to form $(C_3$-$C_8)$cycloalkyl or 3-4 membered heterocycloalkyl containing 1-2 heteroatoms independently selected from nitrogen, oxygen, or sulfur, wherein $R^e$ is optionally substituted with 1-5 $R^g$;

each $R^g$ is independently halo, $R^X$, $OR^X$, $N(R^X)_2$, $C(O)R^X$, $C(O)OR^X$, $OC(O)R^X$, $OC(O)OR^X$, $S(O)_2R^X$, optionally substituted 3-4 membered heterocycloalkyl containing 1-2 heteroatoms independently selected from nitrogen, oxygen, or sulfur, or two $R^g$ on the same carbon are taken together to form an oxo group, or two $R^g$ on the same sulfur are optionally taken together to form an oxo group;

$X^1$ is N or C(H);
$X^2$ is N or C(H);
$X^3$ is N or C(H); and wherein the compound is not one of the following structures:

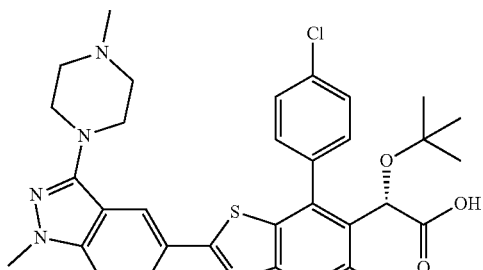

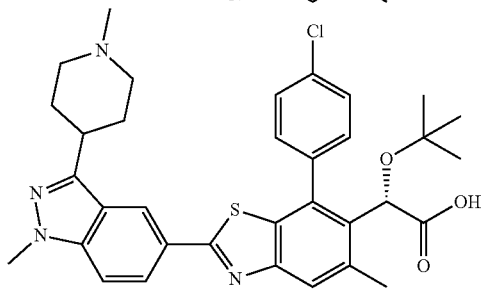

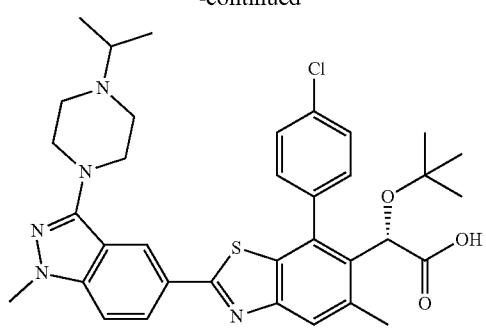

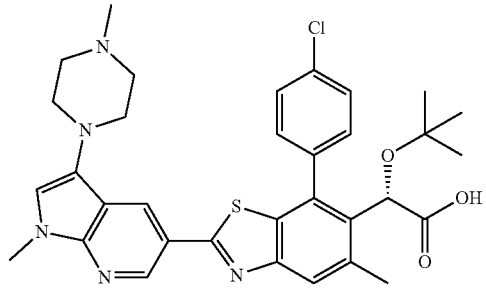

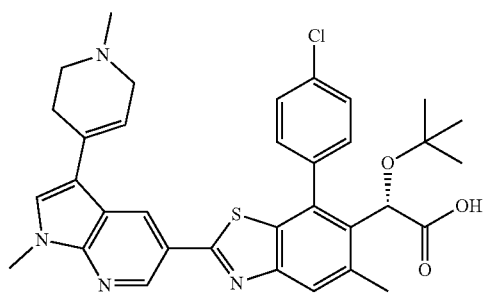

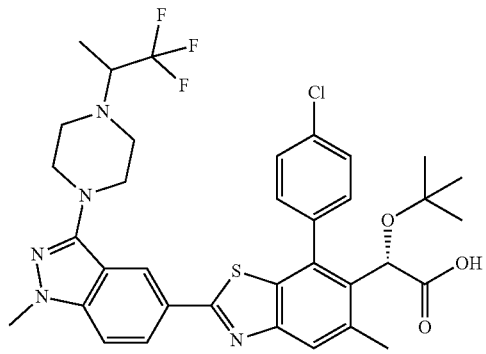

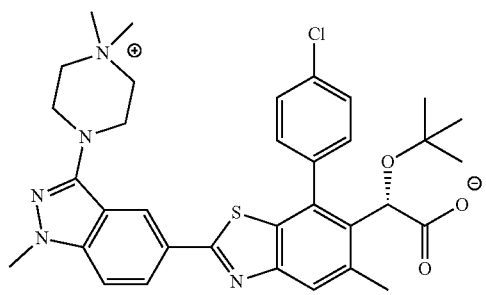

-continued
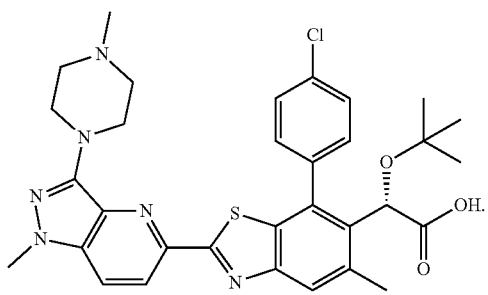
2. The compound of claim 1, wherein Q is a 5-6 membered saturated monocyclic heterocycloalkyl containing one heteroatom selected from nitrogen, oxygen, or sulfur, optionally substituted with 1-2 $R^e$.
3. The compound of claim 2, wherein Q is of the following formula:
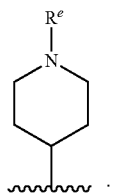
4. The compound of claim 1, of any of the following formulae:
II
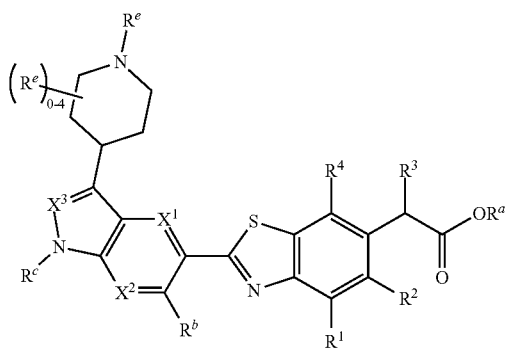
III
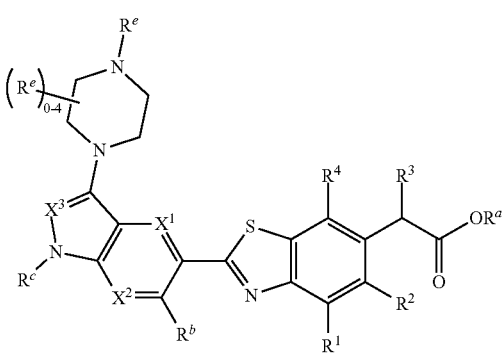
-continued
II-a
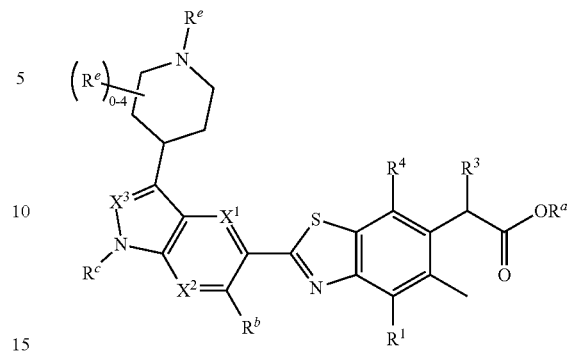
III-a
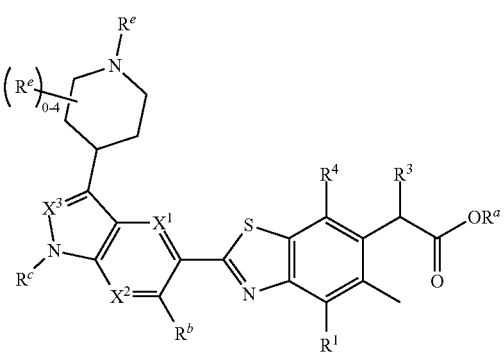
II-b
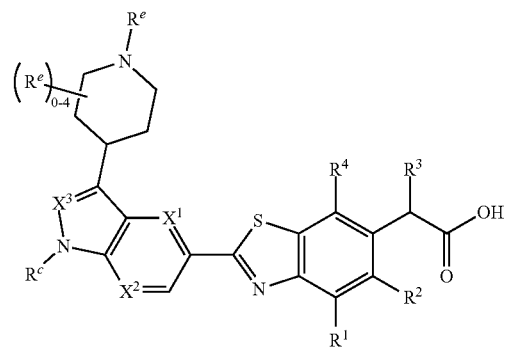
III-b
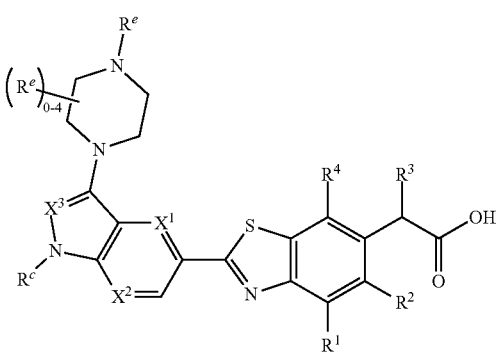

II-c
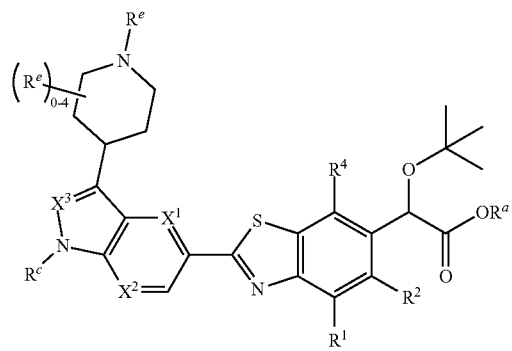
III-c
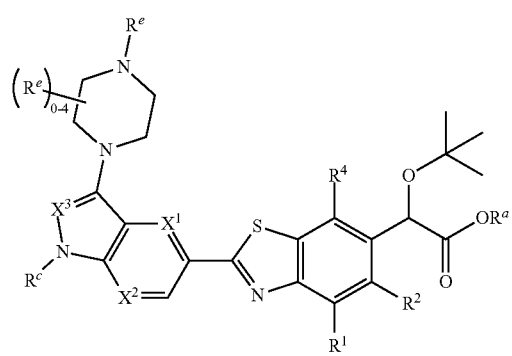
II-d
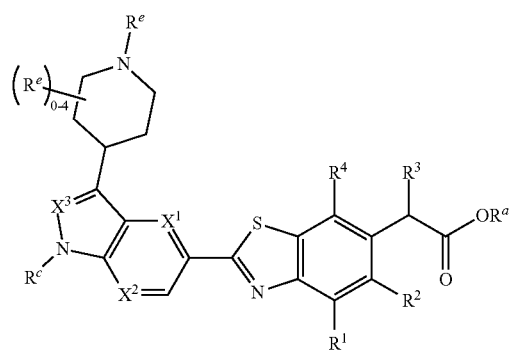
III-d
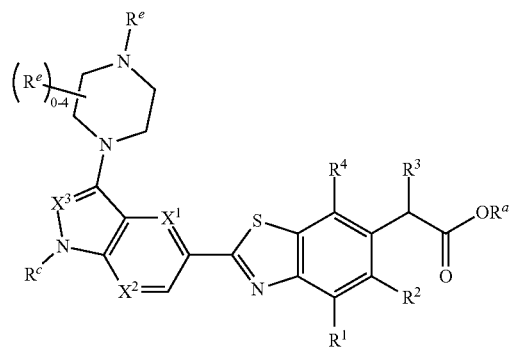
II-e
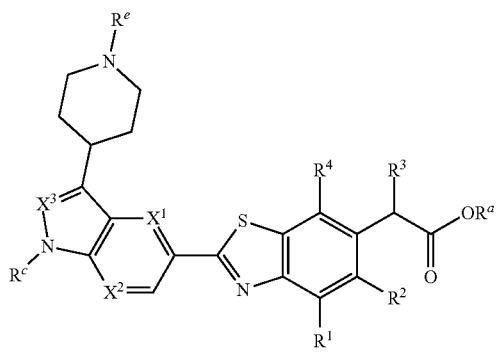
III-e
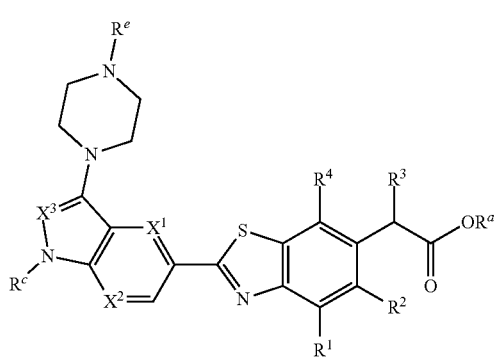
II-f
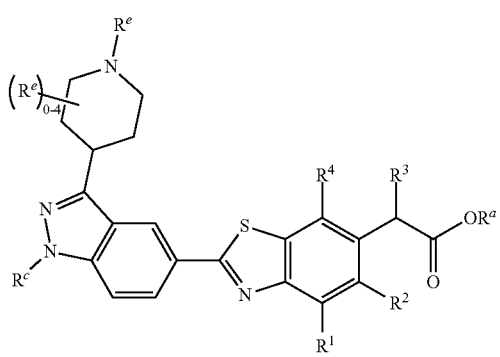
III-f
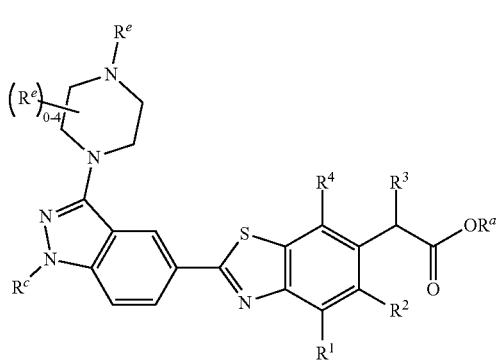

II-g
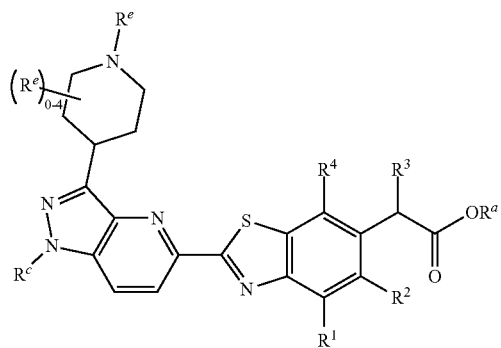
III-g
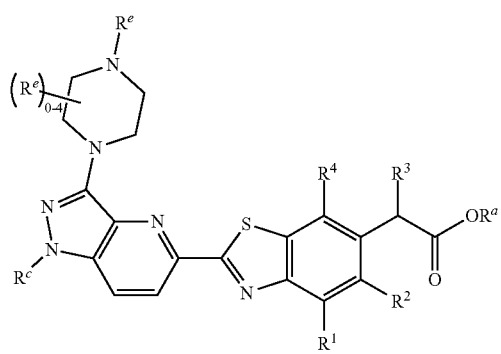
II-h
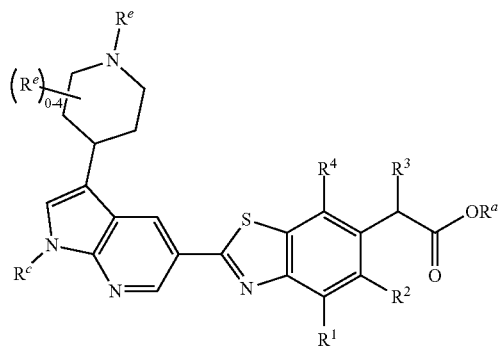
III-h
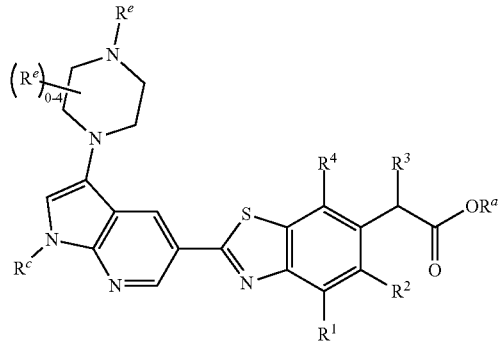
II-i
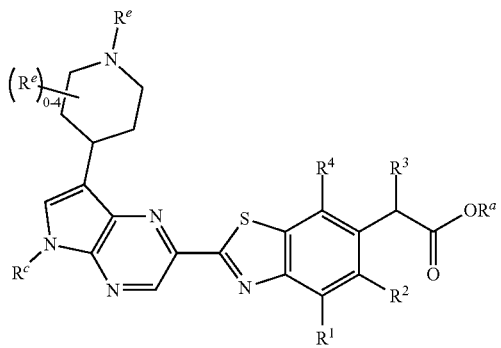
III-i
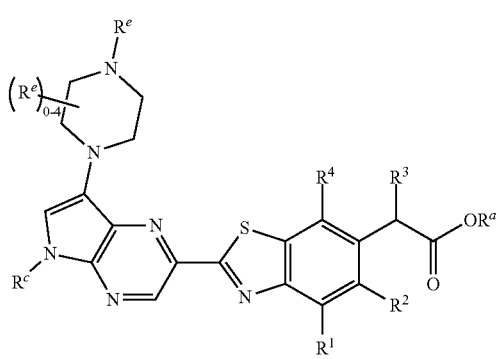
II-j
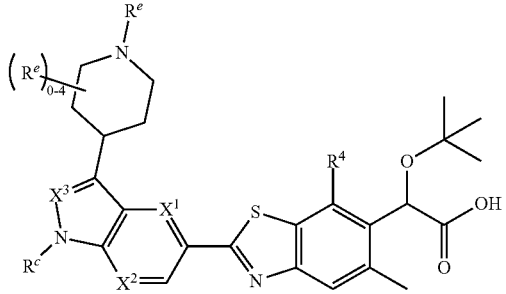
III-j
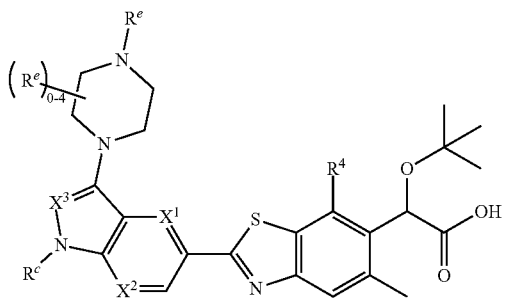

II-k
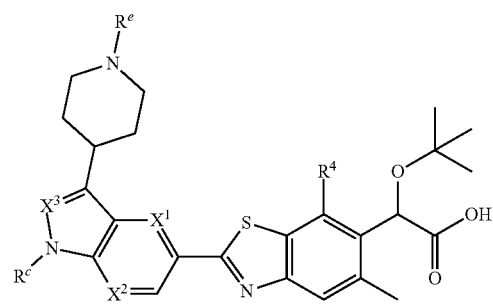
III-k
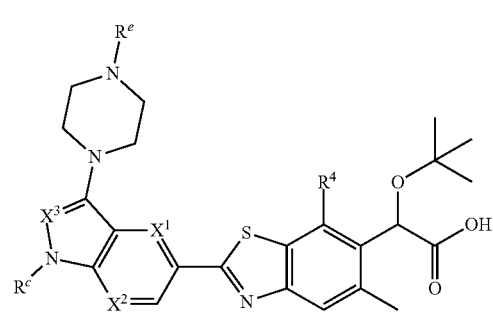
II-l
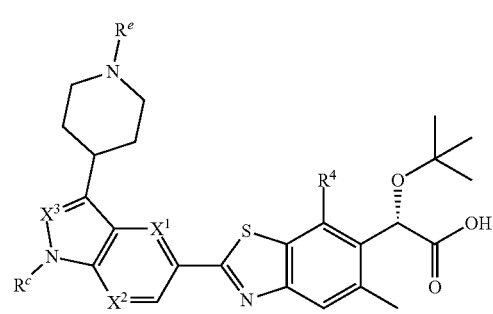
III-l
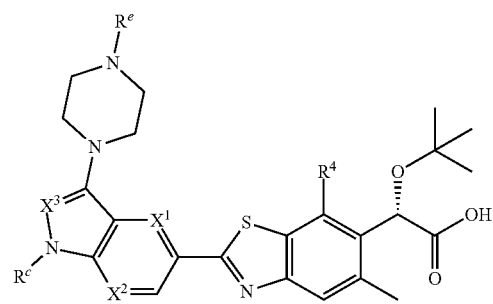
II-m
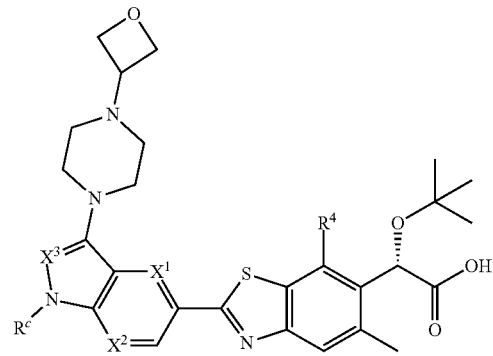
III-m
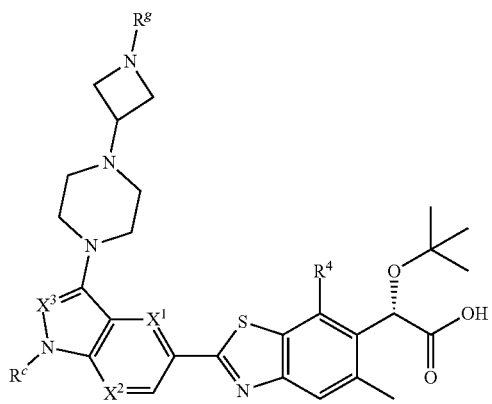
II-n
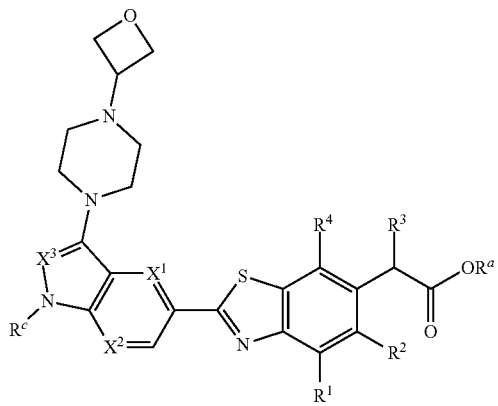
III-n II-o

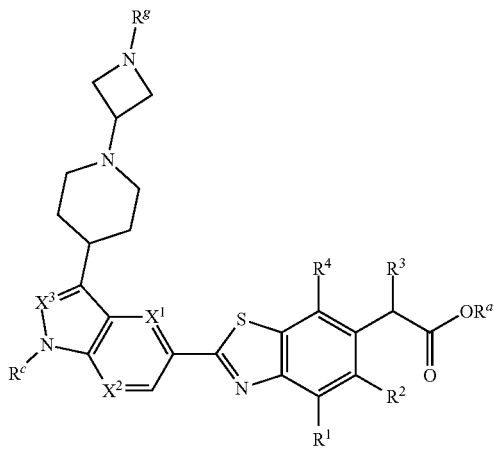

III-o

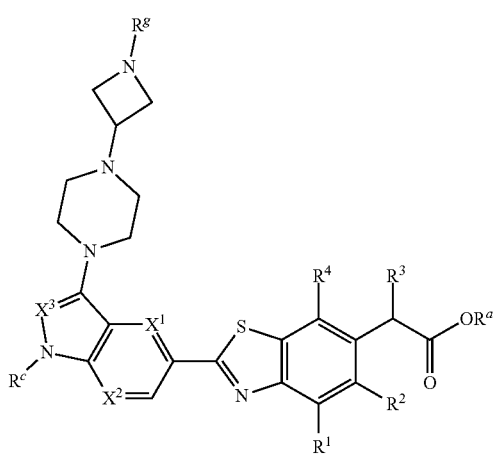

II-p

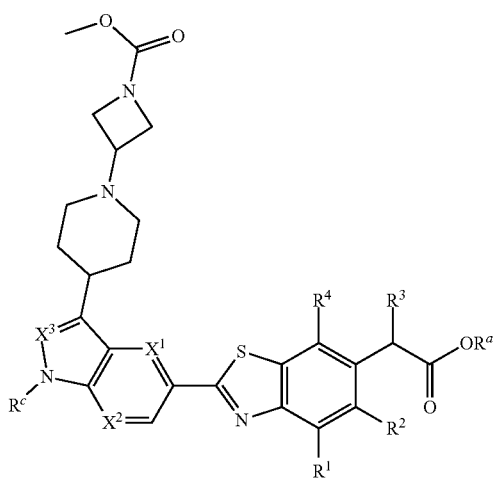

III-p

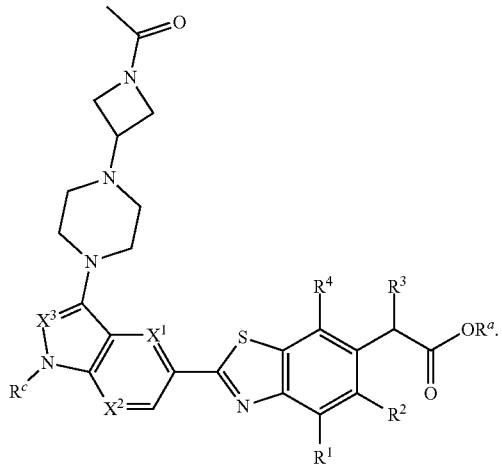

5. The compound of claim 1, wherein $R^1$ is H.
6. The compound of claim 1, wherein $R^2$ is methyl.
7. The compound of claim 1, wherein $R^a$ is H.
8. The compound of claim 1, wherein $R^3$ is selected from O-nPr, O-iPr, O-cyclopropyl, and O-tBu.
9. The compound of claim 8, wherein $R^3$ is O-tBu.
10. The compound of claim 1, wherein $R^4$ is a 3-8 membered saturated, partially unsaturated, or aryl monocyclic ring containing 0-4 heteroatoms independently selected from nitrogen, oxygen, or sulfur.
11. The compound of claim 10, wherein $R^4$ is a 5-6 membered aryl ring having 0-4 heteroatoms independently selected from nitrogen, oxygen, or sulfur, wherein the aryl ring is optionally substituted with 1-4 $R^f$.
12. The compound of claim 11, wherein $R^4$ is phenyl, optionally substituted with 1-4 $R^f$.
13. The compound of claim 12, wherein $R^4$ is phenyl optionally substituted at the para position with one $R^f$.
14. The compound of claim 11, wherein $R^4$ is optionally substituted with 1-4 $R^f$, wherein each $R^f$ is independently halo.
15. The compound of claim 14, wherein $R^4$ is substituted with one $R^f$, wherein $R^f$ is chloro.
16. The compound of claim 15, wherein $R^4$ is

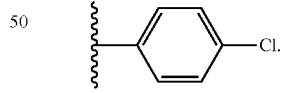

17. The compound of claim 1, wherein $R^b$ is H.
18. The compound of claim 1, wherein $R^c$ is $(C_1-C_6)$alkyl optionally substituted with 1-5 groups independently selected from halo, D, $OR^x$, and $NR^x_2$.
19. The compound of claim 18, wherein $R^c$ is methyl optionally substituted with 1-3 groups independently selected from halo, D, $OR^x$, and $NR^x_2$.
20. The compound of claim 19, wherein $R^c$ is methyl substituted with 1-3 fluoro.
21. The compound of claim 20, wherein $R^c$ is methyl substituted with two fluoro.
22. The compound of claim 18, wherein $R^c$ is methyl.
23. The compound of claim 18, wherein $R^c$ is ethyl.

24. The compound of claim 1, wherein $R^c$ is $(C_3-C_6)$ cycloalkyl optionally substituted with 1-5 groups independently selected from halo, D, $OR^x$, and $NR^x_2$.

25. The compound of claim 24, wherein $R^c$ is cyclopropyl optionally substituted with 1-3 groups independently selected from halo, D, $OR^x$, and $NR^x_2$.

26. The compound of claim 24, wherein $R^c$ is cyclopropyl.

27. The compound of claim 1, wherein at least one $R^e$ is independently a 3-6 membered heterocycloalkyl containing 1-2 heteroatoms independently selected from nitrogen, oxygen, or sulfur.

28. The compound of claim 1, wherein Q is substituted with one $R^e$.

29. The compound of claim 1, wherein $R^e$ is a 3-6 membered heterocycloalkyl containing 1-2 heteroatoms independently selected from nitrogen, oxygen, or sulfur, wherein $R^e$ is optionally substituted with 1-5 $R^g$.

30. The compound of claim 29, wherein $R^e$ is a 4 membered heterocycloalkyl containing one heteroatom independently selected from nitrogen, oxygen or sulfur, wherein $R^e$ is optionally substituted with 1-3 $R^g$.

31. The compound of claim 29, wherein $R^e$ is a 5 membered heterocycloalkyl containing one heteroatom independently selected from nitrogen, oxygen or sulfur, wherein $R^e$ is optionally substituted with 1-3 $R^g$.

32. The compound of claim 30, wherein $R^e$ is azetidine optionally substituted with 1-2 $R^g$.

33. The compound of claim 32, wherein $R^e$ is N-substituted azetidine.

34. The compound of claim 33, wherein $R^e$ is

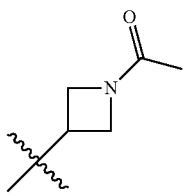

35. The compound of claim 33, wherein $R^e$ is

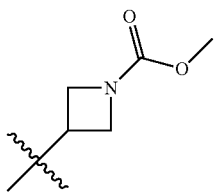

36. The compound of claim 30, wherein $R^e$ is oxetane optionally substituted with 1-2 $R^g$ groups.

37. The compound of claim 36, wherein $R^e$ is

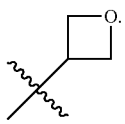

38. The compound of claim 1, wherein each $R^g$ is independently $R^x$, $OR^x$, $C(O)R^x$, or $C(O)OR^x$.

39. The compound of claim 1, wherein $X^1$ is N.

40. The compound of claim 1, wherein $X^1$ is C(H).

41. The compound of claim 1, wherein $X^2$ is N.

42. The compound of claim 1, wherein $X^2$ is C(H).

43. The compound of claim 1, wherein $X^3$ is N.

44. The compound of claim 1, wherein $X^3$ is C(H).

45. The compound of claim 9, wherein $R^3$ is

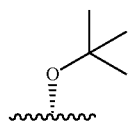

46. The compound of claim 1, selected from:

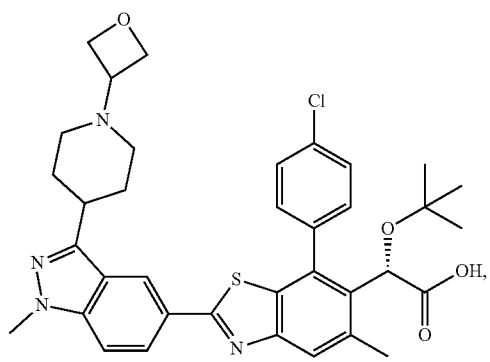

1

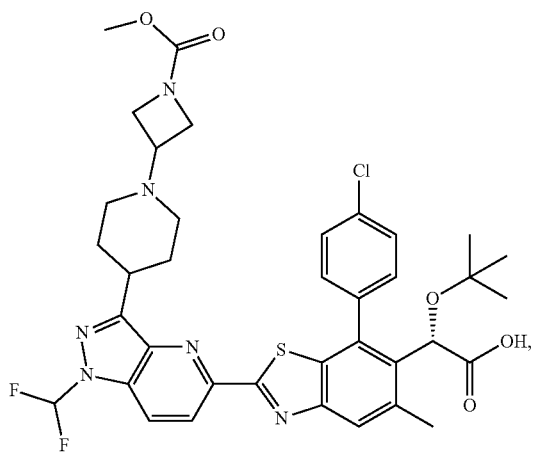

14

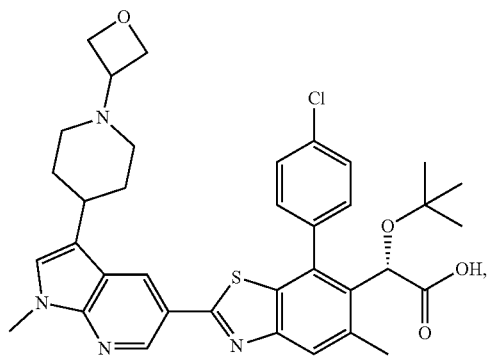

17

515
-continued
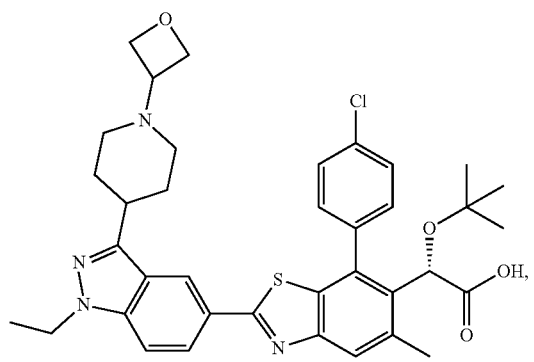
35
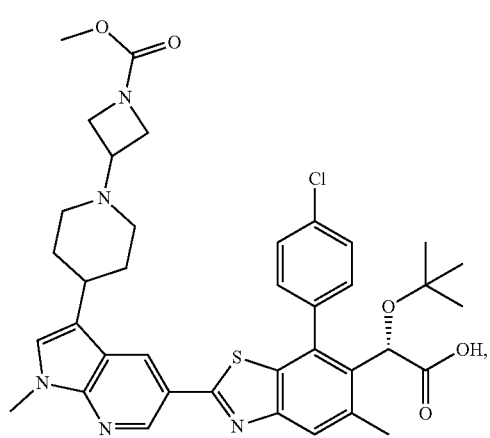
203
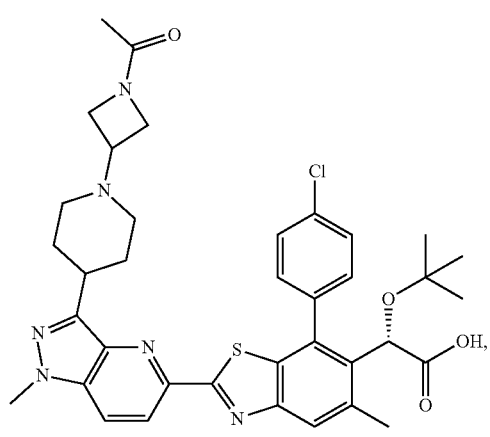
185
516
-continued
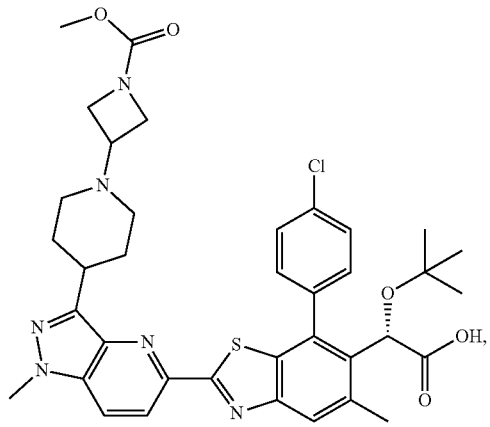
167
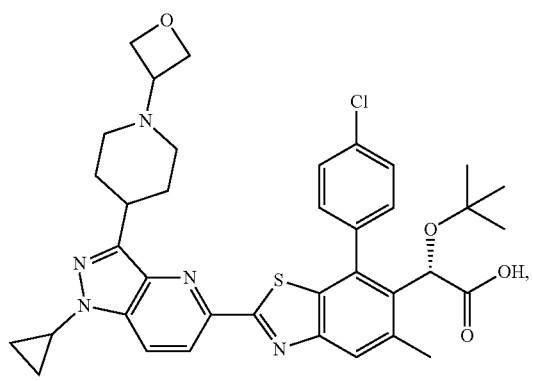
178
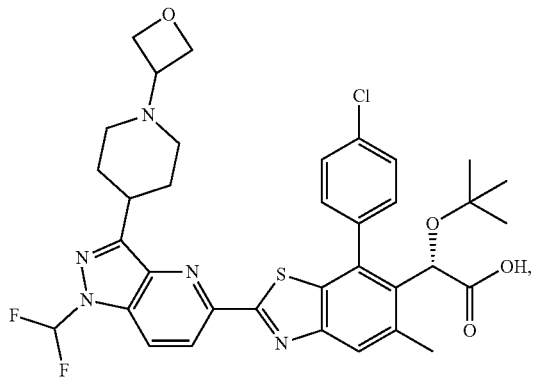
194

-continued

199

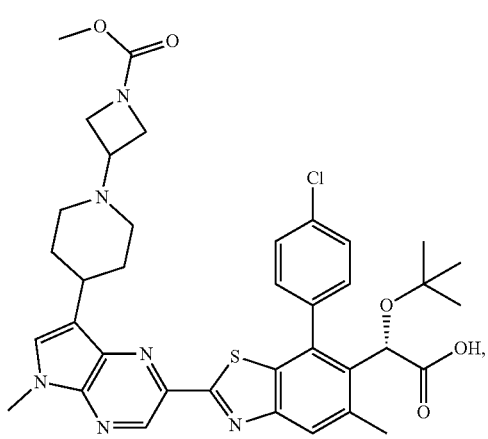

180

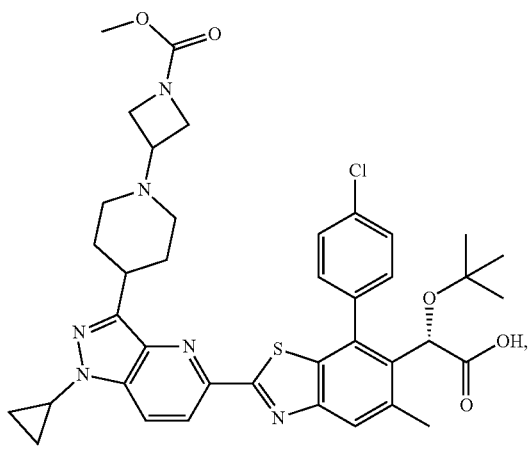

or a pharmaceutically acceptable salt thereof.

47. Compound 1:

1

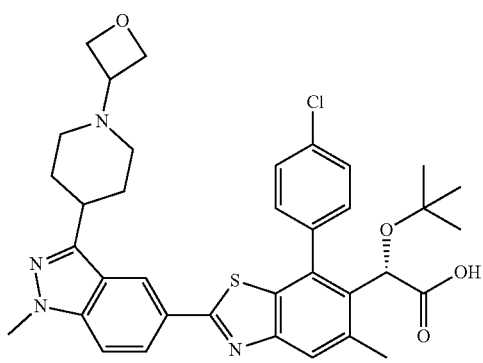

or a pharmaceutically acceptable salt thereof.

48. The compound of claim 1 of formula II-e:

II-e

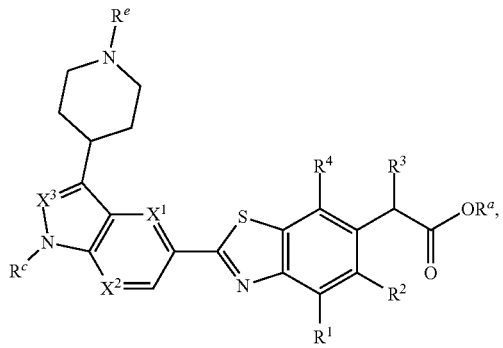

or a pharmaceutically acceptable salt thereof, wherein:
$R^1$ is H;
$R^2$ is $(C_1-C_6)$alkyl;
$R^a$ is H;
$R^3$ is $O(C_1-C_6)$alkyl;
$R^4$ is

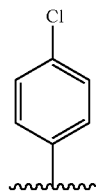

$R^c$ is $(C_1-C_6)$alkyl or $(C_3-C_6)$cycloalkyl, wherein $R^c$ is optionally substituted with 1-5 groups independently selected from halo, D, $OR^X$, and $N(R^X)_2$;
$R^e$ is a 4 membered heterocycloalkyl having one heteroatom selected from N or O, wherein $R^e$ is optionally substituted with 1-2 $R^g$;
each $R^g$ is independently $C(O)R^X$ or $C(O)OR^X$; and
each $R^X$ is independently $C_{1-8}$ aliphatic.

49. The compound of claim 48, wherein $X^1$ is N, $X^2$ is C(H), and $X^3$ is N.

50. The compound of claim 48, wherein $X^1$ is C(H), $X^2$ is C(H), and $X^3$ is N.

51. The compound of claim 48, wherein $X^1$ is C(H), $X^2$ is N, and $X^3$ is C(H).

52. The compound of claim 48, wherein $X^1$ is N, $X^2$ is N, and $X^3$ is C(H).

53. A pharmaceutical composition comprising a compound of Formula I as described in claim 1, or a pharmaceutically acceptable salt thereof, and a pharmaceutically acceptable carrier.

* * * * *